US012624028B2

(12) United States Patent
Giroux et al.

(10) Patent No.: US 12,624,028 B2
(45) Date of Patent: May 12, 2026

(54) 1H-PYRAZOLO[4,3-G]ISOQUINOLINE AND 1H-PYRAZOLO[4,3-G]QUINOLINE DERIVATIVES AS ALPHA-1-ANTITRYPSIN MODULATORS FOR TREATING ALPHA-1-ANTITRYPSIN DEFICIENCY (AATD)

(71) Applicant: Vertex Pharmaceuticals Incorporated, Boston, MA (US)

(72) Inventors: Simon Giroux, Cambridge, MA (US); Philippe Marcel Nuhant, Dorchester, MA (US); Upul Keerthi Bandarage, Lexington, MA (US); Pedro Manuel Garcia Barrantes, Melrose, MA (US); Yusheng Liao, Lexington, MA (US); Zachary Gale-Day, Brookline, MA (US); Wenxin Gu, Concord, MA (US); Alexander S. Karns, Boston, MA (US); Hu Zhang, Newton, MA (US); Emily Elizabeth Allen, Boston, MA (US); Jinwang Xu, Framingham, MA (US); Michael Paul Deninno, Gales Ferry, CT (US); Qing Tang, Boxborough, MA (US); Diane Marie Boucher, Beverly, MA (US); Lev T.D. Fanning, San Marcos, CA (US); Amy B. Hall, Wellesley Hills, MA (US); Dennis James Hurley, San Marcos, CA (US); Mac Arthur Johnson, Jr., Derry, NH (US); John Patrick Maxwell, Hingham, MA (US); Rebecca Jane Swett, Somerville, MA (US); Timothy Lewis Tapley, Cardiff, CA (US); Stephen A. Thomson, Durham, NC (US); Veronique Damagnez, Framingham, MA (US); Kevin Michael Cottrell, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 765 days.

(21) Appl. No.: 17/916,405

(22) PCT Filed: Apr. 2, 2021

(86) PCT No.: PCT/US2021/025616

§ 371 (c)(1),
(2) Date: Sep. 30, 2022

(87) PCT Pub. No.: WO2021/203025

PCT Pub. Date: Oct. 7, 2021

(65) Prior Publication Data

US 2023/0159521 A1 May 25, 2023

Related U.S. Application Data

(60) Provisional application No. 63/004,719, filed on Apr. 3, 2020.

(51) Int. Cl.
*C07D 471/04* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS

| | | | |
|---|---|---|---|
| 2,538,341 | A | 1/1951 | Ullyot |
| 2,612,503 | A | 9/1952 | Ullyot |
| 4,198,415 | A | 4/1980 | Kornfeld et al. |
| 4,647,667 | A | 3/1987 | Schaus et al. |
| 4,778,894 | A | 10/1988 | Schaus et al. |
| 5,216,001 | A | 6/1993 | Perregaard et al. |
| 5,358,949 | A | 10/1994 | Tabusa et al. |
| 6,201,129 | B1 | 3/2001 | Miller et al. |
| 11,623,924 | B2 | 4/2023 | Bandarage et al. |
| 11,884,672 | B2 | 1/2024 | Bandarage et al. |
| 12,331,057 | B2 | 6/2025 | Bandarage et al. |
| 2001/0051620 | A1 * | 12/2001 | Berger et al. |
| 2003/0097000 | A1 | 5/2003 | Bovy et al. |
| 2003/0165712 | A1 | 9/2003 | Lin et al. |
| 2003/0212085 | A1 | 11/2003 | McCall et al. |

(Continued)

FOREIGN PATENT DOCUMENTS

| | | | |
|---|---|---|---|
| CA | 3114672 | A1 | 4/2020 |
| CN | 1704404 | A | 7/2001 |

(Continued)

OTHER PUBLICATIONS

Al-Shaar et al. The Synthesis of Heterocycles via Addition-Elimination Reactions of 4- and 5-aminoimidazoles. J. Chem. Soc. Perkin Trans. 1 (1992). (Year: 1992).*

Carta et al. Reactions of Alkylation of Biologically Interesting triazolo[4,5-g]quinolines and triazolo[4,5-g]quinoline-1-oxides with Electrophilic Reagents. Heterocycles 75(10) 2493-2505 (2008). (Year: 2008).*

American Thoracic Society & European Respiratory Society (2003) "American Thoracic Society/European Respiratory Society Statement: Standards for the Diagnosis and Management of Individuals with Alpha-1 Antitrypsin Deficiency," *Am J Respir Crit Care Med.*, 168:818-900.

Balle, T. et al. (2003) "Synthesis and Structure-Affinity Relationship Investigations of 5-Aminomethyl and 5-Carbamoyl Analogues of the Antipsychotic Sertindole. A New Class of Selective a1 Adrenoceptor Antagonists," *Bioorg. Med. Chem.*, 11:1065-1078.

(Continued)

*Primary Examiner* — Jeffrey S Lundgren
*Assistant Examiner* — Sara Elizabeth Townsley
(74) *Attorney, Agent, or Firm* — Finnegan, Henderson, Farabow, Garrett & Dunner, LLP

(57) ABSTRACT

1H-pyrazolo[4,3-g]isoquinoline and 1H-pyrazolo[4,3-g]quinoline derivatives as alpha-1-antitrypsin modulators for treating alpha-1-antitrypsin deficiency (AATD).

36 Claims, No Drawings

(56) References Cited

U.S. PATENT DOCUMENTS

2004/0077865 A1 4/2004 Zhao et al.
2005/0009754 A1 1/2005 Pan et al.
2005/0043381 A1 2/2005 Johnson et al.
2005/0153957 A1 7/2005 Cuenoud et al.
2007/0027177 A1 2/2007 Trotter et al.
2007/0232682 A1 10/2007 Beard et al.
2007/0248947 A1 10/2007 Cezar
2008/0021056 A1 1/2008 Konradi et al.
2010/0016285 A1 1/2010 Uchida et al.
2010/0076018 A1 3/2010 Liu et al.
2011/0118221 A1 5/2011 Nussbaum et al.
2013/0167932 A1 7/2013 Maeda et al.
2013/0319530 A1 12/2013 Maeda et al.
2014/0135359 A1 5/2014 Martineau
2014/0341899 A1 11/2014 Dinarello et al.
2016/0083363 A1 3/2016 Hamm et al.
2016/0145271 A1 5/2016 Vakalopoulos et al.
2018/0251460 A1 9/2018 Aktoudianakis et al.
2020/0361939 A1 11/2020 Bandarage et al.
2021/0260036 A1 8/2021 Bozic et al.
2023/0157999 A1 5/2023 Clark et al.
2023/0159502 A1 5/2023 Giroux et al.
2023/0159504 A1 5/2023 Giroux et al.
2023/0159580 A1 5/2023 Giroux et al.
2023/0265080 A1 8/2023 Bandarage et al.
2023/0279010 A1 9/2023 Bligh et al.
2023/0339915 A1 10/2023 Giroux et al.
2024/0002386 A1 1/2024 Shi et al.
2024/0012010 A1 1/2024 Penney et al.
2024/0158404 A1 5/2024 Grey, Jr. et al.
2024/0336614 A1 10/2024 Bandarage et al.

FOREIGN PATENT DOCUMENTS

CN 1505613 A 6/2004
CN 102850324 A 1/2013
CN 103239451 8/2013
CN 105061316 A * 11/2015 ......... C07D 491/052
CN 107698505 A 2/2018
CN 109111426 A 1/2019
CN 109414596 A 3/2019
CN 110776459 A 2/2020
CN 113164761 A 7/2021
CN 115361946 A 11/2022
EP 0 465 398 A2 1/1992
EP 1 396 488 A1 3/2004
EP 3571187 B1 11/2019
EP 3 699 179 A1 8/2020
ES 323287 A1 3/1967
JP 4856667 A 8/1973
JP 2000-072751 A 3/2000
JP 2000-281654 A 10/2000
JP 5107589 B2 12/2012
RU 2337915 C1 11/2008
RU 2617405 C2 4/2017
WO WO 1996/037467 A1 11/1996
WO WO-0035919 A2 * 6/2000 ................ A61P 9/12
WO WO 2000/075114 A1 12/2000
WO WO 2001/044197 A2 6/2001
WO WO 2002/008224 A1 1/2002
WO WO 2002/094790 A1 11/2002
WO WO 2003/099824 A1 12/2003
WO WO 2004/065367 A1 8/2004
WO WO 2004/108120 A1 12/2004
WO WO 2006/019831 A1 2/2006
WO WO 2006/093823 A1 9/2006
WO WO 2007/022501 A2 2/2007
WO WO 2007/115315 A2 10/2007
WO WO 2009/060209 A1 5/2009
WO WO 2009/127686 A1 10/2009
WO WO 2009/158587 A1 12/2009
WO WO 2011/056222 A1 5/2011
WO WO 2011/110852 A1 9/2011
WO WO 2012/016695 A2 2/2012
WO WO 2012/038820 A2 3/2012
WO WO-2014179154 A2 * 11/2014 ........... C07D 519/00
WO WO 2016/154051 A1 9/2016
WO WO 2017/035418 A1 3/2017
WO WO 2017/117304 A1 7/2017
WO WO 2017/197240 A1 11/2017
WO WO 2017/207118 A1 12/2017
WO WO 2018/218192 A1 11/2018
WO WO 2019/076336 A1 4/2019
WO WO 2019/089667 A1 5/2019
WO WO 2019/116302 A1 6/2019
WO WO 2019/149522 A1 8/2019
WO WO 2019/243841 A1 12/2019
WO WO 2020/002611 A1 1/2020
WO WO 2020/033288 A1 2/2020
WO WO 2020/048694 A1 3/2020
WO WO 2020/081257 A1 4/2020
WO WO 2020/247160 A1 12/2020
WO WO 2021/067584 A1 4/2021
WO WO 2021/155087 A1 8/2021
WO WO 2021/203007 A1 10/2021
WO WO 2021/203010 A1 10/2021
WO WO 2021/203014 A1 10/2021
WO WO 2021/203023 A1 10/2021
WO WO 2021/203025 A1 10/2021
WO WO 2021/203028 A1 10/2021
WO WO 2022/026372 A2 2/2022
WO WO 2022/104353 A1 5/2022
WO WO 2022/109553 A2 5/2022
WO WO 2024/054624 A1 3/2024

OTHER PUBLICATIONS

Bergin, D.A. et al. (2014) "The circulating proteinase inhibitor alpha-1 antitrypsin regulates neutrophil degranulation and autoimmunity," *Sci Transl Med.*, 6(217):217ra1 (70 pages).
Chemical Abstracts Service, CAS Registry No. 1516110-75-0. CA Index Name: Pyrrolo[2,3-f]benzimidazole-7-methanamine, 6-ethyl-3,5-dihydro-2-methyl-6-Ethyl-3,5-dihydro-2-methylpyrrolo[2,3-f]benzimidazole-7-methanamine Date: Jan. 10, 2014.
Chemical Abstracts Service, CAS Registry No. 2103889-64-9. CA Index Name: Pyrrolo[2,3-f]benzimidazole-7-carbonitrile, 3,5-dihydro-2,5,6-trimethyl Date: Jul. 27, 2017.
Donawade, D.S. et al. (Apr. 2007.) "Synthesis and antimicrobial activity of novel linearly fused 5-substituted-7-acetyl-2,6-dimethyloxazolo[4,5-f] indoles," *Indian Journal of Chemistry*, 46B:690-693.
Forbes, I.T. et al. (1996) "Synthesis, Biological Activity, and Molecular Modeling Studies of Selective 5-$HT_{2C}$/*2B* Receptor Antagonists," *J. Med. Chem.*, 39:4966-4977.
Fregonese, F. & J. Stolk (2008) "Hereditary alpha-1-antitrypsin deficiency and its clinical consequences," *Orphanet J. Rare Dis.*, 3:16 (9 pages).
Geraghty, P. et al. (Dec. 2014.), "α1-Antitrypsin Activates Protein Phosphatase 2A to Counter Lung Inflammatory Responses," *Am J Respir Crit Care Med*, 190(11):1229-1242.
Grant & Hackh's Chemical Dictionary (5th ed. 1987), at p. 148.
Grinev, A.N. et al. (1975), "Synthesis of Aldehydes and Nitriles in the 5-Hydroxyindole Series," *Chem. Heterocycl. Compd.*, 11:1087-1090.
Gadaginamath, G.S. et al. (2000) "Chemoselective Reaction of 3,6-Diacetylindole Towards Hydroxylamine: Synthesis and Antimicrobial Activity of Novel Isoxazolo[4,5-f]indole Derivatives," *Rev. Roum. Chim.*, 45(10):929-933.
Ghorai, J. et al. (2016) "Cobalt(III)-Catalyzed Intramolecular Cross-Dehydrogenative C—H/X—H Coupling: Efficient Synthesis of Indoles and Benzofurans," *Chem. Eur. J.*, 22:16042-16046.
Ghorai, J. et al. (2018) "Divergent Functionalization of N-Alkyl-2-alkenylanilines: Efficient Synthesis of Substituted Indoles and Quinolines," *Chem. Asian J.*, 13(17):2499-2504.
Gosai, S. et al. (Nov. 2010.) "Automated High-Content Live Animal Drug Screening Using *C. elegans* Expressing the Aggregation Prone Serpin αl-antitrypsin Z," *PLoS One*, 5(11): e15460 (16 pages).
He, L. et al. (2014) "Transition-metal-free synthesis of multisubstituted N-arylindoles via reaction of arynes and α-amino ketones," *Tetrahedron*, 70:2400-2405.

(56) References Cited

OTHER PUBLICATIONS

International Search Report and Written Opinion from International Application No. PCT/US2021/025616, mailed Jun. 14, 2021 (12 pages).
Jafarpour, F. et al. (2019) "A Fast Track to Indoles and Annulated Indoles through ortho- vs ipso-Amination of Aryl Halides," *Org. Lett.*, 21:10143-10148.
Jiang, H. et al. (2016) "Multiple Roles of the Pyrimidyl Group in the Rhodium-Catalyzed Regioselective Synthesis and Functionalization of Indole-3-carboxylic Acid Esters," *Advanced Synthesis & Catalysis*, 358:188-194.
Kamat, A.G. et al. (Mar. 1994.), "Synthesis and Antimicrobial Activity of Furoindole Derivatives," *Indian J. Chem. Sect. B*, 33B(3):255-259.
Maity, S. et al. (Sep. 2012) "A Visible-Light-Mediated Oxidative C—N Bond Formation/Aromatization Cascade: A New Photocatalytic Preparation of N-Arylindoles," *Angew Chem Int Ed Engl.*, 51(38):9562-9566. NIH Public Access Author Manuscript; available in PMC Sep. 17, 2013 (11 pages).
Mali, R.S. et al. (1994) "Useful Syntheses of Pyrano- and Pyridoindoles," *Organic Preparations and Procedures International: The New Journal for Organic Synthesis*, 26(5):573-577.
Meti, P. et al. (2017) "Regioselective synthesis of dipyrrolopyrazine (DPP) derivatives via metal free and metal catalyzed amination and investigation of their optical and thermal properties," *RSC Adv.*, 7:18120-18131.
Notice of Allowance and Fee(s) Due for U.S. Appl. No. 16/593,118, mailed Nov. 9, 2022.
Ogushi, F. et al. (1987) "Z-type α1-antitrypsin is less competent than M1-type α1-antitrypsin as an inhibitor of neutrophil elastase," *J Clin Invest.*, 80(5):1366-1374.
Piitulainen, E. & H.A. Tanash (2015), "The Clinical Profile of Subjects Included in the Swedish National Register on Individuals with Severe Alpha 1-Antitrypsin deficiency," *COPD*, 12(S1):36-41.
Saccarello, M.L. et al. (Sep. 1979) "A New Synthesis of 1-Alkyl-3-aminoindoles," *Synthesis*, 1979(9):727-729.
Song, X. et al. (2018) "Regioselective Synthesis of 2-Alkenylindoles and 2-Alkenylindole-3-carboxylates through the Cascade Reactions of N-Nitrosoanilines with Propargyl Alcohols," *J. Org. Chem.*, 83:8509-8521.
Tanash, H.A. et al. (2016) "Cause-specific mortality in individuals with severe alpha 1-antitrypsin deficiency in comparison with the general population in Sweden," *International Journal of COPD*, 2016(11):1663-1669.
Tidwell, R.R. et al. (1978) "Diarylamidine Derivatives with One or Both of the Aryl Moieties Consisting of an Indole or Indole-like Ring. Inhibitors of Arginine-Specific Esteroproteases," J Med Chem, vol. 21, No. 7:613-623.
Wen, W. et al. (2014) "Substituted indoles as selective protease activated receptor 4 (PAR-4) antagonists: Discovery and SAR of ML354," *Bioorg. Med. Chem. Lett.*, http://dx.doi.org/10.1016/j.bmcl.2014.08.021.
*Vertex Provides Update on its Clinical Programs Targeting Alpha-1 Antitrypsin Deficiency*, Vertex (Oct. 14, 2020), https://news.vrtx.com/press-release/vertex-provides-update-its-clinical-programs-targeting-alpha-1-antitrypsin-deficiency (4 pages).
*Vertex Announces Primary Endpoint Achieved in Phase 2 Study of VX-864 in Alpha-1 Antitrypsin Deficiency*, Vertex (Jun. 10, 2021), https://news.vrtx.com/press-release/vertex-announces-primary-endpoint-achieved-phase-2-study-vx-864-alpha-1-antitrypsin (5 pages).
U.S. Appl. No. 17/060,945, filed Oct. 1, 2020, by Bozic et al.
U.S. Appl. No. 17/916,388, filed Sep. 30, 2022, by Giroux et al.
U.S. Appl. No. 17/916,405, filed Sep. 30, 2022, by Giroux et al.
U.S. Appl. No. 17/916,448, filed Sep. 30, 2022, by Clark et al.
U.S. Appl. No. 17/916,453, filed Sep. 30, 2022, by Giroux et al.
U.S. Appl. No. 17/916,481, filed Sep. 30, 2022, by Giroux et al.
U.S. Appl. No. 17/916,484, filed Sep. 30, 2022, by Giroux et al.
Akhapkina, V.I. et al. (2012) "Fundamental bases of modulatory concept and classification of modulatory drugs", Russian Medical Journal, 19: 933-951.
Aldonyte, R. et al. (2004) "Analysis of systemic biomarkers in COPD patients", Journal of Chronic Obstructive Pulmonarydisease, 1(2):155-164.
Belikov, V.G. (2007) "Pharmaceutical Chemistry", textbook, Moscow, MEDpress-inform, pp. 27-29.
Chemical Abstracts Service, CAS Registry No. 2255-53-0. CA Index Name: Carbostyril, 3-ethyl-8-hydroxy-4-methoxy-(8CI) Date: Nov. 16, 1984.
Chemical Abstracts Service, CAS Registry No. 56513-01-0. CA Index Name: 8-Hydroxy-3-methyl-1(2H)-isoquinolinone, Date: Nov. 16, 1984.
Chemical Abstracts Service, CAS Registry No. 73109-03-2. CA Index Name: 7-Hydroxy-3-methyl-2-phenyl-1(2H)-isoquinolinone, Date: Nov. 16, 1984.
Chemical Abstracts Service, CAS Registry No. 73828-43-0. CA Index Name: 1(2H)-Isoquinolinone, 3-ethyl-7-hydroxy- Date: Nov. 16, 1984.
Chemical Abstracts Service, CAS Registry No. 73828-46-3. CA Index Name: 1(2H)-Isoquinolinone, 3-ethyl-7-hydroxy-2-methyl- Date: Nov. 16, 1984.
Chemical Abstracts Service, CAS Registry No. 73828-51-0. CA Index Name: 7-Hydroxy-2-(2-hydroxyethyl)-3-methyl-I(2H)-isoquinolinone. Date: Nov. 16, 1984.
Chemical Abstracts Service, CAS Registry No. 73828-52-1. CA Index Name: 1(2H)-Isoquinolinone, 3-ethyl-7-hydroxy-2-(2-hydroxyethyl)- Date: Nov. 16, 1984.
Chemical Abstracts Service, CAS Registry No. 73828-55-4. CA Index Name: 1(2H)-Isoquinolinone, 3-ethyl- 2,7-dihydroxy- Date: Nov. 16, 1984.
Chemical Abstracts Service, CAS Registry No. 91348-44-6. CA Index Name: 3-(2-Bromoethyl)-8-hydroxy- 2(1H)-quinolinone. Date: Nov. 16, 1984.
Chemical Abstracts Service, CAS Registry No. 872787-19-4. CA Index Name: 1(2H)-Isoquinolinone, 7-amino-3-ethyl- Date: Jan. 27, 2006.
Chemical Abstracts Service, CAS Registry No. 102559-86-4. CA Index Name: 8-Quinolinol, 4-chloro-2-[2-(diethylamino)ethyl]-3-ethyl- Date: Jun. 7, 1986.
Chemical Abstracts Service, CAS Registry No. 1045710-22-2. CA Index Name: 8-Quinolinol, 3-(1-methylethyl)-2-(2-methylpropyl)- Date: Sep. 2, 2008.
Chemical Abstracts Service, CAS Registry No. 105909-75-9. CA Index Name: 8-Quinolinol, 3-ethyl-2-methyl- Date: Dec. 25, 1986.
Chemical Abstracts Service, CAS Registry No. 1078095-05-2. CA Index Name: 8-Quinolinol, 3-ethyl-2-phenyl- Date: Dec. 1, 2008.
Chemical Abstracts Service, CAS Registry No. 1780592-67-7. CA Index Name: 2-(7-hydroxy-2-methoxyquinolin-3-yl)acetic acid. Date: Jun. 15, 2015.
Chemical Abstracts Service, CAS Registry No. 1785114-56-8. CA Index Name: 7-Hydroxy-3-methyl-I-isoquinolinecarboxylic acid. Date: Jun. 21, 2015.
Chemical Abstracts Service, CAS Registry No. 1854272-23-3. CA Index Name: 4-Chloro-3-ethyl-2-methyl-8-(phenylmethoxy)quinoline Date: Jan. 28, 2016.
Chemical Abstracts Service, CAS Registry No. 1869801-41-1. CA Index Name: 3-Ethyl-N-methyl-7-(phenylmethoxy)-2-quinolinamine Date: Feb. 18, 2016.
Chemical Abstracts Service, CAS Registry No. 1873904-99-4. CA Index Name: 4-Chloro-3-ethyl-2-methyl-7-(phenylmethoxy)quinoline Date: Feb. 25, 2016.
Chemical Abstracts Service, CAS Registry No. 1875846-68-6. CA Index Name: N,3-Diethyl-7-(phenylmethoxy)-2-quinolinamine Date: Feb. 29, 2016.
Chemical Abstracts Service, CAS Registry No. 1877816-72-2. CA Index Name: N-Methyl-3-(1-methylethyl)-7-(phenylmethoxy)-2-quinolinamine Date: Mar. 2, 2016.
Chemical Abstracts Service, CAS Registry No. 1878025-01-4. CA Index Name: 4-Chloro-2-methyl-3-(1-methylethyl)-7-(phenylmethoxy)quinoline Date: Mar. 2, 2016.
Chemical Abstracts Service, CAS Registry No. 1880486-29-2. CA Index Name: 4-Chloro-2-methyl-3-(1-methylethyl)-8-(phenylmethoxy)quinoline Date: Mar. 6, 2016.

(56) References Cited

OTHER PUBLICATIONS

Chemical Abstracts Service, CAS Registry No. 1893503-08-6. CA Index Name: 1,2-Dihydro-8-hydroxy-1-methyl-2-oxo-3-quinolineacetic acid Date: Apr. 20, 2016.
Chemical Abstracts Service, CAS Registry No. 1936181-19-9. CA Index Name: 8-Hydroxy-3-(hydroxymethyl)-1(2H)-isoquinolinone Date: Jun. 21, 2016.
Chemical Abstracts Service, CAS Registry No. RN 2106364-27-4. Index Name: Pyrrolo[2,3-f]benzimidazole-7-carboxylic acid, 3,5-dihydro-2,5,6-trimethyl-, ethyl ester Date: Aug. 1, 2017.
Chemical Abstracts Service, CAS Registry No. RN 2137577-83-2. Index Name: 7-Hydroxy-3-(methylamino)-1(2H)-isoquinolinone, Date: Nov. 1, 2017.
Chou, T.-C. (2010) "Drug Combination Studies and Their Synergy Quantification Using the Chou-Talalay Method", Cancer Res; 70(2):440-446.
Dafforn, T. R. et al. (1999) ""A kinetic mechanism for the polymerization of alpha1-antitrypsin", The Journal of Biological Chemistry, 274 (4): 9548-9555."
Eggenschwiler, R. et al. (2013) "Sustained Knockdown of a Disease-Causing Gene in Patient-Specific Induced Pluripotent Stem Cells Using Lentiviral Vector-Based Gene Therapy", Stem Cells Translational Medicine, 2 (9): 641-654.
Ferrarotti, I. et al. (2020) "Quantification of circulating alpha-1-antitrypsin polymers in dried blood spots", Molecular Pathology and Funct. Genomics, 56, p. 326.
Fujisawa, T. (1959) "Studies on the Utilisation of Safrole as Medicinal Raw Materials XII. Synthesis of Indole Derivatives" Journal of the Pharmaceutical Society of Japan, 79(6): 778-783.
Harkevich, D.A. (2010) Pharmacology/Textbook, 10th edition, pp. 72-82.
International Search Report and Written Opinion from International Application No. PCT/US2025/019485, mailed Jul. 2, 2025 (10 pages).
Jiang, B. et al. (2011) "A multi-component domino reaction for the direct access to polyfunctionalized indolesvia intermolecular allylic esterification and indolation," Chem. Commun., 2012,48,808-810.
Kapetanovic IM. (2008). Computer-aided drug discovery and development (CADDD): in silico-chemico-biological approach. Chem Biol Interact. 30;171(2):165-76.
Kathuria, A. et al. (2011). Substrate specificity of acetoxy derivatives of coumarins and quinolones towards Calreticulin mediated transacetylation: Investigations on antiplatelet function. Bioorganic & Medicinal Chemistry, vol. 20: 1624-1638.
Khusnutdinov, R. et al. (2015), "Quinoline Synthesis by the Reaction of Anilines with 1,2-diols Catalyzed by Iron Compounds," J. Heterocyclic Chem., vol. 53: 1022-1029.
Kummerer, K. (2010) "Pharmaceuticals in the environment", Annual Review of Environment and Resources, 35:57-75.
Kuznetsova, GA. (2005) "Methodological instructions", Irkutsk State University, Department of General Physics, pp. 2-3.
Laefranchi, M. et al. (2018) "Heteropolymerization of[alpha]-1-antitrypsin mutants in cell models mimicking heterozygosity", Human Molecular Genetics, 27 (10): 1785-1793.
Liu, M. et al. (2016) "Synthesis and Antifungal Activities of Novel Strobilurin Derivatives Containing Quinolin-2(1H)-one Moiety," Chem. Res. Chin. Univ., 32(4): 600-606.
Lyubchanskaya, V. M. et al., Nenitzescu synthesis of derivatives of 5-hydroxybenzofuran and 5- and 6-hydroxyindoles,Khimiko-Farmatsevtichesik Zhurnal, 1992, 26(9-10), 108-112.
Mashkovsky (2001) MD. Drugs, 14th edition, Moscow, 1:11.
Modi, A. R. et al., "Synthesis of 3-Methyl, 3-Formyl & Other 3-Substituted N-Arylisoquinolones", Indian Journal of Chemistry, 1979, vol. 188, pp. 304-306.
Modi, A. R. et al., "Synthesis of 7-hydroxy-3-alkylisoquinolones and 7-hydroxy-3-alkylisocoumarins from 4-hydroxyhomophthalic acid", Indian Journal of Chemistry, 1979, vol. 178, No. 4, pp. 360-363.
Priya, N. et al. (2010) "Characterization of 4-methyl-2-oxo-1,2-dihydroquinolin-6-yl acetate as an effective antiplatelet agent," Bioorganic & Medicinal Chemistry, vol. 18: 4085-4094.
STOLLER, J.K. "Alpha-1 antitrypsin deficiency: An under-recognized, treatable cause of COPD." *Cleve Clin J Med* 83, No. 7 (2016): 507-14.
U.S. Appl. No. 18/630,559, filed Apr. 9, 2024, by Bozic et al.
Xu, M. et al, Facile Assembly of 11 H-Indolo[3,2-c]quinoline by a Two-Step Protocol Involving a Regioselective 6-endo-Cyclization Promoted by the Hendrickson Reagent, Synthesis 2011, No. 4, pp. 0626-0634.
Zorgdrager, J. et al. (1989) "Synthesis of indoles using (N-arylaminomethyl)diphenylphosphine oxides," *Recueil des Travaux Chimiques des Pays-Bas*, 108 (12): 441-444.

* cited by examiner

1H-PYRAZOLO[4,3-G]ISOQUINOLINE AND 1H-PYRAZOLO[4,3-G]QUINOLINE DERIVATIVES AS ALPHA-1-ANTITRYPSIN MODULATORS FOR TREATING ALPHA-1-ANTITRYPSIN DEFICIENCY (AATD)

This application claims the benefit of priority of U.S. Provisional Application No. 63/004,719, filed Apr. 3, 2020, the contents of which are incorporated by reference herein in their entirety.

The disclosure provides compounds that are capable of modulating alpha-1 antitrypsin (AAT) activity and methods of treating alpha-1 antitrypsin deficiency (AATD) by administering one or more such compounds.

AATD is a genetic disorder characterized by low circulating levels of AAT. While treatments for AATD exist, there is currently no cure. AAT is produced primarily in liver cells and secreted into the blood, but it is also made by other cell types including lung epithelial cells and certain white blood cells. AAT inhibits several serine proteases secreted by inflammatory cells (most notably neutrophil elastase [NE], proteinase 3, and cathepsin G) and thus protects organs such as the lung from protease-induced damage, especially during periods of inflammation.

The mutation most commonly associated with AATD involves a substitution of lysine for glutamic acid (E342K) in the SERPINA1 gene that encodes the AAT protein. This mutation, known as the Z mutation or the Z-allele, leads to misfolding of the translated protein, which is therefore not secreted into the bloodstream and can polymerize within the producing cell. Consequently, circulating AAT levels in individuals homozygous for the Z-allele (PiZZ) are markedly reduced; only approximately 15% of mutant Z-AAT protein folds correctly and is secreted by the cell. An additional consequence of the Z mutation is that the secreted Z-AAT has reduced activity compared to wild-type protein, with 40% to 80% of normal antiprotease activity (American thoracic society/European respiratory society, Am J Respir Crit Care Med. 2003; 168(7):818-900; and Ogushi et al. J Clin Invest. 1987; 80(5):1366-74).

The accumulation of polymerized Z-AAT protein within hepatocytes results in a gain-of-function cytotoxicity that can result in cirrhosis or liver cancer later in life and neonatal liver disease in 12% of patients. This accumulation may spontaneously remit but can be fatal in a small number of children. The deficiency of circulating AAT results in unregulated protease activity that degrades lung tissue over time, resulting in emphysema, a form of chronic obstructive pulmonary disease (COPD). This effect is severe in PiZZ individuals and typically manifests in middle age, resulting in a decline in quality of life and shortened lifespan (mean 68 years of age) (Tanash et al. Int J Chron Obstruct Pulm Dis. 2016; 11:1663-9). The effect is more pronounced in PiZZ individuals who smoke, resulting in an even further shortened lifespan (58 years). (Piitulainen and Tanash, COPD 2015; 12(1):36-41). PiZZ individuals account for the majority of those with clinically relevant AATD lung disease. Accordingly, there is a need for additional and effective treatments for AATD.

A milder form of AATD is associated with the SZ genotype in which the Z-allele is combined with an S-allele. The S-allele is associated with somewhat reduced levels of circulating AAT but causes no cytotoxicity in liver cells. The result is clinically significant lung disease but not liver disease. (Fregonese and Stolk, Orphanet J Rare Dis. 2008; 33:16). As with the ZZ genotype, the deficiency of circulating AAT in subjects with the SZ genotype results in unregulated protease activity that degrades lung tissue over time and can result in emphysema, particularly in smokers.

The current standard of care for AAT deficient individuals who have or show signs of developing significant lung or liver disease is augmentation therapy or protein replacement therapy. Augmentation therapy involves administration of a human AAT protein concentrate purified from pooled donor plasma to augment the missing AAT. Although infusions of the plasma protein have been shown to improve survival or slow the rate of emphysema progression, augmentation therapy is often not sufficient under challenging conditions such as during an active lung infection. Similarly, although protein replacement therapy shows promise in delaying progression of disease, augmentation does not restore the normal physiological regulation of AAT in patients and efficacy has been difficult to demonstrate. In addition, augmentation therapy requires weekly visits for treatment and augmentation therapy cannot address liver disease, which is driven by the toxic gain-of-function of the Z-allele. Thus, there is a continuing need for new and more effective treatments for AATD.

One aspect of the disclosure provides a compound of Formula I:

(I)

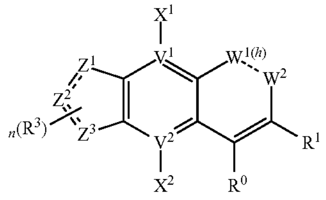

or tautomer thereof, deuterated derivative of that compound or tautomer, or a pharmaceutically acceptable salt of any of the foregoing, wherein:

$Z^1$, $Z^2$, and $Z^3$ are each independently N, —NH, or —CH; provided that at least one of $Z^1$, $Z^2$, and $Z^3$ is N or —NH;

$V^1$ and $V^2$ are each selected from C and N;

$W^1$ and $W^2$ are each selected from —C═O, —$CR^2$, N, and —$NR^2$, wherein:

when $W^1$ is —$CR^2$, then $W^2$ is N;

when $W^2$ is —$CR^2$, then $W^1$ is N or —$NR^2$;

when $W^1$ is —C═O, then $W^2$ is —$NR^2$; and when $W^2$ is —C═O, then $W^1$ is —$NR^2$;

$\overset{\text{----}}{=}$ for each of the two occurrences, is a single bond or a double bond; provided that one is a single bond and the other is a double bond;

*(h)* is a double bond except that when either of one of $W^1$ and $W^2$ is —C═O, then *(h)* is a single bond;

$R^0$ is halogen or

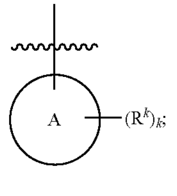

wherein:

Ring A is $C_3$-$C_{12}$ carbocyclyl, 3 to 12-membered heterocyclyl, $C_6$ or $C_{10}$ aryl, or 5 to 10-membered heteroaryl;

$R^1$ is halogen, —CN, $C_1$-$C_6$ alkyl, $C_1$-$C_6$ alkoxy, $C_1$-$C_6$ haloalkoxy, —C(=O)$R^z$, —C(=O)O$R^z$, —C(=O)N$R^wR^x$, —N$R^wR^x$, —N$R^w$C(=O)$R^z$, —N$R^w$C(=O)O$R^z$, —N$R^w$C(=O)N$R^xR^y$, —O$R^z$, —OC(=O)$R^z$, —OC(=O)N$R^wR^x$, S(=O)$_2R^z$, $C_3$-$C_6$ cycloalkyl, or 3 to 6-membered heterocyclyl; wherein:

the $C_1$-$C_6$ alkyl, the $C_3$-$C_6$ cycloalkyl, or the 3 to 6-membered heterocyclyl of $R^1$ is optionally substituted with 1 to 3 groups selected from —O$R^z$, $C_1$-$C_3$ haloalkyl, —CN, and halogen; and $R^w$, $R^x$, $R^y$, and $R^z$ are each independently hydrogen or $C_1$-$C_4$ alkyl;

$X^1$ and $X^2$ are each independently hydrogen, halogen, —CN, $C_1$-$C_3$ alkyl, $C_1$-$C_3$ haloalkyl, $C_1$-$C_3$ alkoxy, $C_1$-$C_3$ haloalkoxy, $C_3$-$C_6$ cycloalkyl, or 5 or 6-membered heteroaryl;

$R^2$ is hydrogen, halogen,

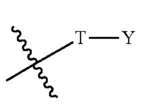

or

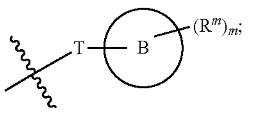

wherein:

T is absent or a bond, or is selected from —O—, —O$CH_2$—, —NH—, —NS(=O)$_2CH_3$, —S—, and —$CH_2$—;

Y is selected from $C_1$-$C_6$ alkyl, —$(CR^aR^a)_p$COOH, —$(CR^aR^a)_p$N$R^b$S(=O)$_2$$(CR^cR^c)_q$OH, —$(CR^aR^a)_p$C(=O)N$R^b$$(CR^cR^c)_q$COOH, and —$(CR^aR^a)_p$(O)$(CR^cR^c)_q$COOH; wherein:

$R^a$, for each occurrence, is independently hydrogen, halogen, —OH, or $C_1$-$C_4$ alkyl optionally substituted with 1 to 3 groups selected from halogen and —OH;

or alternatively, when $R^a$, for each occurrence, is $C_1$-$C_4$ alkyl, two $R^a$ groups together with their intervening carbon atom form cyclopropyl or cyclobutyl;

$R^b$ and $R^c$, for each occurrence, are each independently hydrogen or $C_1$-$C_2$ alkyl; and p and q are each independently an integer selected from 1 and 2;

Ring B is $C_3$-$C_{12}$ carbocyclyl, 3 to 12-membered heterocyclyl, $C_6$ or $C_{10}$ aryl, or 5 to 10-membered heteroaryl;

$R^3$ is —C(=O)O$R^d$; wherein $R^d$ is $C_1$-$C_4$ alkyl optionally substituted with —OC(O)$R^e$, —OC(=O)O$R^e$, or —OP(=O)O$R^fR^f$; wherein:

$R^e$, for each occurrence, is independently hydrogen, —$CH_3$, or —$C_2H_5$;

$R^f$, for each occurrence, is independently —OH, —$CH_3$, —$C_2H_5$, —O$CH_3$, or —O$C_2H_5$;

$R^k$ is halogen, —CN, $C_1$-$C_2$ alkyl, $C_1$-$C_2$ haloalkyl, $C_1$-$C_2$ alkoxy, $C_1$-$C_2$ haloalkoxy, or O—($C_3$-$C_6$ cycloalkyl);

$R^m$, for each occurrence, is independently halogen, —CN, =O, $C_1$-$C_6$ alkyl, $C_1$-$C_6$ alkoxy, —C(=O)$R^r$, —C(=O)O$R^r$, —C(=O)N$R^pR^q$, —C(=O)N$R^p$O$R^r$, —N$R^pR^q$, —N$R^p$C(=O)$R^r$, —N$R^p$S(=O)$_2R^r$, —O$R^r$, S(=O)$_2R^r$, —S(=O)$_2$N$R^pR^q$, —P(=O)$R^sR^t$, $C_3$-$C_6$ cycloalkyl, 3 to 6-membered heterocyclyl, phenyl, or 5 or 6-membered heteroaryl, wherein the $C_1$-$C_6$ alkyl, the phenyl, or the 5 or 6-membered heteroaryl of $R^m$ is optionally substituted with 1 to 3 groups selected from halogen, CN, —C(=O)O$R^r$, —N$R^pR^q$, and —O$R^r$; and wherein the $C_3$-$C_6$ cycloalkyl or the 3 to 6-membered heterocyclyl of $R^m$ is optionally substituted with 1 to 3 groups selected from halogen, CN, =O, —C(=O)O$R^r$, —N$R^pR^q$, and —O$R^r$;

wherein $R^p$ and $R^q$, for each occurrence, are each independently hydrogen or $C_1$-$C_4$ alkyl optionally substituted with 1 to 3 groups selected from —OH, —O$CH_3$, —O$C_2H_5$, and —COOH;

wherein $R^r$, for each occurrence, is each independently hydrogen, $C_1$-$C_4$ alkyl, $C_3$-$C_6$ cycloalkyl, or 3 to 6-membered heterocyclyl; wherein the $C_1$-$C_4$ alkyl, $C_3$-$C_6$ cycloalkyl, or 3 to 6-membered heterocyclyl of $R^r$ is optionally substituted with 1 to 3 groups selected from —OH, —O$CH_3$, —O$C_2H_5$, —$CH_2$OH, —C(=O)O H, —(O)C(=O)OH, and —(O)P(=O)(OH)$_2$; and wherein $R^s$ and $R^t$, for each occurrence, are each independently hydrogen, $C_1$-$C_4$ alkyl, $C_1$-$C_4$ alkoxy, or —OH;

k and m are each independently an integer selected from 0, 1, 2, 3, 4, and 5; and n is an integer selected from 0, 1, and 2.

Other aspects of the disclosure provide compounds of Formulae II, IIIa-d, IVa-c, Va-c, VIa-c, VIIa-f, VIIIa-c, and Compounds 1-262, tautomers thereof, deuterated derivatives of those compounds or tautomers, and pharmaceutically acceptable salts as disclosed herein.

The compounds of Formulae I, II, IIIa-d, IVa-c, Va-c, VIa-c, VIIa-f, and VIIIa-c are modulators of AAT activity. In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay. In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay.

In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $IC_{50}$ of 5.0 μM or less when tested in a Z-AAT Elastase Activity Assay. In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $IC_{50}$ of less than 2.0 μM when tested in a Z-AAT Elastase Activity Assay.

In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay and have an $IC_{50}$ of 5.0 μM or less when tested in a Z-AAT Elastase Activity Assay. In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay and have an $IC_{50}$ of 5.0 μM or less when tested in a Z-AAT Elastase Activity Assay. In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay and have an $IC_{50}$ of less than 2.0 μM when tested in a Z-AAT Elastase Activity Assay. In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay and have an $IC_{50}$ of less than 2.0 μM when tested in a Z-AAT Elastase Activity Assay.

In some embodiments, the compounds of Formulae I, II, IIIa-d, IVa-c, Va-c, VIa-c, VIIa-f, and VIIIa-c, as well as tautomers of those compounds, deuterated derivatives of those tautomers and compounds, and pharmaceutically acceptable salts of those compounds, tautomers, or deuterated derivatives are provided for use in the treatment of AATD.

In one aspect of the disclosure, the compounds of Formulae I, II, IIIa-d, IVa-c, Va-c, VIa-c, VIIa-f, VIIIa-c, and Compounds 1-262, tautomers thereof, deuterated derivatives of those compounds or tautomers, and pharmaceutically acceptable salts of any of the foregoing can be employed in the treatment of AATD.

In some embodiments, the disclosure provides pharmaceutical compositions comprising at least one compound selected from compounds of Formulae I, II, IIIa-d, IVa-c, Va-c, VIa-c, and VIIa-f, and VIIIa-c tautomers thereof, deuterated derivatives of those compounds or tautomers, and pharmaceutically acceptable salts of any of the foregoing. In specific embodiments, the pharmaceutical compositions may comprise a compound selected from Compounds 1-262, tautomers thereof, deuterated derivatives of those compounds or tautomers, and pharmaceutically acceptable salts of any of the foregoing. These compositions may further include at least one additional active pharmaceutical ingredient and/or at least one carrier.

Another aspect of the disclosure provides methods of treating AATD comprising administering to a subject in need thereof, at least one compound selected from compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing or a pharmaceutical composition comprising the at least one compound, tautomer, deuterated derivative or pharmaceutically acceptable salt. In specific embodiments, the methods comprise administering a compound selected from Compounds 1-262, tautomers thereof, deuterated derivatives of those compounds or tautomers, and pharmaceutically acceptable salts of any of the foregoing.

In some embodiments, the methods of treatment include administration of at least one additional active agent to the subject in need thereof, either in the same pharmaceutical composition as the at least one compound selected from compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing, or as separate compositions. In specific embodiments, the methods comprise administering a compound selected from Compounds 1-262, tautomers thereof, deuterated derivatives of those compounds or tautomers, and pharmaceutically acceptable salts of any of the foregoing with at least one additional active agent either in the same pharmaceutical composition or in a separate composition. In some embodiments, the subject in need of treatment carries the ZZ mutation. In some embodiments, the subject in need of treatment carries the SZ mutation.

Also provided are methods of modulating AAT, comprising administering to a subject in need thereof, at least one compound selected from compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing or a pharmaceutical composition comprising the at least one compound, tautomer, deuterated derivative, or salt. In specific embodiments, the methods of modulating AAT comprise administering at least one compound selected from Compounds 1-262, tautomers thereof, deuterated derivatives of those compounds or tautomers, and pharmaceutically acceptable salts of any of the foregoing or a pharmaceutical composition comprising the at least one compound, tautomer, deuterated derivative, or salt.

Also provided is a compound of Formulae I, II, IIIa-d, IVa-c, Va-c, VIa-c, VIIa-f, or VIIIa-c, and tautomers of those compounds, deuterated derivatives of those compounds and tautomers, and pharmaceutically acceptable salts of any of the foregoing, for use in therapy. In some embodiments, there is provided a compound selected from Compounds 1-262, tautomers of those compounds, deuterated derivatives of those compounds and tautomers, and pharmaceutically acceptable salts of any of the foregoing, for use in therapy.

Also provided is a pharmaceutical composition comprising a compound of Formulae I, II, IIIa-d, IVa-c, Va-c, VIa-c, VIIa-f, or VIIIa-c, or tautomers of those compounds, deuterated derivatives of those compounds and tautomers, or pharmaceutically acceptable salts of any of the foregoing, for use in therapy. In some embodiments, there is provided a pharmaceutical composition comprising a compound selected from Compounds 1-262, tautomers of those compounds, deuterated derivatives of those compounds and tautomers, and pharmaceutically acceptable salts of any of the foregoing, for use in therapy.

Definitions

The term "AAT" as used herein means alpha-1 antitrypsin or a mutation thereof, including, but not limited to, the AAT gene mutations such as Z mutations. As used herein, "Z-AAT" means AAT mutants which have the Z mutation.

As used herein, "mutations" can refer to mutations in the SERPINA1 gene (the gene encoding AAT) or the effect of alterations in the gene sequence on the AAT protein. A "SERPINA1 gene mutation" refers to a mutation in the SERPINA1 gene, and an "AAT protein mutation" refers to a mutation that results in an alteration in the amino acid sequence of the AAT protein. A genetic defect or mutation, or a change in the nucleotides in a gene in general, results in a mutation in the AAT protein translated from that gene.

As used herein, a patient who is "homozygous" for a particular gene mutation has the same mutation on each allele.

As used herein, a patient who has the PiZZ genotype is a patient who is homozygous for the Z mutation in the AAT protein.

The term "AATD" as used herein means alpha-1 antitrypsin deficiency, which is a genetic disorder characterized by low circulating levels of AAT.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

Compounds of the disclosure may optionally be substituted with one or more substituents. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from a specific compound of this disclosure only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (F) double bond isomers, and (Z) and (F) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of a compound that exist together in equilibrium, and are readily interchanged by migration of an atom or group within the molecule.

"Stereoisomer" refers to both enantiomers and diastereomers.

As used herein, "deuterated derivative" refers to a compound having the same chemical structure as a reference compound, but with one or more hydrogen atoms replaced by a deuterium atom ("D"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of a compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at lease 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

The term "alkyl," as used herein, means a straight-chain (i.e., linear or unbranched) or branched, substituted or unsubstituted hydrocarbon chain that is completely saturated or may contain one or more units of saturation, without being fully aromatic. Unless otherwise specified, alkyl groups contain 1-12 alkyl carbon atoms. In some embodiments, alkyl groups contain 1-10 aliphatic carbon atoms. In other embodiments, alkyl groups contain 1-8 aliphatic carbon atoms. In still other embodiments, alkyl groups contain 1-6 alkyl carbon atoms, in other embodiments alkyl groups contain 1-4 alkyl carbon atoms, and in yet other embodiments alkyl groups contain 1-3 alkyl carbon atoms.

The term "heteroalkyl" as used herein, refers to aliphatic groups wherein one or two carbon atoms are independently replaced by one or more of oxygen, sulfur, nitrogen, phosphorus, or silicon. Heteroalkyl groups may be substituted or unsubstituted, branched or unbranched.

The term "alkenyl" as used herein, means a straight-chain (i.e., linear or unbranched), branched, substituted or unsubstituted hydrocarbon chain that contains one or more carbon to carbon double bonds.

The terms "cycloalkyl," "carbocycle," and "cyclic alkyl" refer to a fused, spirocyclic, monocyclic, or bridged monocyclic $C_{3-9}$ hydrocarbon or a fused, spirocyclic, bicyclic, bridged bicyclic, tricyclic, or bridged tricyclic $C_{8-14}$ hydrocarbon that is completely saturated or that contains one or more units of unsaturation, but which is not fully aromatic, wherein any individual ring in said bicyclic ring system has 3-9 members. Typically, a cycloalkyl is completely saturated, while a carbocycle may contain one or more units of unsaturation but is not aromatic. In some embodiments, the cycloalkyl or carbocycle group contains 3 to 12 carbon atoms. In some embodiments, the cycloalkyl or carbocycle group contains 3 to 8 carbon atoms. In some embodiments, the cycloalkyl or carbocycle group contains 3 to 6 carbon atoms.

The term "heterocycle", "heterocyclyl", or "heterocyclic" as used herein refers to non-aromatic, monocyclic, bicyclic, or tricyclic, spirocyclic, bridged, or fused ring systems in which one or more ring members is a heteroatom. In some embodiments, the "heterocycle", "heterocyclyl", or "heterocyclic" group has 3 to 14 ring members in which one or more ring members is a heteroatom independently selected from oxygen, sulfur, nitrogen, phosphorus, and silicon and each ring in the system contains 3 to 9 ring members. In some embodiments, the heterocyclyl contains 3 to 12 ring member atoms. In some embodiments, the heterocyclyl contains 3 to 8 ring member atoms. In some embodiments, the heterocyclyl contains 3 to 6 ring member atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NH^+$ (as in N-substituted pyrrolidinyl)).

The term "alkoxy" as used herein, refers to an alkyl group, as previously defined, wherein one carbon of the alkyl group is replaced by an oxygen ("alkoxy") atom, respectively, provided that the oxygen atom is linked between two carbon atoms. A "cyclic alkoxy" refers to a monocyclic, fused, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl.

The terms "haloalkyl" and "haloalkoxy" means an alkyl or alkoxy, as the case may be, which is substituted with one or more halogen atoms. The term "halogen" or means F, Cl, Br, or I. In some embodiments, the halogen is selected from F, Cl, and Br. Examples of haloalkyls include $—CHF_2$, $—CH_2F$, $—CF_3$, $—CF_2—$, or perhaloalkyl, such as, $—CF_2CF_3$.

As used herein, "═O" refers to an oxo group.

As used herein, a "cyano" or "nitrile" groups refers to —C≡N.

As used herein, a "hydroxy" group refers to —OH.

As used herein, "aromatic groups" or "aromatic rings" refer to chemical groups that contain conjugated, planar ring systems with delocalized pi electron orbitals comprised of [4n+2]p orbital electrons, wherein n is an integer ranging from 0 to 6. Nonlimiting examples of aromatic groups include aryl and heteroaryl groups.

The term "aryl" refers to monocyclic, bicyclic, and tricyclic ring systems having a total of 5 to 14 ring members, wherein at least one ring in the system is aromatic and wherein each ring in the system contains 3 to 7 ring members. In some embodiments, an aryl contains 6 or 10 carbon atoms. A nonlimiting example of an aryl group is a phenyl ring.

The term "heteroaryl" refers to monocyclic, bicyclic, and tricyclic ring systems having a total of 5 to 14 ring members, wherein at least one ring in the system is aromatic, at least one ring in the system contains one or more heteroatoms, and wherein each ring in the system contains 3 to 7 ring members. In some embodiments, a heteroaryl contains 6 or 10 ring atoms.

Examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999).

Examples of suitable solvents that may be used in this disclosure include, but not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Examples of suitable bases that may be used in this disclosure include, but not limited to, 1,8-diazabicyclo [5.4.0]undec-7-ene (DBU), potassium tert-butoxide (KOtBu), potassium carbonate ($K_2CO_3$), N-methylmorpholine (NMM), triethylamine ($Et_3N$; TEA), diisopropyl-ethyl amine ($i\text{-}Pr_2EtN$; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the disclosed compounds. A salt of a compound of is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences,* 1977, 66,1-19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2- sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The terms "patient" and "subject" are used interchangeably and refer to an animal including a human.

The terms "effective dose" and "effective amount" are used interchangeably herein and refer to that amount of a compound that produces the desired effect for which it is administered (e.g., improvement in AATD or a symptom of AATD, lessening the severity of AATD or a symptom of AATD, and/or reducing the rate of onset or incidence of AATD or a symptom of AATD). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the term "treatment" and its cognates refer to improving AATD or its symptoms in a subject, delaying the onset of AATD or its symptoms in a subject, or lessening the severity of AATD or its symptoms in a subject. "Treatment" and its cognates as used herein, include, but are not limited to the following: improved liver and/or spleen function, lessened jaundice, improved lung function, lessened lung diseases and/or pulmonary exacerbations (e.g., emphysema), lessened skin disease (e.g., necrotizing panniculitis), increased growth in children, improved appetite, and reduced fatigue. Improvements in or lessening the severity of any of these symptoms can be readily assessed according to methods and techniques known in the art or subsequently developed.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. Typically, the term "about" refers to a variation of up to 10%, up to 5%, or up to 2% of a stated value.

Any one or more of the compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing may be administered once daily, twice daily, or three times daily for the treatment of AATD. In specific embodiments, the any one or more compounds are selected from Compounds 1-262, tautomers thereof, deuterated derivatives of those compounds or tautomers, and pharmaceutically acceptable salts of any of the foregoing. In some embodiments, at least one compound chosen from compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing is administered once daily. In specific embodiments, a compound selected from Compounds 1-262, tautomers thereof, deuterated derivatives of those compounds or tautomers, and pharmaceutically acceptable salts of any of the foregoing is administered once daily. In some embodiments, at least one compound chosen from compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing are administered twice daily. In specific embodiments, a compound selected from Compounds 1-262, tautomers thereof, deuterated derivatives of those compounds or tautomers, and pharmaceutically acceptable salts of any of the foregoing is administered twice daily. In some embodiments, at least one compound chosen from compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing are administered three times daily. In specific embodiments, a compound selected from Compounds 1-262, tautomers thereof, deuterated derivatives of those compounds or tautomers, and pharmaceutically acceptable salts of any of the foregoing of any of the foregoing is administered three times daily.

Any one or more of the compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing may be administered in combination with AAT augmentation therapy or AAT replacement therapy for the treatment of AATD. In specific embodiments, the any one or more compounds are selected from Compounds 1-262, tautomers thereof, deuterated derivatives of those compounds or tautomers, and pharmaceutically acceptable salts of any of the foregoing.

As used herein, "AAT augmentation therapy" refers to the use of alpha-1 antitrypsin protein (AAT) from the blood plasma of healthy human donors to augment (increase) the alpha-1 antitrypsin levels circulating in the blood. "AAT replacement therapy" refers to administration of recombinant AAT.

It should be understood that references herein to methods of treatment (e.g., methods of treating AATD) using one or more compounds (e.g., compounds of Formulae I, II, IIIa-d, IVa-c, Va-c, VIa-c, VIIa-f, and VIIIa-c), as well as tautomers of those compounds, deuterated derivatives of those compounds and tautomers, and pharmaceutically acceptable salts of those compounds) should also be interpreted as references to:

one or more compounds (e.g., compounds of Formulae I, II, IIIa-d, IVa-c, Va-c, VIa-c, VIIa-f, and VIIIa-c), as well as tautomers of those compounds, deuterated derivatives of those compounds and tautomers, and pharmaceutically acceptable salts of those compounds) for use in methods of treating, e.g., AATD; and/or the use of one or more compounds (e.g., compounds of Formulae I, II, IIIa-d, IVa-c, Va-c, VIa-c, VIIa-f, and VIIIa-c), as well as tautomers of those compounds, deuterated derivatives of those compounds and tautomers, and pharmaceutically acceptable salts of those compounds) in the manufacture of a medicament for treating, e.g., AATD.

EXAMPLE EMBODIMENTS

Some non-limiting embodiments of this disclosure include:

1. A compound represented by Formula I (I)

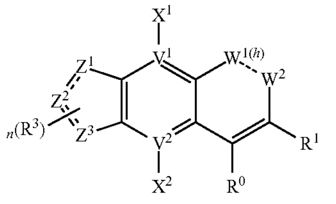

or a tautomer thereof, a deuterated derivative of that compound or tautomer, or a pharmaceutically acceptable salt of any of the foregoing, wherein:

$Z^1$, $Z^2$, and $Z^3$ are each independently —N, —NH, or —CH; provided that at least one of $Z^1$, $Z^2$, and $Z^3$ is N or —NH;

$V^1$ and $V^2$ are each selected from C and N;

$W^1$ and $W^2$ are each selected from —C═O, —$CR^2$, N, and —$NR^2$, wherein:

when $W^1$ is —$CR^2$, then $W^2$ is N;

when $W^2$ is —$CR^2$, then $W^1$ is N or —$NR^2$;

when $W^1$ is —C═O, then $W^2$ is —$NR^2$; and when $W^2$ is —C═O, then $W^1$ is —$NR^2$;

┄┄, for each of the two occurrences, is a single bond or a double bond; provided that one is a single bond and the other is a double bond;

*(h)* is a double bond except that when either of one of $W^1$ and $W^2$ is —C═O, then *(h)* is a single bond;

$R^0$ is halogen or

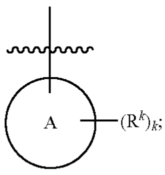

wherein:

Ring A is $C_3$-$C_{12}$ carbocyclyl, 3 to 12-membered heterocyclyl, $C_6$ or $C_{10}$ aryl, or 5 to 10-membered heteroaryl;

$R^1$ is halogen, —CN, $C_1$-$C_6$ alkyl, $C_1$-$C_6$ alkoxy, $C_1$-$C_6$ haloalkoxy, —C(═O)$R^z$, —C(═O)$OR^z$, —C(═O)$NR^wR^x$, —$NR^wR^x$, —$NR^w$C(═O)$R^z$, —$NR^w$C(═O)$OR^z$, —$NR^w$C(═O)$NR^xR^y$, —$OR^z$, —OC(═O)$R^z$, —OC(═O)$NR^wR^x$, S(═O)$_2R^z$, $C_3$-$C_6$ cycloalkyl, or 3 to 6-membered heterocyclyl; wherein:

the $C_1$-$C_6$ alkyl, the $C_3$-$C_6$ cycloalkyl, or the 3 to 6-membered heterocyclyl of $R^1$ is optionally substituted with 1 to 3 groups selected from —$OR^z$, $C_1$-$C_3$ haloalkyl, —CN, and halogen; and $R^w$, $R^x$, $R^y$, and $R^z$ are each independently hydrogen or $C_1$-$C_4$ alkyl;

$X^1$ and $X^2$ are each independently hydrogen, halogen, —CN, $C_1$-$C_3$ alkyl, $C_1$-$C_3$ haloalkyl, $C_1$-$C_3$ alkoxy, $C_1$-$C_3$ haloalkoxy, $C_3$-$C_6$ cycloalkyl, or 5 or 6-membered heteroaryl;

$R^2$ is hydrogen, halogen,

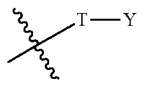

or

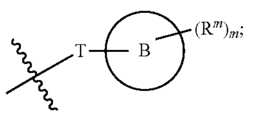

wherein:

T is absent or a bond, or is selected from —O—, —$OCH_2$—, —NH—, —NS(═O)$_2CH_3$, —S—, and —$CH_2$—;

Y is selected from $C_1$-$C_6$ alkyl, —$(CR^aR^a)_p$COOH, —$(CR^aR^a)_pNR^b$S(═O)$_2(CR^cR^c)_q$OH, —$(CR^aR^a)_p$C(═O)$NR^b(CR^cR^c)_q$COOH, and —$(CR^aR^a)_p$(O)$(CR^cR^c)_q$COOH; wherein:

$R^a$, for each occurrence, is independently hydrogen, halogen, —OH, or $C_1$-$C_4$ alkyl optionally substituted with 1 to 3 groups selected from halogen and —OH;

or alternatively, when $R^a$, for each occurrence, is $C_1$-$C_4$ alkyl, two $R^a$ groups together with their intervening carbon atom form cyclopropyl or cyclobutyl;

$R^b$ and $R^c$, for each occurrence, are each independently hydrogen or $C_1$-$C_2$ alkyl; and p and q are each independently an integer selected from 1 and 2;

Ring B is $C_3$-$C_{12}$ carbocyclyl, 3 to 12-membered heterocyclyl, $C_6$ or $C_{10}$ aryl, or 5 to 10-membered heteroaryl;

$R^3$ is —C(═O)$OR^d$; wherein $R^d$ is $C_1$-$C_4$ alkyl optionally substituted with —OC(O)$R^e$, —OC(═O)$OR^e$, or —OP(═O)$OR^fR^f$; wherein:

$R^e$, for each occurrence, is independently hydrogen, —$CH_3$, or —$C_2H_5$;

$R^f$, for each occurrence, is independently —OH, —$CH_3$, —$C_2H_5$, —$OCH_3$, or —$OC_2H_5$;

$R^k$ is halogen, —CN, $C_1$-$C_2$ alkyl, $C_1$-$C_2$ haloalkyl, $C_1$-$C_2$ alkoxy, $C_1$-$C_2$ haloalkoxy, or O—($C_3$-$C_6$ cycloalkyl);

$R^m$, for each occurrence, is independently halogen, —CN, ═O, $C_1$-$C_6$ alkyl, $C_1$-$C_6$ alkoxy, —C(═O)$R^r$, —C(═O)$OR^r$, —C(═O)$NR^pR^q$, —C(═O)$NR^pOR^r$, —$NR^pR^q$, —$NR^p$C(═O)$R^r$, —NRPS(═O)$_2R^r$, —$OR^r$, S(═O)$_2R^r$, —S(═O)$_2NR^pR^q$, —P(═O)$R^sR^t$, $C_3$-$C_6$ cycloalkyl, 3 to 6-membered heterocyclyl, phenyl, or 5 or 6-membered heteroaryl, wherein the $C_1$-$C_6$ alkyl, the phenyl, or the 5 or 6-membered heteroaryl of $R^m$ is optionally substituted with 1 to 3 groups selected from halogen, CN, —C(═O)$OR^r$, —$NR^pR^q$, and —$OR^r$; and wherein the $C_3$-$C_6$ cycloalkyl or the 3 to 6-membered heterocyclyl of $R^m$ is optionally substituted with 1 to 3 groups selected from halogen, CN, ═O, —C(═O)$OR^r$, —$NR^pR^q$, and —$OR^r$;

wherein $R^p$ and $R^q$, for each occurrence, are each independently hydrogen or $C_1$-$C_4$ alkyl optionally substituted with 1 to 3 groups selected from —OH, —$OCH_3$, —$OC_2H_5$, and —COOH;

wherein $R^r$, for each occurrence, is each independently hydrogen, $C_1$-$C_4$ alkyl, $C_3$-$C_6$ cycloalkyl, or 3 to 6-membered heterocyclyl; wherein the $C_1$-$C_4$ alkyl, $C_3$-$C_6$ cycloalkyl, or 3 to 6-membered heterocyclyl of $R^r$ is optionally substituted with 1 to 3 groups selected from —OH, —$OCH_3$, —$OC_2H_5$, —$CH_2$OH, —C(═O)OH, —(O)C(═O)OH, and —(O)P(═O)(OH)$_2$; and wherein $R^s$ and $R^t$, for each occurrence, are each independently hydrogen, $C_1$-$C_4$ alkyl, $C_1$-$C_4$ alkoxy, or —OH;

k and m are each independently an integer selected from 0, 1, 2, 3, 4, and 5; and n is an integer selected from 0, 1, and 2.

2. The compound, tautomer, deuterated derivative, or pharmaceutically acceptable salt according to Embodiment 1, wherein two of $Z^1$, $Z^2$, and $Z^3$ are N or —NH; n is an integer selected from 0 and 1; and wherein all other variables not specifically defined herein are as defined in the preceding Embodiment.

3. The compound, tautomer, deuterated derivative, or pharmaceutically acceptable salt according to Embodiment 1 or Embodiment 2, represented by Formula II (II)

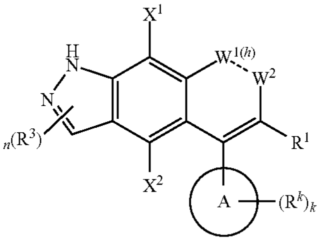

wherein:

$R^3$ is —C(═O)OR$^d$; wherein $R^d$ is $C_1$-$C_4$ alkyl optionally substituted with —OC(O)R$^e$, —OC(═O)OR$^e$, or —OC(═O)OR$^f$R$^f$; wherein:

$R^e$, for each occurrence, is independently hydrogen or —$CH_3$;

$R^f$, for each occurrence, is independently —OH, —$CH_3$, or —$OCH_3$;

n is an integer selected from 0 and 1;

and wherein all other variables not specifically defined herein are as defined in any one of the preceding Embodiments.

4. The compound, tautomer, deuterated derivative, or pharmaceutically acceptable salt according to any one of Embodiments 1 to 3, represented Formulae Ma, Mb, IIIc, or IIId (IIIa)

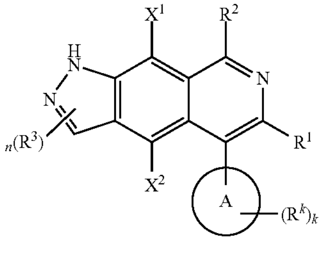

(IIIb)

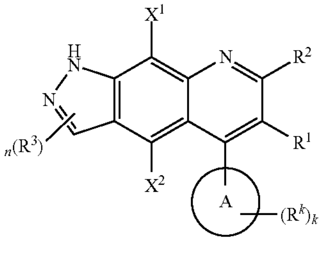

-continued (IIIc)

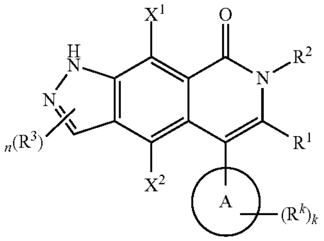

(IIId)

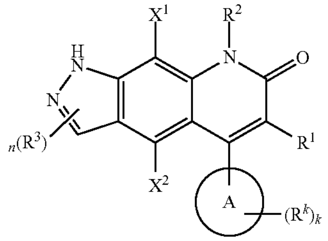

wherein:

Ring A is optionally substituted with $R^k$ and Ring A is 5 or 6-membered carbocyclyl, phenyl, or 5 or 6-membered heteroaryl;

$R^1$ is $C_1$-$C_6$ alkyl, $C_1$-$C_6$ alkoxy-C(═O)OR$^z$, —C(═O)NR$^w$R$^x$, —NR$^w$R$^x$, —OR$^z$, —S(═O)$_2$R$^z$, $C_3$-$C_6$ cycloalkyl, or 3 to 6-membered heterocyclyl; wherein:

the $C_1$-$C_6$ alkyl, the $C_3$-$C_6$ cycloalkyl, or the 3 to 6-membered heterocyclyl of $R^1$ is optionally substituted with 1 to 3 groups selected from —OR$^z$ and halogen; and $R^w$, $R^x$, $R^y$, and $R^z$ are each independently hydrogen or $C_1$-$C_4$ alkyl;

$X^1$ and $X^2$ are each independently hydrogen, halogen, —CN, $C_1$-$C_2$ alkyl, $C_1$-$C_2$ haloalkyl, $C_1$-$C_2$ alkoxy, $C_1$-$C_2$ haloalkoxy or $C_3$-$C_4$ cycloalkyl;

$R^2$ is as defined in Embodiment 1, except when $R^2$ is

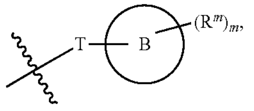

Ring B is optionally substituted with $R^m$ and Ring B is $C_4$-$C_9$ carbocyclyl, phenyl, 4 to 9-membered heterocyclyl, or 5 to 6-membered heteroaryl;

$R^3$ is absent or is —C(═O)O($CH_2$)$_2$(O)P(═O)(OH)$_2$;

$R^k$ is halogen, —CN, —$CH_3$, $C_1$ haloalkyl, or —$OCH_3$;

n is an integer selected from 0 and 1;

and wherein all other variables not specifically defined herein are as defined in any one of the preceding Embodiments.

5. The compound, tautomer, deuterated derivative, or pharmaceutically acceptable salt according to any one of Embodiments 1 to 4, represented Formulae IVa, IVb, or IVc (IVa)

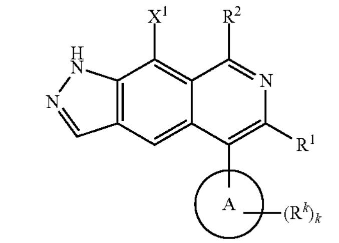

(IVb)

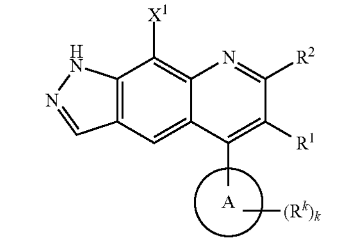

(IVc)

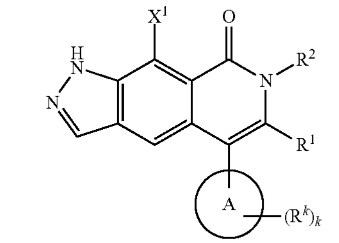

wherein $X^1$ is hydrogen, halogen, —$CH_3$, —$CHF_2$, —$CH_2F$, or —$OCH_3$; and wherein all other variables not specifically defined herein are as defined in any one of the preceding Embodiments.

6. The compound, tautomer, deuterated derivative, or pharmaceutically acceptable salt according to any one of Embodiments 1 to 5, represented Formulae Va, Vb, or Vc:

(Va)

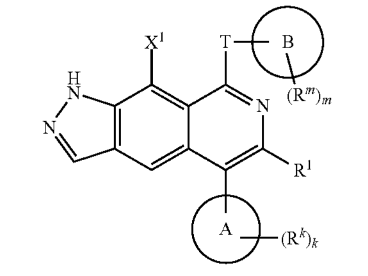

(Vb)

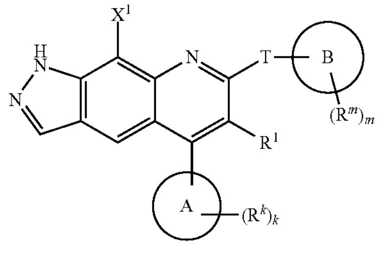

-continued (Vc)

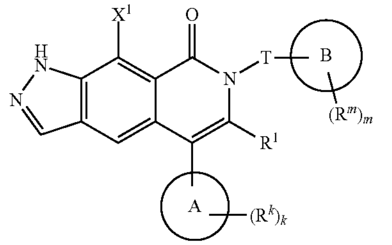

wherein:

$R^1$ is $C_1$-$C_4$ alkyl, $C_1$-$C_4$ alkoxy, —C(═O)$OR^z$, —C(═O)$NR^wR^x$, —$NR^wR^x$, —$OR^z$, —S(═O)$_2R^z$, cyclopropyl, cyclobutyl or 5 or 6-membered heterocyclyl; wherein:

the $C_1$-$C_4$ alkyl, the cyclopropyl, the cyclobutyl, or the 5 or 6-membered heterocyclyl of $R^1$ is optionally substituted with 1 to 3 groups selected from —$OR^z$ and halogen; and $R^w$, $R^x$, $R^y$, and $R^z$ are each independently hydrogen or $C_1$-$C_2$ alkyl; T is absent, or is selected from —O—, —$OCH_2$—, —NH—, and —$CH_2$—;

and wherein all other variables not specifically defined herein are as defined in any one of the preceding Embodiments.

7. The compound, tautomer, deuterated derivative, or pharmaceutically acceptable salt according to any one of Embodiments 1 to 6, wherein Ring A is optionally substituted with $R^k$ and Ring A is phenyl, cyclohexenyl, 3,6-dihydro-2H-pyranyl, pyridinyl, pyridazinyl, thiophenyl, or pyrazolyl; and wherein all other variables not specifically defined herein are as defined in any one of the preceding Embodiments.

8. The compound, tautomer, deuterated derivative, or pharmaceutically acceptable salt according to any one of Embodiments 1 to 7, wherein Ring A is optionally substituted with $R^k$ and Ring A is selected from:

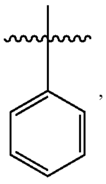
,
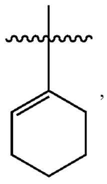
,
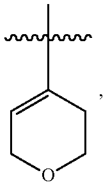
,
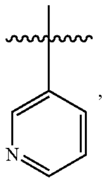
,
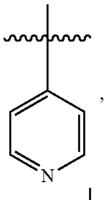
,
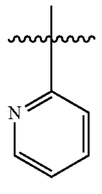
,
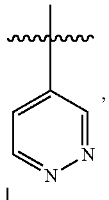
,
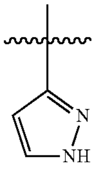
, and
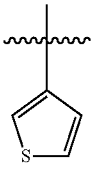
;

and wherein all other variables not specifically defined herein are as defined in any one of the preceding Embodiments.

9. The compound, tautomer, deuterated derivative, or pharmaceutically acceptable salt according to any one of Embodiments 1 to 8, wherein Ring A is optionally substituted with $R^k$ and Ring A is selected from

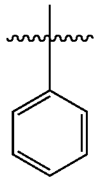
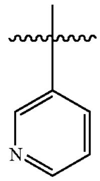
and
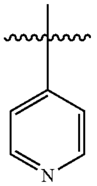
;

and wherein all other variables not specifically defined herein are as defined in any one of the preceding Embodiments.

10. The compound, tautomer, deuterated derivative, or pharmaceutically acceptable salt according to any one of Embodiments 1 to 9, wherein when $R^2$ is

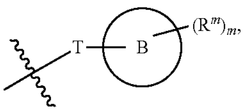

Ring B is optionally substituted with $R^m$ and Ring B is selected from isoindolinyl, azaspiro[3.4]octanyl, spiro[3.3]heptanyl, azaspiro[3.3]heptanyl, oxaspiro[3.3]heptanyl, azabicyclo[3.2.0]heptanyl, phenyl, cyclohexenyl, cyclohexyl, pyridinyl, piperidinyl, morpholinyl, tetrahydro-2H-pyranyl, thiazolyl, pyrazolyl, furanyl, tetrahydrofuranyl, cyclopentyl, bicyclo[1.1.1]pentanyl, pyrrolidinyl, cyclobutyl, azetidinyl, and cyclopropyl; and wherein all other variables not specifically defined herein are as defined in any one of the preceding Embodiments.

11. The compound, tautomer, deuterated derivative, or pharmaceutically acceptable salt according to any one of Embodiments 1 to 10, wherein $R^2$ is

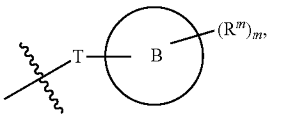

Ring B is optionally substituted with $R^m$ and Ring B is selected from

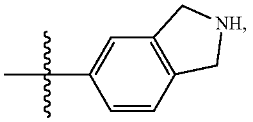
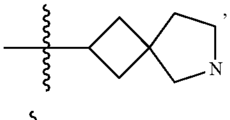
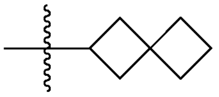
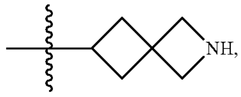
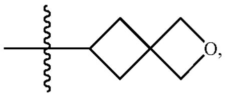
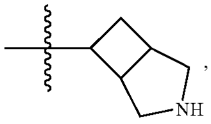

-continued

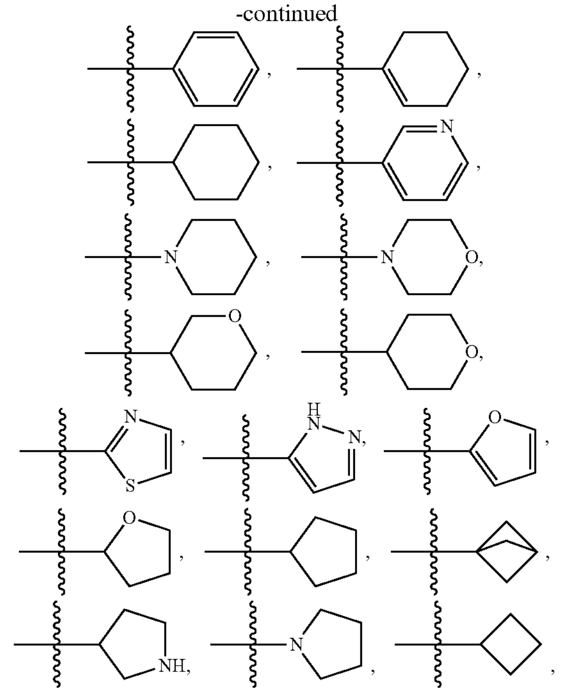
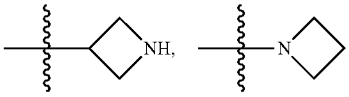
and
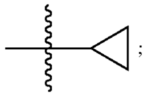
;

and wherein all other variables not specifically defined herein are as defined in any one of the preceding Embodiments.

12. The compound, tautomer, deuterated derivative, or pharmaceutically acceptable salt according to any one of Embodiments 1 to 11, wherein $R^2$ is

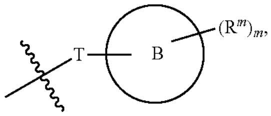

Ring B is optionally substituted with $R^m$ and Ring B is selected from

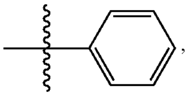
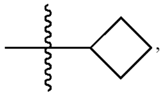
and
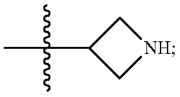

and wherein all other variables not specifically defined herein are as defined in any one of the preceding Embodiments.

13. The compound, tautomer, deuterated derivative, or pharmaceutically acceptable salt according to any one of Embodiments 1 to 12, wherein $R^m$, for each occurrence, is independently halogen, —CN, =O, $C_1$-$C_6$ alkyl, $C_1$-$C_4$ alkoxy, —C(=O)$R^r$, —C(=O)O$R^r$, —C(═O)NR$^p$R$^q$, —C(═O)NR$^p$OR$^r$, —NR$^p$R$^q$, —NR$^p$C(═O)R$^r$, —NR$^p$S(═O)$_2$R$^r$, —OR$^r$, S(═O)$_2$R$^r$, —S(═O)$_2$NR$^p$R$^q$, —P(═O)R$^s$R$^t$, or 5 or 6-membered heterocyclyl; wherein:

the $C_1$-$C_6$ alkyl of R$^m$ is optionally substituted with 1 to 3 groups selected from —C(═O)OH, —C(═O)OCH$_3$, —C(═O)OC$_2$H$_5$, —OH, —OCH$_3$, and —OC$_2$H$_5$; and the 5 or 6-membered heterocyclyl of R$^m$ is optionally substituted with 1 to 3 groups selected from halogen, ═O, —C(═O)OH, and —OH; wherein:

R$^p$ and R$^q$, for each occurrence, are each independently hydrogen or $C_1$-$C_3$ alkyl optionally substituted with 1 to 3 groups selected from —OH, —OCH$_3$, and —C(═O)OH;

R$^r$, for each occurrence, are each independently hydrogen, $C_1$-$C_4$ alkyl, $C_3$-$C_6$ cycloalkyl, or 4 to 6-membered heterocyclyl; wherein the $C_1$-$C_2$ alkyl, $C_3$-$C_6$ cycloalkyl, or 4 to 6-membered heterocyclyl of R$^r$ is optionally substituted with 1 to 3 groups selected from —OH, —OCH$_3$, —OC$_2$H$_5$, —C(═O)OH, —(O)C(═O)OH, and —(O)P(═O)(OH)$_2$; and R$^s$ and R$^t$, for each occurrence, are each independently hydrogen, $C_1$-$C_2$ alkyl, $C_1$-$C_2$ alkoxy, or —OH;

and wherein all other variables not specifically defined herein are as defined in any one of the preceding Embodiments.

14. The compound, tautomer, deuterated derivative, or pharmaceutically acceptable salt according to any one of Embodiments 1 to 13, wherein R$^m$, for each occurrence, is independently halogen, CN, ═O, $C_1$-$C_4$ alkyl, $C_1$-$C_4$ alkoxy, —C(═O)R$^r$, —C(═O)OR$^r$, —C(═O)NR$^p$R$^q$, —C(═O)NR$^p$OR$^r$, —NR$^p$R$^q$, —NR$^p$C(═O)R$^r$, —NR$^p$S(═O)$_2$R$^r$, —OR$^r$, S(═O)$_2$R$^r$, —S(═O)$_2$NR$^p$R$^q$, —P(═O)R$^s$R$^t$, imidazolidinyl, or morpholinyl; wherein:

the $C_1$-$C_4$ alkyl of R$^m$ is optionally substituted with 1 to 3 groups selected from —C(═O)OH, —C(═O)OCH$_3$, —C(═O)OC$_2$H$_5$, —OH, —OCH$_3$, and —OC$_2$H$_5$; and the imidazolidinyl or the morpholinyl of R$^m$ is optionally substituted with 1 to 3 groups selected from oxo (═O) and —OH; wherein:

R$^p$ and R$^q$, for each occurrence, are each independently hydrogen or $C_1$-$C_3$ alkyl optionally substituted with 1 to 3 groups selected from —OH, —OCH$_3$, and —C(═O)OH;

R$^r$, for each occurrence, are each independently hydrogen, $C_1$-$C_2$ alkyl, cyclopropyl, oxetanyl, or azetidinyl; wherein the $C_1$-$C_2$ alkyl, cyclopropyl, oxetanyl, or azetidinyl of R$^r$ is optionally substituted with 1 to 3 groups selected from —OH, —CH$_2$OH, —C(═O)OH, and —(O)P(═O)(OH)$_2$; and R$^s$ and R$^t$, for each occurrence, are each independently —CH$_3$, —OCH$_3$, or —OH;

and wherein all other variables not specifically defined herein are as defined in any one of the preceding Embodiments.

15. The compound, tautomer, deuterated derivative, or pharmaceutically acceptable salt according to any one of Embodiments 1 to 14, wherein R$^m$, for each occurrence, is independently —COOH, —C(═O)CH(OH)CH$_3$, F, —CH$_3$, —C(═O)NH$_2$, —C(═O)NH(OCH$_3$), S(═O)$_2$NH$_2$, —NHS(═O)$_2$CH$_3$, ═O, —OH, —P(═O)(CH$_3$)$_2$, —P(═O)(OH)$_2$, —P(═O)(OCH$_3$)$_2$, —OH, imidazolidin-4yl, —CH$_2$OH, —NHCH$_3$, morpholin-4-yl, —(C═O)NHCH(CH$_3$)CH$_2$OH, —C(═O)N(CH$_3$)CH(CH$_3$)CH$_2$OH, —NCH$_3$C(═O)CH(OH)CH$_3$, —C(═O)CH(CH$_3$)CH$_2$OH, —C(═O)CH(OH)CH$_2$OH, —C(═O)(hydroxymethyl)oxetan-3-yl, —C(═O)(hydroxy)cyclopropyl, —C(═O)CH(OH)CH$_3$, —C(═O)OCH$_3$, —OCH$_3$, —CH$_2$COOH, —CN, —OCH$_2$COOH, —OCH(CH$_3$)COOH, —CH(CH$_3$)COOH, Cl, S(═O)$_2$CH$_3$, S(═O)$_2$NHCH$_3$, —CH$_2$C(═O)OC$_2$H$_5$, —C(═O)OCH$_2$(O)P(═O)(OH)$_2$, —C(═O)NHCH(CH$_3$)COOH, —C(═O)NHCH$_3$, —C═O(3-hydroxyazetidin-1-yl), and —C(═O)(morpholin-4-yl); and wherein all other variables not specifically defined herein are as defined in any one of the preceding Embodiments.

16. The compound, tautomer, deuterated derivative, or pharmaceutically acceptable salt according to any one of Embodiments 1 to 15, wherein at least one occurrence of R$^m$ is —COOH, —CH$_2$COOH, —OCH$_2$COOH, —OCH(CH$_3$)COOH, —CH(CH$_3$)COOH, —C(═O)OCH$_2$(O)P(═O)(OH)$_2$, or —C(═O)NHCH(CH$_3$)COOH; and wherein all other variables not specifically defined herein are as defined in any one of the preceding Embodiments.

17. The compound, tautomer, deuterated derivative, or pharmaceutically acceptable salt according to any one of Embodiments 1 to 16, represented by Formulae VIa, VIb, or VIc (VIa)

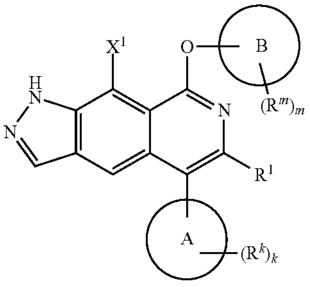

(VIb)

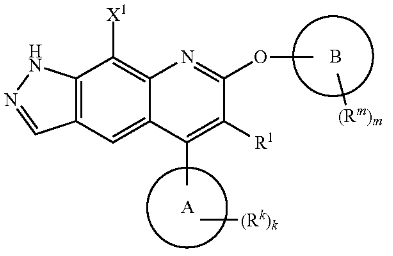

(VIc)

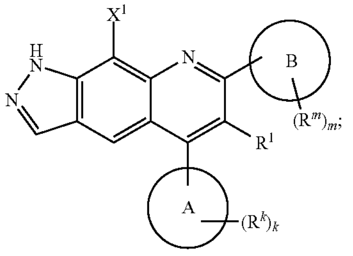

wherein all other variables not specifically defined herein are as defined in any one of the preceding Embodiments.

18. The compound, tautomer, deuterated derivative, or pharmaceutically acceptable salt according to any one of Embodiments 1 to 17, wherein R$^1$ is $C_1$-$C_3$ alkyl, $C_1$-$C_3$ alkoxy, —C(═O)OR$^z$, —C(═O)NR$^w$R$^x$, —$NR^wR^x$, —$OR^z$, —$S(=O)_2R^z$, cyclopropyl, cyclobutyl, or a 6-membered heterocyclyl; wherein:

the $C_1$-$C_3$ alkyl, the cyclopropyl, the cyclobutyl, or the tetrahydro-2H-pyran-4-yl of $R^1$ is optionally substituted with 1 to 3 groups selected from —OH, —$OCH_3$, $C_1$-$C_2$ haloalkyl, —CN, and halogen;

$R^w$, $R^x$, $R^y$, and $R^z$ are each independently hydrogen or —$CH_3$;

and wherein all other variables not specifically defined herein are as defined in any one of the preceding Embodiments.

19. The compound, tautomer, deuterated derivative, or pharmaceutically acceptable salt according to any one of Embodiments 1 to 18, wherein $R^1$ is —$C(CH_3)_2$, —$CF_3$, —$CH_2C(CH_3)_2OCH_3$, —$C(CH_3)_2CH_2OH$, —$OCH_3$, —$O(C)(CH_3)_2$, —$C(=O)OCH_3$, —$C(=O)N(CH_3)_2$, $N(CH_3)_2$, —$S(=O)_2CH_3$, $S(=O)_2C_2H_5$, —$S(=O)_2CH(CH_3)_2$, tetrahydro-2H-pyran-4-yl, cyclopropyl, or cyclobutyl; wherein the cyclopropyl or the cyclobutyl of $R^1$ is optionally substituted with —OH, —$OCH_3$, or —$CF_3$; and wherein all other variables not specifically defined herein are as defined in any one of the preceding Embodiments.

20. The compound, tautomer, deuterated derivative, or pharmaceutically acceptable salt according to any one of Embodiments 1 to 19, represented Formulae VIIa, VIIb, VIIc, VIId, VIIe, or VIIf (VIIa)

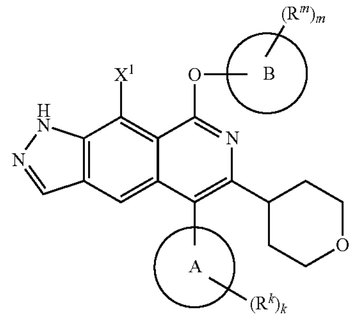

(VIIb)

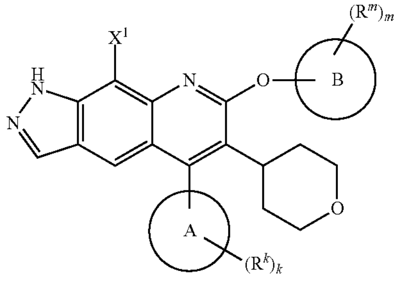

(VIIc)

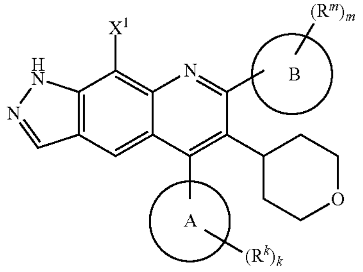

-continued (VIId)

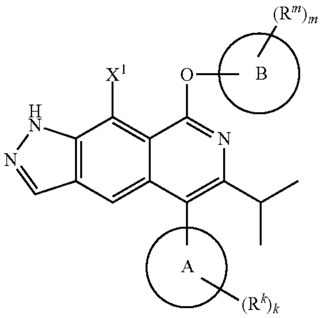

(VIIe)

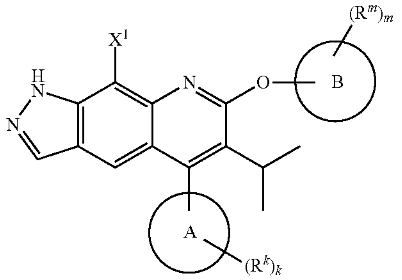

(VIIf)

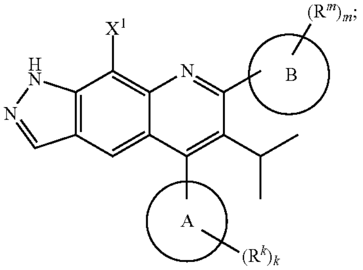

wherein all other variables not specifically defined herein are as defined in any one of the preceding Embodiments.

21. The compound, tautomer, deuterated derivative, or pharmaceutically acceptable salt according to any one of Embodiments 1 to 5, represented Formulae VIIIa, VIIIb, or VIIIc (VIIIa)

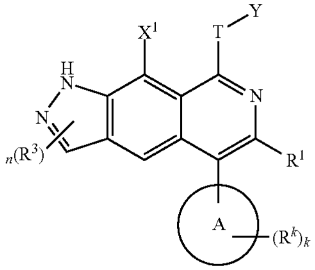

-continued (VIIIb)

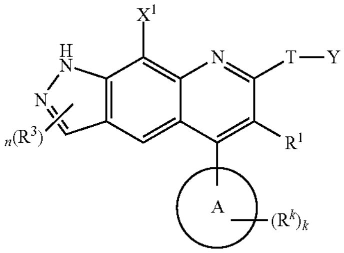

(VIIIc)

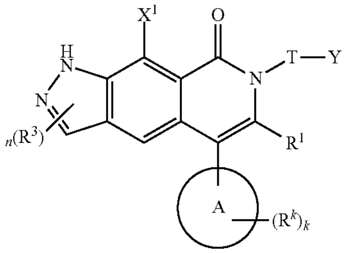

wherein:

Ring A is optionally substituted with $R^k$ and Ring A is phenyl or 5 or 6-membered heteroaryl;

T is absent, or is selected from —O—, —NH—, and —$CH_2$—;

Z is $C_1$-$C_2$ alkyl, —$(CR^aR^a)_p$COOH, —$(CR^aR^a)_p$$NR^b$S(═O)$_2$$(CR^cR^c)_q$OH, —$(CR^aR^a)_p$C(═O)$NR^b$$(CR^cR^c)_q$COOH, or —$(CR^aR^a)_p$(O)$(CR^cR^c)_q$COOH; wherein:

$R^a$, for each occurrence, is independently hydrogen, —OH, —$CH_3$, or —$CH_2$OH; and $R^b$ and $R^c$, for each occurrence, are each independently hydrogen or —$CH_3$;

and wherein all other variables not specifically defined herein are as defined in any one of Embodiments 1 to 5.

22. The compound, tautomer, deuterated derivative, or pharmaceutically acceptable salt according to any one of Embodiments 1 to 5 and 21, wherein

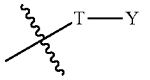

is —$NHCH_3$, —$CH_2$COOH, —$(CH_2)_2$COOH, —CH($CH_3$)$CH_2$COOH, —NHCH($CH_3$)COOH, —$OCH_2$COOH, —O$(CH_2)_2$(O)$CH_2$COOH, —$CH_2$CH($CH_3$)COOH, —OCH($CH_3$)C(═O)$NHCH_2$COOH, or —OCH($CH_2$OH)$CH_2$NHS(═O)$_2$$(CH_2)_2$OH; and wherein all other variables not specifically defined herein are as defined in any one of Embodiments 1 to 5 and 21.

23. The compound, tautomer, deuterated derivative, or pharmaceutically acceptable salt according to any one of Embodiments 1 to 5, 21, and 22, wherein Ring A is optionally substituted with $R^k$ and Ring A is phenyl or pyridinyl; and wherein all other variables not specifically defined herein are as defined in any one of Embodiments 1 to 5, 21, and 22.

24. The compound, tautomer, deuterated derivative, or pharmaceutically acceptable salt according to any one of Embodiments 1 to 5 and 21 to 23, wherein Ring A is optionally substituted with $R^k$ and Ring A is

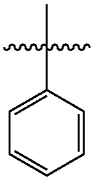 or 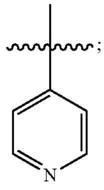;

and wherein all other variables not specifically defined herein are as defined in any one of Embodiments 1 to 5 and 21 to 23.

25. The compound, tautomer, deuterated derivative, or pharmaceutically acceptable salt according to any one of Embodiments 1 to 5 and 21 to 23, wherein Ring A is selected from

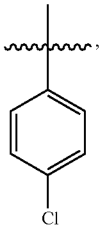, 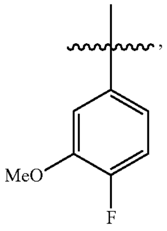, 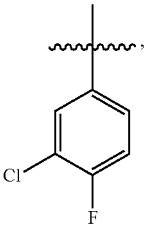, 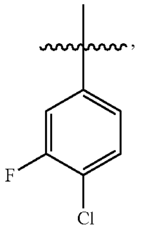, 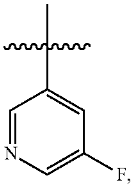 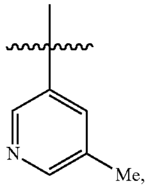 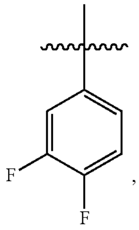, and 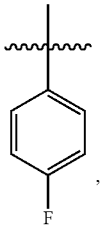, and wherein all other variables not specifically defined herein are as defined in any one of Embodiments 1 to 5 and 21 to 23.

26. The compound, tautomer, deuterated derivative, or pharmaceutically acceptable salt according to any one of Embodiments 1 to 5 and 21 to 23, wherein Ring A is selected from

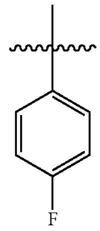, 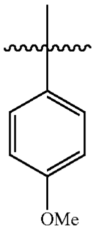, 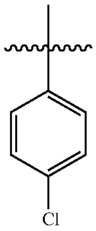, 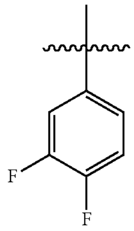,

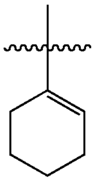, 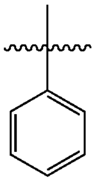, 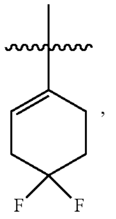, 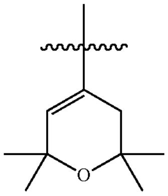,

-continued

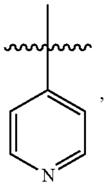 , 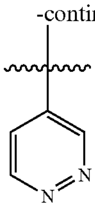 , 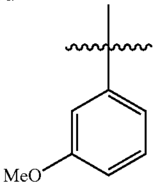 ,

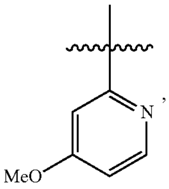 , 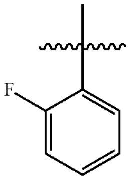 , 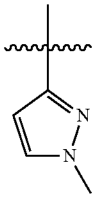 ,

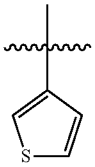 , and 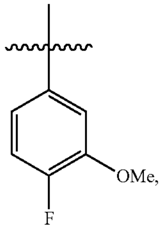

and wherein all other variables not specifically defined herein are as defined in any one of Embodiments 1 to 5 and 21 to 23.

27. The compound, tautomer, deuterated derivative, or pharmaceutically acceptable salt according to any one of Embodiments 1 to 5 and 21 to 26, wherein $R^1$ is halogen, —CN, $C_1$-$C_3$ alkyl, $C_1$-$C_3$ alkoxy, —$NR^wR^x$, —$OR^z$, $C_3$-$C_6$ cycloalkyl, or 5 or 6-membered heterocyclyl; wherein:

the $C_1$-$C_3$ alkyl, the $C_3$-$C_6$ cycloalkyl, or the 5 or 6-membered heterocyclyl of $R^1$ is optionally substituted with 1 to 3 groups selected from —OH, —$OCH_3$, $C_1$-$C_2$ haloalkyl, —CN, and halogen; and $R^w$, $R^x$, $R^y$, and $R^z$ are each independently hydrogen or —$CH_3$;

and wherein all other variable not specifically defined herein are as defined in any one of Embodiments 1 to 5 and 21 to 26.

28. The compound, tautomer, deuterated derivative, or pharmaceutically acceptable salt according to any one of Embodiments 1 to 5 and 21 to 26, wherein $R^1$ is $C_1$-$C_3$ alkyl or 6-membered heterocyclyl; wherein:

the $C_1$-$C_3$ alkyl or the 5 or 6-membered heterocyclyl of $R^1$ is optionally substituted with 1 to 3 groups selected from —OH, —$OCH_3$, $C_1$-$C_2$ haloalkyl, and halogen;

and wherein all other variable not specifically defined herein are as defined in any one of Embodiments 1 to 5 and 21 to 26.

29. The compound, tautomer, deuterated derivative, or pharmaceutically acceptable salt according to any one of Embodiments 1 to 5 and 21 to 26, wherein $R^1$ is —$C(CH_3)_2$ or tetrahydro-2H-pyran-4-yl; and wherein all other variables not specifically defined herein are as defined in any one of Embodiments 1 to 5 and 21 to 26.

30. The compound, tautomer, deuterated derivative, or pharmaceutically acceptable salt according to any one of Embodiments 1 to 5 and 21 to 26, wherein $R^1$ is selected from

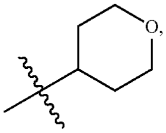 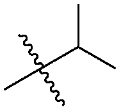 , 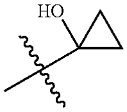 ,

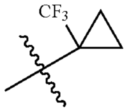 , 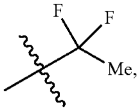 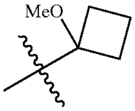 ,

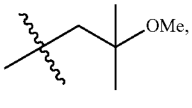 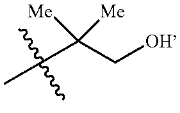 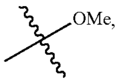

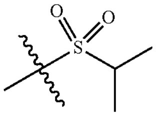 , and 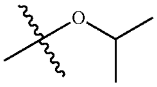

wherein all other variables not specifically defined herein are as defined in any one of Embodiments 1 to 5 and 21 to 26.

31. The compound, tautomer, deuterated derivative, or pharmaceutically acceptable salt according to any one of Embodiments 1 to 5 and 21 to 26, wherein $R^1$ is selected from

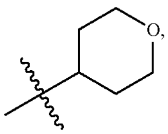 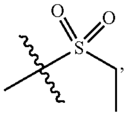 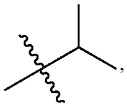 , 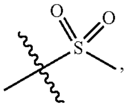 ,

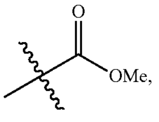 and 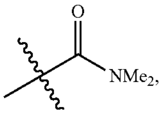

and wherein all other variables not specifically defined herein are as defined in any one of Embodiments 1 to 5 and 21 to 26.

32. The compound, tautomer, deuterated derivative, or pharmaceutically acceptable salt according to any one of Embodiments 1 to 5 and 21 to 31, wherein $R^2$ is chosen from

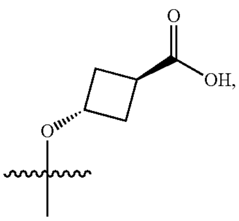 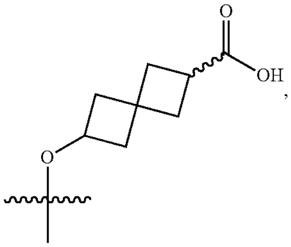 ,

-continued
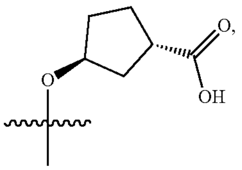
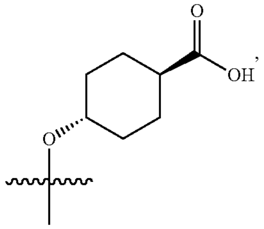
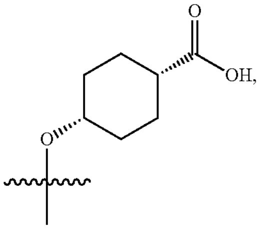
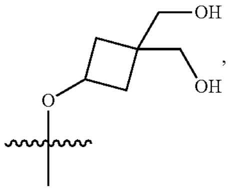
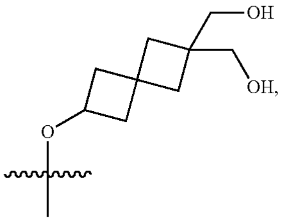
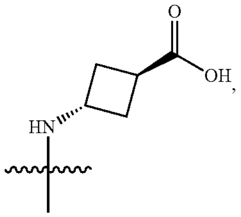
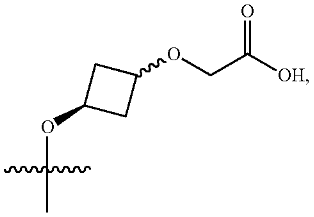
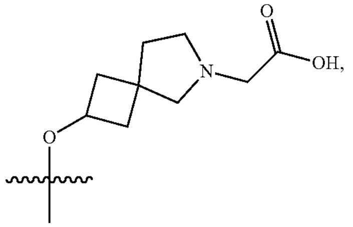
and
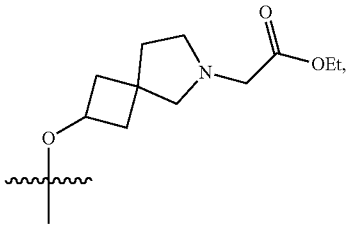
and wherein all other variables not specifically defined herein are as defined in any one of Embodiments 1 to 5 and 21 to 31.
33. The compound, tautomer, deuterated derivative, or pharmaceutically acceptable salt according to any one of Embodiments 1 to 5 and 21-31, wherein $R^2$ is chosen from,
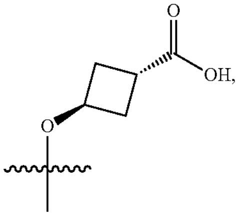
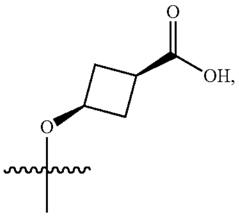
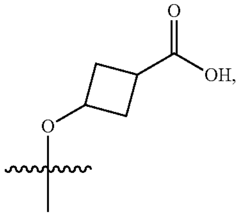
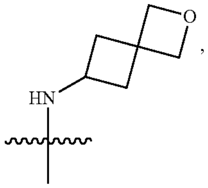
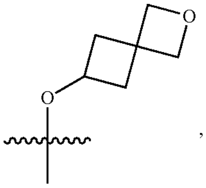
,
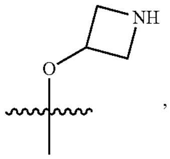
,
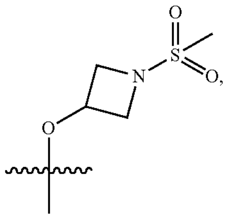
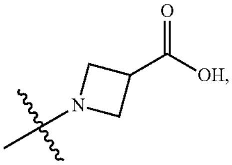
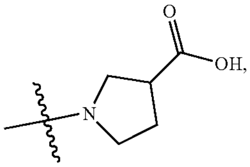
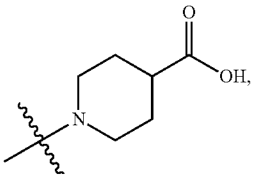
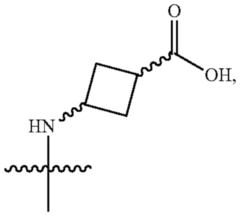
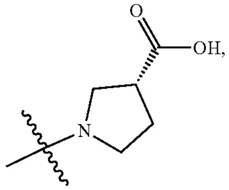
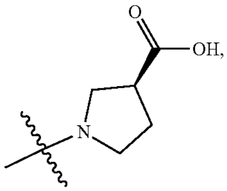
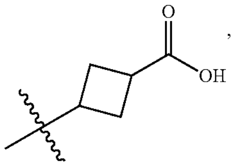
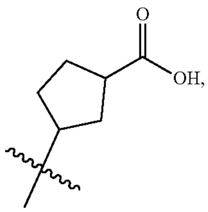
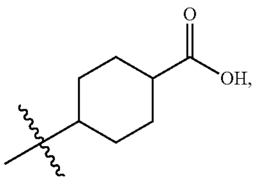

-continued

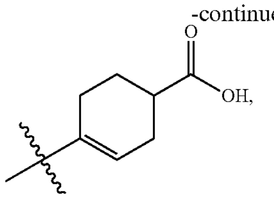

,

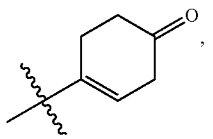

,

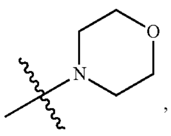

, and

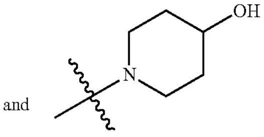

, and wherein all other variables not specifically defined herein are as defined in any one of Embodiments 1 to 5 and 21 to 31.

34. The compound, tautomer, deuterated derivative, or pharmaceutically acceptable salt according to any one of Embodiments 1 to 32, wherein:

$X^1$ is hydrogen, F, or —$CH_3$;

$R^k$ is F, Cl, —$CH_3$, or —$OCH_3$; and k is an integer selected from 0, 1, and 2.

and wherein all other variables not specifically defined herein are as defined in any one of the preceding Embodiments.

35. The compound, tautomer, deuterated derivative, or pharmaceutically acceptable salt according to any one of Embodiments 1 to 34, wherein the compound is selected from the compounds of Table I.

36. A pharmaceutical composition comprising a compound, tautomer, deuterated derivative, or pharmaceutically acceptable salt according to any one of Embodiments 1 to 35 and a pharmaceutically acceptable carrier.

37. A method of modulating alpha-1 antitrypsin (AAT) activity in a subject comprising administering a compound, tautomer, deuterated derivative, or pharmaceutically acceptable salt according to any one of Embodiments 1 to 35, or a pharmaceutical composition according to Embodiment 36.

38. Use of a compound, tautomer, deuterated derivative, or pharmaceutically acceptable salt according to any one of Embodiments 1 to 35 in the manufacture of a medicament for modulating AAT activity.

39. The pharmaceutical composition according to Embodiment 36, for use in modulating AAT activity.

40. A method of treating alpha-1 antitrypsin deficiency (AATD) in a subject comprising administering a compound, tautomer, deuterated derivative, or pharmaceutically acceptable salt according to any one of Embodiments 1 to 35, or a pharmaceutical composition according to Embodiment 36.

41. Use of a compound, tautomer, deuterated derivative, or pharmaceutically acceptable salt according to any one of Embodiments 1 to 35 in the manufacture of a medicament for treating AATD.

42. The pharmaceutical composition according to Embodiment 36, for use in treating AATD.

In some embodiments, 10 mg to 1,500 mg, 100 mg to 1,800 mg, 100 mg to 500 mg, 200 mg to 600 mg, 200 mg to 800 mg, 400 mg to 2,000 mg, 400 mg to 2,500 mg or 400 mg to 600 mg of a compound of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing are administered once daily, twice daily, or three times daily. In specific embodiments, 10 mg to 1,500 mg, 100 mg to 1,800 mg, 100 mg to 500 mg, 200 mg to 600 mg, 200 mg to 800 mg, 400 mg to 2,000 mg, or 400 mg to 600 mg of a compound selected from Compounds 1-262, tautomers thereof, deuterated derivatives of those compounds or tautomers, and pharmaceutically acceptable salts of any of the foregoing are administered once daily, twice daily, or three times daily.

One of ordinary skill in the art would recognize that, when an amount of a compound is disclosed, the relevant amount of a pharmaceutically acceptable salt form of the compound is an amount equivalent to the concentration of the free base of the compound. It is noted that the disclosed amounts of the compounds, tautomers, deuterated derivatives, and pharmaceutically acceptable salts disclosed herein are based upon the free base form of the reference compound. For example, "10 mg of at least one compound chosen from compounds of Formula (I) and pharmaceutically acceptable salts thereof" includes 10 mg of a compound of Formula (I) and a concentration of a pharmaceutically acceptable salt of compounds of Formula (I) equivalent to 10 mg of compounds of Formula (I).

II. Compounds and Compositions

Some embodiments of the disclosure provide a compound represented by Formula I:

(I)

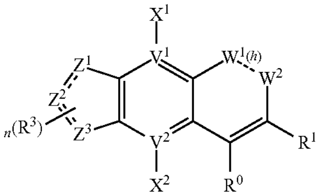

a tautomer thereof, a deuterated derivative of that compound or tautomer, or a pharmaceutically acceptable salt of any of the foregoing, wherein:

$Z^1$, $Z^2$, and $Z^3$ are each independently N, —NH, or —CH; provided that at least one of $Z^1$, $Z^2$, and $Z^3$ is N or —NH;

$V^1$ and $V^2$ are each selected from C and N;

$W^1$ and $W^2$ are each selected from —C═O, —$CR^2$, N, and —$NR^2$, wherein:

when $W^1$ is —$CR^2$, then $W^2$ is N;

when $W^2$ is —$CR^2$, then $W^1$ is N or —$NR^2$;

when $W^1$ is —C═O, then $W^2$ is —$NR^2$; and when $W^2$ is —C═O, then $W^1$ is —$NR^2$;

┄┄ for each of the two occurrences, is a single bond or a double bond; provided that one is a single bond and the other is a double bond;

*(h)* is a double bond except that when either of one of $W^1$ and $W^2$ is —C═O, then *(h)* is a single bond;

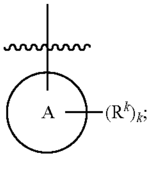

$R^0$ is halogen or wherein:

Ring A is $C_3$-$C_{12}$ carbocyclyl, 3 to 12-membered heterocyclyl, $C_6$ or $C_{10}$ aryl, or 5 to 10-membered heteroaryl;

$R^1$ is halogen, —CN, $C_1$-$C_6$ alkyl, $C_1$-$C_6$ alkoxy, $C_1$-$C_6$ haloalkoxy, —C(═O)$R^z$, —C(═O)O$R^z$, —C(═O)N$R^w R^x$, —N$R^w R^x$, —N$R^w$C(═O)$R^z$, —N$R^w$C(═O)O$R^z$, —N$R^w$C(═O)N$R^x R^y$, —O$R^z$, —OC(═O)$R^z$, —OC(═O)N$R^w R^x$, S(═O)$_2R^z$, $C_3$-$C_6$ cycloalkyl, or 3 to 6-membered heterocyclyl; wherein:

the $C_1$-$C_6$ alkyl, the $C_3$-$C_6$ cycloalkyl, or the 3 to 6-membered heterocyclyl of W is optionally substituted with 1 to 3 groups selected from —O$R^z$, $C_1$-$C_3$ haloalkyl, —CN, and halogen; and $R^w$, $R^x$, $R^y$, and $R^z$ are each independently hydrogen or $C_1$-$C_4$ alkyl;

$X^1$ and $X^2$ are each independently hydrogen, halogen, —CN, $C_1$-$C_3$ alkyl, $C_1$-$C_3$ haloalkyl, $C_1$-$C_3$ alkoxy, $C_1$-$C_3$ haloalkoxy, $C_3$-$C_6$ cycloalkyl, or 5 or 6-membered heteroaryl;

$R^2$ is hydrogen, halogen,

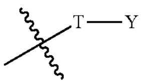

or

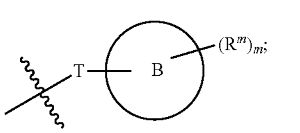

wherein:

T is absent or a bond, or is selected from —O—, —OC$H_2$—, —NH—, —NS(═O)$_2$C$H_3$, —S—, and —C$H_2$—;

Y is selected from $C_1$-$C_6$ alkyl, —(C$R^a R^a$)$_p$COOH, —(C$R^a R^a$)$_p$N$R^b$S(═O)$_2$(C$R^c R^c$)$_q$OH, —(C$R^a R^a$)$_p$C(═O)N$R^b$(C$R^c R^c$)$_q$COOH, and —(C$R^a R^a$)$_p$(O)(C$R^c R^c$)$_q$COOH; wherein:

$R^a$, for each occurrence, is independently hydrogen, halogen, —OH, or $C_1$-$C_4$ alkyl optionally substituted with 1 to 3 groups selected from halogen and —OH;

or alternatively, when $R^a$, for each occurrence, is $C_1$-$C_4$ alkyl, two $R^a$ groups together with their intervening carbon atom form cyclopropyl or cyclobutyl;

$R^b$ and $R^c$, for each occurrence, are each independently hydrogen or $C_1$-$C_2$ alkyl; and p and q are each independently an integer selected from 1 and 2;

Ring B is $C_3$-$C_{12}$ carbocyclyl, 3 to 12-membered heterocyclyl, $C_6$ or $C_{10}$ aryl, or 5 to 10-membered heteroaryl;

$R^3$ is —C(═O)O$R^d$; wherein $R^d$ is $C_1$-$C_4$ alkyl optionally substituted with —OC(O)$R^e$, —OC(═O)O$R^e$, or —OP(═O)O$R^f R^f$; wherein:

$R^e$, for each occurrence, is independently hydrogen, —C$H_3$, or —$C_2H_5$;

$R^f$, for each occurrence, is independently —OH, —C$H_3$, —$C_2H_5$, —OC$H_3$, or —O$C_2H_5$;

$R^k$ is halogen, —CN, $C_1$-$C_2$ alkyl, $C_1$-$C_2$ haloalkyl, $C_1$-$C_2$ alkoxy, $C_1$-$C_2$ haloalkoxy, or O—($C_3$-$C_6$ cycloalkyl);

$R^m$, for each occurrence, is independently halogen, —CN, ═O, $C_1$-$C_6$ alkyl, $C_1$-$C_6$ alkoxy, —C(═O)$R^r$, —C(═O)O$R^r$, —C(═O)N$R^p R^q$, —C(═O)N$R^p$O$R^r$, —N$R^p R^q$, —NRPC(═O)$R^r$, —N$R^p$S(═O)$_2R^r$, —O$R^r$, S(═O)$_2R^r$, —S(═O)$_2$N$R^p R^q$, —P(═O)$R^s R^t$, $C_3$-$C_6$ cycloalkyl, 3 to 6-membered heterocyclyl, phenyl, or 5 or 6-membered heteroaryl, wherein the $C_1$-$C_6$ alkyl, the phenyl, or the 5 or 6-membered heteroaryl of $R^m$ is optionally substituted with 1 to 3 groups selected from halogen, —CN, —C(═O)O$R^r$, —N$R^p R^q$, and —O$R^r$; and wherein the $C_3$-$C_6$ cycloalkyl or the 3 to 6-membered heterocyclyl of $R^m$ is optionally substituted with 1 to 3 groups selected from halogen, CN, ═O, —C(═O)O$R^r$, —N$R^p R^q$, and —O$R^r$;

wherein $R^p$ and $R^q$, for each occurrence, are each independently hydrogen or $C_1$-$C_4$ alkyl optionally substituted with 1 to 3 groups selected from —OH, —OC$H_3$, —O$C_2H_5$, and —COOH;

wherein $R^r$, for each occurrence, is each independently hydrogen, $C_1$-$C_4$ alkyl, $C_3$-$C_6$ cycloalkyl, or 3 to 6-membered heterocyclyl; wherein the $C_1$-$C_4$ alkyl, $C_3$-$C_6$ cycloalkyl, or 3 to 6-membered heterocyclyl of $R^r$ is optionally substituted with 1 to 3 groups selected from —OH, —OC$H_3$, —O$C_2H_5$, —C$H_2$OH, —C(═O)OH, —(O)C(═O)OH, and —(O)P(═O)(OH)$_2$; and wherein $R^s$ and $R^t$, for each occurrence, are each independently hydrogen, $C_1$-$C_4$ alkyl, $C_1$-$C_4$ alkoxy, or —OH;

k and m are each independently an integer selected from 0, 1, 2, 3, 4, and 5; and n is an integer selected from 0, 1, and 2.

In some embodiments, two of $Z^1$, $Z^2$, and $Z^3$ are N or —NH in the compound, tautomer, deuterated derivative, or pharmaceutically acceptable salt of Formula I and n is an integer selected from 0 and 1.

In some embodiments, in the compound, tautomer, deuterated derivative, or pharmaceutically acceptable salt of Formula I, $R^0$ is Cl.

In some embodiments, the compound, tautomer, deuterated derivative, or pharmaceutically acceptable salt of Formula I is a compound, tautomer, deuterated derivative, or pharmaceutically acceptable salt of Formula II:

(II)

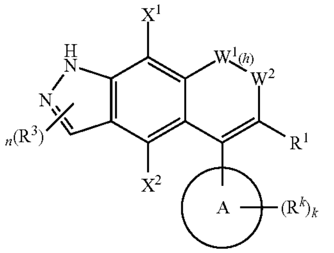

wherein:

$R^3$ is —C(═O)O$R^d$; wherein $R^d$ is $C_1$-$C_4$ alkyl optionally substituted with —OC(O)$R^e$, —OC(═O)O$R^e$, or —OC(═O)O$R^f R^f$; wherein:

$R^e$, for each occurrence, is independently hydrogen or —C$H_3$;

$R^f$, for each occurrence, is independently —OH, —C$H_3$, or —OC$H_3$;

n is an integer selected from 0 and 1;

and wherein all other variables not specifically defined herein are as defined for Formula I.

In some embodiments, the compound, tautomer, deuterated derivative, or pharmaceutically acceptable salt of Formula I is a compound, tautomer, deuterated derivative, or pharmaceutically acceptable salt of Formulae IIIa, Formula IIIb, Formula IIIc, or Formula IIId ("Formulae IIIa-d"):

(IIIa)

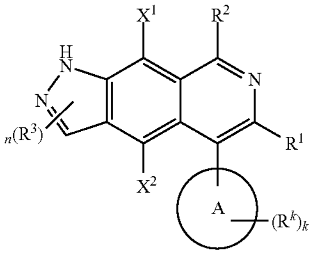

(IIIb)

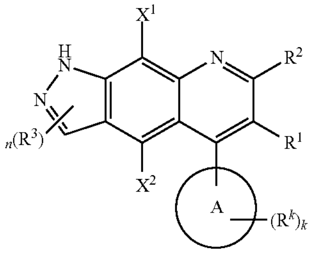

(IIIc)

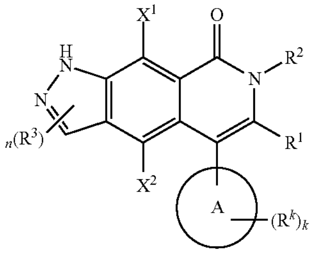

(IIId)

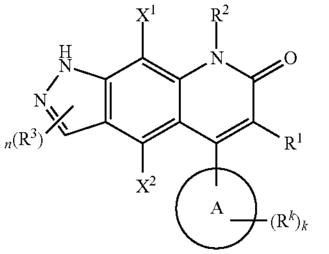

wherein:

Ring A is optionally substituted with $R^k$ and Ring A is 5 or 6-membered carbocyclyl, phenyl, or 5 or 6-membered heteroaryl;

$R^1$ is $C_1$-$C_6$ alkyl, $C_1$-$C_6$ alkoxy-C(=O)$OR^z$, —C(=O)$NR^wR^x$, —$NR^wR^x$, —$OR^z$, —S(=O)$_2R^z$, $C_3$-$C_6$ cycloalkyl, or 3 to 6-membered heterocyclyl; wherein:

the $C_1$-$C_6$ alkyl, the $C_3$-$C_6$ cycloalkyl, or the 3 to 6-membered heterocyclyl of $R^1$ is optionally substituted with 1 to 3 groups selected from —$OR^z$ and halogen; and $R^w$, $R^x$, $R^y$, and $R^z$ are each independently hydrogen or $C_1$-$C_4$ alkyl;

$X^1$ and $X^2$ are each independently hydrogen, halogen, —CN, $C_1$-$C_2$ alkyl, $C_1$-$C_2$ haloalkyl, $C_1$-$C_2$ alkoxy, $C_1$-$C_2$ haloalkoxy, or $C_3$-$C_4$ cycloalkyl;

$R^2$ is as defined for Formula I but when $R^2$ is

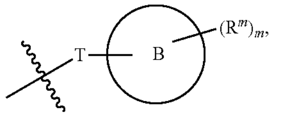

Ring B is optionally substituted with $R^m$ and Ring B is selected from $C_4$-$C_9$ carbocyclyl, phenyl, 4 to 9-membered heterocyclyl, and 5 to 6-membered heteroaryl;

$R^3$ is absent or is —C(=O)O$(CH_2)_2$(O)P(=O)$(OH)_2$;

$R^k$ is halogen, —CN, —$CH_3$, $C_1$ haloalkyl, or —$OCH_3$;

n is an integer selected from 0 and 1;

and wherein all other variables not specifically defined herein are as defined for Formula I or Formula II.

In some embodiments, the compound, tautomer, deuterated derivative, or pharmaceutically acceptable salt of Formula I is a compound, tautomer, deuterated derivative, or pharmaceutically acceptable salt of Formula IVa, Formula IVb, or Formula IVc ("Formulae IVa-c"):

(IVa)

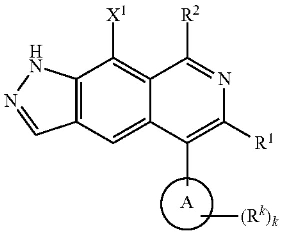

(IVb)

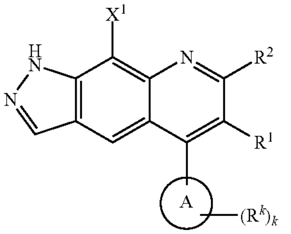

(IVc)

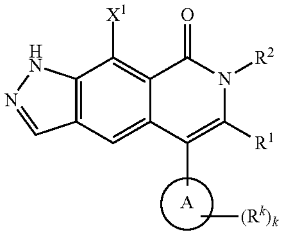

wherein $X^1$ is hydrogen, halogen, —$CH_3$, —$CHF_2$, —$CH_2F$, or —$OCH_3$; and wherein all other variables not specifically defined herein are as defined for Formula I, Formula II, or Formulae IIIa-d.

In some embodiments, the compound, tautomer, deuterated derivative, or pharmaceutically acceptable salt of Formula I is a compound, tautomer, deuterated derivative, or pharmaceutically acceptable salt of Formula Va, Formula Vb, or Formula Vc ("Formulae Va c"):

(Va)

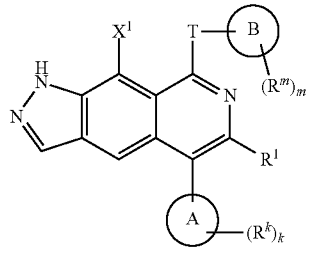

(Vb)

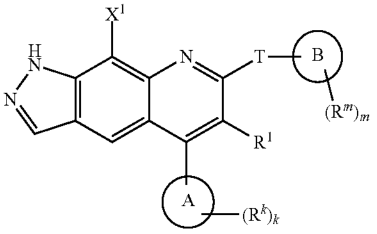

(Vc)

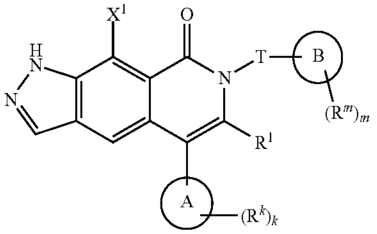

wherein:

$R^1$ is $C_1$-$C_4$ alkyl, $C_1$-$C_4$ alkoxy, —C(═O)OR$^z$, —C(═O)NR$^w$R$^x$, —NR$^w$R$^x$, —OR$^z$, —S(═O)$_2$R$^z$, cyclopropyl, cyclobutyl or 5 or 6-membered heterocyclyl; wherein:

the $C_1$-$C_4$ alkyl, the cyclopropyl, the cyclobutyl, or the 5 or 6-membered heterocyclyl of W is optionally substituted with 1 to 3 groups selected from —OR$^z$ and halogen; and $R^w$, $R^x$, $R^y$, and $R^z$ are each independently hydrogen or $C_1$-$C_2$ alkyl;

T is absent, or is selected from —O—, —OCH$_2$—, —NH—, and —CH$_2$—;

and wherein all other variables not specifically defined herein are as defined for Formula I, Formula II, Formulae IIIa-d, or Formula IVa-c.

In some embodiments, Ring A in the compound, tautomer, deuterated derivative, or pharmaceutically acceptable salt, of any of Formulae I, II, IIIa-d, IVa-c, and Va-c is optionally substituted with $R^k$ and is selected from phenyl, cyclohexenyl, 3,6-dihydro-2H-pyranyl, pyridinyl, pyridazinyl, thiophenyl, and pyrazolyl.

In some embodiments, Ring A in the compound, tautomer, deuterated derivative, or pharmaceutically acceptable salt, of any of Formulae I, II, IIIa-d, IVa-c, and Va-c is optionally substituted with $R^k$ and is selected from:

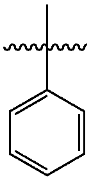, 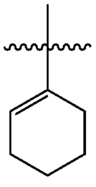, 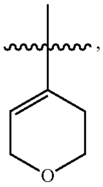, 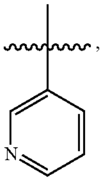, 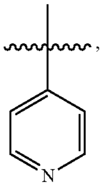,

-continued

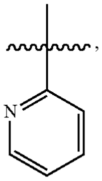, 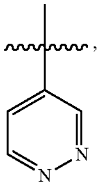, 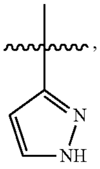, and 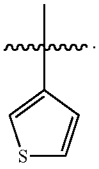.

In some embodiments, Ring A in the compound, tautomer, deuterated derivative, or pharmaceutically acceptable salt, of any of Formulae I, II, IIIa-d, IVa-c, and Va-c is optionally substituted with $R^k$ and is selected from:

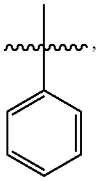, 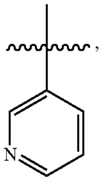, and 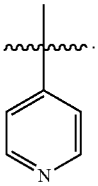.

In some embodiments, $R^2$ in the compound, tautomer, deuterated derivative, or pharmaceutically acceptable salt, of any of Formulae I, II, IIIa-d, IVa-c, and Va-c is

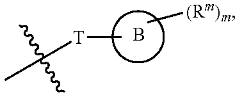

Ring B is optionally substituted with $R^m$ and Ring B is selected from isoindolinyl, azaspiro[3.4]octanyl, spiro[3.3]heptanyl, azaspiro[3.3]heptanyl, oxaspiro[3.3]heptanyl, azabicyclo[3.2.0]heptanyl, phenyl, cyclohexenyl, cyclohexyl, pyridinyl, piperidinyl, morpholinyl, tetrahydro-2H-pyranyl, thiazolyl, pyrazolyl, furanyl, tetrahydrofuranyl, cyclopentyl, bicyclo[1.1.1]pentanyl, pyrrolidinyl, cyclobutyl, azetidinyl, and cyclopropyl.

In some embodiments, $R^2$ in the compound, tautomer, deuterated derivative, or pharmaceutically acceptable salt, of any of Formulae I, II, IIIa-d, IVa-c, and Va-c is

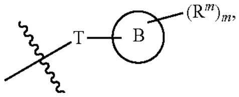

Ring B is optionally substituted with $R^m$ and Ring B is selected from

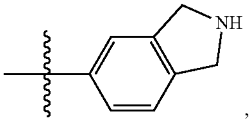, 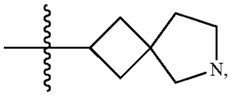

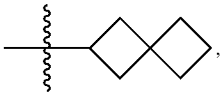, 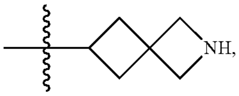

-continued

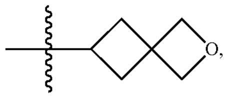, 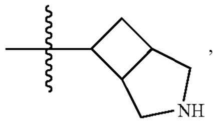,

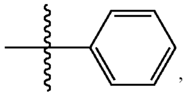, 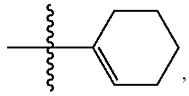, 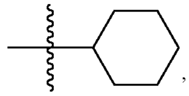,

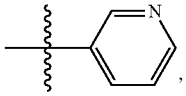, 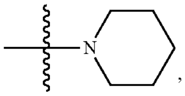, 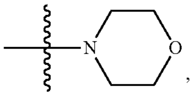,

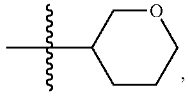, 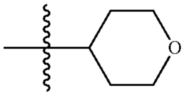, 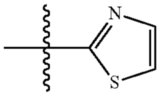,

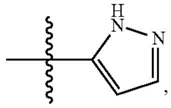, 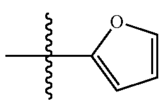, 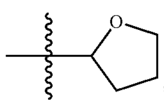,

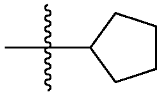, 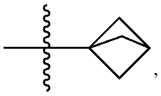, 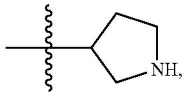,

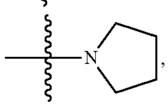, 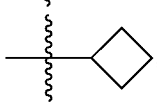, 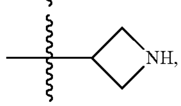

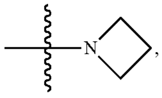, and 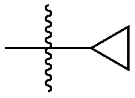.

In some embodiments, $R^2$ in the compound, tautomer, deuterated derivative, or pharmaceutically acceptable salt, of any of Formulae I, II, IIIa-d, IVa-c, and Va-c is

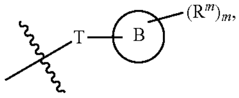

Ring B is optionally substituted with $R^m$ and Ring B is selected from

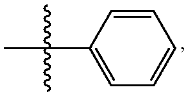, 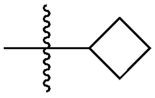, and 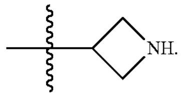.

In some embodiments of Formulae I, II, IIIa-d, IVa-c, and Va-c, for each occurrence in the compound, tautomer, deuterated derivative, or pharmaceutically acceptable salt, $R^m$ is independently selected from halogen, —CN, =O, $C_1$-$C_6$ alkyl, $C_1$-$C_4$ alkoxy, —C(=O)$R^r$, —C(=O)O$R^r$, —C(=O)N$R^pR^q$, —C(=O)N$R^p$O$R^r$, —N$R^pR^q$, —N$R^p$C(=O)$R^r$c, —N$R^p$S(=O)$_2R^r$, —O$R^r$, S(=O)$_2R^r$, —S(=O)$_2$N$R^pR^q$, —P(=O)$R^sR^t$, and 5 and 6-membered heterocyclyl; wherein:

the $C_1$-$C_6$ alkyl of $R^m$ is optionally substituted with 1 to 3 groups selected from —C(=O)OH, —C(=O)$OCH_3$, —C(=O)$OC_2H_5$, —OH, —$OCH_3$, and —$OC_2H_5$; and the 5 or 6-membered heterocyclyl of $R^m$ is optionally substituted with 1 to 3 groups selected from halogen, =O, —C(=O)OH, and —OH; wherein:

$R^p$ and $R^q$, for each occurrence, are each independently hydrogen or $C_1$-$C_3$ alkyl optionally substituted with 1 to 3 groups selected from —OH, —$OCH_3$, and —C(=O)OH;

$R^r$, for each occurrence, are each independently hydrogen, $C_1$-$C_4$ alkyl, $C_3$-$C_6$ cycloalkyl, or 4 to 6-membered heterocyclyl; wherein the $C_1$-$C_2$ alkyl, $C_3$-$C_6$ cycloalkyl, or 4 to 6-membered heterocyclyl of $R^r$ is optionally substituted with 1 to 3 groups selected from —OH, —$OCH_3$, —$OC_2H_5$, —C(=O)OH, —(O)C(=O)OH, and —(O)P(=O)$(OH)_2$; and $R^s$ and $R^t$, for each occurrence, are each independently hydrogen, $C_1$-$C_2$ alkyl, $C_1$-$C_2$ alkoxy, or —OH.

In some embodiments of Formulae I, II, IIIa-d, IVa-c, and Va-c, for each occurrence in the compound, tautomer, deuterated derivative, or pharmaceutically acceptable salt, $R^m$ is independently selected from halogen, CN, =O, $C_1$-$C_4$ alkyl, $C_1$-$C_4$ alkoxy, —C(=O)$R^r$, —C(=O)O$R^r$, —C(=O)N$R^pR^q$, —C(=O)N$R^p$O$R^r$, —N$R^pR^q$, —N$R^p$C(=O)$R^r$, —N$R^p$S(=O)$_2R^r$, —O$R^r$, S(=O)$_2R^r$, —S(=O)$_2$N$R^pR^q$, —P(=O)$R^sR^t$, imidazolidinyl, and morpholinyl; wherein:

the $C_1$-$C_4$ alkyl of $R^m$ is optionally substituted with 1 to 3 groups selected from —C(=O)OH, —C(=O)$OCH_3$, —C(=O)$OC_2H_5$, —OH, —$OCH_3$, and —$OC_2H_5$; and the imidazolidinyl or the morpholinyl of $R^m$ is optionally substituted with 1 to 3 groups selected from oxo (=O) and —OH; wherein:

$R^p$ and $R^q$, for each occurrence, are each independently hydrogen or $C_1$-$C_3$ alkyl optionally substituted with 1 to 3 groups selected from —OH, —$OCH_3$, and —C(=O)OH;

$R^r$, for each occurrence, are each independently hydrogen, $C_1$-$C_2$ alkyl, cyclopropyl, oxetanyl, or azetidinyl; wherein the $C_1$-$C_2$ alkyl, cyclopropyl, oxetanyl, or azetidinyl of $R^r$ is optionally substituted with 1 to 3 groups selected from —OH, —$CH_2$OH, —C(=O)OH, and —(O)P(=O)$(OH)_2$; and $R^s$ and $R^t$, for each occurrence, are each independently —$CH_3$, —$OCH_3$, or —OH.

In some embodiments of Formulae I, II, IIIa-d, IVa-c, and Va-c, for each occurrence in the compound, tautomer, deuterated derivative, or pharmaceutically acceptable salt, $R^m$ is independently selected from —COOH, —C(=O)CH(OH)$CH_3$, F, —$CH_3$, —C(=O)$NH_2$, —C(=O)NH($OCH_3$), S(=O)$_2NH_2$, —NHS(=O)$_2CH_3$, =O, —OH, —P(=O)$(CH_3)_2$, —P(=O)$(OH)_2$, —P(=O)$(OCH_3)_2$, —OH, imidazolidin-4yl, —$CH_2$OH, —NH$CH_3$, morpholin-4-yl, —(C=O)NHCH($CH_3$)$CH_2$OH, —C(=O)N($CH_3$)CH($CH_3$)$CH_2$OH, —N$CH_3$C(=O)CH(OH)$CH_3$, —C(=O)CH($CH_3$)$CH_2$OH, —C(=O)CH(OH)$CH_2$OH, —C(=O)(hydroxymethyl)oxetan-3-yl, —C(=O)(hydroxy)cyclopropyl, —C(=O)CH(OH)$CH_3$, —C(=O)$OCH_3$, —$OCH_3$, —$CH_2$COOH, —CN, —$OCH_2$COOH, —OCH($CH_3$)COOH, —CH($CH_3$)COOH, Cl, S(=O)$_2CH_3$, S(=O)$_2$NH$CH_3$, —$CH_2$C(=O)$OC_2H_5$, —C(=O)$OCH_2$(O)P(=O)$(OH)_2$, —C(=O)NHCH($CH_3$)COOH, —C(=O)NH$CH_3$, —C=O(3-hydroxyazetidin-1-yl), and —C(=O)(morpholin-4-yl).

In some embodiments of Formulae I, II, IIIa-d, IVa-c, and Va-c, for each occurrence in the compound, tautomer, deuterated derivative, or pharmaceutically acceptable salt $R^m$ is independently selected from —COOH, —$CH_2$COOH, —$OCH_2$COOH, —OCH($CH_3$)COOH, —CH($CH_3$)COOH, —C(=O)$OCH_2$(O)P(=O)$(OH)_2$, and —C(=O)NHCH($CH_3$)COOH.

In some embodiments, the compound, tautomer, deuterated derivative, or pharmaceutically acceptable salt of Formula I is a compound, tautomer, deuterated derivative, or pharmaceutically acceptable salt of Formula VIa, Formula VIb, or Formula VIc ("Formulae VIa-c"):

(VIa)

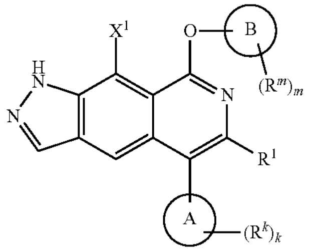

(VIb)

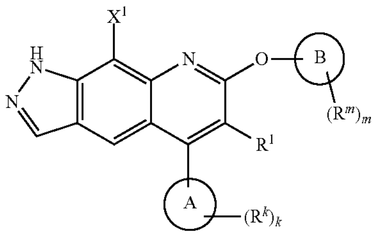

(VIc)

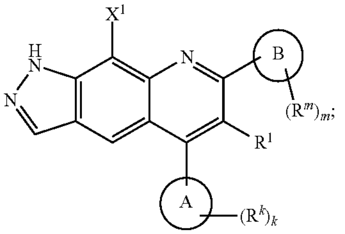

wherein all other variables not specifically defined herein are as defined in any one of Formulae I, II, IIIa-d, IVa-c, and Va-c.

In some embodiments, W in the compound, tautomer, deuterated derivative, or pharmaceutically acceptable salt of Formulae I, II, IIIa-d, IVa-c, Va-c, and VIa-c, is selected from $C_1$-$C_3$ alkyl, $C_1$-$C_3$ alkoxy, —C(═O)OR$^z$, —C(═O)NR$^w$R$^x$, —NR$^w$R$^x$, —OR$^z$, —S(═O)$_2$R$^z$, cyclopropyl, cyclobutyl, and a 6-membered heterocyclyl; wherein:

the $C_1$-$C_3$ alkyl, the cyclopropyl, the cyclobutyl, or the tetrahydro-2H-pyran-4-yl of R$^1$ is optionally substituted with 1 to 3 groups selected from —OH, —$OCH_3$, $C_1$-$C_2$ haloalkyl, and halogen;

R$^w$, R$^x$, R$^y$, and R$^z$ are each independently hydrogen or —$CH_3$.

In some embodiments, R$^1$ in the compound, tautomer, deuterated derivative, or pharmaceutically acceptable salt of Formulae I, II, IIIa-d, IVa-c, Va-c, and VIa-c, is selected from —$C(CH_3)_2$, —$CF_3$, —$CH_2C(CH_3)_2OCH_3$, —$C(CH_3)_2CH_2OH$, —$OCH_3$, —O(C)$(CH_3)_2$, —C(═O)$OCH_3$, —C(═O)N$(CH_3)_2$, N$(CH_3)_2$, —S(═O)$_2CH_3$, S(═O)$_2C_2H_5$, —S(═O)$_2CH(CH_3)_2$, tetrahydro-2H-pyran-4-yl, cyclopropyl, and cyclobutyl; wherein the cyclopropyl or the cyclobutyl of R$^1$ is optionally substituted with —OH, —$OCH_3$, or —$CF_3$.

In some embodiments, the compound, tautomer, deuterated derivative, or pharmaceutically acceptable salt of Formula I is a compound, tautomer, deuterated derivative, or pharmaceutically acceptable salt of Formula VIIa, Formula VIIb, Formula VIIc, Formula VIId, Formula VIIe, or Formula VIIf ("Formulae VIIa-f"):

(VIIa)

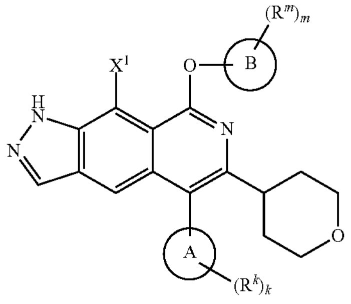

(VIIb)

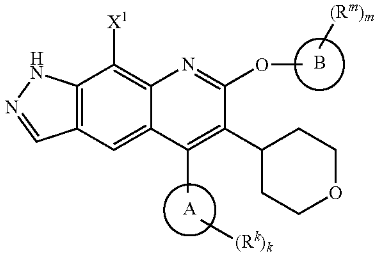

(VIIc)

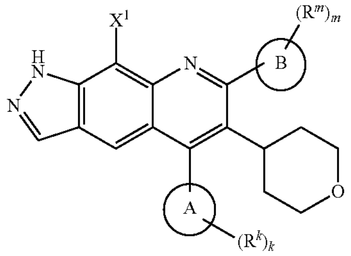

(VIId)

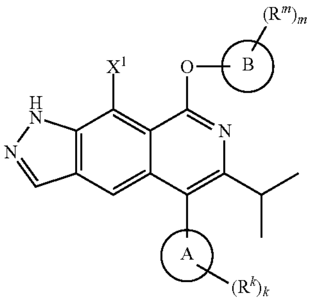

(VIIe)

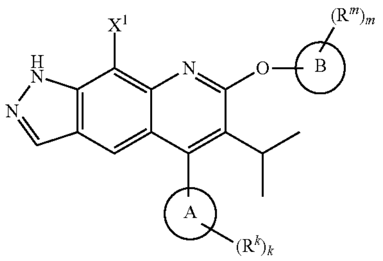

-continued (VIIf)

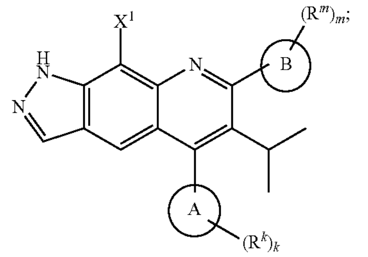

wherein all other variables not specifically defined herein are as defined in any one of Formulae I, II, IIIa-d, IVa-c, Va-c, and VIa-c.

In some embodiments, the compound, tautomer, deuterated derivative, or pharmaceutically acceptable salt of Formula I is a compound, tautomer, deuterated derivative, or pharmaceutically acceptable salt of Formula VIIIa, Formula VIIIb, or Formula VIIIc ("Formulae VIIIa-c"):

(VIIIa)

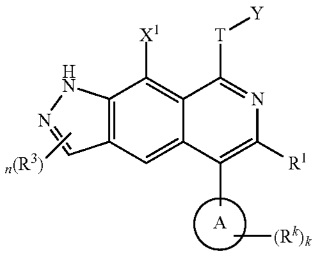

(VIIIb)

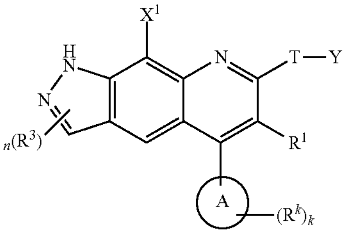

(VIIIc)

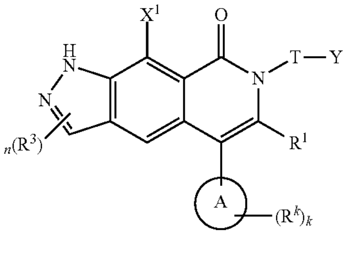

wherein:

Ring A is optionally substituted with $R^k$ and Ring A is phenyl or 5 or 6-membered heteroaryl;

T is absent, or is selected from —O—, —NH—, and —$CH_2$—;

Z is $C_1$-$C_2$ alkyl, —$(CR^aR^a)_pCOOH$, —$(CR^aR^a)_pNR^bS(=O)_2(CR^cR^c)_qOH$, —$(CR^aR^a)_pC(=O)NR^b(CR^cR^c)_qCOOH$, or —$(CR^aR^a)_p(O)(CR^cR^c)_qCOOH$; wherein:

$R^a$, for each occurrence, is independently hydrogen, —OH, —$CH_3$, or —$CH_2OH$; and $R^b$ and $R^c$, for each occurrence, are each independently hydrogen or —$CH_3$;

and wherein all other variables not specifically defined herein are as defined in any one of Formulae I, II, IIIa-d, and IVa-c.

In some embodiments,

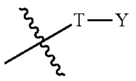

in the compound, tautomer, deuterated derivative, or pharmaceutically acceptable salt of Formulae I, II, IIIa-d, IVa-c, or VIIIa-c is selected from —$NHCH_3$, —$CH_2COOH$, —$(CH_2)_2COOH$, —$CH(CH_3)CH_2COOH$, —$NHCH(CH_3)COOH$, —$OCH_2COOH$, —$O(CH_2)_2(O)CH_2COOH$, —$CH_2CH(CH_3)COOH$, —$OCH(CH_3)C(=O)NHCH_2COOH$, and —$OCH(CH_2OH)CH_2NHS(=O)_2(CH_2)_2OH$.

In some embodiments, Ring A in the compound, tautomer, deuterated derivative, or pharmaceutically acceptable salt of Formulae I, II, IIIa-d, IVa-c, or VIIIa-c is phenyl or pyridinyl optionally substituted with $R^k$.

In some embodiments, Ring A in the compound, tautomer, deuterated derivative, or pharmaceutically acceptable salt of Formulae I, II, IIIa-d, IVa-c, or VIIIa-c is

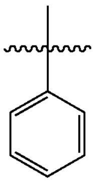 or 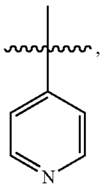, optionally substituted with $R^k$.

In some embodiments, $R^1$ in the compound, tautomer, deuterated derivative, or pharmaceutically acceptable salt of Formulae I, II, IIIa-d, IVa-c, or VIIIa-c is selected from halogen, —CN, $C_1$-$C_3$ alkyl, $C_1$-$C_3$ alkoxy, —$NR^wR^x$, —$OR^z$, $C_3$-$C_6$ cycloalkyl, and 5 or 6-membered heterocyclyl; wherein:

the $C_1$-$C_3$ alkyl, the $C_3$-$C_6$ cycloalkyl, or the 5 or 6-membered heterocyclyl of $R^1$ is optionally substituted with 1 to 3 groups selected from —OH, —$OCH_3$, $C_1$-$C_2$ haloalkyl, and halogen; and $R^w$, $R^x$, $R^y$, and $R^z$ are each independently hydrogen or —$CH_3$.

In some embodiments, IV in the compound, tautomer, deuterated derivative, or pharmaceutically acceptable salt of Formulae I, II, IIIa-d, IVa-c, or VIIIa-c is $C_1$-$C_3$ alkyl or 6-membered heterocyclyl; wherein:

the $C_1$-$C_3$ alkyl or the 5 or 6-membered heterocyclyl of $R^1$ is optionally substituted with 1 to 3 groups selected from —OH, —$OCH_3$, $C_1$-$C_2$ haloalkyl, and halogen.

In some embodiments, $R^1$ in the compound, tautomer, deuterated derivative, or pharmaceutically acceptable salt of Formulae I, II, IIIa-d, IVa-c, or VIIIa-c is —$C(CH_3)_2$ or tetrahydro-2H-pyran-4-yl.

In some embodiments of the compound, tautomer, deuterated derivative, or pharmaceutically acceptable salt of Formulae I, II, IIIa-d, IVa-c, Va-c, VIa-c, VIIa-f, and VIIIa-c:

$X^1$ is hydrogen, F, or —$CH_3$;

$R^k$ is F, Cl, —$CH_3$, or —$OCH_3$; and k is an integer selected from 0, 1, and 2.

In some embodiments, the compound, tautomer, deuterated derivative, or pharmaceutically acceptable salt of Formulae I, II, IIIa-d, IVa-c, Va-c, VIa-c, VIIa-f, and VIIIa-c is selected from Compounds 1-262 as described in Table I below.
TABLE I
| Compounds 1-262 |
|---|
| Compound 1<br>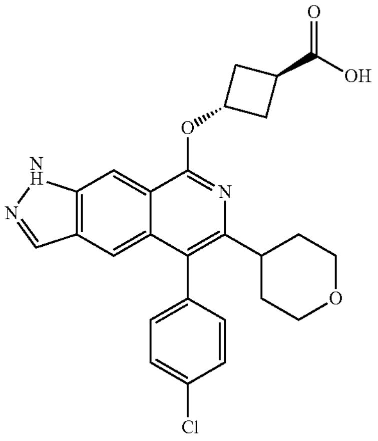 [SMILES: O=C(O)[C@H]1C[C@H](Oc2nc(C3CCOCC3)c(-c3ccc(Cl)cc3)c3cc4cn[nH]c4cc23)C1] |
| Compound 2<br>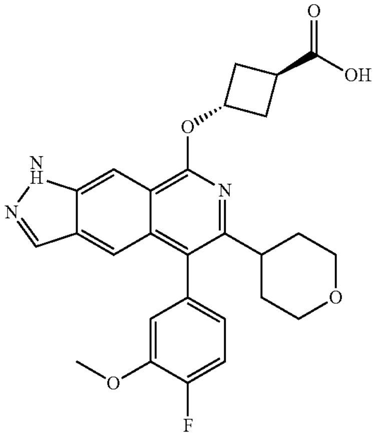 [SMILES: COc1cc(-c2c(C3CCOCC3)nc(O[C@H]3C[C@H](C(=O)O)C3)c3cc4[nH]ncc4cc23)ccc1F] |
| Compound 3<br>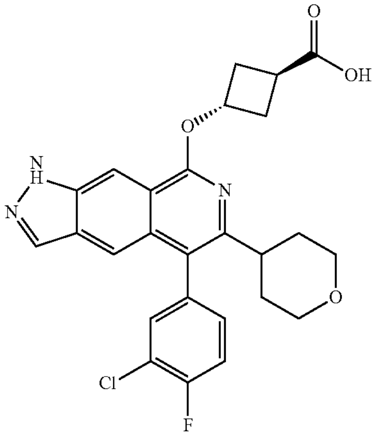 |
TABLE I-continued
| Compounds 1-262 |
|---|
| Compound 4<br>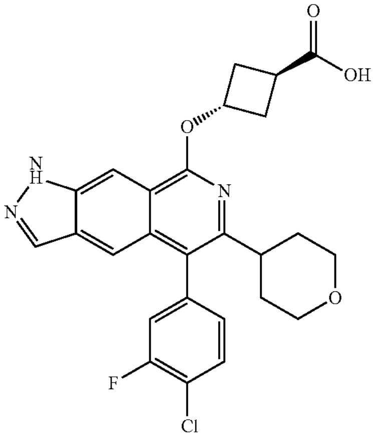 |
| Compound 5<br>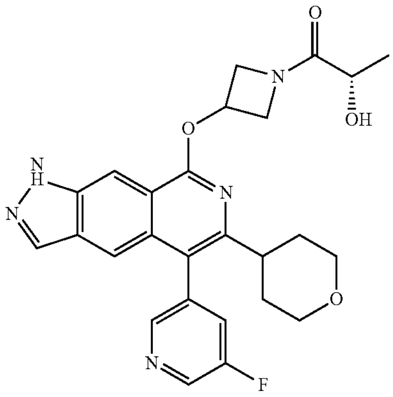 [SMILES: C[C@H](O)C(=O)N1CC(Oc2nc(C3CCOCC3)c(-c3cncc(F)c3)c3cc4cn[nH]c4cc23)C1] |
| Compound 6<br>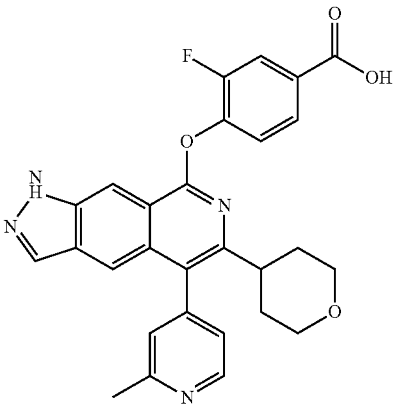 [SMILES: Cc1cc(-c2c(C3CCOCC3)nc(Oc3ccc(C(=O)O)cc3F)c3cc4[nH]ncc4cc23)ccn1] |

TABLE I-continued
| Compounds 1-262 |
| --- |
Compound 7
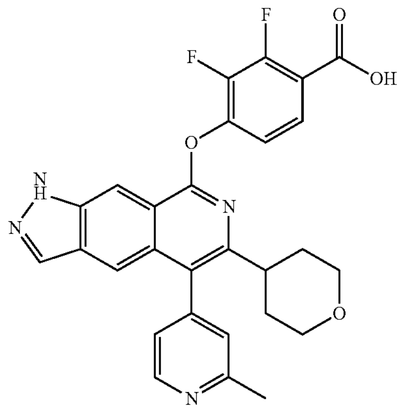 [SMILES: Cc1cc(-c2c(C3CCOCC3)nc(Oc3ccc(C(=O)O)c(F)c3F)c3cc4[nH]ncc4cc23)ccn1]
Compound 8
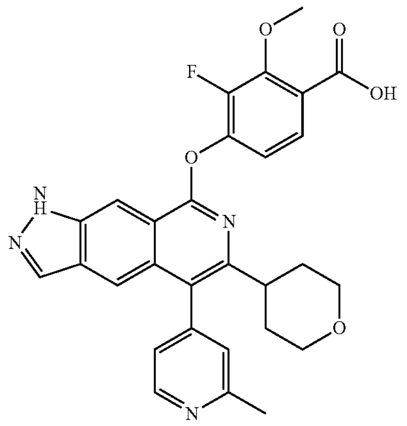 [SMILES: COc1c(C(=O)O)ccc(Oc2nc(C3CCOCC3)c(-c3ccnc(C)c3)c3cc4cn[nH]c4cc23)c1F]
Compound 9
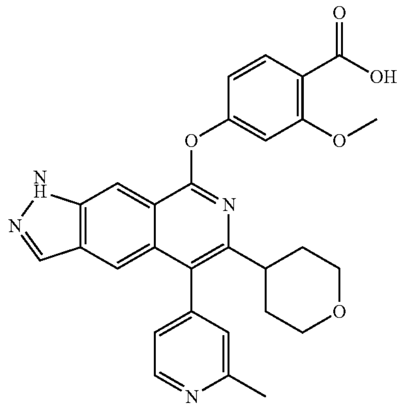 [SMILES: COc1cc(Oc2nc(C3CCOCC3)c(-c3ccnc(C)c3)c3cc4cn[nH]c4cc23)ccc1C(=O)O]
TABLE I-continued
| Compounds 1-262 |
| --- |
Compound 10
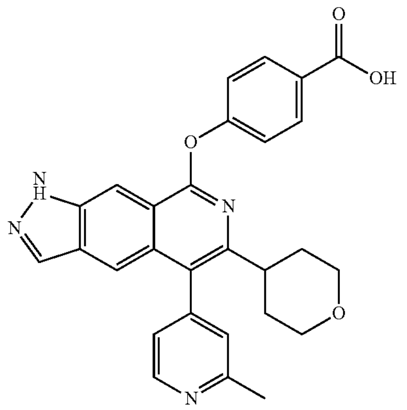 [SMILES: Cc1cc(-c2c(C3CCOCC3)nc(Oc3ccc(C(=O)O)cc3)c3cc4[nH]ncc4cc23)ccn1]
Compound 11
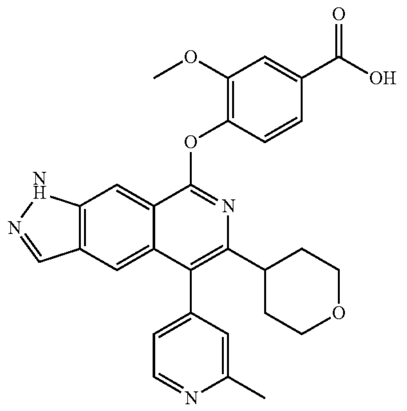 [SMILES: COc1cc(C(=O)O)ccc1Oc1nc(C2CCOCC2)c(-c2ccnc(C)c2)c2cc3cn[nH]c3cc12]
Compound 12
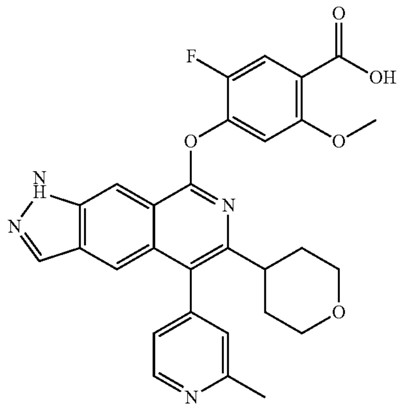 [SMILES: COc1cc(Oc2nc(C3CCOCC3)c(-c3ccnc(C)c3)c3cc4cn[nH]c4cc23)c(F)cc1C(=O)O]

TABLE I-continued
| Compounds 1-262 |
| --- |
Compound 13
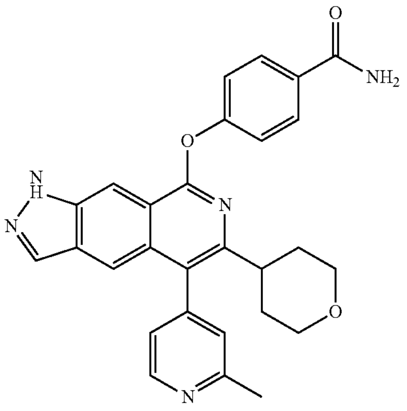 [SMILES: Cc1cc(-c2c(C3CCOCC3)nc(Oc3ccc(C(N)=O)cc3)c3cc4[nH]ncc4cc23)ccn1]
Compound 14
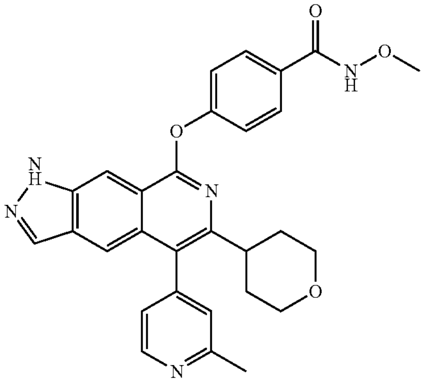 [SMILES: CONC(=O)c1ccc(Oc2nc(C3CCOCC3)c(-c3ccnc(C)c3)c3cc4cn[nH]c4cc23)cc1]
Compound 15
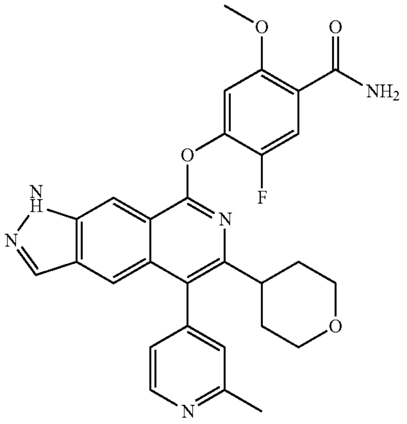 [SMILES: COc1cc(Oc2nc(C3CCOCC3)c(-c3ccnc(C)c3)c3cc4cn[nH]c4cc23)c(F)cc1C(N)=O]
TABLE I-continued
| Compounds 1-262 |
| --- |
Compound 16
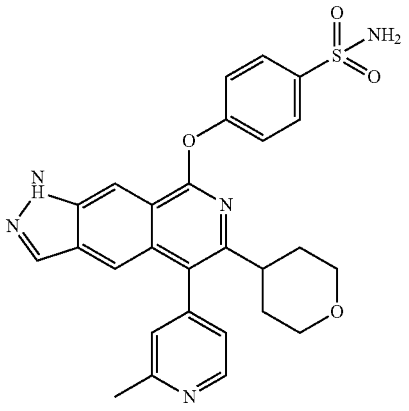 [SMILES: Cc1cc(-c2c(C3CCOCC3)nc(Oc3ccc(S(N)(=O)=O)cc3)c3cc4[nH]ncc4cc23)ccn1]
Compound 17
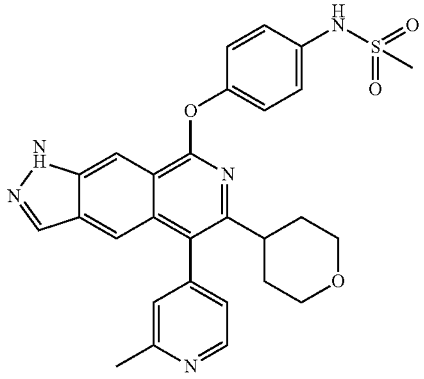 [SMILES: Cc1cc(-c2c(C3CCOCC3)nc(Oc3ccc(NS(C)(=O)=O)cc3)c3cc4[nH]ncc4cc23)ccn1]
Compound 18
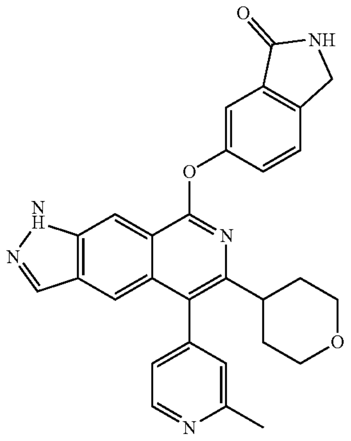 [SMILES: Cc1cc(-c2c(C3CCOCC3)nc(Oc3ccc4c(c3)C(=O)NC4)c3cc4[nH]ncc4cc23)ccn1]

TABLE I-continued
| Compounds 1-262 |
|---|
Compound 19
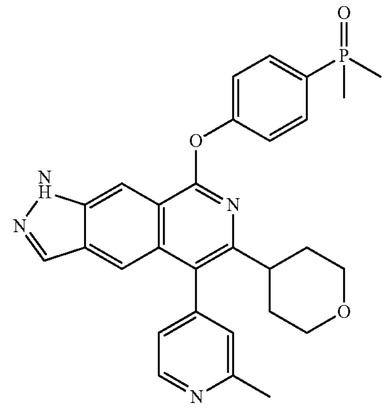 [SMILES: Cc1cc(-c2c(C3CCOCC3)nc(Oc3ccc(P(C)(C)=O)cc3)c3cc4[nH]ncc4cc23)ccn1]
Compound 20
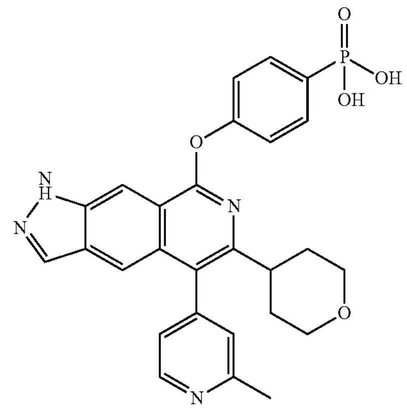 [SMILES: Cc1cc(-c2c(C3CCOCC3)nc(Oc3ccc(P(=O)(O)O)cc3)c3cc4[nH]ncc4cc23)ccn1]
Compound 21
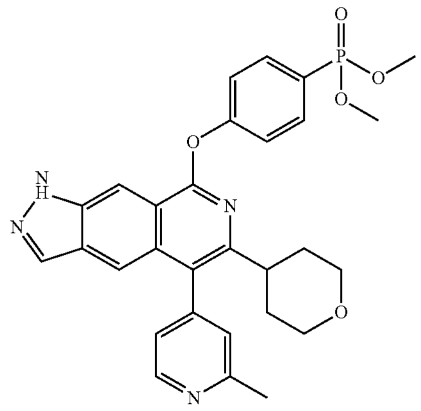 [SMILES: COP(=O)(OC)c1ccc(Oc2nc(C3CCOCC3)c(-c3ccnc(C)c3)c3cc4cn[nH]c4cc23)cc1]
TABLE I-continued
| Compounds 1-262 |
|---|
Compound 22
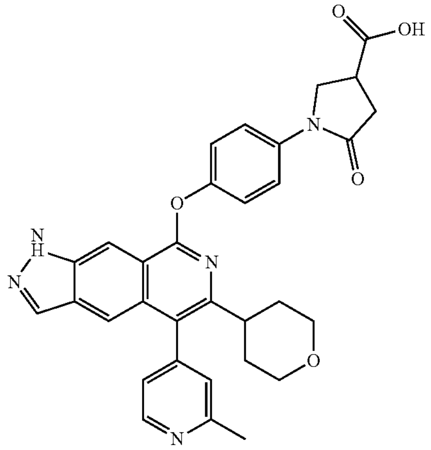 [SMILES: Cc1cc(-c2c(C3CCOCC3)nc(Oc3ccc(N4CC(C(=O)O)CC4=O)cc3)c3cc4[nH]ncc4cc23)ccn1]
Compound 23
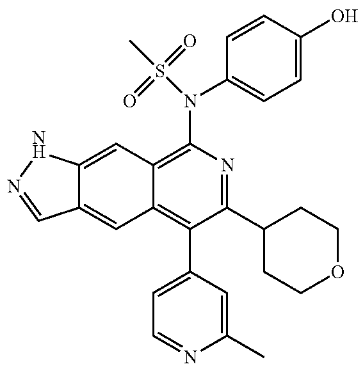 [SMILES: Cc1cc(-c2c(C3CCOCC3)nc(N(c3ccc(O)cc3)S(C)(=O)=O)c3cc4[nH]ncc4cc23)ccn1]
Compound 24
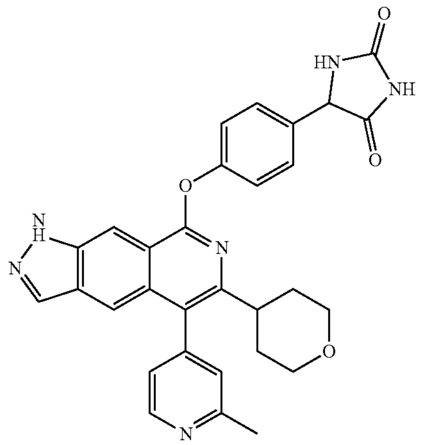 [SMILES: Cc1cc(-c2c(C3CCOCC3)nc(Oc3ccc(C4NC(=O)NC4=O)cc3)c3cc4[nH]ncc4cc23)ccn1]

TABLE I-continued
Compounds 1-262
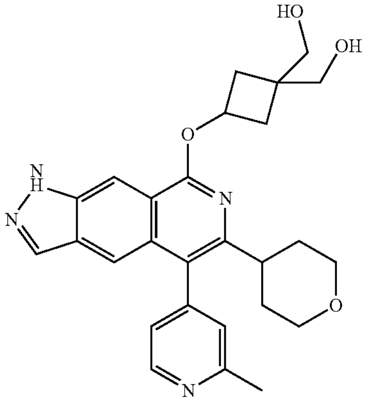 [SMILES: Cc1cc(-c2c(C3CCOCC3)nc(OC3CC(CO)(CO)C3)c3cc4[nH]ncc4cc23)ccn1]
Compound 25
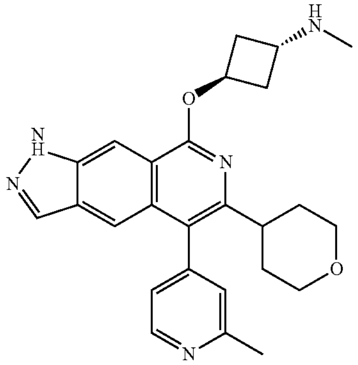 [SMILES: CN[C@H]1C[C@H](Oc2nc(C3CCOCC3)c(-c3ccnc(C)c3)c3cc4cn[nH]c4cc23)C1]
Compound 26
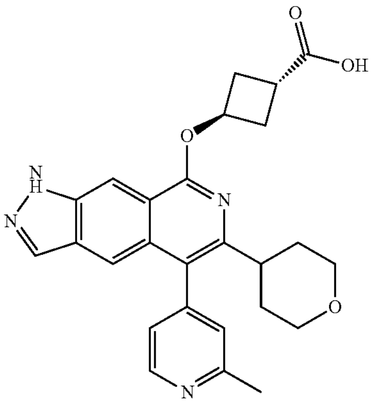 [SMILES: Cc1cc(-c2c(C3CCOCC3)nc(O[C@H]3C[C@H](C(=O)O)C3)c3cc4[nH]ncc4cc23)ccn1]
Compound 27
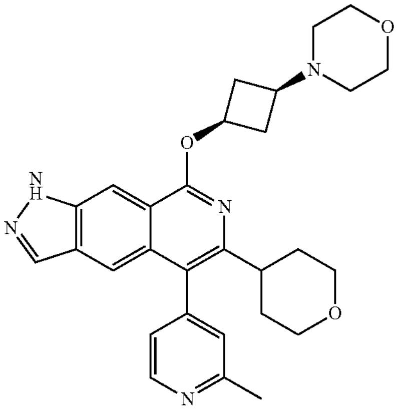 [SMILES: Cc1cc(-c2c(C3CCOCC3)nc(O[C@H]3C[C@@H](N4CCOCC4)C3)c3cc4[nH]ncc4cc23)ccn1]
Compound 28
TABLE I-continued
Compounds 1-262
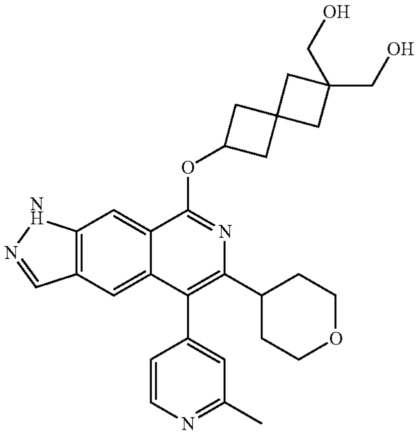 [SMILES: Cc1cc(-c2c(C3CCOCC3)nc(OC3CC4(C3)CC(CO)(CO)C4)c3cc4[nH]ncc4cc23)ccn1]
Compound 29
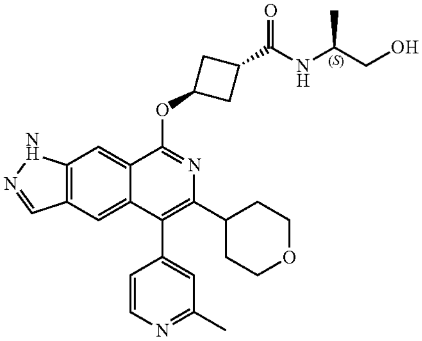
Compound 30
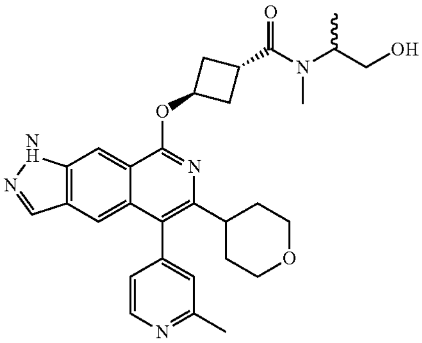 [SMILES: Cc1cc(-c2c(C3CCOCC3)nc(O[C@H]3C[C@H](C(=O)N(C)C(C)CO)C3)c3cc4[nH]ncc4cc23)ccn1]
Compound 31
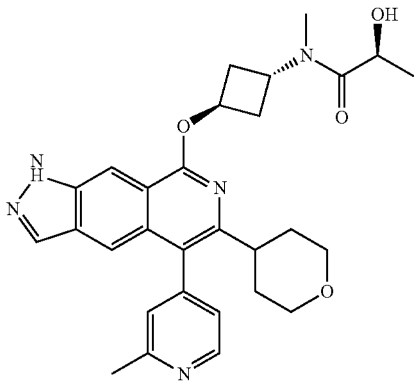 [SMILES: Cc1cc(-c2c(C3CCOCC3)nc(O[C@H]3C[C@H](N(C)C(=O)[C@H](C)O)C3)c3cc4[nH]ncc4cc23)ccn1]
Compound 32

TABLE I-continued
Compounds 1-262
Compound 33
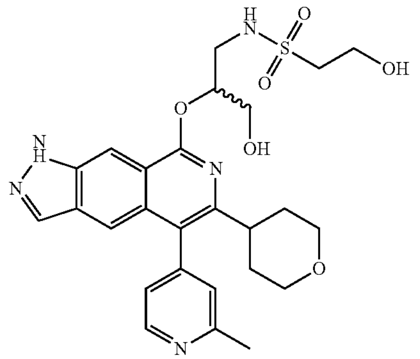 [SMILES: Cc1cc(-c2c(C3CCOCC3)nc(OC(CO)CNS(=O)(=O)CCO)c3cc4[nH]ncc4cc23)ccn1]
Compound 34
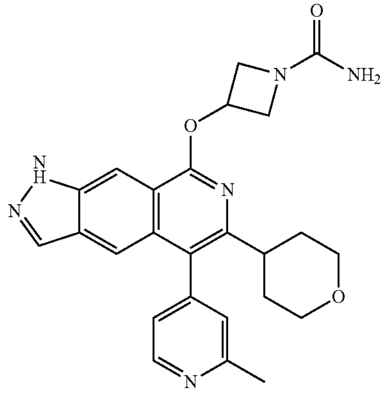 [SMILES: Cc1cc(-c2c(C3CCOCC3)nc(OC3CN(C(N)=O)C3)c3cc4[nH]ncc4cc23)ccn1]
Compound 35
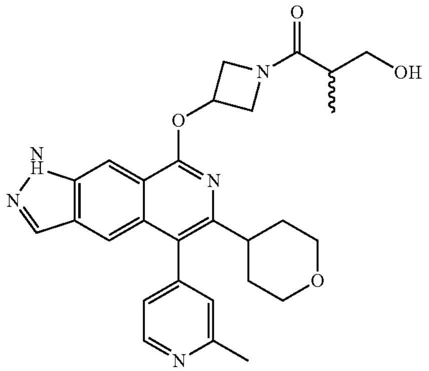 [SMILES: Cc1cc(-c2c(C3CCOCC3)nc(OC3CN(C(=O)C(C)CO)C3)c3cc4[nH]ncc4cc23)ccn1]
Compound 36
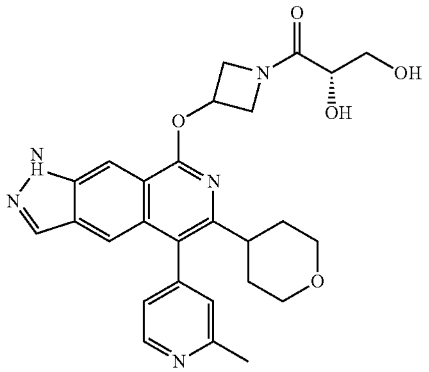 [SMILES: Cc1cc(-c2c(C3CCOCC3)nc(OC3CN(C(=O)[C@@H](O)CO)C3)c3cc4[nH]ncc4cc23)ccn1]
Compound 37
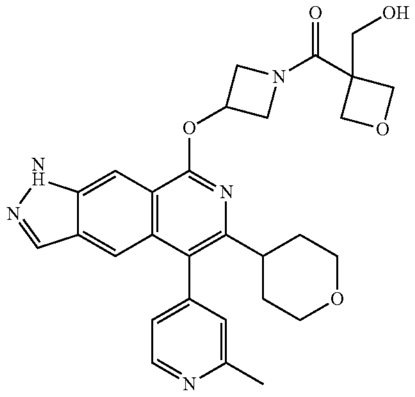 [SMILES: Cc1cc(-c2c(C3CCOCC3)nc(OC3CN(C(=O)C4(CO)COC4)C3)c3cc4[nH]ncc4cc23)ccn1]
Compound 38
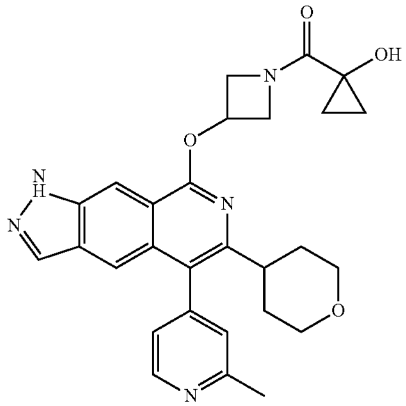 [SMILES: Cc1cc(-c2c(C3CCOCC3)nc(OC3CN(C(=O)C4(O)CC4)C3)c3cc4[nH]ncc4cc23)ccn1]
Compound 39
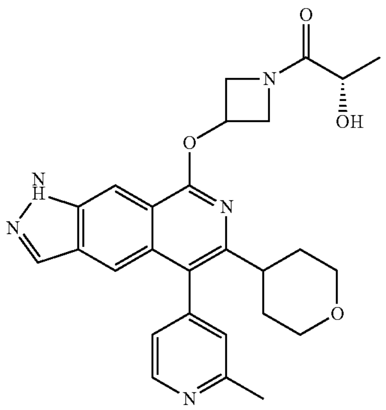 [SMILES: Cc1cc(-c2c(C3CCOCC3)nc(OC3CN(C(=O)[C@H](C)O)C3)c3cc4[nH]ncc4cc23)ccn1]

TABLE I-continued
Compounds 1-262
Compound 40
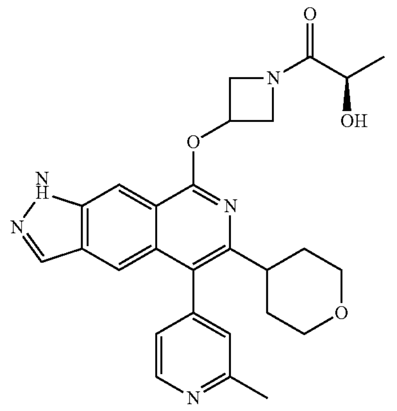 [SMILES: Cc1cc(-c2c(C3CCOCC3)nc(OC3CN(C(=O)[C@@H](C)O)C3)c3cc4[nH]ncc4cc23)ccn1]
Compound 41
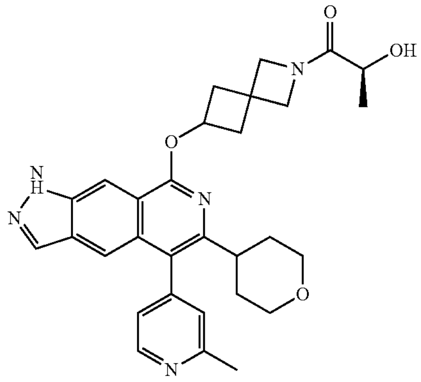 [SMILES: Cc1cc(-c2c(C3CCOCC3)nc(OC3CC4(C3)CN(C(=O)[C@H](C)O)C4)c3cc4[nH]ncc4cc23)ccn1]
Compound 42
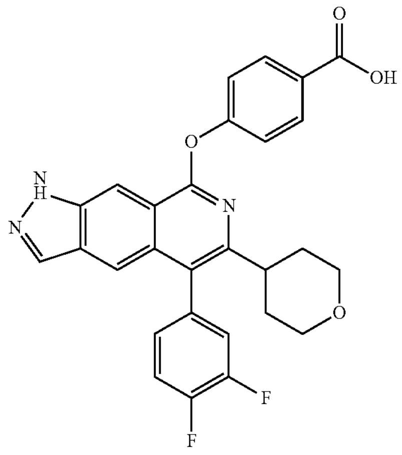 [SMILES: O=C(O)c1ccc(Oc2nc(C3CCOCC3)c(-c3ccc(F)c(F)c3)c3cc4cn[nH]c4cc23)cc1]
Compound 43
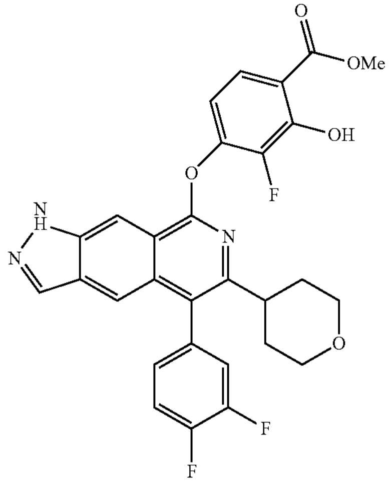 [SMILES: COC(=O)c1ccc(Oc2nc(C3CCOCC3)c(-c3ccc(F)c(F)c3)c3cc4cn[nH]c4cc23)c(F)c1O]
Compound 44
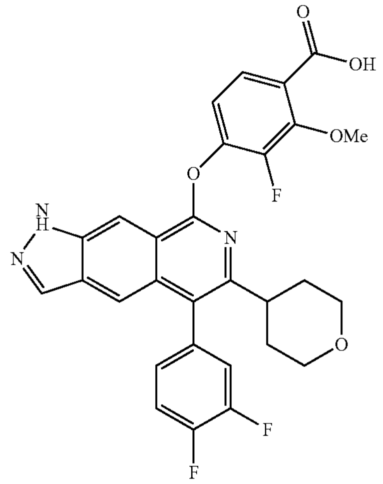 [SMILES: COc1c(C(=O)O)ccc(Oc2nc(C3CCOCC3)c(-c3ccc(F)c(F)c3)c3cc4cn[nH]c4cc23)c1F]
Compound 45
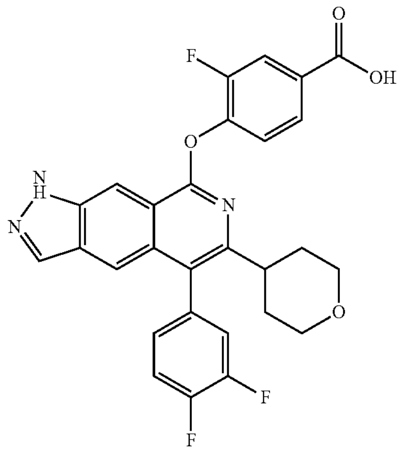 [SMILES: O=C(O)c1ccc(Oc2nc(C3CCOCC3)c(-c3ccc(F)c(F)c3)c3cc4cn[nH]c4cc23)c(F)c1]

TABLE I-continued
Compounds 1-262
Compound 46
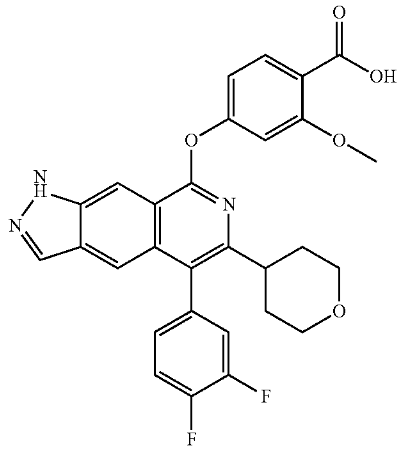 [SMILES: COc1cc(Oc2nc(C3CCOCC3)c(-c3ccc(F)c(F)c3)c3cc4cn[nH]c4cc23)ccc1C(=O)O]
Compound 47
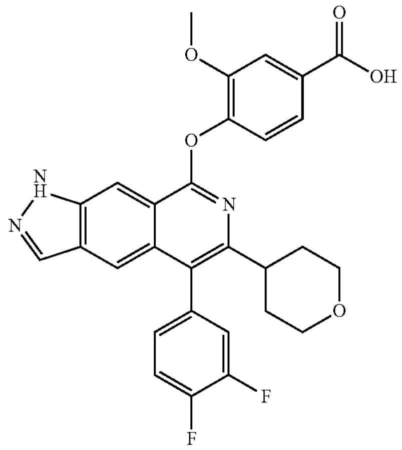 [SMILES: COc1cc(C(=O)O)ccc1Oc1nc(C2CCOCC2)c(-c2ccc(F)c(F)c2)c2cc3cn[nH]c3cc12]
Compound 48
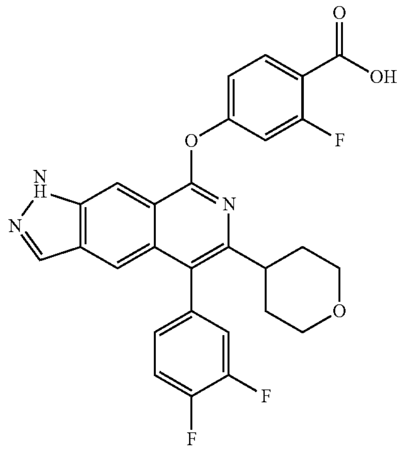 [SMILES: O=C(O)c1ccc(Oc2nc(C3CCOCC3)c(-c3ccc(F)c(F)c3)c3cc4cn[nH]c4cc23)cc1F]
TABLE I-continued
Compounds 1-262
Compound 49
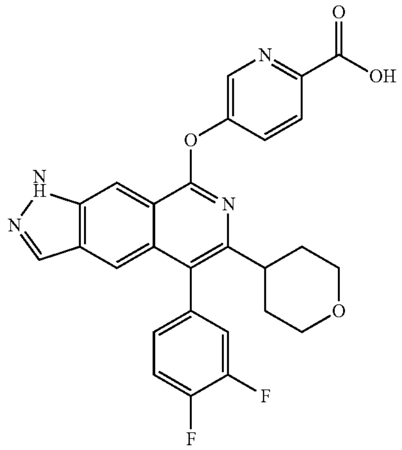 [SMILES: O=C(O)c1ccc(Oc2nc(C3CCOCC3)c(-c3ccc(F)c(F)c3)c3cc4cn[nH]c4cc23)cn1]
Compound 50
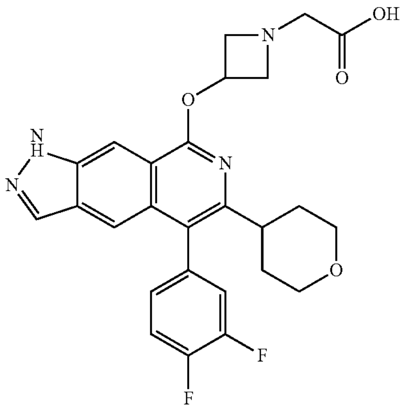 [SMILES: O=C(O)CN1CC(Oc2nc(C3CCOCC3)c(-c3ccc(F)c(F)c3)c3cc4cn[nH]c4cc23)C1]
Compound 51
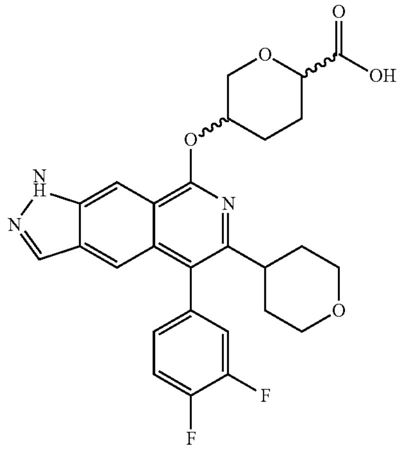 [SMILES: O=C(O)C1CCC(Oc2nc(C3CCOCC3)c(-c3ccc(F)c(F)c3)c3cc4cn[nH]c4cc23)CO1]

TABLE I-continued
Compounds 1-262
Compound 52
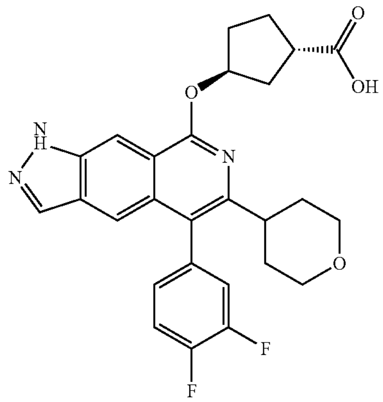 [SMILES: O=C(O)[C@H]1CC[C@H](Oc2nc(C3CCOCC3)c(-c3ccc(F)c(F)c3)c3cc4cn[nH]c4cc23)C1]
Compound 53
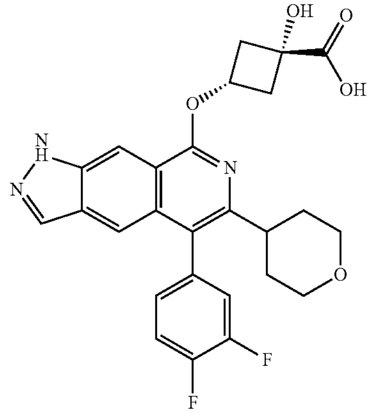 [SMILES: O=C(O)[C@]1(O)C[C@@H](Oc2nc(C3CCOCC3)c(-c3ccc(F)c(F)c3)c3cc4cn[nH]c4cc23)C1]
Compound 54
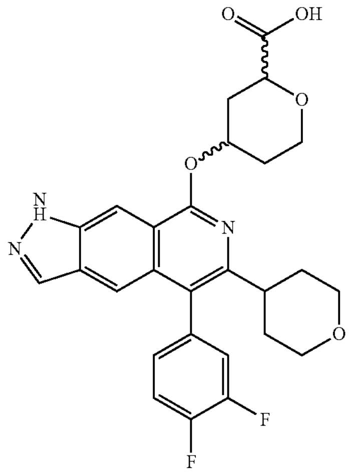 [SMILES: O=C(O)C1CC(Oc2nc(C3CCOCC3)c(-c3ccc(F)c(F)c3)c3cc4cn[nH]c4cc23)CCO1]
TABLE I-continued
Compounds 1-262
Compound 55
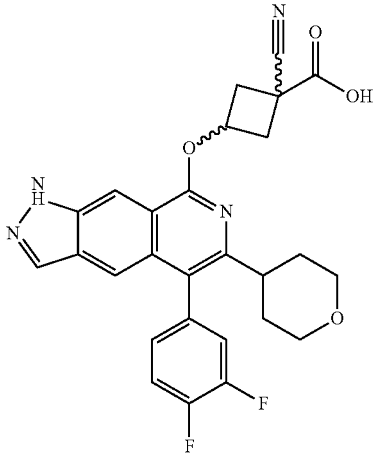 [SMILES: N#CC1(C(=O)O)CC(Oc2nc(C3CCOCC3)c(-c3ccc(F)c(F)c3)c3cc4cn[nH]c4cc23)C1]
Compound 56
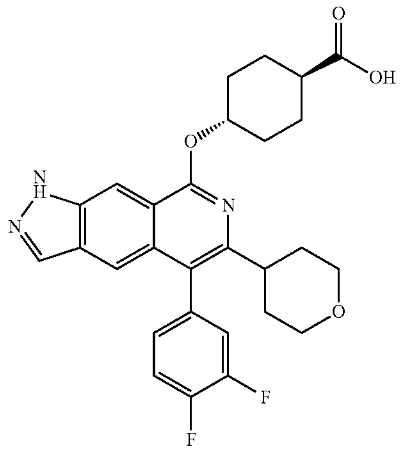 [SMILES: O=C(O)[C@H]1CC[C@H](Oc2nc(C3CCOCC3)c(-c3ccc(F)c(F)c3)c3cc4cn[nH]c4cc23)CC1]
Compound 57
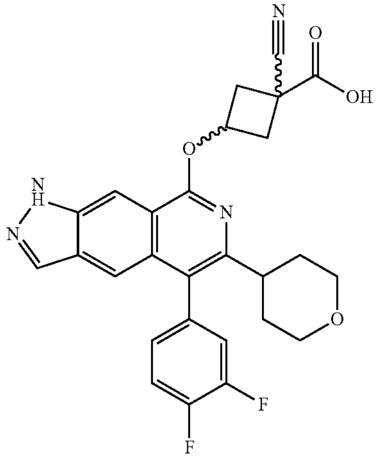 [SMILES: N#CC1(C(=O)O)CC(Oc2nc(C3CCOCC3)c(-c3ccc(F)c(F)c3)c3cc4cn[nH]c4cc23)C1]

TABLE I-continued
Compounds 1-262
Compound 58
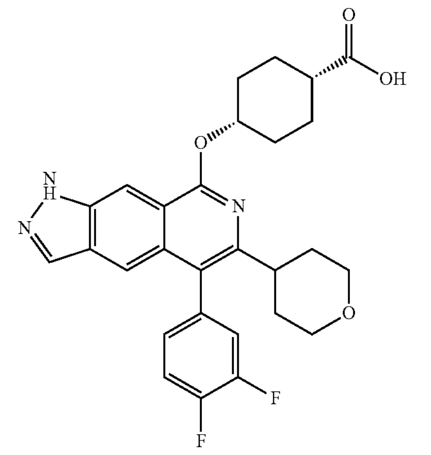 [SMILES: O=C(O)[C@H]1CC[C@@H](Oc2nc(C3CCOCC3)c(-c3ccc(F)c(F)c3)c3cc4cn[nH]c4cc23)CC1]
Compound 59
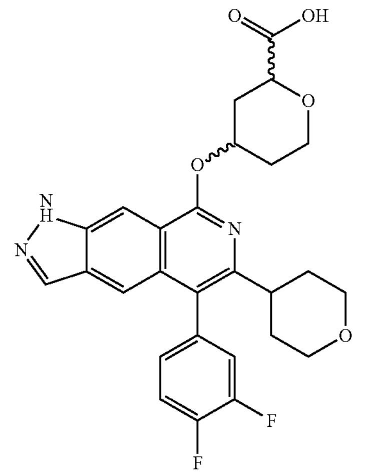 [SMILES: O=C(O)C1CC(Oc2nc(C3CCOCC3)c(-c3ccc(F)c(F)c3)c3cc4cn[nH]c4cc23)CCO1]
Compound 60
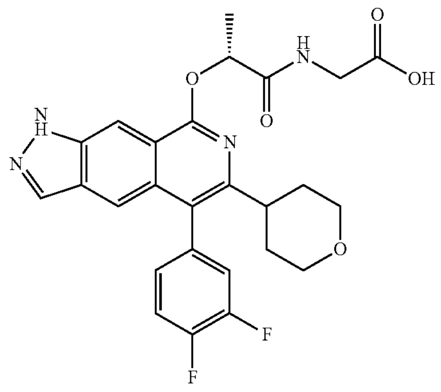 [SMILES: C[C@@H](Oc1nc(C2CCOCC2)c(-c2ccc(F)c(F)c2)c2cc3cn[nH]c3cc12)C(=O)NCC(=O)O]
Compound 61
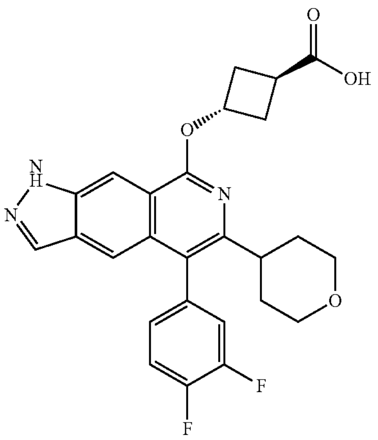 [SMILES: O=C(O)[C@H]1C[C@H](Oc2nc(C3CCOCC3)c(-c3ccc(F)c(F)c3)c3cc4cn[nH]c4cc23)C1]
Compound 62
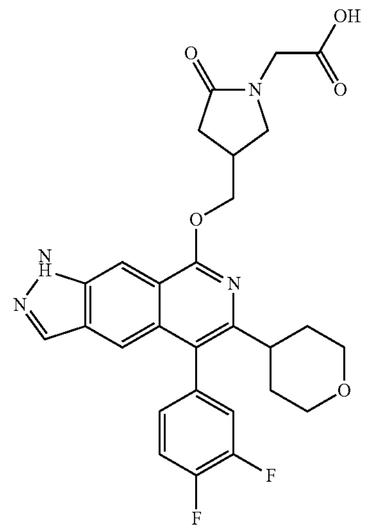 [SMILES: O=C(O)CN1CC(COc2nc(C3CCOCC3)c(-c3ccc(F)c(F)c3)c3cc4cn[nH]c4cc23)CC1=O]
Compound 63
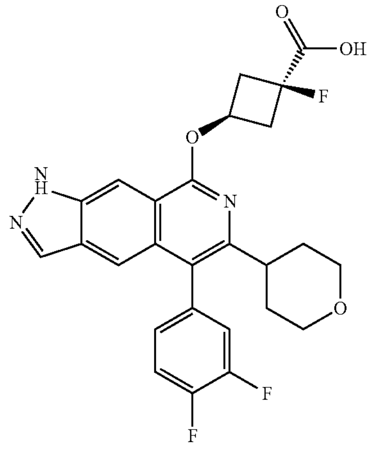 [SMILES: O=C(O)[C@]1(F)C[C@@H](Oc2nc(C3CCOCC3)c(-c3ccc(F)c(F)c3)c3cc4cn[nH]c4cc23)C1]

TABLE I-continued
| Compounds 1-262 |
|---|
Compound 64
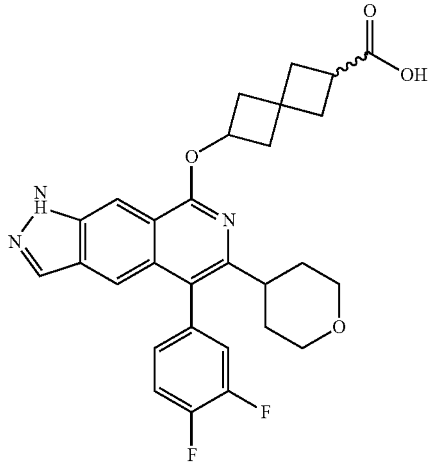 [SMILES: O=C(O)C1CC2(CC(Oc3nc(C4CCOCC4)c(-c4ccc(F)c(F)c4)c4cc5cn[nH]c5cc34)C2)C1]
Compound 65
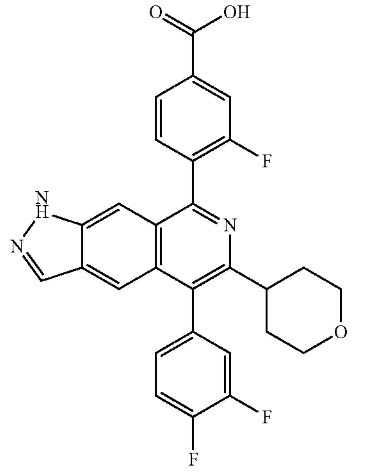 [SMILES: O=C(O)c1ccc(-c2nc(C3CCOCC3)c(-c3ccc(F)c(F)c3)c3cc4cn[nH]c4cc23)c(F)c1]
Compound 66
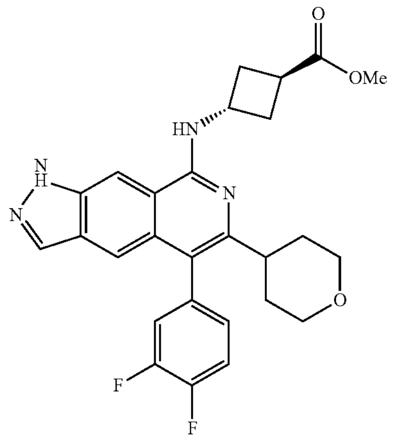 [SMILES: COC(=O)[C@H]1C[C@H](Nc2nc(C3CCOCC3)c(-c3ccc(F)c(F)c3)c3cc4cn[nH]c4cc23)C1]
TABLE I-continued
| Compounds 1-262 |
|---|
Compound 67
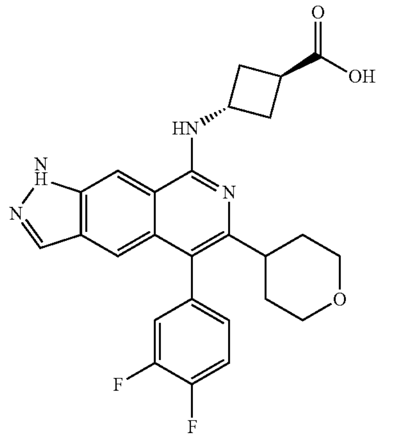 [SMILES: O=C(O)[C@H]1C[C@H](Nc2nc(C3CCOCC3)c(-c3ccc(F)c(F)c3)c3cc4cn[nH]c4cc23)C1]
Compound 68
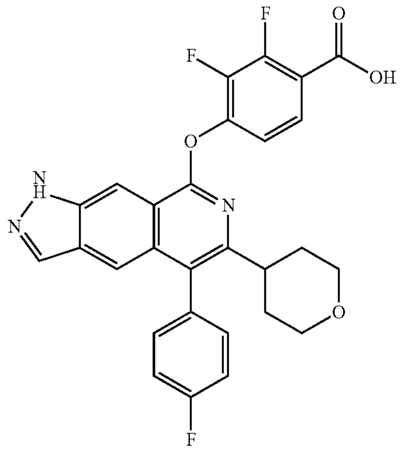 [SMILES: O=C(O)c1ccc(Oc2nc(C3CCOCC3)c(-c3ccc(F)cc3)c3cc4cn[nH]c4cc23)c(F)c1F]
Compound 69
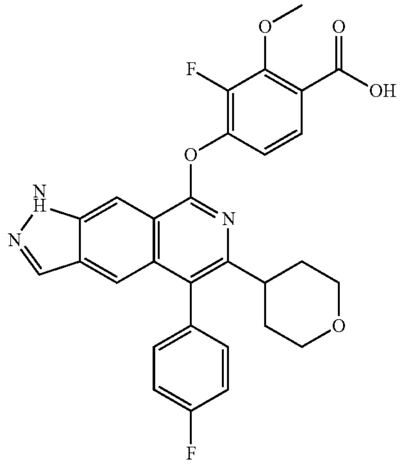 [SMILES: COc1c(C(=O)O)ccc(Oc2nc(C3CCOCC3)c(-c3ccc(F)cc3)c3cc4cn[nH]c4cc23)c1F]

TABLE I-continued
| Compounds 1-262 |
| --- |
| Compound 70 |
| 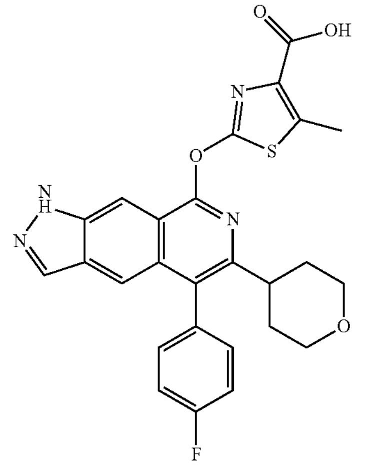 [SMILES: Cc1sc(Oc2nc(C3CCOCC3)c(-c3ccc(F)cc3)c3cc4cn[nH]c4cc23)nc1C(=O)O] |
| Compound 71 |
| 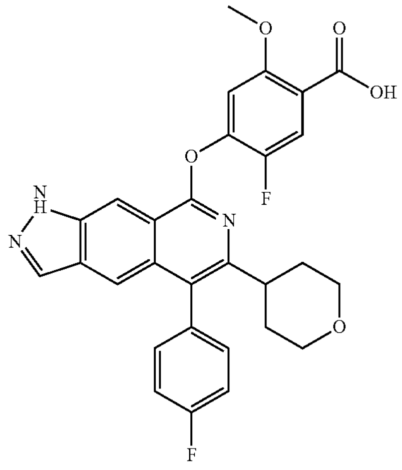 [SMILES: COc1cc(Oc2nc(C3CCOCC3)c(-c3ccc(F)cc3)c3cc4cn[nH]c4cc23)c(F)cc1C(=O)O] |
| Compound 72 |
| 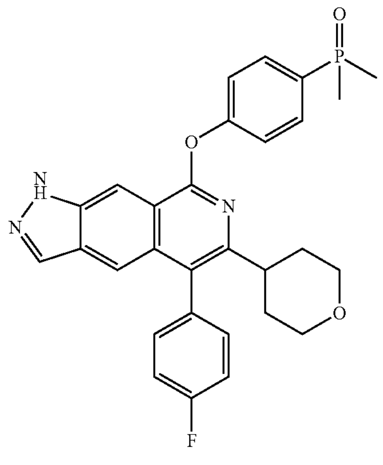 [SMILES: CP(C)(=O)c1ccc(Oc2nc(C3CCOCC3)c(-c3ccc(F)cc3)c3cc4cn[nH]c4cc23)cc1] |
TABLE I-continued
| Compounds 1-262 |
| --- |
| Compound 73 |
| 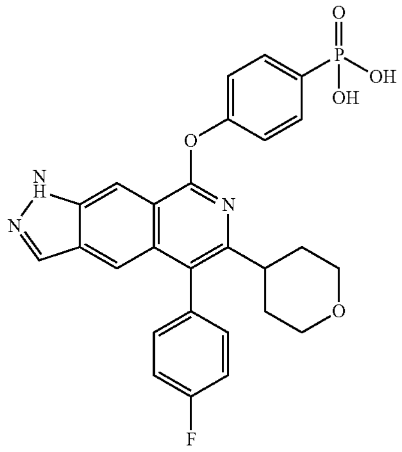 [SMILES: O=P(O)(O)c1ccc(Oc2nc(C3CCOCC3)c(-c3ccc(F)cc3)c3cc4cn[nH]c4cc23)cc1] |
| Compound 74 |
| 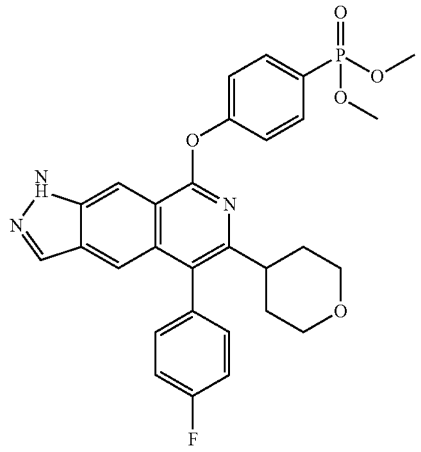 [SMILES: COP(=O)(OC)c1ccc(Oc2nc(C3CCOCC3)c(-c3ccc(F)cc3)c3cc4cn[nH]c4cc23)cc1] |
| Compound 75 |
| 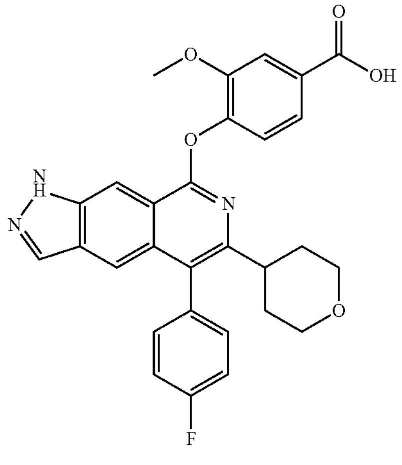 [SMILES: COc1cc(C(=O)O)ccc1Oc1nc(C2CCOCC2)c(-c2ccc(F)cc2)c2cc3cn[nH]c3cc12] |

TABLE I-continued
Compounds 1-262
Compound 76
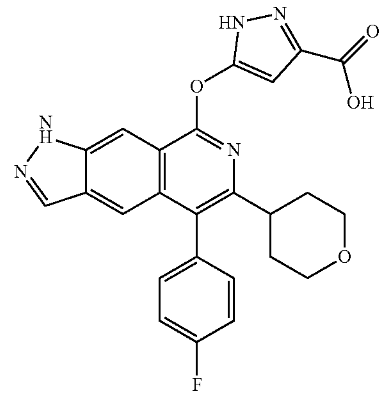 [SMILES: O=C(O)c1cc(Oc2nc(C3CCOCC3)c(-c3ccc(F)cc3)c3cc4cn[nH]c4cc23)[nH]n1]
Compound 77
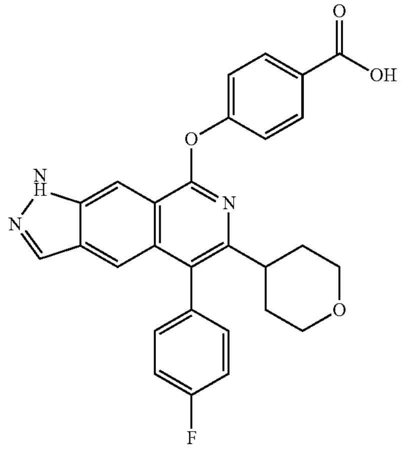 [SMILES: O=C(O)c1ccc(Oc2nc(C3CCOCC3)c(-c3ccc(F)cc3)c3cc4cn[nH]c4cc23)cc1]
Compound 78
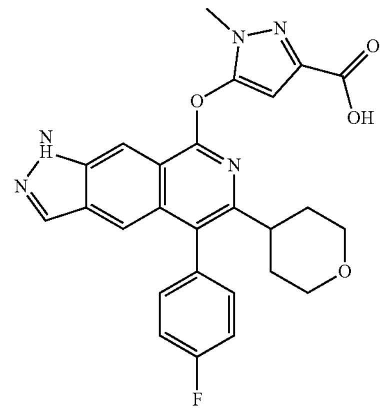 [SMILES: Cn1nc(C(=O)O)cc1Oc1nc(C2CCOCC2)c(-c2ccc(F)cc2)c2cc3cn[nH]c3cc12]
Compound 79
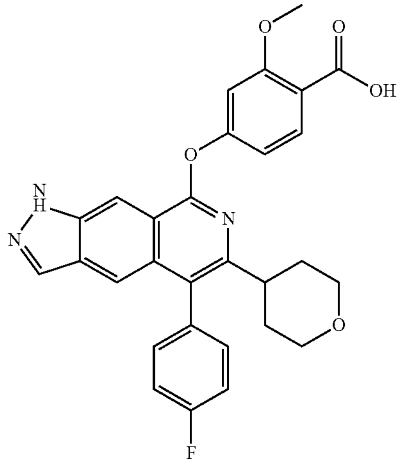 [SMILES: COc1cc(Oc2nc(C3CCOCC3)c(-c3ccc(F)cc3)c3cc4cn[nH]c4cc23)ccc1C(=O)O]
Compound 80
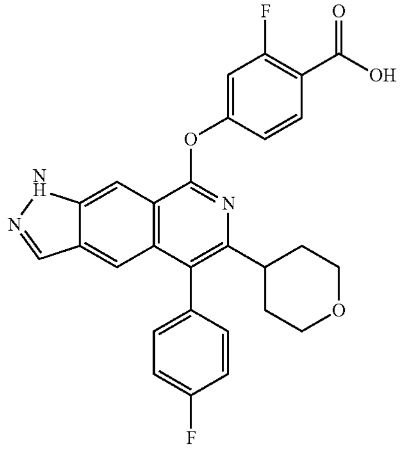 [SMILES: O=C(O)c1ccc(Oc2nc(C3CCOCC3)c(-c3ccc(F)cc3)c3cc4cn[nH]c4cc23)cc1F]
Compound 81
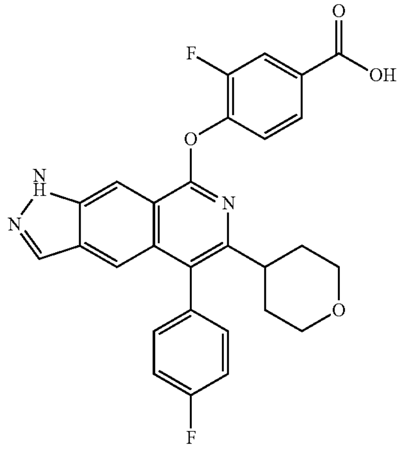 [SMILES: O=C(O)c1ccc(Oc2nc(C3CCOCC3)c(-c3ccc(F)cc3)c3cc4cn[nH]c4cc23)c(F)c1]

TABLE I-continued
Compounds 1-262
Compound 82
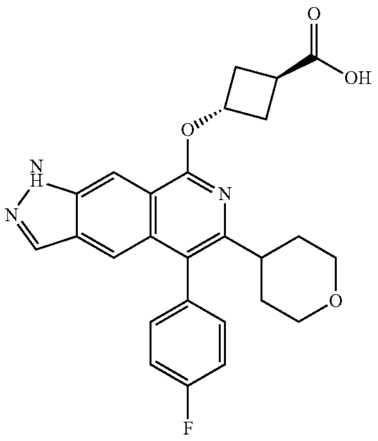 [SMILES: O=C(O)[C@H]1C[C@H](Oc2nc(C3CCOCC3)c(-c3ccc(F)cc3)c3cc4cn[nH]c4cc23)C1]
Compound 83
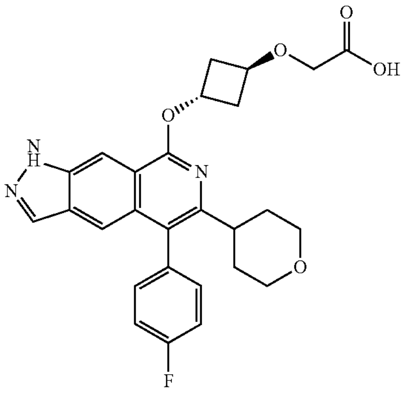 [SMILES: O=C(O)CO[C@H]1C[C@H](Oc2nc(C3CCOCC3)c(-c3ccc(F)cc3)c3cc4cn[nH]c4cc23)C1]
Compound 84
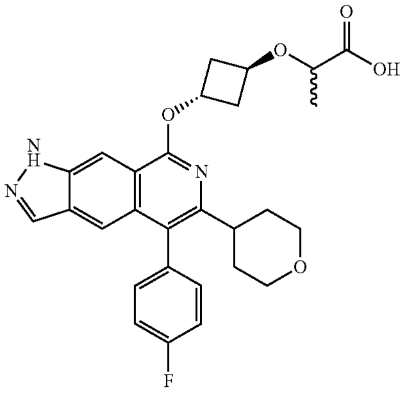 [SMILES: CC(O[C@H]1C[C@H](Oc2nc(C3CCOCC3)c(-c3ccc(F)cc3)c3cc4cn[nH]c4cc23)C1)C(=O)O]
Compound 85
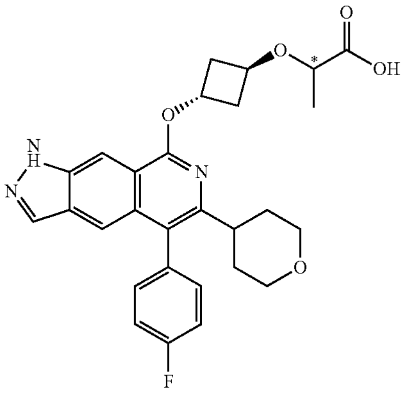 [SMILES: CC(O[C@H]1C[C@H](Oc2nc(C3CCOCC3)c(-c3ccc(F)cc3)c3cc4cn[nH]c4cc23)C1)C(=O)O]
Compound 86
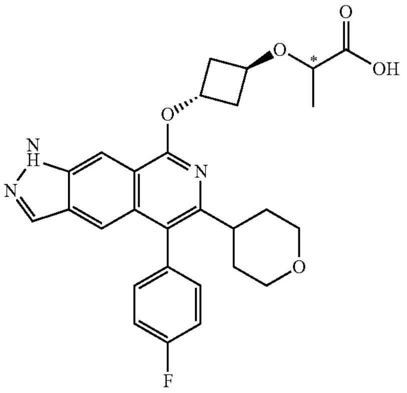 [SMILES: CC(O[C@H]1C[C@H](Oc2nc(C3CCOCC3)c(-c3ccc(F)cc3)c3cc4cn[nH]c4cc23)C1)C(=O)O]
Compound 87
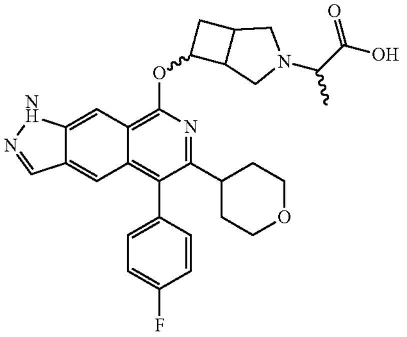 [SMILES: CC(C(=O)O)N1CC2CC(Oc3nc(C4CCOCC4)c(-c4ccc(F)cc4)c4cc5cn[nH]c5cc34)C2C1]
Compound 88
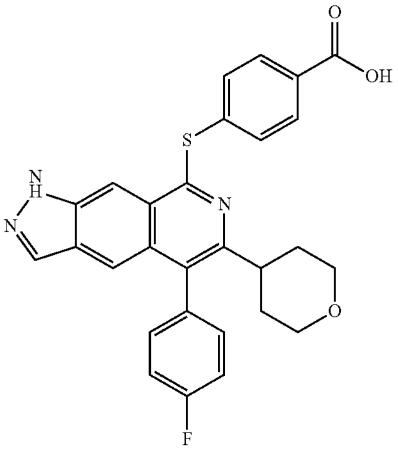

TABLE I-continued
| Compounds 1-262 |
| --- |
Compound 89
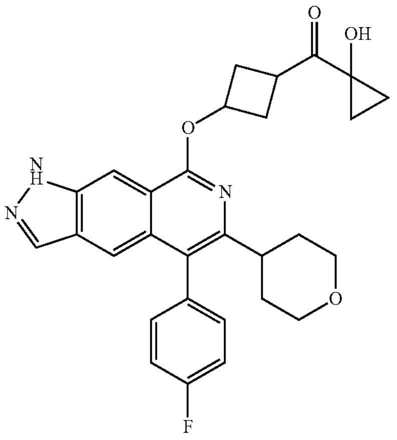
Compound 90
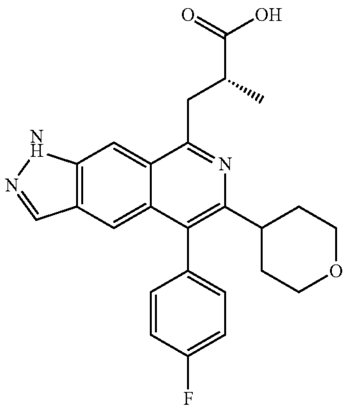 [SMILES: C[C@H](Cc1nc(C2CCOCC2)c(-c2ccc(F)cc2)c2cc3cn[nH]c3cc12)C(=O)O]
Compound 91
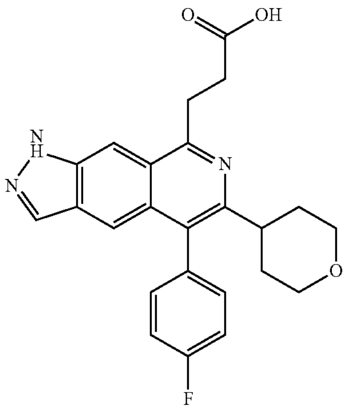 [SMILES: O=C(O)CCc1nc(C2CCOCC2)c(-c2ccc(F)cc2)c2cc3cn[nH]c3cc12]
TABLE I-continued
| Compounds 1-262 |
| --- |
Compound 92
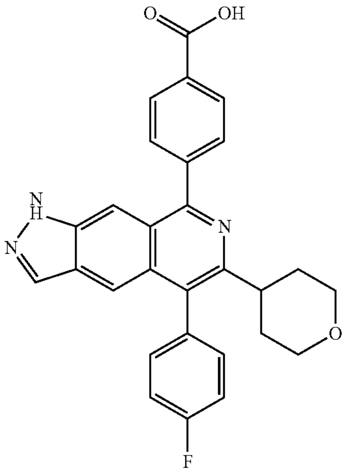 [SMILES: O=C(O)c1ccc(-c2nc(C3CCOCC3)c(-c3ccc(F)cc3)c3cc4cn[nH]c4cc23)cc1]
Compound 93
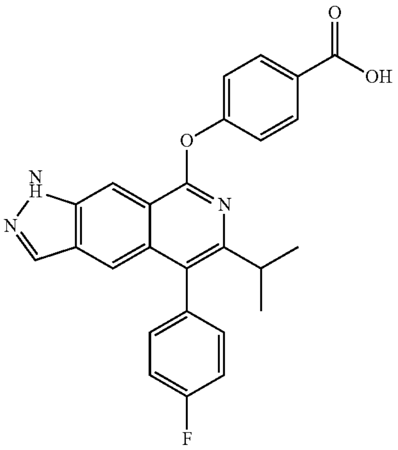 [SMILES: CC(C)c1nc(Oc2ccc(C(=O)O)cc2)c2cc3[nH]ncc3cc2c1-c1ccc(F)cc1]
Compound 94
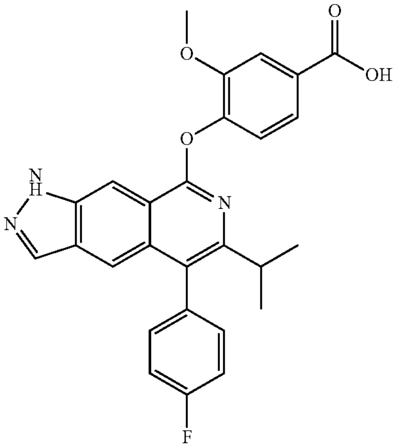 [SMILES: COc1cc(C(=O)O)ccc1Oc1nc(C(C)C)c(-c2ccc(F)cc2)c2cc3cn[nH]c3cc12]

TABLE I-continued
| Compounds 1-262 |
|---|
Compound 95
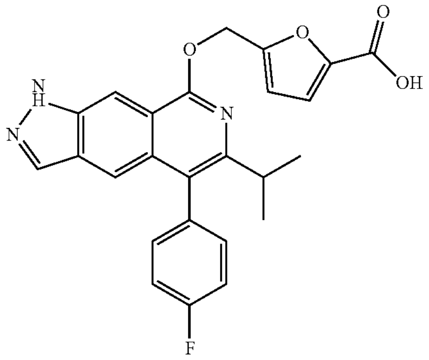 [SMILES: CC(C)c1nc(OCc2ccc(C(=O)O)o2)c2cc3[nH]ncc3cc2c1-c1ccc(F)cc1]
Compound 96
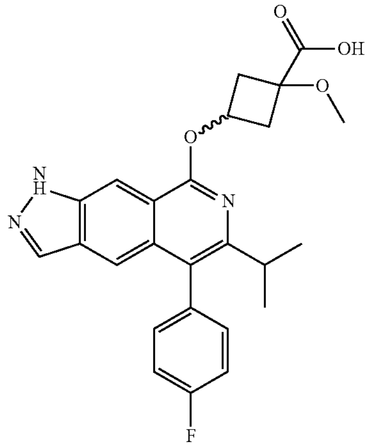 [SMILES: COC1(C(=O)O)CC(Oc2nc(C(C)C)c(-c3ccc(F)cc3)c3cc4cn[nH]c4cc23)C1]
Compound 97
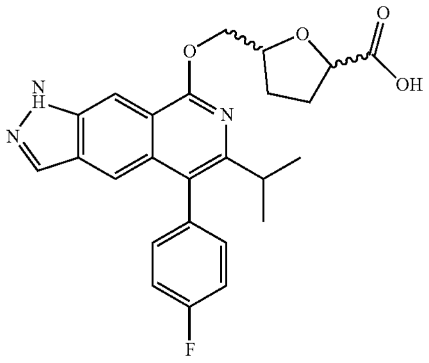 [SMILES: CC(C)c1nc(OCC2CCC(C(=O)O)O2)c2cc3[nH]ncc3cc2c1-c1ccc(F)cc1]
Compound 98
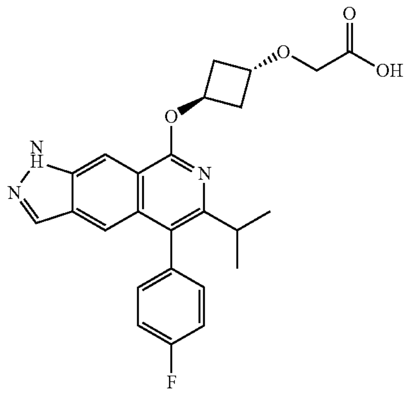 [SMILES: CC(C)c1nc(O[C@H]2C[C@H](OCC(=O)O)C2)c2cc3[nH]ncc3cc2c1-c1ccc(F)cc1]
TABLE I-continued
| Compounds 1-262 |
|---|
Compound 99
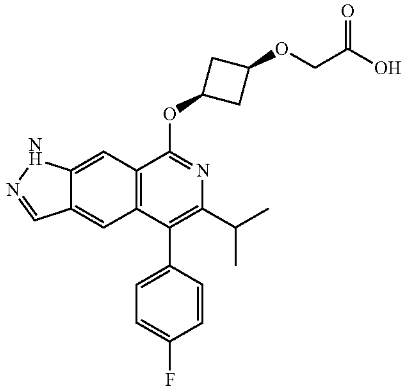 [SMILES: CC(C)c1nc(O[C@H]2C[C@@H](OCC(=O)O)C2)c2cc3[nH]ncc3cc2c1-c1ccc(F)cc1]
Compound 100
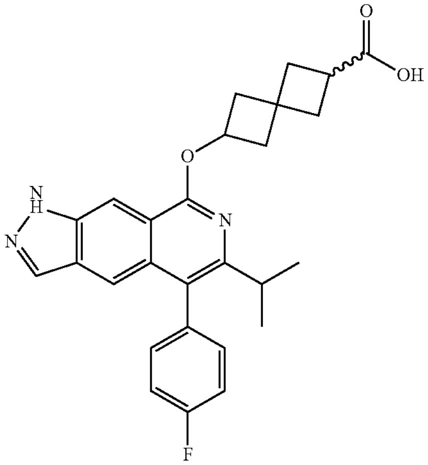 [SMILES: CC(C)c1nc(OC2CC3(C2)CC(C(=O)O)C3)c2cc3[nH]ncc3cc2c1-c1ccc(F)cc1]
Compound 101
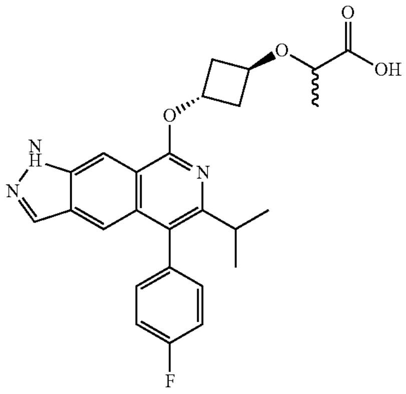 [SMILES: CC(O[C@H]1C[C@H](Oc2nc(C(C)C)c(-c3ccc(F)cc3)c3cc4cn[nH]c4cc23)C1)C(=O)O]

TABLE I-continued
| Compounds 1-262 |
| --- |
| Compound 102 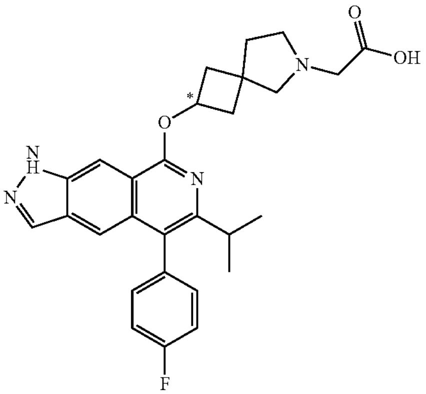 [SMILES: CC(C)c1nc(OC2CC3(CCN(CC(=O)O)C3)C2)c2cc3[nH]ncc3cc2c1-c1ccc(F)cc1] |
| Compound 103 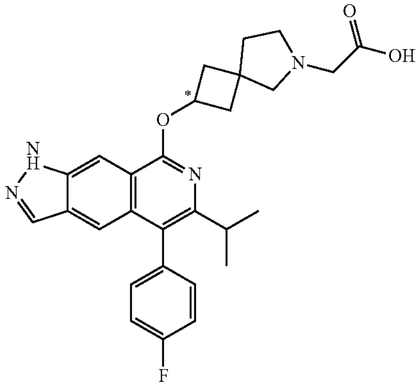 [SMILES: CC(C)c1nc(OC2CC3(CCN(CC(=O)O)C3)C2)c2cc3[nH]ncc3cc2c1-c1ccc(F)cc1] |
| Compound 104 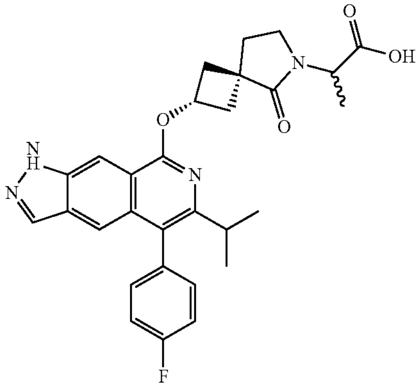 [SMILES: CC(C)c1nc(O[C@H]2C[C@@]3(CCN(C(C)C(=O)O)C3=O)C2)c2cc3[nH]ncc3cc2c1-c1ccc(F)cc1] |
TABLE I-continued
| Compounds 1-262 |
| --- |
| Compound 105 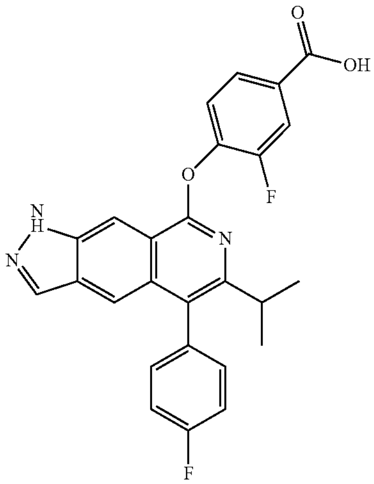 [SMILES: CC(C)c1nc(Oc2ccc(C(=O)O)cc2F)c2cc3[nH]ncc3cc2c1-c1ccc(F)cc1] |
| Compound 106 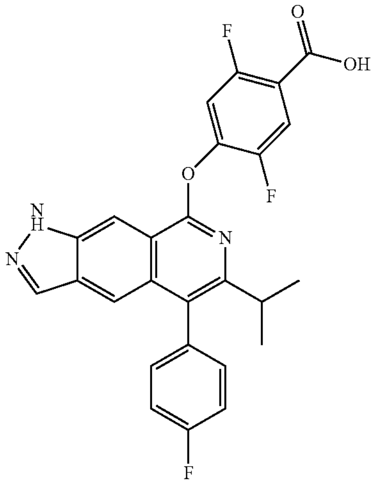 [SMILES: CC(C)c1nc(Oc2cc(F)c(C(=O)O)cc2F)c2cc3[nH]ncc3cc2c1-c1ccc(F)cc1] |
| Compound 107 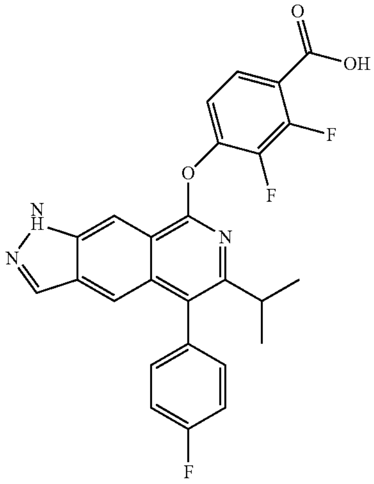 [SMILES: CC(C)c1nc(Oc2ccc(C(=O)O)c(F)c2F)c2cc3[nH]ncc3cc2c1-c1ccc(F)cc1] |

TABLE I-continued
Compounds 1-262
Compound 108
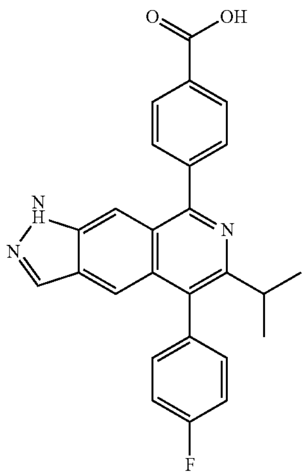 [SMILES: CC(C)c1nc(-c2ccc(C(=O)O)cc2)c2cc3[nH]ncc3cc2c1-c1ccc(F)cc1]
Compound 109
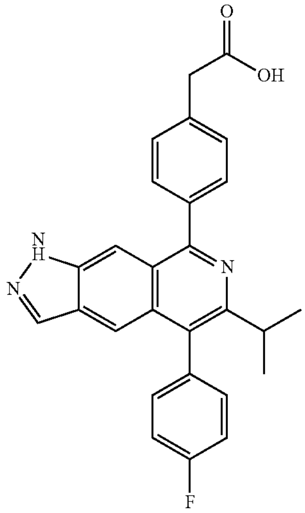 [SMILES: CC(C)c1nc(-c2ccc(CC(=O)O)cc2)c2cc3[nH]ncc3cc2c1-c1ccc(F)cc1]
Compound 110
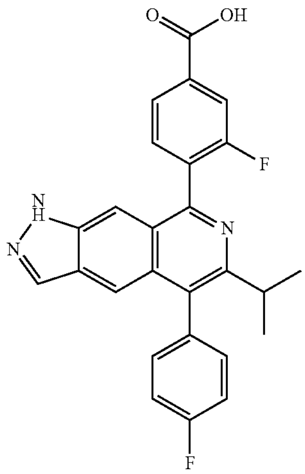 [SMILES: CC(C)c1nc(-c2ccc(C(=O)O)cc2F)c2cc3[nH]ncc3cc2c1-c1ccc(F)cc1]
TABLE I-continued
Compounds 1-262
Compound 111
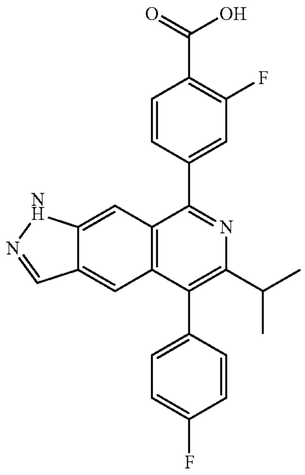 [SMILES: CC(C)c1nc(-c2ccc(C(=O)O)c(F)c2)c2cc3[nH]ncc3cc2c1-c1ccc(F)cc1]
Compound 112
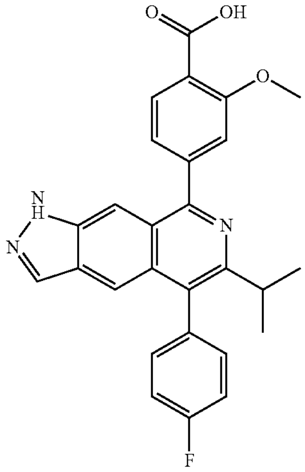
Compound 113
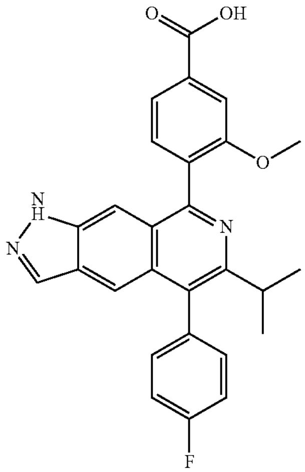

TABLE I-continued
Compounds 1-262
Compound 114
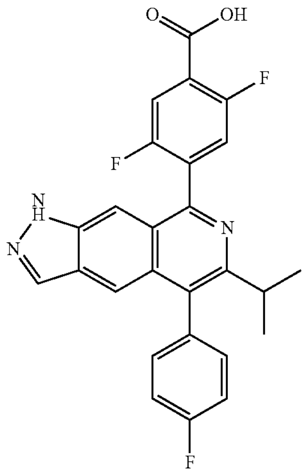
Compound 115
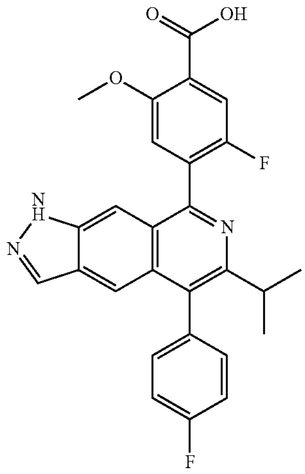 [SMILES: COc1cc(-c2nc(C(C)C)c(-c3ccc(F)cc3)c3cc4cn[nH]c4cc23)c(F)cc1C(=O)O]
Compound 116
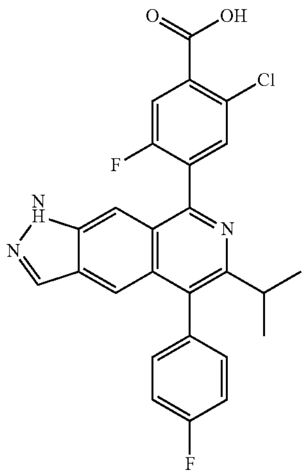
TABLE I-continued
Compounds 1-262
Compound 117
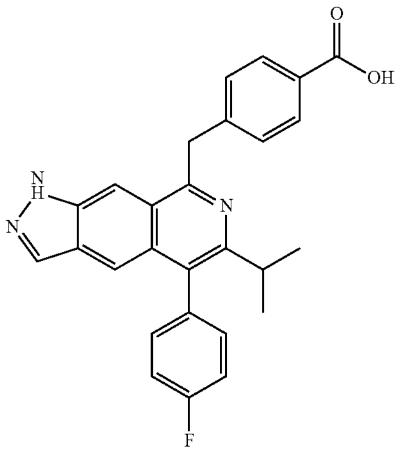 [SMILES: CC(C)c1nc(Cc2ccc(C(=O)O)cc2)c2cc3[nH]ncc3cc2c1-c1ccc(F)cc1]
Compound 118
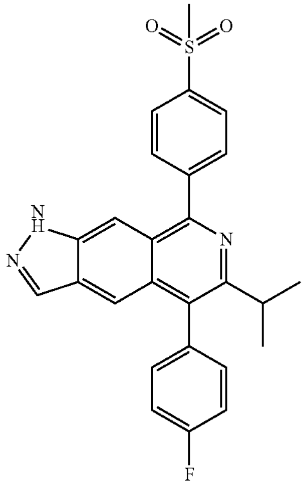 [SMILES: CC(C)c1nc(-c2ccc(S(C)(=O)=O)cc2)c2cc3[nH]ncc3cc2c1-c1ccc(F)cc1]
Compound 119
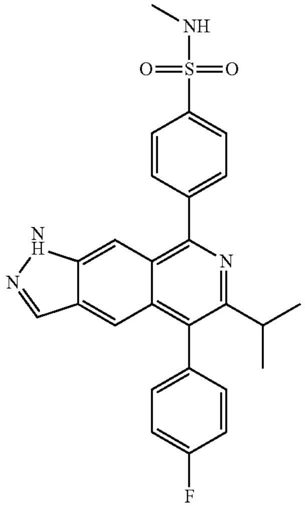 [SMILES: CNS(=O)(=O)c1ccc(-c2nc(C(C)C)c(-c3ccc(F)cc3)c3cc4cn[nH]c4cc23)cc1]

TABLE I-continued
Compounds 1-262
Compound 120
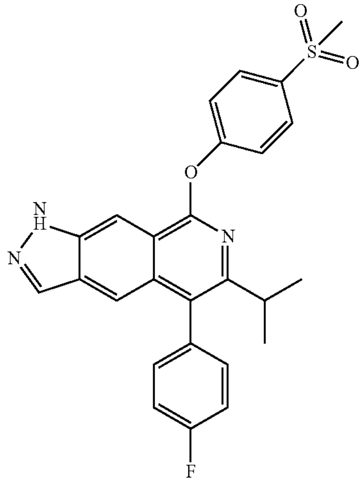 [SMILES: CC(C)c1nc(Oc2ccc(S(C)(=O)=O)cc2)c2cc3[nH]ncc3cc2c1-c1ccc(F)cc1]
Compound 121
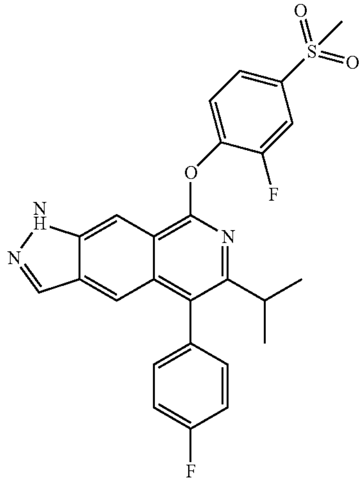 [SMILES: CC(C)c1nc(Oc2ccc(S(C)(=O)=O)cc2F)c2cc3[nH]ncc3cc2c1-c1ccc(F)cc1]
Compound 122
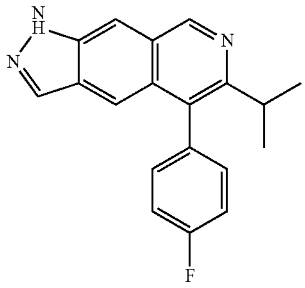 [SMILES: CC(C)c1ncc2cc3[nH]ncc3cc2c1-c1ccc(F)cc1]
TABLE I-continued
Compounds 1-262
Compound 123
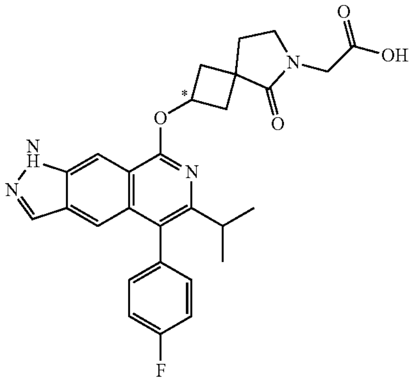 [SMILES: CC(C)c1nc(OC2CC3(CCN(CC(=O)O)C3=O)C2)c2cc3[nH]ncc3cc2c1-c1ccc(F)cc1]
Compound 124
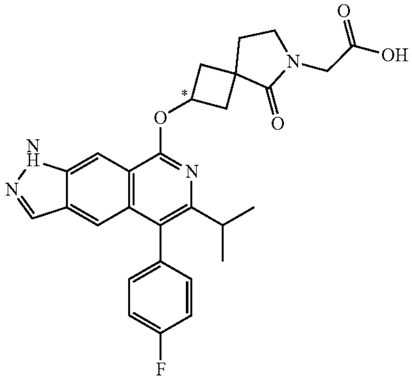 [SMILES: CC(C)c1nc(OC2CC3(CCN(CC(=O)O)C3=O)C2)c2cc3[nH]ncc3cc2c1-c1ccc(F)cc1]
Compound 125
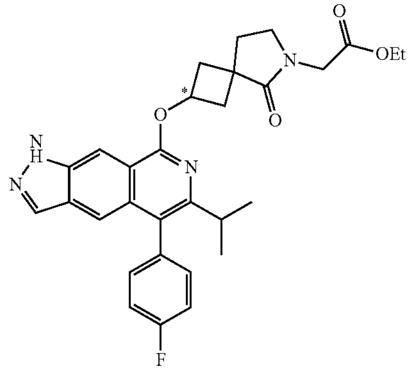 [SMILES: CCOC(=O)CN1CCC2(CC(Oc3nc(C(C)C)c(-c4ccc(F)cc4)c4cc5cn[nH]c5cc34)C2)C1=O]
Compound 126
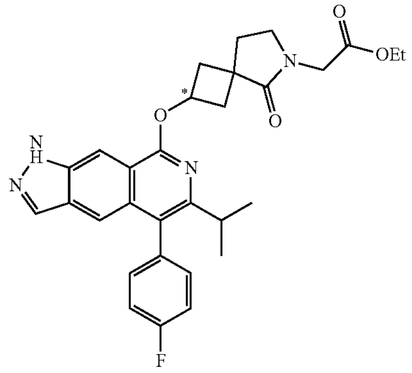 [SMILES: CCOC(=O)CN1CCC2(CC(Oc3nc(C(C)C)c(-c4ccc(F)cc4)c4cc5cn[nH]c5cc34)C2)C1=O]

TABLE I-continued
Compounds 1-262
Compound 127
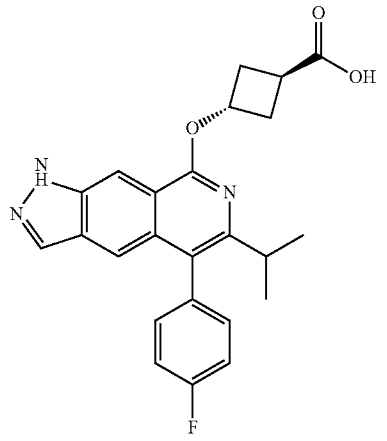 [SMILES: CC(C)c1nc(O[C@H]2C[C@H](C(=O)O)C2)c2cc3[nH]ncc3cc2c1-c1ccc(F)cc1]
Compound 128
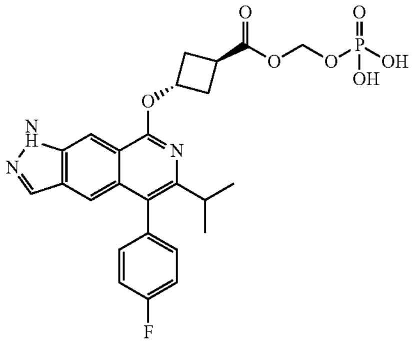 [SMILES: CC(C)c1nc(O[C@H]2C[C@H](C(=O)OCOP(=O)(O)O)C2)c2cc3[nH]ncc3cc2c1-c1ccc(F)cc1]
Compound 129
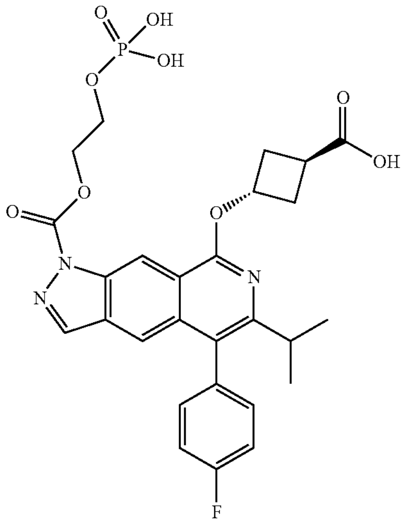 [SMILES: CC(C)c1nc(O[C@H]2C[C@H](C(=O)O)C2)c2cc3c(cnn3C(=O)OCCOP(=O)(O)O)cc2c1-c1ccc(F)cc1]
Compound 130
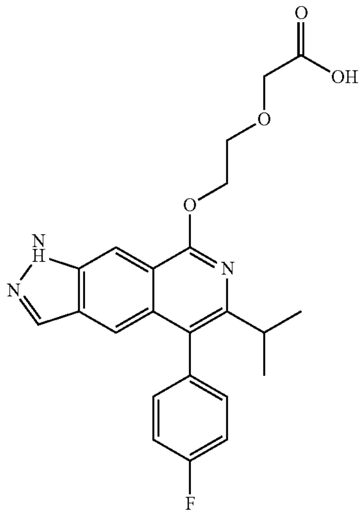 [SMILES: CC(C)c1nc(OCCOCC(=O)O)c2cc3[nH]ncc3cc2c1-c1ccc(F)cc1]
Compound 131
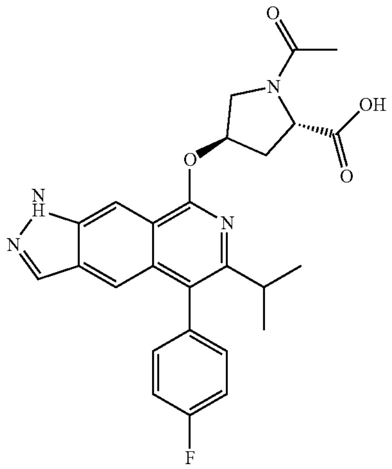 [SMILES: CC(=O)N1C[C@H](Oc2nc(C(C)C)c(-c3ccc(F)cc3)c3cc4cn[nH]c4cc23)C[C@H]1C(=O)O]
Compound 132
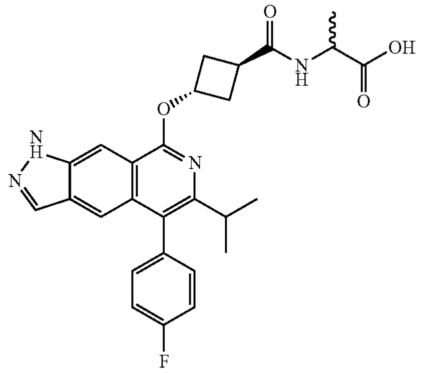 [SMILES: CC(NC(=O)[C@H]1C[C@H](Oc2nc(C(C)C)c(-c3ccc(F)cc3)c3cc4cn[nH]c4cc23)C1)C(=O)O]

TABLE I-continued
Compounds 1-262
Compound 133
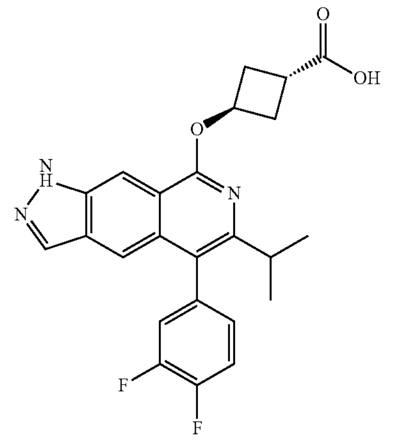 [SMILES: CC(C)c1nc(O[C@H]2C[C@H](C(=O)O)C2)c2cc3[nH]ncc3cc2c1-c1ccc(F)c(F)c1]
Compound 134
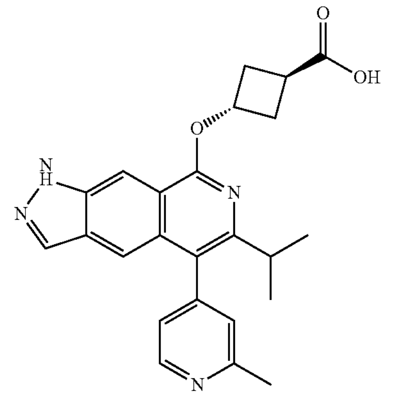 [SMILES: Cc1cc(-c2c(C(C)C)nc(O[C@H]3C[C@H](C(=O)O)C3)c3cc4[nH]ncc4cc23)ccn1]
Compound 135
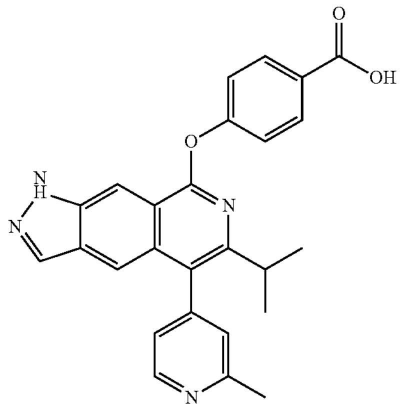 [SMILES: Cc1cc(-c2c(C(C)C)nc(Oc3ccc(C(=O)O)cc3)c3cc4[nH]ncc4cc23)ccn1]
TABLE I-continued
Compounds 1-262
Compound 136
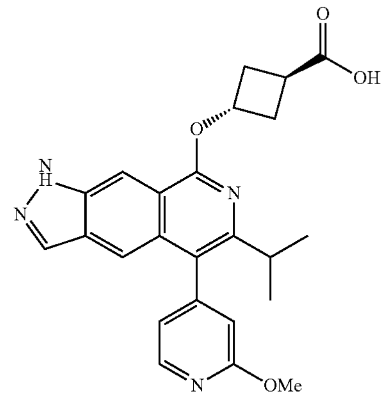 [SMILES: COc1cc(-c2c(C(C)C)nc(O[C@H]3C[C@H](C(=O)O)C3)c3cc4[nH]ncc4cc23)ccn1]
Compound 137
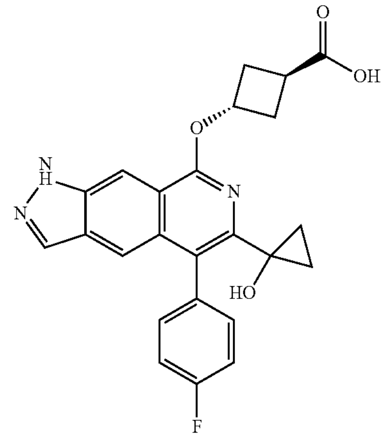 [SMILES: O=C(O)[C@H]1C[C@H](Oc2nc(C3(O)CC3)c(-c3ccc(F)cc3)c3cc4cn[nH]c4cc23)C1]
Compound 138
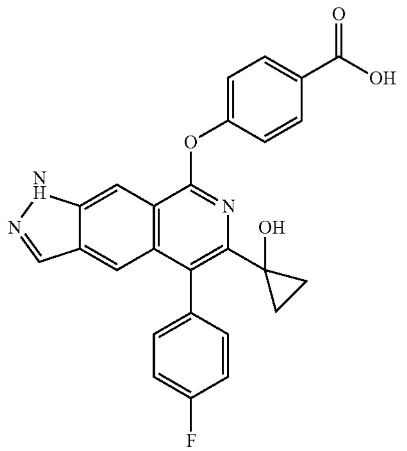 [SMILES: O=C(O)c1ccc(Oc2nc(C3(O)CC3)c(-c3ccc(F)cc3)c3cc4cn[nH]c4cc23)cc1]

TABLE I-continued
Compounds 1-262
Compound 139
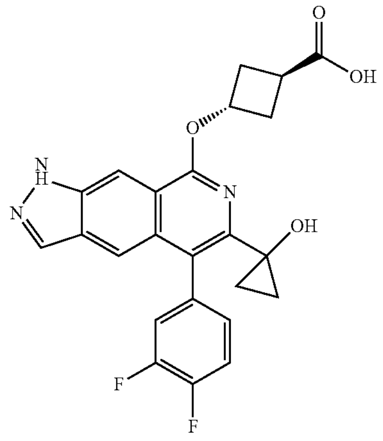 [SMILES: O=C(O)[C@H]1C[C@H](Oc2nc(C3(O)CC3)c(-c3ccc(F)c(F)c3)c3cc4cn[nH]c4cc23)C1]
Compound 140
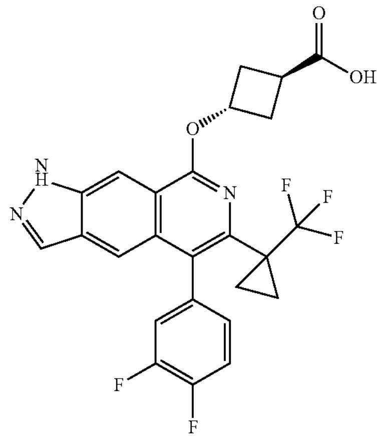 [SMILES: O=C(O)[C@H]1C[C@H](Oc2nc(C3(C(F)(F)F)CC3)c(-c3ccc(F)c(F)c3)c3cc4cn[nH]c4cc23)C1]
Compound 141
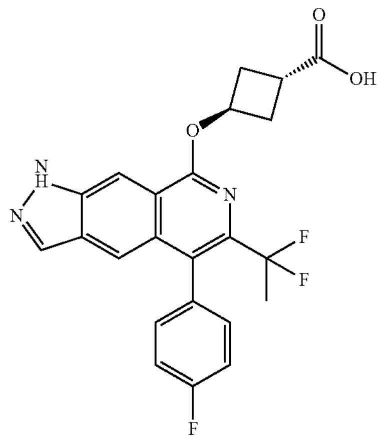 [SMILES: CC(F)(F)c1nc(O[C@H]2C[C@H](C(=O)O)C2)c2cc3[nH]ncc3cc2c1-c1ccc(F)cc1]
TABLE I-continued
Compounds 1-262
Compound 142
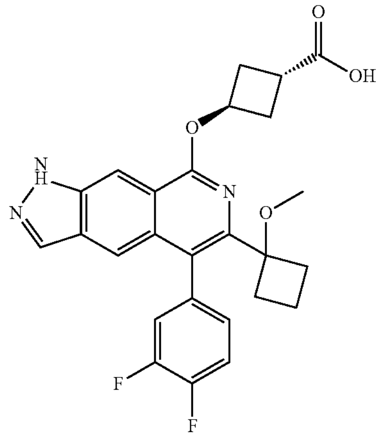 [SMILES: COC1(c2nc(O[C@H]3C[C@H](C(=O)O)C3)c3cc4[nH]ncc4cc3c2-c2ccc(F)c(F)c2)CCC1]
Compound 143
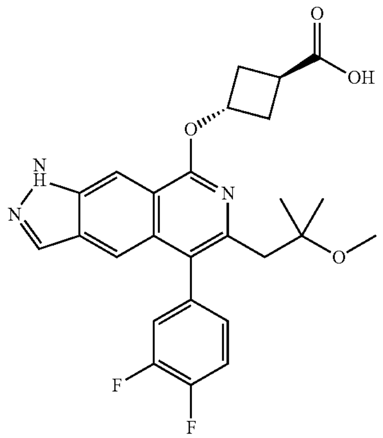 [SMILES: COC(C)(C)Cc1nc(O[C@H]2C[C@H](C(=O)O)C2)c2cc3[nH]ncc3cc2c1-c1ccc(F)c(F)c1]
Compound 144
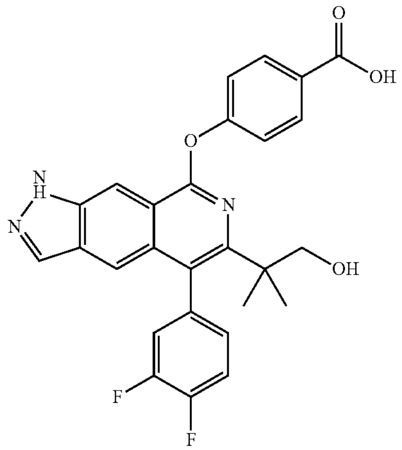 [SMILES: CC(C)(CO)c1nc(Oc2ccc(C(=O)O)cc2)c2cc3[nH]ncc3cc2c1-c1ccc(F)c(F)c1]

TABLE I-continued
Compounds 1-262
Compound 145
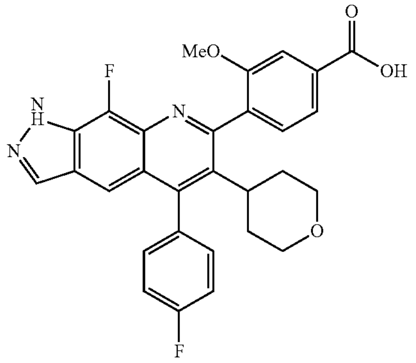 [SMILES: COc1cc(C(=O)O)ccc1-c1nc2c(F)c3[nH]ncc3cc2c(-c2ccc(F)cc2)c1C1CCOCC1]
Compound 146
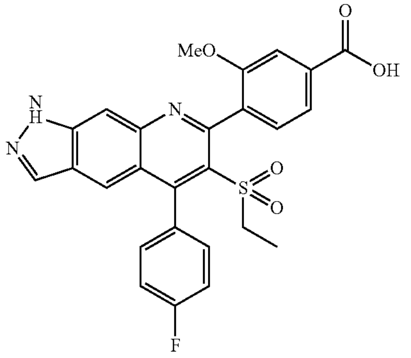 [SMILES: CCS(=O)(=O)c1c(-c2ccc(C(=O)O)cc2OC)nc2cc3[nH]ncc3cc2c1-c1ccc(F)cc1]
Compound 147
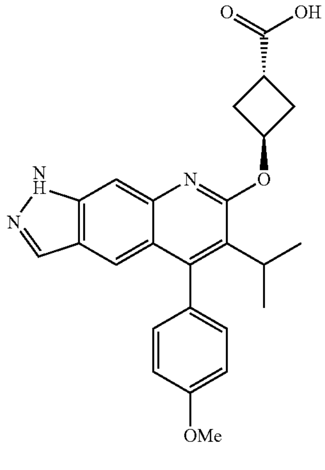 [SMILES: COc1ccc(-c2c(C(C)C)c(O[C@H]3C[C@H](C(=O)O)C3)nc3cc4[nH]ncc4cc23)cc1]
Compound 148
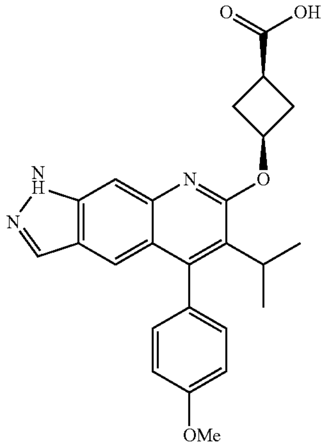 [SMILES: COc1ccc(-c2c(C(C)C)c(O[C@H]3C[C@@H](C(=O)O)C3)nc3cc4[nH]ncc4cc23)cc1]
Compound 149
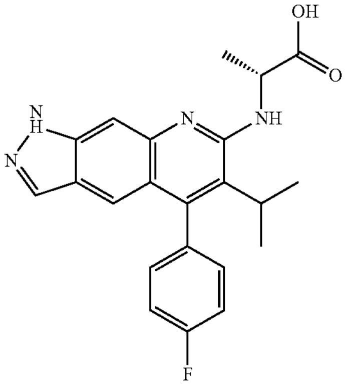 [SMILES: CC(C)c1c(N[C@H](C)C(=O)O)nc2cc3[nH]ncc3cc2c1-c1ccc(F)cc1]
Compound 150
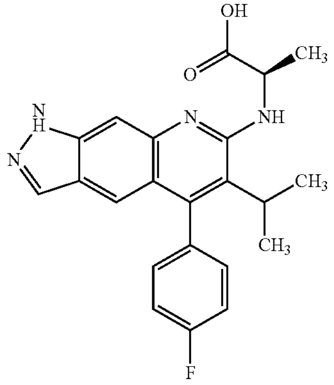 [SMILES: CC(C)c1c(N[C@H](C)C(=O)O)nc2cc3[nH]ncc3cc2c1-c1ccc(F)cc1]
Compound 151
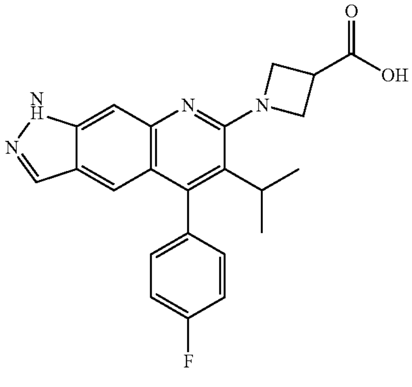 [SMILES: CC(C)c1c(N2CC(C(=O)O)C2)nc2cc3[nH]ncc3cc2c1-c1ccc(F)cc1]

TABLE I-continued
| Compounds 1-262 |
| --- |
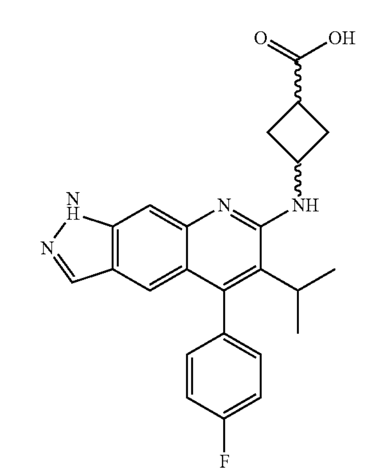 [SMILES: CC(C)c1c(NC2CC(C(=O)O)C2)nc2cc3[nH]ncc3cc2c1-c1ccc(F)cc1]
Compound 152
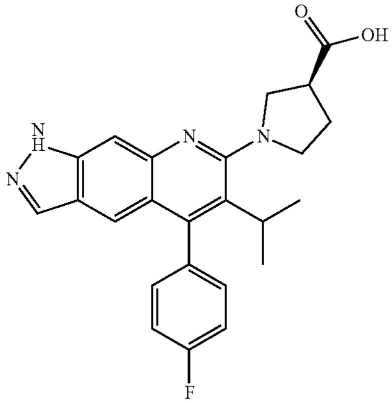 [SMILES: CC(C)c1c(N2CC[C@H](C(=O)O)C2)nc2cc3[nH]ncc3cc2c1-c1ccc(F)cc1]
Compound 153
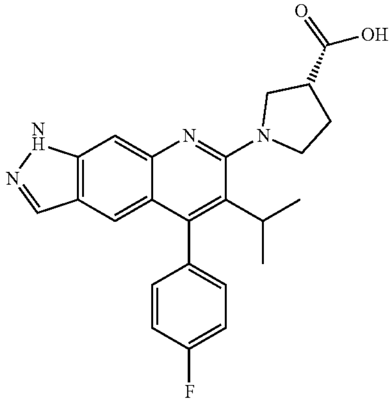
Compound 154
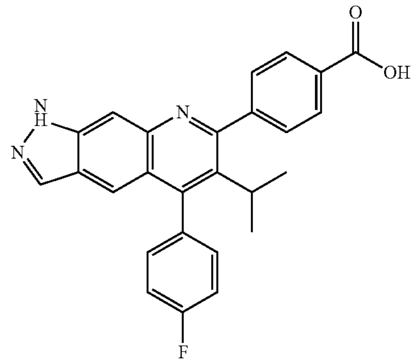 [SMILES: CC(C)c1c(-c2ccc(C(=O)O)cc2)nc2cc3[nH]ncc3cc2c1-c1ccc(F)cc1]
Compound 155
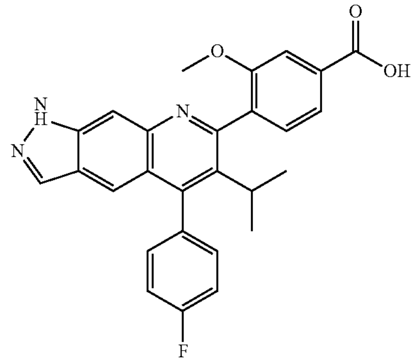 [SMILES: COc1cc(C(=O)O)ccc1-c1nc2cc3[nH]ncc3cc2c(-c2ccc(F)cc2)c1C(C)C]
Compound 156
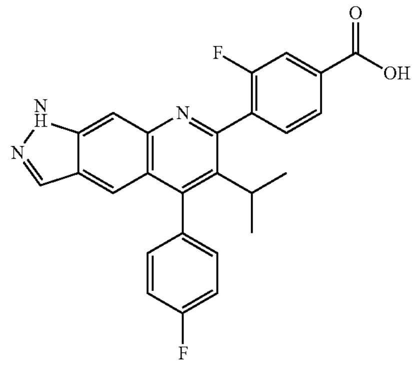 [SMILES: CC(C)c1c(-c2ccc(C(=O)O)cc2F)nc2cc3[nH]ncc3cc2c1-c1ccc(F)cc1]
Compound 157
Compound 158
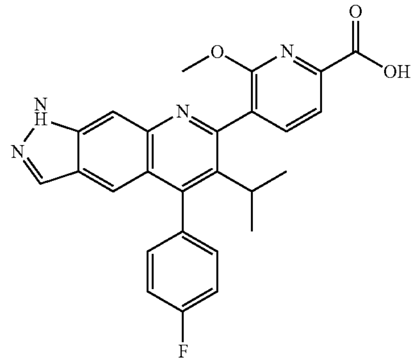 [SMILES: COc1nc(C(=O)O)ccc1-c1nc2cc3[nH]ncc3cc2c(-c2ccc(F)cc2)c1C(C)C]

TABLE I-continued
| Compounds 1-262 |
| --- |
| Compound 159 |
| 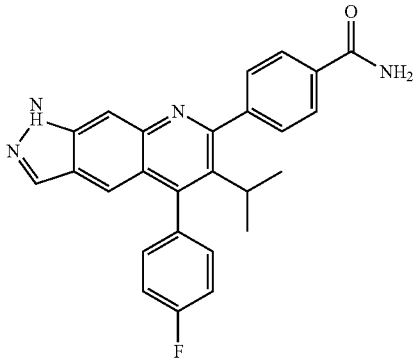 [SMILES: CC(C)c1c(-c2ccc(C(N)=O)cc2)nc2cc3[nH]ncc3cc2c1-c1ccc(F)cc1] |
| Compound 160 |
| 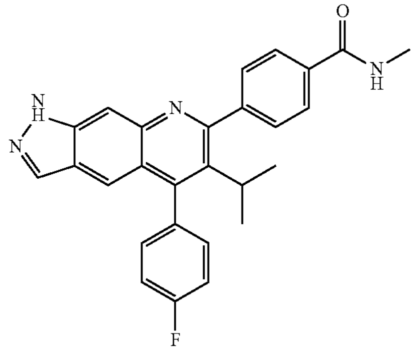 [SMILES: CNC(=O)c1ccc(-c2nc3cc4[nH]ncc4cc3c(-c3ccc(F)cc3)c2C(C)C)cc1] |
| Compound 161 |
| 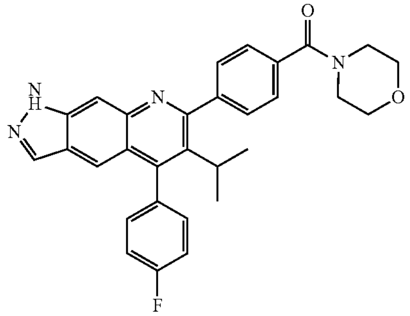 [SMILES: CC(C)c1c(-c2ccc(C(=O)N3CCOCC3)cc2)nc2cc3[nH]ncc3cc2c1-c1ccc(F)cc1] |
| Compound 162 |
| 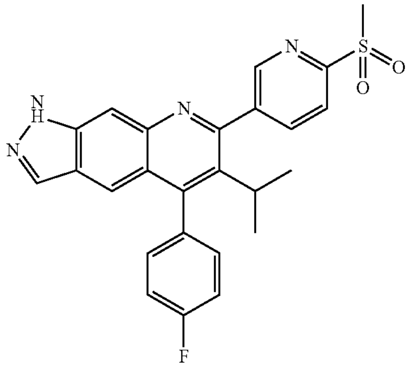 [SMILES: CC(C)c1c(-c2ccc(S(C)(=O)=O)nc2)nc2cc3[nH]ncc3cc2c1-c1ccc(F)cc1] |
TABLE I-continued
| Compounds 1-262 |
| --- |
| Compound 163 |
| 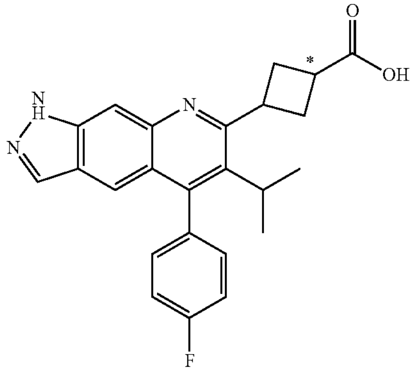 [SMILES: CC(C)c1c(C2CC(C(=O)O)C2)nc2cc3[nH]ncc3cc2c1-c1ccc(F)cc1] |
| Compound 164 |
| 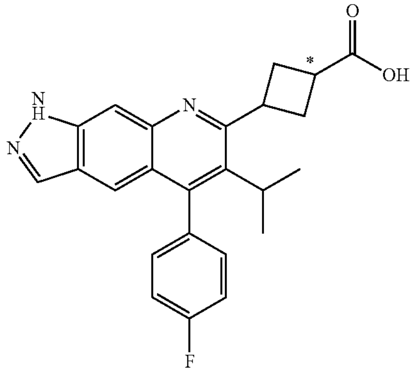 [SMILES: CC(C)c1c(C2CC(C(=O)O)C2)nc2cc3[nH]ncc3cc2c1-c1ccc(F)cc1] |
| Compound 165 |
| 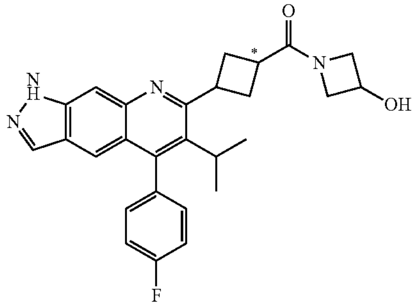 [SMILES: CC(C)c1c(C2CC(C(=O)N3CC(O)C3)C2)nc2cc3[nH]ncc3cc2c1-c1ccc(F)cc1] |
| Compound 166 |
| 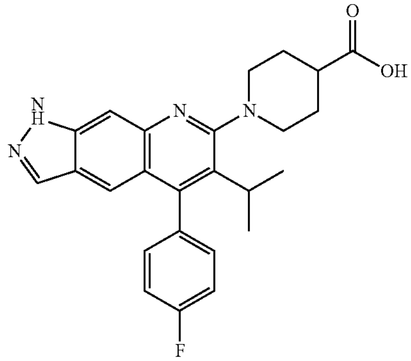 [SMILES: CC(C)c1c(N2CCC(C(=O)O)CC2)nc2cc3[nH]ncc3cc2c1-c1ccc(F)cc1] |

TABLE I-continued
| Compounds 1-262 |
| --- |
Compound 167
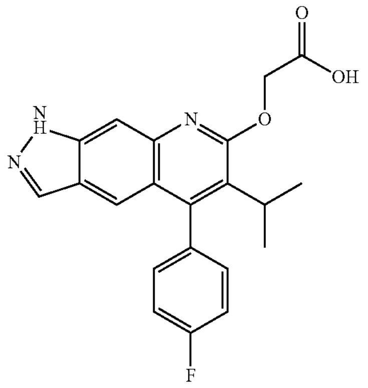 [SMILES: CC(C)c1c(OCC(=O)O)nc2cc3[nH]ncc3cc2c1-c1ccc(F)cc1]
Compound 168
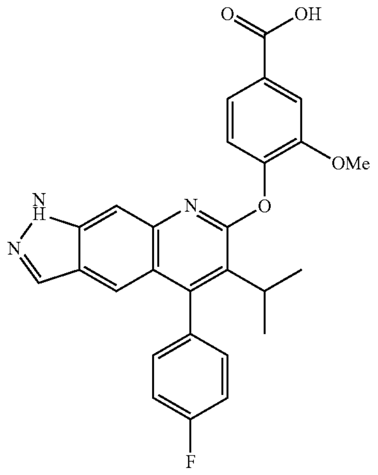 [SMILES: COc1cc(C(=O)O)ccc1Oc1nc2cc3[nH]ncc3cc2c(-c2ccc(F)cc2)c1C(C)C]
Compound 169
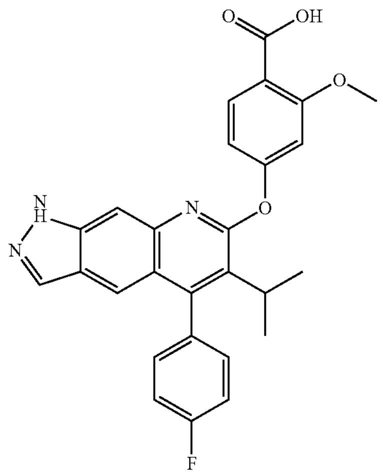 [SMILES: COc1cc(Oc2nc3cc4[nH]ncc4cc3c(-c3ccc(F)cc3)c2C(C)C)ccc1C(=O)O]
TABLE I-continued
| Compounds 1-262 |
| --- |
Compound 170
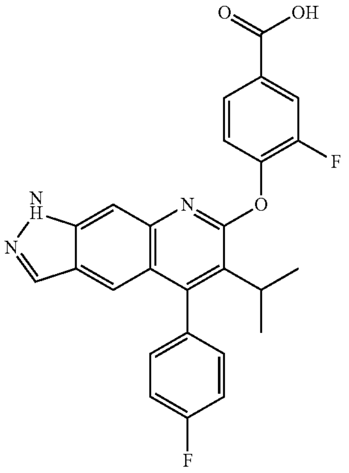 [SMILES: CC(C)c1c(Oc2ccc(C(=O)O)cc2F)nc2cc3[nH]ncc3cc2c1-c1ccc(F)cc1]
Compound 171
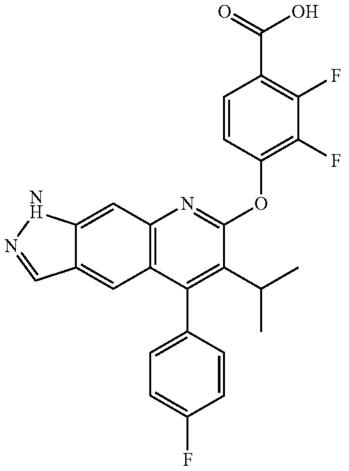 [SMILES: CC(C)c1c(Oc2ccc(C(=O)O)c(F)c2F)nc2cc3[nH]ncc3cc2c1-c1ccc(F)cc1]
Compound 172
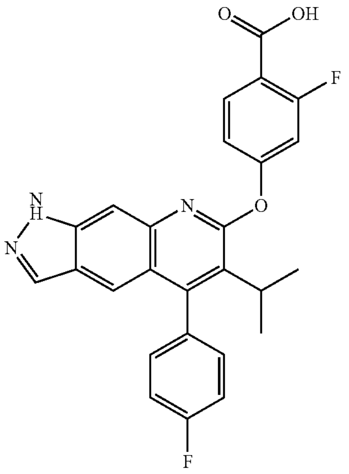 [SMILES: CC(C)c1c(Oc2ccc(C(=O)O)c(F)c2)nc2cc3[nH]ncc3cc2c1-c1ccc(F)cc1]

TABLE I-continued
| Compounds 1-262 |
| --- |
Compound 173
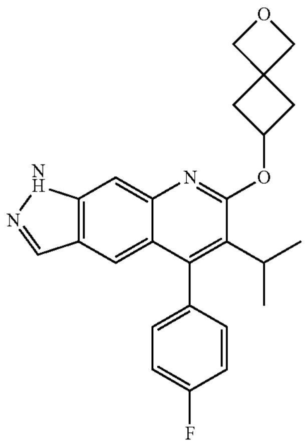 [SMILES: CC(C)c1c(OC2CC3(COC3)C2)nc2cc3[nH]ncc3cc2c1-c1ccc(F)cc1]
Compound 174
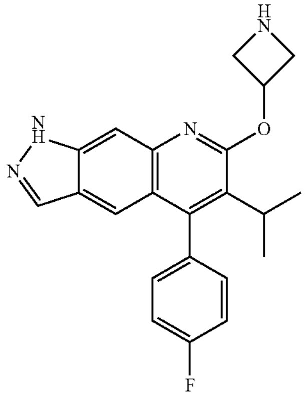 [SMILES: CC(C)c1c(OC2CNC2)nc2cc3[nH]ncc3cc2c1-c1ccc(F)cc1]
Compound 175
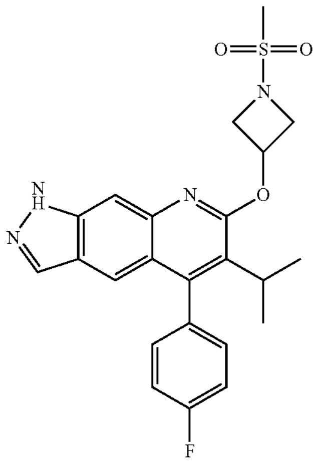 [SMILES: CC(C)c1c(OC2CN(S(C)(=O)=O)C2)nc2cc3[nH]ncc3cc2c1-c1ccc(F)cc1]
TABLE I-continued
| Compounds 1-262 |
| --- |
Compound 176
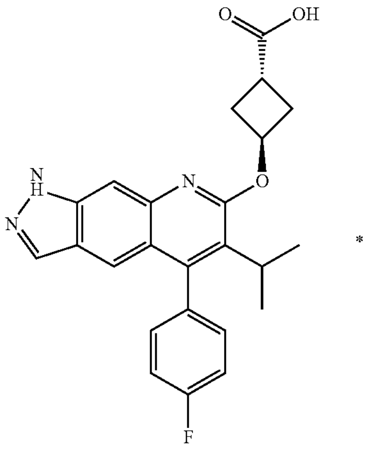 [SMILES: CC(C)c1c(O[C@H]2C[C@H](C(=O)O)C2)nc2cc3[nH]ncc3cc2c1-c1ccc(F)cc1]
Compound 177
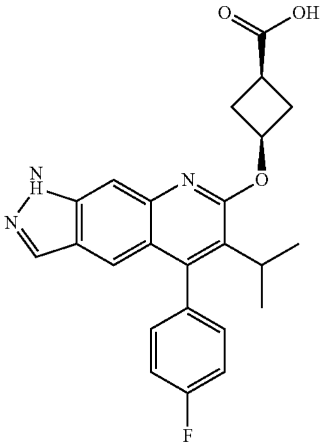 [SMILES: CC(C)c1c(O[C@H]2C[C@@H](C(=O)O)C2)nc2cc3[nH]ncc3cc2c1-c1ccc(F)cc1]
Compound 178
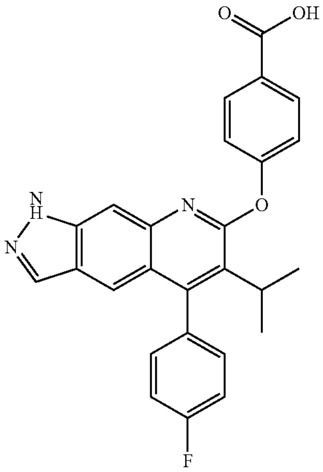 [SMILES: CC(C)c1c(Oc2ccc(C(=O)O)cc2)nc2cc3[nH]ncc3cc2c1-c1ccc(F)cc1]

TABLE I-continued
| Compounds 1-262 |
| --- |
| 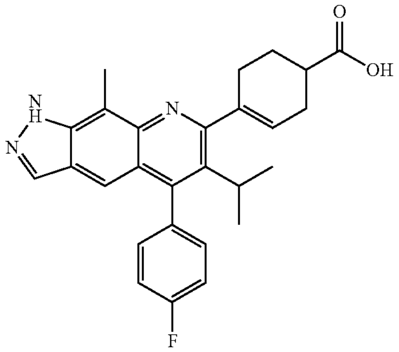 [SMILES: Cc1c2nc(C3=CCC(C(=O)O)CC3)c(C(C)C)c(-c3ccc(F)cc3)c2cc2cn[nH]c12] Compound 179 |
| Compound 180 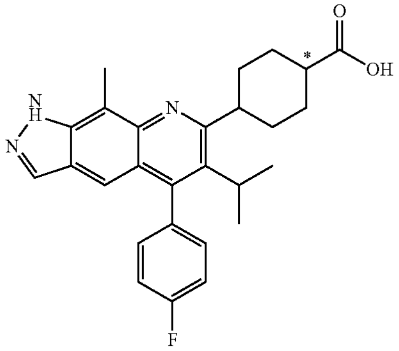 [SMILES: Cc1c2nc(C3CCC(C(=O)O)CC3)c(C(C)C)c(-c3ccc(F)cc3)c2cc2cn[nH]c12] |
| Compound 181 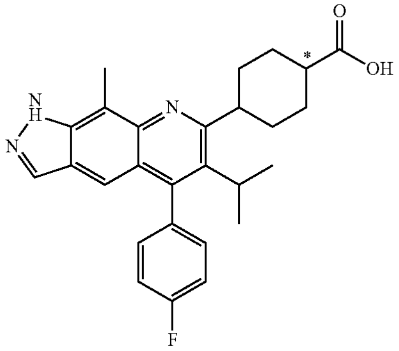 [SMILES: Cc1c2nc(C3CCC(C(=O)O)CC3)c(C(C)C)c(-c3ccc(F)cc3)c2cc2cn[nH]c12] |
| 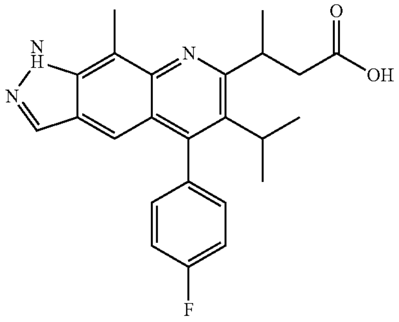 [SMILES: Cc1c2nc(C(C)CC(=O)O)c(C(C)C)c(-c3ccc(F)cc3)c2cc2cn[nH]c12] Compound 182 |
TABLE I-continued
| Compounds 1-262 |
| --- |
| 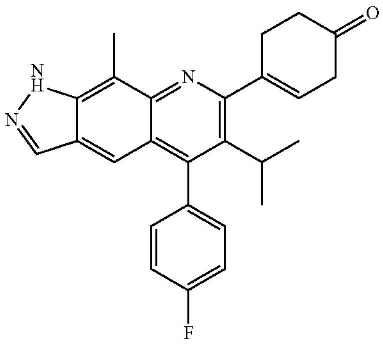 [SMILES: Cc1c2nc(C3=CCC(=O)CC3)c(C(C)C)c(-c3ccc(F)cc3)c2cc2cn[nH]c12] Compound 183 |
| 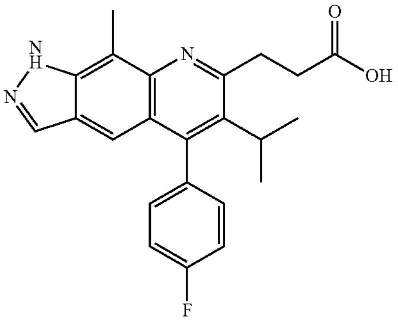 [SMILES: Cc1c2nc(CCC(=O)O)c(C(C)C)c(-c3ccc(F)cc3)c2cc2cn[nH]c12] Compound 184 |
| 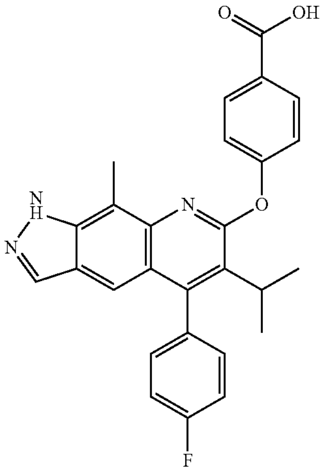 Compound 185 |
| 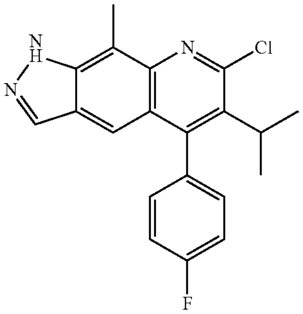 [SMILES: Cc1c2nc(Cl)c(C(C)C)c(-c3ccc(F)cc3)c2cc2cn[nH]c12] Compound 186 |

TABLE I-continued
| Compounds 1-262 |
| --- |
| 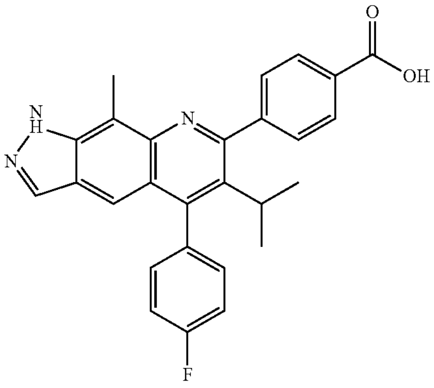 [SMILES: Cc1c2nc(-c3ccc(C(=O)O)cc3)c(C(C)C)c(-c3ccc(F)cc3)c2cc2cn[nH]c12] Compound 187 |
| 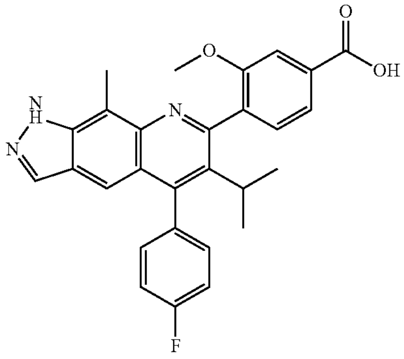 [SMILES: COc1cc(C(=O)O)ccc1-c1nc2c(C)c3[nH]ncc3cc2c(-c2ccc(F)cc2)c1C(C)C] Compound 188 |
| 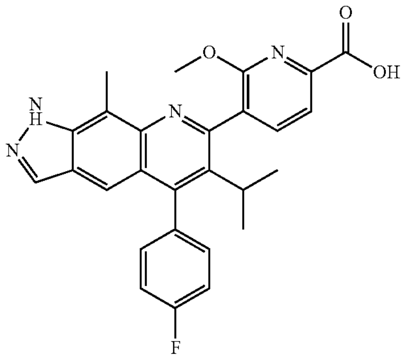 [SMILES: COc1nc(C(=O)O)ccc1-c1nc2c(C)c3[nH]ncc3cc2c(-c2ccc(F)cc2)c1C(C)C] Compound 189 |
| 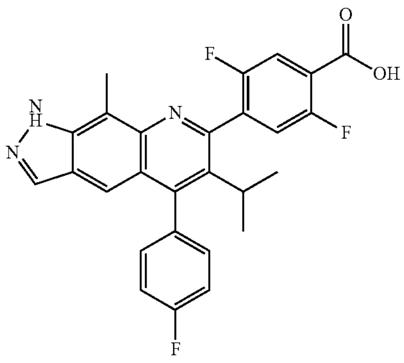 [SMILES: Cc1c2nc(-c3cc(F)c(C(=O)O)cc3F)c(C(C)C)c(-c3ccc(F)cc3)c2cc2cn[nH]c12] Compound 190 |
TABLE I-continued
| Compounds 1-262 |
| --- |
| 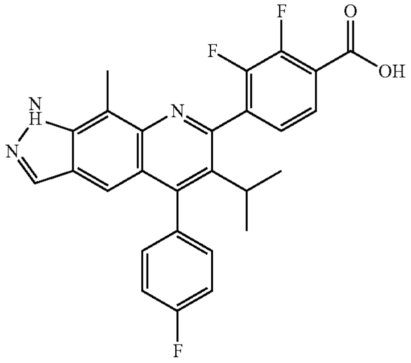 [SMILES: Cc1c2nc(-c3ccc(C(=O)O)c(F)c3F)c(C(C)C)c(-c3ccc(F)cc3)c2cc2cn[nH]c12] Compound 191 |
| 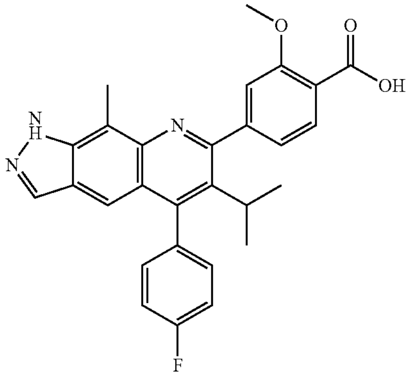 [SMILES: COc1cc(-c2nc3c(C)c4[nH]ncc4cc3c(-c3ccc(F)cc3)c2C(C)C)ccc1C(=O)O] Compound 192 |
| 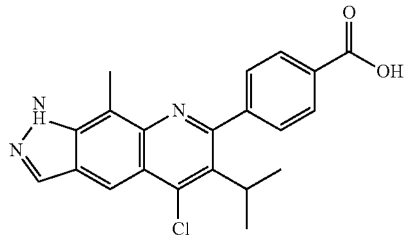 [SMILES: Cc1c2nc(-c3ccc(C(=O)O)cc3)c(C(C)C)c(Cl)c2cc2cn[nH]c12] Compound 193 |
| 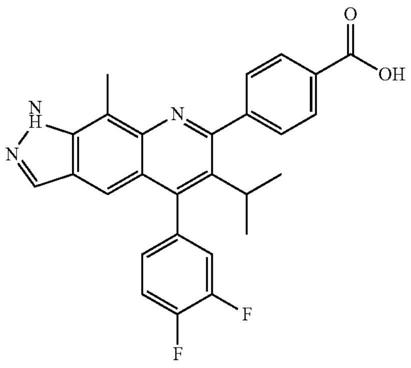 [SMILES: Cc1c2nc(-c3ccc(C(=O)O)cc3)c(C(C)C)c(-c3ccc(F)c(F)c3)c2cc2cn[nH]c12] Compound 194 |

TABLE I-continued
Compounds 1-262
Compound 195
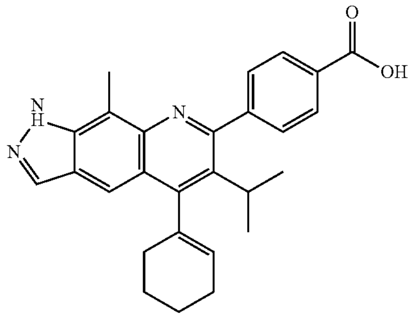 [SMILES: Cc1c2nc(-c3ccc(C(=O)O)cc3)c(C(C)C)c(C3=CCCCC3)c2cc2cn[nH]c12]
Compound 196
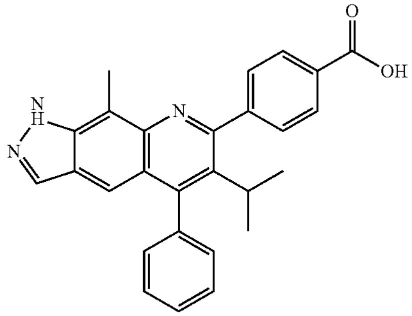 [SMILES: Cc1c2nc(-c3ccc(C(=O)O)cc3)c(C(C)C)c(-c3ccccc3)c2cc2cn[nH]c12]
Compound 197
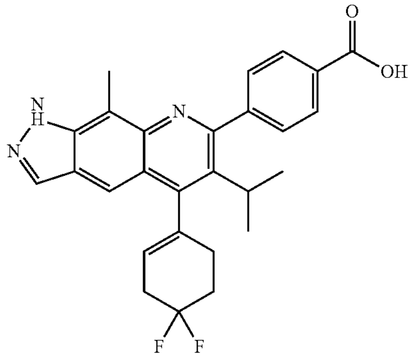 [SMILES: Cc1c2nc(-c3ccc(C(=O)O)cc3)c(C(C)C)c(C3=CCC(F)(F)CC3)c2cc2cn[nH]c12]
Compound 198
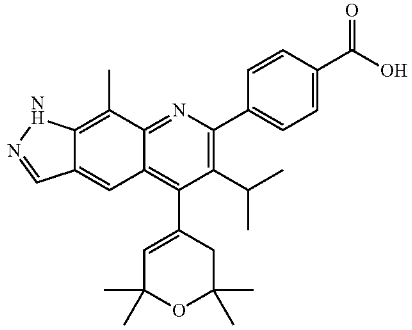 [SMILES: Cc1c2nc(-c3ccc(C(=O)O)cc3)c(C(C)C)c(C3=CC(C)(C)OC(C)(C)C3)c2cc2cn[nH]c12]
TABLE I-continued
Compounds 1-262
Compound 199
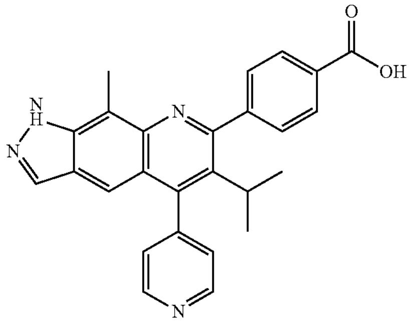 [SMILES: Cc1c2nc(-c3ccc(C(=O)O)cc3)c(C(C)C)c(-c3ccncc3)c2cc2cn[nH]c12]
Compound 200
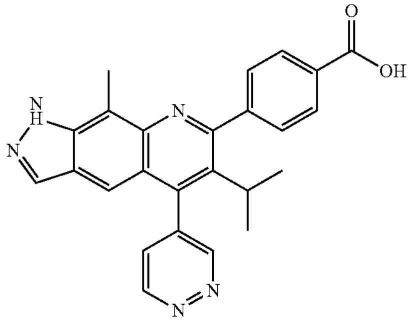 [SMILES: Cc1c2nc(-c3ccc(C(=O)O)cc3)c(C(C)C)c(-c3ccnnc3)c2cc2cn[nH]c12]
Compound 201
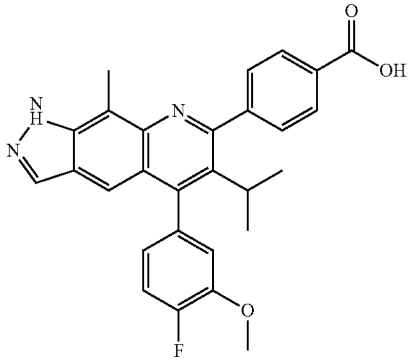 [SMILES: COc1cc(-c2c(C(C)C)c(-c3ccc(C(=O)O)cc3)nc3c(C)c4[nH]ncc4cc23)ccc1F]
Compound 202
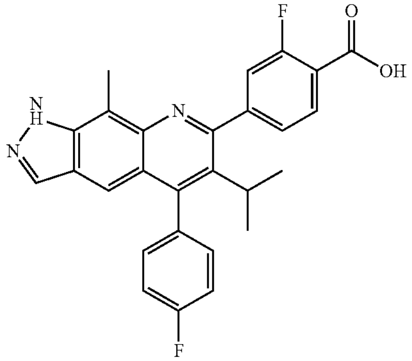 [SMILES: Cc1c2nc(-c3ccc(C(=O)O)c(F)c3)c(C(C)C)c(-c3ccc(F)cc3)c2cc2cn[nH]c12]

TABLE I-continued
Compounds 1-262
Compound 203
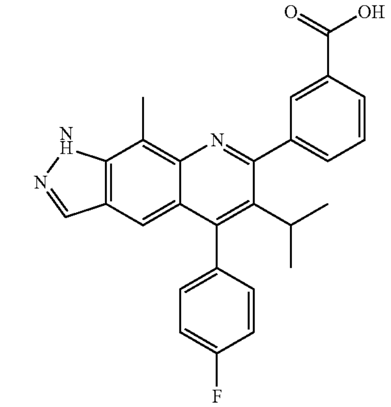 [SMILES: Cc1c2nc(-c3cccc(C(=O)O)c3)c(C(C)C)c(-c3ccc(F)cc3)c2cc2cn[nH]c12]
Compound 204
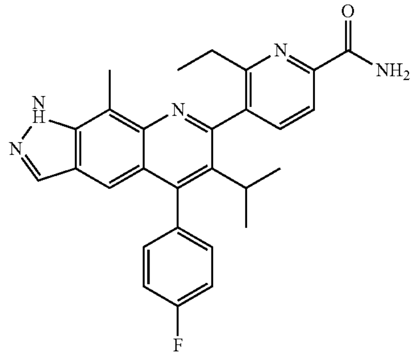 [SMILES: CCc1nc(C(N)=O)ccc1-c1nc2c(C)c3[nH]ncc3cc2c(-c2ccc(F)cc2)c1C(C)C]
Compound 205
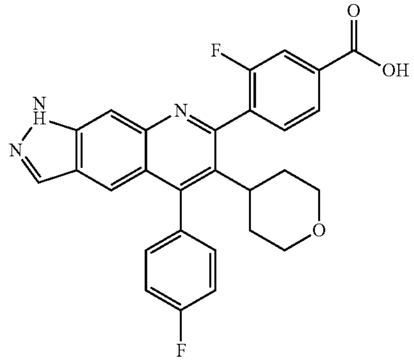 [SMILES: O=C(O)c1ccc(-c2nc3cc4[nH]ncc4cc3c(-c3ccc(F)cc3)c2C2CCOCC2)c(F)c1]
Compound 206
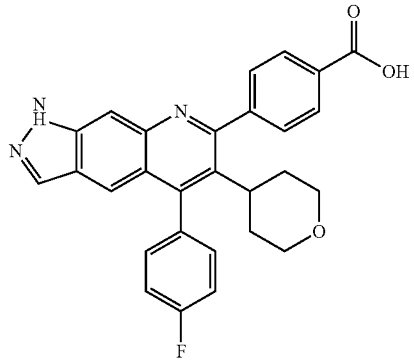 [SMILES: O=C(O)c1ccc(-c2nc3cc4[nH]ncc4cc3c(-c3ccc(F)cc3)c2C2CCOCC2)cc1]
Compound 207
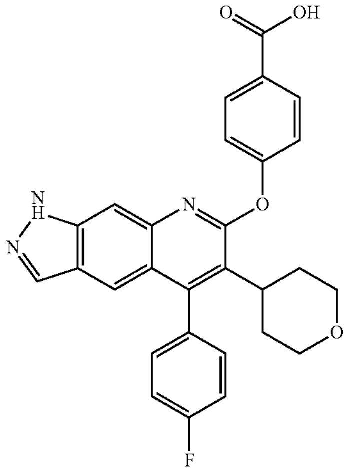 [SMILES: O=C(O)c1ccc(Oc2nc3cc4[nH]ncc4cc3c(-c3ccc(F)cc3)c2C2CCOCC2)cc1]
Compound 208
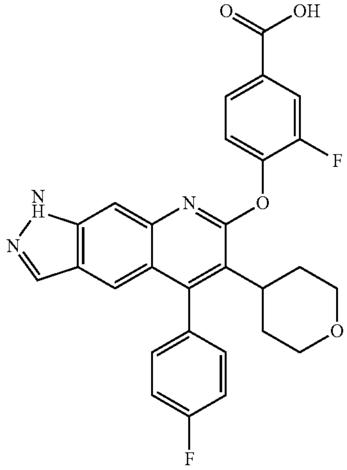 [SMILES: O=C(O)c1ccc(Oc2nc3cc4[nH]ncc4cc3c(-c3ccc(F)cc3)c2C2CCOCC2)c(F)c1]
Compound 209
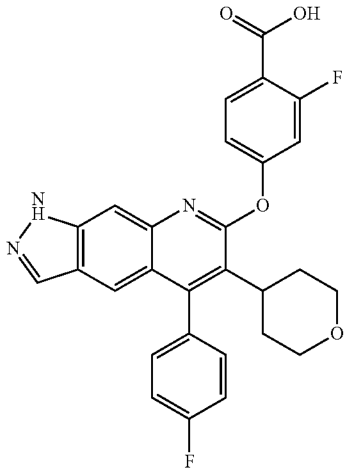 [SMILES: O=C(O)c1ccc(Oc2nc3cc4[nH]ncc4cc3c(-c3ccc(F)cc3)c2C2CCOCC2)cc1F]

TABLE I-continued
| Compounds 1-262 |
| --- |
| 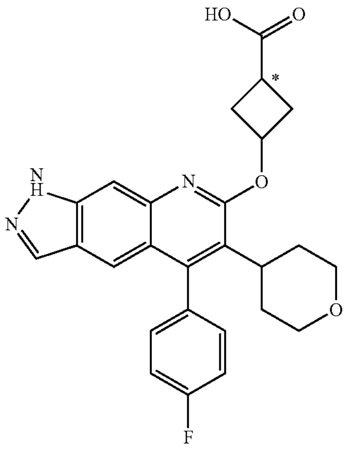 [SMILES: O=C(O)C1CC(Oc2nc3cc4[nH]ncc4cc3c(-c3ccc(F)cc3)c2C2CCOCC2)C1] Compound 210 |
| 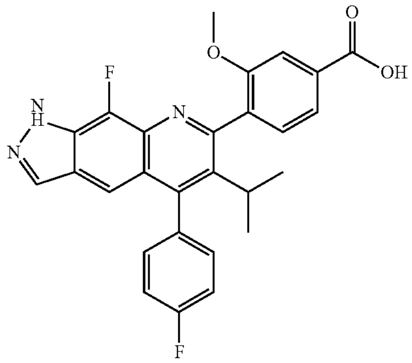 [SMILES: COc1cc(C(=O)O)ccc1-c1nc2c(F)c3[nH]ncc3cc2c(-c2ccc(F)cc2)c1C(C)C] Compound 211 |
| 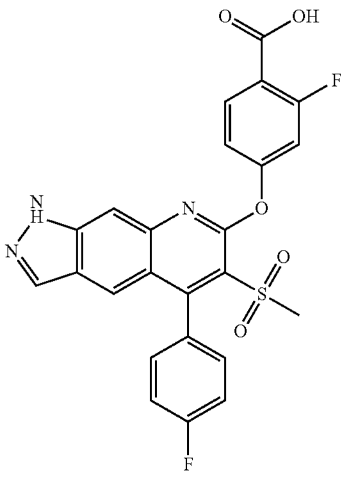 [SMILES: CS(=O)(=O)c1c(Oc2ccc(C(=O)O)c(F)c2)nc2cc3[nH]ncc3cc2c1-c1ccc(F)cc1] Compound 212 |
TABLE I-continued
| Compounds 1-262 |
| --- |
| 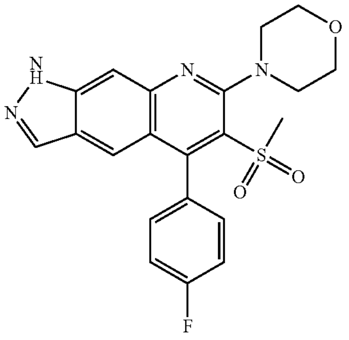 [SMILES: CS(=O)(=O)c1c(N2CCOCC2)nc2cc3[nH]ncc3cc2c1-c1ccc(F)cc1] Compound 213 |
| 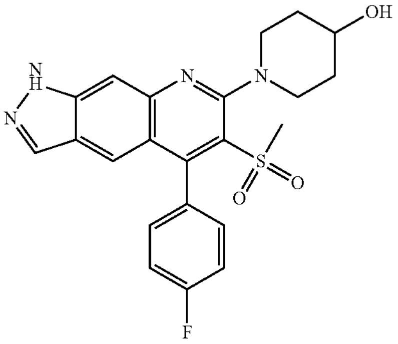 [SMILES: CS(=O)(=O)c1c(N2CCC(O)CC2)nc2cc3[nH]ncc3cc2c1-c1ccc(F)cc1] Compound 214 |
| 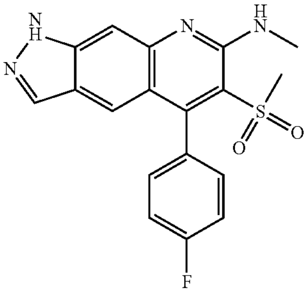 [SMILES: CNc1nc2cc3[nH]ncc3cc2c(-c2ccc(F)cc2)c1S(C)(=O)=O] Compound 215 |
| 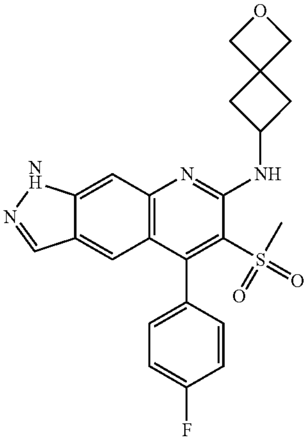 [SMILES: CS(=O)(=O)c1c(NC2CC3(COC3)C2)nc2cc3[nH]ncc3cc2c1-c1ccc(F)cc1] Compound 216 |

TABLE I-continued
Compounds 1-262
Compound 217
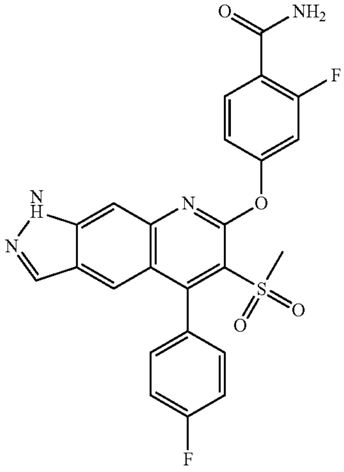 [SMILES: CS(=O)(=O)c1c(Oc2ccc(C(N)=O)c(F)c2)nc2cc3[nH]ncc3cc2c1-c1ccc(F)cc1]
Compound 218
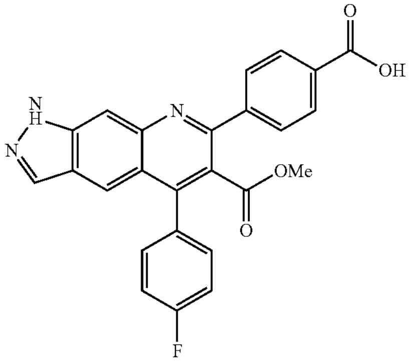 [SMILES: COC(=O)c1c(-c2ccc(C(=O)O)cc2)nc2cc3[nH]ncc3cc2c1-c1ccc(F)cc1]
Compound 219
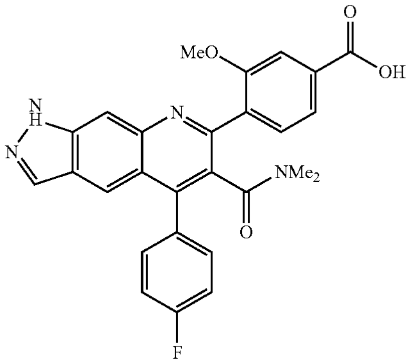 [SMILES: COc1cc(C(=O)O)ccc1-c1nc2cc3[nH]ncc3cc2c(-c2ccc(F)cc2)c1C(=O)N(C)C]
Compound 220
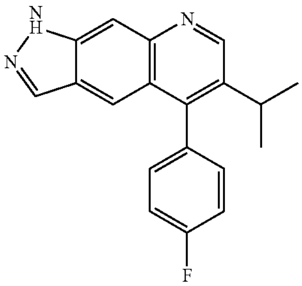 [SMILES: CC(C)c1cnc2cc3[nH]ncc3cc2c1-c1ccc(F)cc1]
Compound 221
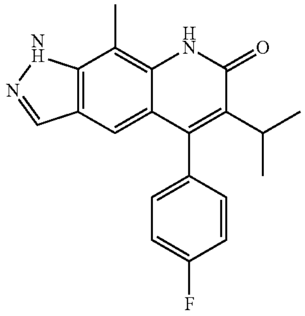 [SMILES: Cc1c2[nH]ncc2cc2c(-c3ccc(F)cc3)c(C(C)C)c(=O)[nH]c12]
Compound 222
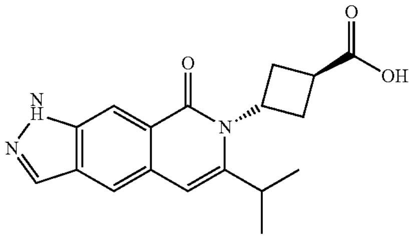
Compound 223
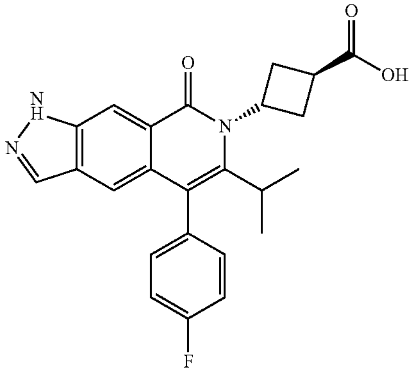
Compound 224
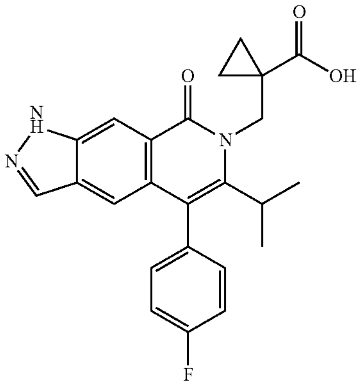 [SMILES: CC(C)c1c(-c2ccc(F)cc2)c2cc3cn[nH]c3cc2c(=O)n1CC1(C(=O)O)CC1]

TABLE I-continued
Compounds 1-262
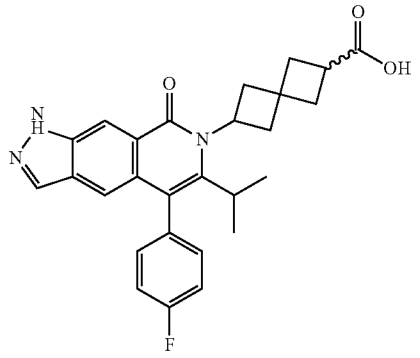 [SMILES: CC(C)c1c(-c2ccc(F)cc2)c2cc3cn[nH]c3cc2c(=O)n1C1CC2(CC(C(=O)O)C2)C1]
Compound 225
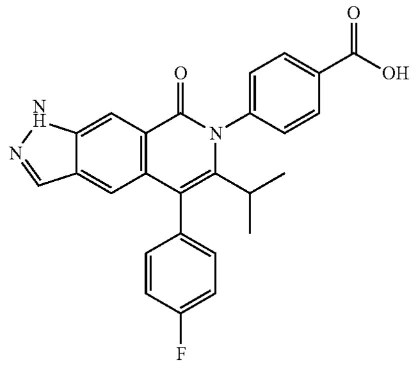 [SMILES: CC(C)c1c(-c2ccc(F)cc2)c2cc3cn[nH]c3cc2c(=O)n1-c1ccc(C(=O)O)cc1]
Compound 226
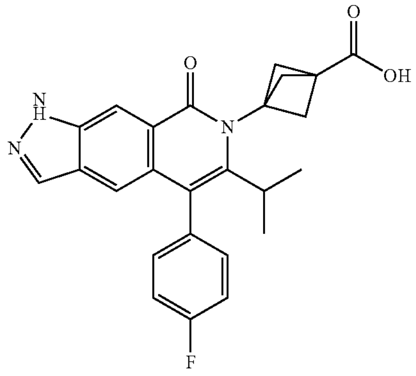 [SMILES: CC(C)c1c(-c2ccc(F)cc2)c2cc3cn[nH]c3cc2c(=O)n1C12CC(C(=O)O)(C1)C2]
Compound 227
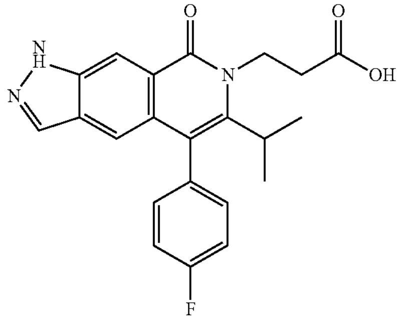 [SMILES: CC(C)c1c(-c2ccc(F)cc2)c2cc3cn[nH]c3cc2c(=O)n1CCC(=O)O]
Compound 228
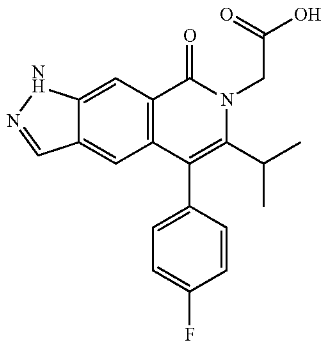 [SMILES: CC(C)c1c(-c2ccc(F)cc2)c2cc3cn[nH]c3cc2c(=O)n1CC(=O)O]
Compound 229
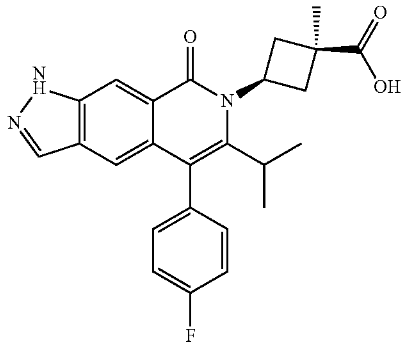 [SMILES: CC(C)c1c(-c2ccc(F)cc2)c2cc3cn[nH]c3cc2c(=O)n1[C@H]1C[C@@](C)(C(=O)O)C1]
Compound 230
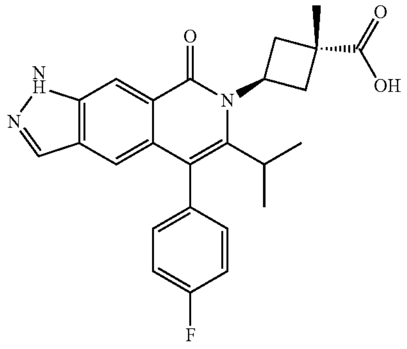 [SMILES: CC(C)c1c(-c2ccc(F)cc2)c2cc3cn[nH]c3cc2c(=O)n1[C@H]1C[C@](C)(C(=O)O)C1]
Compound 231
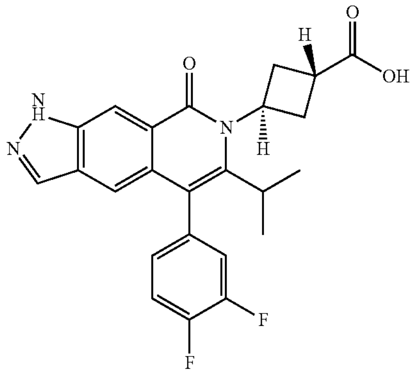 [SMILES: CC(C)c1c(-c2ccc(F)c(F)c2)c2cc3cn[nH]c3cc2c(=O)n1[C@H]1C[C@H](C(=O)O)C1]
Compound 232

TABLE I-continued
| Compounds 1-262 |
| --- |
| Compound 233 |
| 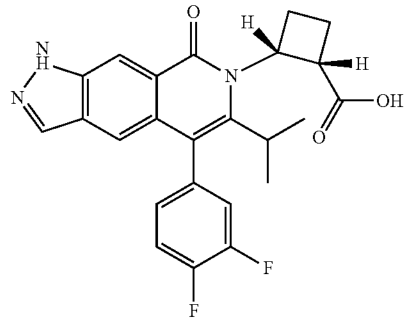 [SMILES: CC(C)c1c(-c2ccc(F)c(F)c2)c2cc3cn[nH]c3cc2c(=O)n1[C@@H]1CC[C@@H]1C(=O)O] |
| Compound 234 |
| 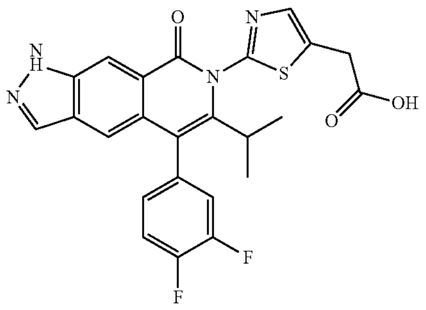 [SMILES: CC(C)c1c(-c2ccc(F)c(F)c2)c2cc3cn[nH]c3cc2c(=O)n1-c1ncc(CC(=O)O)s1] |
| Compound 235 |
| 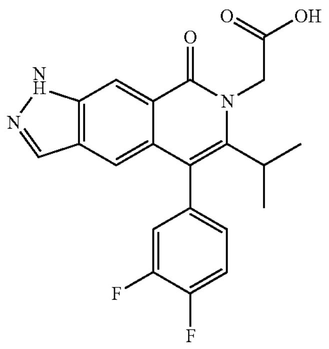 [SMILES: CC(C)c1c(-c2ccc(F)c(F)c2)c2cc3cn[nH]c3cc2c(=O)n1CC(=O)O] |
| Compound 236 |
| 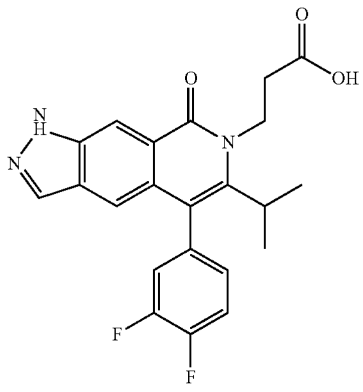 [SMILES: CC(C)c1c(-c2ccc(F)c(F)c2)c2cc3cn[nH]c3cc2c(=O)n1CCC(=O)O] |
TABLE I-continued
| Compounds 1-262 |
| --- |
| Compound 237 |
| 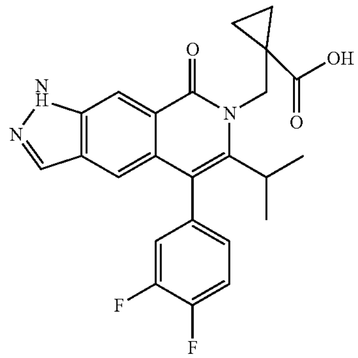 [SMILES: CC(C)c1c(-c2ccc(F)c(F)c2)c2cc3cn[nH]c3cc2c(=O)n1CC1(C(=O)O)CC1] |
| Compound 238 |
| 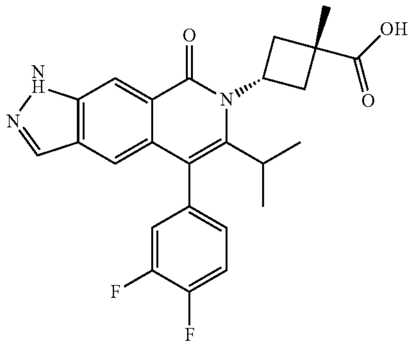 [SMILES: CC(C)c1c(-c2ccc(F)c(F)c2)c2cc3cn[nH]c3cc2c(=O)n1[C@H]1C[C@@](C)(C(=O)O)C1] |
| Compound 239 |
| 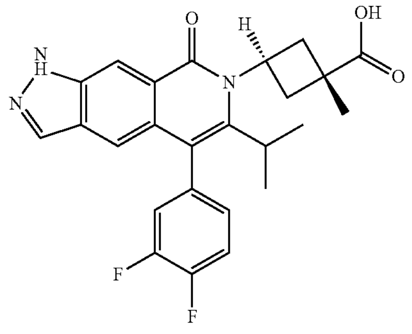 [SMILES: CC(C)c1c(-c2ccc(F)c(F)c2)c2cc3cn[nH]c3cc2c(=O)n1[C@H]1C[C@](C)(C(=O)O)C1] |
| Compound 240 |
| 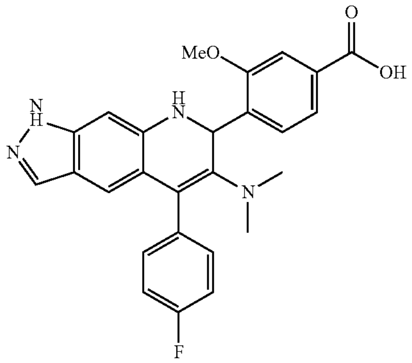 [SMILES: COc1cc(C(=O)O)ccc1C1Nc2cc3[nH]ncc3cc2C(c2ccc(F)cc2)=C1N(C)C] |

TABLE I-continued
Compounds 1-262
Compound 241
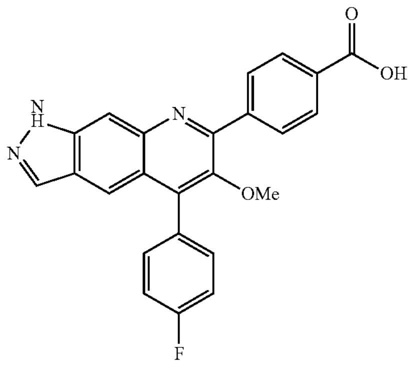 [SMILES: COc1c(-c2ccc(C(=O)O)cc2)nc2cc3[nH]ncc3cc2c1-c1ccc(F)cc1]
Compound 242
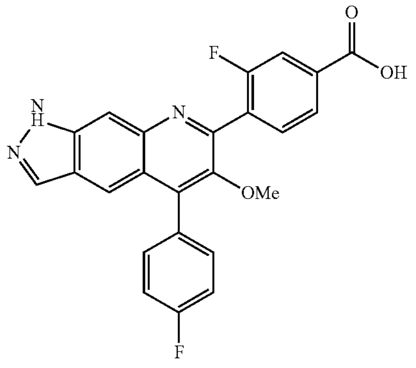 [SMILES: COc1c(-c2ccc(C(=O)O)cc2F)nc2cc3[nH]ncc3cc2c1-c1ccc(F)cc1]
Compound 243
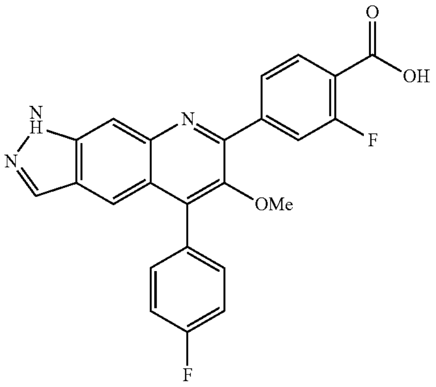
Compound 244
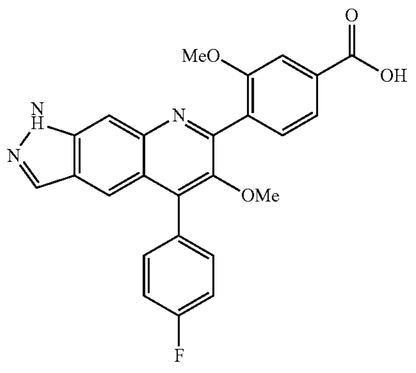 [SMILES: COc1cc(C(=O)O)ccc1-c1nc2cc3[nH]ncc3cc2c(-c2ccc(F)cc2)c1OC]
TABLE I-continued
Compounds 1-262
Compound 245
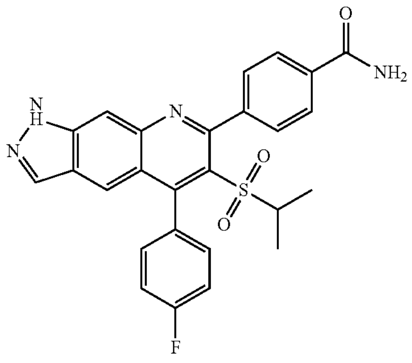 [SMILES: CC(C)S(=O)(=O)c1c(-c2ccc(C(N)=O)cc2)nc2cc3[nH]ncc3cc2c1-c1ccc(F)cc1]
Compound 246
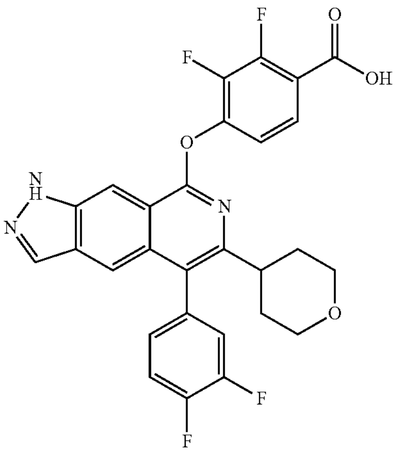 [SMILES: O=C(O)c1ccc(Oc2nc(C3CCOCC3)c(-c3ccc(F)c(F)c3)c3cc4cn[nH]c4cc23)c(F)c1F]
Compound 247
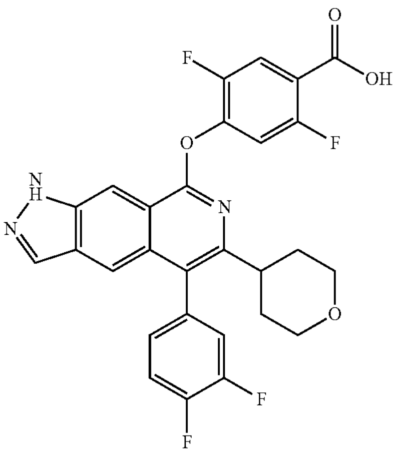 [SMILES: O=C(O)c1cc(F)c(Oc2nc(C3CCOCC3)c(-c3ccc(F)c(F)c3)c3cc4cn[nH]c4cc23)cc1F]

TABLE I-continued
Compounds 1-262
Compound 248
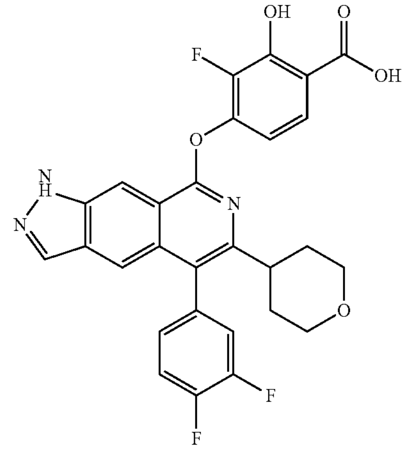 [SMILES: O=C(O)c1ccc(Oc2nc(C3CCOCC3)c(-c3ccc(F)c(F)c3)c3cc4cn[nH]c4cc23)c(F)c1O]
Compound 249
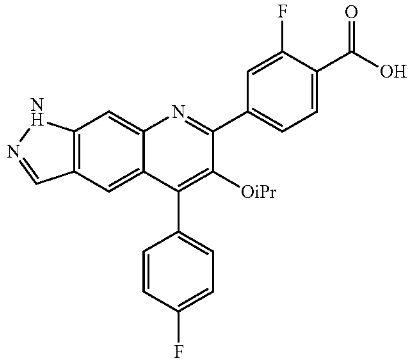 [SMILES: CC(C)Oc1c(-c2ccc(C(=O)O)c(F)c2)nc2cc3[nH]ncc3cc2c1-c1ccc(F)cc1]
Compound 250
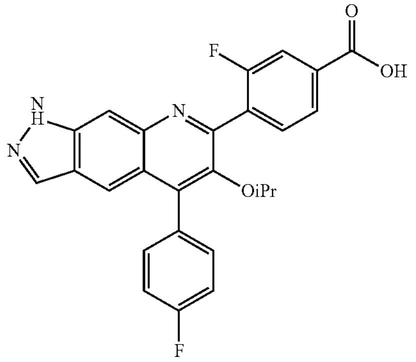 [SMILES: CC(C)Oc1c(-c2ccc(C(=O)O)cc2F)nc2cc3[nH]ncc3cc2c1-c1ccc(F)cc1]
Compound 251
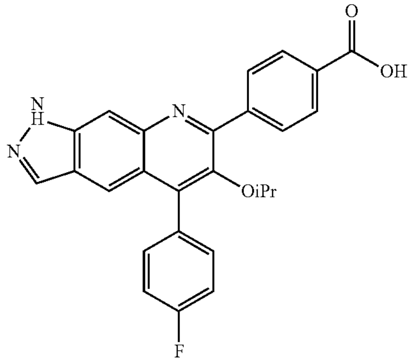 [SMILES: CC(C)Oc1c(-c2ccc(C(=O)O)cc2)nc2cc3[nH]ncc3cc2c1-c1ccc(F)cc1]
TABLE I-continued
Compounds 1-262
Compound 252
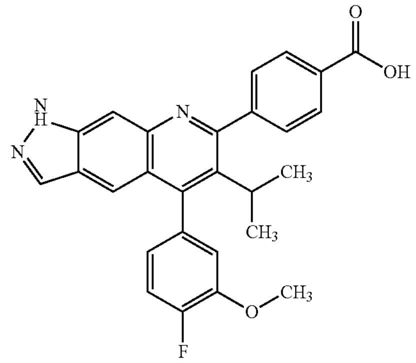 [SMILES: COc1cc(-c2c(C(C)C)c(-c3ccc(C(=O)O)cc3)nc3cc4[nH]ncc4cc23)ccc1F]
Compound 253
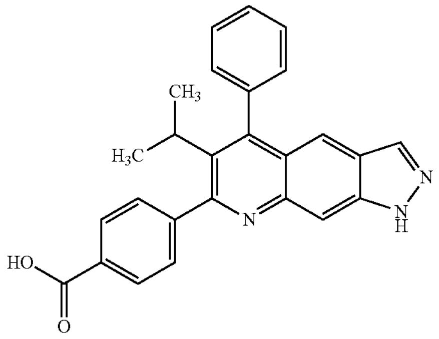 [SMILES: CC(C)c1c(-c2ccc(C(=O)O)cc2)nc2cc3[nH]ncc3cc2c1-c1ccccc1]
Compound 254
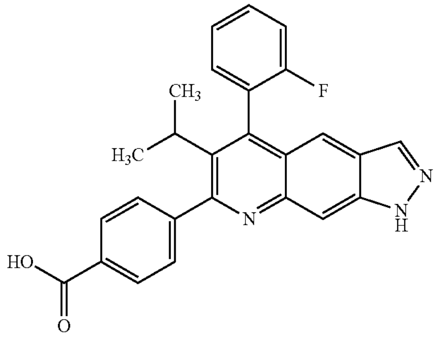 [SMILES: CC(C)c1c(-c2ccc(C(=O)O)cc2)nc2cc3[nH]ncc3cc2c1-c1ccccc1F]
Compound 255
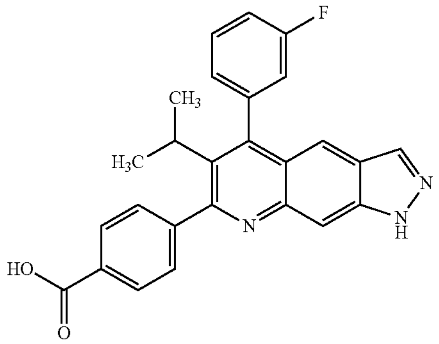 [SMILES: CC(C)c1c(-c2ccc(C(=O)O)cc2)nc2cc3[nH]ncc3cc2c1-c1cccc(F)c1]

TABLE I-continued

Compounds 1-262

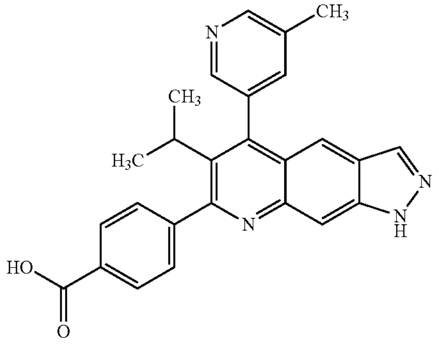 [SMILES: Cc1cncc(-c2c(C(C)C)c(-c3ccc(C(=O)O)cc3)nc3cc4[nH]ncc4cc23)c1]

Compound 256

Compound 257

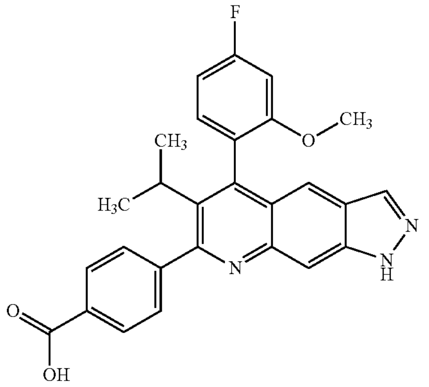 [SMILES: COc1cc(F)ccc1-c1c(C(C)C)c(-c2ccc(C(=O)O)cc2)nc2cc3[nH]ncc3cc12]

Compound 258

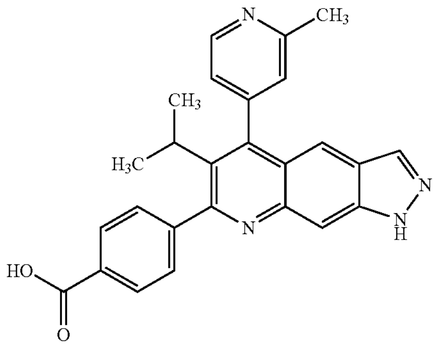 [SMILES: Cc1cc(-c2c(C(C)C)c(-c3ccc(C(=O)O)cc3)nc3cc4[nH]ncc4cc23)ccn1]

Compound 259

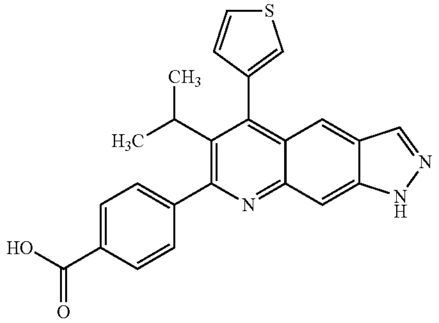 [SMILES: CC(C)c1c(-c2ccc(C(=O)O)cc2)nc2cc3[nH]ncc3cc2c1-c1ccsc1]

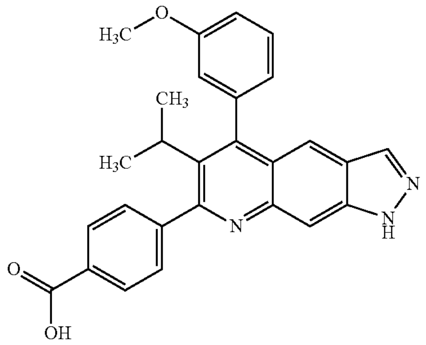 [SMILES: COc1cccc(-c2c(C(C)C)c(-c3ccc(C(=O)O)cc3)nc3cc4[nH]ncc4cc23)c1]

Compound 260

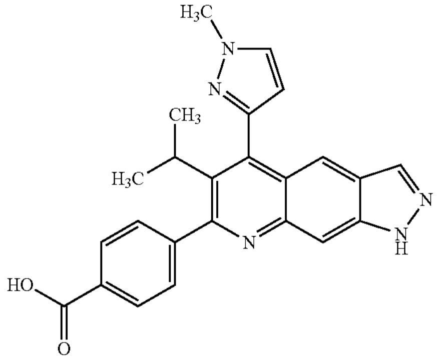 [SMILES: CC(C)c1c(-c2ccc(C(=O)O)cc2)nc2cc3[nH]ncc3cc2c1-c1ccn(C)n1]

Compound 261

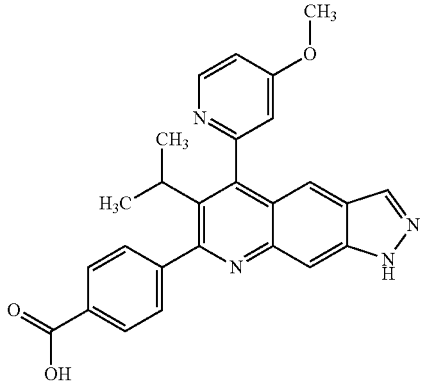 [SMILES: COc1ccnc(-c2c(C(C)C)c(-c3ccc(C(=O)O)cc3)nc3cc4[nH]ncc4cc23)c1]

Compound 262

Some embodiments of the disclosure include derivatives of Compounds 1-262 or compounds of Formulae I, II, IIIa-d, IVa-c, Va-c, VIa-c, VIIa-f, and VIIIa-c. In some embodiments, the derivatives are silicon derivatives in which at least one carbon atom in a compound selected from Compounds 1-262 or compounds of Formulae I, II, IIIa-d, IVa-c, Va-c, VIa-c, VIIa-f, and VIIIa-c has been replaced by silicon. In some embodiments, the derivatives are boron derivatives, in which at least one carbon atom in a compound selected from Compounds 1-262 or compounds of Formulae I, II, IIIa-d, IVa-c, Va-c, VIa-c, VIIa-f, and VIIIa-c has been replaced by boron. In other embodiments, the derivatives are phosphate derivatives, in which at least one carbon atom in a compound selected from Compounds 1-262 or compounds of Formulae I, II, IIIa-d, IVa-c, Va-c, VIa-c, VIIa-f, and VIIIa-c has been replaced by phosphorus. Because the general properties of silicon, boron, and phosphorus are similar to those of carbon, replacement of carbon by silicon, boron, or phosphorus can result in compounds with similar biological activity to a carbon containing original compound.

In some embodiments, the derivative is a silicon derivative in which one carbon atom in a compound selected from Compounds 1-262 or compounds of Formulae I, II, IIIa-d, IVa-c, Va-c, VIa-c, VIIa-f, and VIIIa-c has been replaced by silicon. In other embodiments, two carbon atoms have been replaced by silicon. The carbon replaced by silicon may be a non-aromatic carbon. In some embodiments a quaternary carbon atom of a tert-butyl moiety, may be replaced by silicon. In certain embodiments, the silicon derivatives of the disclosure may include one or more hydrogen atoms replaced by deuterium. For example, one or more hydrogens of a tert-butyl moiety in which the carbon has been replaced by silicon, may be replaced by deuterium. In other embodiments, a silicon derivative of a compound selected from Compounds 1-262 or compounds of Formulae I, II, IIIa-d, IVa-c, Va-c, VIa-c, VIIa-f, and VIIIa-c may have silicon incorporated into a heterocycle ring.

Another aspect of the disclosure provides pharmaceutical compositions comprising a compound according to any one formula chosen from Formulae I, II, IIIa-d, IVa-c, Va-c, VIa-c, VIIa-f, and VIIIa-c and Compounds 1-262, tautomers thereof, deuterated derivatives of those compounds or tautomers, and pharmaceutically acceptable salts of any of the foregoing. In some embodiments, the pharmaceutical composition comprising at least one compound chosen from Formulae I, II, IIIa-d, IVa-c, Va-c, VIa-c, VIIa-f, and VIIIa-c, and Compounds 1-262, tautomers thereof, deuterated derivatives of those compounds or tautomers, and pharmaceutically acceptable salts of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include another active therapeutic agent. Alternatively, a pharmaceutical composition comprising at least one compound of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing can be administered as a separate composition concurrently with, prior to, or subsequent to, a composition comprising at least one other active therapeutic agent. In specific embodiments, a pharmaceutical composition comprising at least one compound selected from Compounds 1-262, tautomers thereof, deuterated derivatives of those compounds or tautomers, and pharmaceutically acceptable salts of any of the foregoing can be administered as a separate composition concurrently with, prior to, or subsequent to, a composition comprising at least one other active therapeutic agent.

In some embodiments, a compound of Formula I, II, IIIa-d, IVa-c, Va-c, VIa-c, VIIa-f, or VIIIa-c, tautomers of those compounds, deuterated derivatives of those compounds and tautomers, or pharmaceutically acceptable salts of any of the foregoing, is combined with at least one additional active agent for simultaneous, separate, or sequential use in the treatment of AATD. In some embodiments, when the use is simultaneous, the compound of Formula I, II, IIIa-d, IVa-c, Va-c, VIa-c, VIIa-f, or VIIIa-c, tautomers of those compounds, deuterated derivatives of those compounds and tautomers, and pharmaceutically acceptable salts of any of the foregoing, and the at least one additional active agent are in separate pharmaceutical compositons. In some embodiments, when the use is simultaneous, the compound of Formula I, II, IIIa-d, IVa-c, Va-c, VIa-c, VIIa-f, or VIIIa-c, tautomers of those compounds, deuterated derivatives of those compounds and tautomers, or pharmaceutically acceptable salts of any of the foregoing, and the at least one additional active agent are together in the same pharmaceutical composition. In some embodiments, the compound is a compound selected from Compounds 1-262, tautomers of those compounds, deuterated derivatives of those compounds and tautomers, and pharmaceutically acceptable salts of any of the foregoing.

In some embodiments, a compound of Formula I, II, IIIa-d, IVa-c, Va-c, VIa-c, VIIa-f, or VIIIa-c, tautomers of those compounds, deuterated derivatives of those compounds and tautomers, or pharmaceutically acceptable salts of any of the foregoing, is provided for use in a method of treating AATD, wherein the method comprises co-administering the compound and an additional active agent. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-262, tautomers of those compounds, deuterated derivatives of those compounds and tautomers, and pharmaceutically acceptable salts of any of the foregoing.

In some embodiments, a combination of a compound of Formula I, II, IIIa-d, IVa-c, Va-c, VIa-c, VIIa-f, or VIIIa-c, tautomers of those compounds, deuterated derivatives of those compounds and tautomers, or pharmaceutically acceptable salts of any of the foregoing, and an additional active agent, is provided for use in a method of treating AATD. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-262, tautomers of those compounds, deuterated derivatives of those compounds and tautomers, and pharmaceutically acceptable salts of any of the foregoing.

In some embodiments, an additional active agent is provided for use in a method of treating AATD, wherein the method comprises co-administrating the additional active agent and a compound of Formula (I), (IIa)-(IIc), (III), (IV), (Va)-(Vc), (VIa)-(VIc), or (VIIa)-(VIIe), tautomers of those compounds, deuterated derivatives of those compounds and tautomers, or pharmaceutically acceptable salts of any of the foregoing. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-262, tautomers of those compounds, deuterated derivatives of those compounds and tautomers, and pharmaceutically acceptable salts of any of the foregoing.

In some embodiments, a compound of Formula I, II, IIIa-d, IVa-c, Va-c, VIa-c, VIIa-f, or VIIIa-c, tautomers of those compounds, deuterated derivatives of those compounds and tautomers, or pharmaceutically acceptable salts of any of the foregoing, is provided for use in a method of treating AATD, wherein the compound is prepared for administration in combination with an additional active agent. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-262, tautomers of those compounds, deuterated derivatives of those compounds and tautomers, and pharmaceutically acceptable salts of any of the foregoing.

In some embodiments, a combination of a compound of Formula I, II, IIIa-d, IVa-c, Va-c, VIa-c, VIIa-f, or VIIIa-c, tautomers of those compounds, deuterated derivatives of those compounds and tautomers, or pharmaceutically acceptable salts of any of the foregoing, and an additional active agent, is provided for use in a method of treating AATD. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-262, tautomers of those compounds, deuterated derivatives of those compounds and tautomers, and pharmaceutically acceptable salts of any of the foregoing.

In some embodiments, an additional active agent is provided for use in a method of treating AATD, wherein the additional active agent is prepared for administration in combination with a compound of Formula I, II, IIIa-d, IVa-c, Va-c, VIa-c, VIIa-f, or VIIIa-c, tautomers of those compounds, deuterated derivatives of those compounds and tautomers, or pharmaceutically acceptable salts of any of the foregoing. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-262, tautomers of those compounds, deuterated derivatives of those compounds and tautomers, and pharmaceutically acceptable salts of any of the foregoing.

In some embodiments, the additional active agent is selected the group consisting of alpha-1 antitrypsin protein (AAT) from the blood plasma of healthy human donors and recombinant AAT. In some embodiments, the additional active agent is alpha-1 antitrypsin protein (AAT) from the blood plasma of healthy human donors. In some embodiments, the additional active agent is alpha-1 antitrypsin protein (AAT) from the blood plasma of healthy human donors.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In another aspect of the disclosure, the compounds and the pharmaceutical compositions, described herein, are used to treat AATD. In some embodiments, the subject in need of treatment with the compounds and compositions of the disclosure carries the ZZ mutation. In some embodiments, the subject in need of treatment with the compounds and compositions of the disclosure carries the SZ mutation.

In some embodiments, the methods of the disclosure comprise administering to a patient in need thereof a compound chosen from any of the compounds of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing. In some embodiments, the compound of any one of Formulae I, II, IIIa-d, IVa-c, Va-c, VIa-c, VIIa-f, and VIIIa-c, is selected from Compounds 1-262, tautomers thereof, deuterated derivatives of those compounds or tautomers, and pharmaceutically acceptable salts of any of the foregoing. In some embodiments, said patient in need thereof has a Z mutation in the alpha-1 antitrypsin gene. In some embodiments said patient in need thereof is homozygous for the Z-mutation in the alpha-1 antitrypsin gene.

Another aspect of the disclosure provides methods of modulating alpha-1 antitrypsin activity comprising the step of contacting said alpha-1-antitrypsin with at least one compound of Formulae I, II, IIIa-d, IVa-c, Va-c, VIa-c, VIIa-f, and VIIIa-c, tautomers thereof, deuterated derivatives of those compounds or tautomers, and pharmaceutically acceptable salts of any of the foregoing. In specific embodiments, the methods of modulating alpha-1 antitrypsin activity comprising the step of contacting said alpha-1-antitrypsin with at least one compound selected from Compounds 1-262, tautomers thereof, deuterated derivatives of those compounds or tautomers, and pharmaceutically acceptable salts of any of the foregoing.

In some embodiments, the methods of modulating alpha-1 antitrypsin activity take place in vivo. In some embodiments, the methods of modulating alpha-1 antitrypsin activity take place ex vivo and said alpha-1-antitrypsin is from a biological sample obtained from a human subject. In some embodiments, the methods of modulating AAT take place in vitro and said alpha-1-antitrypsin is from a biological sample obtained from a human subject. In some embodiments, the biological sample is a blood sample. In some embodiments, the biological sample is a sample taken from a liver biopsy.

III. Preparation of Compounds

All the generic, subgeneric, and specific compound formulae disclosed herein are considered part of the disclosure.

A. Compounds of Formula I

The compounds of the disclosure may be made according to standard chemical practices or as described herein. Throughout the following synthetic schemes and in the descriptions for preparing compounds of Formulae I, II, IIIa-d, IVa-c, Va-c, VIa-c, VIIa-f, and VIIIa-c, and Compounds 1-262, tautomers thereof, deuterated derivatives of those compounds or tautomers, and pharmaceutically acceptable salts of any of the foregoing, the following abbreviations are used:

Abbreviations

BrettPhos Pd G1=Chloro[2-(dicyclohexylphosphino)-3,6-dimethoxy-2',4',6'-triisopropyl-1,1'-biphenyl][2-(2-aminoethyl)phenyl]palladium(II) or (BrettPhos) palladium (II) phenethylamine chloride BrettPhos Pd G4=dicyclohexyl-[3,6-dimethoxy-2-[2,4,6-tri (propan-2-yl)phenyl]phenyl]phosphane; methanesulfonic acid; N-methyl-2-phenylaniline; palladium CBzCl=Benzyl chloroformate Cphos=2-Dicyclohexylphosphino-2',6'-bis(N,N-dimethylamino)biphenyl DIPEA=N,N-Diisopropylethylamine or N-ethyl-N-isopropyl-propan-2-amine DMAP=dimethylamino pyridine DMF=dimethylformamide DMSO=dimethyl sulfoxide EtOAc=Ethyl Acetate HATU=[dimethylamino(triazolo[4,5-b]pyridin-3-yloxy) methylene]-dimethyl-ammonium (Phosphorus Hexafluoride Ion)

IPA=isopropyl alcohol

MeOH=methanol

MP-TMT scavenger resin=a macroporous polystyrene-bound trimercaptotriazine, a resin bound equivalent of 2,4,6-trimercaptotriazine (TMT).

MTBE=Methyl tert-butyl ether $Pd(dppf)_2Cl_2$=[1,1'-Bis(diphenylphosphino)ferrocene]dichloropalladium(II)

$PdCl_2(PPh_3)_2$=Bis(triphenylphosphine)palladium(II) dichloride

PTSA=p-Toluenesulfonic acid monohydrate

SFC=super critical fluid chromatography

TBAF=Tetrabutylammonium fluoride tBuXPhos Pd G1=Chloro[2-(di-tert-butylphosphino)-2',4',6'-triisopropyl-1,1'-biphenyl][2-(2-aminoethyl)phenyl)] palladium(II) or t-BuXPhos palladium(II) phenethylamine chloride tBuXPhos Pd G3=[(2-Di-tert-butylphosphino-2',4',6'-triisopropyl-1,1'-biphenyl)-2-(2'-amino-1,1'-biphenyl)]palladium(II) methanesulfonate TFA=trifluoroacetic acid THF=tetrahydrofuran THP=tetrahydropyran XPhos Pd G1=(2-Dicyclohexylphosphino-2',4',6'-triisopropyl-1,1'-biphenyl)[2-(2-aminoethyl)phenyl)]palladium (II) chloride or (XPhos) palladium(II) phenethylamine chloride In some embodiments, processes for preparing compounds of Formula I, tautomers, pharmaceutically acceptable salts of those compounds or tautomers, or deuterated derivatives of any of the foregoing, comprise reacting a compound of Formulae I, II, IIIa-d, IVa-c, Va-c, VIa-c, VIIa-f, and VIIa-c, and Compounds 1-262, tautomers thereof, deuterated derivatives of those compounds or tautomers, and pharmaceutically acceptable salts of any of the foregoing:

General Synthetic Schemes (IIIa')

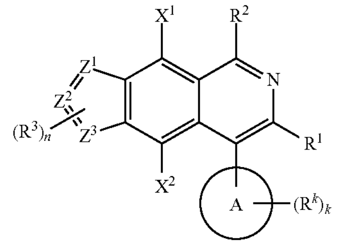

(IIIb')

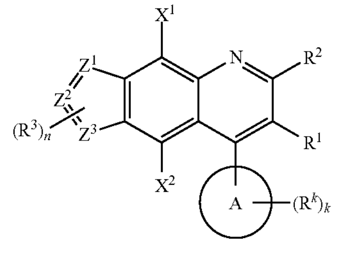

-continued (IIIc')

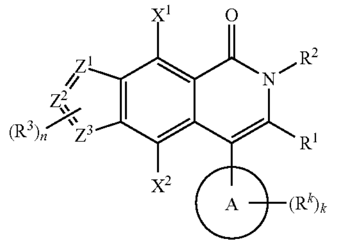

(IIId')

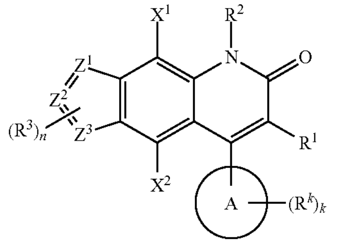

Scheme 1 refers to the preparation of compounds of Formula IIIa'.

Definitions: $PG^1$ is a suitable nitrogen atom protecting group, such as THP. $PG^1$ may also be Cbz, pivalolyl, tosyl, phenyl sulfonyl.

Compounds of Formula IIIa' may be prepared from compounds of Formula 1-1 using any suitable method for the removal of a nitrogen protecting group. In some embodiments, where $PG^1$ is a THP, a reagent such trifluoroacetic acid may be used.

Scheme 1

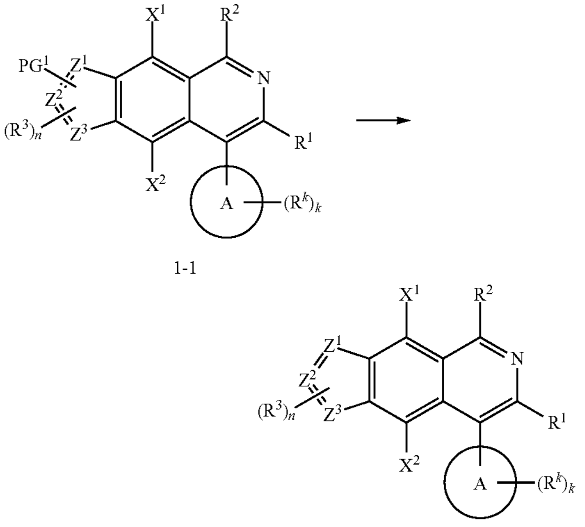

1-1

(IIIa)

Scheme 2 refers to a process for the preparation of compounds of Formula 1-1.

Definitions: $Y^1$ is a halogen (e.g. Br, Cl or I). $R^{11}$ is any alkyl group such as Me, Et, or tBu. $E^1$ is H or $SiMe_3$. $PG^1$ is defined as above. $R^{11}$ is OH, alkyl, or cyclic alkyl where $R^{11}$ groups are linked by a carbon-carbon bond.

A compound of formula 2-2 may be prepared from 2-1 using a suitable method for the addition of a protecting group onto a nitrogen atom. For example, where $PG^1$ is a THP group, treatment with dihydropyran and p-toluenesulfonic acid affords compounds of formula 2-2. Compounds of formula 2-3 may be prepared from formula 2-3 using any suitable method for reduction of an ester to an alcohol (e.g. DiBALH, or $LiAlH_4$). Oxidation of compounds of Formula 2-3 to aldehydes of formula 2-4 may be performed with any suitable oxidizing reagent. In some embodiments, 4-acetamido-TEMPO and $NaHCO_3$ may be used. Sonagashira coupling of compounds of formula 2-4 with an alkyne of formula 2-5 using a reagent system such as $Pd(PPh_3)_2Cl_2$, CuI, and an amine base such as $NEt_3$. Compounds of Formula 2-7 may be prepared from compounds of Formula 2-6 by a condensation reaction with hydroxylamine in the presence of a base such as pyridine. Compounds of Formula 2-8 may be prepared from compound 2-7 by intramolecular cyclization of the amine group onto the alkyne. In some embodiments, a reagent such as molecular iodine, in the presence of a base such as $K_2CO_3$, may be used. Compounds of formula 2-10 may be prepared by from 2-8 by Suzuki coupling with a boronic acid or ester of formula 2-9. Compound 2-11 may be prepared by any suitable method for the preparation of an aryl chloride. For example, a reagent such as $POCl_3$, or oxalyl chloride and $iPr_2NH$ may be used. Compounds of formula 1-1 may be prepared using any suitable condition for coupling an organometallic reagent (e.g. boronic ester, Alkyl zinc) 2-12 with an aryl chloride 2-11.

Scheme 2

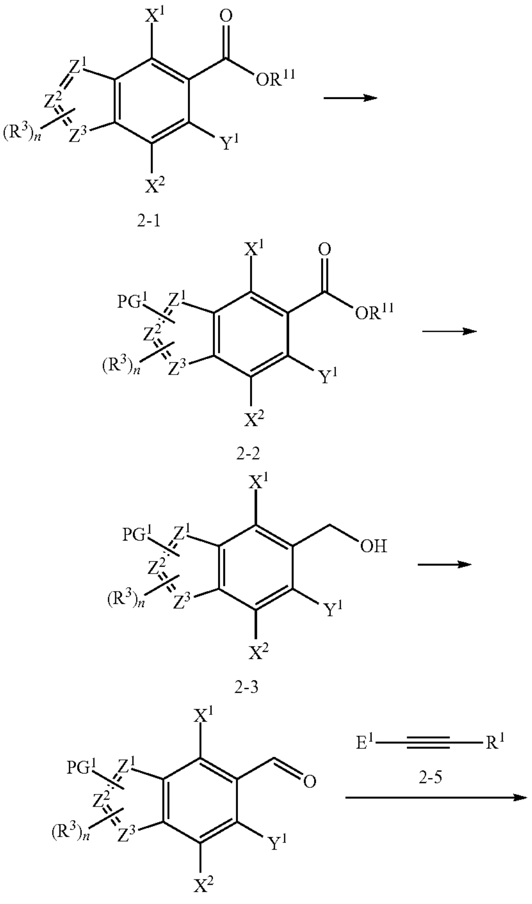

2-1

2-2

2-3

2-4

-continued

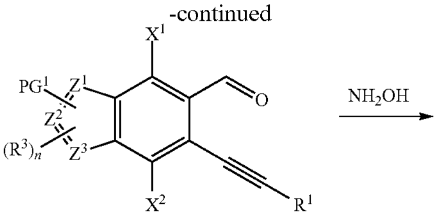

2-6

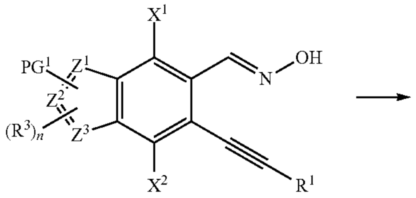

2-7

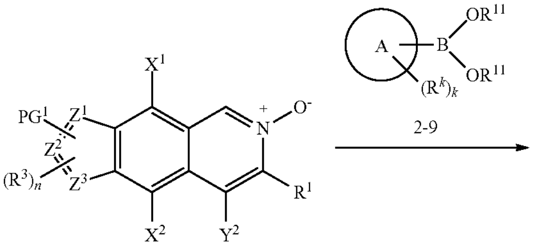

2-8

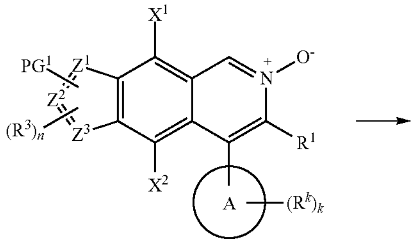

2-10

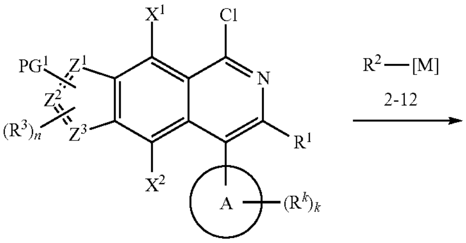

2-11

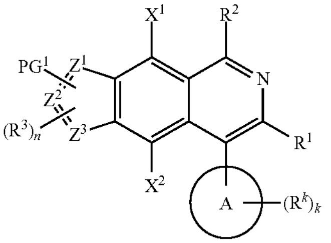

1-1

Scheme 3 provides processes for the preparation of compounds of formula 2-10.

Definitions: $Y^3$ is a halogen such as Br, or I. $PG^1$ is defined as above.

Arylation of compounds of Formula 3-2 with aryl halides of formula 3-1 affords compounds of formula 3-3. In some embodiments, palladium catalyzed coupling conditions such as $Pd(dppf)Cl_2$ and cesium carbonate were used. Compound of formula 2-10 may be prepared from compounds 3-3 by treatment with $NH_2OH$.

Scheme 3

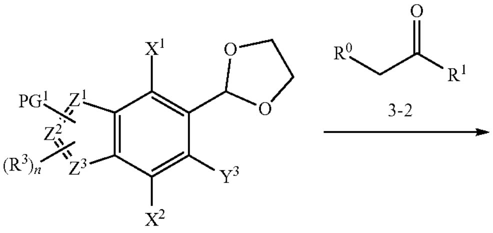

3-1

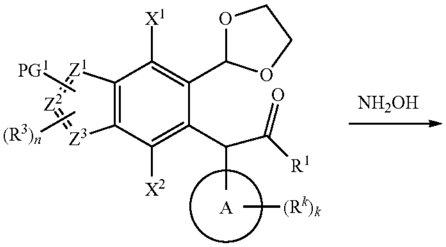

3-3

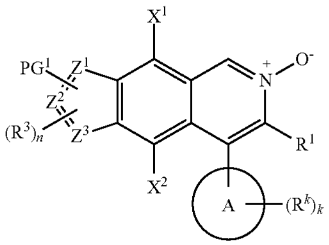

2-10

Scheme 4 depicts processes for the preparation of compounds of formula 4-1 from compounds of formula 2-10. In some embodiments, reagents such as DABCO in the presence of TFAA are used. A solvent such as dichloromethane may be used.

Scheme 4

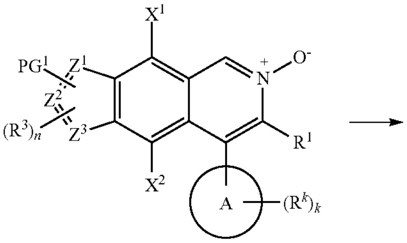

2-10

-continued

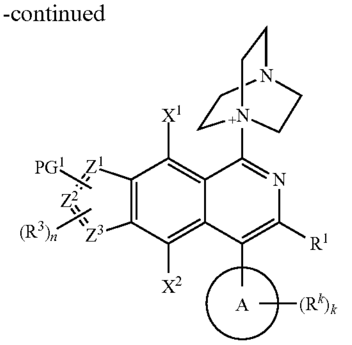

4-1

Scheme 5 shows one possible method for preparation of compounds of formula 5-3. Compounds of Formula 5-2 may be prepared from aryl chlorides of formula 2-11 and alcohols of formula 5-1. In some embodiments, bases such as NaH, $Cs_2CO_3$ or $K_2CO_3$ may be used. A solvent such as DMSO may be used. The reaction may be performed in the presence of added heat (e.g. 50° C.).

Definitions: $R^{12}$ may be alkyl or aryl.

A compound of formula 5-3 may be prepared from 5-2 using any suitable conditions for the removal of a nitrogen protecting group. For example, trifluoroacetic acid may be used.

Scheme 5

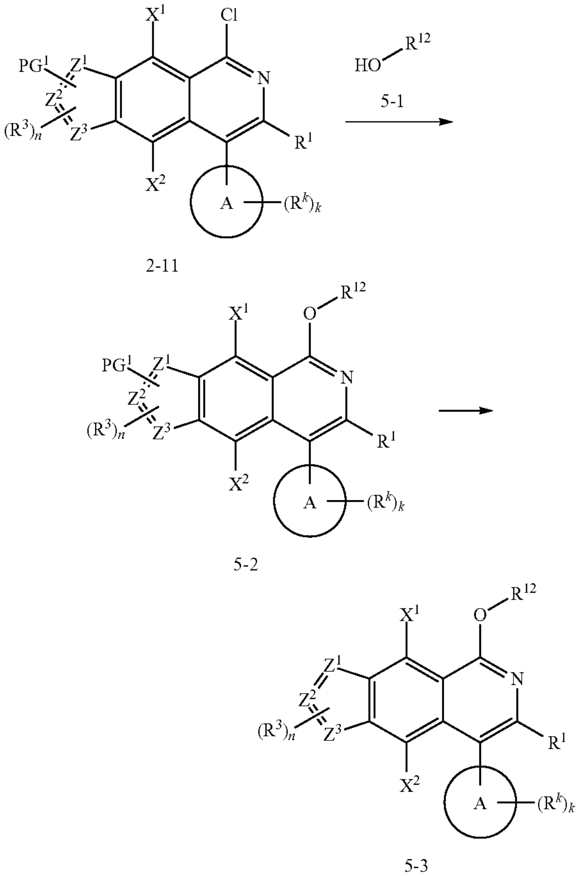

2-11

5-1

5-2

5-3

Scheme 6 depicts processes for the preparation of compound 6-3. Definitions: $R^{13}$ may be OMe, halogen, Phosphonate, phosphite, —$CO_2R^{50}$. In some embodiments, a compound of formula 6-2 may be prepared from compound of formula 2-10 and 6-1 by treatment with 2-isopropoxy-phos-phonoyloxypropane, DIPEA. A solvent system such as $CCl_4$ and MeCN may be used. The reaction may be performed in the presence of additional heat (e.g. 40° C.). Compounds of formula 6-3 may be prepared from 6-2 using a suitable reagent for removal of $PG^1$. Where $PG^1$ is a THP group, TFA in dichloromethane may be used.

Scheme 6

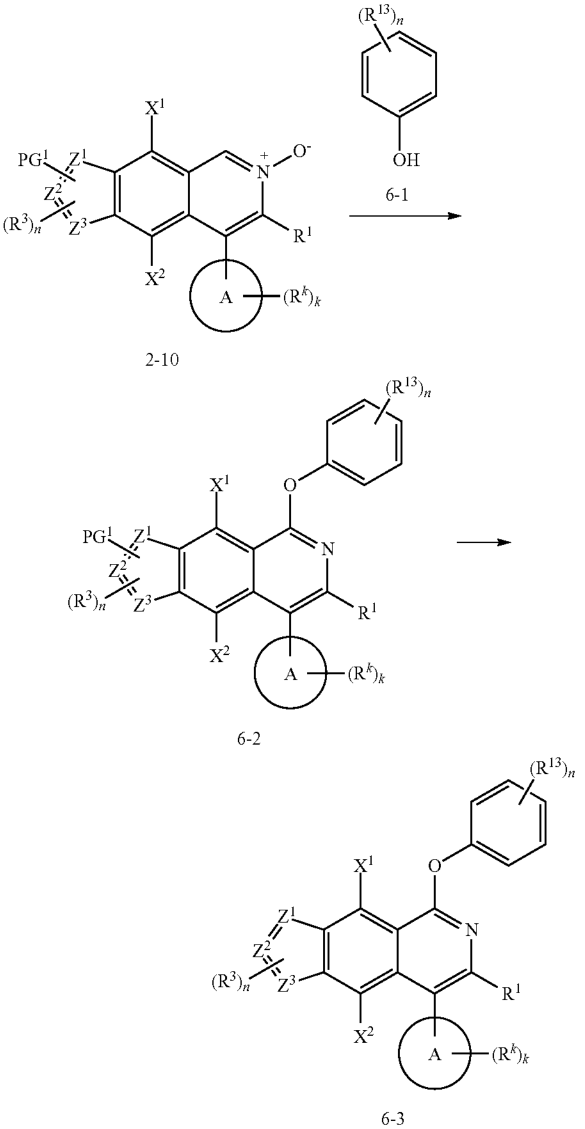

2-10

6-1

6-2

6-3

Processes for the preparation of compounds of Formula 7-4 are shown in Scheme 7.

Definitions: $R^{14}$=alkyl such as Me, Et, tBu; $L^1$=any linear, branched or cyclic alkyl.

A compound of formula 7-2 may be prepared from a compound of Formula 2-10 and an amine of Formula 7-1 using a suitable reagent for coupling an amine to a pyridine N-oxide compound. For example, in some embodiments PyBrop and DIPEA may be used. A compound of Formula 7-3 may be prepared from 7-2 using any suitable method for the hydrolysis of an ester. For example, a base such as NaOH in a solvent such as MeOH may be used. Compounds of Formula 7-4 may be prepared using any suitable method for the removal of a protecting group (e.g. THP) from a nitrogen atom.

Scheme 7

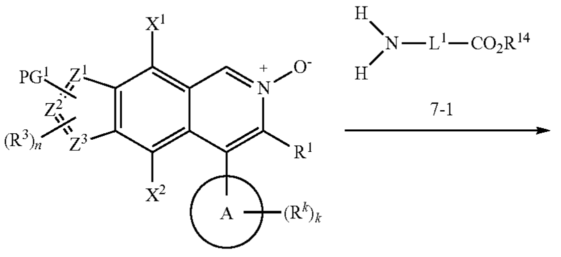

2-10

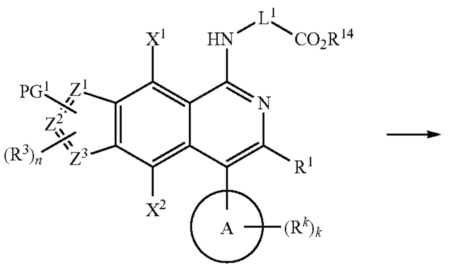

7-2

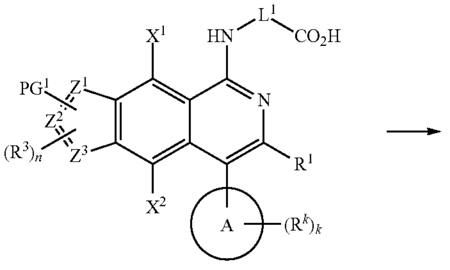

7-3

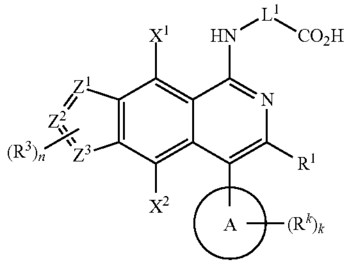

7-4

Compounds of Formula 8-2 may be prepared from intermediate 4-1 and alcohols of formula 8-1 using a suitable base (for example, NaH). A solvent such as DMSO may be used. A compound of formula 8-3 may be prepared from 8-2 by any suitable method for hydrolysis of an ester. Compounds of formula 8-4 may be prepared from 8-3 by treatment with a suitable reagent for removal of a nitrogen protecting group.

Definitions: $R^{15}$=alkyl such as Me, Et or tBu. $L^2$=any linear, branched or cyclic alkyl, or an aryl group.

Scheme 8

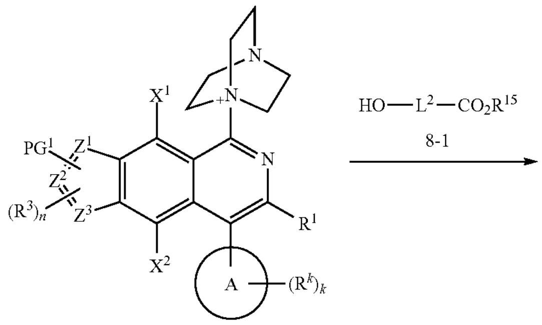

4-1

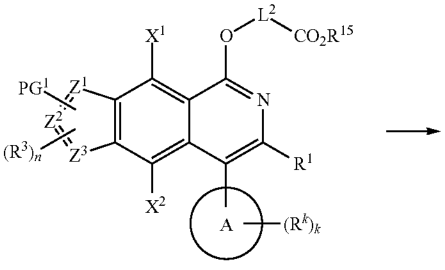

8-2

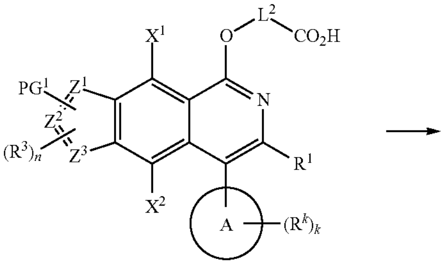

8-3

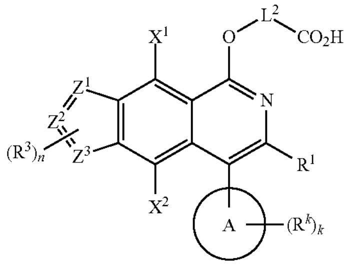

8-4

Scheme 9 describes the preparation of compounds of Formula IIIb' from compounds of Formula 9-1, wherein $PG^1$ is a suitable nitrogen protecting group as defined above. Any suitable method for the removal of a nitrogen protecting group may be used. For example, when $PG^1$ is a Tosyl group, then removal may be achieved by treatment with a base such as NaOH or LiOH in a solvent such as THF and water, with added heat. For example, in some embodiments the reaction may be performed at 50° C.

Scheme 9

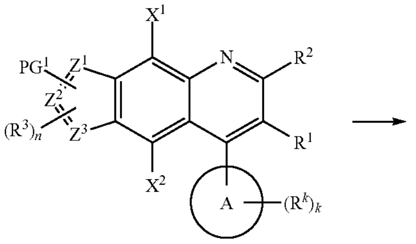

9-1

-continued

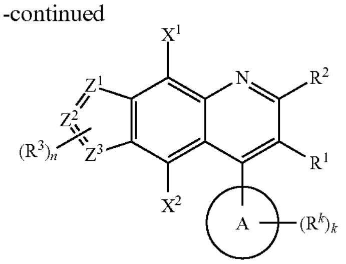

(IIIb')

Scheme 10 provides methods for the preparation of compounds of Formula IIIb' and formula 9-1 from a compound of Formula 10-1.

Definitions: $Y^4$=halogens (e.g. Cl).

Compounds of Formula IIIb' may be prepared from 10-1 by any method known to those skilled in the art for coupling of an aryl halide 10-1 with an organometallic reagent of formula $R^2$-[M]. Compounds of formula 9-1 may be prepared by coupling an organometallic reagent with compounds of formula 10-2.

Scheme 10

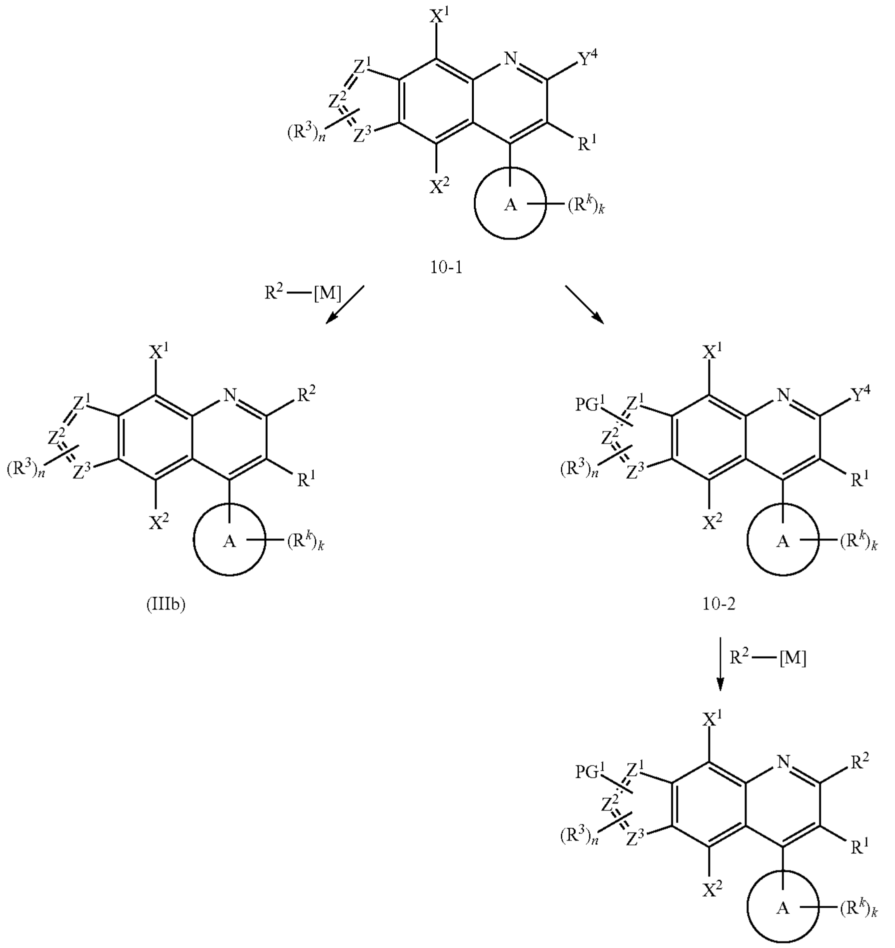

10-1

(IIIb)

10-2

9-1

Scheme 11 refers to methods for the preparation of compounds of Formula 10-1 from compounds of Formula 11-1. Compounds of formula 11-1 may be converted to compounds of formula 11-2 using any suitable method for reduction of an ester to an alcohol. In some embodiments, this may be performed with $NaBH_4$ in the presence of a reagent such as ethyl chloroformate. Compounds of formula 11-3 may be prepared by the oxidation of compounds of formula 11-2 with a suitable reagent system for the oxidation of alcohols to aldehydes. In some examples, oxalyl chloride, $NEt_3$ in DMSO may be used. Compounds of formula 11-4 may be prepared using any suitable reagent for reaction of orthohalogen-substituted aryl aldehydes 11-3 to form a five-membered heterocyclic ring. For example, in some embodiments where $Z^1$ and $Z^2$ are nitrogen atoms, and $Z^3$ is CH, hydroxylamine and $K_2CO_3$, followed by hydrazine may be used to give compounds of formula 11-4. Compounds for formula 11-5 may be prepared from 11-4 by treatment with an oxidizing reagent such as mCPBA. A compound of formula 10-1 may be prepared by treatment with any suitable reagent for conversion of a pyridyl N-oxide to an aryl halide. For example, $POCl_3$ may be used.

Definitions: $R^{16}$ is an alkyl (e.g. Me, Et, tBu). $Y^5$ is a halogen such as F. $Y^4$=Cl or Br.

Scheme 11

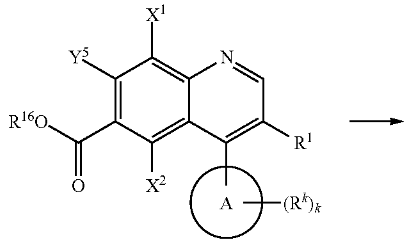

11-1

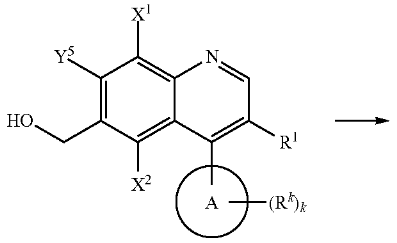

11-2

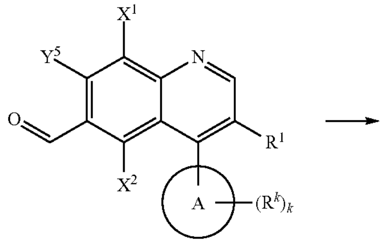

11-3

-continued

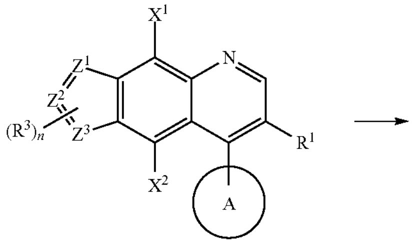

11-4

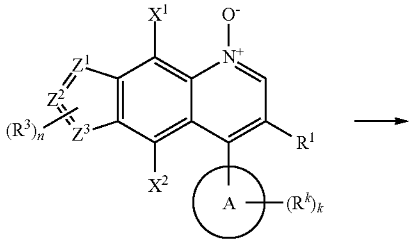

11-5

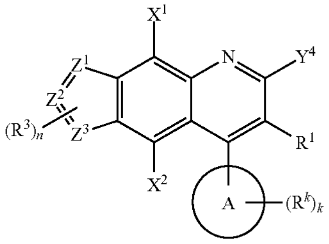

10-1

Scheme 12 depicts processing for the preparation of compounds of formula 12-3 and 12-6 from formula 11-5 and amines of formula 12-1 and 12-4. Any suitable method for addition of amines to N-oxides may be used in the preparation of compounds 12-2 and 12-5. In some embodiments, PyBrop and DIPEA in a solvent such as dichloromethane may be used. Compounds of formula 12-3 may be prepared from 12-2 by any suitable method for ester hydrolysis. In some embodiments, a base such as NaOH or LiOH may be used. A solvent such as THF or MeOH may be used. Compounds 12-6 may be prepared from 12-5 using any method suitable for the hydrolysis of an alkyl ester.

Definitions: $R^{17}$=alkyl groups (e.g. Me, Et, tBu). $L^3$, $L^4$ and $L^5$ are any alkyl linker groups.

Scheme 12

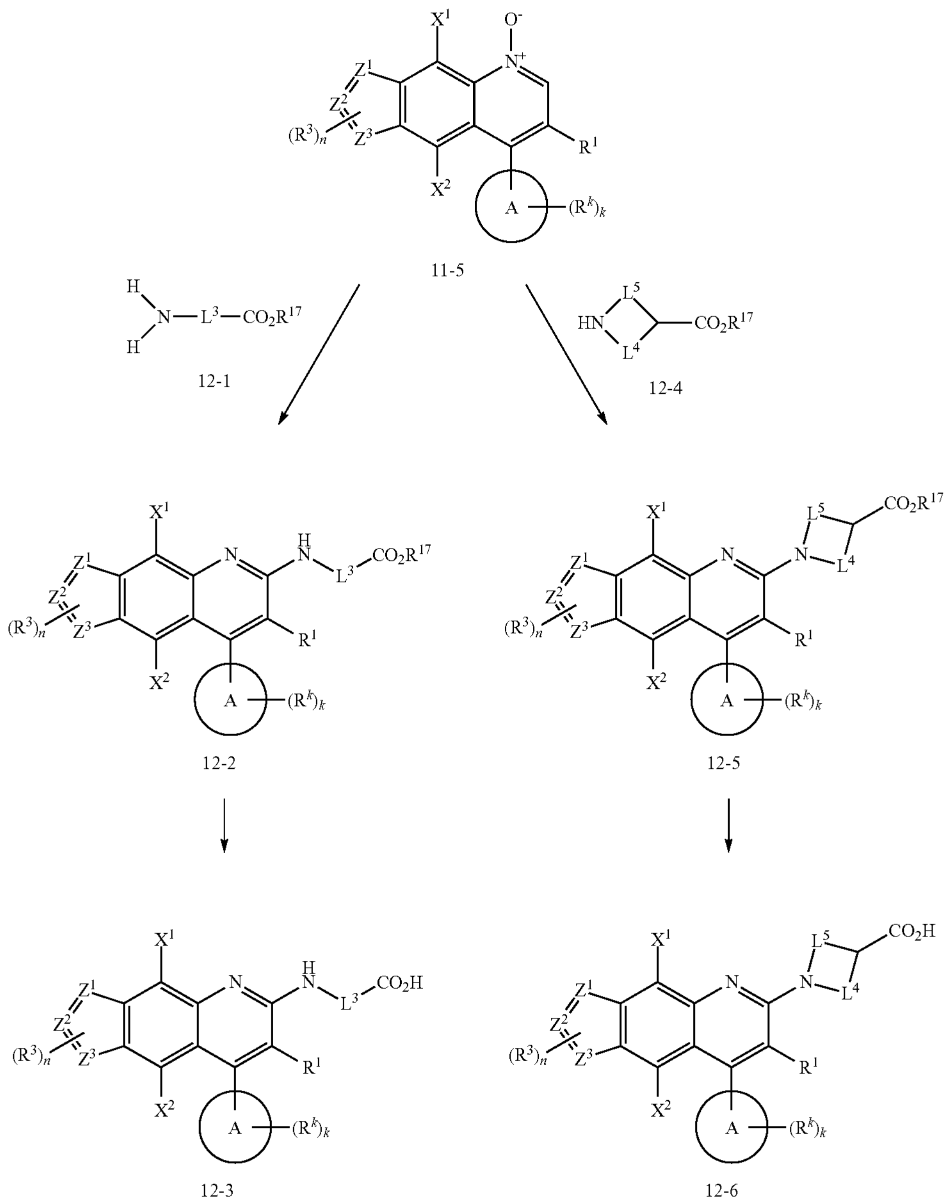

Scheme 13 refers to methods for the preparation of compounds of formula 13-10 from a compound of formula 13-1. Compounds of formula 13-3 may be prepared from 13-1 using any suitable method for the formation of an amide. In some embodiments, the reaction of an acyl halide of formula 13-2, in the presence of a base such as DIPEA may be used. Compounds of formula 13-5 may be prepared from 13-3 by reaction with a compound of formula 13-4. A reagent system such as ammonium sulfooxyhydrogen sulfate and $Pd(TFA)_2$ may be used. Compounds of Formula 13-5 may be transformed into compounds of formula 13-6 by treatment with any suitable reagent for performing an intramolecular condensation onto a ketone. For example, in some embodiments, a base such as LiOMe in a solvent such as DMF may be used. Additional heat (e.g. 80° C.) may be added. Compounds of formula 13-7 may be prepared from 13-6 by treatment with a reagent such as $POCl_3$ at elevated temperature (e.g. 100° C.). A compound of formula 13-8 may be prepared by treatment of compounds of formula 13-7 with a halogenating reagent such as N-bromosuccinimide in $CCl_4$ in the presence of compact fluorescence light. Compounds of formula 13-8 may be prepared from 13-9 by any method suitable for transformation of a benzyl halide to an aldehyde. For example, N-methyl morpholine oxide in the presence of 4 A molecular sieves may be used. The reaction may be performed in a solvent such as MeCN. Compounds of formula 13-10 may be prepared by treatment of compounds of formula 13-9 with a reagent such as tosyl hydrazine and $Cu_2O$. The reaction may be performed at elevated temperature (e.g. 130° C.) in a solvent such as tBuOH.

Definitions: $Y^6$, $Y^7$=halogens such as F, Cl or Br. $PG^2$=Ts. $Y^8$=Cl.

Scheme 13

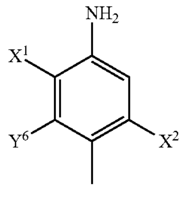

13-1

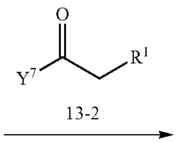

13-2

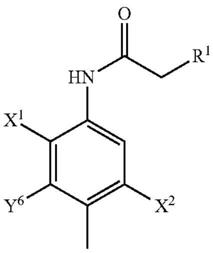

13-3

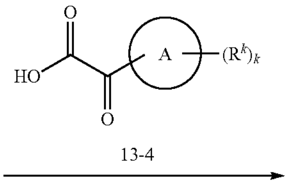

13-4

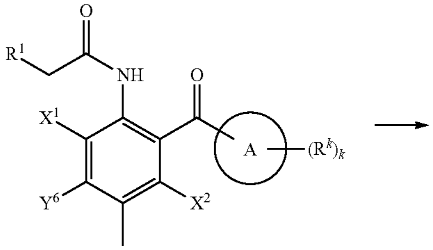

13-5

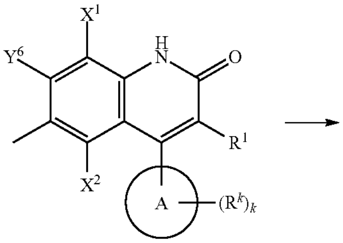

13-6

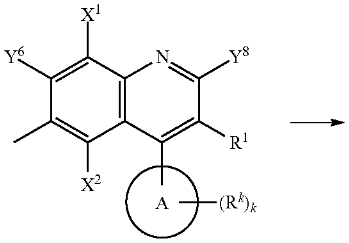

13-7

-continued

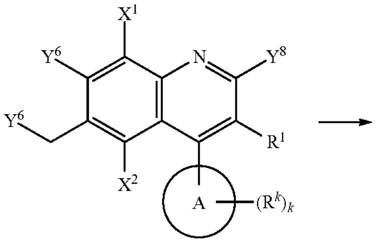

13-8

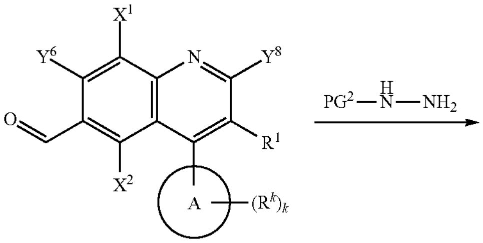

13-9

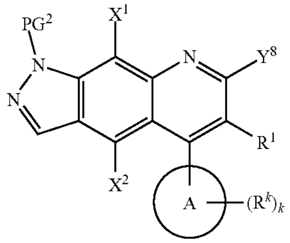

13-10

Scheme 14 shows a method for the preparation of compounds of formula 14-5.

Definitions: $Y^6$ is defined as above. $Y^8$ is a halogen such as Cl.

$PG^3$ may be tosyl or any suitable nitrogen protecting group. $L^6$=alkyl or aryl. Compounds of formula 14-2 may be prepared by addition of alcohols of formula 14-1 to compounds of formula 13-9. Bases such as KOtBu, $K_2CO_3$ or NaH may be used. Solvents such as THF or DMF may be used. Compounds of formula 14-4 may be prepared from 14-2 and an N-protected hydrazine of formula 14-3 in the presence of $Cu_2O$ in a solvent such as EtOH. The reaction may be performed in the presence of added heat (e.g. 130° C.). Compounds of formula 14-4 may be converted to a compound of formula 14-5 using any suitable conditions for simultaneous remove of a N-tosyl protecting group and hydrolysis of an ester. In some embodiments, the reaction is performed in the presence of a base such as LiOH in a solvent such as MeOH, THF and water. The reaction may be performed in the presence of additional heat (e.g. at 50° C.).

Scheme 14

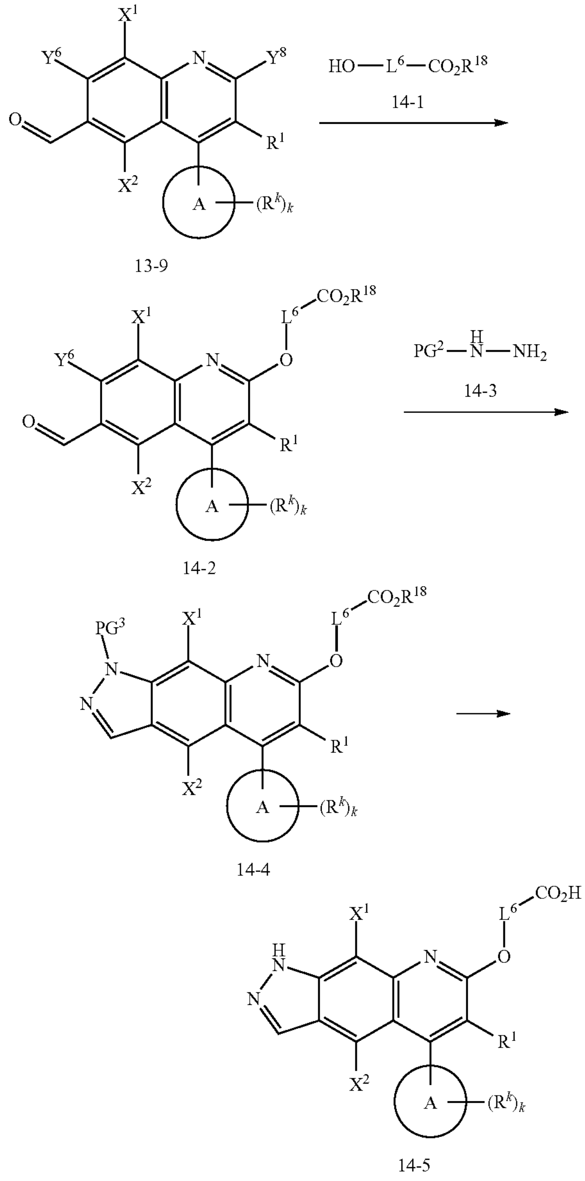
13-9
14-1
14-2
14-3
14-4
14-5

Scheme 15 depicts processes for the preparation of compounds of formula 15-8.

Definitions: $Y^9$=halogens (e.g. Cl, Br, I). $R^{19}$=alkyl group. $R^{20}$ is any suitable group which forms a suitable boronic ester or acid (e.g. H or alkyl). $PG^4$ is a THP group. $E^1$ as defined above. Compounds of formula 15-2 may be prepared from 3-1 by Sonagashira coupling of an alkyne of formula 15-1 using methods know to those skilled in the art. Compounds of formula 15-3 may be prepared from 15-2 by treatment with a reagent system such as molecular iodine and a base such as $NaHCO_3$. A solvent such as dichloromethane may be used. A compound of formula 15-5 may be prepared by Suzuki coupling a compound of formula 15-3 with a boronic acid or ester 15-4. Any suitable method for a Suzuki coupling may be used. For example, a RuPhos Pd G4 catalyst system, with a $K_3PO_4$ and NaOH mixture as the base may be used. A compound of formula 15-7 may be prepared by treatment of 15-5 with an amine such as 15-6, together with pyridine and molecular sieves. Where $PG^4$ is a group such as THP, a compound of formula 15-8 may be prepared by treatment compounds of formula 15-7 with an acid such as HCl or p-toluene sulfonic acid, then ester hydrolysis with a base such as LiOH.

Scheme 15

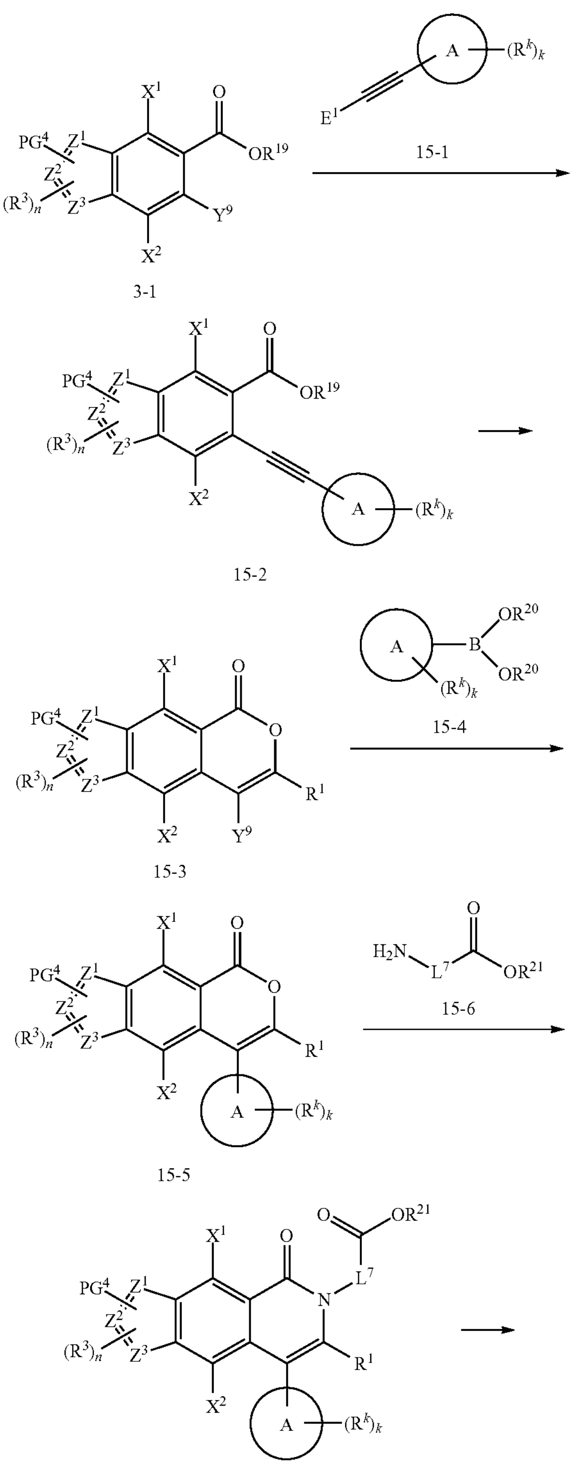
3-1
15-1
15-2
15-3
15-4
15-5
15-6
15-7

-continued

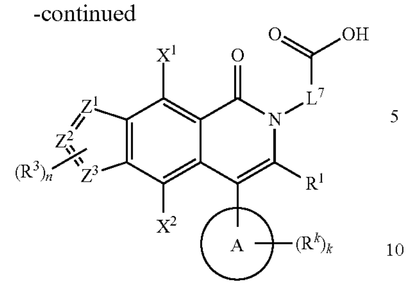

15-8

Scheme 16 described processes for the preparation of compounds of formula 16-4 and 16-7. Definitions: $L^8$ is an alkyl group. $R^{22}$ is any suitable alkyl (e.g. Me, Et, tBu). $PG^4$ is defined as above.

A compound of formula 16-1 may be prepared from 15-5 by treatment with a base such as NaOH in a solvent such as EtOH under reflux temperatures. Compounds of formula 16-3 or 16-6 may be prepared from 16-1 by coupling of an appropriate amine, such as 16-2 or 16-5, using an amide coupling reagent such as HATU in the presence of an organic base (e.g. DIPEA). A solvent such as DMF may be used. Compounds of formula 16-4 may be prepared from 16-3 in two steps using reagents for removal of a nitrogen atom protecting group, then suitable reagents for ester hydrolysis. For example, in some embodiments, treatment of 16-3 by p-toluene sulfonic acid at elevated temperature (e.g. 65° C.), followed by hydrolysis with a base such as NaOH provides compounds of formula 16-4. Compounds of formula 16-7 may be prepared from compounds of formula a 16-6 by treatment with acid such as p-toluene sulfonic acid or HCl.

Scheme 16

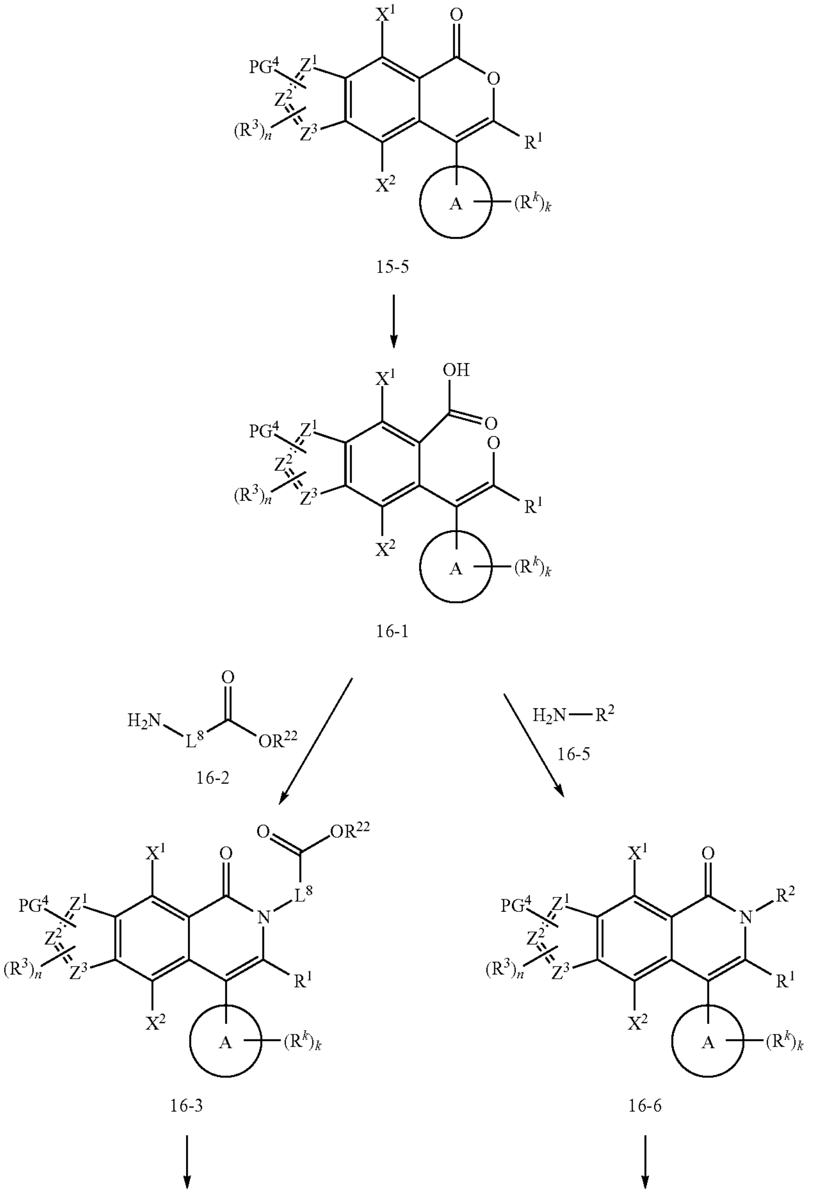

15-5

16-1

16-2

16-5

16-3

16-6

-continued

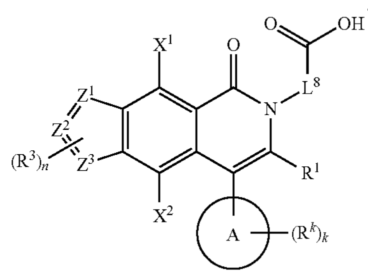

16-4

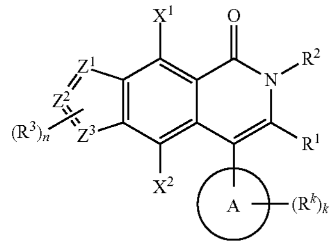

16-7

Synthesis of Starting Materials

The following describes synthetic routes to intermediates used in the synthesis of compounds 1-262.

Preparation of S1

5-iodo-7-oxido-1-tetrahydropyran-2-yl-6-tetrahydropyran-4-yl-pyrazolo[4,3-g]isoquinolin-7-ium (S1)

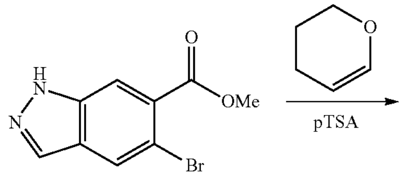

C1

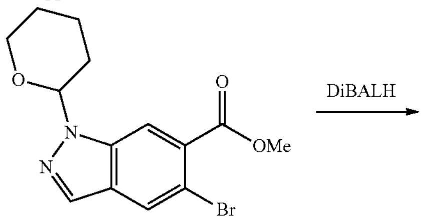

C2

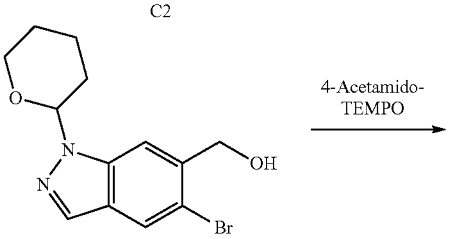

C3

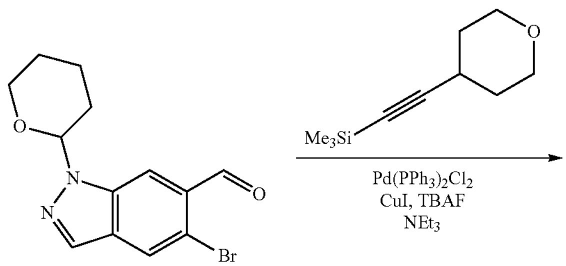

C4

-continued

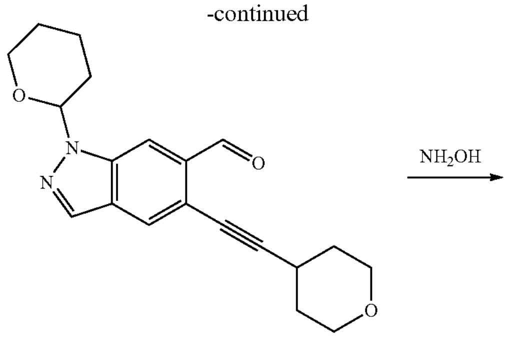

C5

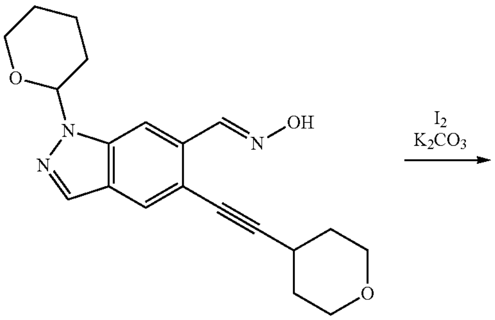

C6

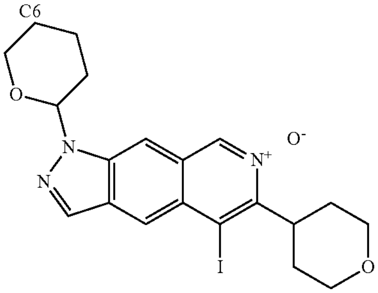

S1

Step 1. Synthesis of methyl 5-bromo-1-tetrahydropyran-2-yl-indazole-6-carboxylate (C2)

In a 5 L 3-neck flask, to a solution/suspension of methyl 5-bromo-1H-indazole-6-carboxylate (200 g, 784.1 mmol) in dichloromethane (2.4 L) at room temperature was added DHP (92 mL, 1.008 mol) followed by 4-methylbenzenesulfonic acid monohydrate (1.8 g, 9.463 mmol). After ~20 min, suspension is consumed, clear solution achieved. The mixture was allowed to stir at room temperature overnight. The mixture was washed with saturated aqueous $NaHCO_3$ (2×1 L), then brine (1 L), dried over ($MgSO_4$), filtered and concentrated to afford the product. Methyl 5-bromo-1-tetrahydropyran-2-yl-indazole-6-carboxylate (266 g, 100%). $^1$H NMR (300 MHz, Chloroform-d) δ 8.04 (t, J=0.7 Hz, 1H), 8.02 (d, J=0.5 Hz, 1H), 8.00 (d, J=0.9 Hz, 1H), 5.74 (dd, J=9.0, 2.7 Hz, 1H), 4.04-3.96 (m, 1H), 3.98 (s, 3H), 3.83-3.67 (m, 1H), 2.62-2.43 (m, 1H), 2.22-2.02 (m, 2H), 1.87-1.62 (m, 3H).

Step 2. Synthesis of (5-bromo-1-tetrahydropyran-2-yl-indazol-6-yl)methanol (C3)

DIBALH (50 mL of 1 M, 50.00 mmol) was added via syringe over 15 minutes to a solution of methyl 5-bromo-1-tetrahydropyran-2-yl-indazole-6-carboxylate (6.5 g, 19.16 mmol) in dichloromethane (60 mL) at −78° C. After one hour, the mixture was quenched by the addition of ethyl acetate (10 mL) and saturated Rochelle's salt (100 mL) and the mixture warmed to room temperature and stirred vigorously until the layers became clear (~2 hours). The layers were separated and the aqueous layer was re-extracted with dichloromethane. The combined organic layers were washed with brine, dried over sodium sulfate, filtered and concentrated to afford (5-bromo-1-tetrahydropyran-2-yl-indazol-6-yl)methanol (5.81 g, 97%) as an off-white solid. $^1$H NMR (300 MHz, Chloroform-d) δ 7.96 (d, J=0.9 Hz, 1H), 7.91 (s, 1H), 7.77-7.66 (m, 1H), 5.72 (dd, J=9.5, 2.6 Hz, 1H), 4.83 (d, J=1.2 Hz, 2H), 4.11-3.95 (m, 1H), 3.85-3.70 (m, 1H), 2.66-2.48 (m, 1H), 2.40 (s, 1H), 2.25-1.98 (m, 2H), 1.89-1.41 (m, 3H). LCMS m/z 311.2 $[M+H]^+$.

Step 3. Synthesis of 5-bromo-1-tetrahydropyran-2-yl-indazole-6-carbaldehyde (C4)

In a 12 L 3-neck flask equipped with a temp probe and mechanical stirrer, to a solution of (5-bromo-1-tetrahydropyran-2-yl-indazol-6-yl)methanol (100 g, 321.4 mmol) in dichloromethane (2.75 L) at 3° C. (ice-water bath) was added water (750 mL) followed by $NaHCO_3$ (44.5 g, 529.7 mmol), NaBr (2.08 g, 20.22 mmol), 4-Acetamido-TEMPO, free radical (1.05 g, 4.923 mmol). To the resulting stirred biphasic mixture was added sodium hypochlorite (250 mL of 2 M, 500.0 mmol) (10-15% aq, 2 M used as approximate concentration) dropwise via addition funnel over the course of 20 minutes. Mildly exothermic, internal temperature rises to 6° C. The mixture was stirred for a further 1 h in ice-water bath to achieve an internal temp of 2° C. The layers were separated and the aqueous layer was extracted with dichloromethane (500 mL). Combined dichloromethane layers were dried ($MgSO_4$), filtered and concentrated to afford the product as a yellow/brown solid. 5-bromo-1-tetrahydropyran-2-yl-indazole-6-carbaldehyde (99 g, 100%) $^1$H NMR (400 MHz, Chloroform-d) δ 10.55 (s, 1H), 8.25 (t, J=0.8 Hz, 1H), 8.06 (d, J=1.0 Hz, 1H), 8.04 (d, J=0.6 Hz, 1H), 5.79 (dd, J=9.6, 2.6 Hz, 1H), 4.12-4.03 (m, 1H), 3.86-3.75 (m, 1H), 2.63-2.48 (m, 1H), 2.25-2.06 (m, 2H), 1.89-1.59 (m, 3H).

Step 4. Synthesis of 1-tetrahydropyran-2-yl-5-(2-tetrahydropyran-4-ylethynyl)indazole-6-carbaldehyde (C5)

A solution of 5-bromo-1-tetrahydropyran-2-yl-indazole-6-carbaldehyde (5 g, 16.17 mmol) and trimethyl(2-tetrahydropyran-4-ylethynyl)silane (3.1 mL, 16.83 mmol) in triethylamine (70 mL), 1,4-dioxane (8 mL) and water (580 μL, 32.19 mmol) was sparged with nitrogen for 15 minutes at 50° C. $Pd(PPh_3)_2Cl_2$ (552 mg, 0.7864 mmol) and CuI (226 mg, 1.187 mmol) were added, followed by the addition of TBAF (18 mL of 1 M, 18.00 mmol) (in THF) via syringe over 2 minutes. The mixture turned dark. Upon sparging the mixture with nitrogen for 5 minutes, the flask was placed under nitrogen and stirred at 50° C. for 6 hours. The reaction was cooled and the majority of the solvents were removed in vacuo. The residue was dissolved in EtOAc and washed with 1 M HCl (2×) and ammonium chloride solution (1×) and brine, dried over sodium sulfate, filtered and concentrated in vacuo to a dark oil. The residue was dissolved in dichloromethane (~15 mL) and IPA (50 mL) was added, and then the mixture was concentrated in vacuo to ~25 mL. The solution was seeded with crystals and the flask scraped with a spatula to induce crystallization. After sitting for 1 hour, the solid was collected by vacuum filtration and washed with cold IPA and dried under vacuum to afford 3.3 g as a tan solid. The residue was concentrated and the purified by flash chromatography on silica gel (Gradient: 5-30% EtOAc/heptanes) to afford an additional 1.1 g of product. 1-tetrahydropyran-2-yl-5-(2-tetrahydropyran-4-ylethynyl)indazole-6-carbaldehyde (4.4 g, 80%). $^1$H NMR (300 MHz, Chloroform-d) δ 10.71 (s, 1H), 8.20 (s, 1H), 8.08 (d, J=0.9 Hz, 1H), 7.94 (d, J=0.7 Hz, 1H), 5.79 (dd, J=9.7, 2.5 Hz, 1H), 4.14-3.92 (m, 3H), 3.80 (ddd, J=13.4, 10.6, 3.0 Hz, 1H), 3.60 (ddd, J=11.7, 8.7, 3.0 Hz, 2H), 2.96 (tt, J=8.6, 4.2 Hz, 1H), 2.67-2.42 (m, 1H), 2.25-1.92 (m, 4H), 1.80 (dddd, J=21.2, 18.3, 9.9, 5.4 Hz, 5H). LCMS m/z 339.0 $[M+H]^+$.

Step 5. Synthesis of (6E)-1-tetrahydropyran-2-yl-5-(2-tetrahydropyran-4-ylethynyl)indazole-6-carbaldehyde oxime (C6)

A solution of hydroxylamine (Hydrochloride salt) (1.4 g, 20.15 mmol) in pyridine (10 mL, 123.6 mmol) was added over two minutes to a solution of 1-tetrahydropyran-2-yl-5-(2-tetrahydropyran-4-ylethynyl)indazole-6-carbaldehyde (2.23 g, 6.590 mmol) in acetonitrile (30 mL) at room temperature. After stirring at room temperature for 1 hour, the mixture was concentrated in vacuo to remove the acetonitrile, and the residue was partitioned between EtOAc and water. The organic layer was washed with water (3×), 1 M HCl (1×) and brine, dried over sodium sulfate, filtered and concentrated to afford the product. (6E)-1-tetrahydropyran-2-yl-5-(2-tetrahydropyran-4-ylethynyl)indazole-6-carbaldehyde oxime (2.32 g, 100%) as a tan solid which was used without further purification. LCMS m/z 354.0 $[M+H]^+$.

Step 6. Synthesis of 5-iodo-7-oxido-1-tetrahydropyran-2-yl-6-tetrahydropyran-4-yl-pyrazolo[4,3-g]isoquinolin-7-ium (S1)

(6E)-1-tetrahydropyran-2-yl-5-(2-tetrahydropyran-4-ylethynyl)indazole-6-carbaldehyde oxime (790 mg, 2.235 mmol) (as a solution in 15 mL dichloromethane) was added to a mixture of molecular iodine (1.56 g, 6.146 mmol) and $K_2CO_3$ (940 mg, 6.801 mmol) in dry dichloromethane (20 mL) at room temperature over 30 minutes. After stirring at room temperature for an additional 30 minutes, the reaction was quenched by the addition of sodium bicarbonate and sodium thiosulfate solutions (4:1). The layers were separated and the aqueous layer extracted with dichloromethane and the combined organic layers were dried over sodium sulfate, filtered and concentrated. The residue was purified by flash chromatography on silica gel (Gradient: 0-5% MeOH in dichloromethane, then isocratic 5% methanol in dichloromethane) to afford the product as a dark brown solid. 5-iodo-7-oxido-1-tetrahydropyran-2-yl-6-tetrahydropyran-4-yl-pyrazolo[4,3-g]isoquinolin-7-ium (740 mg, 69%). $^{1}$H NMR (300 MHz, Chloroform-d) δ 8.83 (s, 1H), 8.61 (s, 1H), 8.34 (d, J=1.1 Hz, 1H), 7.77 (s, 1H), 5.85 (dd, J=9.1, 2.5 Hz, 1H), 4.18 (dd, J=11.2, 4.4 Hz, 2H), 4.06 (dd, J=12.0, 4.2 Hz, 1H), 3.84 (ddd, J=11.4, 9.4, 3.5 Hz, 1H), 3.61 (t, J=11.8 Hz, 2H), 3.24 (s, 2H), 2.73-2.51 (m, 1H), 2.18 (d, J=12.6 Hz, 2H), 1.94-1.70 (m, 3H), 1.62 (d, J=13.1 Hz, 3H). LCMS m/z 480.0 [M+H]$^{+}$.

Preparation of S2 and S3

5-(2-methyl-4-pyridyl)-7-oxido-1-tetrahydropyran-2-yl-6-tetrahydropyran-4-yl-pyrazolo[4,3-g]isoquinolin-7-ium (S2) and 8-chloro-5-(2-methyl-4-pyridyl)-1-tetrahydropyran-2-yl-6-tetrahydropyran-4-yl-pyrazolo[4,3-g]isoquinoline (S3)

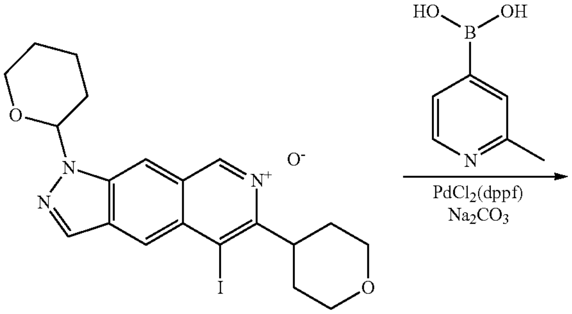

S1

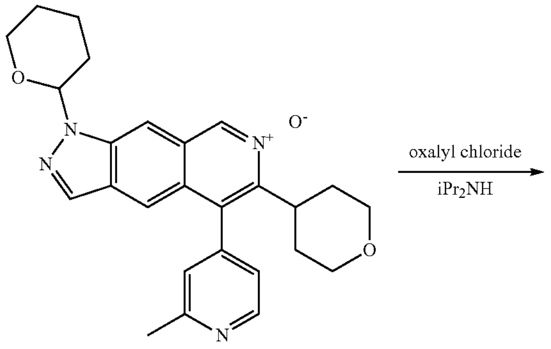

S2

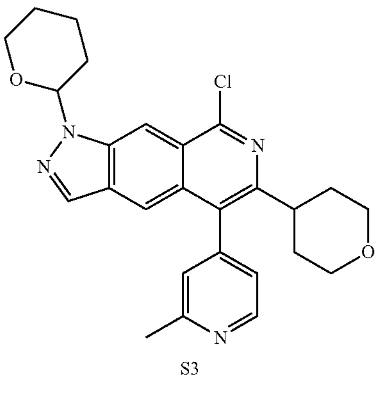

S3

Step 1. Synthesis of 5-(2-methyl-4-pyridyl)-7-oxido-1-tetrahydropyran-2-yl-6-tetrahydropyran-4-yl-pyrazolo[4,3-g]isoquinolin-7-ium (S2)

Sodium carbonate (6 mL of 2 M, 12.00 mmol) was added to a solution of 5-iodo-7-oxido-1-tetrahydropyran-2-yl-6-tetrahydropyran-4-yl-pyrazolo[4,3-g]isoquinolin-7-ium (3 g, 6.259 mmol) and (2-methyl-4-pyridyl)boronic acid (1.3 g, 9.493 mmol) in DMSO (60 mL) at room temperature. The mixture was bubbled with nitrogen for 5 min, then Pd(dppf)$Cl_2$ (280 mg, 0.3429 mmol) was added and the reaction heated at 100° C. for 2 h. The mixture was cooled and diluted with EtOAc and washed with water (3×). The organic layer was then extracted with 2 M HCl (3×) and the aqueous layer was washed with EtOAc (1×) then carefully basified with solid potassium carbonate, and the mixture extracted with dichloromethane (2×). The organic layers were combined and dried over sodium sulfate, filtered and concentrated in vacuo. Purification by silica gel chromatography (Gradient: 0-5% MeOH in dichloromethane) yielded the product. 5-(2-methyl-4-pyridyl)-7-oxido-1-tetrahydropyran-2-yl-6-tetrahydropyran-4-yl-pyrazolo[4,3-g]isoquinolin-7-ium (1.9 g, 68%) as a tan solid. LCMS m/z 445.0 [M+H]$^{+}$.

Step 2. Synthesis of 8-chloro-5-(2-methyl-4-pyridyl)-1-tetrahydropyran-2-yl-6-tetrahydropyran-4-yl-pyrazolo[4,3-g]isoquinoline (S3)

A solution of 5-(2-methyl-4-pyridyl)-7-oxido-1-tetrahydropyran-2-yl-6-tetrahydropyran-4-yl-pyrazolo[4,3-g]isoquinolin-7-ium (660 mg, 1.485 mmol), DIPEA (950 μL, 5.454 mmol) in dichloromethane (10 mL) at −78° C. was treated with a solution of oxalyl dichloride (1 mL of 2 M, 2.000 mmol) over 10 minutes. The reaction was stirred at −78° C. for one hour, then quenched with 5 mL MeOH and concentrated. Purification by silica gel chromatography (Gradient: 0-8% MeOH in dichloromethane). 8-chloro-5-(2-methyl-4-pyridyl)-1-tetrahydropyran-2-yl-6-tetrahydropyran-4-yl-pyrazolo[4,3-g]isoquinoline (520 mg, 76%). $^{1}$H NMR (400 MHz, Chloroform-d) δ 8.75 (d, J=5.0 Hz, 1H), 8.61 (q, J=1.1 Hz, 1H), 8.27-8.16 (m, 1H), 7.68 (d, J=1.0 Hz, 1H), 7.21-7.05 (m, 2H), 5.96 (ddd, J=9.0, 2.8, 1.0 Hz, 1H), 4.25-3.96 (m, 1H), 3.96-3.72 (m, 1H), 3.45-3.23 (m, 2H), 2.84-2.51 (m, 6H), 2.41-2.11 (m, 5H), 1.97-1.66 (m, 2H), 1.61-1.37 (m, 2H). LCMS m/z 463.0 [M+H]$^{+}$.

Preparation of S4

8-(4-aza-1-azoniabicyclo[2.2.2]octan-1-yl)-5-(3,4-difluorophenyl)-1-tetrahydropyran-2-yl-6-tetrahydropyran-4-yl-pyrazolo[4,3-g]isoquinoline (S4)

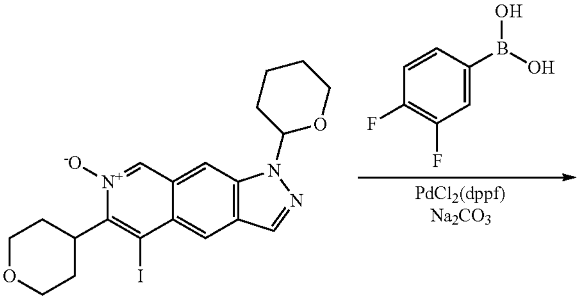

S1

-continued

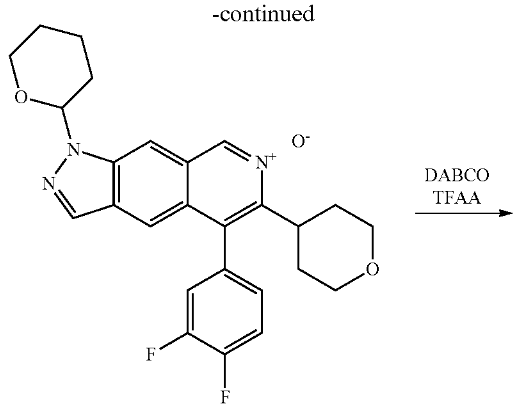

C7

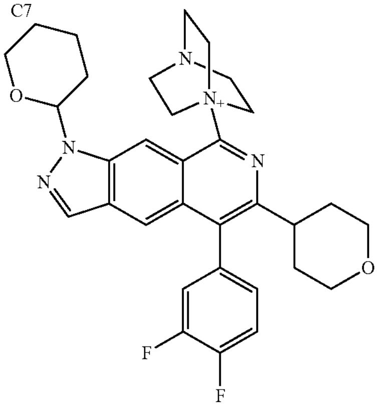

S4

Step 1. Synthesis of 5-(3,4-difluorophenyl)-7-oxido-1-tetrahydropyran-2-yl-6-tetrahydropyran-4-yl-pyrazolo[4,3-g]isoquinolin-7-ium (C7)

To a mixture of 5-iodo-7-oxido-1-tetrahydropyran-2-yl-6-tetrahydropyran-4-yl-pyrazolo[4,3-g]isoquinolin-7-ium (460 mg, 0.9348 mmol), (3,4-difluorophenyl)boronic acid (295 mg, 1.868 mmol) and $Pd(PPh_3)_4$ (63 mg, 0.05452 mmol) in DMF (10 mL) under nitrogen was added $Na_2CO_3$ (2.5 mL of 2 M, 5.000 mmol). The reaction mixture was microwaved at 125° C. for 60 min. Water was added and the mixture was extracted with EtOAc. The combined organic layers were washed with water, brine and dried. Silica gel chromatography (Gradient: 0-10% MeOH in dichloromethane) afforded the product. 5-(3,4-difluorophenyl)-7-oxido-1-tetrahydropyran-2-yl-6-tetrahydropyran-4-yl-pyrazolo[4,3-g]isoquinolin-7-ium (386 mg, 89%). $^1$H NMR (300 MHz, Chloroform-d) δ 8.99 (s, 1H), 8.14 (d, J=0.9 Hz, 1H), 7.87 (d, J=1.3 Hz, 1H), 7.53 (d, J=1.1 Hz, 1H), 7.50-7.37 (m, 1H), 7.18 (ddd, J=10.0, 7.4, 2.1 Hz, 1H), 7.08 (ddd, J=8.3, 4.0, 1.8 Hz, 1H), 5.84 (dd, J=9.1, 2.5 Hz, 1H), 4.03 (t, J=12.3 Hz, 3H), 3.91-3.73 (m, 1H), 3.32 (q, J=11.0 Hz, 3H), 2.94-2.37 (m, 3H), 2.15 (d, J=15.9 Hz, 2H), 1.96-1.70 (m, 3H), 1.49 (s, 2H) ppm. LCMS m/z 466.33 $[M+H]^+$.

Step 2. Synthesis of 8-(4-aza-1-azoniabicyclo[2.2.2]octan-1-yl)-5-(3,4-difluorophenyl)-1-tetrahydropyran-2-yl-6-tetrahydropyran-4-yl-pyrazolo[4,3-g]isoquinoline (S4)

To a solution of 5-(3,4-difluorophenyl)-7-oxido-1-tetrahydropyran-2-yl-6-tetrahydropyran-4-yl-pyrazolo[4,3-g]isoquinolin-7-ium (200 mg, 0.4297 mmol) and 1,4-diazabicyclo[2.2.2]octane (250 mg, 2.229 mmol) in $CH_2Cl_2$ (5 mL) at 0° C. was added TFAA (366 mg, 1.743 mmol). The reaction was stirred at 0° C. for 1 hour, then allowed to warm to ambient temperature and continue stirring for additional 3 hours. The reaction mixture was concentrated in vacuo to afford the product, which was used in the next reaction without further purification. 8-(4-aza-1-azoniabicyclo[2.2.2]octan-1-yl)-5-(3,4-difluorophenyl)-1-tetrahydropyran-2-yl-6-tetrahydropyran-4-yl-pyrazolo[4,3-g]soquinoline (Trifluoroacetic Acid (3)) (388 mg, 100%) LCMS m/z 560.84 $[M+H]^+$.

Preparation of S5 and S6

8-(4-aza-1-azoniabicyclo[2.2.2]octan-1-yl)-5-(3,4-difluorophenyl)-6-tetrahydropyran-4-yl-1H-pyrazolo[4,3-g]isoquinoline (S5) and 8-chloro-5-(3,4-difluorophenyl)-1-tetrahydropyran-2-yl-6-tetrahydropyran-4-yl-pyrazolo[4,3-g]isoquinoline (S6)

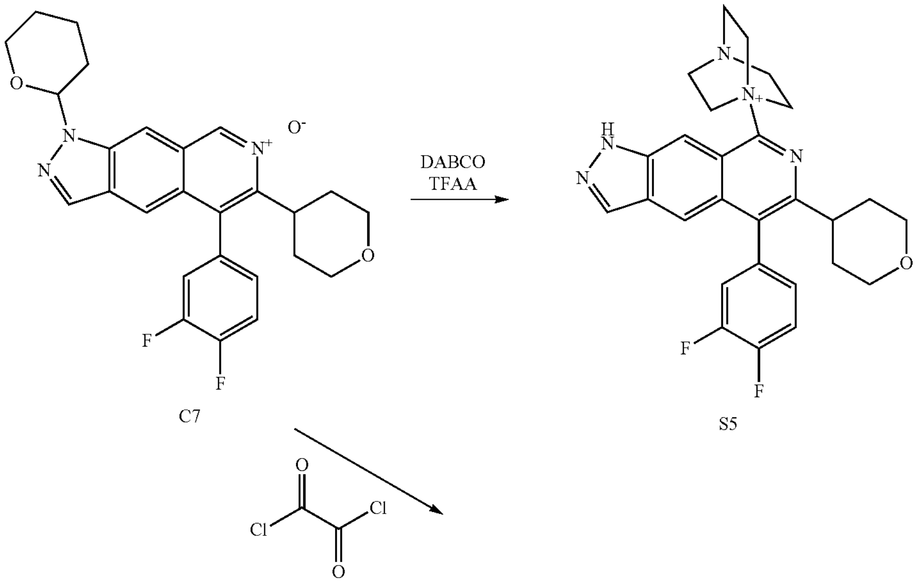

C7

S5

-continued

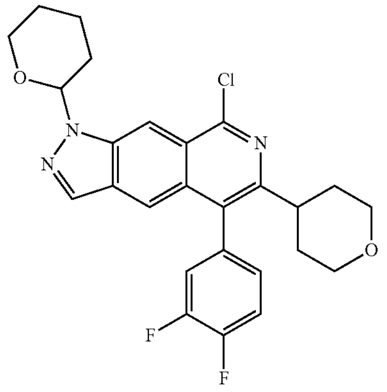

S6

Step 1. Synthesis of 8-(4-aza-1-azoniabicyclo[2.2.2]octan-1-yl)-5-(3,4-difluorophenyl)-6-tetrahydropyran-4-yl-1H-pyrazolo[4,3-g]isoquinoline (S5)

A solution of 5-(3,4-difluorophenyl)-7-oxido-6-tetrahydropyran-4-yl-1H-pyrazolo[4,3-g]isoquinolin-7-ium (Hydrochloride salt) (254 mg, 0.5268 mmol), 1,4-diazabicyclo[2.2.2]octane (300 mg, 2.674 mmol) in dichloromethane (2 mL) was added TFAA (300 μL, 2.158 mmol) at room temperature. The mixture was allowed to stir for 1 hour. The mixture was concentrated and dissolved in DMSO. Purification by reversed-phase chromatography (Column: C18. Gradient: 10-100% MeCN in water with 0.1% trifluoroacetic acid) afforded the product.8-(4-aza-1-azoniabicyclo[2.2.2]octan-1-yl)-5-(3,4-difluorophenyl)-6-tetrahydropyran-4-yl-1H-pyrazolo[4,3-g]isoquinoline (Trifluoroacetic Acid (2)) (321 mg, 85%). LCMS m/z 476.38 $[M+H]^+$.

Step 2. Synthesis of 8-chloro-5-(3,4-difluorophenyl)-1-tetrahydropyran-2-yl-6-tetrahydropyran-4-yl-pyrazolo[4,3-g]isoquinoline (S6)

A solution of 5-(3,4-difluorophenyl)-7-oxido-1-tetrahydropyran-2-yl-6-tetrahydropyran-4-yl-pyrazolo[4,3-g]isoquinolin-7-ium (1.9 g, 4.082 mmol), DIPEA (2.85 mL, 16.36 mmol) in dichloromethane (20 mL) at −78° C. was treated with a dropwise solution of oxalyl chloride (4.2 mL of 2 M, 8.400 mmol) over 1 minute. The reaction was stirred at −78° C. for 1 h and then stirred for 1 hour at 0° C. The mixture was quenched with MeOH (5 mL) and concentrated. The residue was treated with MeOH (5 mL), sonicated for 1 min to give a suspension, then filtered. The collected solid was washed with MeOH (3×1 mL) then dried under suction for 30 minutes. The solid was transferred to a 250 mL flask then dried on rotovap (65° C., 3 mbar) for 1 hour. 10 mL of cold MeOH was added to the crude residue and the solution was filtered. The resulting brown solid was washed with ice cold MeOH and dried under vacuum to afford. 8-chloro-5-(3,4-difluorophenyl)-1-tetrahydropyran-2-yl-6-tetrahydropyran-4-yl-pyrazolo[4,3-g]isoquinoline (1.2 g, 61%). $^1H$ NMR (300 MHz, DMSO-$d_6$) δ 8.65 (d, J=1.0 Hz, 1H), 8.46 (d, J=0.9 Hz, 1H), 7.85 (d, J=1.0 Hz, 1H), 7.78-7.50 (m, 2H), 7.28 (d, J=5.1 Hz, 1H), 6.20 (dd, J=9.3, 2.3 Hz, 1H), 3.88 (d, J=7.3 Hz, 4H), 3.22 (td, J=11.4, 6.5 Hz, 2H), 2.81-2.63 (m, 1H), 2.43 (d, J=9.3 Hz, 1H), 2.00 (td, J=13.9, 9.0 Hz, 4H), 1.82 (d, J=11.5 Hz, 1H), 1.57 (dd, J=23.8, 10.2 Hz, 4H). LCMS m/z 484.19 $[M+H]^+$.

Preparation of S7 and S8

5-(4-fluorophenyl)-7-oxido-1-tetrahydropyran-2-yl-6-tetrahydropyran-4-yl-pyrazolo[4,3-g]isoquinolin-7-ium (S7) and 8-(4-aza-1-azoniabicyclo[2.2.2]octan-1-yl)-5-(4-fluorophenyl)-1-tetrahydropyran-2-yl-6-tetrahydropyran-4-yl-pyrazolo[4,3-g]isoquinoline (S8)

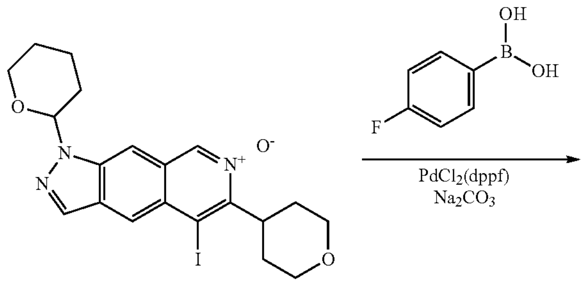

S1

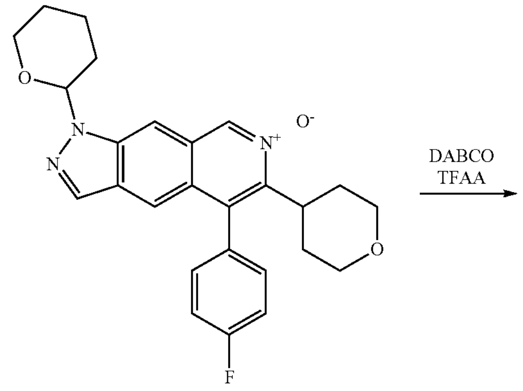

S7

-continued

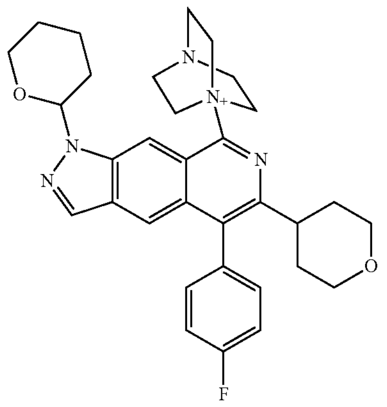

S8

Compounds S7 and S8 were prepared as described from S1 using the method described for the preparation of S4.

5-(4-fluorophenyl)-7-oxido-1-tetrahydropyran-2-yl-6-tetrahydropyran-4-yl-pyrazolo[4,3-g]isoquinolin-7-ium (S7) $^{1}H$ NMR (400 MHz, Chloroform-d) δ 8.97 (s, 1H), 8.10 (d, J=0.9 Hz, 1H), 7.84 (d, J=1.1 Hz, 1H), 7.52 (t, J=1.0 Hz, 1H), 7.29 (m, 4H), 5.82 (dd, J=9.1, 2.7 Hz, 1H), 4.04 (d, J=11.4 Hz, 1H), 4.00-3.90 (m, 2H), 3.87-3.74 (m, 1H), 3.28 (m, 3H), 2.98-2.36 (m, 3H), 2.26-2.06 (m, 2H), 1.93-1.67 (m, 3H), 1.46 (d, J=12.5 Hz, 2H). LCMS m/z 448.25 $[M+H]^+$.

8-(4-aza-1-azoniabicyclo[2.2.2]octan-1-yl)-5-(4-fluorophenyl)-1-tetrahydropyran-2-yl-6-tetrahydropyran-4-yl-pyrazolo[4,3-g]isoquinoline (S8) LCMS m/z 542.0 $[M+H]^+$.

Preparation of S9

8-chloro-5-(4-fluorophenyl)-1-tetrahydropyran-2-yl-6-tetrahydropyran-4-yl-pyrazolo[4,3-g]isoquinoline (S9)

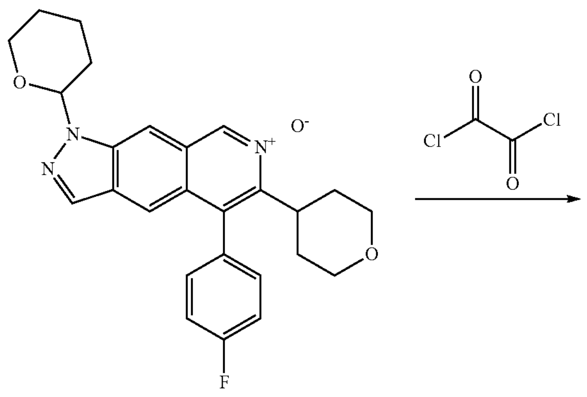

S7

-continued

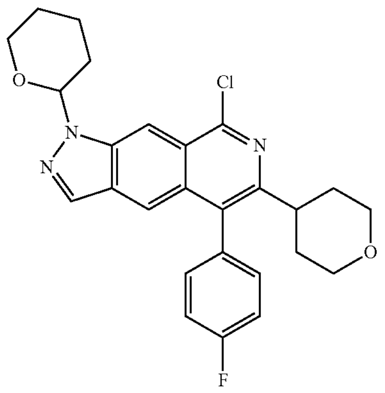

S9

Step 1. Synthesis of 8-chloro-5-(4-fluorophenyl)-1-tetrahydropyran-2-yl-6-tetrahydropyran-4-yl-pyrazolo[4,3-g]isoquinoline (S9)

A solution of 5-(4-fluorophenyl)-7-oxido-1-tetrahydropyran-2-yl-6-tetrahydropyran-4-yl-pyrazolo[4,3-g]isoquinolin-7-ium (500 mg, 1.117 mmol), DIPEA (600 μL, 3.445 mmol) in dichloromethane (5 mL) at −78° C. was treated with a dropwise solution of oxalyl chloride (1.15 mL of 2 M, 2.300 mmol) over 10 minutes. The reaction stirred at −78° C. for 1 hour. The reaction was quenched with MeOH (5 mL) and concentrated. Purification by silica gel chromatography (Gradient: 0-10% EtOAc in dichloromethane) yielded the product. 8-chloro-5-(4-fluorophenyl)-1-tetrahydropyran-2-yl-6-tetrahydropyran-4-yl-pyrazolo[4,3-g]isoquinoline (390 mg, 75%). $^{1}H$ NMR (400 MHz, Chloroform-d) δ 8.58 (t, J=1.1 Hz, 1H), 8.20 (d, J=0.9 Hz, 1H), 7.74 (d, J=1.0 Hz, 1H), 7.32-7.20 (m, 3H), 5.95 (dd, J=9.3, 2.7 Hz, 1H), 4.23-4.01 (m, 3H), 3.98-3.81 (m, 1H), 3.44-3.23 (m, 2H), 2.91-2.58 (m, 2H), 2.39-2.14 (m, 3H), 2.00-1.70 (m, 4H), 1.63-1.44 (m, 2H), 1.31-1.19 (m, 1H). LCMS m/z 466.0 $[M+H]^+$.

Preparation of S10 and S11

5-(4-fluorophenyl)-6-isopropyl-7-oxido-1-tetrahydropyran-2-yl-pyrazolo[4,3-g]isoquinolin-7-ium (S10) and 8-(4-aza-1-azoniabicyclo[2.2.2]octan-1-yl)-5-(4-fluorophenyl)-6-isopropyl-1H-pyrazolo[4,3-g]isoquinoline (S11)

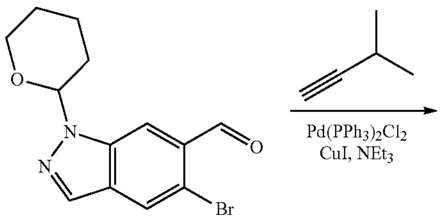

C8

-continued

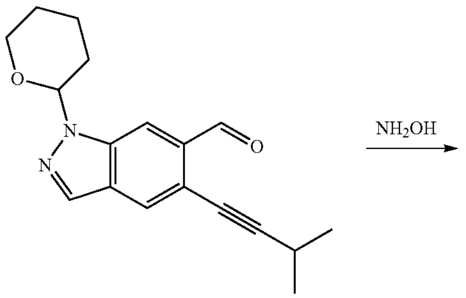

C9

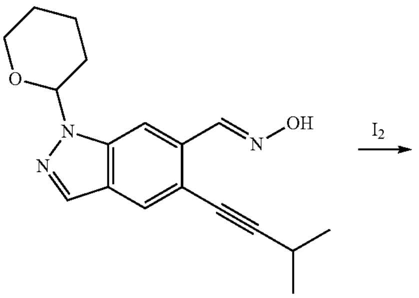

C10

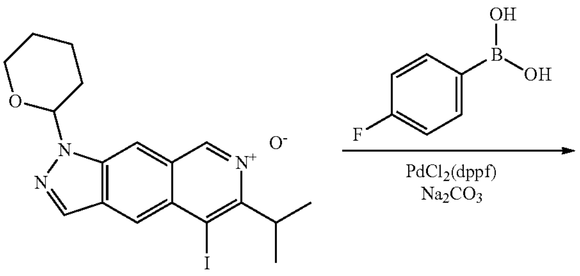

C11

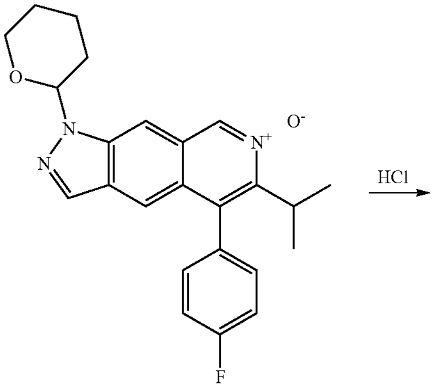

S10

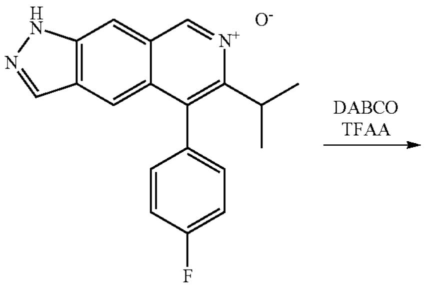

C12

-continued

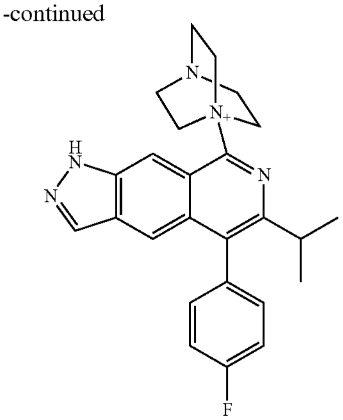

S11

Step 1. Synthesis of 5-(3-methylbut-1-ynyl)-1-tetrahydropyran-2-yl-indazole-6-carbaldehyde (C9)

In a 3 L 4-neck flask (equipped with mechanical stirrer, temp probe, heating jacket) a solution of 5-bromo-1-tetrahydropyran-2-yl-indazole-6-carbaldehyde (113 g, 365.5 mmol) in DMF (1.1 L) was bubbled through with nitrogen for 15 minutes, then diisopropylamine (103 mL, 734.9 mmol) was added. Bubbling of nitrogen was continued for 15 min, then 3-methylbut-1-yne (54 mL, 554.9 mmol) was added followed by $Pd(PPh_3)_2Cl_2$ (8.0 g, 11.40 mmol) and CuI (4.18 g, 21.95 mmol). Placed under a slight positive pressure of nitrogen then heated to 50° C. for 3 h. The mixture was cooled to 25° C., then water (1 L) was added while stirring. The internal temp rises to 41° C., and a precipitate was observed. The mixture was extracted with EtOAc (2×1.5 L). Combined EtOAc extracts were washed successively with 1:1 water:saturated brine, 1:1 saturated aqueous $NH_4Cl$:saturated aqueous $NaHCO_3$, 0.3 M aqueous HCl, brine (1.5 L each). The organics layer was dried ($MgSO_4$), filtered, and concentrated. $^1H$ NMR (200 MHz, Chloroform-d) δ 10.71 (s, 1H), 8.19 (t, J=0.9 Hz, 1H), 8.07 (d, J=1.0 Hz, 1H), 7.91 (d, J=0.7 Hz, 1H), 5.78 (dd, J=9.7, 2.6 Hz, 1H), 4.08 (ddt, J=11.8, 3.8, 1.9 Hz, 1H), 3.85-3.75 (m, 1H), 2.88 (hept, J=6.9 Hz, 1H), 2.56 (dddd, J=13.7, 11.9, 9.8, 4.0 Hz, 1H), 2.24-2.05 (m, 2H), 1.88-1.64 (m, 3H), 1.34 (d, J=6.9 Hz, 6H). LCMS m/z 297.03 $[M+H]^+$. Melting point=100° C.

Step 2. Synthesis of (6E)-5-(3-methylbut-1-ynyl)-1-tetrahydropyran-2-yl-indazole-6-carbaldehyde oxime (C10)

In a 5 L 3-neck flask equipped with mechanical stirring, temperature probe and heating jacket, to a suspension of hydroxylamine (Hydrochloride salt) (70.0 g, 1.007 mol) in MeCN (1.0 L) at room temperature was added pyridine (550 mL, 6.800 mol). The mixture was heated to 50° C., then a solution of 5-(3-methylbut-1-ynyl)-1-tetrahydropyran-2-yl-indazole-6-carbaldehyde (100 g, 337.4 mmol) in dichloromethane (750 mL) was added. The mixture was stirred for 1 hour at 50° C. and then concentrated. The residue was dissolved in EtOAc (2 L), washed successively with water (2×), then brine (1.5 L each), dried ($MgSO_4$) filtered and concentrated. The residue is concentrating from a solution of EtOAc/heptane to afford a dark solid. The solid was treated with MTBE (200 mL), and heated to reflux for 5 minutes, to give a uniform suspension, then treated with heptane (500 mL). The resulting suspension was allowed to stand at room temperature for 18 hour. Crystals were isolated via filtration, washing with heptane (3×100 mL), then dried under suction for 30 minutes, then dried on rotovap (65° C., 3 mbar) for 1 hour to afford the product (6E)-5-(3-methylbut-1-ynyl)-1-tetrahydropyran-2-yl-indazole-6-carbaldehyde oxime (92.7 g, 88%) as a yellow solid. $^1$H NMR (400 MHz, Chloroform-d) δ 8.82-8.75 (m, 1H), 8.07 (s, 1H), 8.00 (d, J=0.9 Hz, 1H), 7.84 (d, J=0.8 Hz, 1H), 7.62 (s, 1H), 5.74 (dd, J=9.7, 2.7 Hz, 1H), 4.07 (dd, J=11.5, 3.0 Hz, 1H), 3.78 (td, J=11.1, 3.0 Hz, 1H), 2.87 (hept, J=6.9 Hz, 1H), 2.64-2.51 (m, 1H), 2.12 (ddd, J=31.8, 11.3, 4.1 Hz, 2H), 1.87-1.57 (m, 3H), 1.33 (d, J=6.9 Hz, 6H). LCMS m/z 312.1 [M+H]$^+$.

Step 3. Synthesis of 5-iodo-6-isopropyl-7-oxido-1-tetrahydropyran-2-yl-pyrazolo[4,3-g]isoquinolin-7-ium (C11)

Compound C11 was prepared from C10 by iodination as described for the preparation of S1.

5-iodo-6-isopropyl-7-oxido-1-tetrahydropyran-2-yl-pyrazolo[4,3-g]isoquinolin-7-ium (1.2 g, 84%) as a yellow foam. 1H NMR (400 MHz, Chloroform-d) δ 8.82 (s, 1H), 8.60 (s, 1H), 8.34 (d, J=1.0 Hz, 1H), 7.77 (q, J=0.9 Hz, 1H), 5.85 (dd, J=9.1, 2.6 Hz, 1H), 4.22 (s, 1H), 4.12-4.00 (m, 1H), 3.90-3.78 (m, 1H), 2.62 (qd, J=9.5, 5.2 Hz, 1H), 2.29-2.11 (m, 2H), 1.93-1.69 (m, 3H), 1.62 (d, J=6.9 Hz, 6H). LCMS m/z 438.03 [M+1]$^+$.

Step 4. Synthesis of 5-(4-fluorophenyl)-6-isopropyl-7-oxido-1-tetrahydropyran-2-yl-pyrazolo[4,3-g]isoquinolin-7-ium (S10)

Compound S10 was prepared from C11 by Suzuki coupling with 4-fluorophenyl boronic acid as described in the preparation of compound S2. $Pd(PPh_3)_4$ was used as the catalyst in this example. Purification by silica gel chromatography (Gradient: 0-10% EtOAc in dichloromethane) yielded the product which was used in the subsequent reaction without further purification. 5-(4-fluorophenyl)-6-isopropyl-7-oxido-1-tetrahydropyran-2-yl-pyrazolo[4,3-g]isoquinolin-7-ium. LCMS m/z 406.08 [M+1]$^+$.

Step 5. Synthesis of 5-(4-fluorophenyl)-6-isopropyl-7-oxido-1H-pyrazolo[4,3-g]isoquinolin-7-ium (C12)

5-(4-fluorophenyl)-6-isopropyl-7-oxido-1-tetrahydropyran-2-yl-pyrazolo[4,3-g]isoquinolin-7-ium (1050 mg, 2.590 mmol) was treated with hydrogen chloride (30 mL of 4 M, 120.0 mmol) at room temperature. The reaction mixture was stirred for 18 hours. The solvent was removed to afford 5-(4-fluorophenyl)-6-isopropyl-7-oxido-1H-pyrazolo[4,3-g]isoquinolin-7-ium (830 mg, 100%). LCMS m/z 322.37 [M+H]$^+$.

Step 6. Synthesis of 8-(4-aza-1-azoniabicyclo[2.2.2]octan-1-yl)-5-(4-fluorophenyl)-6-isopropyl-1H-pyrazolo[4,3-g]isoquinoline (S11)

To a solution of 5-(4-fluorophenyl)-6-isopropyl-7-oxido-1H-pyrazolo[4,3-g]isoquinolin-7-ium (830 mg, 2.583 mmol) and 1,4-diazabicyclo[2.2.2]octane (2.6 g, 23.18 mmol) in $CH_2Cl_2$ (22 mL) at 0° C. was added TFAA (2.5 mL, 17.99 mmol). The reaction was stirred at 0° C. for 1 hours, then allowed to warm to ambient temperature and stirring for additional 3 hours. The reaction mixture was concentrated in vacuo. The crude product was triturated with EtOAc to provide product. 8-(4-aza-1-azoniabicyclo[2.2.2]octan-1-yl)-5-(4-fluorophenyl)-6-isopropyl-1H-pyrazolo[4,3-g]isoquinoline (Trifluoroacetic Acid) (3.2 g, 96%). $^1$H NMR (300 MHz, Chloroform-d) δ 14.16 (s, 1H), 10.13 (s, 1H), 8.22 (s, 1H), 7.92 (s, 1H), 7.32 (d, J=7.0 Hz, 4H), 4.38 (t, J=7.4 Hz, 6H), 3.71 (t, J=7.4 Hz, 6H), 3.03 (q, J=6.7 Hz, 1H), 1.25 (d, J=6.7 Hz, 6H) ppm. LCMS m/z 416.28 [M+H]$^+$.

Preparation of S12 and S13

8-chloro-5-(4-fluorophenyl)-6-isopropyl-1-tetrahydropyran-2-yl-pyrazolo[4,3-g]isoquinoline (S12) and 8-(4-aza-1-azoniabicyclo[2.2.2]octan-1-yl)-5-(4-fluorophenyl)-6-isopropyl-1-tetrahydropyran-2-yl-pyrazolo[4,3-g]isoquinoline (S13)

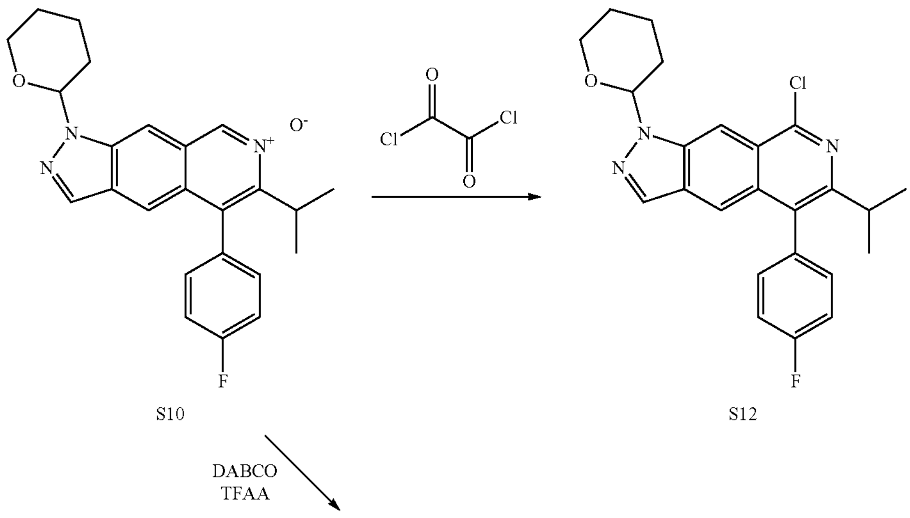

S10 S12

-continued

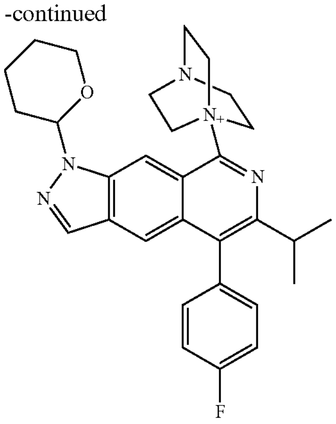

S13

Preparation of 8-chloro-5-(4-fluorophenyl)-6-isopropyl-1-tetrahydropyran-2-yl-pyrazolo[4,3-g]isoquinoline (S12)

Compound S12 was prepared from S10 using the method described for the preparation of S10 to afford the product. 8-chloro-5-(4-fluorophenyl)-6-isopropyl-1-tetrahydropyran-2-yl-pyrazolo[4,3-g]isoquinoline (5.3 g, 82%). LCMS m/z 424.14 $[M+H]^+$.

Preparation of 8-(4-aza-1-azoniabicyclo[2.2.2]octan-1-yl)-5-(4-fluorophenyl)-6-isopropyl-1-tetrahydropyran-2-yl-pyrazolo[4,3-g]isoquinoline (S13)

Compound S10 was prepared from S13 using the method described for the preparation of S8. 8-(4-aza-1-azoniabicyclo[2.2.2]octan-1-yl)-5-(4-fluorophenyl)-6-isopropyl-1-tetrahydropyran-2-yl-pyrazolo[4,3-g]isoquinoline (Trifluoroacetic Acid) (374 mg, 100%). LCMS m/z 500.9 $[M+H]^+$.

Preparation of S14 and S15

6-isopropyl-5-(2-methyl-4-pyridyl)-7-oxido-1-tetrahydropyran-2-yl-pyrazolo[4,3-g]isoquinolin-7-ium (S14) and 8-chloro-6-isopropyl-5-(2-methyl-4-pyridyl)-1-tetrahydropyran-2-yl-pyrazolo[4,3-g]isoquinoline (S15)

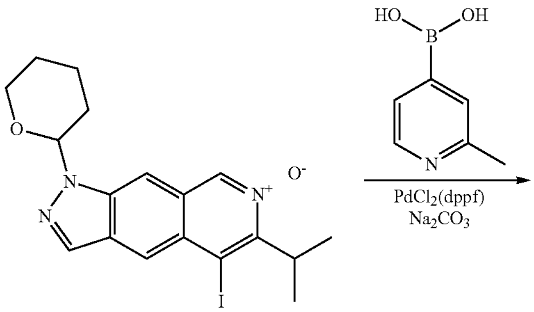

C11

-continued

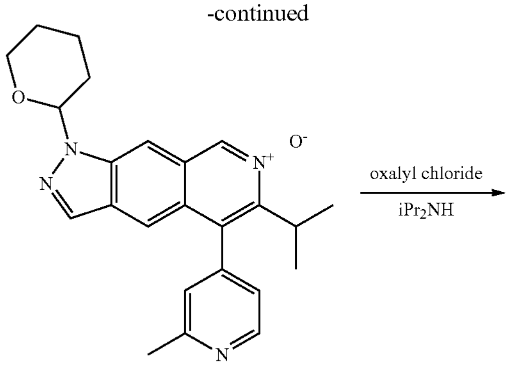

S14

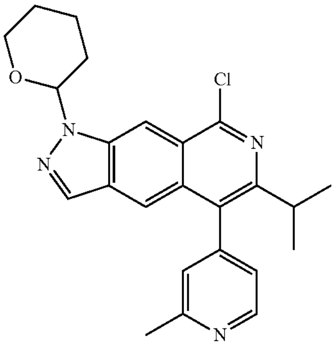

S15

Synthesis of 6-isopropyl-5-(2-methyl-4-pyridyl)-7-oxido-1-tetrahydropyran-2-yl-pyrazolo[4,3-g]isoquinolin-7-ium (S14)

Compound S14 was prepared from C11 by Suzuki coupling with 2-methyl-4-pyridyl boronic acid using the method described for the preparation of S2. 6-isopropyl-5-(2-methyl-4-pyridyl)-7-oxido-1-tetrahydropyran-2-yl-pyrazolo[4,3-g]isoquinolin-7-ium (900 mg, 65%) as a tan solid. LCMS m/z 403.0 $[M+H]^+$.

Synthesis of 8-chloro-6-isopropyl-5-(2-methyl-4-pyridyl)-1-tetrahydropyran-2-yl-pyrazolo[4,3-g]isoquinoline (S15)

Compound S15 was prepared from S14 using the method described for the preparation of compound S3. 8-chloro-6- isopropyl-5-(2-methyl-4-pyridyl)-1-tetrahydropyran-2-yl-pyrazolo[4,3-g]isoquinoline (280 mg, 77%). LCMS m/z 421.0 $[M+H]^+$.

Preparation of S16

8-(4-aza-1-azoniabicyclo[2.2. 2]octan-1yl)-6-isopropyl-5-(2-methoxy-4-pyridyl)-1-tetrahydropyran-2-yl-pyrazolo[4,3-g]isoquinoline (S16)

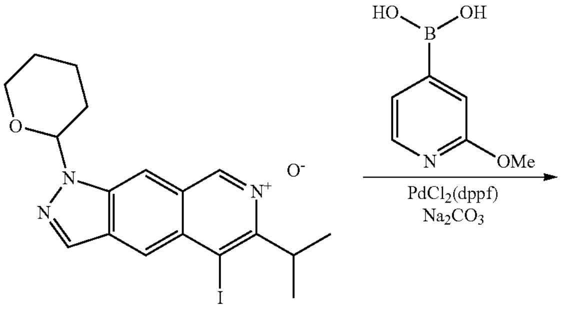

C11

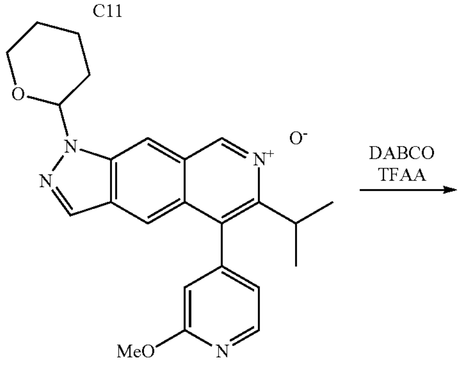

C13

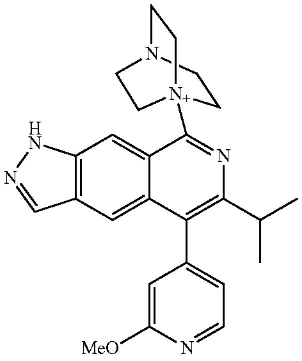

S16

Step 1. Synthesis of 6-isopropyl-5-(2-methoxy-4-pyridyl)-7-oxido-1-tetrahydropyran-2-yl-pyrazolo[4,3-g]isoquinolin-7-ium (C13)

Compound C13 was prepared by Suzuki coupling with C11 and 2-methoxy-4-pyridyl boronic acid using the method described for the preparation of S2. Purification by silica gel chromatography (Gradient: 0-5% of MeOH in dichloromethane) afforded the product as a pale red solid. 6-isopropyl-5-(2-methoxy-4-pyridyl)-7-oxido-1-tetrahydropyran-2-yl-pyrazolo[4,3-g]isoquinolin-7-ium (168.5 mg, 92%). $^1H$ NMR (400 MHz, Chloroform-d) δ 8.87 (s, 1H), 8.31 (m, 1H), 8.04 (d, J=1.0 Hz, 1H), 7.77 (s, 1H), 7.49 (s, 1H), 6.79 (m, 1H), 6.69-6.65 (m, 1H), 5.75 (dd, J=9.1, 2.7 Hz, 1H), 4.00 (m, 4H), 3.81-3.70 (m, 1H), 3.25-3.00 (m, 1H), 2.59-2.47 (m, 1H), 2.19-2.01 (m, 2H), 1.71 (m, 3H), 1.39 (d, J=6.9 Hz, 6H). LCMS m/z 419.26 $[M+H]^+$.

Step 2. Synthesis of 8-(4-aza-1-azoniabicyclo[2.2.2]octan-1-yl)-6-isopropyl-5-(2-methoxy-4-pyridyl)-1-tetrahydropyran-2-yl-pyrazolo[4,3-g]isoquinoline (S16)

Compound S16 was prepared from C13 using the method described for the preparation of compound S4. Purification by reversed-phase chromatography (Column: C18. Gradient: 0-50% MeCN in water with 0.1% trifluoroacetic acid) afforded the product. 8-(4-aza-1-azoniabicyclo[2.2.2]octan-1-yl)-6-isopropyl-5-(2-methoxy-4-pyridyl)-1-tetrahydropyran-2-yl-pyrazolo[4,3-g]isoquinoline (Trifluoroacetate salt) (182 mg, 74%). LCMS m/z 513.43 $[M]^+$.

Preparation of S17

8-(4-aza-1-azoniabicyclo[2.2.2]octan-1-yl)-6-(1-benzyloxycyclopropyl)-5-(4-fluorophenyl)-1H-pyrazolo[4,3-g]isoquinoline (S17)

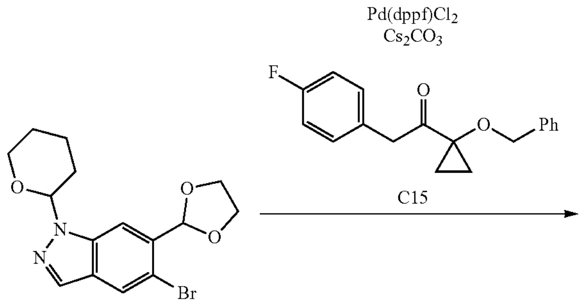

C14

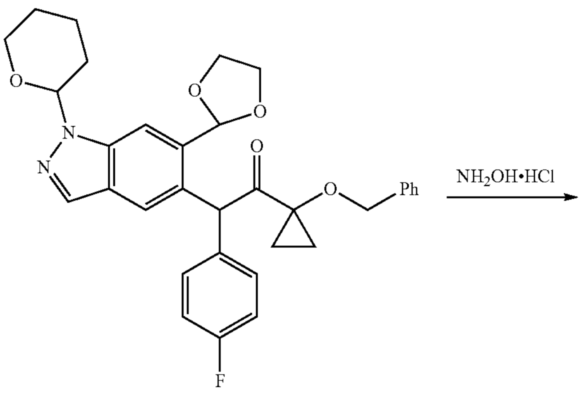

C16

-continued

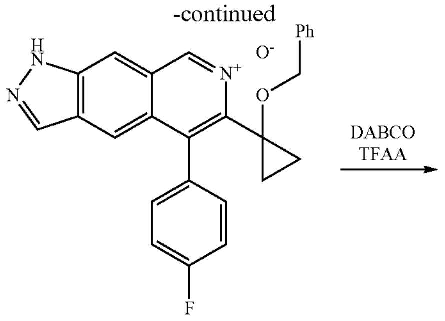

C17

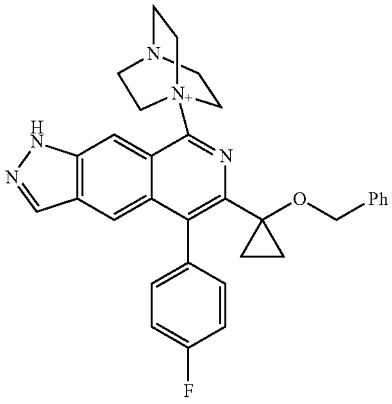

S17

Step 1. Synthesis of 6-(1-benzyloxycyclopropyl)-5-(4-fluorophenyl)-7-oxido-1H-pyrazolo[4,3-g]isoquinolin-7-ium (C17)

Part A. To a 20 mL vial was added 5-bromo-6-(1,3-dioxolan-2-yl)-1-tetrahydropyran-2-yl-indazole (1.15 g, 3.256 mmol), $Cs_2CO_3$ (2.44 g, 7.489 mmol), and Pd(dppf) $Cl_2$ (212 mg, 0.3253 mmol). The vial was sealed and flushed with nitrogen. THF (7.9 mL) was added, followed by 1-(1-benzyloxycyclopropyl)-2-(4-fluorophenyl)ethanone (1.2 g, 4.221 mmol). The reaction mixture was heated to 70° C. overnight, then cooled to room temperature and diluted with EtOAc. The organic solution was washed with brine, dried with $Na_2SO_4$, concentrated in vacuo. The mixture was then purified by silica gel chromatography (Gradient: 10-25% EtOAc in heptane) to afford C16.

Part B. Hydroxylamine (Hydrochloride salt) (1.13 g, 16.26 mmol) in EtOH (14.5 mL)/$H_2O$ (1.5 mL) was added to the product of part A (C16). The reaction mixture was heated under microwave for 2 hours at 90° C. The reaction was concentrated and the product was purified by silica gel chromatography (Gradient: 30-80% EtOAc in heptane) to afford 6-(1-benzyloxycyclopropyl)-5-(4-fluorophenyl)-7-oxido-1H-pyrazolo[4,3-g]isoquinolin-7-ium (600 mg, 43%). LCMS m/z 426.21 $[M+H]^+$.

Step 2. Synthesis of 8-(4-aza-1-azoniabicyclo[2.2.2]octan-1-yl)-6-(1-benzyloxycyclopropyl)-5-(4-fluorophenyl)-1H-pyrazolo[4,3-g]isoquinoline (S17)

To a solution of 6-(1-benzyloxycyclopropyl)-5-(4-fluorophenyl)-7-oxido-1H-pyrazolo[4,3-g]isoquinolin-7-ium (Hydrochloride salt) (600 mg, 1.299 mmol) and DABCO (1.29 g, 11.50 mmol) in dichloromethane (12 mL) was added TFAA (1.24 mL, 8.921 mmol) dropwise over 1 minute at room temperature. The reaction mixture was stirred for 1 hour. The reaction mixture was concentrated in vacuo to provide a dark brown solid. Purification by reversed-phase chromatography (Column: C18. Gradient: 0-100% MeCN in water with 0.1% TFA) afforded the product. 8-(4-aza-1-azoniabicyclo[2.2.2]octan-1-yl)-6-(1-benzyloxycyclopropyl)-5-(4-fluorophenyl)-1H-pyrazolo[4,3-g]isoquinoline (Trifluoroacetic Acid (2)) (620 mg, 63%) LCMS m/z 520.3 $[M+H]^+$.

Preparation of S18

8-(4-aza-1-azoniabicyclo[2.2. 2]octan-1-yl)-6-(1-benzyloxycyclopropyl)-5-(3,4-difluorophenyl)-1H-pyrazolo[4,3-g]isoquinoline (S18)

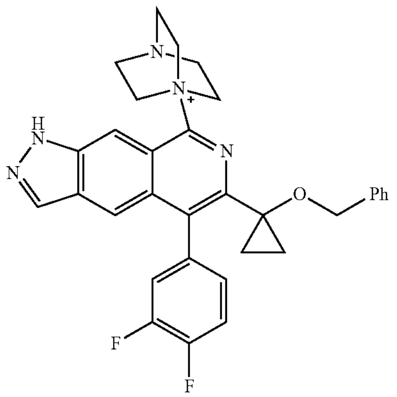 [SMILES: Fc1ccc(-c2c(C3(OCc4ccccc4)CC3)nc([N+]34CCN(CC3)CC4)c3cc4[nH]ncc4cc23)cc1F]

Compound S18 was prepared using the method described for compound S17 from C14 and 1-(1-benzyloxycyclopropyl)-2-(3,4-difluorophenyl)ethanone. Purification by reversed-phase chromatography (Column: C18. Gradient: 0-100% MeCN in water with 0.1% TFA) afforded the product. 8-(4-aza-1-azoniabicyclo[2.2.2]octan-1-yl)-6-(1-benzyloxycyclopropyl)-5-(3,4-difluorophenyl)-1H-pyrazolo[4,3-g]isoquinoline (Trifluoroacetic Acid (2)) (122 mg, 51%) LCMS m/z 538.55 $[M+H]^+$.

Preparation of S19

8-(4-aza-1-azoniabicyclo[2.2.2]octan-1-yl)-5-(3,4-difluorophenyl)-6-[1-(trifluoromethyl)cyclopropyl]-1H-pyrazolo[4,3-g]isoquinoline (S19)

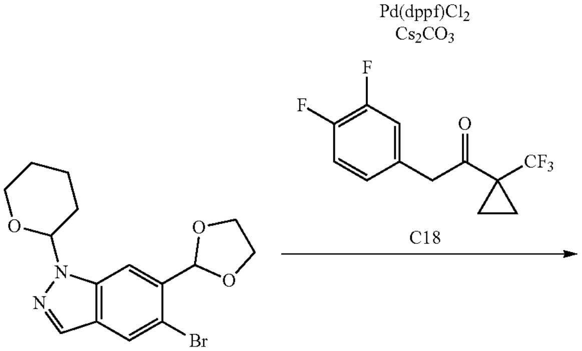

C14

-continued

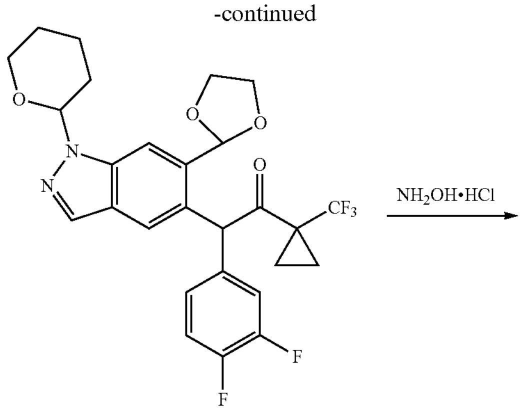

C19

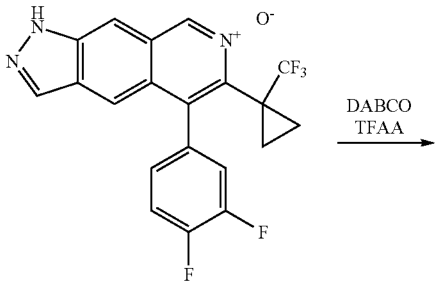

C20

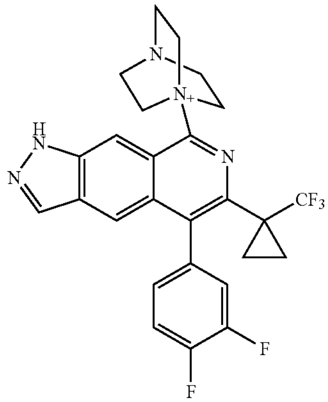

S19

Compound S19 was prepared from C14 and C18 using the method described for the preparation of S17. Purification by reversed-phase chromatography (Column: C18. Gradient: 0-100% MeCN in water with 0.1% trifluoroacetic acid) afforded the product. 8-(4-aza-1-azoniabicyclo[2.2.2]octan-1-yl)-5-(3,4-difluorophenyl)-6-[1-(trifluoromethyl)cyclopropyl]-1H-pyrazolo[4,3-g]isoquinoline (Trifluoroacetate salt) (91 mg, 52%) LCMS m/z 500.49 [M+H]$^+$.

Preparation of S20

6-(1,1-difluoroethyl)-5-(4-fluorophenyl)-7-oxido-1H-pyrazolo[4,3-g]isoquinolin-7-ium (S20)

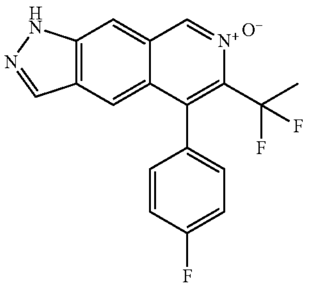

S20 was prepared from C14 and 3,3-difluoro-1-(4-fluorophenyl)butan-2-one (160 mg, 0.7914 mmol) as described for the preparation of C20. The reaction was concentrated and the product was purified by ISCO (40 g silica, 100% EtOAc in heptane) to afford. 6-(1,1-difluoroethyl)-5-(4-fluorophenyl)-7-oxido-1H-pyrazolo[4,3-g]isoquinolin-7-ium (100 mg, 50%). LCMS m/z 344.18 [M+H]$^+$.

Preparation of S21

5-(3,4-difluorophenyl)-6-(1-methoxycyclobutyl)-7-oxido-1-tetrahydropyran-2-yl-pyrazolo[4,3-g]isoquinolin-7-ium (S21)

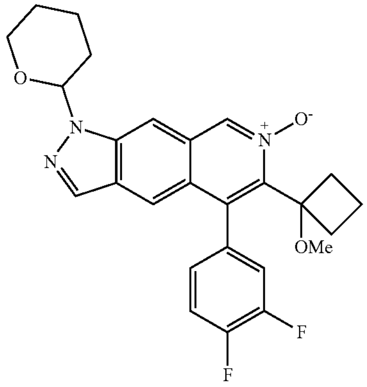

Compound S21 was prepared from 2-(3,4-difluorophenyl)-1-(1-methoxycyclobutyl)ethanone and C14 as described for the preparation of compound S17. The THP protecting group remained during the cyclization step. $^1$H NMR (300 MHz, Chloroform-d) δ 8.92 (s, 1H), 8.16 (d, J=0.9 Hz, 1H), 7.87 (d, J=1.3 Hz, 1H), 7.73 (d, J=1.1 Hz, 1H), 7.40-7.23 (m, 3H), 7.18 (dq, J=8.5, 2.3, 1.9 Hz, 1H), 5.84 (dd, J=9.1, 2.5 Hz, 1H), 4.09-3.99 (m, 1H), 3.89-3.76 (m, 1H), 3.48 (s, 3H), 2.69-2.50 (m, 1H), 2.36 (dt, J=10.9, 8.5 Hz, 2H), 2.25-2.09 (m, 1H), 2.04-1.88 (m, 1H), 1.88-1.67 (m, 1H), 1.58 (dt, J=11.4, 8.9 Hz, 1H). LCMS m/z 563.09 [M+H]$^+$.

Preparation of S22

8-(4-aza-1-azoniabicyclo[2.2.2]octan-1-yl)-5-(3,4-difluorophenyl)-6-(2-methoxy-2-methyl-propyl)-1-tetrahydropyran-2-yl-pyrazolo[4,3-g]isoquinoline (S22)

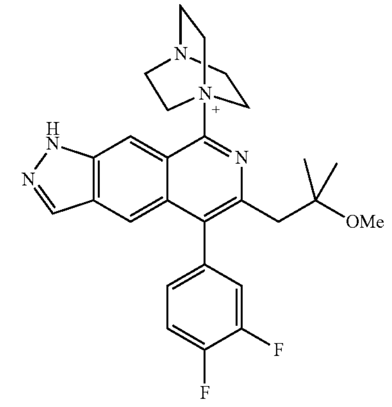

Compound S22 was prepared from 1-(3,4-difluorophenyl)-4-methoxy-4-methyl-pentan-2-one and C14 as described for the preparation of S22. 8-(4-aza-1-azoniabicyclo[2.2.2]octan-1-yl)-5-(3,4-difluorophenyl)-6-(2-methoxy-2-methyl-propyl)-1-tetrahydropyran-2-yl-pyrazolo[4,3-g]isoquinoline (Trifluoroacetic Acid (3)) (160 mg, 56%) LCMS m/z 563.09 $[M+1]^+$.

Preparation of S23

[6-(2-benzyloxy-1,1-dimethyl-ethyl)-5-(3,4-difluorophenyl)-1-tetrahydropyran-2-yl-pyrazolo[4,3-g]isoquinolin-8-yl]trifluoromethanesulfonate (S23)

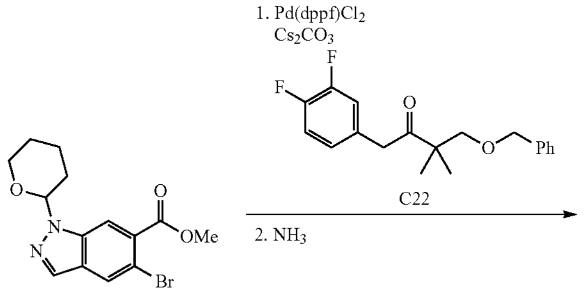

C21

C22

-continued

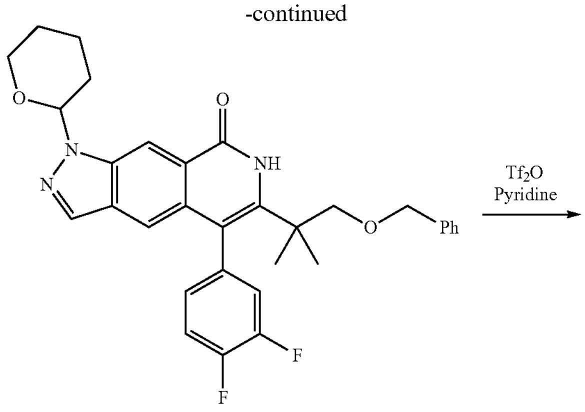

C23

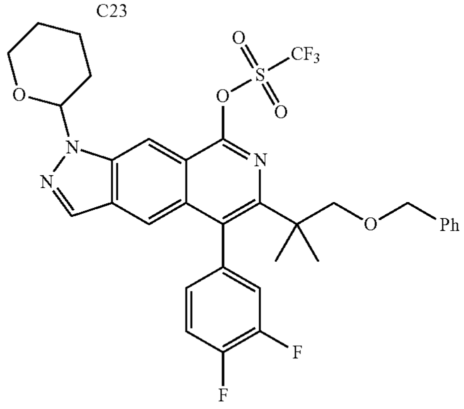

S23

Step 1. Synthesis of 6-(2-benzyloxy-1,1-dimethyl-ethyl)-5-(3,4-difluorophenyl)-1-tetrahydropyran-2-yl-7H-pyrazolo[4,3-g]isoquinolin-8-one (C23)

Part A. To a 20 mL vial was added methyl 5-bromo-1-tetrahydropyran-2-yl-indazole-6-carboxylate (1.23 g, 3.626 mmol), $Cs_2CO_3$ (2.72 g, 8.348 mmol), and $Pd(dppf)Cl_2$ (236 mg, 0.3621 mmol). The vial was sealed and flushed with nitrogen. THF (10 mL) was added, followed by 4-benzyloxy-1-(3,4-difluorophenyl)-3,3-dimethyl-butan-2-one (1.5 g, 4.712 mmol), both by syringe. The reaction mixture was heated to 70° C. overnight. The reaction was cooled to room temperature and diluted with EtOAc. The organic solution was washed with brine, dried with $Na_2SO_4$, concentrated in vacuo. The reaction mixture was then purified by silica gel chromatography (Gradient: 10% to 25% EtOAc in heptane) and the product used in the subsequent reaction.

Part B. To the product from part A was added $NH_3$ (10 mL of 7 M, 70.00 mmol) in methanol in a 10-20 mL microwave vial. The reaction mixture was heated under microwave for 5 hours at 120° C. The reaction was concentrated and the product was purified by silica gel chromatography (Gradient: 30-80% EtOAc in heptane) to afford 6-(2-benzyloxy-1,1-dimethyl-ethyl)-5-(3,4-difluorophenyl)-1-tetrahydropyran-2-yl-7H-pyrazolo[4,3-g]isoquinolin-8-one (850 mg, 43%). $^1H$ NMR (300 MHz, Chloroform-d) δ 10.23 (s, 1H), 8.73 (q, J=1.0 Hz, 1H), 8.06 (d, J=0.9 Hz, 1H), 7.48-7.20 (m, 7H), 7.10-6.94 (m, 2H), 5.87 (dd, J=9.9, 2.4 Hz, 1H), 4.65 (s, 2H), 4.16-4.02 (m, 1H), 3.83 (td, J=11.1, 2.9 Hz, 1H), 3.47 (t, J=1.7 Hz, 2H), 2.71-2.53 (m, 1H), 2.27-2.01 (m, 2H), 1.88-1.63 (m, 3H), 1.12 (dd, J=6.3, 4.3 Hz, 6H). LCMS m/z 577.44 $[M+H]^+$.

Step 2. Synthesis of [6-(2-benzyloxy-1,1-dimethyl-ethyl)-5-(3,4-difluorophenyl)-1-tetrahydropyran-2yl-pyrazolo[4,3g]isoquinolin-8yl]trifluoromethane-sulfonate (S23)

To a solution of 6-(2-benzyloxy-1,1-dimethyl-ethyl)-5-(3,4-difluorophenyl)-1-tetrahydropyran-2-yl-7H-pyrazolo[4,3-g]isoquinolin-8-one (200 mg, 0.3652 mmol) and pyridine (100 μL, 1.236 mmol) in dichloromethane (2.8 mL) was added trifluoromethylsulfonyl trifluoromethanesulfonate (90 0.5349 mmol) at 0° C. The reaction was stirred for 30 minutes at 0° C. and then room temperature for 1 hour. The reaction was quench with $NaHCO_3$, washed with dichloromethane, concentrated and purified by silica gel chromatography (Gradient: 0-30% EtOAc in heptane) to afford [6-(2-benzyloxy-1,1-dimethyl-ethyl)-5-(3,4-difluorophenyl)-1-tetrahydropyran-2-yl-pyrazolo[4,3-g]isoquinolin-8-yl] trifluoromethanesulfonate (220 mg, 89%). LCMS m/z 676.25 $[M+H]^+$.

Exemplary Compounds 1-262

In order that the disclosure described herein may be more fully understood, the following examples are set forth. It should be understood that these examples are for illustrative purposes only and are not to be construed as limiting this disclosure in any manner.

All the specific and generic compounds, and the intermediates disclosed for making those compounds, are considered to be part of the disclosure disclosed herein.

Compound 1

3-[[5-(4-chlorophenyl)-6-tetrahydropyran-4-yl-1H-pyrazolo[4,3-g]isoquinolin-8-yl]oxy]cyclobutanecarboxylic acid (1)

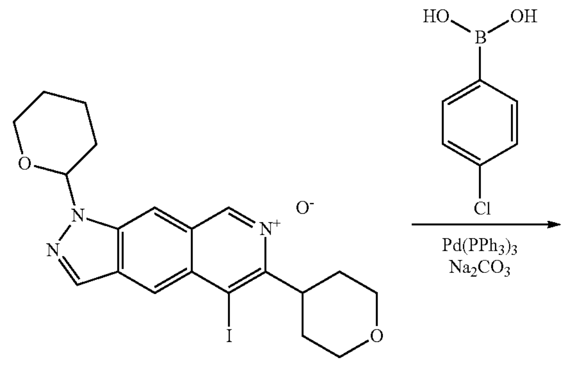

S1

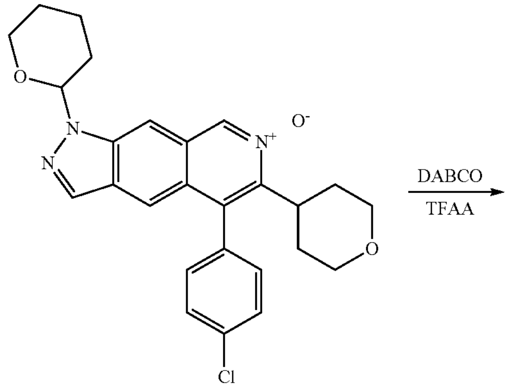

C24

-continued

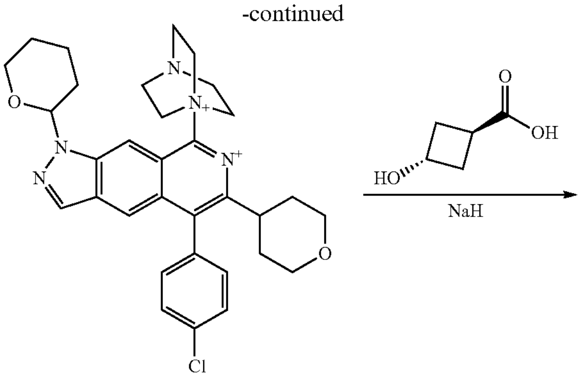

C25

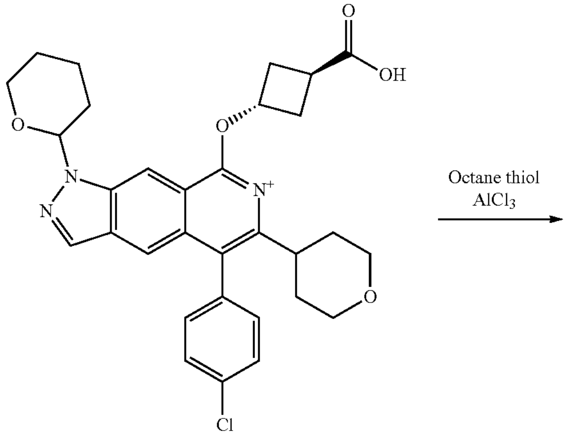

C26

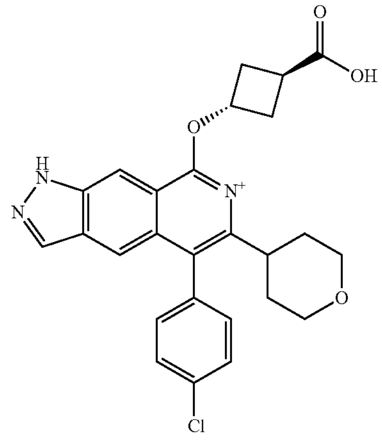

1

Step 1. Synthesis of 5-(4-chlorophenyl)-7-oxido-1-tetrahydropyran-2-yl-6-tetrahydropyran-4-yl-pyrazolo[4,3-g]isoquinolin-7-ium (C24)

In a microwave vial, 5-iodo-7-oxido-1-tetrahydropyran-2-yl-6-tetrahydropyran-4-yl-pyrazolo[4,3-g]isoquinolin-7-ium (500 mg, 0.9994 mmol), (4-chlorophenyl)boronic acid (310 mg, 1.982 mmol) and $Pd(PPh_3)_4$ (70 mg, 0.060 mmol) were dissolved in DMF (7 mL). $Na_2CO_3$ (2 mL of 2 M, 4.000 mmol) was added. The reaction mixture was heated under microwave conditions at 125° C. for 1 hour. Water and dichloromethane was added to the reaction. The mixture was extracted with dichloromethane (×3). The organic phases were filtered through a phase separator, combined and the volatiles were evaporated in vacuo. Purification by silica gel chromatography (Gradient: 0-5% of MeOH in dichloromethane) afforded the product. 5-(4-chlorophenyl)-7-oxido-1-tetrahydropyran-2-yl-6-tetrahydropyran-4-yl-pyrazolo[4,3-g]isoquinolin-7-ium (390 mg, 84%). %). $^1$H NMR (400 MHz, Chloroform-d) δ 8.91 (s, 1H), 8.04 (d, J=0.9 Hz, 1H), 7.78 (m, 1H), 7.55-7.48 (m, 2H), 7.44 (t, J=1.0 Hz, 1H), 7.21-7.16 (m, 3H), 5.75 (dd, J=9.1, 2.7 Hz, 1H), 4.02-3.94 (m, 1H), 3.91 (dd, J=11.3, 4.1 Hz, 2H), 3.75 (m, 1H), 3.22 (m, 3H), 2.93-2.27 (m, 3H), 2.18-2.00 (m, 2H), 1.83-1.64 (m, 3H), 1.39 (d, J=12.5 Hz, 2H). LCMS m/z 444.24 $[M+H]^+$.

Step 2. Synthesis of 8-(4-aza-1-azoniabicyclo[2.2.2]octan-1-yl)-5-(4-chlorophenyl)-1-tetrahydropyran-2-yl-6-tetrahydropyran-4-yl-pyrazolo[4,3-g]isoquinoline (C25)

5-(4-chlorophenyl)-7-oxido-1-tetrahydropyran-2-yl-6-tetrahydropyran-4-yl-pyrazolo[4,3-g]isoquinolin-7-ium (281 mg, 0.6057 mmol) and 1,4-diazabicyclo[2.2.2]octane (340 mg, 3.031 mmol) were suspended in $CH_2Cl_2$ (6.5 mL) and the reaction was cooled to 0° C. (2,2,2-trifluoroacetyl) 2,2,2-trifluoroacetate (250 μL, 1.799 mmol) was added and the reaction was stirred at 0° C. for 1 hour. The volatiles were evaporated in vacuo. Purification by flash column chromatography (Gradient: 0-50% of $CH_3CN$ in water with 0.1% TFA). The product fractions were concentrated and the acetonitrile was removed in vacuo. The water was removed by lyophilization to afford the product as a pale yellow solid. 8-(4-aza-1-azoniabicyclo[2.2.2]octan-1-yl)-5-(4-chlorophenyl)-1-tetrahydropyran-2-yl-6-tetrahydropyran-4-yl-pyrazolo[4,3-g]isoquinoline (Trifluoroacetate salt) (385 mg, 94%). LCMS m/z 558.35 $[M]^+$.

Step 3. Synthesis of 3-[5-(4-chlorophenyl)-1-tetrahydropyran-2-yl-6-tetrahydropyran-4-yl-pyrazolo[4,3-g]isoquinolin-8-yl]oxycyclobutanecarboxylic acid (C26)

In a vial, 8-(4-aza-1-azoniabicyclo[2.2.2]octan-1-yl)-5-(4-chlorophenyl)-1-tetrahydropyran-2-yl-6-tetrahydropyran-4-yl-pyrazolo[4,3-g]isoquinoline (Trifluoroacetate salt) (250 mg, 0.3714 mmol) and 3-hydroxycyclobutanecarboxylic acid (130 mg, 1.120 mmol) were dissolved in DMSO (3.7 mL). Then, at room temperature and under nitrogen, NaH (90 mg of 60% w/w, 2.250 mmol) was added. The reaction was stirred for 2 hours. Purification by reverse-phase flash chromatography (Column: C18. Gradient: 0-100% MeCN in water with 0.1% trifluoroacetic acid) product. Product containing fractions were pooled, and the acetonitrile was evaporated in vacuo. The aqueous mixture was extracted with $CHCl_3$:IPA (3:1). The organic phases were combined, dried with $MgSO_4$ and the volatiles were evaporated in vacuo to afford the product 3-[5-(4-chlorophenyl)-1-tetrahydropyran-2-yl-6-tetrahydropyran-4-yl-pyrazolo[4,3-g]isoquinolin-8-yl]oxycyclobutanecarboxylic acid (161.1 mg, 77%). LCMS m/z 562.26 $[M+H]^+$.

Step 4. Synthesis of 3-[[5-(4-chlorophenyl)-6-tetrahydropyran-4-yl-1H-pyrazolo[4,3-g]isoquinolin-8-yl]oxy]cyclobutanecarboxylic acid (1)

In a vial, 3-[5-(4-chlorophenyl)-1-tetrahydropyran-2-yl-6-tetrahydropyran-4-yl-pyrazolo[4,3-g]isoquinolin-8-yl]oxycyclobutanecarboxylic acid (160 mg, 0.2847 mmol) was dissolved in dichloromethane (1.5 mL). Then, octane-1-thiol (108 μL, 0.6223 mmol) was added. In a separate vial, $AlCl_3$ (76 mg, 0.5700 mmol) was dissolved in $CH_3NO_2$ (1.5 mL) and added to the mixture. The reaction was stirred at room temperature for 1 hour. Saturated $NaHCO_3$ was added and the mixture was extracted with dichloromethane. The organic phases were combined, filtered through a phase separator and the volatiles were evaporated in vacuo. The crude mixture was purified by flash column chromatography (Gradient: 0-5% of MeOH in dichloromethane). The purification was repeated twice, as the impurities co-eluted with the product. The crude was then purified by reversed phase chromatography (Column: C18. gradient: 5-100% of $CH_3CN$ in water with 0.1% TFA) to afford the product. 3-[[5-(4-chlorophenyl)-6-tetrahydropyran-4-yl-1H-pyrazolo[4,3-g]isoquinolin-8-yl]oxy]cyclobutanecarboxylic acid (32 mg, 23%). $^1$H NMR (400 MHz, DMSO-$d_6$) δ 13.35 (s, 1H), 12.38 (s, 1H), 8.35 (s, 1H), 8.32 (s, 1H), 7.63 (d, J=7.9 Hz, 2H), 7.58 (s, 1H), 7.38 (d, J=7.9 Hz, 2H), 5.58 (m, 1H), 3.88 (dd, J=11.7, 4.2 Hz, 2H), 3.19 (t, J=11.9 Hz, 3H), 2.88-2.75 (m, 2H), 2.69-2.57 (m, 3H), 2.03 (m, 2H), 1.47 (dd, J=13.1, 3.3 Hz, 2H). LCMS m/z 478.27 $[M+H]^+$.

Compound 2

3-[[5-(4-fluoro-3-methoxy-phenyl)-6-tetrahydropyran-4-yl-1H-pyrazolo[4,3-g]isoquinolin-8-yl]oxy]cyclobutanecarboxylic acid (2)

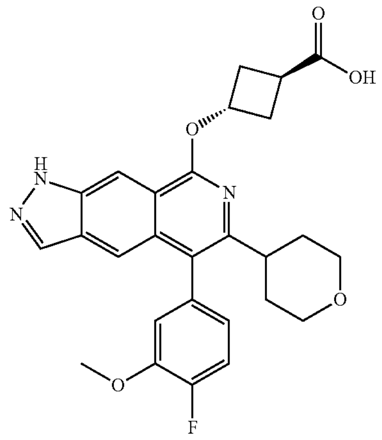 [SMILES: COc1cc(-c2c(C3CCOCC3)nc(O[C@H]3C[C@H](C(=O)O)C3)c3cc4[nH]ncc4cc23)ccc1F]

Compound 2 was prepared from S1 and (4-fluoro-3-methoxy-phenyl)boronic acid as described for compound 1. HCl was used for the final THP deprotection step. 3-[[5-(4-fluoro-3-methoxy-phenyl)-6-tetrahydropyran-4-yl-1H-pyrazolo[4,3-g]isoquinolin-8-yl]oxy]cyclobutanecarboxylic acid (80.7 mg). $^1$H NMR (400 MHz, Methanol-$d_4$:Chloroform-d 3:1) δ 8.41 (s, 1H), 8.12 (d, J=1.2 Hz, 1H), 7.64 (d, J=1.1 Hz, 1H), 7.22 (dd, J=11.3, 8.1 Hz, 1H), 6.93 (dd, J=8.2, 2.0 Hz, 1H), 6.83 (m, 1H), 5.74-5.62 (p, J=8.0 Hz, 1H), 3.97 (m, 2H), 3.84 (s, 3H), 3.42-3.33 (m, 2H), 3.24 (tt, J=9.6, 4.1 Hz, 1H), 2.94 (m, 2H), 2.75 (tt, J=11.5, 3.7 Hz, 1H), 2.65 (m, 2H), 2.21 (m, 2H), 1.51 (m, 2H). LCMS m/z 492.27 $[M+H]^+$ Compound 3

3-[[5-(3-chloro-4-fluoro-phenyl)-6-tetrahydropyran-4-yl-1H-pyrazolo[4,3-g]isoquinolin-8-yl]oxy]cyclobutanecarboxylic acid (3)

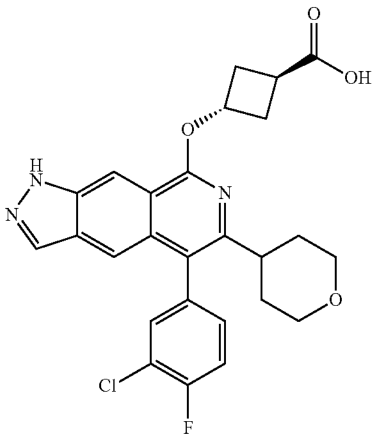

Compound 3 was prepared from S1 and 4-fluoro, 3-chlorophenyl boronic acid as described for compound 1. Purification by reversed-phase chromatography (Column: C18. Gradient: 5-100% MeCN in water with 0.1% trifluoroacetic acid) afforded the product. A pale yellow solid was obtained 3-[[5-(3-chloro-4-fluoro-phenyl)-6-tetrahydropyran-4-yl-1H-pyrazolo[4,3-g]isoquinolin-8-yl]oxy]cyclobutanecarboxylic acid (75.3 mg, 48%). $^{1}H$ NMR (400 MHz, DMSO-$d_6$) δ 13.37 (s, 1H), 12.38 (s, 1H), 8.36 (s, 1H), 8.33 (s, 1H), 7.69-7.55 (m, 3H), 7.38 (m, 1H), 5.59 (m, 1H), 3.97-3.81 (m, 2H), 3.28-3.11 (m, 3H), 2.90-2.71 (m, 2H), 2.62 (m, 3H), 2.12-1.92 (m, 2H), 1.58-1.40 (m, 2H). LCMS m/z 496.23 $[M+H]^+$.

Compound 4

3-[[5-(4-chloro-3-fluoro-phenyl)-6-tetrahydropyran-4-yl-1H-pyrazolo[4,3-g]isoquinolin-8-yl]oxy]cyclobutanecarboxylic acid (4)

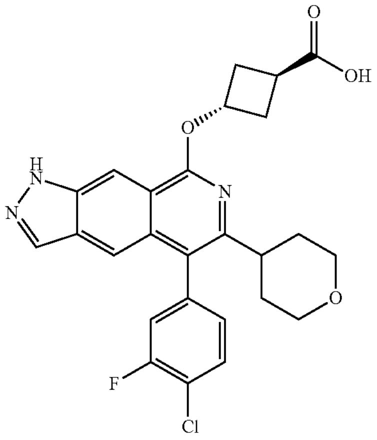

Compound 4 was prepared from S1 and 4-chloro, 3-fluorophenyl boronic acid as described for compound 1. Purification by reversed-phase chromatography (Column: C18. Gradient: 0-50% MeCN in water with 0.2% formic acid) afforded the product. A pale yellow solid was obtained, 3-[[5-(4-chloro-3-fluoro-phenyl)-6-tetrahydropyran-4-yl-1H-pyrazolo[4,3-g]isoquinolin-8-yl]oxy]cyclobutanecarboxylic acid (33.3 mg, 24%). $^{1}H$ NMR (400 MHz, Methanol-$d_4$:Chloroform-d 3:1) δ 8.43 (t, J=1.1 Hz, 1H), 8.14 (d, J=1.2 Hz, 1H), 7.65-7.56 (m, 2H), 7.16 (dd, J=9.6, 1.9 Hz, 1H), 7.09 (dd, J=8.0, 1.9 Hz, 1H), 5.68 (p, J=6.8 Hz, 1H), 3.97 (d, J=11.5 Hz, 2H), 3.37 (m, 2H), 3.20-3.27 (m, 1H), 3.01-2.87 (m, 2H), 2.77-2.59 (m, 3H), 2.29-2.24 (m, 2H), 1.50 (d, J=13.5 Hz, 2H). LCMS m/z 496.23 $[M+H]^+$.

Compound 5

1-[5-(5-fluoro-3-pyridyl)-8-[1-[(2S)-2-hydroxypropanoyl]azetidin-3-yl]oxy-6-tetrahydropyran-4-yl-pyrazolo[4,3-g]isoquinolin-1-yl]-2-hydroxy-propan-1-one (5)

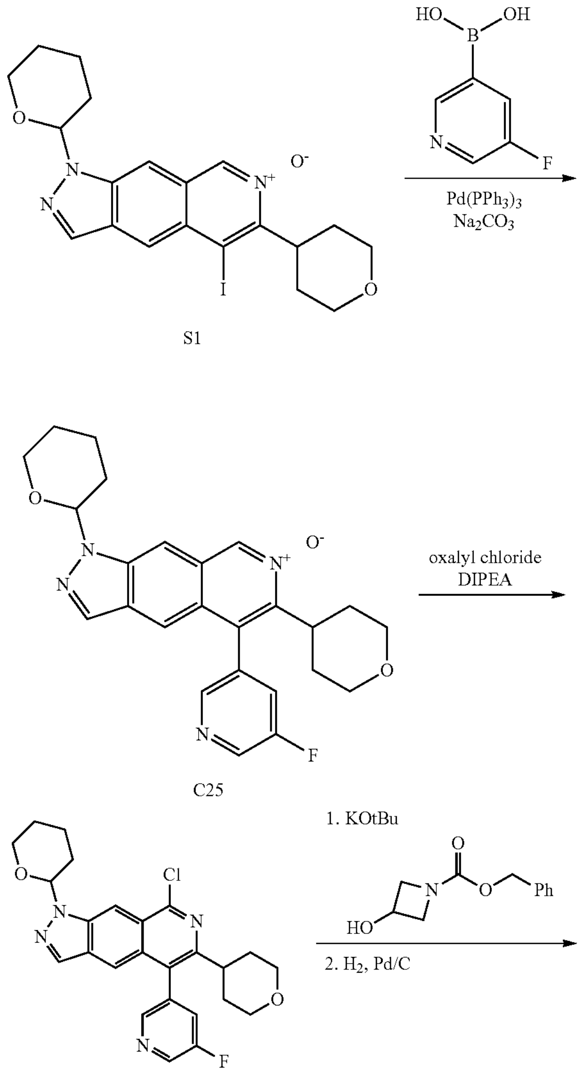

S1

C25

C26

-continued

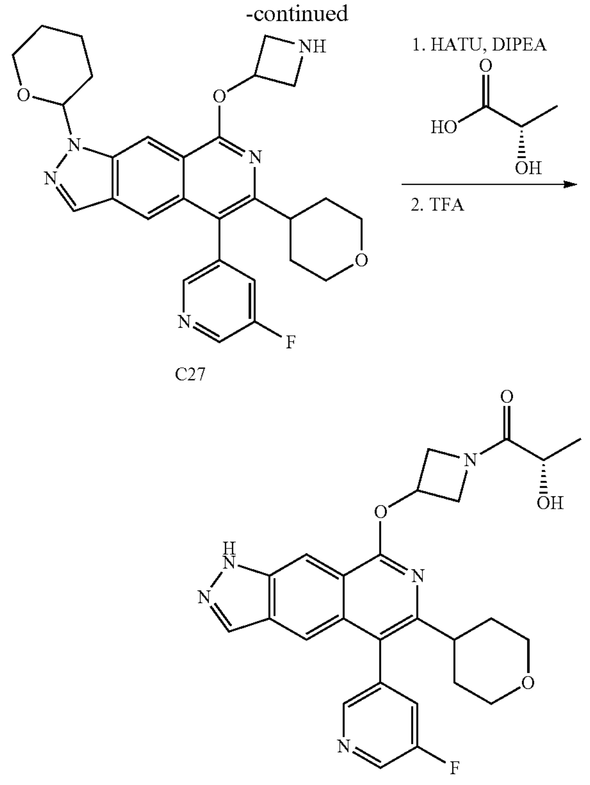

C27

5

Step 1. Synthesis of 5-(5-fluoro-3-pyridyl)-7-oxido-1-tetrahydropyran-2-yl-6-tetrahydropyran-4-yl-pyrazolo[4,3-g]isoquinolin-7-ium (C25)

A mixture of 5-iodo-7-oxido-1-tetrahydropyran-2-yl-6-tetrahydropyran-4-yl-pyrazolo[4,3-g]isoquinolin-7-ium (1 g, 1.997 mmol), (5-fluoro-3-pyridyl)boronic acid (360 mg, 2.555 mmol) and Pd(dppf)$Cl_2$ (100 mg, 0.1225 mmol) in DMSO (10 mL) was bubbled with nitrogen. $Na_2CO_3$ (2 mL of 2 M, 4.000 mmol) was added and the mixture was stirred overnight at 90° C. The mixture was diluted with EtOAc, washed with $H_2O$, dried over $Na_2SO_4$ and then concentrated. Purification by silica gel chromatography (Gradient: 0-10% MeOH/dichloromethane) yielded the product, which was used in the next step without further purification. 5-(5-fluoro-3-pyridyl)-7-oxido-1-tetrahydropyran-2-yl-6-tetrahydropyran-4-yl-pyrazolo[4,3-g]isoquinolin-7-ium (850 mg, 61%). The product was carried to next step. LCMS m/z 449.0 $[M+H]^+$.

Step 2. Synthesis of 8-chloro-5-(5-fluoro-3-pyridyl)-1-tetrahydropyran-2-yl-6-tetrahydropyran-4-yl-pyrazolo[4,3-g]isoquinoline (C26)

A solution of 5-(5-fluoro-3-pyridyl)-7-oxido-1-tetrahydropyran-2-yl-6-tetrahydropyran-4-yl-pyrazolo[4,3-g]isoquinolin-7-ium (850 mg, 1.895 mmol) in dichloromethane (20 mL) was added DIPEA (1 mL, 5.741 mmol) and oxalyl chloride (2 mL of 2 M, 4.0 mmol) at 0° C. The mixture was stirred for 1 hour, then concentrated. Purification by silica gel chromatography (Gradient: 0-10% MeOH in dichloromethane) afforded the product. 8-chloro-5-(5-fluoro-3-pyridyl)-1-tetrahydropyran-2-yl-6-tetrahydropyran-4-yl-pyrazolo[4,3-g]isoquinoline (500 mg, 57%). LCMS m/z 467.0 $[M+H]^+$.

Step 3. Synthesis of 8-(azetidin-3-yloxy)-5-(5-fluoro-3-pyridyl)-1-tetrahydropyran-2-yl-6-tetrahydropyran-4-yl-pyrazolo[4,3-g]isoquinoline (C27)

Part A. A solution of benzyl 3-hydroxyazetidine-1-carboxylate (90 mg, 0.4343 mmol) in DMSO (1 mL) was added KOtBu (48 mg, 0.4278 mmol) and stirred for 10 min. To the mixture was added 8-chloro-5-(5-fluoro-3-pyridyl)-1-tetrahydropyran-2-yl-6-tetrahydropyran-4-yl-pyrazolo[4,3-g]isoquinoline (100 mg, 0.2142 mmol) and stirred for 30 min at 50° C. The reaction was then diluted with EtOAc, washed with $H_2O$, dried over $Na_2SO_4$ and concentrated. Purified by silica gel chromatography (Gradient: 0-10% MeOH in dichloromethane) afforded the product. Benzyl-3-[5-(5-fluoro-3-pyridyl)-1-tetrahydropyran-2-yl-6-tetrahydropyran-4-yl-pyrazolo[4,3-g]isoquinolin-8-yl]oxyazetidine-1-carboxylate (130 mg, 95%). LCMS m/z 638.0 $[M+H]^+$.

Part B. To a solution of benzyl 3-[5-(5-fluoro-3-pyridyl)-1-tetrahydropyran-2-yl-6-tetrahydropyran-4-yl-pyrazolo[4,3-g]isoquinolin-8-yl]oxyazetidine-1-carboxylate (130 mg, 95%) in methanol (5 mL) was added Pd/C (70 mg of 10% w/w, 0.06578 mmol) and stirred for 1 h under a H2 balloon. The mixture was filtered over a layer of Celite®, and the filtrate was concentrated. 8-(azetidin-3-yloxy)-5-(5-fluoro-3-pyridyl)-1-tetrahydropyran-2-yl-6-tetrahydropyran-4-yl-pyrazolo[4,3-g]isoquinoline (90 mg, 83%), LCMS m/z 504.0 $[M+H]^+$.

Step 4. Synthesis of (2S)-1-[3-[[5-(5-fluoro-3-pyridyl)-6-tetrahydropyran-4-yl-1H-pyrazolo[4,3-g]isoquinolin-8-yl]oxy]azetidin-1-yl]-2-hydroxy-propan-1-one (5)

Part A. To a mixture of 8-(azetidin-3-yloxy)-5-(5-fluoro-3-pyridyl)-1-tetrahydropyran-2-yl-6-tetrahydropyran-4-yl-pyrazolo[4,3-g]isoquinoline (90 mg, 0.1787 mmol), (2S)-2-hydroxypropanoic acid (25 mg, 0.2775 mmol) in DMF (1 mL) was added HATU (100 mg, 0.2630 mmol) and DIPEA (75 μL, 0.4306 mmol). The mixture was stirred for 30 minutes. Purification by reversed-phase chromatography (Column: C18. Gradient: 0-100% MeCN in water with 0.2% formic acid) afforded the product, which was used in part B. (2S)-1-[3-[5-(5-fluoro-3-pyridyl)-1-tetrahydropyran-2-yl-6-tetrahydropyran-4-yl-pyrazolo[4,3-g]isoquinolin-8-yl]oxyazetidin-1-yl]-2-hydroxy-propan-1-one (65 mg, 63%). LCMS m/z 576.0 $[M+H]^+$.

Part B. A solution of (2S)-1-[3-[5-(5-fluoro-3-pyridyl)-1-tetrahydropyran-2-yl-6-tetrahydropyran-4-yl-pyrazolo[4,3-g]isoquinolin-8-yl]oxyazetidin-1-yl]-2-hydroxy-propan-1-one (65 mg) in dichloromethane (5 mL) was added TFA (200 μL, 2.596 mmol). The mixture was stirred for 2 hours at room temperature. Purification by reversed-phase chromatography (Column: C18. Gradient: 10-100% MeCN in water with 0.1% formic acid) and then silica gel chromatography (Gradient: 0-15% MeOH in dichloromethane). (2S)-1-[3-[[5-(5-fluoro-3-pyridyl)-6-tetrahydropyran-4-yl-1H-pyrazolo[4,3-g]isoquinolin-8-yl]oxy]azetidin-1-yl]-2-hydroxy-propan-1-one (14.1 mg, 16%). $^1H$ NMR (400 MHz, Methanol-$d_4$) δ 8.67 (d, J=2.7 Hz, 1H), 8.50 (t, J=1.1 Hz, 1H), 8.38 (q, J=1.8 Hz, 1H), 8.22 (d, J=1.1 Hz, 1H), 7.78-7.69 (m, 1H), 7.64 (d, J=1.1 Hz, 1H), 5.74 (tq, J=6.6, 4.3 Hz, 1H), 5.01 (tdd, J=11.1, 6.6, 1.6 Hz, 1H), 4.75-4.55 (m, 2H), 4.43-4.19 (m, 3H), 3.98 (dd, J=11.5, 4.2 Hz, 2H), 3.39-3.33 (m, 2H), 2.73-2.54 (m, 1H), 2.21 (tdd, J=12.8, 10.5, 8.3, 5.2 Hz, 2H), 1.54 (dd, J=11.3, 5.0 Hz, 2H), 1.38 (d, J=6.7 Hz, 3H). LCMS m/z 492.0 [M+H]$^+$.

Compound 6

3-fluoro-4-[[5-(2-methyl-4-pyridyl)-6-tetrahydropyran-4-yl-1H-pyrazolo[4,3-g]isoquinolin-8-yl]oxy]benzoic acid (6)

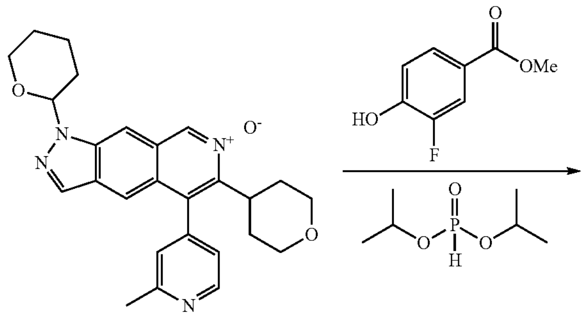

S2

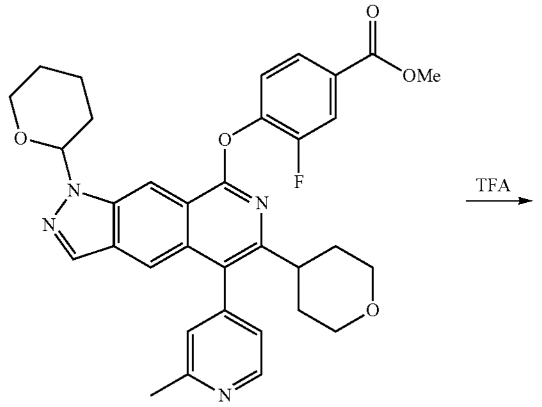

C28

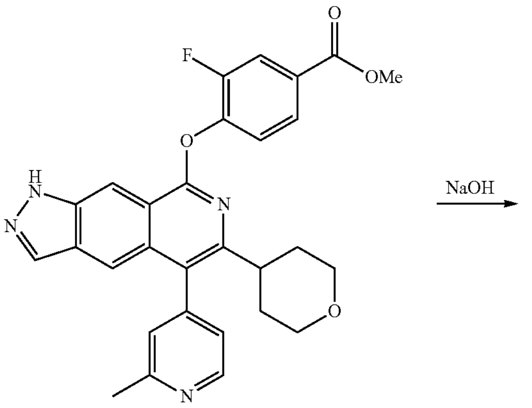

C29

-continued

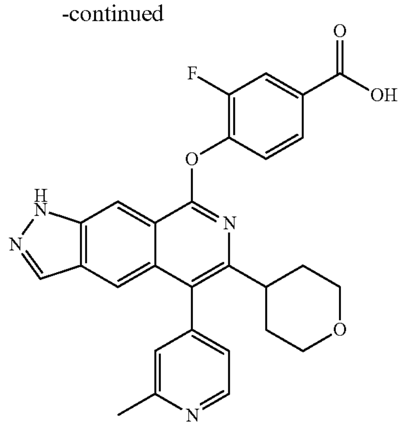

6

Step 1. Synthesis of 3-fluoro-4-[[5-(2-methyl-4-pyridyl)-6-tetrahydropyran-4-yl-1H-pyrazolo[4,3-g]isoquinolin-8-yl]oxy]benzoic acid (C28)

To a mixture of methyl 3-fluoro-4-hydroxy-benzoate (30 mg, 0.1763 mmol), $CCl_4$ (150 μL, 1.554 mmol), DIPEA (40 μL, 0.2296 mmol), 5-(2-methyl-4-pyridyl)-7-oxido-1-tetrahydropyran-2-yl-6-tetrahydropyran-4-yl-pyrazolo[4,3-g]soquinolin-7-ium; 5-(2-methyl-4-pyridyl)-7-oxido-2-tetrahydropyran-2-yl-6-tetrahydropyran-4-yl-pyrazolo[4,3-g]soquinolin-7-ium (50 mg, 0.1125 mmol) in MeCN (2 mL) was added 2-isopropoxyphosphonoyloxypropane (38 mg, 0.2287 mmol). The mixture was stirred at 40° C. overnight. The mixture was diluted with dichloromethane, and washed with $H_2O$. Purification by silica gel chromatography (Gradient: 0-8% MeOH in dichloromethane) yielded the product. Methyl 3-fluoro-4-[5-(2-methyl-4-pyridyl)-1-tetrahydropyran-2-yl-6-tetrahydropyran-4-yl-pyrazolo[4,3-g]soquinolin-8-yl]oxy-benzoate (32 mg, 48%). LCMS m/z 597.0 [M+H]$^+$.

Step 2. Synthesis of methyl 3-fluoro-4-[[5-(2-methyl-4-pyridyl)-6-tetrahydropyran-4-yl-1H-pyrazolo[4,3-g]isoquinolin-8-y]oxy]benzoate(C29)

A solution of methyl 3-fluoro-4-[5-(2-methyl-4-pyridyl)-1-tetrahydropyran-2-yl tetrahydropyran-4-yl-pyrazolo[4,3-g]isoquinolin-8-yl]oxy-benzoate (32 mg, 48%) in dichloromethane (3 mL) was added TFA (800 10.38 mmol) and stirred for 1 h. The mixture was concentrated to afford the product. methyl 3-fluoro-4-[[5-(2-methyl-4-pyridyl)-6-tetrahydropyran-4-yl-1H-pyrazolo[4,3-g]isoquinolin-8-yl]oxy]benzoate (25 mg, 43%). LCMS m/z 513.0 [M+H]$^+$.

Step 3. Synthesis of 3-fluoro-4-[[5-(2-methyl-4-pyridyl)-6-tetrahydropyran-4-yl-1H-pyrazolo[4,3-g]isoquinolin-8-yl]oxy]benzoic acid (6)

A solution of methyl 3-fluoro-4-[[5-(2-methyl-4-pyridyl)-6-tetrahydropyran-4-yl-1H-pyrazolo[4,3-g]isoquinolin-8-yl]oxy]benzoate (25 mg, 43%) in MeOH (5 mL) was added NaOH (300 μL of 6 M, 1.800 mmol) and stirred for 1 hour at 40° C. The pH of the mixture was adjusted to pH=3 by the addition of 1 M HCl, and then concentrated. Purification by reversed-phase chromatography (Column: C18. Gradient: 10-100% MeCN in water with 0.1% formic acid) afforded the product. 3-fluoro-4-[[5-(2-methyl-4-pyridyl)-6-tetrahydropyran-4-yl-1H-pyrazolo[4,3-g]isoquinolin-8-yl]oxy]

benzoic acid (18.8 mg, 32%). $^1$H NMR (400 MHz, Methanol-$d_4$) δ 8.69-8.54 (m, 2H), 8.27 (d, J=1.1 Hz, 1H), 8.12 (s, 2H), 8.05-7.96 (m, 1H), 7.92 (dd, J=10.9, 2.0 Hz, 1H), 7.74 (d, J=1.1 Hz, 1H), 7.56 (dd, J=8.4, 7.5 Hz, 1H), 7.40-7.34 (m, 1H), 7.29 (ddd, J=5.2, 1.7, 0.7 Hz, 1H), 3.83 (dd, J=11.6, 4.3 Hz, 2H), 3.27-3.18 (m, 1H), 2.66 (s, 3H), 2.49-2.39 (m, 1H), 1.90-1.60 (m, 2H), 1.44 (d, J=13.4 Hz, 2H), 0.81-0.67 (m, 1H), LCMS m/z 499.0 [M+H]$^+$.

Compounds 7-24

Compounds 7-24 (Table 1) were prepared from S2 and the appropriate aryl alcohol according to the method described for the preparation of compound 6. The ester hydrolysis step was omitted as appropriate. Modifications to this procedure are noted in the table footnotes.

TABLE 1

Method of preparation, structure and physicochemical data for compounds 7-24

| Compound | Product | Reagent | $^1$H NMR; LCMS m/z [M + H]$^+$ |
|---|---|---|---|
| 7 | 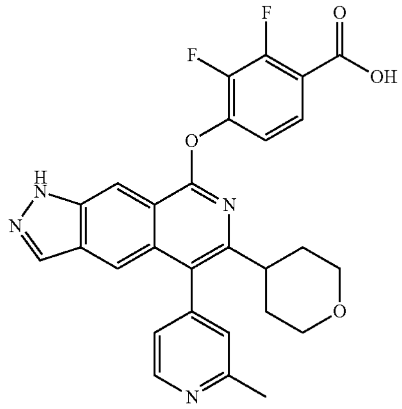 [SMILES: Cc1cc(-c2c(C3CCOCC3)nc(Oc3ccc(C(=O)O)c(F)c3F)c3cc4[nH]ncc4cc23)ccn1] | 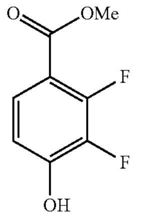 [SMILES: COC(=O)c1ccc(O)c(F)c1F] | $^1$H NMR (400 MHz, Methanol-$d_4$) δ 8.64 (t, J = 1.1 Hz, 1H), 8.62 (dd, J = 5.1, 0.8 Hz, 1H), 8.27 (d, J = 1.1 Hz, 1H), 8.22 (s, 2H), 7.80 (ddd, J = 9.6, 7.4, 2.2 Hz, 1H), 7.75 (d, J = 1.1 Hz, 1H), 7.40-7.36 (m, 1H), 7.36-7.25 (m, 2H), 3.84 (dd, J = 11.5, 4.3 Hz, 2H), 3.29-3.19 (m, 2H), 2.66 (s, 4H), 1.98-1.74 (m, 2H), 1.45 (d, J = 13.2 Hz, 2H). LCMS m/z 517.0 [M + H]$^+$. |
| 8 | 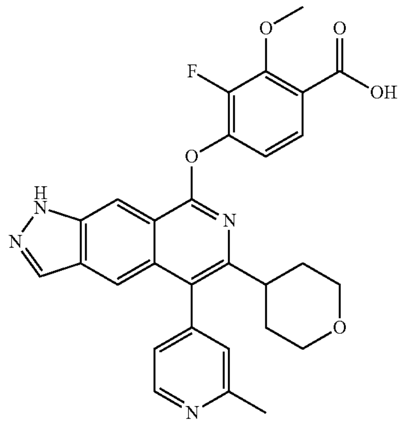 [SMILES: COc1c(C(=O)O)ccc(Oc2nc(C3CCOCC3)c(-c3ccnc(C)c3)c3cc4cn[nH]c4cc23)c1F] | 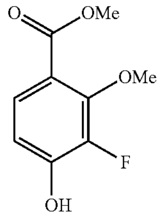 [SMILES: COC(=O)c1ccc(O)c(F)c1OC] | $^1$H NMR (400 MHz, Methanol-$d_4$) δ 8.70-8.55 (m, 2H), 8.27 (d, J = 1.1 Hz, 1H), 8.12 (s, 1H), 7.82-7.68 (m, 2H), 7.42-7.36 (m, 1H), 7.34-7.13 (m, 2H), 4.01 (d, J = 0.8 Hz, 3H), 3.83 (dd, J = 11.6, 4.2 Hz, 2H), 3.24 (d, J = 11.8 Hz, 2H), 2.66 (s, 4H), 1.87 (q, J = 12.6 Hz, 2H), 1.45 (d, J = 13.2 Hz, 2H). LCMS m/z 528.98 [M + H]$^+$. |
| 9 | 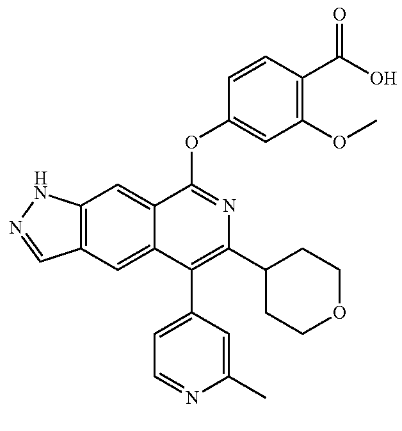 [SMILES: COc1cc(Oc2nc(C3CCOCC3)c(-c3ccnc(C)c3)c3cc4cn[nH]c4cc23)ccc1C(=O)O] | 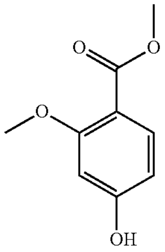 | $^1$H NMR (400 MHz, Methanol-$d_4$) δ 8.73-8.52 (m, 2H), 8.25 (dt, J = 3.1, 1.2 Hz, 1H), 8.10 (d, J = 0.8 Hz, 2H), 8.01 (ddd, J = 8.5, 2.7, 1.2 Hz, 1H), 7.73 (dt, J = 2.7, 1.2 Hz, 1H), 7.38 (s, 1H), 7.34-7.17 (m, 2H), 7.03 (dq, J = 8.6, 2.1 Hz, 1H), 3.95 (d, J = 1.5 Hz, 3H), 3.87 (dd, J = 11.5, 4.3 Hz, 2H), 3.26 (m, 2H), 2.67 (m, 4H), 2.09-1.83 (m, 2H), 1.50 (d, J = 13.4 Hz, 2H). LCMS m/z 511.0 [M + H]$^+$. |

TABLE 1-continued

Method of preparation, structure and physicochemical data for compounds 7-24

| Compound | Product | Reagent | $^1H$ NMR; LCMS m/z $[M + H]^+$ |
|---|---|---|---|
| 10 | 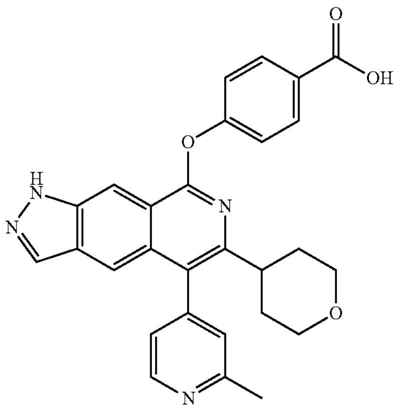 [SMILES: Cc1cc(-c2c(C3CCOCC3)nc(Oc3ccc(C(=O)O)cc3)c3cc4[nH]ncc4cc23)ccn1] | 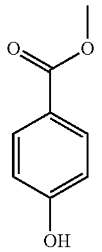 | $^1H$ NMR (400 MHz, Methanol-$d_4$) δ 8.68-8.57 (m, 2H), 8.32-8.22 (m, 1H), 8.16 (dt, J = 10.1, 2.6 Hz, 4H), 7.73 (t, J = 1.3 Hz, 1H), 7.55-7.42 (m, 2H), 7.37 (s, 1H), 7.29 (d, J = 5.2 Hz, 1H), 3.85 (dd, J = 11.6, 4.3 Hz, 2H), 3.25 (d, J = 11.8 Hz, 2H), 2.66 (s, 4H), 1.91 (q, J = 12.6 Hz, 2H), 1.47 (d, J = 13.6 Hz, 2H). LCMS m/z 481.0 $[M + H]^+$. |
| 11 | 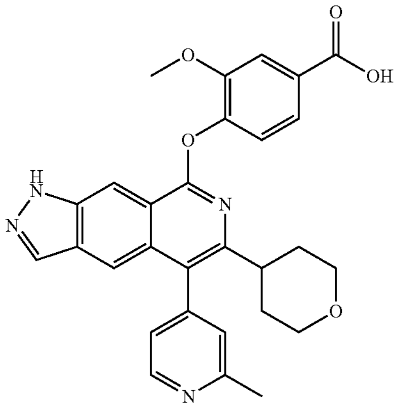 [SMILES: COc1cc(C(=O)O)ccc1Oc1nc(C2CCOCC2)c(-c2ccnc(C)c2)c2cc3cn[nH]c3cc12] | 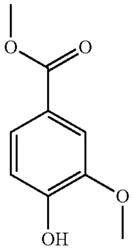 | $^1H$ NMR (400 MHz, Methanol-$d_4$) δ 8.67-8.50 (m, 2H), 8.24 (d, J = 1.1 Hz, 1H), 8.12 (s, 1H), 7.78 (d, J = 7.7 Hz, 2H), 7.71 (d, J = 1.1 Hz, 1H), 7.44-7.34 (m, 2H), 7.28 (dd, J = 5.1, 1.6 Hz, 1H), 3.80 (s, 5H), 3.27-3.13 (m, 2H), 2.66 (s, 3H), 2.59-2.58(m, 1H), 1.80 (ddt, J = 16.6, 12.3, 6.1 Hz, 2H), 1.50-1.22 (m, 2H). LCMS m/z 511.0 $[M + H]^+$. |
| 12 | 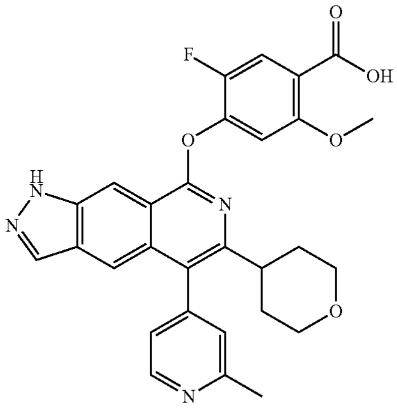 [SMILES: COc1cc(Oc2nc(C3CCOCC3)c(-c3ccnc(C)c3)c3cc4cn[nH]c4cc23)c(F)cc1C(=O)O] | 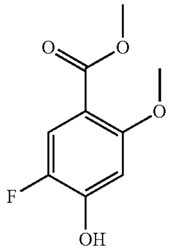 | $^1H$ NMR (400 MHz, Methanol-$d_4$) δ 8.68-8.57 (m, 2H), 8.27 (dd, J = 7.6, 1.1 Hz, 1H), 7.82-7.70 (m, 2H), 7.41-7.25 (m, 3H), 4.00-3.71 (m, 5H), 3.29-3.20 (m, 2H), 2.67 (d, J = 4.0 Hz, 4H), 2.01-1.74 (m, 2H), 1.46 (d, J = 13.4 Hz, 2H). LCMS m/z 529.02 $[M + H]^+$. |

TABLE 1-continued

Method of preparation, structure and physicochemical data for compounds 7-24

| Compound | Product | Reagent | $^1$H NMR; LCMS m/z [M + H]$^+$ |
| --- | --- | --- | --- |
| 13 | 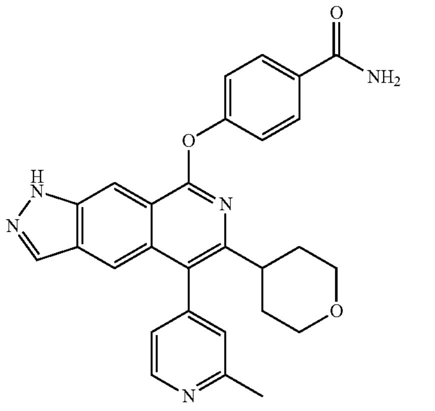 [SMILES: Cc1cc(-c2c(C3CCOCC3)nc(Oc3ccc(C(N)=O)cc3)c3cc4[nH]ncc4cc23)ccn1] | 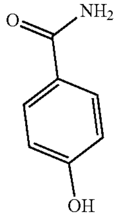 | $^1$H NMR (400 MHz, Methanol-$d_4$) δ 8.71-8.52 (m, 2H), 8.25 (d, J = 1.1 Hz, 1H), 8.12 (s, 2H), 8.08-7.90 (m, 2H), 7.73 (d, J = 1.1 Hz, 1H), 7.51-7.40 (m, 2H), 7.40-7.16 (m, 2H), 3.84 (dd, J = 11.6, 4.3 Hz, 2H), 3.26 (t, J = 1.6 Hz, 2H), 2.66 (s, 4H), 2.04-1.78 (m, 2H), 1.46 (d, J = 13.3 Hz, 2H). LCMS m/z 480.0 [M + H]$^+$. |
| 14 | 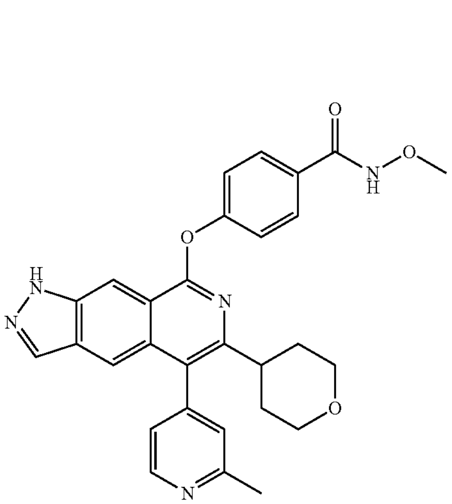 [SMILES: CONC(=O)c1ccc(Oc2nc(C3CCOCC3)c(-c3ccnc(C)c3)c3cc4cn[nH]c4cc23)cc1] | 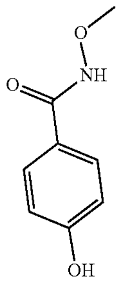 | $^1$H NMR (400 MHz, Methanol-$d_4$) δ 8.70-8.56 (m, 2H), 8.29-8.21 (m, 1H), 8.09 (s, 2H), 7.98-7.91 (m, 2H), 7.73 (d, J = 1.1 Hz, 1H), 7.48 (d, J = 8.7 Hz, 2H), 7.41-7.35 (m, 1H), 7.35-7.17 (m, 1H), 3.85 (s, 5H), 3.26 (m, 2H), 2.75-2.43 (m, 4H), 1.89 (dddd, J = 17.0, 12.5, 8.4, 4.4 Hz, 2H), 1.46 (d, J = 13.5 Hz, 2H). LCMS m/z 510.0 [M + H]$^+$. |
| 15 | 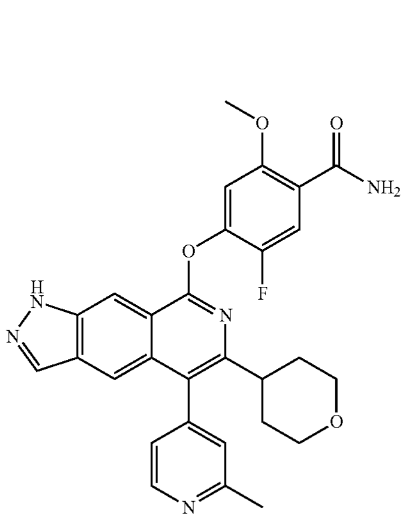 [SMILES: COc1cc(Oc2nc(C3CCOCC3)c(-c3ccnc(C)c3)c3cc4cn[nH]c4cc23)c(F)cc1C(N)=O] | 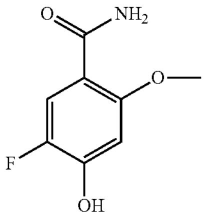 | $^1$H NMR (400 MHz, Methanol-$d_4$) δ 8.69-8.51 (m, 2H), 8.32-8.22 (m, 2H), 7.92 (d, J = 11.3 Hz, 1H), 7.74 (d, J = 1.1 Hz, 1H), 7.44-7.32 (m, 2H), 7.28 (ddd, J = 5.1, 1.7, 0.6 Hz, 1H), 4.03 (s, 3H), 3.84 (dd, J = 11.4, 4.3 Hz, 2H), 3.29-3.20 (m, 2H), 2.66 (m, 5H), 1.89 (ddt, J = 16.7, 12.4, 6.1 Hz, 2H), 1.46 (d, J = 13.2 Hz, 2H), 1.24 (d, J = 6.1 Hz, 1H). LCMS m/z 528.0 [M + H]$^+$. |

TABLE 1-continued

| Method of preparation, structure and physicochemical data for compounds 7-24 | | | |
|---|---|---|---|
| Compound | Product | Reagent | $^1$H NMR; LCMS m/z $[M + H]^+$ |
| 16 | 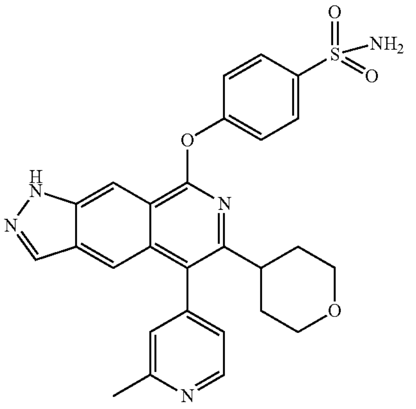 [SMILES: Cc1cc(-c2c(C3CCOCC3)nc(Oc3ccc(S(N)(=O)=O)cc3)c3cc4[nH]ncc4cc23)ccn1] | 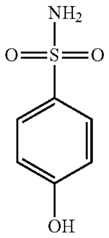 | $^1$H NMR (400 MHz, Methanol-$d_4$) δ 8.69-8.57 (m, 2H), 8.26 (d, J = 1.1 Hz, 1H), 8.11 (s, 2H), 8.05 (d, J = 8.8 Hz, 2H), 7.73 (d, J = 1.1 Hz, 1H), 7.58-7.53 (m, 2H), 7.42-7.20 (m, 1H), 3.92-3.76 (m, 2H), 3.26 (m, 1H), 2.67 (m, 5H), 1.89 (dtd, J = 17.0, 12.4, 4.4 Hz, 2H), 1.47 (d, J = 13.1 Hz, 2H). LCMS m/z 516.0 $[M + H]^+$. |
| 17 | 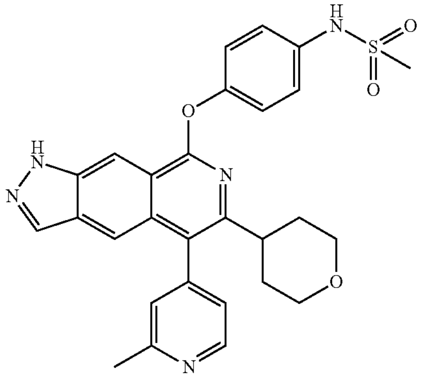 [SMILES: Cc1cc(-c2c(C3CCOCC3)nc(Oc3ccc(NS(C)(=O)=O)cc3)c3cc4[nH]ncc4cc23)ccn1] | 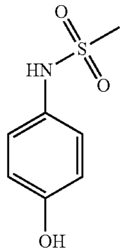 | $^1$H NMR (400 MHz, Methanol-$d_4$) δ 8.69-8.56 (m, 2H), 8.24 (d, J = 1.1 Hz, 1H), 8.12 (s, 2H), 7.70 (d, J = 1.1 Hz, 1H), 7.47-7.17 (m, 6H), 3.91-3.77 (m, 2H), 3.25 (t, J = 11.8 Hz, 2H), 3.00 (s, 3H), 2.66 (m, 4H), 1.88 (ddt, J = 16.8, 12.2, 6.2 Hz, 2H), 1.44 (d, J = 13.3 Hz, 2H). LCMS m/z 530.0 $[M + H]^+$. |
| 18 | 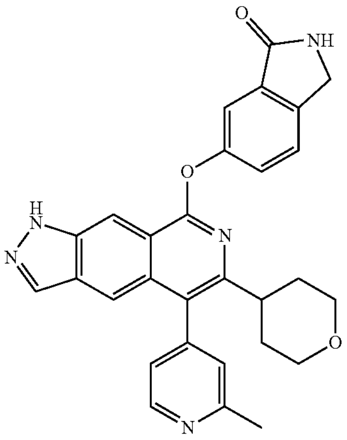 [SMILES: Cc1cc(-c2c(C3CCOCC3)nc(Oc3ccc4c(c3)C(=O)NC4)c3cc4[nH]ncc4cc23)ccn1] | 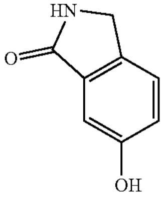 [SMILES: O=C1NCc2ccc(O)cc21] | $^1$H NMR (400 MHz, Methanol-$d_4$) δ 8.67 (t, J = 1.1 Hz, 1H), 8.62 (dd, J = 5.1, 0.8 Hz, 1H), 8.26 (d, J = 1.1 Hz, 1H), 8.11 (s, 2H), 7.78-7.70 (m, 3H), 7.62 (dd, J = 8.2, 2.2 Hz, 1H), 7.42-7.36 (m, 1H), 7.34-7.22 (m, 1H), 4.55 (s, 2H), 3.81 (dd, J = 11.5, 4.3 Hz, 2H), 3.24 (t, J = 11.7 Hz, 2H), 2.66 (s, 4H), 1.94-1.76 (m, 2H), 1.44 (d, J = 13.1 Hz, 2H). LCMS m/z 492.0 $[M + H]^+$. |

TABLE 1-continued

Method of preparation, structure and physicochemical data for compounds 7-24

| Compound | Product | Reagent | $^1$H NMR; LCMS m/z [M + H]$^+$ |
|---|---|---|---|
| 19 | 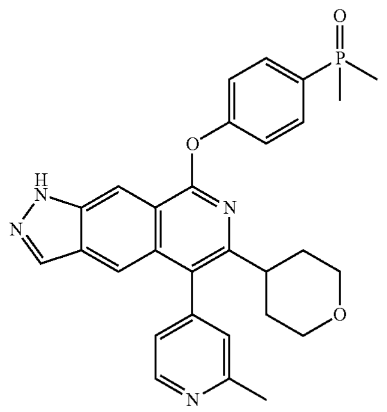 [SMILES: Cc1cc(-c2c(C3CCOCC3)nc(Oc3ccc(P(C)(C)=O)cc3)c3cc4[nH]ncc4cc23)ccn1] | 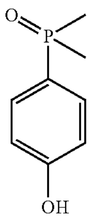 | $^1$H NMR (400 MHz, Methanol-$d_4$) δ 8.68-8.57 (m, 2H), 8.25 (d, J = 1.1 Hz, 1H), 8.02-7.88 (m, 2H), 7.73 (d, J = 1.1 Hz, 1H), 7.59 (dq, J = 9.1, 2.4 Hz, 2H), 7.40-7.33 (m, 1H), 7.31-7.23 (m, 1H), 3.84 (dd, J = 11.5, 4.3 Hz, 2H), 3.28-3.17 (m, 2H), 2.66 (s, 5H), 1.86 (d, J = 13.4 Hz, 7H), 1.50-1.40 (m, 2H). LCMS m/z 513.0 [M + H]$^+$. |
| 20* | 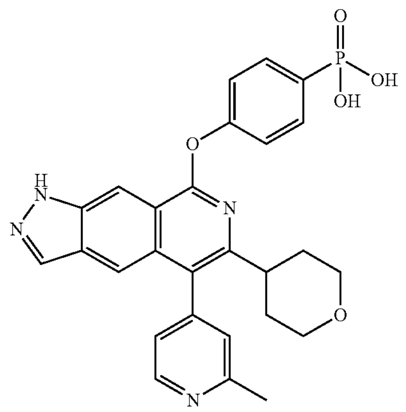 [SMILES: Cc1cc(-c2c(C3CCOCC3)nc(Oc3ccc(P(=O)(O)O)cc3)c3cc4[nH]ncc4cc23)ccn1] | 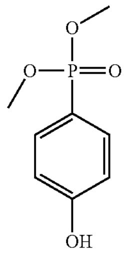 | $^1$H NMR (400 MHz, Methanol-$d_4$) δ 8.68-8.60 (m, 2H), 8.24 (d, J = 1.1 Hz, 1H), 7.96 (dd, J = 12.1, 8.4 Hz, 2H), 7.71 (d, J = 1.1 Hz, 1H), 7.47-7.35 (m, 3H), 7.31 (d, J = 5.1 Hz, 1H), 3.82 (dd, J = 11.4, 4.3 Hz, 2H), 3.23 (t, J = 12.0 Hz, 2H), 2.67 (s, 4H), 1.98-1.82 (m, 2H), 1.43 (d, J = 12.8 Hz, 2H). LCMS m/z 517.0 [M + H]$^+$. |
| 21 | 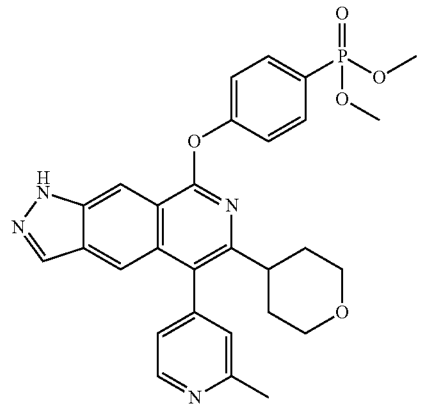 [SMILES: COP(=O)(OC)c1ccc(Oc2nc(C3CCOCC3)c(-c3ccnc(C)c3)c3cc4cn[nH]c4cc23)cc1] | 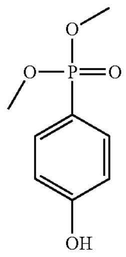 | $^1$H NMR (400 MHz, Methanol-$d_4$) δ 8.69-8.58 (m, 2H), 8.31-8.20 (m, 2H), 8.03-7.87 (m, 2H), 7.74 (d, J = 1.1 Hz, 1H), 7.62-7.54 (m, 2H), 7.40-7.34 (m, 1H), 7.31-7.12 (m, 1H), 3.82 (d, J = 11.2 Hz, 8H), 3.24 (d, J = 11.9 Hz, 2H), 2.66 (s, 4H), 1.98-1.79 (m, 2H), 1.51-1.36 (m, 2H). LCMS m/z 545.0 [M + H]$^+$. |

TABLE 1-continued

Method of preparation, structure and physicochemical data for compounds 7-24

| Compound | Product | Reagent | $^1H$ NMR; LCMS m/z [M + H]$^+$ |
|---|---|---|---|
| 22 | 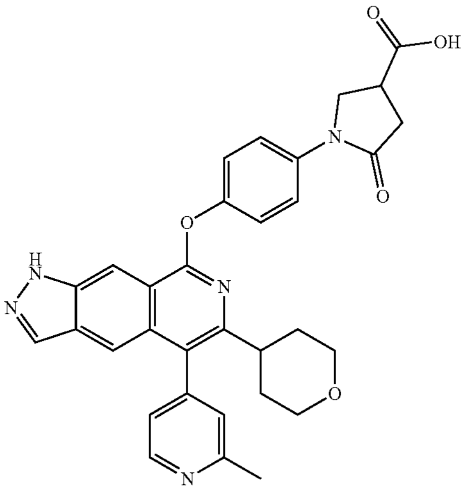 [SMILES: Cc1cc(-c2c(C3CCOCC3)nc(Oc3ccc(N4CC(C(=O)O)CC4=O)cc3)c3cc4[nH]ncc4cc23)ccn1] | 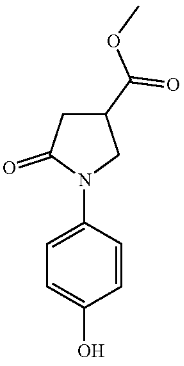 | $^1H$ NMR (400 MHz, Methanol-$d_4$) δ 8.68-8.55 (m, 2H), 8.24 (d, J = 1.1 Hz, 1H), 8.11 (s, 2H), 7.80-7.73 (m, 2H), 7.70 (d, J = 1.1 Hz, 1H), 7.46-7.34 (m, 2H), 7.31-7.15 (m, 1H), 4.28-4.12 (m, 2H), 3.84 (dd, J = 11.5, 4.2 Hz, 2H), 3.51-3.38 (m, 1H), 3.28-3.15 (m, 2H), 2.92 (d, J = 8.2 Hz, 2H), 2.66 (s, 4H), 1.99-1.79 (m, 2H), 1.45 (d, J = 13.2 Hz, 2H). LCMS m/z 564.0 [M + H]$^+$. |
| 23 | 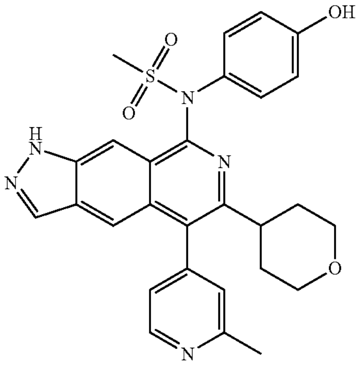 [SMILES: Cc1cc(-c2c(C3CCOCC3)nc(N(c3ccc(O)cc3)S(C)(=O)=O)c3cc4[nH]ncc4cc23)ccn1] | 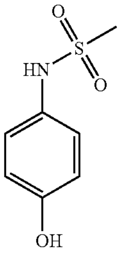 | $^1H$ NMR (400 MHz, Methanol-$d_4$) δ 8.69-8.56 (m, 2H), 8.24 (d, J = 1.1 Hz, 1H), 8.12 (s, 2H), 7.70 (d, J = 1.1 Hz, 1H), 7.47-7.17 (m, 6H), 3.91-3.77 (m, 2H), 3.25 (t, J = 11.8 Hz, 2H), 3.00 (s, 3H), 2.66 (m, 4H), 1.88 (ddt, J = 16.8, 12.2, 6.2 Hz, 2H), 1.44 (d, J = 13.3 Hz, 2H). LCMS m/z 530.0 [M + H]$^+$. |
| 24 | 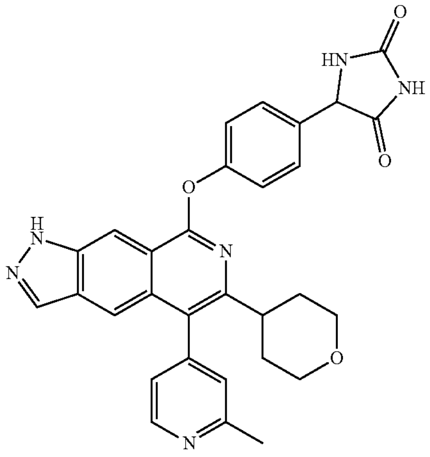 [SMILES: Cc1cc(-c2c(C3CCOCC3)nc(Oc3ccc(C4NC(=O)NC4=O)cc3)c3cc4[nH]ncc4cc23)ccn1] | 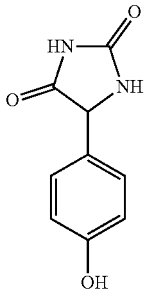 [SMILES: O=C1NC(=O)C(c2ccc(O)cc2)N1] | $^1H$ NMR (400 MHz, Methanol-$d_4$) δ 8.65-8.58 (m, 2H), 8.25 (d, J = 1.1 Hz, 1H), 7.71 (d, J = 1.1 Hz, 1H), 7.59-7.51 (m, 2H), 7.45-7.40 (m, 2H), 7.35 (d, J = 1.4 Hz, 1H), 7.27 (dd, J = 5.1, 1.5 Hz, 1H), 5.26 (s, 1H), 3.83 (dd, J = 11.3, 4.2 Hz, 2H), 3.24 (d, J = 11.8 Hz, 2H), 2.66 (s, 4H), 1.96-1.78 (m, 2H), 1.44 (d, J = 13.3 Hz, 2H). LCMS m/z 535.0 [M + H]$^+$. |

*The phosphonate ester was hydrolyzed by treatment with TMSBr in dichloromethane at room temperature.

Compounds 25-29

Compounds 25-29 were prepared from aryl chloride S3 by the addition of the appropriate alcohol reagent using KOtBu in DMSO. The THP group was deprotected with TFA in dichloromethane. Modifications to this procedure are noted in the table footnotes.

TABLE 2

Method of preparation, structure and physicochemical data for compounds 25-29

| Compound | Product | Reagent | $^1$H NMR; LCMS m/z $[M + H]^+$ |
|---|---|---|---|
| 25* | 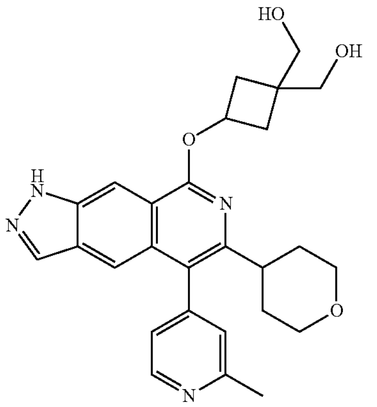 [SMILES: Cc1cc(-c2c(C3CCOCC3)nc(OC3CC(CO)(CO)C3)c3cc4[nH]ncc4cc23)ccn1] | 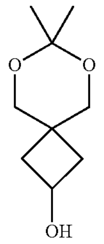 | $^1$H NMR (400 MHz, Methanol-$d_4$) δ 8.59 (dd, J = 5.1, 0.8 Hz, 1H), 8.46 (t, J = 1.1 Hz, 1H), 8.37 (s, 1H), 8.18 (d, J = 1.2 Hz, 1H), 7.60 (d, J = 1.1 Hz, 1H), 7.32 (dd, J = 1.6, 0.8 Hz, 1H), 7.24 (ddd, J = 5.1, 1.6, 0.7 Hz, 1H), 5.52 (t, J = 7.1 Hz, 1H), 3.97 (dd, J = 11.5, 4.3 Hz, 3H), 3.73 (s, 2H), 3.65 (s, 2H), 3.36 (d, J = 12.0 Hz, 2H), 2.75-2.48 (m, 7H), 2.24 (ddd, J = 17.6, 12.9, 6.3 Hz, 4H), 1.53 (d, J = 14.2 Hz, 1H). LCMS m/z 475.0 $[M + H]^+$ |
| 26** | 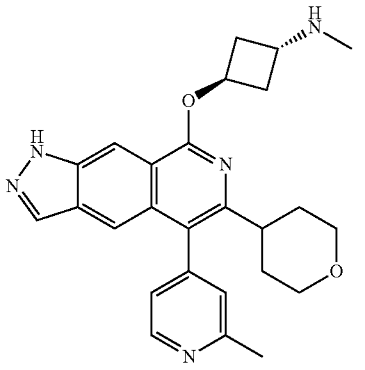 [SMILES: CN[C@H]1C[C@H](Oc2nc(C3CCOCC3)c(-c3ccnc(C)c3)c3cc4cn[nH]c4cc23)C1] | 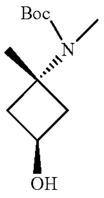 | $^1$H NMR (400 MHz, Methanol-$d_4$) δ 8.65 (dd, J = 5.3, 0.8 Hz, 1H), 8.48 (t, J = 1.1 Hz, 1H), 8.21 (d, J = 1.1 Hz, 1H), 8.07 (s, 2H), 7.66 (d, J = 1.1 Hz, 1H), 7.48-7.43 (m, 1H), 7.40-7.34 (m, 1H), 5.83-5.71 (m, 1H), 4.12-3.90 (m, 3H), 3.36 (t, J = 12.0 Hz, 2H), 2.97-2.85 (m, 4H), 2.75 (s, 3H), 2.70 (s, 4H), 2.22 (qt, J = 12.1, 5.1 Hz, 2H), 1.56 (d, J = 13.3 Hz, 2H). LCMS m/z 444.0 $[M + H]^+$. |
| 27*** | 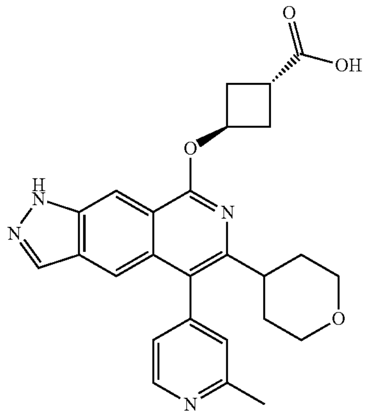 [SMILES: Cc1cc(-c2c(C3CCOCC3)nc(O[C@H]3C[C@H](C(=O)O)C3)c3cc4[nH]ncc4cc23)ccn1] | 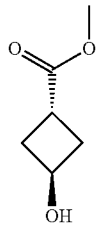 | $^1$H NMR (400 MHz, Methanol-$d_4$) δ 8.61 (d, J = 5.1 Hz, 1H), 8.46 (dt, J = 4.4, 1.2 Hz, 1H), 8.19 (t, J = 1.2 Hz, 1H), 8.10 (s, 2H), 7.62 (d, J = 1.1 Hz, 1H), 7.37 (d, J = 1.7 Hz, 1H), 7.29 (dd, J = 5.2, 1.7 Hz, 1H), 5.49 (dd, J = 8.5, 6.9 Hz, 1H), 3.98 (dd, J = 11.4, 4.3 Hz, 2H), 3.36 (d, J = 12.2 Hz, 2H), 3.07-2.90 (m, 3H), 2.67 (m, 4H), 2.54 (m, 2H), 2.25 (tt, J = 12.3, 6.4 Hz, 2H), 1.54 (d, J = 13.1 Hz, 2H). LCMS m/z 459.0 $[M + H]^+$. |

TABLE 2-continued

Method of preparation, structure and physicochemical data for compounds 25-29

| Compound | Product | Reagent | $^1$H NMR; LCMS m/z $[M + H]^+$ |
|---|---|---|---|
| 28 | 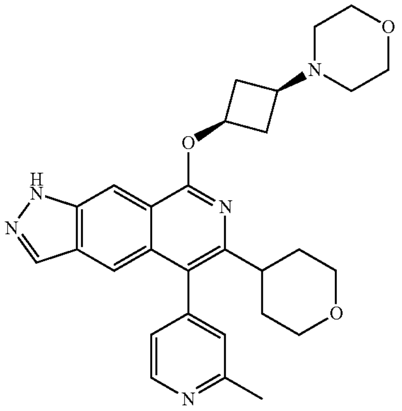 [SMILES: Cc1cc(-c2c(C3CCOCC3)nc(O[C@H]3C[C@@H](N4CCOCC4)C3)c3cc4[nH]ncc4cc23)ccn1] | 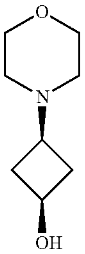 [SMILES: O[C@H]1C[C@@H](N2CCOCC2)C1] | $^1$H NMR (400 MHz, Methanol-$d_4$) δ 8.60 (dd, J = 5.1, 0.8 Hz, 1H), 8.44 (t, J = 1.2 Hz, 1H), 8.30-8.12 (m, 2H), 7.62 (d, J = 1.1 Hz, 1H), 7.39-7.16 (m, 2H), 5.36 (q, J = 7.1 Hz, 1H), 3.97 (dd, J = 11.5, 4.4 Hz, 2H), 3.80 (t, J = 4.7 Hz, 4H), 3.44-3.35 (m, 2H), 3.03 (q, J = 9.5 Hz, 2H), 2.84-2.61 (m, 9H), 2.41-2.06 (m, 4H), 1.55 (d, J = 13.3 Hz, 2H). LCMS m/z 500.0 $[M + H]^+$. |
| 29* | 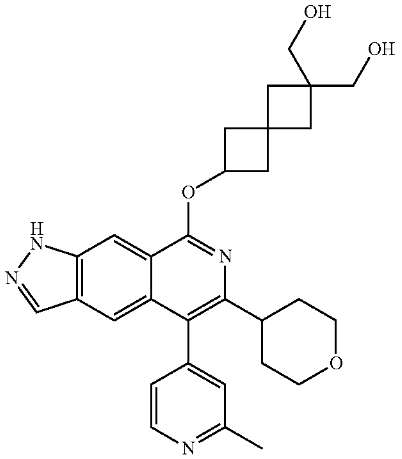 [SMILES: Cc1cc(-c2c(C3CCOCC3)nc(OC3CC4(C3)CC(CO)(CO)C4)c3cc4[nH]ncc4cc23)ccn1] | 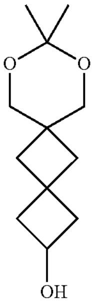 | $^1$H NMR (400 MHz, Methanol-$d_4$) δ 8.48 (dd, J = 5.1, 0.9 Hz, 1H), 8.31 (t, J = 1.1 Hz, 1H), 8.12 (s, 1H), 8.07 (d, J = 1.1 Hz, 1H), 7.48 (d, J = 1.1 Hz, 1H), 7.21 (d, J = 1.5 Hz, 1H), 7.13 (dd, J = 5.0, 1.9 Hz, 1H), 5.31 (t, J = 7.0 Hz, 1H), 3.87 (dd, J = 11.4, 4.2 Hz, 2H), 3.46 (s, 4H), 3.25 (d, J = 12.1 Hz, 2H), 2.68 (ddd, J = 10.1, 6.9, 3.0 Hz, 2H), 2.54 (s, 4H), 2.35 (td, J = 6.9, 1.5 Hz, 2H), 2.30-2.06 (m, 2H), 1.97 (s, 2H), 1.87 (m, 1H), 1.73-1.50 (m, 1H), 1.42 (d, J = 13.2 Hz, 2H), 0.69-0.54 (m, 2H). LCMS m/z 515.0 $[M + H]^+$. |

*Acetonide deprotection occurred during THP deprotection with TFA. Trifluoroacetate esters of the products 25 and 29 were also observed in the acetonide deprotection. These esters were converted to products 25 and 29 by hydrolysis with NaOH.

**The Boc group was removed during the THP deprotection with TFA.

***Methyl ester hydrolysis was performed by treatment with NaOH prior to the THP deprotection step.

Compound 30

N-[(1S)-2-hydroxy-1-methyl-ethyl]-3-[[5-(2-methyl-4-pyridyl)-6-tetrahydropyran-4-yl-1H-pyrazolo[4,3-g]isoquinolin-8-yl]oxy]cyclobutanecarboxamide (30)

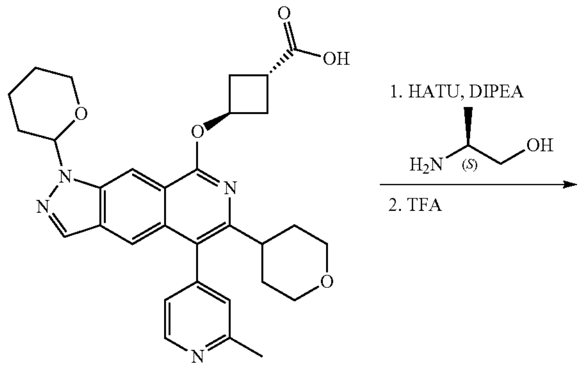

C30

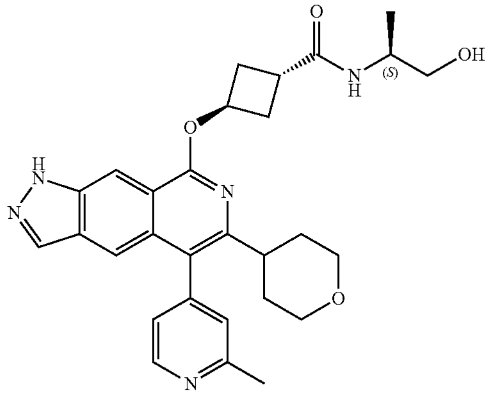

30

Compound 30 was prepared in two steps from C30.

Part A. To a mixture of 3-[5-(2-methyl-4-pyridyl)-1-tetrahydropyran-2-yl-6-tetrahydropyran-4-yl-pyrazolo[4,3-g]isoquinolin-8-yl]oxycyclobutanecarboxylic acid (15 mg, 0.02764 mmol), (2S)-2-aminopropan-1-ol (3 mg, 0.03994 mmol) in DMF (0.5 mL) was added HATU (15 mg, 0.03945 mmol) and DIPEA (20 μL, 0.1148 mmol). The mixture was stirred for 1 hour. Purification by reversed-phase chromatography (Column: C18. Gradient: 0-100% MeCN in water with 0.1% formic acid) afforded the product. N-[(1S)-2-hydroxy-1-methyl-ethyl]-3-[5-(2-methyl-4-pyridyl)-1-tetrahydropyran-2-yl-6-tetrahydropyran-4-yl-pyrazolo[4,3-g]isoquinolin-8-yl]oxy-cyclobutanecarboxamide (8 mg, 48%), LCMS m/z 600.0 $[M+H]^+$.

Part B. A solution of N-[(1S)-2-hydroxy-1-methyl-ethyl]-3-[5-(2-methyl-4-pyridyl)-1-tetrahydropyran-2-yl-6-tetrahydropyran-4-yl-pyrazolo[4,3-g]isoquinolin-8-yl]oxy-cyclobutanecarboxamide (8 mg) in dichloromethane (2 mL) was added TFA (200 μL, 2.596 mmol). The mixture was stirred for 1 hour. Purification by reversed-phase chromatography (Column: C18. Gradient: 10-100% MeCN in water with 0.1% formic acid) afforded the product. N-[(1S)-2-hydroxy-1-methyl-ethyl]-3-[[5-(2-methyl-4-pyridyl)-6-tetrahydropyran-4-yl-1H-pyrazolo[4,3-g]isoquinolin-8-yl]oxy]cyclobutanecarboxamide (3.0 mg, 20%), $^1H$ NMR (400 MHz, Methanol-$d_4$) δ 8.59 (dd, J=5.1, 0.9 Hz, 1H), 8.46 (dt, J=3.7, 1.1 Hz, 1H), 8.38 (s, 1H), 8.19 (t, J=1.2 Hz, 1H), 7.61 (d, J=1.1 Hz, 1H), 7.39-7.31 (m, 1H), 7.30-7.20 (m, 1H), 5.48 (q, J=7.2, 6.7 Hz, 1H), 4.07-3.88 (m, 3H), 3.59-3.43 (m, 2H), 3.36 (d, J=11.9 Hz, 2H), 2.98-2.76 (m, 4H), 2.76-2.48 (m, 6H), 2.25 (dq, J=12.1, 6.4, 6.0 Hz, 2H), 1.55 (d, J=13.0 Hz, 2H), 1.16 (d, J=6.8 Hz, 4H). LCMS m/z 516.0 $[M+H]^+$.

Compound 31

N-(2-hydroxy-1-methyl-ethyl)-N-methyl-3-[[5-(2-methyl-4-pyridyl)-6-tetrahydropyran-4-yl-1H-pyrazolo[4,3-g]isoquinolin-8-yl]oxy]cyclobutanecarboxamide (31)

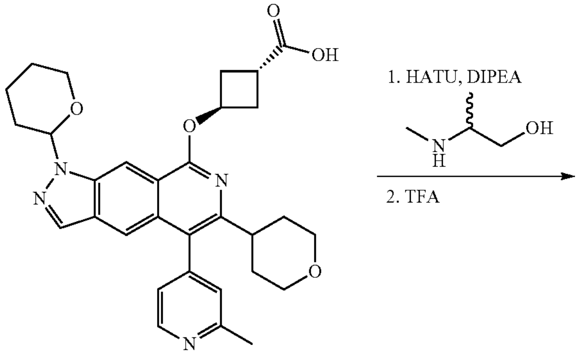

C30

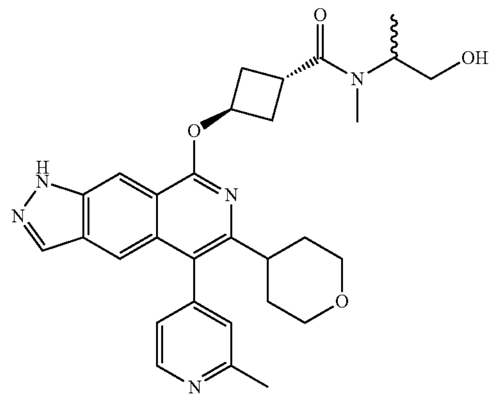

31

Compound 31 was prepared from C30 and 2-(methylamino)propan-1-ol according to the method described for the preparation of compound 30. N-(2-hydroxy-1-methyl-ethyl)-N-methyl-3-[[5-(2-methyl-4-pyridyl)-6-tetrahydropyran-4-yl-1H-pyrazolo[4,3-g]isoquinolin-8-yl]oxy]cyclobutanecarboxamide (2.7 mg, 17%). $^1H$ NMR (400 MHz, Methanol-$d_4$) δ 8.59 (d, J=5.0 Hz, 1H), 8.44 (t, J=1.1 Hz, 1H), 8.28 (s, 2H), 8.24-8.09 (m, 1H), 7.61 (d, J=1.1 Hz, 1H), 7.33 (s, 1H), 7.25 (d, J=5.1 Hz, 1H), 5.52 (q, J=7.5 Hz, 1H), 4.75-4.63 (m, 2H), 4.19-3.98 (m, 4H), 3.69-3.47 (m, 2H), 3.35-3.30 (m, 2H), 2.96 (m, 3H), 2.83-2.43 (m, 6H), 2.42-2.21 (m, 2H), 1.55 (d, J=12.9 Hz, 2H), 1.23-1.03 (m, 3H). LCMS m/z 530.0 $[M+H]^+$.

Compound 32

(2S)-2-hydroxy-N-methyl-N-[3-[[5-(2-methyl-4-pyridyl)-6-tetrahydropyran-4-yl-1H-pyrazolo[4,3-g]isoquinolin-8-yl]oxy]cyclobutyl]propanamide (32)

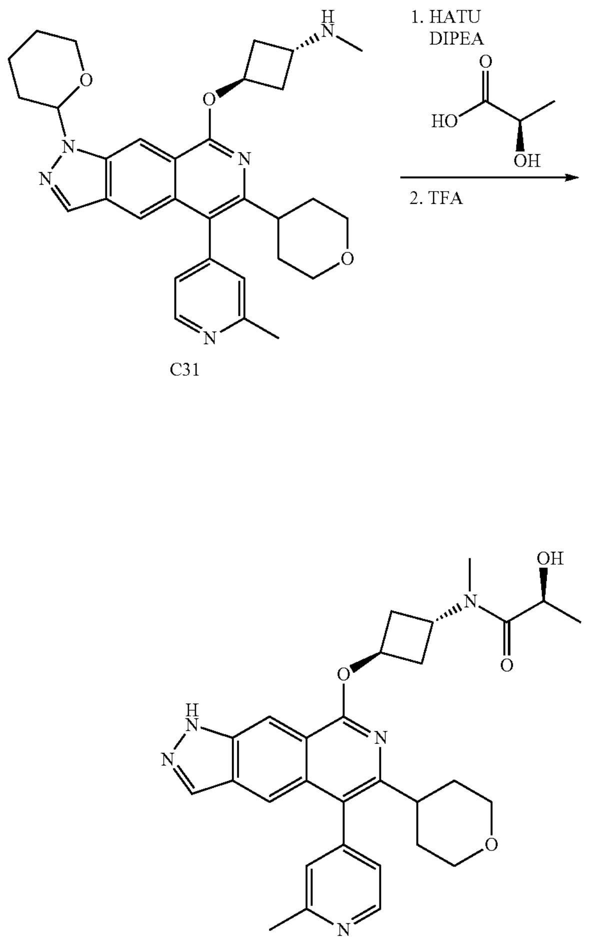

C31

32

Compound 32 was prepared from C31 and (2S)-2-hydroxypropanoic acid according to the method described for compound 30. (2S)-2-hydroxy-N-methyl-N-[3-[[5-(2-methyl-4-pyridyl)-6-tetrahydropyran-4-yl-1H-pyrazolo[4,3-g]isoquinolin-8-yl]oxy]cyclobutyl]propanamide (11.4 mg, 40%). $^1$H NMR (400 MHz, Methanol-$d_4$) δ 8.60 (dd, J=5.1, 0.8 Hz, 1H), 8.51 (t, J=1.1 Hz, 1H), 8.20 (d, J=1.1 Hz, 1H), 8.11 (s, 2H), 7.63 (d, J=1.1 Hz, 1H), 7.35 (s, 1H), 7.27 (d, J=5.1 Hz, 1H), 5.63 (d, J=7.7 Hz, 1H), 4.71-4.51 (m, 1H), 4.02-3.92 (m, 2H), 3.36 (d, J=11.9 Hz, 2H), 3.23-3.09 (m, 3H), 3.10-2.85 (m, 3H), 2.80-2.62 (m, 5H), 2.23 (tt, J=12.6, 7.0 Hz, 2H), 1.54 (d, J=13.3 Hz, 2H), 1.33 (t, J=7.4 Hz, 3H). LCMS m/z 516.0 [M+H]$^+$.

Compound 33

2-hydroxy-N-[3-hydroxy-2-[[5-(2-methyl-4-pyridyl)-6-tetrahydropyran-4-yl-1H-pyrazolo[4,3-g]isoquinolin-8-yl]oxy]propyl]ethanesulfonamide (33)

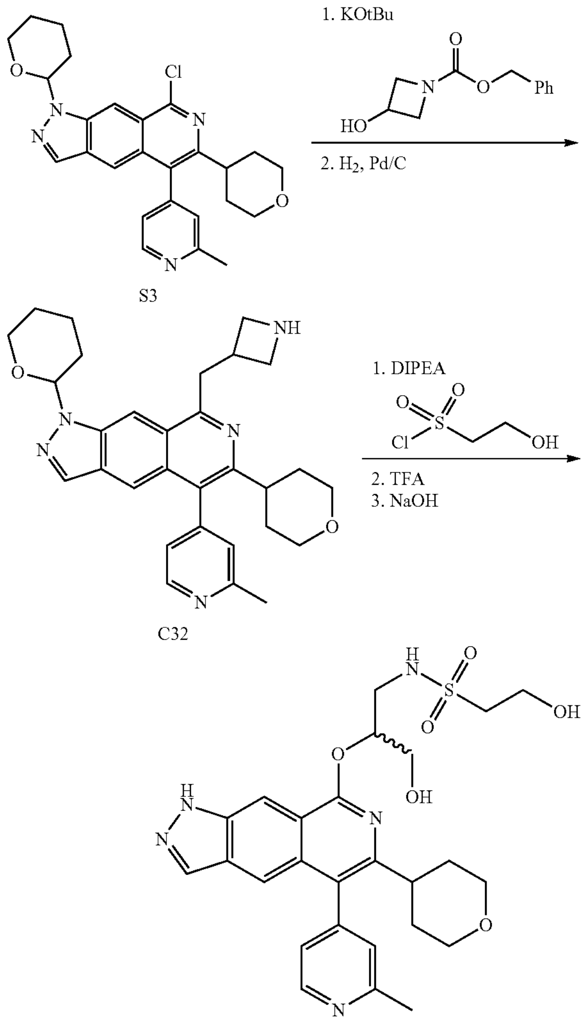

S3

C32

33

Step 1. Synthesis of benzyl 3-[5-(2-methyl-4-pyridyl)-1-tetrahydropyran-2-yl-6-tetrahydropyran-4-yl-pyrazolo[4,3-g]isoquinolin-8-yl]oxyazetidine-1-carboxylate To a solution of benzyl 3-hydroxyazetidine-1-carboxylate (150 mg, 0.7238 mmol) in DMSO (2 mL) was added KOtBu (82 mg, 0.7308 mmol) and the mixture was stirred for 10 minutes. The mixture was added to a vial of 8-chloro-5-(2-methyl-4-pyridyl)-1-tetrahydropyran-2-yl-6-tetrahydropyran-4-yl-pyrazolo[4,3-g]isoquinoline (170 mg, 0.3672 mmol). The mixture was stirred for 1 h at 50° C. The mixture was diluted with EtOAc, washed with $H_2O$, dried over $Na_2SO_4$, and concentrated. Purification by silica gel chromatography (Gradient with 0-5% MeOH in dichloromethane) afforded the product. Benzyl 3-[5-(2-methyl-4-pyridyl)-1-tetrahydropyran-2-yl-6-tetrahydropyran-4-ylpyrazolo[4,3-g]isoquinolin-8-yl]oxyazetidine-1-carboxylate (222 mg, 95%) LCMS m/z 634.0 [M+H]$^+$.

Step 2. Synthesis of 8-(azetidin-3-yloxy)-5-(2-methyl-4-pyridyl)-1-tetrahydropyran-2-yl-6-tetrahydropyran-4-yl-pyrazolo[4,3-g]isoquinoline (C32)

A solution of benzyl 3-[5-(2-methyl-4-pyridyl)-1-tetrahydropyran-2-yl-6-tetrahydropyran-4-yl-pyrazolo[4,3-g]isoquinolin-8-yl]oxyazetidine-1-carboxylate (222 mg, 0.3503 mmol) in MeOH (5 mL) and EtOAc (5 mL) was added Pd/C (120 mg of 10% w/w, 0.1128 mmol) and stirred for 1 hour under hydrogen balloon. The Pd catalyst was filtered off and the filtrate was concentrated. Purification by silica gel chromatography (Gradient: 0-20% MeOH in dichloromethane) afforded the product. 8-(azetidin-3-yloxy)-5-(2-methyl-4-pyridyl)-1-tetrahydropyran-2-yl-6-tetrahydropyran-4-yl-pyrazolo[4,3-g]isoquinoline (132 mg, 75%), LCMS m/z 500.0 [M+H]$^+$. $^1$H NMR (400 MHz, Methanol-$d_4$) δ 8.74-8.50 (m, 2H), 8.21 (d, J=0.9 Hz, 1H), 7.65 (d, J=1.1 Hz, 1H), 7.32 (d, J=2.0 Hz, 2H), 7.24 (dt, J=5.1, 1.6 Hz, 1H), 6.03 (dd, J=9.5, 2.6 Hz, 1H), 5.82 (p, J=6.3 Hz, 1H), 4.70 (dd, J=12.3, 6.9 Hz, 2H), 4.45 (dt, J=12.4, 6.8 Hz, 2H), 4.04-3.81 (m, 5H), 3.42-3.34 (m, 2H), 2.81-2.44 (m, 4H), 2.29-2.02 (m, 4H), 2.00-1.83 (m, 1H), 1.73 (dq, J=9.1, 4.3 Hz, 2H), 1.65-1.48 (m, 2H).

Step 3. Synthesis of 2-hydroxy-N-[3-hydroxy-2-[[5-(2-methyl-4-pyridyl)-6-tetrahydropyran-4-yl-1H-pyrazolo[4,3-g]isoquinolin-8-yl]oxy]propyl]ethanesulfonamide (33)

Part A. A solution of 8-(azetidin-3-yloxy)-5-(2-methyl-4-pyridyl)-1-tetrahydropyran-2-yl-6-tetrahydropyran-4-yl-pyrazolo[4,3-g]isoquinoline (20 mg, 0.04003 mmol) in DMF (0.5 mL) was added DIPEA (15 μL, 0.08612 mmol) and 2-hydroxyethanesulfonyl chloride (10 mg, 0.06917 mmol). The mixture was stirred for 30 minutes, and then concentrated. Purification by reversed-phase chromatography (Column: C18. Gradient: 0-100% MeCN in water with 0.2% formic acid) afforded the product. 2-[3-[5-(2-methyl-4-pyridyl)-1-tetrahydropyran-2-yl-6-tetrahydropyran-4-yl-pyrazolo[4,3-g]isoquinolin-8-yl]oxyazetidin-1-yl]sulfonylethanol (21 mg, 86%). LCMS m/z 608.0 [M+H]$^+$.

Part B and Part C. A solution of 2-[3-[5-(2-methyl-4-pyridyl)-1-tetrahydropyran-2-yl-6-tetrahydropyran-4-yl-pyrazolo[4,3-g]isoquinolin-8-yl]oxyazetidin-1-yl]sulfonylethanol (21 mg, 86%) in dichloromethane (2 mL) was added TFA (100 μL, 1.298 mmol). The mixture was stirred overnight. The mixture was concentrated, then diluted with MeOH (2 mL), NaOH (400 of 1 M, 0.4000 mmol) was added and stirred for 130 minutes. Purification by reversed-phase chromatography (Column: C18. Gradient: 10-100% MeCN in water with 0.2% formic acid) afforded the product. 2-hydroxy-N-[3-hydroxy-2-[[5-(2-methyl-4-pyridyl)-6-tetrahydropyran-4-yl-1H-pyrazolo[4,3-g]isoquinolin-8-yl]oxy]propyl]ethanesulfonamide (8.8 mg, 39%), $^1$H NMR (400 MHz, Methanol-$d_4$) δ 8.65-8.53 (m, 2H), 8.14 (s, 1H), 8.09 (t, J=0.9 Hz, 1H), 7.42-7.35 (m, 1H), 7.34-7.23 (m, 1H), 7.15 (s, 1H), 4.54 (dd, J=14.1, 3.8 Hz, 1H), 4.41-4.18 (m, 3H), 3.98 (t, J=6.1 Hz, 2H), 3.90-3.73 (m, 2H), 3.34 (m, 5H), 2.66 (d, J=2.1 Hz, 3H), 1.77 (m, 2H), 1.61 (m, 2H). LCMS m/z 542.0 [M+H]$^+$.

Compound 34

3-[[5-(2-methyl-4-pyridyl)-6-tetrahydropyran-4-yl-1H-pyrazolo[4,3-g]isoquinolin-8-yl]oxy]azetidine-1-carboxamide (34)

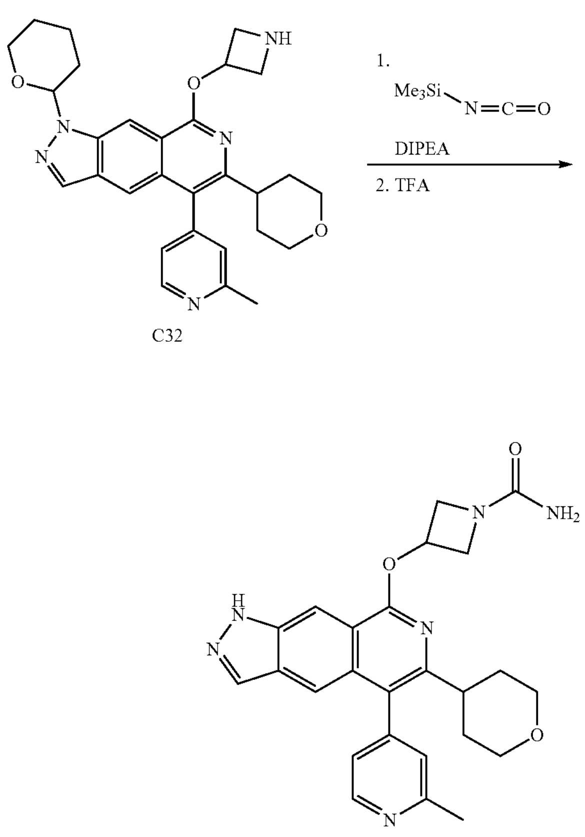

C32

34

To a solution of 8-(azetidin-3-yloxy)-5-(2-methyl-4-pyridyl)-1-tetrahydropyran-2-yl-6-tetrahydropyran-4-yl-pyrazolo[4,3-g]isoquinoline (10 mg, 0.02002 mmol) in dichloromethane (1 mL) was added DIPEA (20 μL, 0.1148 mmol) and isocyanato(trimethyl)silane (10 μL, 0.07387 mmol). The mixture was stirred for 1 hour, then concentrated in vacuo. Purification by silica gel chromatography (Gradient: 0-10% MeOH in dichloromethane) yielded the product. 3-[5-(2-methyl-4-pyridyl)-1-tetrahydropyran-2-yl-6-tetrahydropyran-4-yl-pyrazolo[4,3-g]isoquinolin-8-yl]oxyazetidine-1-carboxamide (7 mg, 64%). LCMS m/z 543.0 [M+H]$^+$. To a solution of 3-[5-(2-methyl-4-pyridyl)-1-tetrahydropyran-2-yl-6-tetrahydropyran-4-yl-pyrazolo[4,3-g]isoquinolin-8-yl]oxyazetidine-1-carboxamide (7 mg, 64%) in dichloromethane (2 mL) was added TFA (200 μL, 2.596 mmol) and stirred for 1 h and then in vacuo. Purification by reversed-phase chromatography (Column: C18. Gradient: 10-100% MeCN in water with 0.2% formic acid) afforded the product. 3-[[5-(2-methyl-4-pyridyl)-6-tetrahydropyran-4-yl-1H-pyrazolo[4,3-g]isoquinolin-8-yl]oxy]azetidine-1-carboxamide (4.2 mg, 43%). $^1$H NMR (400 MHz, Methanol-$d_4$) δ 8.77-8.66 (m, 2H), 8.40 (d, J=1.1 Hz, 1H), 8.10 (s, 2H), 7.78 (s, 1H), 7.43 (s, 1H), 7.35 (d, J=4.9 Hz, 1H), 5.81 (t, J=8.4 Hz, 1H), 5.32 (t, J=10.5 Hz, 1H), 5.15 (t, J=9.1 Hz, 1H), 4.04-3.76 (m, 3H), 3.31 (m, 2H), 3.18 (m, 2H), 2.68 (d, J=18.1 Hz, 4H), 1.77 (s, 3H). LCMS m/z 459.0 [M+H]$^+$.

Compound 35

3-hydroxy-2-methyl-1-[3-[[5-(2-methyl-4-pyridyl)-6-tetrahydropyran-4-yl-1H-pyrazolo[4,3-g]isoquinolin-8-yl]oxy]azetidin-1-yl]propan-1-one (35)

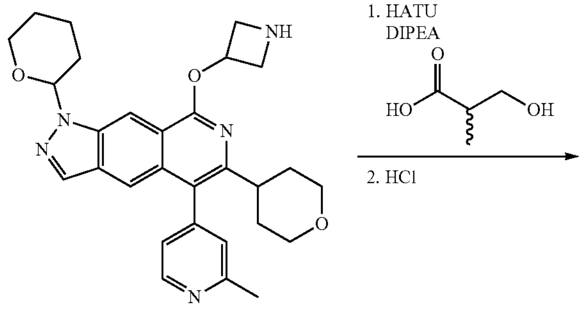

C32

-continued

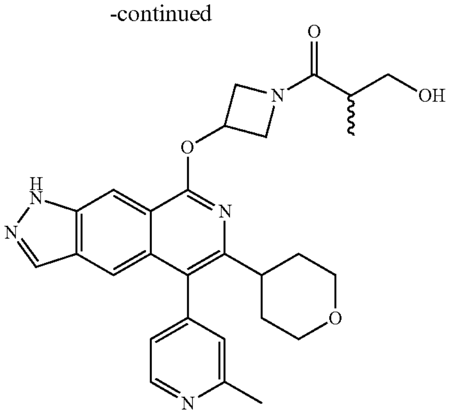

35

Compound 35 was prepared from C32 as described for compound 32. 3-hydroxy-2-methyl-1-[3-[[5-(2-methyl-4-pyridyl)-6-tetrahydropyran-4-yl-1H-pyrazolo[4,3-g]isoquinolin-8-yl]oxy]azetidin-1-yl]propan-1-one (2.0 mg, 13%). $^1$H NMR (400 MHz, Methanol-$d_4$) δ 8.61 (d, J=5.1 Hz, 1H), 8.51 (dt, J=7.0, 1.1 Hz, 1H), 8.21 (t, J=1.3 Hz, 1H), 7.66 (t, J=1.2 Hz, 1H), 7.36 (d, J=4.2 Hz, 1H), 7.28 (t, J=4.5 Hz, 1H), 5.82-5.67 (m, 1H), 4.75-4.40 (m, 2H), 4.33-4.17 (m, 1H), 4.02-3.93 (m, 2H), 3.80-3.63 (m, 1H), 3.54 (ddd, J=10.6, 8.5, 5.4 Hz, 1H), 3.37 (d, J=12.2 Hz, 2H), 2.67 (s, 5H), 2.21 (s, 3H), 1.56 (d, J=13.2 Hz, 2H), 1.07 (dd, J=10.1, 6.8 Hz, 3H). LCMS m/z 502.0 [M+H]$^+$.

Compounds 36-41

Compound 36-41 (Table 3) were prepared from C32 using the method described for the preparation of compound 32.

TABLE 3

Method of preparation, structure and physicochemical data for compounds 36-41

| Compound | Product | Reagent | $^1$H NMR; LCMS m/z [M + H]$^+$ |
|---|---|---|---|
| 36 | 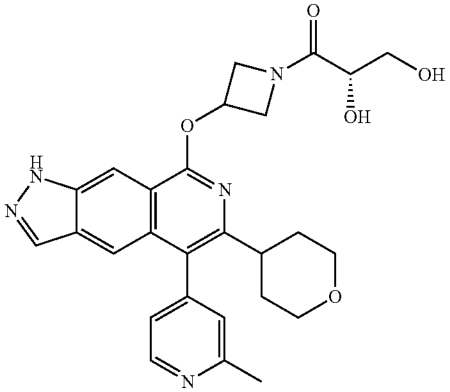 [SMILES: Cc1cc(-c2c(C3CCOCC3)nc(OC3CN(C(=O)[C@@H](O)CO)C3)c3cc4[nH]ncc4cc23)ccn1] | 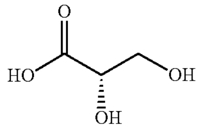 | $^1$H NMR (400 MHz, Methanol-$d_4$) δ 8.61 (dd, J = 5.1, 2.7 Hz, 1H), 8.56-8.44 (m, 2H), 8.22 (dd, J = 6.5, 1.1 Hz, 1H), 7.67 (dd, J = 9.2, 1.1 Hz, 1H), 7.34 (s, 1H), 7.26 (d, J = 4.9 Hz, 1H), 5.86-5.73 (m, 1H), 5.07-4.93 (m, 1H), 4.67 (q, J = 11.0, 9.3 Hz, 2H), 4.36-4.21 (m, 1H), 3.98 (d, J = 11.6 Hz, 2H), 3.76 (d, J = 4.9 Hz, 1H), 3.36 (d, J = 12.1 Hz, 2H), 3.04 (s, 4H), 2.66 (s, 3H), 2.20 (s, 2H), 1.56 (d, J = 13.6 Hz, 2H). LCMS m/z 504.0 [M + H]$^+$. |

TABLE 3-continued

Method of preparation, structure and physicochemical data for compounds 36-41

| Compound | Product | Reagent | $^1$H NMR; LCMS m/z $[M + H]^+$ |
|---|---|---|---|
| 37 | 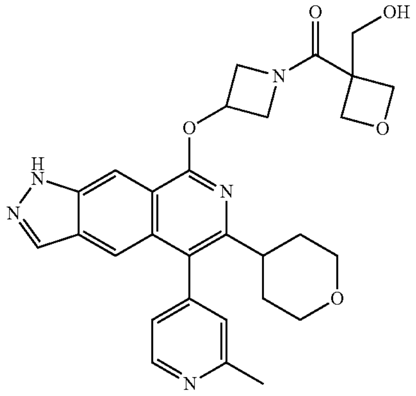 [SMILES: Cc1cc(-c2c(C3CCOCC3)nc(OC3CN(C(=O)C4(CO)COC4)C3)c3cc4[nH]ncc4cc23)ccn1] | 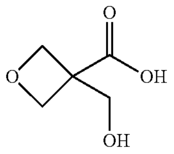 | $^1$H NMR (400 MHz, Methanol-$d_4$) δ 8.60 (d, J = 5.1 Hz, 1H), 8.54-8.49 (m, 2H), 8.21 (d, J = 1.1 Hz, 1H), 7.66 (d, J = 1.1 Hz, 1H), 7.33 (d, J = 4.8 Hz, 1H), 7.24 (d, J = 4.9 Hz, 1H), 5.74 (ddd, J = 11.1, 6.8, 4.4 Hz, 1H), 5.02-4.93 (m, 3H), 4.83-4.59 (m, 2H), 4.55-4.41 (m, 3H), 4.31 (m, 2H), 4.08 (m, 2H), 3.98 (d, J = 11.6 Hz, 2H), 2.65 (s, 5H), 2.18 (s, 2H), 1.55 (d, J = 13.3 Hz, 2H). LCMS m/z 530.0 $[M + H]^+$. |
| 38 | 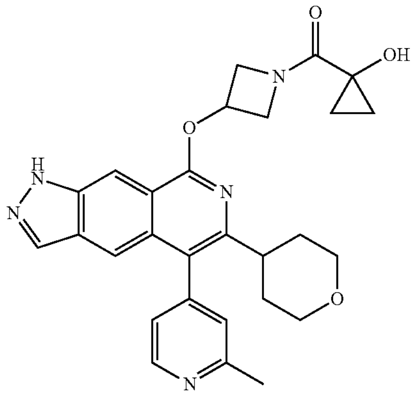 [SMILES: Cc1cc(-c2c(C3CCOCC3)nc(OC3CN(C(=O)C4(O)CC4)C3)c3cc4[nH]ncc4cc23)ccn1] | 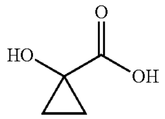 | $^1$H NMR (400 MHz, Methanol-$d_4$) δ 8.61 (d, J = 5.1 Hz, 1H), 8.52 (t, J = 1.1 Hz, 1H), 8.22 (d, J = 1.1 Hz, 1H), 8.13 (s, 1H), 7.66 (d, J = 1.1 Hz, 1H), 7.35 (s, 1H), 7.27 (d, J = 5.4 Hz, 1H), 5.80-5.64 (m, 1H), 5.20 (dd, J = 11.5, 6.5 Hz, 1H), 4.80-4.51 (m, 2H), 4.26 (d, J = 10.9 Hz, 1H), 3.97 (d, J = 11.4 Hz, 2H), 2.66 (s, 4H), 2.21 (s, 2H), 1.64-1.39 (m, 3H), 1.35-0.86 (m, 6H). LCMS m/z 500.0 $[M + H]^+$. |
| 39 | 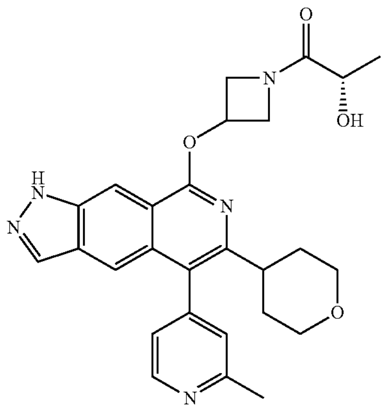 [SMILES: Cc1cc(-c2c(C3CCOCC3)nc(OC3CN(C(=O)[C@H](C)O)C3)c3cc4[nH]ncc4cc23)ccn1] | 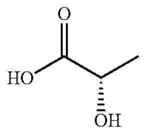 | $^1$H NMR (400 MHz, Methanol-$d_4$) δ 8.60 (d, J = 5.1 Hz, 1H), 8.51 (t, J = 1.1 Hz, 1H), 8.21 (d, J = 1.1 Hz, 1H), 7.66 (d, J = 1.1 Hz, 1H), 7.34 (s, 1H), 7.25 (dt, J = 4.1, 1.9 Hz, 1H), 5.86-5.67 (m, 1H), 5.10-4.97 (m, 1H), 4.62 (ddd, J = 20.0, 10.0, 4.8 Hz, 2H), 4.44-4.20 (m, 1H), 3.98 (d, J = 12.1 Hz, 2H), 3.82-3.60 (m, 1H), 3.22 (q, J = 7.4 Hz, 1H), 2.66 (s, 4H), 2.19 (d, J = 16.6 Hz, 2H), 1.64-1.23 (m, 8H). LCMS m/z 488.0 $[M + H]^+$ |

TABLE 3-continued

Method of preparation, structure and physicochemical data for compounds 36-41

| Compound | Product | Reagent | $^1$H NMR; LCMS m/z [M + H]+ |
|---|---|---|---|
| 40 | 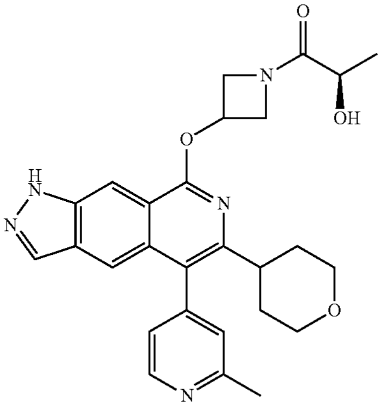 | 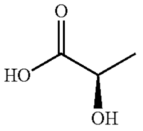 | $^1$H NMR (400 MHz, Methanol-$d_4$) δ 8.61 (d, J = 5.1 Hz, 1H), 8.51 (t, J = 1.1 Hz, 1H), 8.22 (d, J = 1.1 Hz, 1H), 7.66 (d, J = 1.1 Hz, 1H), 7.38-7.20 (m, 2H), 5.84-5.62 (m, 1H), 5.09-4.94 (m, 2H), 4.60 (m, 3H), 4.36 (m, 3H), 3.98 (d, J = 11.7 Hz, 3H), 2.66 (s, 4H), 2.20-5-2.20 (m, 2H), 1.56 (d, J = 13.1 Hz, 2H), 1.38 (d, J = 6.8 Hz, 3H). LCMS m/z 488.0 $[M + H]^+$ |
| 41 | 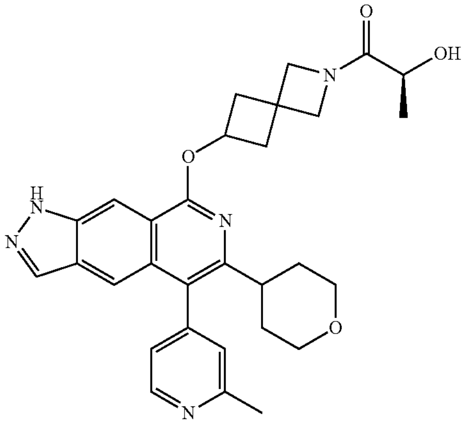 [SMILES: Cc1cc(-c2c(C3CCOCC3)nc(OC3CC4(C3)CN(C(=O)[C@H](C)O)C4)c3cc4[nH]ncc4cc23)ccn1] | 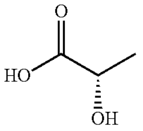 | $^1$H NMR (400 MHz, Methanol-$d_4$)) δ 8.59 (dd, J = 5.1, 0.8 Hz, 1H), 8.43 (dt, J = 2.0, 1.1 Hz, 1H), 8.35 (s, 1H), 8.19 (d, J = 1.1 Hz, 1H), 7.61 (d, J = 1.1 Hz, 1H), 7.32 (s, 1H), 7.28-7.15 (m, 1H), 5.46 (td, J = 7.0, 2.5 Hz, 1H), 4.62-4.37 (m, 2H), 4.36-4.04 (m, 3H), 3.98 (dd, J = 11.5, 4.3 Hz, 2H), 3.37 (d, J = 12.1 Hz, 2H), 3.01 (ddd, J = 10.9, 7.2, 3.6 Hz, 2H), 2.75-2.51 (m, 5H), 2.25 (dq, J = 12.5, 6.7, 6.1 Hz, 2H), 1.62-1.39 (m, 3H), 1.33 (t, J = 7.0 Hz, 3H). LCMS m/z 528.0 $[M + H]^+$ |

Compound 42

4-[[5-(3,4-difluorophenyl)-6-tetrahydropyran-4-yl-1H-pyrazolo[4,3-g]isoquinolin-8-yl]oxy]benzoic acid (42)

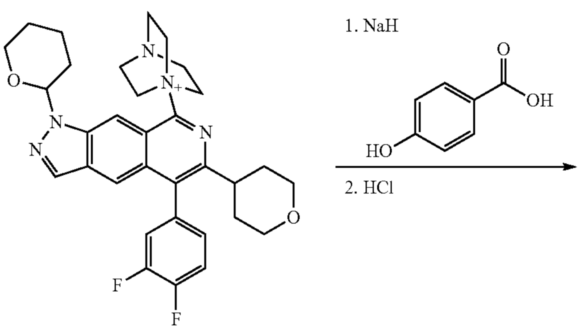

S4

-continued

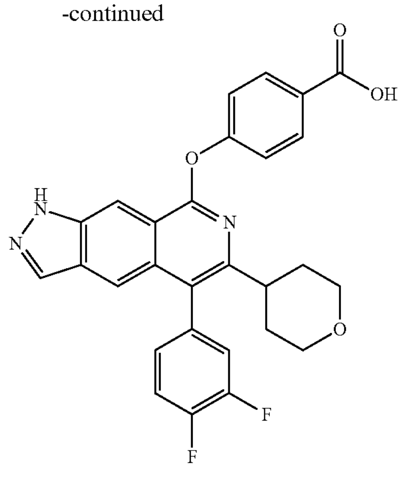

42

Compound 42 was prepared from S4 by treatment with 4-hydroxy-benzoic acid and sodium hydride, followed by THP deprotection with HCl as described for the preparation of compound 1. $^1$H NMR (300 MHz, Chloroform-d+Methanol-$d_4$) δ 8.62 (d, J=1.2 Hz, 1H), 8.28-8.11 (m, 3H), 7.71 (d, J=1.1 Hz, 1H), 7.45 (d, J=2.1 Hz, 1H), 7.42-7.34 (m, 2H), 7.18 (ddd, J=10.4, 7.6, 2.1 Hz, 1H), 7.13-7.04 (m, 1H), 3.90 (d, J=11.5 Hz, 2H), 3.29 (dt, J=11.1, 5.7 Hz, 2H), 2.69 (ddd, J=11.5, 7.7, 3.8 Hz, 1H), 1.94 (q, J=12.3 Hz, 2H), 1.44 (d, J=13.3 Hz, 2H) ppm. LCMS m/z 502.29 $[M+H]^+$.
Compounds 43 and 44
4-[[5-(3,4-difluorophenyl)-6-tetrahydropyran-4-yl-1H-pyrazolo[4,3-g]isoquinolin-8-yl]oxy]-3-fluoro-2-methoxy-benzoic acid (43) and methyl 4-[[5-(3,4-difluorophenyl)-6-tetrahydropyran-4-yl-1H-pyrazolo[4,3-g]isoquinolin-8-yl]oxy]-3-fluoro-2-hydroxy-benzoate (44)
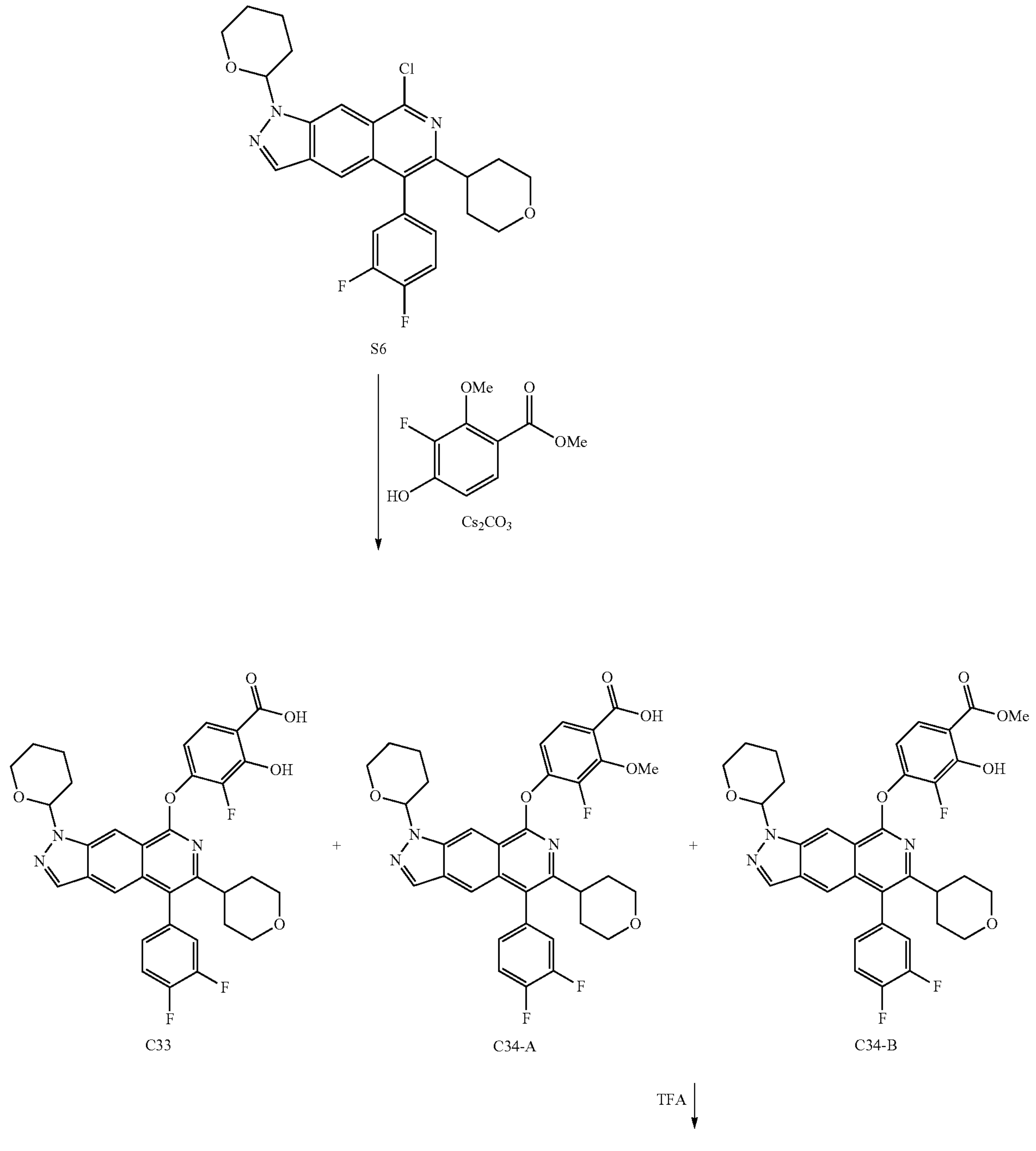

-continued

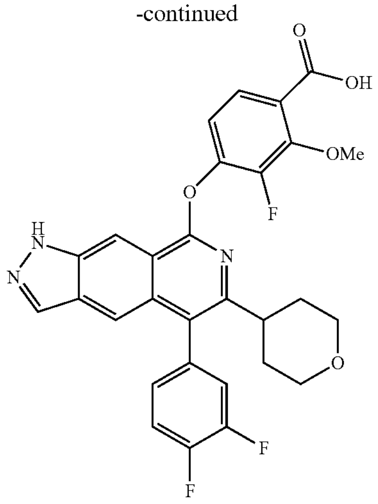

44

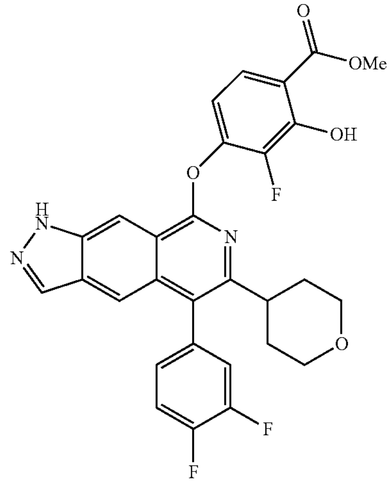

43

Step 1. Synthesis of 4-[5-(3,4-difluorophenyl)-1-tetrahydropyran-2-yl-6-tetrahydropyran-4-yl-pyrazolo[4,3-g]isoquinolin-8-yl]oxy-3-fluoro-2-hydroxy-benzoic acid (C33), 4-[5-(3,4-difluorophenyl)-1-tetrahydropyran-2-yl-6-tetrahydropyran-4-yl-pyrazolo[4,3-g]isoquinolin-8-yl]oxy-3-fluoro-2-methoxy-benzoic acid (C34-A) and Methyl 4-[5-(3,4-difluorophenyl)-1-tetrahydropyran-2-yl-6-tetrahydropyran-4-yl-pyrazolo[4,3-g]isoquinolin-8-yl]oxy-3-fluoro-2-hydroxy-benzoate (C34-B)

To a mixture of 8-chloro-5-(3,4-difluorophenyl)-1-tetrahydropyran-2-yl-6-tetrahydropyran 4-yl-pyrazolo[4,3-g]isoquinoline (99 mg, 0.2046 mmol) and methyl 3-fluoro-4-hydroxy-2-methoxy-benzoate (140 mg, 0.6994 mmol) in dry DMF (4 mL) at room temperature under nitrogen was added $Cs_2CO_3$ (539 mg, 1.654 mmol). The reaction mixture was microwaved at 150° C. under nitrogen for 20 hours. The reaction mixture was quenched with water (1 mL) and 1 M HCl (~2 mL until pH=6 was achieved). The desired product was extracted with EtOAc, washed with water, sat. NaCl and dried. Purification by silica gel chromatography (Gradient: 0-10% MeOH in dichloromethane, then 0-20% MeOH in dichloromethane) yielded the products. 4-[5-(3,4-difluorophenyl)-1-tetrahydropyran-2-yl-6-tetrahydropyran-4-yl-pyrazolo[4,3-g]isoquinolin-8-yl]oxy-3-fluoro-2-methoxy-benzoic acid C34-A (60 mg, 46%). LCMS m/z 634.11 $[M+H]^+$ was obtained as an inseparable mixture with a minor amount of Methyl 4-[5-(3,4-difluorophenyl)-1-tetrahydropyran-2-yl-6-tetrahydropyran-4-yl-pyrazolo[4,3-g]isoquinolin-8-yl]oxy-3-fluoro-2-hydroxy-benzoate (C34-B).

Compound C33 was isolated as a single compound. 4-[5-(3,4-difluorophenyl)-1-tetrahydropyran-2-yl-6-tetrahydropyran-4-yl-pyrazolo[4,3-g]isoquinolin-8-yl]oxy-3-fluoro-2-hydroxy-benzoic acid C33 (10 mg, 8%). LCMS m/z 620.16 $[M+H]^+$.

Step 2. Synthesis of 4-[[5-(3,4-difluorophenyl)-6-tetrahydropyran-4-yl-1H-pyrazolo[4,3-g]isoquinolin-8-yl]oxy]-3-fluoro-2-methoxy-benzoic acid (43) and methyl 4-[[5-(3,4-difluorophenyl)-6-tetrahydropyran-4-yl-1H-pyrazolo[4,3-g]isoquinolin-8-yl]oxy]-3-fluoro-2-hydroxy-benzoate (44)

The mixture of 4-[5-(3,4-difluorophenyl)-1-tetrahydropyran-2-yl-6-tetrahydropyran-4-yl-pyrazolo[4,3-g]isoquinolin-8-yl]oxy-3-fluoro-2-methoxy-benzoic acid C34-A (60 mg, 0.09469 mmol) containing minor impurity of C34-B was dissolved in dichloromethane (4 mL). The mixture was treated with TFA (2 mL, 25.96 mmol) for 90 min. The excess solvent was removed and the mixture was purified by reversed-phase HPLC. (Method: C18 Waters Sunfire column (30×150 mm, 5 micron). Gradient: MeCN in $H_2O$ with 0.2% formic acid.)

Product A: 4-[[5-(3,4-difluorophenyl)-6-tetrahydropyran-4-yl-1H-pyrazolo[4,3-g]isoquinolin-8-yl]oxy]-3-fluoro-2-methoxy-benzoic acid (Hydrochloride salt) (44) (15 mg, 26%). $^1H$ NMR (300 MHz, Chloroform-d+Methanol-$d_4$) δ 8.64 (t, J=1.1 Hz, 1H), 8.22 (d, J=1.1 Hz, 1H), 7.84 (dd, J=8.8, 2.1 Hz, 1H), 7.73 (d, J=1.1 Hz, 1H), 7.38 (dd, J=10.3, 8.3 Hz, 1H), 7.31-7.14 (m, 2H), 7.09 (ddd, J=8.6, 4.4, 1.8 Hz, 1H), 4.08 (d, J=1.2 Hz, 3H), 3.88 (d, J=11.3 Hz, 2H), 3.29 (dt, J=9.9, 5.8 Hz, 2H), 2.74-2.62 (m, 1H), 1.89 (q, J=12.2 Hz, 2H), 1.43 (d, J=13.3 Hz, 2H) ppm. LCMS m/z 550.21 $[M+H]^+$.

Product B: Methyl 4-[[5-(3,4-difluorophenyl)-6-tetrahydropyran-4-yl-1H-pyrazolo[4,3-g]isoquinolin-8-yl]oxy]-3-fluoro-2-hydroxy-benzoate (3 mg, 5%) (43). $^1H$ NMR (300 MHz, Chloroform-$d^+$-Methanol-$d_4$) δ 8.63 (t, J=1.1 Hz, 1H), 8.21 (d, J=1.1 Hz, 1H), 7.87-7.66 (m, 2H), 7.40 (dt, J=10.4, 8.3 Hz, 1H), 7.28-7.05 (m, 2H), 7.00 (dd, J=8.9, 6.5 Hz, 1H), 4.04 (s, 3H), 3.90 (d, J=11.5 Hz, 2H), 3.33-3.19 (m, 2H), 2.73-2.62 (m, 1H), 1.90 (q, J=12.0 Hz, 2H), 1.43 (d, J=13.1 Hz, 2H) ppm. LCMS m/z 550.21 $[M+H]^+$.

Compounds 45-64

Compounds 45-62 were prepared from S5 by treatment with NaH and the appropriate alcohol reagent as described for the preparation of compound 42. Compounds 62-64 were prepared from S4 by treatment with NaH and the appropriate alcohol reagent, followed by treatment with HCl to remove the THP protecting group.

TABLE 4

Method of preparation, structure and physicochemical data for compounds 45-64

| Compound | Product | Reagent | $^1$H NMR; LCMS m/z [M + H]$^+$ |
| --- | --- | --- | --- |
| 45 | 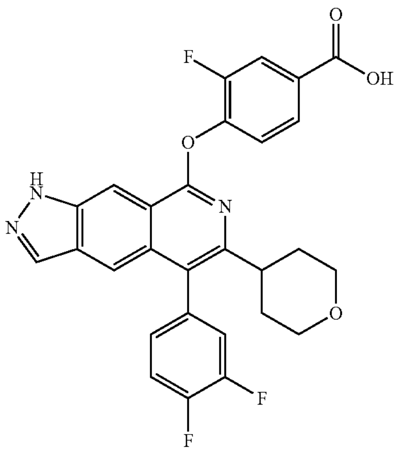 | 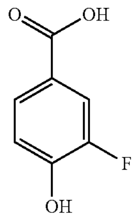 [SMILES: O=C(O)c1ccc(O)c(F)c1] | 1H NMR (300 MHz, Chloroform-d + Methanol-$d_4$) δ 8.65 (t, J = 1.1 Hz, 1H), 8.22 (d, J = 1.1 Hz, 1H), 8.07-7.86 (m, 2H), 7.73 (d, J = 1.1 Hz, 1H), 7.53-7.47 (m, 1H), 7.41 (dt, J = 10.4, 8.3 Hz, 1H), 7.26-6.96 (m, 2H), 3.88 (d, J = 11.1 Hz, 2H), 3.29 (tdd, J = 8.0, 6.1, 2.0 Hz, 2H), 2.67 (ddt, J = 11.5, 7.5, 3.7 Hz, 1H), 1.86 (q, J = 13.0 Hz, 2H), 1.54-1.32 (m, 2H) ppm. LCMS m/z 520.14 [M + H]$^+$ |
| 46 | 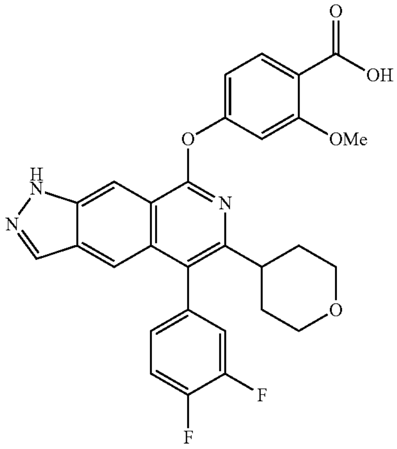 [SMILES: COc1cc(Oc2nc(C3CCOCC3)c(-c3ccc(F)c(F)c3)c3cc4cn[nH]c4cc23)ccc1C(=O)O] | 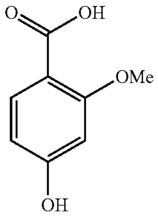 [SMILES: COc1cc(O)ccc1C(=O)O] | $^1$H NMR (300 MHz, Chloroform-d + Methanol-$d_4$) δ 8.61 (d, J = 3.1 Hz, 1H), 8.21 (d, J = 3.3 Hz, 1H), 8.10 (dt, J = 7.8, 3.9 Hz, 1H), 7.73 (d, J = 3.0 Hz, 1H), 7.40 (t, J = 8.3 Hz, 1H), 7.26-6.98 (m, 4H), 4.06-3.80 (m, 5H), 3.29 (s, 2H), 2.72 (s, 1H), 1.99 (d, J = 13.2 Hz, 2H), 1.47 (d, J = 13.2 Hz, 2H) pm. LCMS m/z 532.13 [M + H]$^+$ |
| 47 | 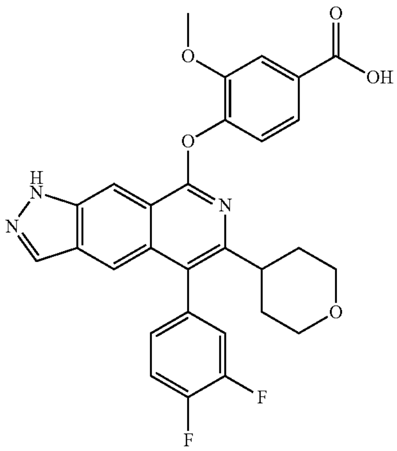 | 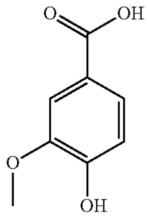 | $^1$H NMR (300 MHz, Chloroform-d + Methanol-$d_4$) δ 8.67 (t, J = 1.2 Hz, 1H), 8.20 (d, J = 1.1 Hz, 1H), 7.87-7.65 (m, 3H), 7.46-7.33 (m, 2H), 7.25-7.03 (m, 2H), 3.84 (s, 5H), 3.33-3.22 (m, 2H), 2.65 (ddt, J = 11.3, 7.4, 3.7 Hz, 1H), 1.82 (q, J = 12.6 Hz, 2H), 1.47-1.33 (m, 2H) ppm. LCMS m/z 532.2 [M + H]$^+$ |

TABLE 4-continued

| Method of preparation, structure and physicochemical data for compounds 45-64 | | | |
|---|---|---|---|
| Compound | Product | Reagent | $^1$H NMR; LCMS m/z $[M + H]^+$ |
| 48 | 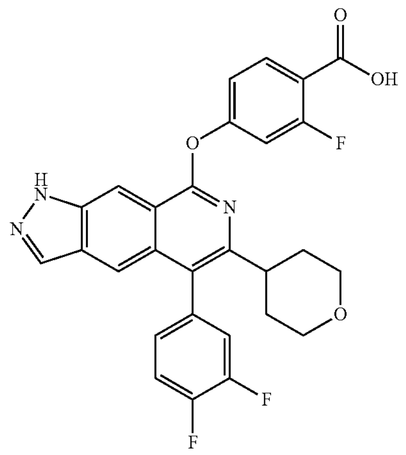 [SMILES: O=C(O)c1ccc(Oc2nc(C3CCOCC3)c(-c3ccc(F)c(F)c3)c3cc4cn[nH]c4cc23)cc1F] | 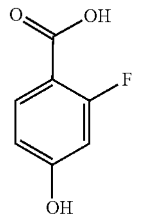 [SMILES: O=C(O)c1ccc(O)cc1F] | $^1$H NMR (300 MHz, Chloroform-d + Methanol-$d_4$) δ 8.58 (t, J = 1.1 Hz, 1H), 8.21 (d, J = 1.1 Hz, 1H), 8.11 (t, J = 8.6 Hz, 1H), 7.72 (d, J =1.1 Hz, 1H), 7.39-7.34 (m, 1H), 7.30-7.02 (m, 4H), 3.93 (d, J = 11.3 Hz, 2H), 3.36-3.23 (m, 2H), 2.70 (ddt, J = 11.4, 7.4, 3.7 Hz, 1H), 1.97 (q, J = 12.2 Hz, 2H), 1.55-1.34 (m, 2H) ppm. LCMS m/z 520.21 $[M + H]^+$ |
| 49 | 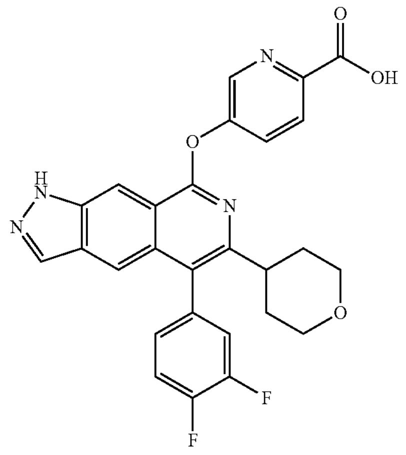 [SMILES: O=C(O)c1ccc(Oc2nc(C3CCOCC3)c(-c3ccc(F)c(F)c3)c3cc4cn[nH]c4cc23)cn1] | 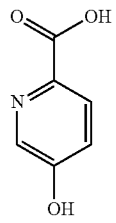 | $^1$H NMR (300 MHz, Chloroform-d + Methanol-$d_4$) δ 8.97 (s, 1H), 8.66 (s, 1H), 8.45 (d, J = 8.5 Hz, 1H), 8.25 (d, J = 8.9 Hz, 2H), 7.75 (s, 1H), 7.42-7.30 (m, 1H), 7.24-7.14 (m, 1H), 7.10 (d, J = 6.4 Hz, 1H), 3.92 (d, J = 11.4 Hz, 2H), 3.36-3.21 (m, 2H), 2.74 (t, J = 12.0 Hz, 1H), 1.92 (d, J = 13.0 Hz, 2H), 1.48 (d, J = 13.2 Hz, 2H) ppm. LCMS m/z 503.11 $[M + H]^+$ |
| 50 | 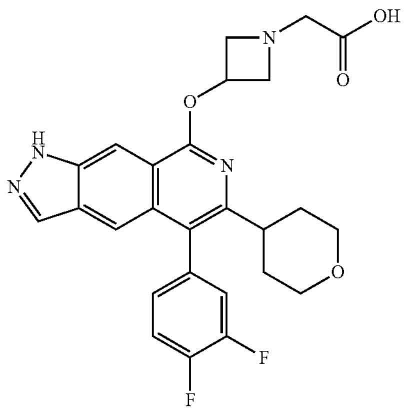 [SMILES: O=C(O)CN1CC(Oc2nc(C3CCOCC3)c(-c3ccc(F)c(F)c3)c3cc4cn[nH]c4cc23)C1] | 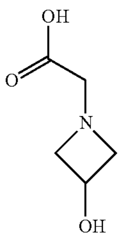 | $^1$H NMR (300 MHz, DMSO-$d_6$) δ 13.41 (s, 1H), 8.37 (t, J = 1.1 Hz, 1H), 8.33 (s, 1H), 7.71-7.56 (m, 2H), 7.56-7.43 (m, 1H), 5.49 (d, J = 5.5 Hz, 1H), 4.25-4.10 (m, 2H), 3.88 (d, J = 11.2 Hz, 2H), 3.65 (s, 3H), 2.63 (s, 1H), 2.11-1.89 (m, 2H), 1.48 (s, 2H). LCMS m/z 495.44 $[M + H]^+$ |

TABLE 4-continued

Method of preparation, structure and physicochemical data for compounds 45-64

| Compound | Product | Reagent | $^1$H NMR; LCMS m/z $[M + H]^+$ |
|---|---|---|---|
| 51 | 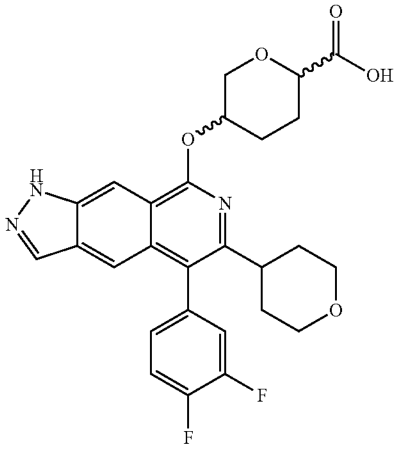 [SMILES: O=C(O)C1CCC(Oc2nc(C3CCOCC3)c(-c3ccc(F)c(F)c3)c3cc4cn[nH]c4cc23)CO1] | 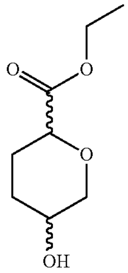 | $^1$H NMR (300 MHz, Chloroform-d + Methanol-$d_4$) δ 8.41 (t, J = 1.1 Hz, 1H), 8.14 (d, J = 1.1 Hz, 1H), 7.60 (d, J =1.1 Hz, 1H), 7.39 (d, J = 8.6 Hz, 1H), 7.14 (t, J = 8.4 Hz, 1H), 7.10-6.97 (m, 1H), 5.54 (dd, J = 9.2, 4.6 Hz, 1H), 4.56 (dd, J = 11.2, 4.4 Hz, 1H), 4.24-4.12 (m, 1H), 4.01 (d, J = 11.5 Hz, 2H), 3.70 (dd, J = 11.1, 8.7 Hz, 1H), 3.42 (s, 1H), 2.89-2.64 (m, 1H), 2.52 (s, 1H), 2.43-2.12 (m, 3H), 2.00 (t, J = 9.3 Hz, 2H), 1.67-1.37 (m, 3H) ppm. LCMS m/z 510.14 $[M + H]^+$ |
| 52 | 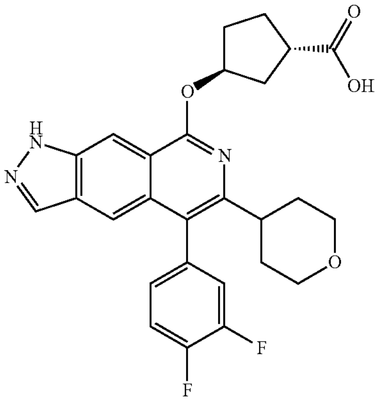 [SMILES: O=C(O)[C@H]1CC[C@H](Oc2nc(C3CCOCC3)c(-c3ccc(F)c(F)c3)c3cc4cn[nH]c4cc23)C1] | 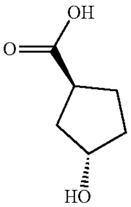 | $^1$H NMR (300 MHz, Chloroform-d + Methanol-$d_4$) δ 8.41 (t, J = 1.1 Hz, 1H), 8.15 (d, J = 1.1 Hz, 1H), 7.40 (dt, J = 10.5, 8.3 Hz, 1H), 7.25-6.96 (m, 2H), 5.97-5.81 (m, 1H), 4.33 (s, 1H), 4.02 (d, J = 11.2 Hz, 2H), 3.52-3.36 (m, 2H), 3.18 (q, J = 8.1 Hz, 1H), 2.84-2.67 (m, 1H), 2.50-1.95 (m, 8H), 1.55 (d, J = 13.2 Hz, 2H) ppm. LCMS m/z 494.46 $[M + H]^+$ |
| 53 | 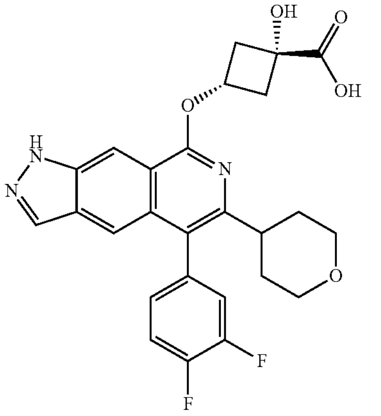 [SMILES: O=C(O)[C@]1(O)C[C@@H](Oc2nc(C3CCOCC3)c(-c3ccc(F)c(F)c3)c3cc4cn[nH]c4cc23)C1] | 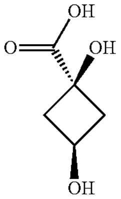 | $^1$H NMR (400 MHz, Methanol-$d_4$) δ 8.45 (s, 1H), 8.26-8.15 (m, 1H), 7.68-7.62 (m, 1H), 7.46 (dt, J = 10.8, 8.4 Hz, 1H), 7.35-7.21 (m, 1H), 7.14 (d, J = 5.1 Hz, 1H), 5.46 (q, J = 7.1 Hz, 1H), 3.98 (d, J = 11.3 Hz, 2H), 3.31 (p, J = 1.6 Hz, 4H), 2.85-2.69 (m, 1H), 2.57 (d, J = 10.6 Hz, 2H), 2.23 (q, J = 12.9, 12.3 Hz, 2H), 1.53 (d, J = 13.4 Hz, 2H). LCMS m/z 496.32 $[M + H]^+$ |

TABLE 4-continued

| Method of preparation, structure and physicochemical data for compounds 45-64 | | | |
|---|---|---|---|
| Compound | Product | Reagent | $^1$H NMR; LCMS m/z [M + H]$^+$ |
| 54 | 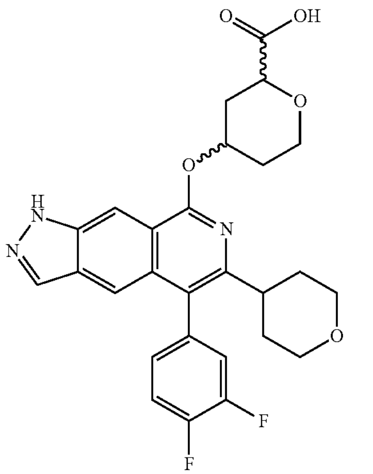 [SMILES: O=C(O)C1CC(Oc2nc(C3CCOCC3)c(-c3ccc(F)c(F)c3)c3cc4cn[nH]c4cc23)CCO1] | 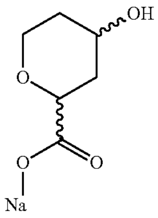 | $^1$H NMR (300 MHz, DMSO-$d_6$) δ 13.41 (s, 1H), 8.37 (d, J = 1.1 Hz, 1H), 8.33 (s, 1H), 7.62 (d, J = 8.5 Hz, 2H), 7.56-7.45 (m, 1H), 7.21 (s, 1H), 5.49 (d, J = 5.5 Hz, 1H), 4.24-4.11 (m, 2H), 3.88 (d, J = 10.8 Hz, 2H), 3.65 (s, 2H), 3.25-3.15 (m, 4H), 2.64 (s, 1H), 2.16-1.88 (m, 2H), 1.48 (t, J = 13.0 Hz, 2H). |
| 55 | 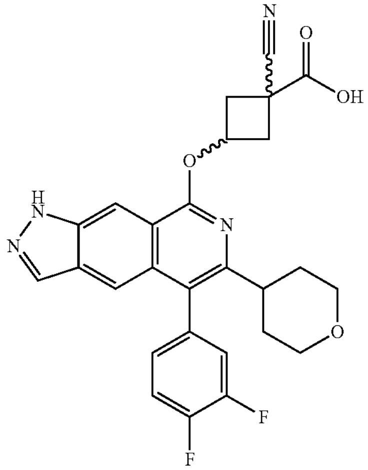 [SMILES: N#CC1(C(=O)O)CC(Oc2nc(C3CCOCC3)c(-c3ccc(F)c(F)c3)c3cc4cn[nH]c4cc23)C1] | 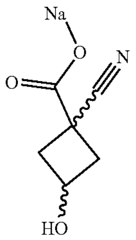 | $^1$H NMR (400 MHz, 1:1 Chloroform-d + Methanol-$d_4$) δ 8.44 (t, J = 1.2 Hz, 1H), 8.16 (d, J = 1.1 Hz, 1H), 7.63 (d, J = 1.1 Hz, 1H), 7.40 (dt, J = 10.5, 8.3 Hz, 1H), 7.17 (ddd, J = 10.8, 7.6, 2.1 Hz, 1H), 7.13-7.05 (m, 1H), 5.75 (p, J = 7.6 Hz, 1H), 4.04 (dd, J = 10.6, 5.1Hz, 2H), 3.50-3.39 (m, 2H), 3.31 (dt, J = 9.1, 2.4 Hz, 2H), 3.19-3.06 (m, 2H), 2.75 (tt, J = 11.6, 3.8 Hz, 1H), 2.24 (ddt, J = 19.3, 12.8, 6.1 Hz, 2H), 1.55 (d, J = 12.9 Hz, 2H). LCMS m/z 505.0 [M + H]$^+$ |
| 56 | 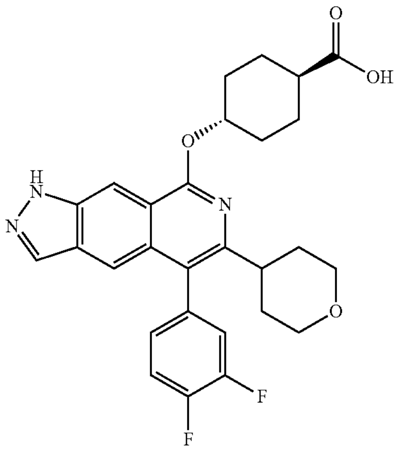 [SMILES: O=C(O)[C@H]1CC[C@H](Oc2nc(C3CCOCC3)c(-c3ccc(F)c(F)c3)c3cc4cn[nH]c4cc23)CC1] | 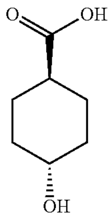 | $^1$H NMR (300 MHz, Chloroform-d + Methanol-$d_4$) δ 8.43 (s, 1H), 8.14 (s, 1H), 7.60 (s, 1H), 7.40-7.25 (m, 1H), 7.26-6.95 (m, 2H), 5.40 (d, J = 9.3 Hz, 1H), 4.01 (s, 2H), 3.38-3.26 (m, 2H), 2.72 (dd, J = 13.4, 9.8 Hz, 1H), 2.58-2.32 (m, 3H), 2.34-2.06 (m, 4H), 1.95-1.60 (m, 4H), 1.52 (d, J = 13.3 Hz, 2H) ppm. LCMS m/z 508.4 [M + H]$^+$ |

TABLE 4-continued

Method of preparation, structure and physicochemical data for compounds 45-64

| Compound | Product | Reagent | $^1$H NMR; LCMS m/z $[M + H]^+$ |
|---|---|---|---|
| 57 | 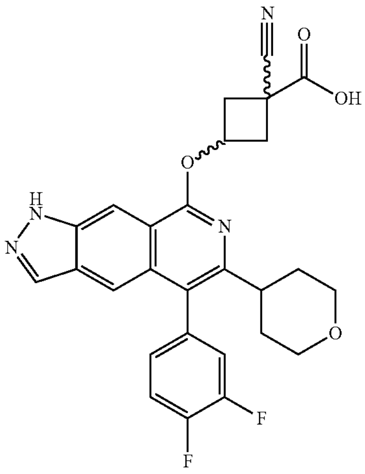 [SMILES: N#CC1(C(=O)O)CC(Oc2nc(C3CCOCC3)c(-c3ccc(F)c(F)c3)c3cc4cn[nH]c4cc23)C1] | 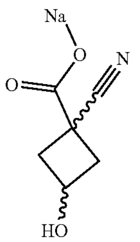 | $^1$H NMR (400 MHz, DMSO-$d_6$) δ 14.17 (s, 1H), 13.43 (s, 1H), 8.41 (t, J = 1.1 Hz, 1H), 8.34 (d, J = 1.1 Hz, 1H), 7.73-7.57 (m, 2H), 7.51 (ddd, J = 11.3, 7.9, 2.1 Hz, 1H), 7.27-7.14 (m, 1H), 5.63 (p, J = 6.8 Hz, 1H), 4.00-3.81 (m, 2H), 3.38-3.29 (m, 2H), 3.21 (tdd, J = 12.1, 9.3, 4.1 Hz, 2H), 2.99 (dddd, J = 13.4, 6.0, 4.7, 1.5 Hz, 2H), 2.71-2.59 (m, 1H), 2.00 (qd, J = 12.6, 4.6 Hz, 2H), 1.57-1.42 (m, 2H). LCMS m/z 505.29 $[M + H]^+$ |
| 58 | 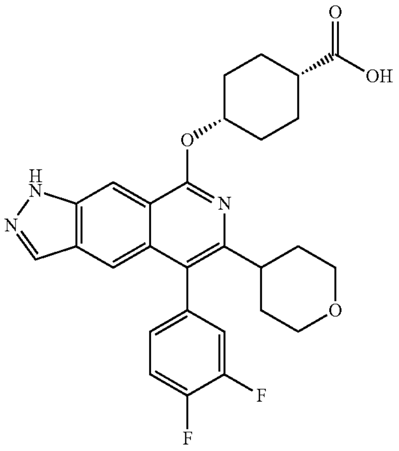 [SMILES: O=C(O)[C@H]1CC[C@@H](Oc2nc(C3CCOCC3)c(-c3ccc(F)c(F)c3)c3cc4cn[nH]c4cc23)CC1] | 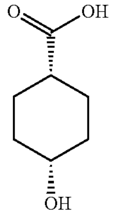 | $^1$H NMR (300 MHz, Chloroform-d + Methanol-$d_4$) δ 8.50(t, J = 1.1 Hz, 1H), 8.15 (d, J = 1.1 Hz, 1H), 7.61 (d, J = 1.1 Hz, 1H), 7.37 (dt, J = 10.4, 8.3 Hz, 1H), 7.24-6.96 (m, 2H), 5.72 (s, 1H), 4.02 (d, J = 11.0 Hz, 2H), 3.42 (dd, J = 11.5, 6.2 Hz, 2H), 2.84-2.64 (m, 1H), 2.54 (td, J = 10.5, 5.2 Hz, 1H), 2.41-2.02 (m, 6H), 2.02-1.67 (m, 4H), 1.54 (d, J = 13.3 Hz, 2H) ppm. LCMS m/z 508.32 $[M + H]^+$ |
| 59 | 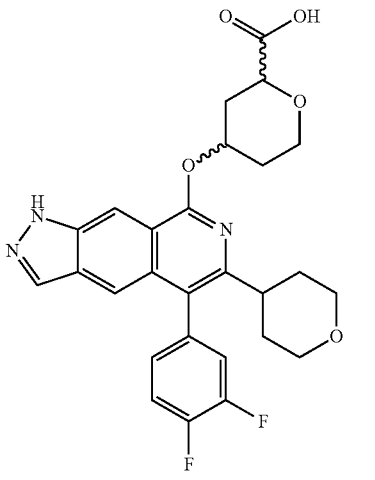 [SMILES: O=C(O)C1CC(Oc2nc(C3CCOCC3)c(-c3ccc(F)c(F)c3)c3cc4cn[nH]c4cc23)CCO1] | 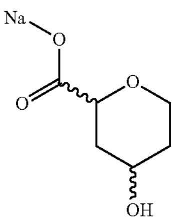 | $^1$H NMR (400 MHz, Methanol-$d_4$) δ 8.38 (s, 1H), 8.17 (s, 1H), 7.61 (s, 1H), 7.46 (dtd, J = 10.7, 8.4, 3.7 Hz, 1H), 7.27 (tdd, J = 11.2, 7.7, 2.0 Hz, 1H), 7.19-7.07 (m, 1H), 5.70 (s, 1H), 4.26 (d, J = 43.3 Hz, 2H), 4.06-3.91 (m, 2H), 3.79 (s, 1H), 3.35 (m, 2H), 2.83-2.67 (m, 2H), 2.48-2.12 (m, 3H), 1.96 (d, J = 20.0 Hz, 2H), 1.55 (s, 2H). |

TABLE 4-continued

Method of preparation, structure and physicochemical data for compounds 45-64

| Compound | Product | Reagent | $^1$H NMR; LCMS m/z $[M + H]^+$ |
|---|---|---|---|
| 60 | 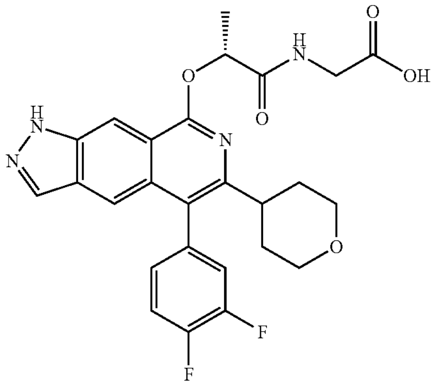 [SMILES: C[C@@H](Oc1nc(C2CCOCC2)c(-c2ccc(F)c(F)c2)c2cc3cn[nH]c3cc12)C(=O)NCC(=O)O] | 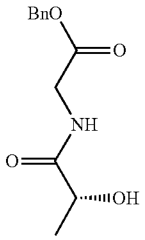 | $^1$H NMR (300 MHz, DMSO-$d_6$) δ 13.38 (s, 1H), 12.56 (s, 1H), 8.48 (d, J = 1.2 Hz, 1H), 8.32 (s, 1H), 7.69-7.54 (m, 2H), 7.53-7.42 (m, 1H), 7.19 (s, 1H), 5.68 (q, J = 6.8 Hz, 1H), 4.03-3.68 (m, 4H), 3.28-3.11 (m, 2H), 2.68-2.54 (m, 1H), 2.21-1.84 (m, 2H), 1.66 (d, J = 6.8 Hz, 3H), 1.43 (dt, J = 23.7, 11.8 Hz, 2H). LCMS m/z 511.38 $[M + H]^+$ |
| 61 | 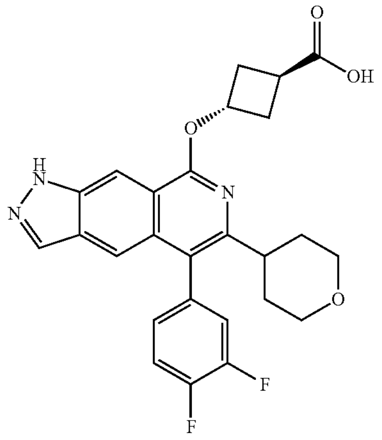 [SMILES: O=C(O)[C@H]1C[C@H](Oc2nc(C3CCOCC3)c(-c3ccc(F)c(F)c3)c3cc4cn[nH]c4cc23)C1] | 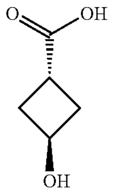 | $^1$H NMR (300 MHz, Chloroform-d + Methanol-$d_4$) δ 8.46 (t, J = 1.1 Hz, 1H), 8.15 (d, J = 1.1 Hz, 1H), 7.62 (d, J =1.1 Hz, 1H), 7.38 (dt, J = 10.4, 8.3 Hz, 1H), 7.25-7.02 (m, 2H), 5.79-5.63 (m, 1H), 4.01 (d, J = 11.4 Hz, 2H), 3.43 (d, J = 6.2 Hz, 1H), 3.34-3.21 (m, 2H), 3.09-2.88 (m, 2H), 2.69 (tdd, J = 10.3, 8.8, 4.8 Hz, 3H), 2.35-2.12 (m, 2H), 1.51 (d, J = 13.3 Hz, 2H) ppm. LCMS m/z 480.38 $[M + H]^+$ |
| 62* | 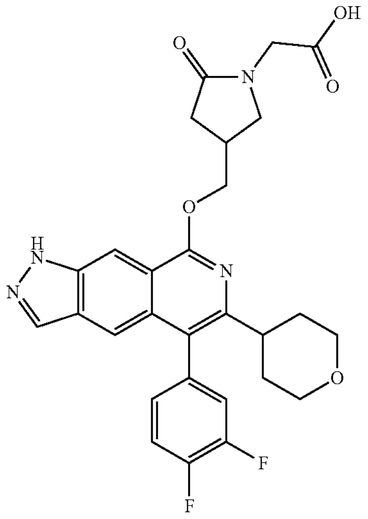 [SMILES: O=C(O)CN1CC(COc2nc(C3CCOCC3)c(-c3ccc(F)c(F)c3)c3cc4cn[nH]c4cc23)CC1=O] | 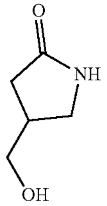 | $^1$H NMR (300 MHz, DMSO-$d_6$) δ 13.36 (s, 1H), 12.82 (s, 1H), 8.35-8.27 (m, 2H), 7.63 (d, J = 10.0 Hz, 2H), 7.49 (t, J = 9.7 Hz, 1H), 7.20 (s, 1H), 4.61 (t, J = 7.3 Hz, 2H), 4.10-3.93 (m, 2H), 3.88 (d, J = 10.2 Hz, 2H), 3.74 (t, J = 8.8 Hz, 1H), 3.48 (dd, J = 9.5, 5.1 Hz, 1H), 3.22 (dd, J = 16.1, 10.2 Hz, 2H), 2.69-2.57 (m, 2H), 2.38 (dd, J = 17.0, 6.1 Hz, 2H), 2.17-2.01 (m, 2H), 1.49 (t, J = 12.1 Hz, 2H). LCMS m/z 537.44 $[M + H]^+$ |

TABLE 4-continued

| Method of preparation, structure and physicochemical data for compounds 45-64 | | | |
|---|---|---|---|
| Compound | Product | Reagent | $^{1}$H NMR; LCMS m/z [M + H]$^{+}$ |
| 63 | 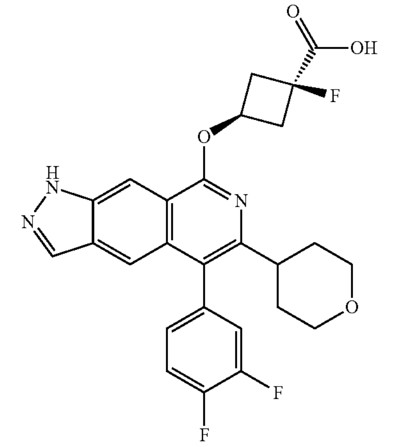 [SMILES: O=C(O)[C@]1(F)C[C@@H](Oc2nc(C3CCOCC3)c(-c3ccc(F)c(F)c3)c3cc4cn[nH]c4cc23)C1] | 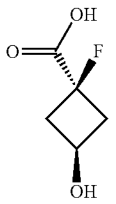 | LCMS m/z 498.27 [M + H]$^{+}$ |
| 64 | 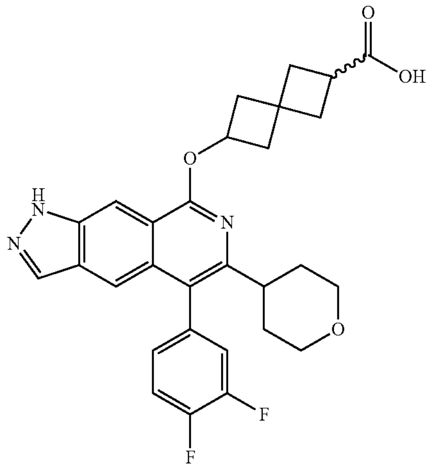 [SMILES: O=C(O)C1CC2(CC(Oc3nc(C4CCOCC4)c(-c4ccc(F)c(F)c4)c4cc5cn[nH]c5cc34)C2)C1] | 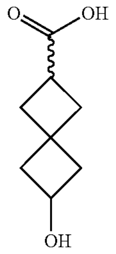 [SMILES: O=C(O)C1CC2(CC(O)C2)C1] | $^{1}$H NMR (300 MHz, Chloroform-d + Methanol-$d_4$) δ 8.41 (p, J = 1.3 Hz, 1H), 8.19-8.05 (m, 1H), 7.67-7.55 (m, 1H), 7.36 (s, 1H), 7.12 (dd, J = 23.2, 13.8 Hz, 2H), 5.54-5.36 (m, 1H), 4.03 (d, J = 11.5 Hz, 2H), 3.40 (q, J = 8.0, 5.7 Hz, 3H), 3.11 (d, J = 8.5 Hz, 1H), 2.86 (d, J = 5.6 Hz, 1H), 2.73 (dd, J = 12.3, 4.7 Hz, 2H), 2.56-2.11 (m, 7H), 1.60-1.41 (m, 2H) ppm. LCMS m/z 520.38 [M + H]$^{+}$ |

*Compound 62 was prepared from S4 and 4-(hydroxymethyl)pyrrolidin-2-one to give intermediate 4-[[5-(3,4-difluorophenyl)-1-tetrahydropyran-2-yl-6-tetrahydropyran-4-yl-pyrazolo[4,3-g]isoquinolin-8-yl]oxymethyl]pyrrolidin-2-one. Alkylation of this intermediate with benzyl 2-bromoacetate afforded benzyl 2-4-[[5-(3,4-difluorophenyl)-1-tetrahydropyran-2-yl-6-tetrahydropyran-4-yl-pyrazolo[4,3-g]isoquinolin-8-yl]oxymethyl]-2-oxo-pyrrolidin-1-yl]acetate. THP deprotection with HCl, followed by hydrogenation afforded compound 62.

Compound 65

4-[5-(3,4-difluorophenyl)-6-tetrahydropyran-4-yl-1H-pyrazolo[4,3-g]isoquinolin-8-yl]-3-fluoro-benzoic acid (65)

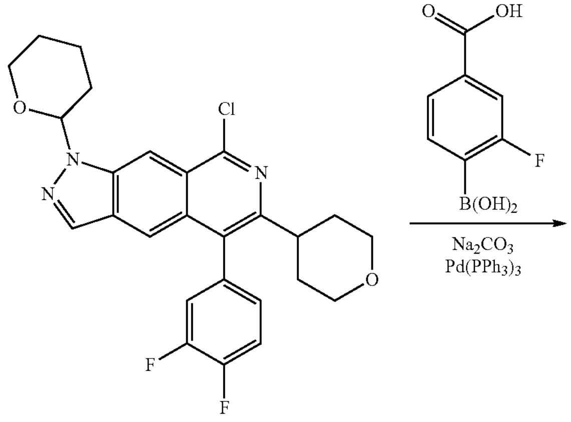

S6

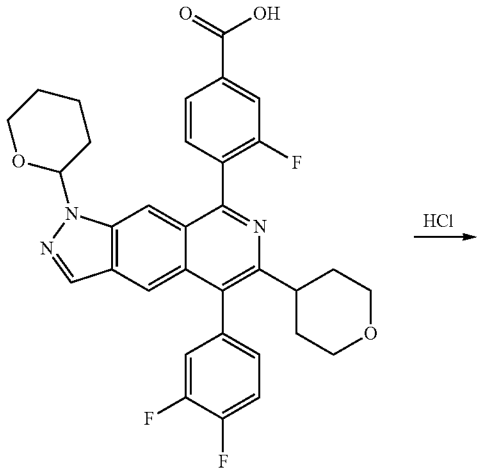

C35

-continued

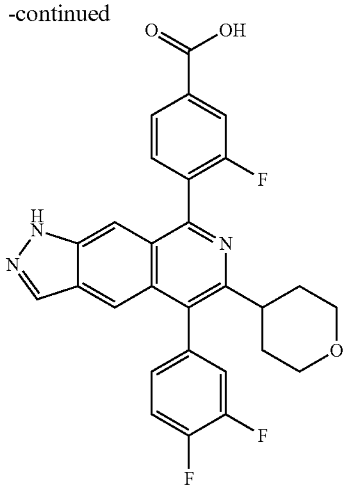

65

Step 1. Synthesis of 4-[5-(3,4-difluorophenyl)-1-tetrahydropyran-2-yl-6-tetrahydropyran-4-yl-pyrazolo[4,3-g]isoquinolin-8-yl]-3-fluoro-benzoic acid (C35)

To a mixture of 8-chloro-5-(3,4-difluorophenyl)-1-tetrahydropyran-2-yl-6-tetrahydropyran-4-yl-pyrazolo[4,3-g] isoquinoline S6 (95 mg, 0.1786 mmol), 4-borono-3-fluoro-benzoic acid (50 mg, 0.2718 mmol) and $Pd(PPh_3)_4$ (15 mg, 0.01298 mmol) in DMF (4 mL) under nitrogen was added $Na_2CO_3$ (600 μL of 2 M, 1.200 mmol). The reaction mixture was microwaved at 130° C. for 2 hours. Water was added and the mixture was extracted with EtOAc, and the combined organic layers were washed with water, sat NaCl and dried over $Na_2SO_4$. Purification by silica gel chromatography (Gradient: 0-10% MeOH in dichloromethane), then reverse-phase HPLC (Method: C18 Waters Sunfire column (30×150 mm, 5 micron). Gradient: MeCN in $H_2O$ with 0.2% formic acid) afforded the product.4-[5-(3,4-difluorophenyl)-1-tetrahydropyran-2-yl-6-tetrahydropyran-4-yl-pyrazolo[4,3-g]soquinolin-8-yl]-3-fluoro-benzoic acid (100 mg, 95%) LCMS m/z 588.28 $[M+H]^+$.

Step 2. Synthesis of 4-[5-(3,4-difluorophenyl)-6-tetrahydropyran-4-yl-1H-pyrazolo[4,3-g]isoquinolin-8-yl]-3-fluoro-benzoic acid (65)

4-[5-(3,4-difluorophenyl)-1-tetrahydropyran-2-yl-6-tetrahydropyran-4-yl-pyrazolo[4,3-g]isoquinolin-8-yl]-3-fluoro-benzoic acid (100 mg, 0.1702 mmol) was treated with HCl (4.5 mL of 4 M, 18.00 mmol) in 1,4-dioxane. The reaction mixture was microwaved at 80° C. for 50 minutes. The excess solvent was removed and the mixture was purified by reversed-phase HPLC. Method: C18 Waters Sunfire column (30×150 mm, 5 micron). Gradient: MeCN in $H_2O$ with 0.2% formic acid to afford the product. 4-[5-(3,4-difluorophenyl)-6-tetrahydropyran-4-yl-1H-pyrazolo[4,3-g]isoquinolin-8-yl]-3-fluoro-benzoic acid (Trifluoroacetate salt) (62 mg, 56%). $^1H$ NMR (300 MHz, Methanol-$d_4$) δ 8.22 (d, J=1.0 Hz, 1H), 8.09 (dd, J=7.8, 1.5 Hz, 1H), 8.03-7.89 (m, 2H), 7.87-7.64 (m, 2H), 7.51-7.41 (m, 1H), 7.30-7.09 (m, 2H), 4.10 (d, J=11.0 Hz, 1H), 3.95 (d, J=9.9 Hz, 1H), 3.51-3.38 (m, 2H), 2.88 (d, J=12.0 Hz, 1H), 2.33 (d, J=13.4 Hz, 2H), 1.72-1.46 (m, 2H) ppm. LCMS m/z 504.15 $[M+H]^+$.

Compounds 66 and 67
Methyl 3-[[5-(3,4-difluorophenyl)-6-tetrahydropyran-4-yl-1H-pyrazolo[4,3-g]isoquinolin-8-yl]amino]cyclobutanecarboxylate (66) and 3-[[5-(3,4-difluorophenyl)-6-tetrahydropyran-4-yl-1H-pyrazolo[4,3-g]isoquinolin-8-yl]amino]cyclobutanecarboxylic acid (67)
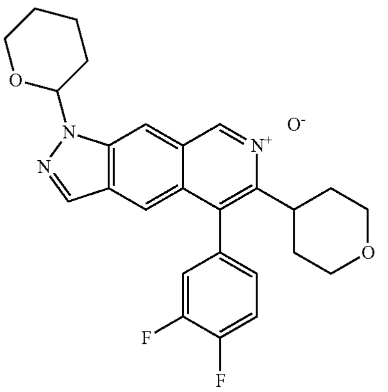
C7
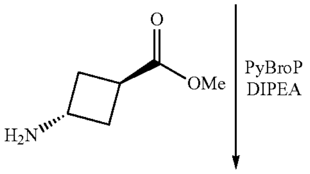
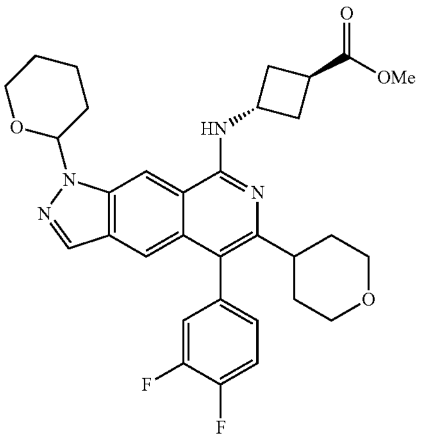
C36
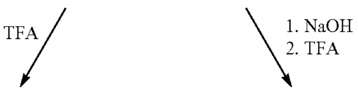

-continued

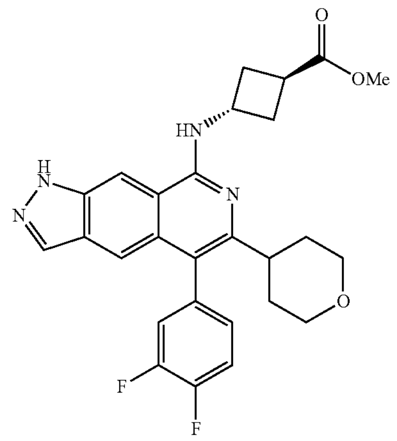

66

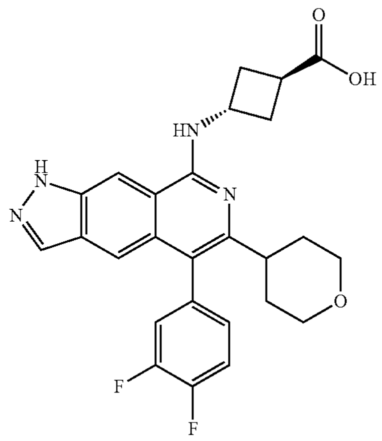

67

Step 1. Synthesis of methyl 3-[[5-(3,4-difluorophenyl)-1-tetrahydropyran-2-yl-6-tetrahydropyran-4-yl-pyrazolo[4,3-g]isoquinolin-8-yl]amino]cyclobutanecarboxylate (C36)

To a solution of 5-(3,4-difluorophenyl)-7-oxido-1-tetrahydropyran-2-yl-6-tetrahydropyran-4-yl-pyrazolo[4,3-g]isoquinolin-7-ium (150 mg, 0.1642 mmol), methyl 3-aminocyclobutanecarboxylate (Hydrochloride salt) (100 mg, 0.6038 mmol) and DIPEA (750 μL, 4.306 mmol) in dichloromethane (2 mL) was added PyBroP (560 mg, 1.201 mmol) and the reaction was stirred at 80° C. overnight. Additional PyBrop (560 mg, 1.201 mmol) was added and the reaction was stirred at 80° C. overnight. The mixture was concentrated in vacuo, then purification by reversed-phase HPLC (Method: C18 Waters Sunfire column (30×150 mm, 5 micron). Gradient: MeCN in $H_2O$ with 0.1% trifluoroacetic acid) afforded the product. methyl 3-[[5-(3,4-difluorophenyl)-1-tetrahydropyran-2-yl-6-tetrahydropyran-4-yl-pyrazolo[4,3-g]isoquinolin-8-yl]amino]cyclobutanecarboxylate (74 mg, 62%). LCMS m/z 577.34 $[M+H]^+$.

Synthesis of methyl 3-[[5-(3,4-difluorophenyl)-6-tetrahydropyran-4-yl-1H-pyrazolo[4,3-g]isoquinolin-8-yl]amino]cyclobutanecarboxylate (66)

Methyl 3-[[5-(3,4-difluorophenyl)-1-tetrahydropyran-2-yl-6-tetrahydropyran-4-yl-pyrazolo[4,3-g]isoquinolin-8-yl]amino]cyclobutanecarboxylate (70 mg, 0.09635 mmol) in a solution of hydrogen chloride (5 mL of 4 M, 20.00 mmol) in 1,4-Dioxane (5 mL) was stirred for 50 minutes. $Et_2O$ was added and stirred for 10 minutes. The mixture was filtered and the cake was washed with $Et_2O$, and filtered. The cake was then dried under vacuum. Purification by reverse-phase HPLC. Method: C18 Waters Sunfire column (30×150 mm, 5 micron). Gradient: MeCN in $H_2O$ with 0.1% trifluoroacetic acid afforded the product. Methyl 3-[[5-(3,4-difluorophenyl)-6-tetrahydropyran-4-yl-1H-pyrazolo[4,3-g]isoquinolin-8-yl]amino]cyclobutanecarboxylate (Trifluoroacetate salt) (45 mg, 72%). $^1$H NMR (400 MHz, Methanol-$d_4$) δ 8.94 (s, 1H), 8.28 (d, J=1.1 Hz, 1H), 7.67 (d, J=1.0 Hz, 1H), 7.53 (dt, J=10.5, 8.3 Hz, 1H), 7.36 (ddd, J=10.9, 7.6, 2.1 Hz, 1H), 7.20 (ddt, J=8.1, 3.8, 1.7 Hz, 1H), 5.17-4.99 (m, 2H), 4.08-3.94 (m, 2H), 3.79 (s, 3H), 3.36 (ddd, J=12.7, 6.4, 4.1 Hz, 3H), 2.97 (dddd, J=12.9, 6.7, 5.1, 2.8 Hz, 3H), 2.77 (dtt, J=10.4, 7.1, 2.9 Hz, 2H), 2.04 (qd, J=12.3, 4.6 Hz, 2H), 1.69 (d, J=13.3 Hz, 2H). LCMS m/z 493.31 $[M+H]^+$.

Synthesis of 3-[[5-(3,4-difluorophenyl)-6-tetrahydropyran-4-yl-1H-pyrazolo[4,3-g]isoquinolin-8-yl]amino]cyclobutanecarboxylic acid (67)

NaOH (2000 μL of 2 M, 4.000 mmol) was added to a solution of methyl 3-[[5-(3,4-difluorophenyl)-6-tetrahydropyran-4-yl-1H-pyrazolo[4,3-g]isoquinolin-8-yl]amino]cyclobutanecarboxylate (Trifluoroacetate salt) (45 mg, 0.06932 mmol) in MeOH (6 mL) and the mixture was allowed to stir for 30 minutes. TFA (250 μL, 3.245 mmol) was added and the mixture was evaporated to dryness. Purification by reverse-phase HPLC. Method: C18 Waters Sunfire column (30×150 mm, 5 micron). Gradient: MeCN in $H_2O$ with 0.2% formic acid afforded the product. 3-[[5-(3,4-difluorophenyl)-6-tetrahydropyran-4-yl-1H-pyrazolo[4,3-g]isoquinolin-8-yl]amino]cyclobutanecarboxylic acid (12.8 mg, 37%) $^1$H NMR (400 MHz, Methanol-$d_4$) δ 8.39 (d, J=1.1 Hz, 1H), 8.15-8.09 (m, 2H), 7.54 (d, J=1.0 Hz, 1H), 7.41 (dt, J=10.8, 8.4 Hz, 1H), 7.20 (ddd, J=11.3, 7.8, 2.1 Hz, 1H), 7.07 (ddd, J=8.0, 3.9, 1.9 Hz, 1H), 4.95 (d, J=7.9 Hz, 1H), 3.97 (dt, J=10.5, 4.7 Hz, 2H), 3.39-3.31 (m, 2H), 3.26-3.14 (m, 1H), 2.88-2.77 (m, 2H), 2.67 (tt, J=11.6, 3.8 Hz, 1H), 2.53 (tdd, J=10.1, 7.4, 2.4 Hz, 2H), 2.26 (qt, J=12.6, 4.7 Hz, 2H), 1.57-1.42 (m, 2H). LCMS m/z 479.31 $[M+H]^+$.

Compounds 68-74

Compounds 68-74 (Table 5) were prepared from S7 according to the method described for the preparation of compound 6. Modifications to this procedure are noted in the table footnotes.

TABLE 5

| Method of preparation, structure and physicochemical data for compounds 68-74 | | | |
|---|---|---|---|
| Compound | Product | Reagent | 1H NMR; LCMS m/z [M + H]$^+$ |
| 68 | 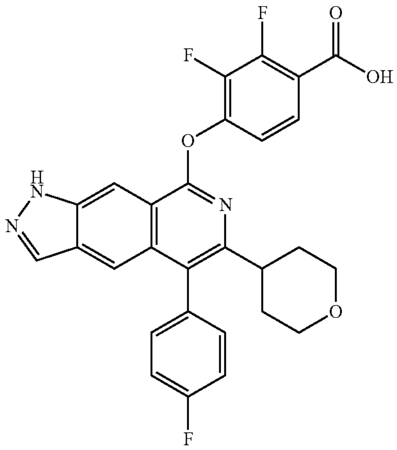 [SMILES: O=C(O)c1ccc(Oc2nc(C3CCOCC3)c(-c3ccc(F)cc3)c3cc4cn[nH]c4cc23)c(F)c1F] | 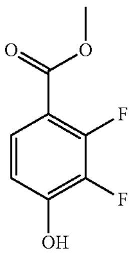 | $^1$H NMR (400 MHz, Methanol-$d_4$) δ 8.61 (t, J = 1.1 Hz, 1H), 8.25 (d, J = 1.1 Hz, 1H), 7.88 (s, 0H), 7.78 (d, J = 1.1 Hz, 1H), 7.44-7.22 (m, 5H), 3.92-3.76 (m, 2H), 3.28-3.13 (m, 2H), 2.72 (tt, J = 11.6, 3.7 Hz, 1H), 1.83 (dd, J = 12.5, 4.4 Hz, 2H), 1.44 (d, J = 12.9 Hz, 2H). LCMS m/z 520.0 [M + H]$^+$ |
| 69 | 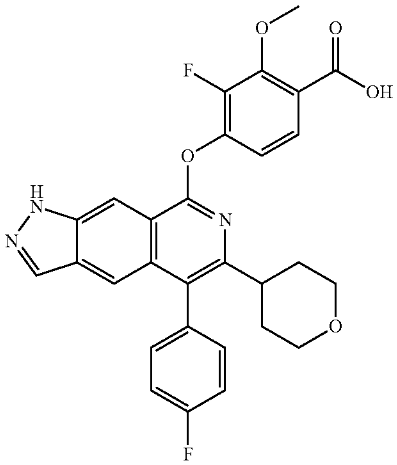 [SMILES: COc1c(C(=O)O)ccc(Oc2nc(C3CCOCC3)c(-c3ccc(F)cc3)c3cc4cn[nH]c4cc23)c1F] | 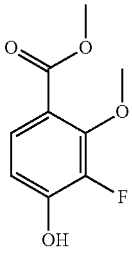 | $^1$H NMR (400 MHz, Methanol-$d_4$) δ 8.61 (t, J = 1.1 Hz, 1H), 8.25 (d, J = 1.1 Hz, 1H), 7.82-7.66 (m, 2H), 7.44-7.15 (m, 5H), 4.01 (d, J = 0.9 Hz, 3H), 3.82 (dd, J = 11.4, 4.3 Hz, 2H), 3.27-3.11 (m, 2H), 2.71 (tt, J = 11.6, 3.8 Hz, 1H), 1.86 (qd, J = 12.6, 4.5 Hz, 2H), 1.43 (d, J = 12.3 Hz, 2H). LCMS m/z 532.0 [M + H]$^+$ |
| 70 | 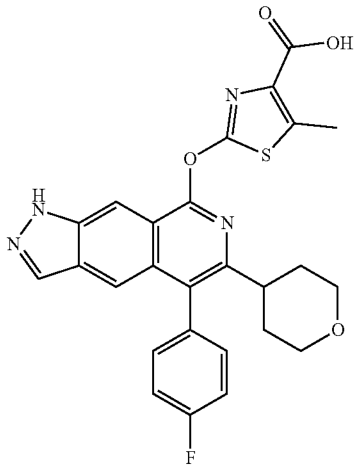 [SMILES: Cc1sc(Oc2nc(C3CCOCC3)c(-c3ccc(F)cc3)c3cc4cn[nH]c4cc23)nc1C(=O)O] | 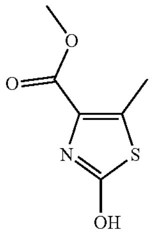 | $^1$H NMR (400 MHz, Methanol-$d_4$) δ 8.25 (d, J = 1.1 Hz, 1H), 8.13 (t, J = 1.1 Hz, 1H), 7.84 (d, J = 1.1 Hz, 1H), 7.52-7.27 (m, 4H), 3.94 (dt, J = 10.8, 5.0 Hz, 2H), 3.3-3.4 (m, 2H), 2.85 (ddt, J = 11.6, 7.5, 3.8 Hz, 1H), 2.64 (d, J = 11.9 Hz, 4H), 2.16 (dtd, J = 26.8, 12.7, 6.2 Hz, 2H), 1.54 (dd, J = 32.1, 13.5 Hz, 2H). LCMS m/z 505.0 [M + H]$^+$ |

TABLE 5-continued

Method of preparation, structure and physicochemical data for compounds 68-74

| Compound | Product | Reagent | 1H NMR; LCMS m/z $[M + H]^+$ |
|---|---|---|---|
| 71 | 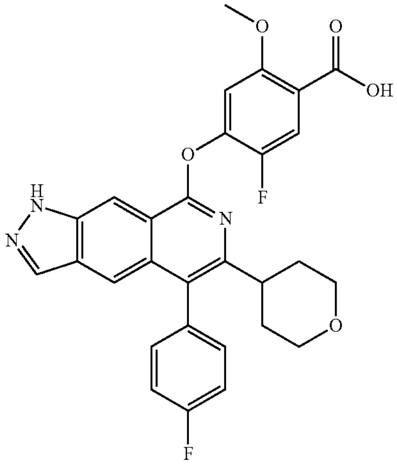 [SMILES: COc1cc(Oc2nc(C3CCOCC3)c(-c3ccc(F)cc3)c3cc4cn[nH]c4cc23)c(F)cc1C(=O)O] | 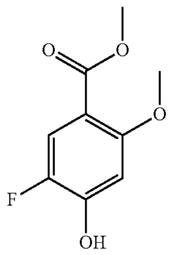 | $^1H$ NMR (400 MHz, Methanol-$d_4$) δ 8.61 (t, J = 1.1 Hz, 1H), 8.24 (d, J = 1.1 Hz, 1H), 7.84-7.68 (m, 2H), 7.43-7.23 (m, 5H), 3.94 (s, 3H), 3.85 (dd, J = 11.5, 4.2 Hz, 2H), 3.28-3.14 (m, 2H), 2.72 (tt, J = 11.5, 3.8 Hz, 1H), 1.88 (qd, J = 12.6, 4.5 Hz, 2H), 1.52-1.42 (m, 2H). LCMS m/z 532.0 $[M + H]^+$ |
| 72 | 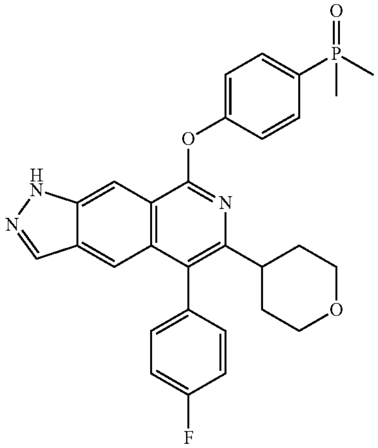 [SMILES: CP(C)(=O)c1ccc(Oc2nc(C3CCOCC3)c(-c3ccc(F)cc3)c3cc4cn[nH]c4cc23)cc1] | 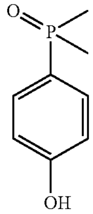 | 1H NMR (400 MHz, Methanol-$d_4$) δ 8.60 (t, J = 1.1 Hz, 1H), 8.23 (d, J = 1.1 Hz, 1H), 8.03-7.90 (m, 2H), 7.76 (d, J = 1.1 Hz, 1H), 7.64-7.53 (m, 2H), 7.42-7.23 (m, 5H), 3.90-3.75 (m, 2H), 3.24 (td, J = 12.1, 2.0 Hz, 2H), 2.74 (tt, J = 11.4, 3.8 Hz, 1H), 1.86 (d, J = 13.4 Hz, 8H), 1.45 (dd, J = 12.8, 3.7 Hz, 2H). LCMS m/z 516.0 $[M + H]^+$ |
| 73* | 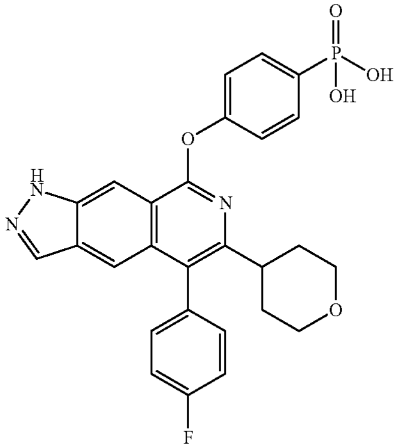 [SMILES: O=P(O)(O)c1ccc(Oc2nc(C3CCOCC3)c(-c3ccc(F)cc3)c3cc4cn[nH]c4cc23)cc1] | 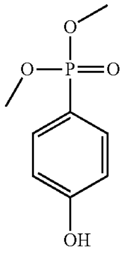 | $^1H$ NMR (300 MHz, Methanol-$d_4$) δ 6 8.60 (d, J = 1.2 Hz, 1H), 8.46 (s, 2H), 8.22 (d, J = 1.1 Hz, 1H), 8.04-7.87 (m, 2H), 7.73 (d, J = 1.1 Hz, 1H), 7.42-7.17 (m, 7H), 3.90-3.71 (m, 2H), 3.28-3.06 (m, 2H), 2.79-2.59 (m, 1H), 1.89 (qd, J = 12.7, 4.6 Hz, 2H), 1.51-1.28 (m, 2H). LCMS m/z 520.0 $[M + H]^+$ |

TABLE 5-continued

| Method of preparation, structure and physicochemical data for compounds 68-74 | | | |
|---|---|---|---|
| Compound | Product | Reagent | 1H NMR; LCMS m/z $[M + H]^+$ |
| 74 | 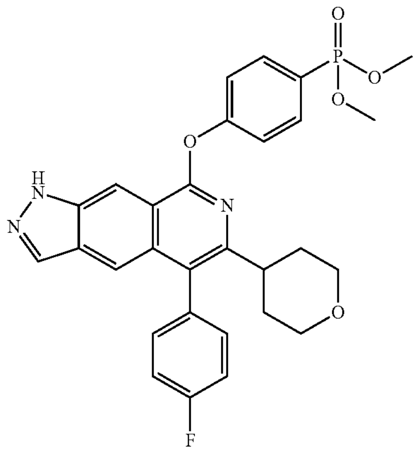 [SMILES: COP(=O)(OC)c1ccc(Oc2nc(C3CCOCC3)c(-c3ccc(F)cc3)c3cc4cn[nH]c4cc23)cc1] | 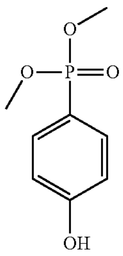 | $^1$H NMR (400 MHz, Methanol-$d_4$) δ 8.60 (t, J = 1.1 Hz, 1H), 8.24 (d, J = 1.1 Hz, 1H), 7.93 (dd, J = 13.0, 8.6 Hz, 2H), 7.76 (d, J = 1.1 Hz, 1H), 7.57 (dd, J = 8.7, 3.6 Hz, 2H), 7.41-7.25 (m, 5H), 3.82 (d, J = 11.2 Hz, 8H), 3.29-3.18 (m, 2H), 2.73 (tt, J = 11.6, 3.9 Hz, 1H), 1.88 (qd, J = 12.6, 4.5 Hz, 2H), 1.50-1.36 (m, 2H). LCMS m/z 548.0 $[M + H]^+$ |

*The phosphonate ester was hydrolyzed by treatment with TMSBr in dichloromethane at room temperature.

Compounds 75-88

Compounds 75-88 (Table 6) were prepared from S8 using the method described for the preparation of compound 42. The THP protecting group was removed by treatment with and TFA, HCl, or TFA. Any modifications are noted in the table footnotes.

TABLE 6

| Method of preparation, structure and physicochemical data for compounds 75-88 | | | |
|---|---|---|---|
| Compound | Product | Reagent | $^1$H NMR; LCMS m/z $[M + H]^+$ |
| 75 | 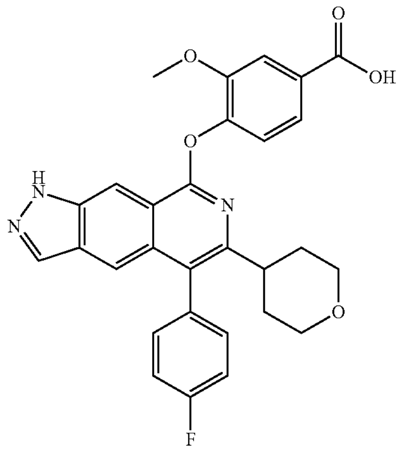 [SMILES: COc1cc(C(=O)O)ccc1Oc1nc(C2CCOCC2)c(-c2ccc(F)cc2)c2cc3cn[nH]c3cc12] | 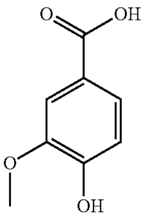 | $^1$H NMR (400 MHz, Methanol-$d_4$) δ 8.61 (t, J = 1.1 Hz, 1H), 8.22 (d, J = 1.1 Hz, 1H), 7.84-7.66 (m, 3H), 7.45-7.22 (m, 5H), 3.80 (s, 5H), 3.21 (m, 2H), 2.78-2.60 (m, 1H), 1.79 (dd, J = 12.5, 4.4 Hz, 2H), 1.48-1.19 (m, 2H). LCMS m/z 514.18 $[M + H]^+$ |

TABLE 6-continued

Method of preparation, structure and physicochemical data for compounds 75-88

| Compound | Product | Reagent | $^1$H NMR; LCMS m/z [M + H]$^+$ |
|---|---|---|---|
| 76 | 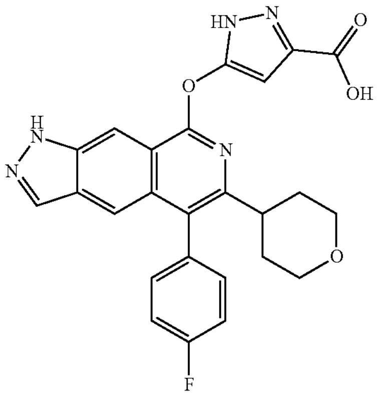 [SMILES: O=C(O)c1cc(Oc2nc(C3CCOCC3)c(-c3ccc(F)cc3)c3cc4cn[nH]c4cc23)[nH]n1] | 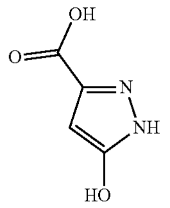 | $^1$H NMR (400 MHz, DMSO-$d_6$) δ 13.52 (d, J = 46.8 Hz, 2H), 8.50 (t, J = 1.1 Hz, 1H), 8.38 (d, J = 1.1 Hz, 1H), 7.69 (d, J = 1.0 Hz, 1H), 7.42 (d, J = 7.3 Hz, 4H), 6.85 (s, 1H), 3.95-3.69 (m, 2H), 3.25-2.99 (m, 2H), 2.65 (s, 1H), 1.83 (dd, J = 12.3, 4.3 Hz, 2H), 1.44 (dd, J = 12.1, 3.1 Hz, 2H). LCMS m/z 474.0 [M + H]$^+$ |
| 77 | 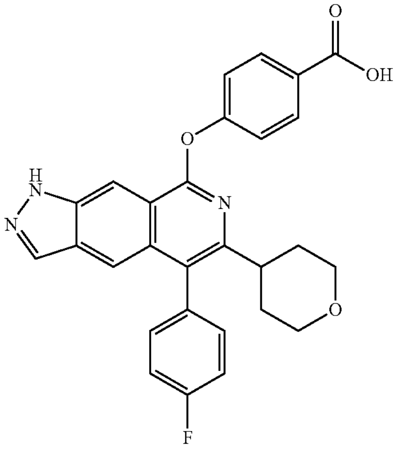 | 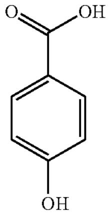 | $^1$H NMR (400 MHz, Methanol-$d_4$) δ 8.64-8.55 (m, 1H), 8.23 (d, J = 1.1 Hz, 1H), 8.19-8.11 (m, 2H), 7.76 (d, J = 1.1 Hz, 1H), 7.54-7.41 (m, 2H), 7.41-7.24 (m, 4H), 3.93-3.75 (m, 2H), 3.29-3.19 (m, 2H), 2.72 (m, 1H), 1.90 (dd, J = 12.5, 4.4 Hz, 2H), 1.46 (d, J = 3.6 Hz, 2H). LCMS m/z 484.0 [M + H]$^+$ |
| 78 | 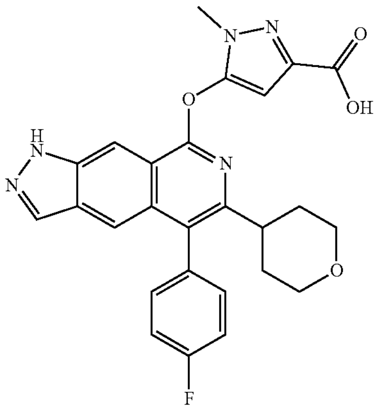 [SMILES: Cn1nc(C(=O)O)cc1Oc1nc(C2CCOCC2)c(-c2ccc(F)cc2)c2cc3cn[nH]c3cc12] | 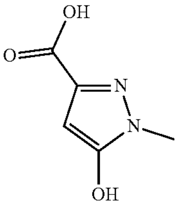 | $^1$H NMR (400 MHz, Methanol-$d_4$) δ 8.67-8.57 (m, 1H), 8.26 (d, J = 1.1 Hz, 1H), 8.09 (s, 1H), 7.80 (d, J =1.1 Hz, 1H), 7.42-7.25 (m, 4H), 6.78 (s, 1H), 3.90 (s, 4H), 3.29-3.21 (m, 2H), 2.77 (ddd, J = 11.6, 7.9, 3.7 Hz, 1H), 2.66 (s, 1H), 1.95 (dd, J = 12.5, 4.4 Hz, 2H), 1.56-1.39 (m, 2H), 1.02-0.91 (m, 1H). LCMS m/z 488.13 [M + H]$^+$ |

TABLE 6-continued

| Method of preparation, structure and physicochemical data for compounds 75-88 | | | |
|---|---|---|---|
| Compound | Product | Reagent | $^1H$ NMR; LCMS m/z $[M + H]^+$ |
| 79 | 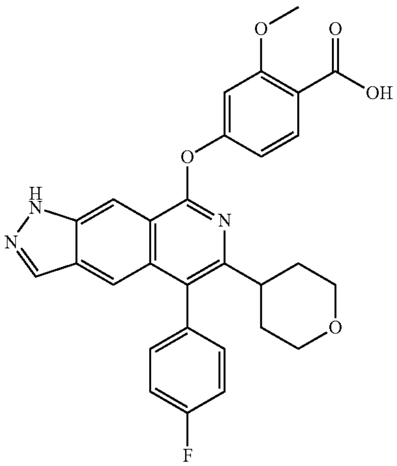 [SMILES: COc1cc(Oc2nc(C3CCOCC3)c(-c3ccc(F)cc3)c3cc4cn[nH]c4cc23)ccc1C(=O)O] | 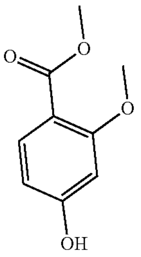 | $^1H$ NMR (400 MHz, Methanol-$d_4$) δ 8.60 (t, J = 1.1 Hz, 1H), 8.23 (d, J = 1.1 Hz, 1H), 7.91 (d, J = 8.5 Hz, 1H), 7.75 (d, J = 1.1 Hz, 1H), 7.46-7.26 (m, 4H), 7.23 (d, J = 2.1 Hz, 1H), 7.00 (dd, J = 8.5, 2.1 Hz, 1H), 3.99-3.80 (m, 5H), 3.25 (dd, J = 12.5, 10.7 Hz, 2H), 2.73-2.68 (m, 1H), 1.97 (dd, J = 12.5, 4.4 Hz, 2H), 1.47 (d, J = 12.3 Hz, 2H). LCMS m/z 514.2 $[M + H]^+$ |
| 80 | 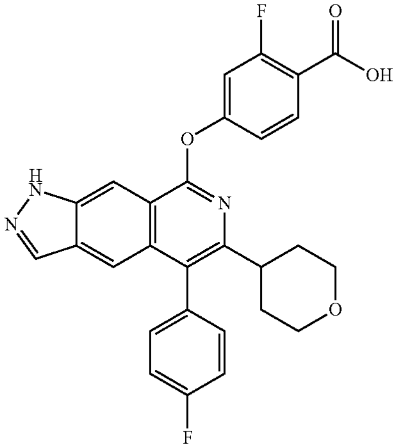 [SMILES: O=C(O)c1ccc(Oc2nc(C3CCOCC3)c(-c3ccc(F)cc3)c3cc4cn[nH]c4cc23)cc1F] | 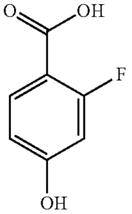 [SMILES: O=C(O)c1ccc(O)cc1F] | $^1H$ NMR (400 MHz, Methanol-$d_4$) δ 8.58 (t, J = 1.1 Hz, 1H), 8.24 (d, J = 1.1 Hz, 1H), 8.08 (t, J = 8.7 Hz, 1H), 7.77 (d, J = 1.2 Hz, 1H), 7.44-7.22 (m, 6H), 3.88 (dd, J = 11.7, 4.1 Hz, 2H), 3.29-3.22 (m, 2H), 2.86-2.70 (m, 1H), 2.14-1.85 (m, 2H), 1.48 (d, J = 12.0 Hz, 2H). LCMS m/z 502.0 $[M + H]^+$ |
| 81 | 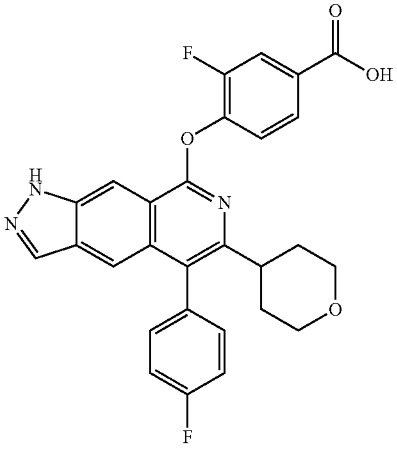 [SMILES: O=C(O)c1ccc(Oc2nc(C3CCOCC3)c(-c3ccc(F)cc3)c3cc4cn[nH]c4cc23)c(F)c1] | 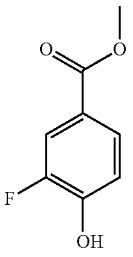 | $^1H$ NMR (400 MHz, Methanol-$d_4$) δ 8.62 (t, J = 1.1 Hz, 1H), 8.24 (d, J = 1.1 Hz, 1H), 8.11-7.86 (m, 2H), 7.76 (d, J = 1.1 Hz, 1H), 7.56 (dd, J = 8.4, 7.5 Hz, 1H), 7.44-7.22 (m, 4H), 3.92-3.75 (m, 2H), 3.26-3.14 (m, 2H), 2.70 (ddd, J = 11.5, 7.7, 3.8 Hz, 1H), 1.94-1.70 (m, 2H), 1.42 (d, J = 13.1 Hz, 2H). LCMS m/z 502.17 $[M + H]^+$ |

TABLE 6-continued

Method of preparation, structure and physicochemical data for compounds 75-88

| Compound | Product | Reagent | $^1$H NMR; LCMS m/z $[M + H]^+$ |
|---|---|---|---|
| 82 | 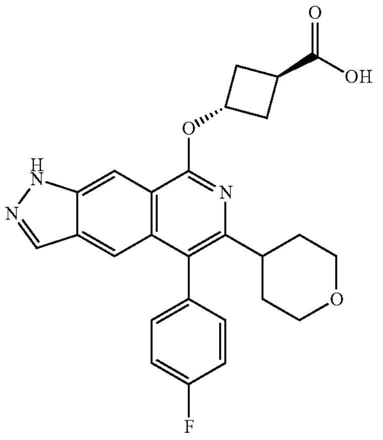 [SMILES: O=C(O)[C@H]1C[C@H](Oc2nc(C3CCOCC3)c(-c3ccc(F)cc3)c3cc4cn[nH]c4cc23)C1] | 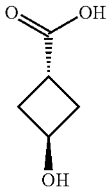 | $^1$H NMR (300 MHz, DMSO-$d_6$) δ 13.34 (s, 1H), 12.37 (s, 1H), 8.35 (t, J = 1.1 Hz, 1H), 8.32 (d, J = 1.0 Hz, 1H), 7.58 (d, J = 1.0 Hz, 1H), 7.42-7.35 (m, 4H), 5.59 (p, J = 7.0 Hz, 1H), 3.88 (dd, J = 11.1, 4.1 Hz, 2H), 3.18 (dd, J = 13.3, 10.3 Hz, 3H), 2.82 (ddt, J = 11.0, 7.4, 3.7 Hz, 2H), 2.66-2.56 (m, 3H), 2.12-1.95 (m, 2H), 1.46 (d, J = 12.2 Hz, 2H) ppm. LCMS m/z 462.28 $[M + H]^+$ |
| 83 | 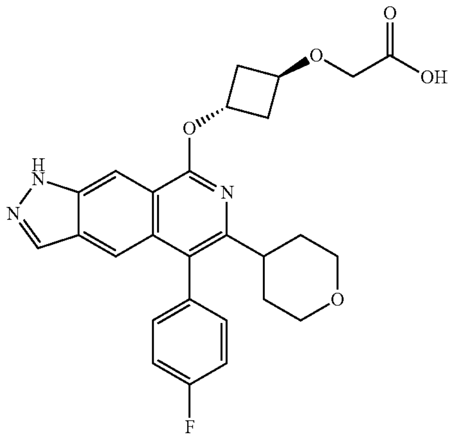 [SMILES: O=C(O)CO[C@H]1C[C@H](Oc2nc(C3CCOCC3)c(-c3ccc(F)cc3)c3cc4cn[nH]c4cc23)C1] | 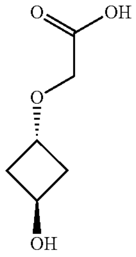 | $^1$H NMR (400 MHz, Methanol-$d_4$) δ 8.42 (t, J = 1.1 Hz, 1H), 8.17 (d, J = 1.1 Hz, 1H), 7.63 (d, J = 1.1 Hz, 1H), 7.42-7.19 (m, 4H), 5.78-5.60 (m, 1H), 4.47 (d, J = 4.2 Hz, 1H), 4.08 (s, 2H), 3.97 (dd, J = 11.3, 4.4 Hz, 2H), 3.35 (d, J = 2.4 Hz, 1H), 2.74 (ddd, J = 13.0, 7.1, 3.8 Hz, 3H), 2.67-2.55 (m, 2H), 2.32-2.12 (m, 1H), 1.60-1.46 (m, 2H), 1.26 (dd, J = 11.6, 6.2 Hz, 2H). LCMS m/z 492.2 $[M + H]^+$ |
| 84 | 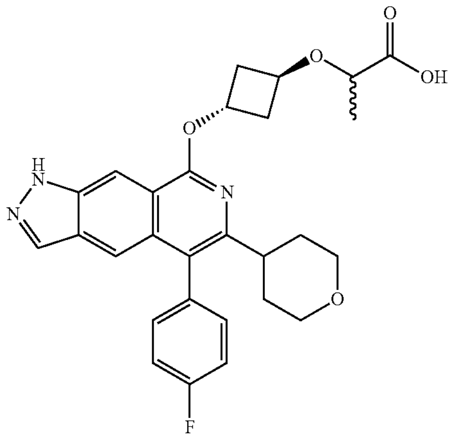 [SMILES: CC(O[C@H]1C[C@H](Oc2nc(C3CCOCC3)c(-c3ccc(F)cc3)c3cc4cn[nH]c4cc23)C1)C(=O)O] | 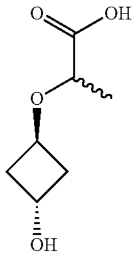 | $^1$H NMR (400 MHz, Methanol-$d_4$) δ 8.42 (t, J = 1.2 Hz, 1H), 8.17 (d, J = 1.1 Hz, 1H), 7.63 (d, J = 1.1 Hz, 1H), 7.41-7.19 (m, 4H), 5.81-5.55 (m, 1H), 4.60-4.37 (m, 1H), 4.03 (d, J = 6.8 Hz, 4H), 3.48-3.41 (m, 2H), 2.86-2.46 (m, 4H), 2.23 (q, J = 11.9, 11.5 Hz, 2H), 1.51 (d, J = 12.8 Hz, 2H), 1.43 (d, J = 6.8 Hz, 3H). LCMS m/z 506.0 $[M + H]^+$ |

TABLE 6-continued

Method of preparation, structure and physicochemical data for compounds 75-88

| Compound | Product | Reagent | $^1$H NMR; LCMS m/z [M + H]$^+$ |
|---|---|---|---|
| 85 | 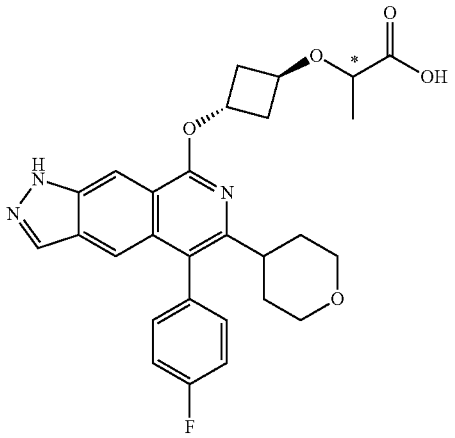 [SMILES: CC(O[C@H]1C[C@H](Oc2nc(C3CCOCC3)c(-c3ccc(F)cc3)c3cc4cn[nH]c4cc23)C1)C(=O)O] | From 84 | $^1$H NMR (400 MHz, Methanol-$d_4$) δ 8.42 (t, J = 1.1 Hz, 1H), 8.16 (d, J = 1.1 Hz, 1H), 7.63 (d, J = 1.1 Hz, 1H), 7.39-7.13 (m, 4H), 4.03-3.73 (m, 4H), 2.87-2.48 (m, 4H), 2.31-2.14 (m, 3H), 1.57-1.22 (m, 6H), 1.24-1.00 (m, 3H). LCMS m/z 506.0 [M + H]$^+$ |
| 86 | 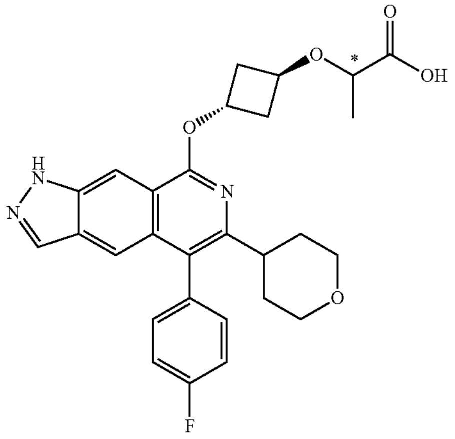 [SMILES: CC(O[C@H]1C[C@H](Oc2nc(C3CCOCC3)c(-c3ccc(F)cc3)c3cc4cn[nH]c4cc23)C1)C(=O)O] | From 84 | $^1$H NMR (300 MHz, Methanol-$d_4$) δ 8.42 (t, J = 1.1 Hz, 1H), 8.16 (d, J = 1.1 Hz, 1H), 7.63 (d, J = 1.0 Hz, 1H), 7.38-7.21 (m, 4H), 5.66 (s, 1H), 3.97 (dd, J =11.4, 4.3 Hz, 3H), 2.90-2.39 (m, 5H), 2.34-1.98 (m, 3H), 1.66-1.21 (m, 7H). LCMS m/z 506.1 [M + H]$^+$ |
| 87* | 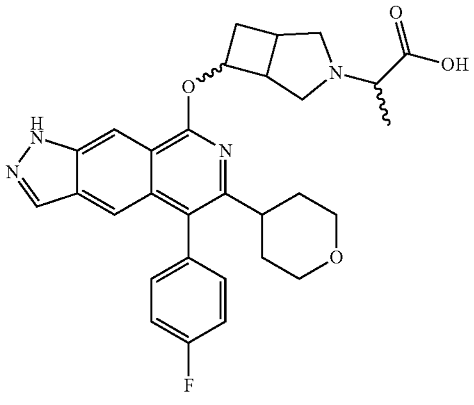 [SMILES: CC(C(=O)O)N1CC2CC(Oc3nc(C4CCOCC4)c(-c4ccc(F)cc4)c4cc5cn[nH]c5cc34)C2C1] | 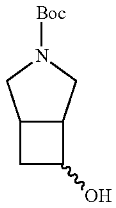 [SMILES: CC(C)(C)OC(=O)N1CC2CC(O)C2C1] | $^1$H NMR (400 MHz, Methanol-$d_4$) δ 8.87-8.64 (m, 1H), 8.21-8.08 (m, 2H), 7.63 (dd, J = 7.4, 1.1 Hz, 1H), 7.36-7.23 (m, 4H), 5.77-5.61 (m, 1H), 4.08-3.42 (m, 7H), 3.31-3.34 (m, 2H), 3.13 (d, J = 6.6 Hz, 1H), 2.75 (m, 1H), 2.18 (dd, J = 12.7, 4.7 Hz, 3H), 1.73-1.45 (m, 6H). LCMS m/z 531.0 [M + H]$^+$ |

TABLE 6-continued

Method of preparation, structure and physicochemical data for compounds 75-88

| Compound | Product | Reagent | $^1$H NMR; LCMS m/z $[M + H]^+$ |
|---|---|---|---|
| 88 | 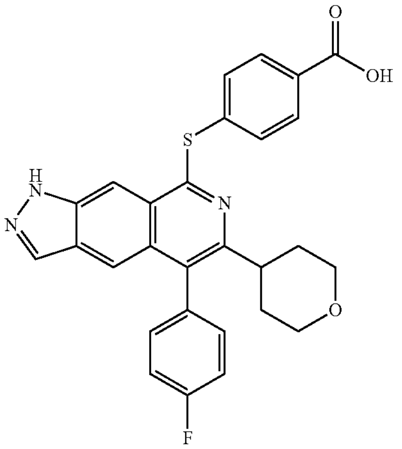 | 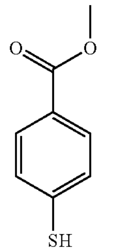 | $^1$H NMR (400 MHz, DMSO-$d_6$) δ 13.49 (s, 1H), 8.45 (t, J = 1.1 Hz, 1H), 8.39 (d, J = 1.1 Hz, 1H), 8.08-7.96 (m, 2H), 7.74 (dd, J = 7.6, 1.4 Hz, 3H), 7.41 (d, J = 7.2 Hz, 4H), 3.81-3.52 (m, 2H), 3.29-2.93 (m, 2H), 2.67-2.55 (m, 1H), 1.63 (qd, J = 12.6, 4.4 Hz, 2H), 1.42-1.22 (m, 2H). LCMS m/z 500.0 $[M + H]^+$ |

*Compound 87 was prepared by addition of tert-butyl 6-hydroxy-3-azabicyclo[3.2.0]heptane-3-carboxylate to S8 . The resulting Boc-protected product was treated with TFA to afford 8-(3-azabicyclo[3.2.0]heptan-6-yloxy)-5-(4-fluorophenyl)-6-tetrahydropyran-4-yl-1H-pyrazolo[4,3-g]isoquinoline (Trifluoroacetate salt). Alkylation of the amine by treatment with tert-butyl-2-bromopropanoate and $K_2CO_3$ in DMF. Tert-Butyl ester group was then removed with TFA to afford the product.

Compound 89

[3-[[5-(4-fluorophenyl)-6-tetrahydropyran-4-yl-1H-pyrazolo[4,3-g]isoquinolin-8-yl]oxy]azetidin-1-yl]-(1-hydroxycyclopropyl)methanone (89)

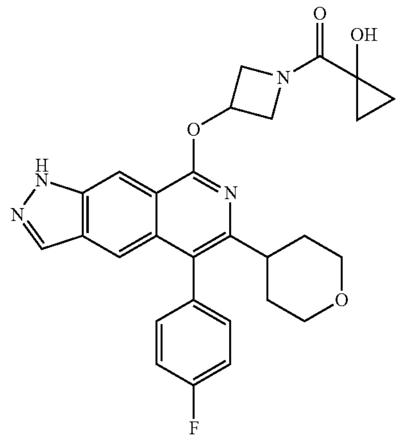 [SMILES: O=C(N1CC(Oc2nc(C3CCOCC3)c(-c3ccc(F)cc3)c3cc4cn[nH]c4cc23)C1)C1(O)CC1]

Compound 89 was prepared from S9 according to the method described for the preparation of compound 35. Purification by reversed-phase HPLC. Method: C18 Waters Sunfire column (30×150 mm, 5 micron). Gradient: MeCN in $H_2O$ with 0.2% formic acid. [3-[[5-(4-fluorophenyl)-6-tetrahydropyran-4-yl-1H-pyrazolo[4,3-g]isoquinolin-8-yl]oxy]azetidin-1-yl]-(1-hydroxycyclopropyl)methanone (4.0 mg, 32%). $^1$H NMR (400 MHz, Methanol-$d_4$) δ 8.68 (s, 1H), 8.45 (s, 2H), 8.23 (d, J=0.9 Hz, 1H), 7.53 (s, 1H), 7.38 (d, J=7.5 Hz, 3H), 4.70 (s, 1H), 4.37 (d, J=13.1 Hz, 1H), 4.04-3.79 (m, 3H), 3.72 (d, J=13.9 Hz, 1H), 3.22 (d, J=27.2 Hz, 2H), 1.76 (d, J=12.9 Hz, 1H), 1.63 (d, J=13.3 Hz, 1H). LCMS m/z 503.0 $[M+H]^+$ Compound 90

(2R)-3-[5-(4-fluorophenyl)-6-tetrahydropyran-4-yl-1H-pyrazolo[4,3-g]isoquinolin-8-yl]-2-methyl-propanoic acid (Hydrochloride Salt) (90)

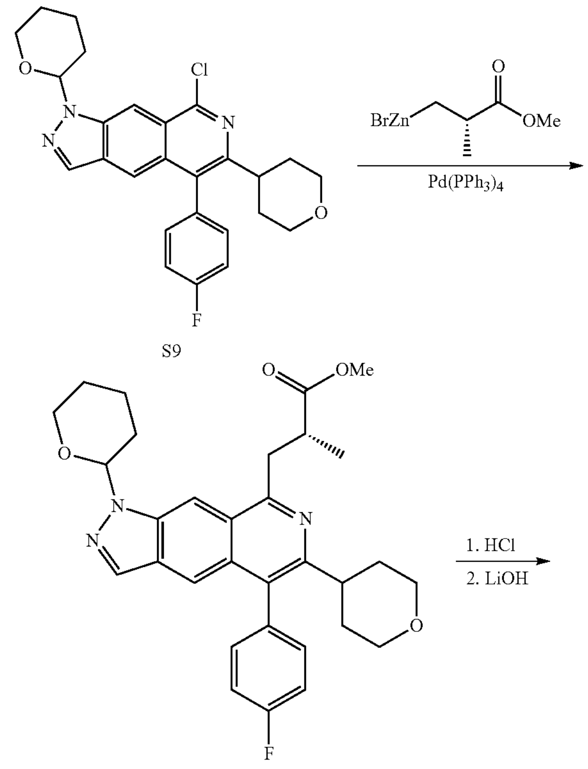

S9

C37

-continued

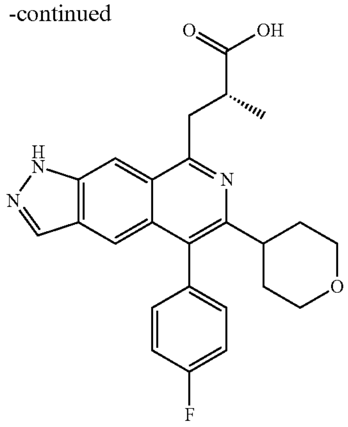

90

Step 1. Synthesis of methyl (2R)-3-[5-(4-fluorophenyl)-1-tetrahydropyran-2-yl-6-tetrahydropyran-4-yl-pyrazolo[4,3-g]isoquinolin-8-yl]-2-methyl-propanoate (C37)

To a mixture of 8-chloro-5-(4-fluorophenyl)-1-tetrahydropyran-2-yl-6-tetrahydropyran-4-yl-pyrazolo[4,3-g]isoquinoline (107 mg, 0.2296 mmol) and $Pd(PPh_3)_4$ (20 mg, 0.01731 mmol) in THF (2 mL) under nitrogen was added bromo-[(2S)-3-methoxy-2-methyl-3-oxo-propyl]zinc (1.9 mL of 0.5 M, 0.9500 mmol). The reaction mixture was heated at 90° C. for 4 h. The solvent was evaporated and the residue was dissolved in dichloromethane. The organic solution was washed with NaOH (0.5M/6 mL), water, brine, dried over $Na_2SO_4$ and concentrated. Purification by silica gel chromatography (Gradient: 10-100% EtOAc in heptane) yielded the product.3-[5-(4-fluorophenyl)-1-tetrahydropyran-2-yl-6-tetrahydropyran-4-yl-pyrazolo[4,3-g]isoquinolin-8-yl]-2-methyl-propanoate (115 mg, 94%). $^1$H NMR (300 MHz, Chloroform-d) δ 8.32 (dt, J=3.7, 1.1 Hz, 1H), 8.15 (d, J=0.9 Hz, 1H), 7.71 (d, J=1.0 Hz, 1H), 7.28-7.17 (m, 4H), 5.95 (dd, J=8.9, 2.7 Hz, 1H), 4.08-3.98 (m, 3H), 3.92 (dd, J=8.1, 6.1 Hz, 1H), 3.81 (s, 3H), 3.68-3.47 (m, 2H), 3.43-3.27 (m, 2H), 2.90-2.60 (m, 2H), 2.47-2.31 (m, 1H), 2.27-2.12 (m, 3H), 1.99-1.69 (m, 3H), 1.48 (dd, J=7.0, 2.2 Hz, 4H), 0.95-0.85 (m, 3H) ppm. LCMS m/z 531.81 $[M+H]^+$.

Step 2. Synthesis of methyl (2R)-3-[5-(4-fluorophenyl)-6-tetrahydropyran-4-yl-1H-pyrazolo[4,3-g]isoquinolin-8-yl]-2-methyl-propanoate (C37)

Methyl (2R)-3-[5-(4-fluorophenyl)-1-tetrahydropyran-2-yl-6-tetrahydropyran-4-yl-pyrazolo[4,3-g]isoquinolin-8-yl]-2-methyl-propanoate (110 mg, 0.2069 mmol) in was treated with HCl (5 mL of 4 M, 20.00 mmol) in 1,4-dioxane. The reaction mixture was stirred at room temperature for 1 h. MeOH (1 mL, 24.69 mmol) was added and the resultant clear reaction mixture was stirred at room temperature for 3 h. The excess solvent was removed and the residue was triturated with $CH_3CN$, water, dichloromethane, MeOH, and then dried to give methyl (2R)-3-[5-(4-fluorophenyl)-6-tetrahydropyran-4-yl-1H-pyrazolo[4,3-g]isoquinolin-8-yl]-2-methyl-propanoate (56 mg, 60%) LCMS m/z 447.5 $[M+H]^+$.

Step 3. Synthesis of (2R)-3-[5-(4-fluorophenyl)-6-tetrahydropyran-4-yl-1H-pyrazolo[4,3-g]isoquinolin-8-yl]-2-methyl-propanoic acid (90)

A mixture of methyl (2R)-3-[5-(4-fluorophenyl)-6-tetrahydropyran-4-yl-1H-pyrazolo[4,3-g]isoquinolin-8-yl]-2-methyl-propanoate (55 mg, 0.1229 mmol) and $LiOH{\cdot}H_2O$ (135 mg, 3.217 mmol) in THF (4 mL) and $H_2O$ (2 mL) was stirred for 3 h. The reaction mixture was acidified with HCl (4 mL of 1 M, 4.000 mmol) and extracted with EtOAc. Organic layer was concentrated. Purification by silica gel chromatography (Gradient: 0-10% MeOH in dichloromethane) afforded the product. (2R)-3-[5-(4-fluorophenyl)-6-tetrahydropyran-4-yl-1H-pyrazolo[4,3-g]isoquinolin-8-yl]-2-methyl-propanoic acid (Hydrochloride salt) (25 mg, 41%). $^1$H NMR (300 MHz, DMSO-$d_6$) δ 13.35 (s, 1H), 12.08 (s, 1H), 8.44-8.26 (m, 2H), 7.67 (d, J=0.9 Hz, 1H), 7.50-7.29 (m, 4H), 3.99-3.68 (m, 3H), 3.55-3.36 (m, 2H), 3.18 (t, J=11.9 Hz, 2H), 2.77-2.61 (m, 1H), 2.29-2.09 (m, 2H), 1.54-1.23 (m, 5H) ppm. LCMS m/z 434.43 $[M+H]^+$.

Compound 91

3-[5-(4-fluorophenyl)-6-tetrahydropyran-4-yl-1H-pyrazolo[4,3-g]isoquinolin-8-yl]propanoic acid (91)

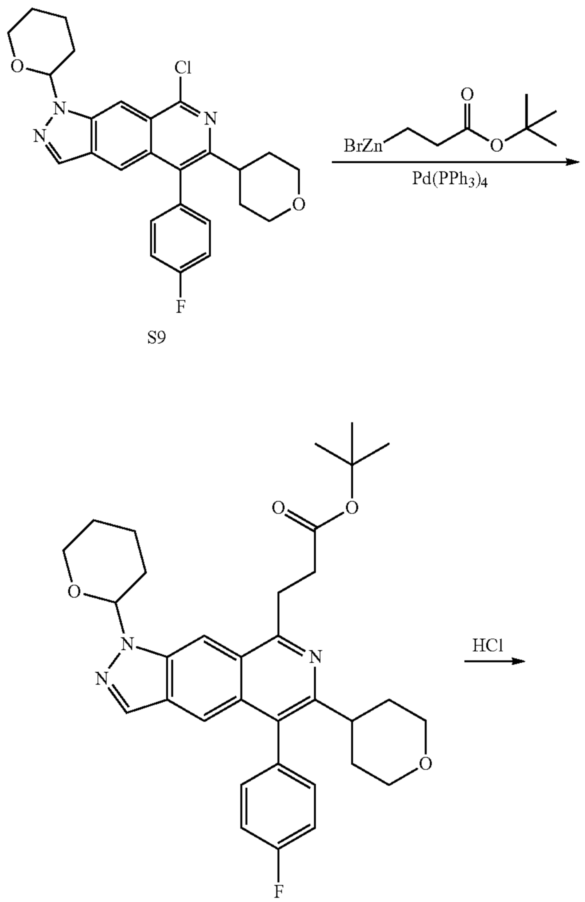

S9

C38

-continued

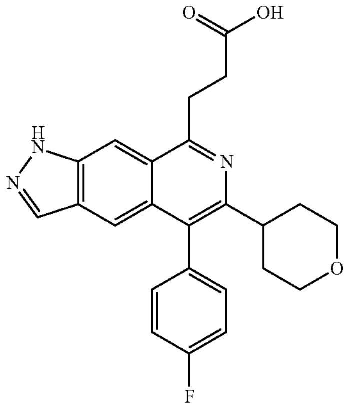

91

Compound 91 was prepared from S9 as described for compound 90. Tert-butyl ester and THP deprotection was performed by treatment of C38 with HCl. 3-[5-(4-fluorophenyl)-6-tetrahydropyran-4-yl-1H-pyrazolo[4,3-g]isoquinolin-8-yl]propanoic acid (Hydrochloride salt) (25 mg, 29%) $^1$H NMR (400 MHz, Chloroform-d+Methanol-$d_4$) δ 8.34 (d, J=1.2 Hz, 1H), 8.15 (d, J=1.0 Hz, 1H), 7.74 (d, J=1.1 Hz, 1H), 7.32-7.21 (m, 4H), 4.01 (dd, J=11.5, 4.2 Hz, 2H), 3.41-3.34 (m, 4H), 3.09 (t, J=6.6 Hz, 2H), 2.80 (tt, J=11.8, 3.8 Hz, 1H), 2.32 (qd, J=12.8, 4.5 Hz, 2H), 1.51 (d, J=12.2 Hz, 2H) ppm. LCMS m/z 420.39 $[M+H]^+$.

Compound 92

4-[5-(4-fluorophenyl)-6-tetrahydropyran-4-yl-1H-pyrazolo[4,3-g]isoquinolin-8-yl]benzoic acid (92)

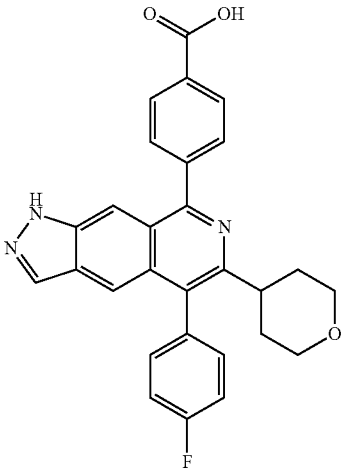 [SMILES: O=C(O)c1ccc(-c2nc(C3CCOCC3)c(-c3ccc(F)cc3)c3cc4cn[nH]c4cc23)cc1]

Compound 92 was prepared from S9 by Suzuki coupling with tert-butyl 4-(4,4,5,5-tetramethyl-1,3,2-dioxaborolan-2-yl)benzoate, then treatment with HCl. 4-[5-(4-fluorophenyl)-6-tetrahydropyran-4-yl-1H-pyrazolo[4,3-g]isoquinolin-8-yl]benzoic acid (Hydrochloride salt) (49 mg, 89%). $^1$H NMR (400 MHz, DMSO-$d_6$) δ 13.26 (s, 1H), 8.39 (d, J=1.0 Hz, 1H), 8.26-8.18 (m, 2H), 8.16 (t, J=1.1 Hz, 1H), 8.01-7.91 (m, 2H), 7.80 (d, J=1.1 Hz, 1H), 7.55-7.43 (m, 4H), 3.74-3.63 (m, 2H), 3.21 (t, J=11.8 Hz, 2H), 2.90-2.75 (m, 1H), 2.13 (qd, J=12.6, 4.6 Hz, 2H), 1.55 (d, J=12.3 Hz, 2H) ppm. LCMS m/z 468.26 $[M+H]^+$.

Compounds 93-103

Compounds 93-103 (Table 7) were prepared from S11 by addition of the appropriate alcohol in the presence of NaH in DMSO. Any modifications are noted in the table footnotes.

TABLE 7

Method of preparation, structure and physicochemical data for compounds 93-103

| Compound | Product | Reagent | $^1$H NMR; LCMS m/z $[M + H]^+$ |
|---|---|---|---|
| 93 | 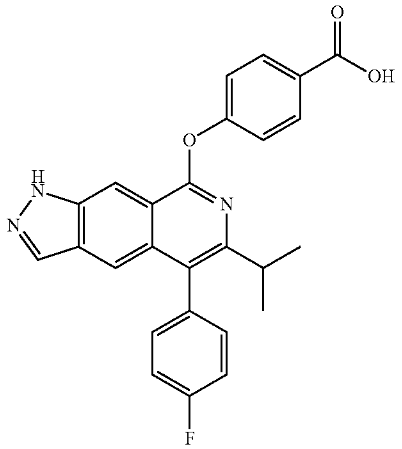 [SMILES: CC(C)c1nc(Oc2ccc(C(=O)O)cc2)c2cc3[nH]ncc3cc2c1-c1ccc(F)cc1] | 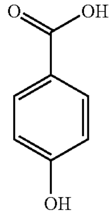 | $^1$H NMR (300 MHz, Chloroform-d + Methanol-$d_4$) δ 8.58 (s, 1H), 8.20-8.15 (m, 2H), 7.92 (d, J = 8.8 Hz, 2H), 7.48 (s, 1H), 7.34-7.22 (m, 3H), 6.84 (d, J = 8.8 Hz, 2H), 2.84 (p, J = 6.7 Hz, 1H), 1.05 (d, J = 6.7 Hz, 6H) ppm. LCMS m/z 442.44 $[M + H]^+$ |

TABLE 7-continued

| Method of preparation, structure and physicochemical data for compounds 93-103 | | | |
|---|---|---|---|
| Compound | Product | Reagent | $^1$H NMR; LCMS m/z [M + H]$^+$ |
| 94 | 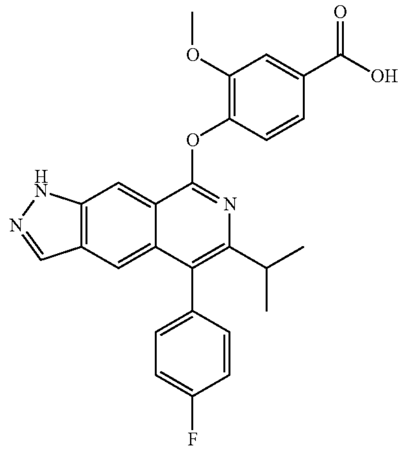 [SMILES: COc1cc(C(=O)O)ccc1Oc1nc(C(C)C)c(-c2ccc(F)cc2)c2cc3cn[nH]c3cc12] | 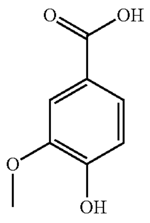 | $^1$H NMR (300 MHz, Chloroform-d Methanol-$d_4$) δ 8.64 (t, J = 1.1 Hz, 1H), 8.17 (d, J = 1.1 Hz, 1H), 7.83-7.74 (m, 2H), 7.71 (d, J = 1.1 Hz, 1H), 7.41-7.35 (m, 1H), 7.35-7.20 (m, 4H), 3.84 (s, 3H), 2.77 (p, J = 6.6 Hz, 1H), 0.94 (d, J = 6.7 Hz, 6H) ppm. LCMS m/z 472.45 [M + H]$^+$ |
| 95 | 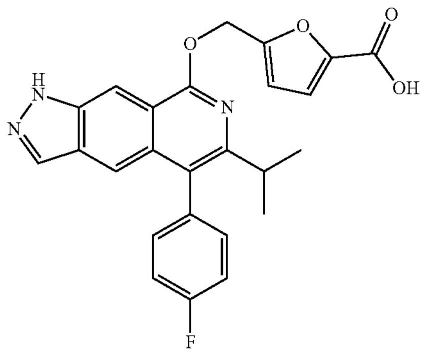 [SMILES: CC(C)c1nc(OCc2ccc(C(=O)O)o2)c2cc3[nH]ncc3cc2c1-c1ccc(F)cc1] | 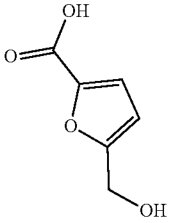 | $^1$H NMR (300 MHz, Methanol-$d_4$) δ 8.45 (t, J = 1.1 Hz, 1H), 8.11 (d, J = 1.1 Hz, 1H), 7.62 (d, J = 1.1 Hz, 1H), 7.35-7.17 (m, 5H), 6.69 (d, J = 3.4 Hz, 1H), 5.74 (s, 2H), 2.88 (h, J = 6.8 Hz, 1H), 1.23 (d, J = 6.7 Hz, 6H). LCMS m/z 446.44 [M + H]$^+$ |
| 96 | 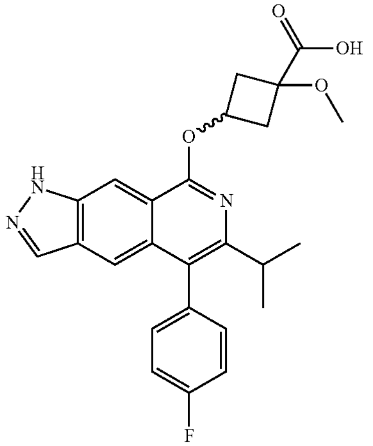 [SMILES: COC1(C(=O)O)CC(Oc2nc(C(C)C)c(-c3ccc(F)cc3)c3cc4cn[nH]c4cc23)C1] | 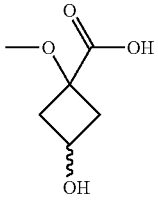 | $^1$H NMR (300 MHz, Chloroform-d + Methanol-$d_4$) δ 8.42 (t, J = 1.1 Hz, 1H), 8.11 (d, J = 1.1 Hz, 1H), 7.61 (d, J = 1.1 Hz, 1H), 7.36-7.08 (m, 4H), 5.68 (p, J = 7.1 Hz, 1H), 3.43 (s, 3H), 3.10-2.67 (m, 5H), 1.19 (d, J = 6.7 Hz, 6H) ppm. LCMS m/z 450.01 [M + H]$^+$ |

TABLE 7-continued

| Method of preparation, structure and physicochemical data for compounds 93-103 | | | |
|---|---|---|---|
| Compound | Product | Reagent | $^1$H NMR; LCMS m/z [M + H]$^+$ |
| 97 | 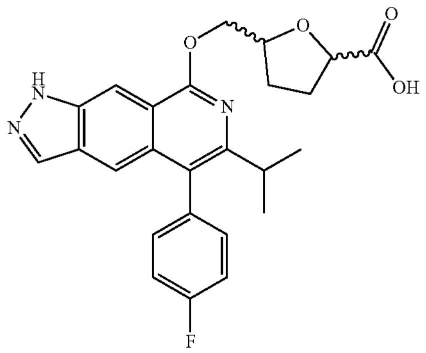 [SMILES: CC(C)c1nc(OCC2CCC(C(=O)O)O2)c2cc3[nH]ncc3cc2c1-c1ccc(F)cc1] | 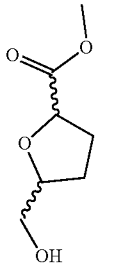 | $^1$H NMR (300 MHz, Methanol-$d_4$) δ 8.50 (s, 1H), 8.11 (d, J = 1.1 Hz, 1H), 7.60 (d, J = 1.1 Hz, 1H), 7.36-7.13 (m, 4H), 4.96-4.75 (m, 2H), 4.73-4.56 (m, 2H), 2.87 (p, J = 6.6 Hz, 1H), 2.49-2.02 (m, 4H), 1.20 (dd, J = 6.7, 1.3 Hz, 6H) ppm. LCMS m/z 450.14 [M + H]$^+$ |
| 98 | 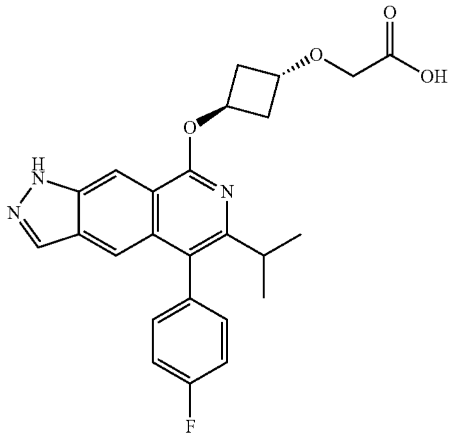 [SMILES: CC(C)c1nc(O[C@H]2C[C@H](OCC(=O)O)C2)c2cc3[nH]ncc3cc2c1-c1ccc(F)cc1] | 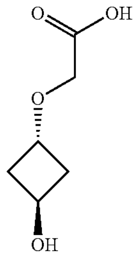 | $^1$H NMR (400 MHz, Methanol-$d_4$) δ 8.41 (q, J = 1.4 Hz, 1H), 8.21-8.11 (m, 1H), 7.62 (d, J = 1.1 Hz, 1H), 7.42-7.21 (m, 4H), 5.68 (s, 1H), 4.46 (ddd, J = 7.0, 4.2, 2.8 Hz, 1H), 4.07 (s, 2H), 2.78-2.48 (m, 3H), 1.20 (d, J = 6.7 Hz, 6H), 0.97-0.81 (m, 2H). LCMS m/z 450.0 [M + H]$^+$ |
| 99* | 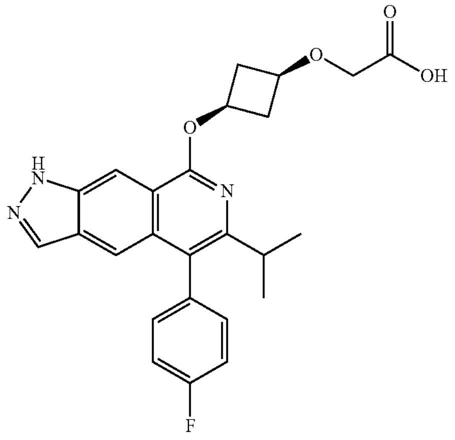 [SMILES: CC(C)c1nc(O[C@H]2C[C@@H](OCC(=O)O)C2)c2cc3[nH]ncc3cc2c1-c1ccc(F)cc1] | 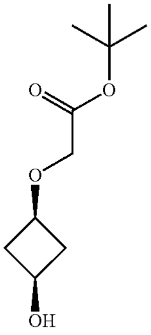 | $^1$H NMR (400 MHz, Chloroform-$d_4$) δ 8.66 (t, J = 1.1 Hz, 1H), 8.20 (d, J = 0.9 Hz, 1H), 8.09-7.82 (m, 2H), 7.52 (dd, J = 8.3, 7.4 Hz, 1H), 7.35-7.16 (m, 4H), 5.95 (dd, J = 9.4, 2.6 Hz, 1H), 4.10 (d, J = 11.7 Hz, 1H), 4.01 (s, 2H), 3.93-3.82 (m, 3H), 3.33-3.20 (m, 2H), 2.67 (tt, J = 11.5, 3.4 Hz, 2H), 2.32-2.05 (m, 2H), 1.46-1.30 (m, 2H). LCMS m/z 450.0 [M + H]$^+$ |

TABLE 7-continued

| Method of preparation, structure and physicochemical data for compounds 93-103 | | | |
|---|---|---|---|
| Compound | Product | Reagent | $^1$H NMR; LCMS m/z [M + H]$^+$ |
| 100 | 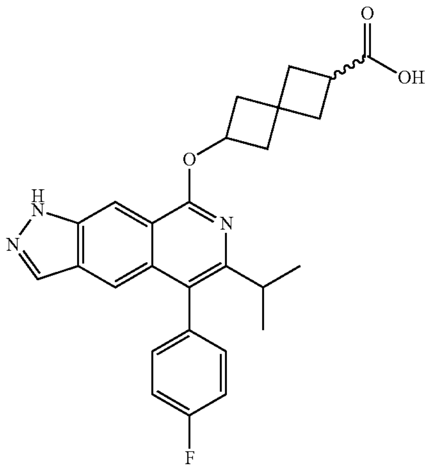 [SMILES: CC(C)c1nc(OC2CC3(C2)CC(C(=O)O)C3)c2cc3[nH]ncc3cc2c1-c1ccc(F)cc1] | 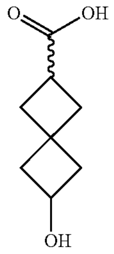 [SMILES: O=C(O)C1CC2(CC(O)C2)C1] | $^1$H NMR (300 MHz, Chloroform-d + Methanol-$d_4$) δ 8.39 (t, J = 1.1 Hz, 1H), 8.10 (d, J = 1.1 Hz, 1H), 7.60 (d, J = 1.1 Hz, 1H), 7.32-7.11 (m, 4H), 5.42 (p, J = 7.2 Hz, 1H), 3.11 (q, J = 8.5 Hz, 1H), 2.85 (p, J = 5.9 Hz, 2H), 2.70 (dt, J = 12.0, 6.0 Hz, 1H), 2.53-2.22 (m, 6H), 1.19 (dd, J = 6.7, 1.7 Hz, 6H). ppm LCMS m/z 460.48 [M + H]$^+$ |
| 101** | 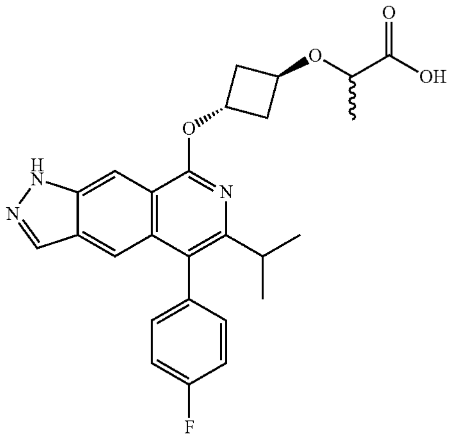 [SMILES: CC(O[C@H]1C[C@H](Oc2nc(C(C)C)c(-c3ccc(F)cc3)c3cc4cn[nH]c4cc23)C1)C(=O)O] | 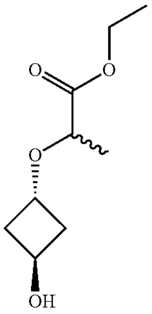 | 1H NMR (400 MHz, Methanol-$d_4$) δ 8.41 (t, J = 1.1 Hz, 1H), 8.15 (d, J = 1.1 Hz, 1H), 7.61 (d, J = 1.1 Hz, 1H), 7.40-7.15 (m, 4H), 5.66 (ddd, J = 7.1, 4.6, 2.6 Hz, 1H), 4.47 (tt, J = 6.9, 4.6 Hz, 1H), 4.03 (t, J = 6.9 Hz, 1H), 2.93-2.43 (m, 5H), 1.43 (d, J = 6.9 Hz, 3H), 1.36-1.13 (m, 8H). LCMS m/z 464.0 [M + H]$^+$ |

*Tert-butyl ester was removed under the reaction conditions.
**Ethyl ester was removed under the reaction conditions.

Compound 102 and Compound 103
2-[2-[[5-(4-fluorophenyl)-6-isopropyl-1H-pyrazolo[4,3-g]isoquinolin-8-yl]oxy]-6-azaspiro[3.4]octan-6-yl]acetic acid [isomer-1] (102) and 2-[2-[[5-(4-fluorophenyl)-6-isopropyl-1H-pyrazolo[4,3-g]isoquinolin-8-y]oxy]-6-azaspiro[3.4]octan-6-yl]acetic acid [isomer-2] (103)
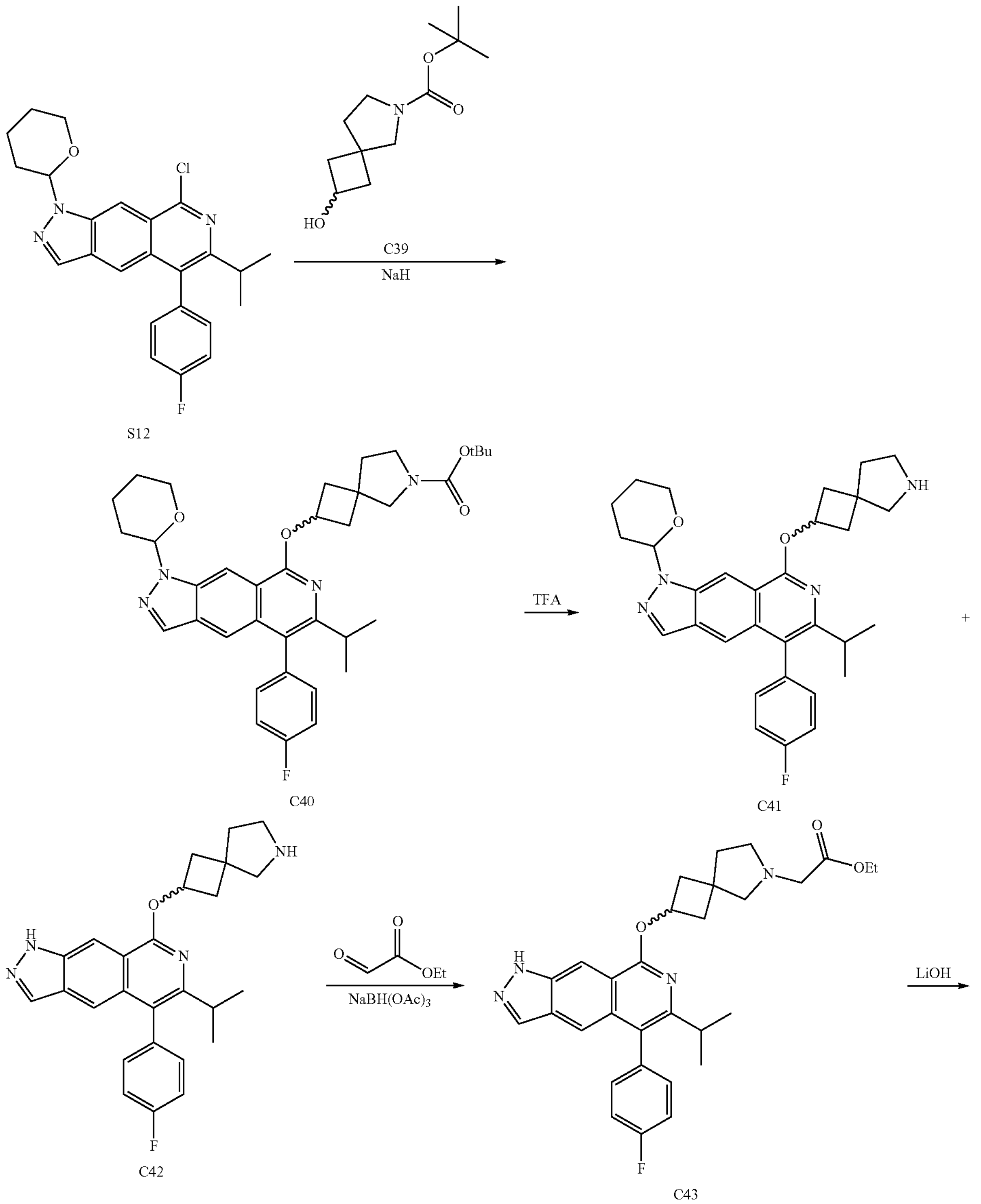

-continued

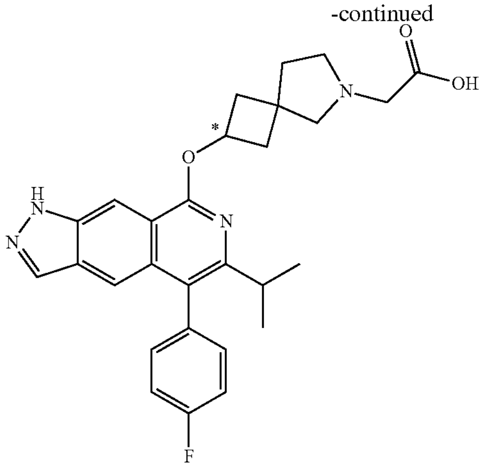

102

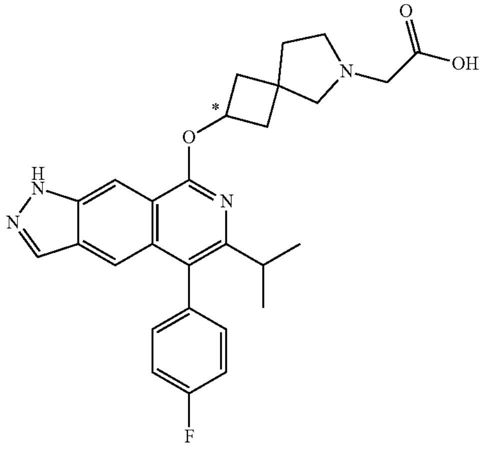

103

Steps 1 & 2

A mixture of compounds C41 and C42 were prepared in two steps from S11 and C39 using the method described for the preparation of compound C32. Compound C43 was prepared from the mixture of C41 and C42 by reductive amination with ethyl 2-oxoacetate.

Step 3. Synthesis of ethyl 2-[2-[[5-(4-fluorophenyl)-6-isopropyl-1H-pyrazolo[4,3-g]isoquinolin-8-yl]oxy]-6-azaspiro[3.4]octan-6-yl]acetate (C43)

To a solution of 8-(6-azaspiro[3.4]octan-2-yloxy)-5-(4-fluorophenyl)-6-isopropyl-1-tetrahydropyran-2-yl-pyrazolo[4,3-g]isoquinoline (67 mg, 0.1302 mmol), 8-(6-azaspiro[3.4]octan-2-yloxy)-5-(4-fluorophenyl)-6-isopropyl-1H-pyrazolo[4,3-g]isoquinoline (50 mg, 0.1161 mmol), ethyl 2-oxoacetate (155 mg of 50% w/w, 0.7591 mmol) and acetic acid (8 μL, 0.1407 mmol) in dichloromethane (10 mL) was added sodium triacetoxyborohydride (275 mg, 1.298 mmol). The mixture was stirred for 18 hours then diluted with dichloromethane and slowly quenched with MeOH and sat. $NaHCO_3$ (50 mL). After separation, the organic layer was washed with water, sat. NaCl and dried. The excess solvent was pumped down. Purification by silica gel chromatography (Gradient: 0-100% EtOAc in heptane) afforded C43 and the THP protected analog. Compound C43 was the first eluting product. ethyl 2-[2-[[5-(4-fluorophenyl)-6-isopropyl-1H-pyrazolo[4,3-g]isoquinolin-8-yl]oxy]-6-azaspiro[3.4]octan-6-yl]acetate (30 mg, 45%). LCMS m/z 517.5 $[M+H]^+$. Ethyl 2-[2-[5-(4-fluorophenyl)-6-isopropyl-1-tetrahydropyran-2-yl-pyrazolo[4,3-g]isoquinolin-8-yl]oxy-6-azaspiro[3.4]octan-6-yl]acetate (43 mg, 55%). LCMS m/z 601.61 $[M+H]^+$.

Step 4. Preparation of 2-[2-[[5-(4-fluorophenyl)-6-isopropyl-1H-pyrazolo[4,3-g]isoquinolin-8-yl]oxy]-6-azaspiro[3.4]octan-6-yl]acetic acid [isomer-1] (102) and 2-[2-[[5-(4-fluorophenyl)-6-isopropyl-1H-pyrazolo[4,3-g]isoquinolin-8-yl]oxy]-6-azaspiro[3.4]octan-6-yl]acetic acid [isomer-2] (103)

A mixture of ethyl 2-[2-[[5-(4-fluorophenyl)-6-isopropyl-1H-pyrazolo[4,3-g]isoquinolin-8-yl]oxy]-6-azaspiro[3.4]octan-6-yl]acetate C43 (30 mg, 0.05807 mmol) and LiOH (25 mg, 0.5957 mmol) in water (1 mL) and THF (1 mL) was stirred at room temperature for 3 h. The reaction mixture was treated with 1 M HCl until pH=7 was reached. The excess solvent was removed. Purification by reverse-phase HPLC. Method: C18 Waters Sunfire column (30×150 mm, 5 micron). Gradient: MeCN in $H_2O$ with 0.1% trifluoroacetic acid afforded the two isomers compound 102 and compound 103.

Compound 102. $^1H$ NMR (300 MHz, Chloroform-d+Methanol-$d_4$) δ 7.52 (s, 1H), 7.48-7.45 (m, 1H), 7.35 (s, 1H), 7.20 (d, J=7.1 Hz, 4H), 5.46 (t, J=6.9 Hz, 1H), 4.23 (d, J=2.1 Hz, 2H), 4.08 (s, 2H), 3.32 (s, 2H), 2.90-2.71 (m, 3H), 2.56-2.33 (m, 4H), 1.13 (d, J=6.7 Hz, 6H) ppm. LCMS m/z 489.36 $[M+H]^+$.

Compound 103. $^1H$ NMR (300 MHz, Chloroform-d+Methanol-$d_4$) δ 8.40 (d, J=1.1 Hz, 1H), 8.12 (d, J=1.1 Hz, 1H), 7.62 (d, J=1.1 Hz, 1H), 7.25 (dtd, J=11.1, 8.6, 5.9 Hz, 4H), 5.50 (p, J=6.9 Hz, 1H), 4.05 (s, 2H), 3.70 (d, J=14.4 Hz, 4H), 3.10-2.77 (m, 3H), 2.54 (dd, J=13.2, 6.5 Hz, 2H), 2.38 (t, J=7.2 Hz, 2H), 1.18 (d, J=6.7 Hz, 6H) ppm. LCMS m/z 489.36 $[M+H]^+$.

Compound 104

2-[2-[[5-(4-fluorophenyl)-6-isopropyl-1H-pyrazolo[4,3-g]isoquinolin-8-yl]oxy]-5-oxo-6-azaspiro[3.4]octan-6-yl]propanoic acid (104)

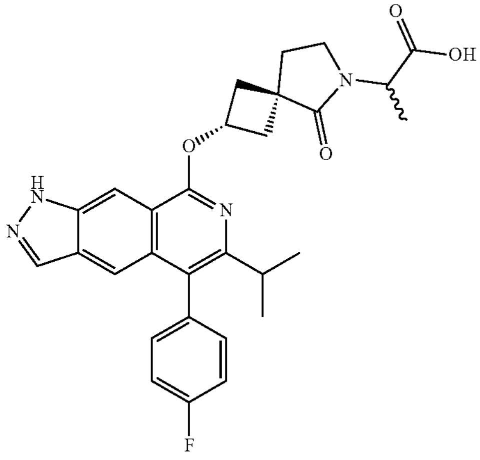 [SMILES: CC(C)c1nc(O[C@H]2C[C@@]3(CCN(C(C)C(=O)O)C3=O)C2)c2cc3[nH]ncc3cc2c1-c1ccc(F)cc1]

Compound 104 was prepared from S11 and sodium 2-(2-hydroxy-5-oxo-6-azaspiro[3.4]octan-6-yl)propanoate as described for compounds 93-103. LCMS m/z 517.28 $[M+H]^+$.

Compounds 105-128

Compounds 105-107 and 120-121 (Table 8) were prepared from S12 using the method described for compound 43. Compounds 108-119 were prepared by Suzuki or Negishi coupling onto S12 and ester deprotection as appropriate. Any modifications are noted in the Table footnotes.

TABLE 8

Method of preparation, structure and physicochemical data for compounds 105-128

| Compound | Product | Reagent | $^1H$ NMR; LCMS m/z $[M + H]^+$ |
|---|---|---|---|
| 105 | 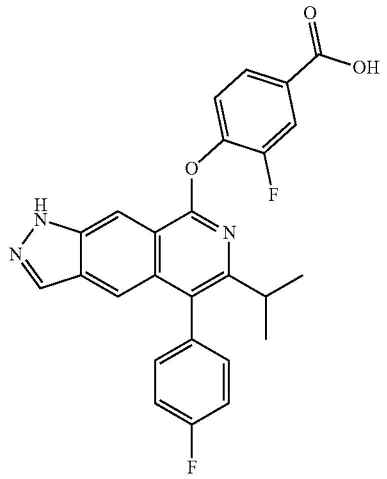 [SMILES: CC(C)c1nc(Oc2ccc(C(=O)O)cc2F)c2cc3[nH]ncc3cc2c1-c1ccc(F)cc1] | 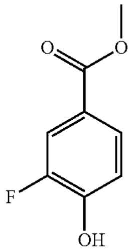 | $^1H$ NMR (300 MHz, Chloroform-d + Methanol-$d_4$) δ 8.62 (t, J = 1.2 Hz, 1H), 8.18 (d, J = 1.1 Hz, 1H), 8.05-7.85 (m, 2H), 7.72 (d, J = 1.1 Hz, 1H), 7.54 (dd, J = 8.3, 7.4 Hz, 1H), 7.38-7.09 (m, 4H), 2.80 (p, J = 6.6 Hz, 1H), 0.98 (d, J = 6.7 Hz, 6H) ppm. LCMS m/z 460.31 $[M + H]^+$ |
| 106 | 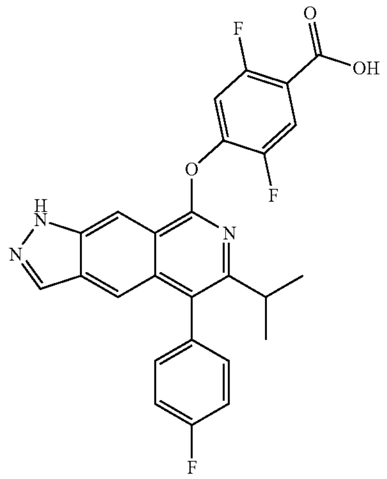 [SMILES: CC(C)c1nc(Oc2cc(F)c(C(=O)O)cc2F)c2cc3[nH]ncc3cc2c1-c1ccc(F)cc1] | 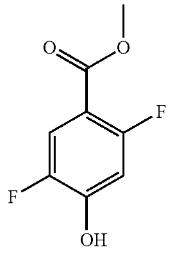 | $^1H$ NMR (300 MHz, Chloroform-d + Methanol-$d_4$) δ 8.59 (q, J = 1.7, 1.1 Hz, 1H), 8.19 (d, J = 1.3 Hz, 1H), 7.87 (dd, J = 10.4, 6.6 Hz, 1H), 7.74 (d, J = 1.3 Hz, 1H), 7.44-7.13 (m, 5H), 2.83 (p, J = 6.6 Hz, 1H), 1.03 (d, J = 6.7 Hz, 6H) ppm. LCMS m/z 478.12 $[M + H]^+$ |

TABLE 8-continued

Method of preparation, structure and physicochemical data for compounds 105-128

| Compound | Product | Reagent | $^1$H NMR; LCMS m/z [M + H]$^+$ |
|---|---|---|---|
| 107 | 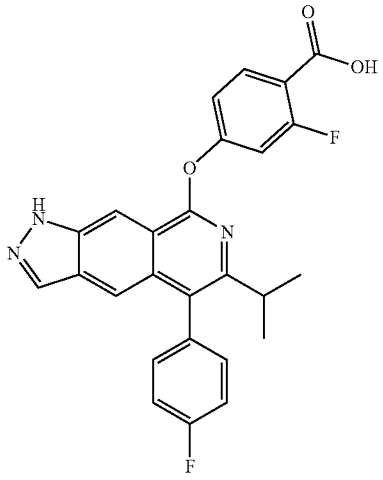 | 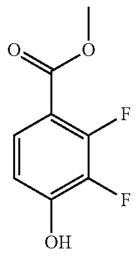 | $^1$H NMR (300 MHz, Chloroform-d + Methanol-$d_4$) δ 8.59 (t, J = 1.1 Hz, 1H), 8.18 (d, J = 1.1 Hz, 1H), 7.87 (ddd, J = 8.9, 7.4, 2.3 Hz, 1H), 7.73 (d, J = 1.1 Hz, 1H), 7.37-7.14 (m, 5H), 2.81 (p, J = 6.7 Hz, 1H), 1.00 (d, J = 6.7 Hz, 6H) ppm. LCMS m/z 478.09 [M + H]$^+$ |
| 108 | 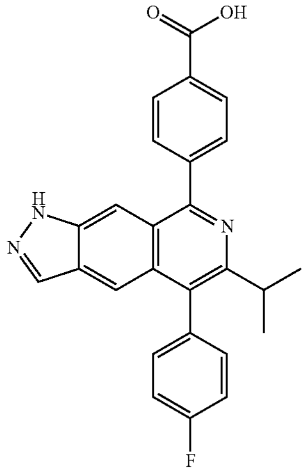 [SMILES: CC(C)c1nc(-c2ccc(C(=O)O)cc2)c2cc3[nH]ncc3cc2c1-c1ccc(F)cc1] | 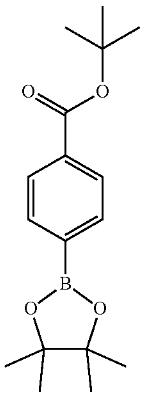 | $^1$H NMR (300 MHz, DMSO-$d_6$) δ 13.30 (s, 1H), 8.41 (d, J = 1.1 Hz, 1H), 8.27-8.17 (m, 2H), 8.15 (t, J = 1.1 Hz, 1H), 8.01-7.90 (m, 2H), 7.82 (d, J = 1.1 Hz, 1H), 7.55-7.40 (m, 4H), 2.97 (p, J = 6.7 Hz, 1H), 1.25 (d, J = 6.8 Hz, 6H) ppm. LCMS m/z 426.51 [M + H]$^+$ |
| 109 | 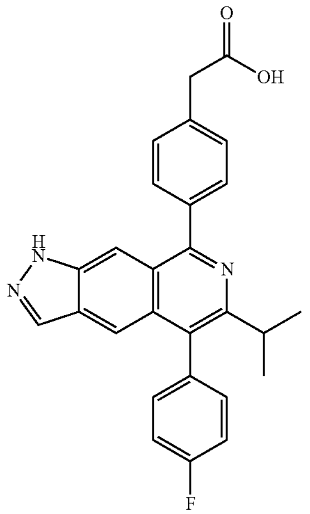 [SMILES: CC(C)c1nc(-c2ccc(CC(=O)O)cc2)c2cc3[nH]ncc3cc2c1-c1ccc(F)cc1] | 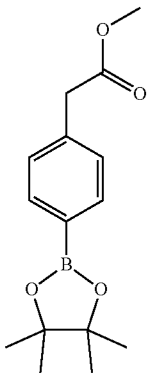 | $^1$H NMR (400 MHz, Chloroform-d + Methanol-$d_4$) δ 8.35 (dd, J = 2.9, 1.1 Hz, 2H), 8.00 (d, J = 1.1 Hz, 1H), 7.84-7.74 (m, 2H), 7.72-7.61 (m, 2H), 7.46-7.31 (m, 4H), 3.88 (s, 2H), 3.24 (p, J = 7.1 Hz, 1H), 1.39 (d, J = 7.0 Hz, 6H) ppm. LCMS m/z 440.17 [M + H]$^+$ |

TABLE 8-continued

Method of preparation, structure and physicochemical data for compounds 105-128

| Compound | Product | Reagent | $^1$H NMR; LCMS m/z [M + H]$^+$ |
|---|---|---|---|
| 110 | 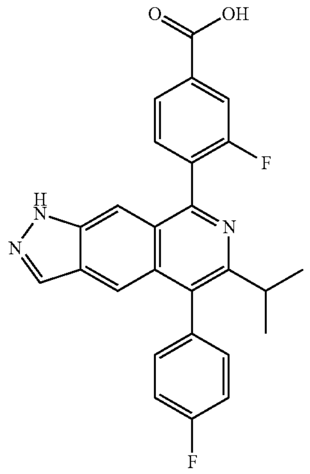 | 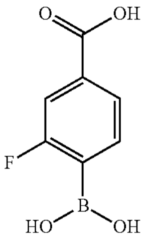 | $^1$H NMR (400 MHz, Chloroform-d Methanol-$d_4$) δ 8.29 (d, J = 1.1 Hz, 1H), 8.16 (dd, J = 7.9, 1.5 Hz, 1H), 8.11-8.00 (m, 2H), 7.95 (d, J = 1.1 Hz, 1H), 7.82 (dd, J = 7.9, 6.8 Hz, 1H), 7.43 (d, J = 8.2 Hz, 1H), 7.40 (s, 1H), 7.35 (t, J = 8.7 Hz, 2H), 3.17 (p, J = 6.9 Hz, 1H), 1.36 (d, J = 6.9 Hz, 6H) ppm. LCMS m/z 444.12 [M + H]$^+$ |
| 111 | 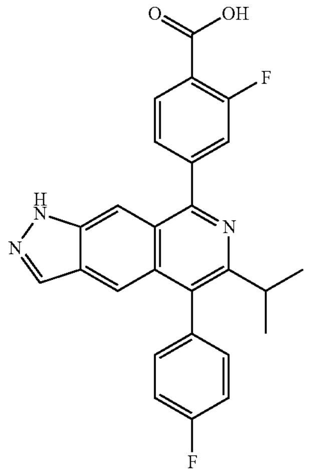 | 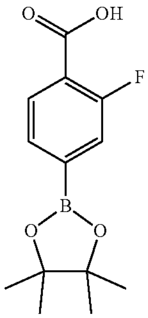 | $^1$H NMR (300 MHz, DMSO-$d_6$) δ 13.28 (s, 1H), 8.40 (d, J = 1.1 Hz, 1H), 8.21-8.03 (m, 2H), 7.88-7.69 (m, 3H), 7.47 (d, J = 8.3 Hz, 4H), 2.96 (p, J = 6.7 Hz, 1H), 1.23 (d, J = 6.7 Hz, 6H) ppm. LCMS m/z 444.46 [M + H]$^+$ |
| 112 | 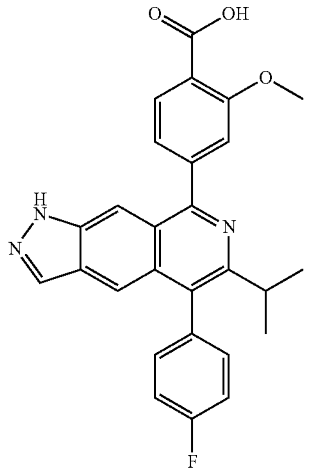 [SMILES: COc1cc(-c2nc(C(C)C)c(-c3ccc(F)cc3)c3cc4cn[nH]c4cc23)ccc1C(=O)O] | 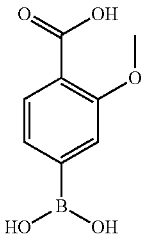 | $^1$H NMR (300 MHz, Chloroform-d + Methanol-$d_4$) δ 7.19 (d, J = 7.1 Hz, 3H), 6.86 (s, 1H), 6.51 (d, J = 6.0 Hz, 2H), 6.44-6.17 (m, 4H), 3.08 (d, J = 4.2 Hz, 3H), 2.10 (dd, J = 13.8, 7.2 Hz, 1H), 0.31 (d, J = 6.6 Hz, 6H) ppm. LCMS m/z 456.04 [M + H]$^+$ |

TABLE 8-continued

Method of preparation, structure and physicochemical data for compounds 105-128

| Compound | Product | Reagent | $^1$H NMR; LCMS m/z [M + H]$^+$ |
|---|---|---|---|
| 113 | 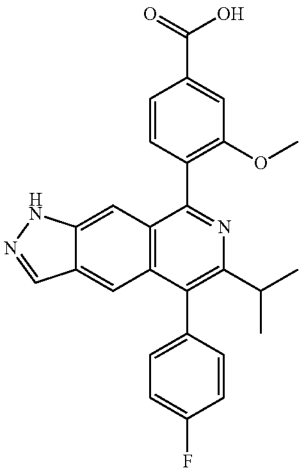 | 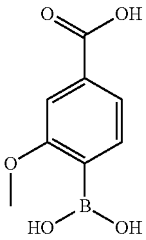 | $^1$H NMR (300 MHz, Chloroform-d + Methanol-$d_4$) δ 8.35 (s, 1H), 8.16 (s, 1H), 8.07-7.88 (m, 3H), 7.68 (d, J = 7.7 Hz, 1H), 7.55-7.41 (m, 2H), 7.38 (d, J = 8.7 Hz, 2H), 3.91 (s, 3H), 3.25 (p, J = 6.9 Hz, 1H), 1.41 (d, J = 7.1 Hz, 6H) ppm. LCMS m/z 456.17 [M + H]$^+$ |
| 114 | 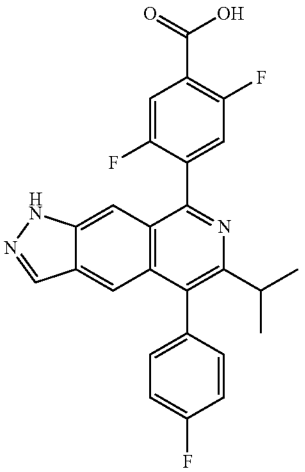 | 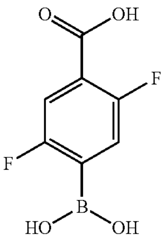 [SMILES: O=C(O)c1cc(F)c(B(O)O)cc1F] | $^1$H NMR (300 MHz, Chloroform-d + Methanol-$d_4$) δ 8.20 (d, J = 1.1 Hz, 1H), 7.97-7.80 (m, 3H), 7.51 (d, J = 5.4 Hz, 1H), 7.44-7.23 (m, 4H), 3.06 (p, J = 6.8 Hz, 1H), 1.28 (d, J = 6.8 Hz, 6H) ppm. LCMS m/z 462.06 [M + H]$^+$ |
| 115 | 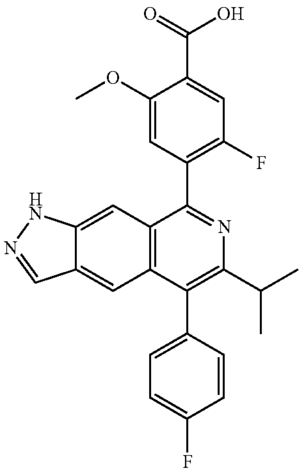 [SMILES: COc1cc(-c2nc(C(C)C)c(-c3ccc(F)cc3)c3cc4cn[nH]c4cc23)c(F)cc1C(=O)O] | 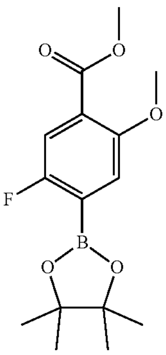 | 1H NMR (300 MHz, Chloroform-d + Methanol-$d_4$) δ 8.30-8.13 (m, 1H), 8.06-7.68 (m, 3H), 7.43-7.27 (m, 5H), 4.14-3.89 (m, 3H), 3.10 (p, J = 7.0 Hz, 1H), 1.50-1.05 (m, 6H) ppm. LCMS m/z 474.15 [M + H]$^+$ |

TABLE 8-continued

Method of preparation, structure and physicochemical data for compounds 105-128

| Compound | Product | Reagent | $^1$H NMR; LCMS m/z [M + H]$^+$ |
| --- | --- | --- | --- |
| 116 | 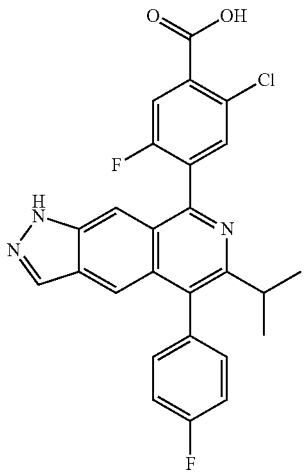 | 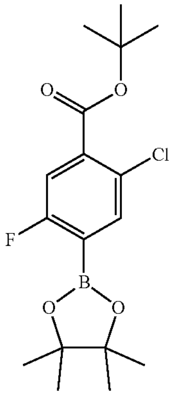 | $^1$H NMR (300 MHz, Chloroform-d Methanol-$d_4$) δ 8.20 (d, J = 1.1 Hz, 1H), 7.95-7.81 (m, 3H), 7.77 (d, J = 6.1 Hz, 1H), 7.44-7.21 (m, 4H), 3.06 (p, J = 6.8 Hz, 1H), 1.28 (d, J = 6.8 Hz, 6H) ppm. LCMS m/z 478.09 [M + H]$^+$ |
| 117* | 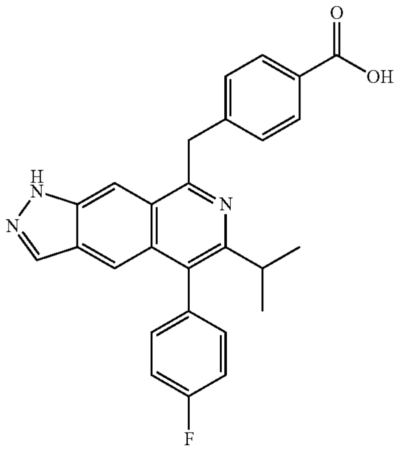 [SMILES: CC(C)c1nc(Cc2ccc(C(=O)O)cc2)c2cc3[nH]ncc3cc2c1-c1ccc(F)cc1] | 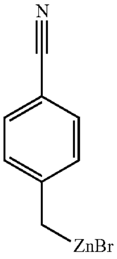 | $^1$H NMR (300 MHz, Chloroform-d + Methanol-$d_4$) δ 8.83 (s, 1H), 8.33 (d, J = 1.0 Hz, 1H), 8.08-7.93 (m, 3H), 7.61-7.48 (m, 2H), 7.38 (d, J = 6.9 Hz, 4H), 5.55 (s, 2H), 3.28 (p, J = 7.2 Hz, 1H), 1.56 (d, J = 7.1 Hz, 6H) ppm. LCMS m/z 440.17 [M + H]$^+$ |
| 118 | 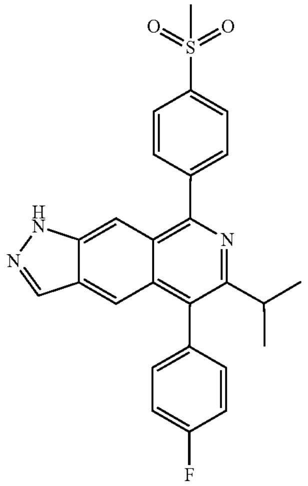 [SMILES: CC(C)c1nc(-c2ccc(S(C)(=O)=O)cc2)c2cc3[nH]ncc3cc2c1-c1ccc(F)cc1] | 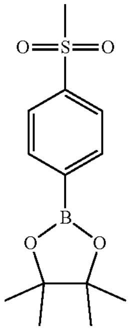 | $^1$H NMR (300 MHz, Chloroform-d) δ 10.22 (s, 1H), 8.32-8.11 (m, 4H), 8.06 (d, J = 8.0 Hz, 2H), 7.88 (d, J = 1.0 Hz, 1H), 7.47-7.29 (m, 4H), 3.20 (s, 3H), 3.09 (p, J = 6.7 Hz, 1H), 1.32 (d, J = 6.7 Hz, 6H) ppm. LCMS m/z 460.11 [M + H]$^+$ |

TABLE 8-continued

Method of preparation, structure and physicochemical data for compounds 105-128

| Compound | Product | Reagent | $^1$H NMR; LCMS m/z $[M + H]^+$ |
|---|---|---|---|
| 119 | 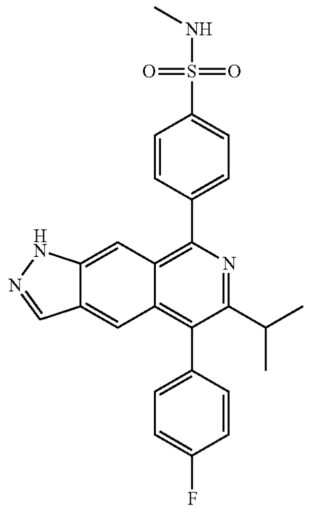 [SMILES: CNS(=O)(=O)c1ccc(-c2nc(C(C)C)c(-c3ccc(F)cc3)c3cc4cn[nH]c4cc23)cc1] | 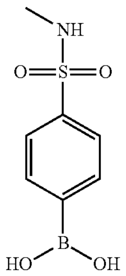 | $^1$H NMR (300 MHz, DMSO-$d_6$) δ 13.26 (s, 1H), 8.40 (d, J = 1.1 Hz, 1H), 8.09 (d, J = 21.0 Hz, 5H), 7.87-7.66 (m, 2H), 7.61-7.26 (m, 4H), 2.97 (p, J = 6.7 Hz, 1H), 2.57 (d, J = 4.5 Hz, 3H), 1.24 (d, J = 6.7 Hz, 6H) ppm. LCMS m/z 475.15 $[M + H]^+$ |
| 120 | 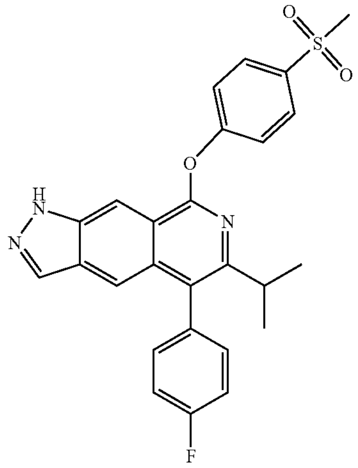 [SMILES: CC(C)c1nc(Oc2ccc(S(C)(=O)=O)cc2)c2cc3[nH]ncc3cc2c1-c1ccc(F)cc1] | 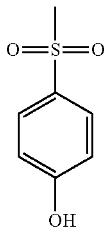 | $^1$H NMR (300 MHz, Chloroform-d + Methanol-$d_4$) 6 8.57 (t, J = 1.1 Hz, 1H), 8.19 (d, J = 1.1 Hz, 1H), 8.12-7.98 (m, 2H), 7.82-7.56 (m, 3H), 7.39-7.14 (m, 4H), 3.19(s, 3H), 2.87 (p, J = 6.7 Hz, 1H), 1.06 (d, J = 6.7 Hz, 6H) ppm. LCMS m/z 476.14 $[M + H]^+$ |
| 121 | 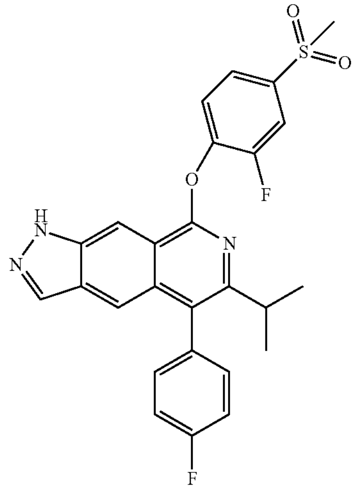 [SMILES: CC(C)c1nc(Oc2ccc(S(C)(=O)=O)cc2F)c2cc3[nH]ncc3cc2c1-c1ccc(F)cc1] | 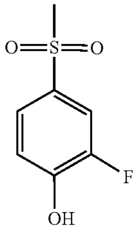 | 1H NMR (300 MHz, Methanol-$d_4$) δ 8.59 (t, J = 1.1 Hz, 1H), 8.19 (d, J = 1.1 Hz, 1H), 7.95-7.80 (m, 2H), 7.79-7.65 (m, 2H), 7.35-7.16 (m, 4H), 3.19 (s, 3H), 2.82 (p, J = 6.7 Hz, 1H), 0.99 (d, J = 6.7 Hz, 6H). LCMS m/z 494.12 $[M + H]^+$ |

TABLE 8-continued

| Method of preparation, structure and physicochemical data for compounds 105-128 | | | |
|---|---|---|---|
| Compound | Product | Reagent | $^{1}$H NMR; LCMS m/z $[M + H]^+$ |
| 122** | 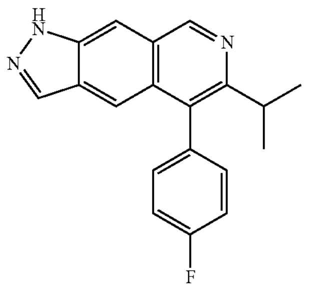 [SMILES: CC(C)c1ncc2cc3[nH]ncc3cc2c1-c1ccc(F)cc1] | | $^{1}$H NMR (300 MHz, Methanol-$d_4$) δ 9.91 (s, 1H), 8.74 (s, 1H), 8.37 (s, 1H), 7.98 (s, 1H), 7.38 (d, J = 6.9 Hz, 4H), 3.20 (p, J = 6.9 Hz, 1H), 1.44 (d, J = 7.0 Hz, 6H) ppm. LCMS m/z 305.99 $[M + H]^+$ |

*Compound 117 was prepared by Negishi coupling as described for compound 90. The nitrile group was converted to the carboxylic acid by hydrolysis with NaOH in EtOH at 110 °C. under microwave conditions.
**Compound 122 was obtained as a by-product in the preparation of compound 112.

Compound 123 and Compound 124

2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid (Hydrochloride Salt) (123)

and

2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid (Hydrochloride Salt) (124)

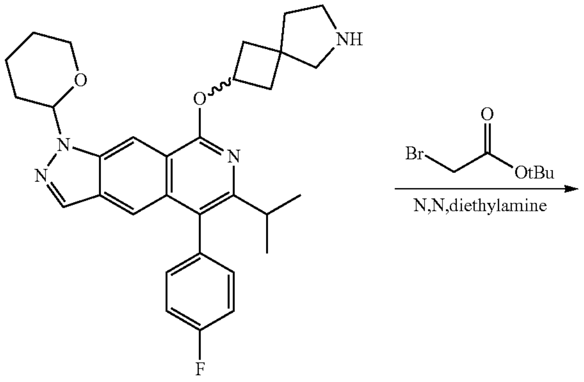

C41

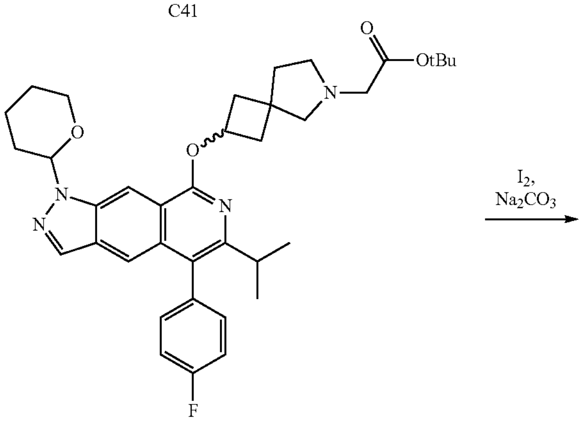

C44

-continued

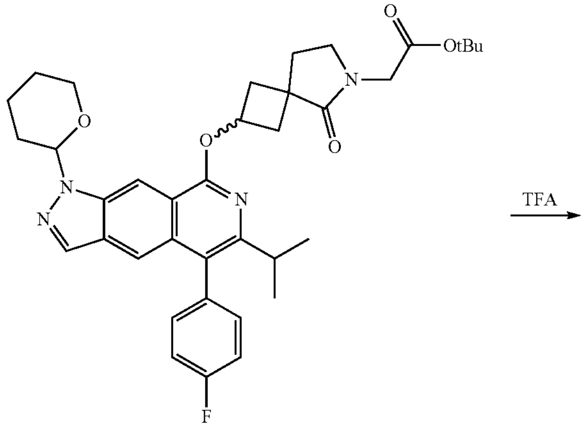

C45

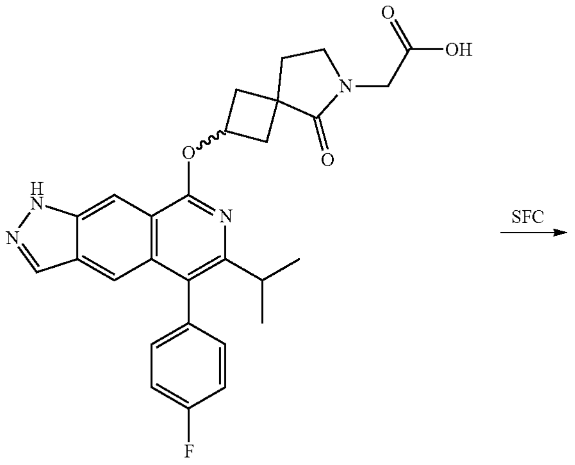

C46

-continued

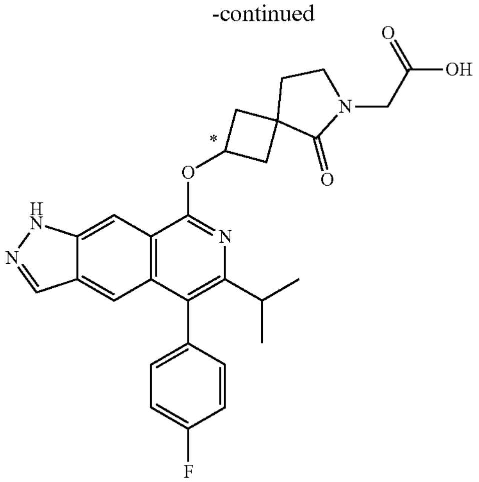

123

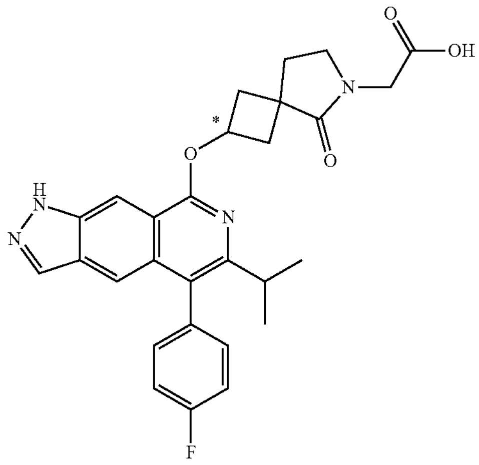

124

Step 1. Synthesis of tert-butyl 2-[2-[5-(4-fluorophenyl)-6-isopropyl-1-tetrahydropyran-2-yl-pyrazolo[4,3-g]isoquinolin-8-yl]oxy-6-azaspiro[3.4]octan-6-yl]acetate (C44)

To a solution of 8-(6-azaspiro[3.4]octan-2-yloxy)-5-(4-fluorophenyl)-6-isopropyl-1-tetrahydropyran-2-yl-pyrazolo[4,3-g]isoquinoline (200 mg, 0.3886 mmol), tert-butyl 2-bromoacetate (86 mg, 0.4409 mmol) in dichloromethane (4 mL) was added N,N-diethylethanamine (62 μL, 0.4448 mmol). DMSO (2 mL) was added to the reaction mixture and the resultant mixture was stirred at room temperature for 18 hours. The excess solvent was removed. Silica gel chromatography (Gradient: 0-20% MeOH in dichloromethane) afforded the product. Tert-butyl 2-[2-[5-(4-fluorophenyl)-6-isopropyl-1-tetrahydropyran-2-yl-pyrazolo[4,3-g]isoquinolin-8-yl]oxy-6-azaspiro[3.4]octan-6-yl]acetate (138 mg, 56%). LCMS m/z 629.4 $[M+H]^+$. The THP deprotected product was also observed. Tert-butyl 2-[2-[[5-(4-fluorophenyl)-6-isopropyl-1H-pyrazolo[4,3-g]isoquinolin-8-yl]oxy]-6-azaspiro[3.4]octan-6-yl]acetate (20 mg, 9%). LCMS m/z 545.23 $[M+1]^+$.

Step 2. Synthesis of tert-butyl 2-[2-[5-(4-fluorophenyl)-6-isopropyl-1-tetrahydropyran-2-yl-pyrazolo[4,3-g]isoquinolin-8-yl]oxy-5-oxo-6-azaspiro[3.4]octan-6-yl]acetate (C45)

To a mixture of tert-butyl 2-[2-[5-(4-fluorophenyl)-6-isopropyl-1-tetrahydropyran-2-yl-pyrazolo[4,3-g]isoquinolin-8-yl]oxy-6-azaspiro[3.4]octan-6-yl]acetate C44 (138 mg, 0.2195 mmol) and ethyl 2-[2-[5-(4-fluorophenyl)-6-isopropyl-1-tetrahydropyran-2-yl-pyrazolo[4,3-g]isoquinolin-8-yl]oxy-6-azaspiro[3.4]octan-6-yl]acetate (C47) (132 mg, 0.2197 mmol) in THF (10 mL) was added $NaHCO_3$ (19 mg, 0.2262 mmol) molecular iodine (450 mg, 1.773 mmol). The reaction mixture was stirred for 3 hours. The reaction was quenched with sat. $NaHCO_3$ (1 mL), and sodium thiosulfate (10 mL). Silica gel chromatography (Gradient: 0-20% MeOH in dichloromethane) and then (Gradient: 10-50% EtOAc in hexane) afforded the product.

Tert-butyl 2-[2-[5-(4-fluorophenyl)-6-isopropyl-1-tetrahydropyran-2-yl-pyrazolo[4,3-g]isoquinolin-8-yl]oxy-5-oxo-6-azaspiro[3.4]octan-6-yl]acetate C45 (36 mg, 26%) LCMS m/z 643.55 $[M+H]^+$. ethyl 2-[2-[5-(4-fluorophenyl)-6-isopropyl-1-tetrahydropyran-2-yl-pyrazolo[4,3-g]isoquinolin-8-yl]oxy-5-oxo-6-azaspiro[3.4]octan-6-yl]acetate and tert-butyl 2-[2-[5-(4-fluorophenyl)-6-isopropyl-1-tetrahydropyran-2-yl-pyrazolo[4,3-g]isoquinolin-8-yl]oxy-7-oxo-6-azaspiro[3.4]octan-6-yl]acetate were also obtained. Ethyl 2-[2-[5-(4-fluorophenyl)-6-isopropyl-1-tetrahydropyran-2-yl-pyrazolo[4,3-g]isoquinolin-8-yl]oxy-5-oxo-6-azaspiro[3.4]octan-6-yl]acetate (33 mg, 24%) LCMS m/z 615.52 $[M+H]^+$. Tert-butyl 2-[2-[5-(4-fluorophenyl)-6-isopropyl-1-tetrahydropyran-2-yl-pyrazolo[4,3-g]isoquinolin-8-yl]oxy-7-oxo-6-azaspiro[3.4]octan-6-yl]acetate (10 mg, 7%) LCMS m/z 643.52 $[M+H]^+$.

Step 3. Preparation of 2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid (123) and -[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid (124)

Tert-butyl 2-[2-[5-(4-fluorophenyl)-6-isopropyl-1-tetrahydropyran-2-yl-pyrazolo[4,3-g]isoquinolin-8-yl]oxy-5-oxo-6-azaspiro[3.4]octan-6-yl]acetate C45 (36 mg, 0.05601 mmol) in dichloromethane (2 mL) was treated with TFA (1 mL, 12.98 mmol) for 1 hours. The excess solvent was removed. Purification by reverse-phase HPLC. Method: C18 Waters Sunfire column (30×150 mm, 5 micron). Gradient: MeCN in $H_2O$ with 0.2% formic acid afforded compound 123 and compound 124.

Compound 123 2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid (Hydrochloride salt) (123) (4 mg, 25%). $^1H$ NMR (300 MHz, Chloroform-d+Methanol-$d_4$) δ 8.44 (t, J=1.1 Hz, 1H), 8.12 (d, J=1.1 Hz, 1H), 7.62 (d, J=1.1 Hz, 1H), 7.42-7.08 (m, 4H), 5.70 (q, J=6.7 Hz, 1H), 4.10 (s, 2H), 3.51 (t, J=6.8 Hz, 2H), 3.20-3.02 (m, 2H), 2.85 (p, J=6.7 Hz, 1H), 2.54-2.20 (m, 4H), 1.19 (d, J=6.7 Hz, 6H). LCMS m/z 503.14 $[M+H]^+$.

Compound 124 2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid (Hydrochloride salt) (124) (3 mg, 19%). $^1H$ NMR (300 MHz, Chloroform-d+Methanol-$d_4$) δ 8.46 (t, J=1.1 Hz, 1H), 8.12 (d, J=1.1 Hz, 1H), 7.61 (d, J=1.1 Hz, 1H), 7.42-7.08 (m, 4H), 5.66 (p, J=7.7 Hz, 1H), 4.09 (s, 2H), 3.54 (t, J=6.8 Hz, 2H), 2.95-2.54 (m, 5H), 2.44 (t, J=6.8 Hz, 2H), 1.20 (d, J=6.7 Hz, 6H) ppm. LCMS m/z 503.11 $[M+H]^+$.

Compound 125 and Compound 126

2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid [ENANT-1] (125) and 2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid [ENANT-2] (126)

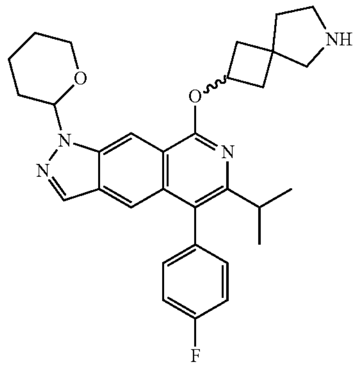

C41

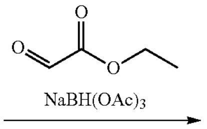

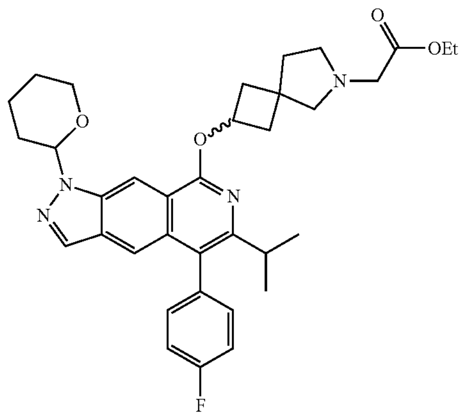

C47

$I_2$,
$Na_2CO_3$

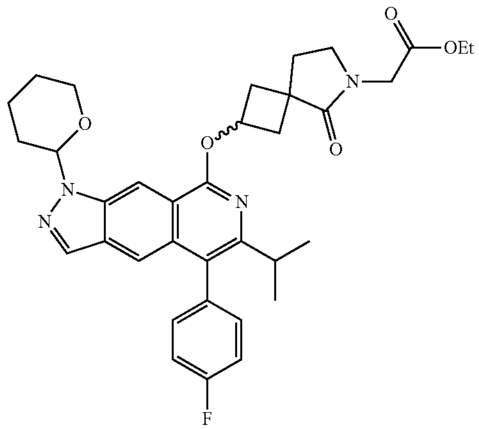

C48

1. TFA
2. SFC

-continued

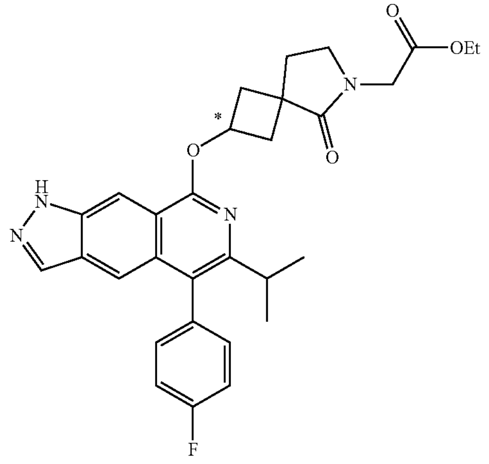

125

+

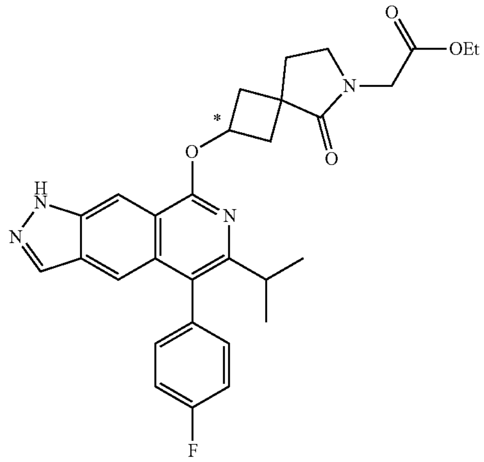

126

Compound 125 and 126 were prepared from C41 using the methods described in the preparation of C43 and compounds 123 and 124.

Compound 125: 2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid [ENANT-1] (125). $^1$H NMR (300 MHz, Chloroform-d+Methanol-$d_4$) δ 8.43 (t, J=1.1 Hz, 1H), 8.12 (d, J=1.1 Hz, 1H), 7.62 (d, J=1.1 Hz, 1H), 7.33-7.18 (m, 4H), 5.71 (p, J=6.8 Hz, 1H), 4.23 (t, J=7.2 Hz, 2H), 4.11 (s, 2H), 3.82-3.69 (m, 1H), 3.49 (t, J=6.8 Hz, 2H), 3.22-2.99 (m, 2H), 2.85 (p, J=6.6 Hz, 1H), 2.48-2.40 (m, 1H), 2.35 (t, J=6.8 Hz, 2H), 1.32 (t, J=7.1 Hz, 3H), 1.19 (d, J=6.7 Hz, 6H) ppm. LCMS m/z 530.93 $[M+H]^+$.

Compound 126: 2-[2-[[5-(4-fluorophenyl)-6-isopropyl-1H-pyrazolo[4,3-g]isoquinolin-8-yl]oxy]-5-oxo-6-azaspiro[3.4]octan-6-yl]acetic acid [ENANT-2] (126). 1H NMR (300 MHz, Chloroform-d+Methanol-$d_4$) δ 8.45 (t, J=1.1 Hz, 1H), 8.10 (d, J=1.1 Hz, 1H), 7.60 (d, J=1.1 Hz, 1H), 7.37-7.10 (m, 4H), 5.65 (p, J=7.7 Hz, 1H), 4.22 (q, J=7.1 Hz, 2H), 4.10 (s, 2H), 3.52 (t, J=6.8 Hz, 2H), 2.99-2.54 (m, 5H), 2.43 (t, J=6.8 Hz, 2H), 1.30 (t, J=7.1 Hz, 3H), 1.19 (d, J=6.7 Hz, 6H) ppm. LCMS m/z 531.32 $[M+H]^+$ Compound 127

3-[[5-(4-fluorophenyl)-6-isopropyl-1H-pyrazolo[4,3-g]isoquinolin-8-yl]oxy]cyclobutanecarboxylic acid (127)

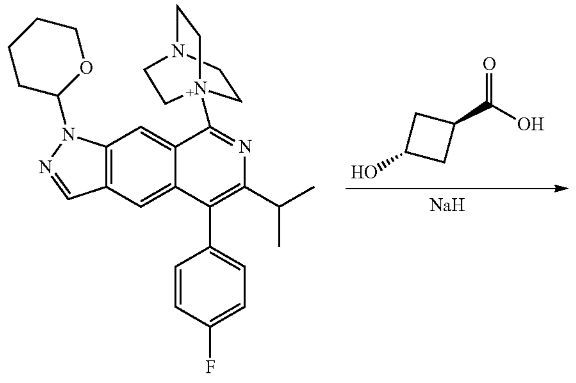

S13

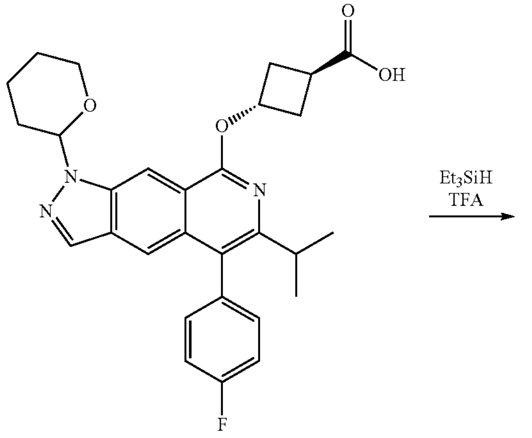

C49

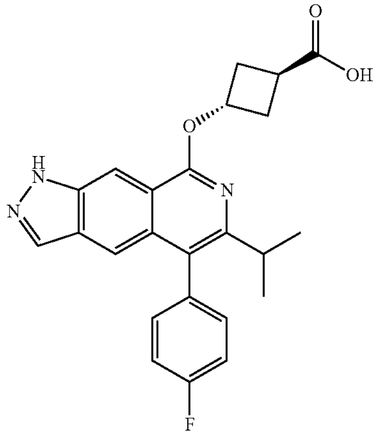

127

Step 1. Synthesis of 3-[5-(4-fluorophenyl)-6-isopropyl-1-tetrahydropyran-2-yl-pyrazolo[4,3-g]isoquinolin-8-yl]oxycyclobutanecarboxylic acid (C49)

In a vial, 8-(4-aza-1-azoniabicyclo[2.2.2]octan-1-yl)-5-(4-fluorophenyl)-6-isopropyl-1-tetrahydropyran-2-yl-pyrazolo[4,3-g]isoquinoline (Trifluoroacetate salt) (350 mg, 0.5694 mmol) and 3-hydroxycyclobutanecarboxylic acid (200 mg, 1.722 mmol) were dissolved in DMSO (6 mL). Then, at room temperature and under nitrogen, NaH (140 mg of 60% w/w, 3.500 mmol) was added. The reaction was stirred for 1 hour. Purification by reversed-phase chromatography (Column: C18. Gradient: 0-100% MeCN in water with 0.1% trifluoroacetic acid) afforded the product. Fractions containing the product were pooled and the acetonitrile was evaporated in vacuo. The aqueous mixture was extracted with $CHCl_3$:IPA (3:1). The organic phases were combined, dried with $MgSO_4$ and the volatiles were evaporated in vacuo. A yellow solid was obtained. 3-[5-(4-fluorophenyl)-6-isopropyl-1-tetrahydropyran-2-yl-pyrazolo[4,3-g]-isoquinolin-8-yl]oxycyclobutanecarboxylic acid (225.8 mg, 79%). LCMS m/z 504.29 $[M+H]^+$.

Step 2. Synthesis of 3-[[5-(4-fluorophenyl)-6-isopropyl-1H-pyrazolo[4,3-g]isoquinolin-8-yl]oxy]cyclobutanecarboxylic acid (127)

In a 3 L 4-neck flask equipped with mechanical stirrer and temperature probe, to a solution/suspension of 3-[5-(4-fluorophenyl)-6-isopropyl-1-tetrahydropyran-2-yl-pyrazolo[4,3-g]isoquinolin-8-yl]oxycyclobutanecarboxylic acid (Dicyclohexylamine) (28.2 g, 41.17 mmol) in dichloromethane (560 mL) at room temperature, was added $Et_3SiH$ (13.2 mL, 82.64 mmol) followed by TFA (224 mL). The reaction mixture was stirred for 2 h, then concentrated (rotovap bath at 50° C.). The resulting thick yellow oil/paste was treated with water (850 mL), solid was scraped off wall of flask, the resulting suspension was spun on rotovap (no vacuum) with the bath set at 65° C. for 30 minutes. The resulting suspension was cooled to 28° C., then filtered. The collected solid was washed with water (500 mL) then dried under suction, then transferred to a 1 L flask, and then dissolved/suspended in AcOH (300 mL). The suspension was heated at 75° C. on rotovap (no vacuum) for 20 minutes, to give a uniform suspension. The mixture was then sonicated for 2 minutes, and treated with water (300 mL). The mixture was then heated at 75° C. on rotovap (no vacuum) for 20 minutes, then cooled to 23° C. and filtered. The material was suspended in AcOH (1.5 L), heated to 90° C. After 30 minutes at 90° C., the suspension was cooled to room temperature, treated with water (1.5 L), then filtered. The residue was dissolved in DMSO (200 mL). Water (200 mL) was added via dropwise over the course of 15 minutes to give a suspension. The mixture was stirred for a further 20 minutes, then filtered, washing with water (200 mL). The solid was dried under suction for 30 minutes, then on rotovap (75° C., 3 mbar) for 1 hour, then dried in a vacuum oven, 75° C. for 18 hours. Gives 16.1 g yellow powder. $^1H$ NMR (4 MHz, DMSO-$d_6$) δ 13.34 (s, 1H), 12.36 (s, 1H), 8.35 (t, J=1.2 Hz, 1H), 8.31 (d, J=1.1 Hz, 1H), 7.57 (d, J=1.1 Hz, 1H), 7.45-7.31 (m, 4H), 5.59 (p, J=7.0 Hz, 1H), 3.25-3.12 (m, 1H), 2.80 (ddt, J=13.5, 11.0, 5.3 Hz, 3H), 2.59 (ddt, J=10.3, 6.5, 3.1 Hz, 2H), 1.16 (d, J=6.7 Hz, 6H). $^{19}F$ NMR (376 MHz, DMSO-$d_6$) δ −115.17. LCMS m/z 420.02 $[M+H]^+$. Melting point=311° C.

Compound 128

Phosphonooxymethyl 3-[[5-(4-fluorophenyl)-6-isopropyl-1H-pyrazolo[4,3-g]isoquinolin-8-yl]oxy]cyclobutanecarboxylate (128)

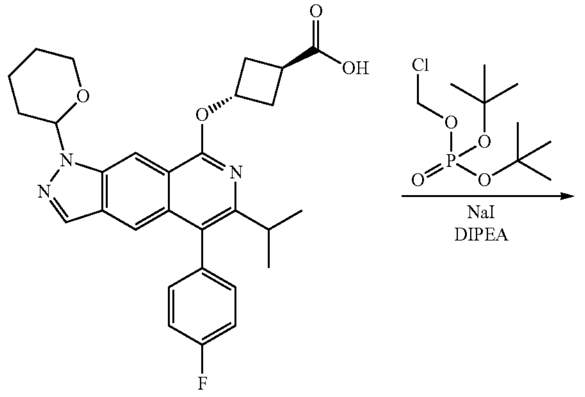

C49

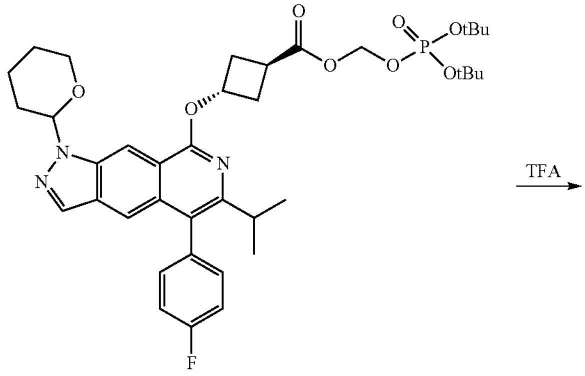

C50

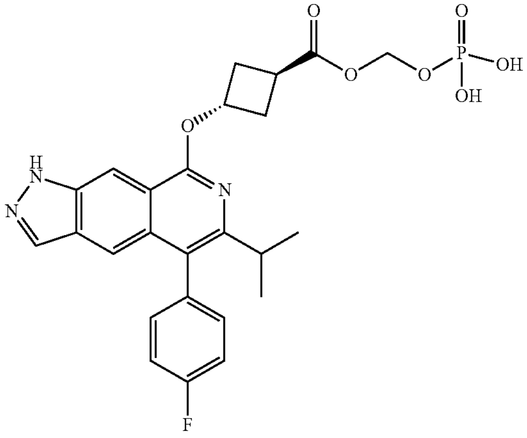

128

Step 1. Synthesis of ditert-butoxyphosphoryloxymethyl 3-[5-(4-fluorophenyl)-6-isopropyl-1-tetrahydropyran-2-yl-pyrazolo[4,3-g]isoquinolin-8-yl]oxycyclobutanecarboxylate (C50)

To a solution of 3-[5-(4-fluorophenyl)-6-isopropyl-1-tetrahydropyran-2-yl-pyrazolo[4,3-g]isoquinolin-8-yl]oxycyclobutanecarboxylic acid (735 mg, 1.460 mmol) in DMF (12 mL) at rt was added NaI (68 mg, 0.4537 mmol), DIPEA (0.80 mL, 4.593 mmol) and ditert-butyl chloromethyl phosphate (950 mg, 3.673 mmol). The mixture was heated to 75° C. After 2.5 hours, additional DIPEA (1.0 mL, 5.741 mmol) and ditert-butyl chloromethyl phosphate (800 mg, 3.093 mmol) were added. The reaction was stirred a further 2.5 hours at 75° C., then cooled to room temperature. The mixture was partitioned between water and EtOAc (80 mL each). The organic layer was separated, washed with 5 wt % aq citric acid, water, brine (80 mL each), dried ($MgSO_4$) filtered and concentrated. Purification by silica gel chromatography (Gradient: 0-100% EtOAc in heptane) yielded the product. ditert-butoxyphosphoryloxymethyl 3-[5-(4-fluorophenyl)-6-isopropyl-1-tetrahydropyran-2-yl-pyrazolo[4,3-g]isoquinolin-8-yl]oxycyclobutanecarboxylate (610 mg, 58%) as a yellow glassy solid. $^1$H NMR (400 MHz, Chloroform-d) δ 8.43 (t, J=1.1 Hz, 1H), 8.14 (d, J=0.9 Hz, 1H), 7.60 (d, J=1.0 Hz, 1H), 7.32-7.19 (m, 4H), 5.94 (dd, J=9.2, 2.8 Hz, 1H), 5.78-5.68 (m, 3H), 4.07 (d, J=12.0 Hz, 1H), 3.93-3.82 (m, 1H), 3.40 (tdd, J=9.8, 5.0, 4.0 Hz, 1H), 3.10-2.99 (m, 2H), 2.85 (h, J=6.7 Hz, 1H), 2.81-2.63 (m, 2H), 2.31-2.20 (m, 1H), 2.15 (d, J=13.6 Hz, 1H), 1.96-1.68 (m, 3H), 1.54 (d, J=0.6 Hz, 18H), 1.19 (dd, J=6.7, 3.1 Hz, 6H). $^{19}$F NMR (376 MHz, Chloroform-d) δ −115.36. $^{31}$P NMR (162 MHz, Chloroform-d) δ −11.54. LCMS m/z 726.36 $[M+1]^+$.

Step 2. Synthesis of phosphonooxymethyl 3-[[5-(4-fluorophenyl)-6-isopropyl-1H-pyrazolo[4,3-g]isoquinolin-8-yl]oxy]cyclobutanecarboxylate (128)

To a solution of ditert-butoxyphosphoryloxymethyl 3-[5-(4-fluorophenyl)-6-isopropyl-1-tetrahydropyran-2-yl-pyrazolo[4,3-g]isoquinolin-8-yl]oxycyclobutanecarboxylate (596 mg, 0.8212 mmol) in dichloromethane (40 mL) at room temperature was added TFA (26 mL). The mixture was allowed to stir for 2 hours, then concentrated on a rotovap (60° C.). The residue was dissolved in MeOH (5 mL), and purified. Purification by reversed-phase chromatography (Column: C18. Gradient: 0-100% MeCN in water with 0.1% trifluoroacetic acid) then lyophilization afforded the product. The powder was slurried in water (10 mL) for 45 minutes, then filtered, washing with water (10 mL). Drying under suction for 30 min, then on a rotovap (2 mbar, 60° C.) for 1 hour to afford phosphonooxymethyl 3-[[5-(4-fluorophenyl)-6-isopropyl-1H-pyrazolo[4,3-g]isoquinolin-8-yl]oxy]cyclobutanecarboxylate (192 mg, 40%) as a yellow powder. $^1$H NMR (400 MHz, DMSO-$d_6$) δ 13.34 (s, 1H), 8.35 (t, J=1.1 Hz, 1H), 8.31 (d, J=1.1 Hz, 1H), 7.57 (d, J=1.1 Hz, 1H), 7.43-7.34 (m, 4H), 5.64-5.55 (m, 1H), 5.57 (d, J=13.8 Hz, 2H), 3.39-3.28 (m, 1H), 2.88 (ddq, J=11.2, 7.3, 3.8, 3.2 Hz, 2H), 2.77 (p, J=6.7 Hz, 1H), 2.65 (dddd, J=13.4, 10.3, 6.7, 2.8 Hz, 2H), 1.16 (d, J=6.6 Hz, 6H). $^{19}$F NMR (282 MHz, DMSO-$d_6$) δ −115.18. $^{31}$P NMR (162 MHz, DMSO-$d_6$) δ −2.56. LCMS m/z 530.14 $[M+H]^+$.

Compound 129

3-[5-(4-fluorophenyl)-6-isopropyl-1-(2-phosphonooxyethoxycarbonyl)pyrazolo[4,3-g]isoquinolin-8-yl]oxycyclobutanecarboxylic acid (129)

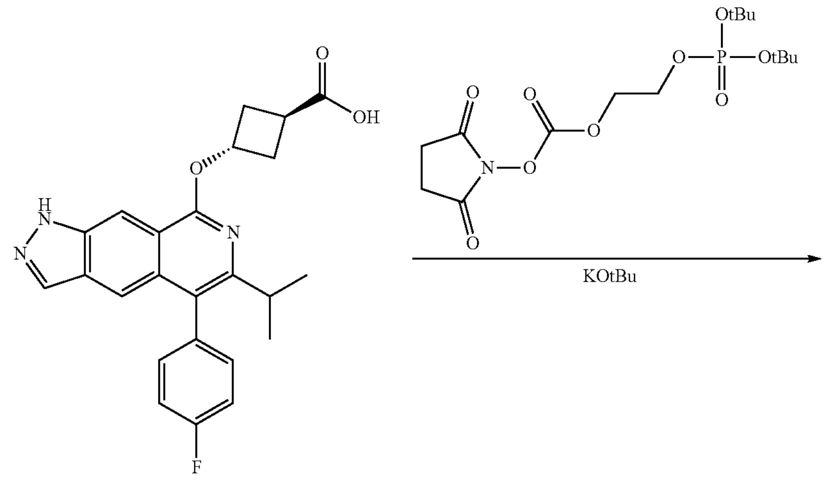

127

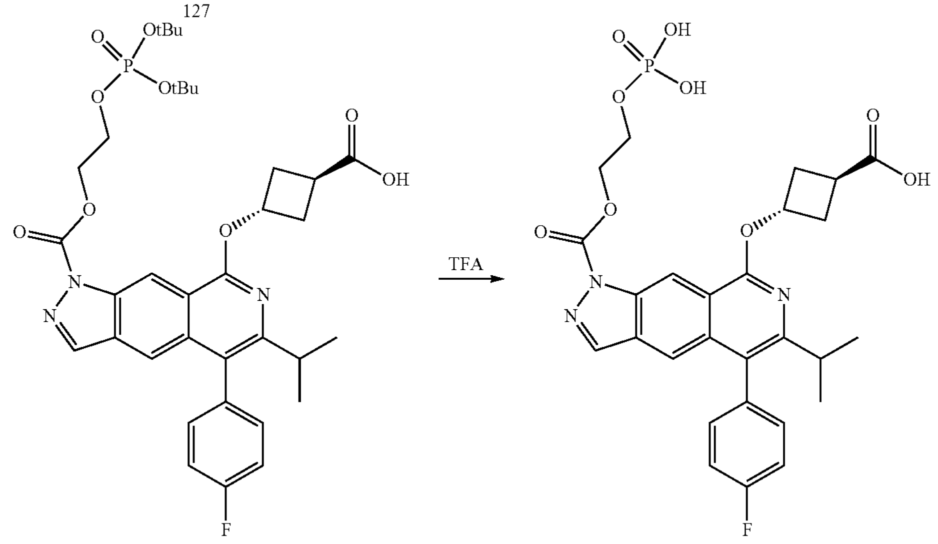

C51 129

Step 1. Synthesis of 3-[1-(2-ditert-butoxyphosphoryloxyethoxycarbonyl)-5-(4-fluorophenyl)-6-isopropyl-pyrazolo[4,3-g]isoquinolin-8-yl]oxycyclobutanecarboxylic acid (C51)

To a solution of 3-[[5-(4-fluorophenyl)-6-isopropyl-1H-pyrazolo[4,3-g]isoquinolin-8-yl]oxy]cyclobutanecarboxylic acid (188 mg, 0.4452 mmol) in THF (10 mL) at 0° C. under nitrogen, was added KOtBu (1.4 mL of 1 M, 1.400 mmol) (solution in THF), to give a suspension of yellow solid, stirring is hindered. 2-Ditert-butoxyphosphoryloxyethyl (2,5-dioxopyrrolidin-1-yl) carbonate (540 mg, 1.366 mmol) was added (as a solid), and the reaction mixture turned slightly red in color, and the yellow solid is consumed ~5 minutes. After a total of 8 minutes, the reaction was quenched with saturated aqueous $NH_4Cl$ (10 mL). The mixture was partitioned between EtOAc and water (80 mL each). The organic layer was separated, washed with water, then brine (80 mL each), and dried ($MgSO_4$) filtered and concentrated. Purification by silica gel chromatography (Gradient: 0-100% EtOAc in heptane) yielded the product. 3-[1-(2-ditert-butoxyphosphoryloxyethoxycarbonyl)-5-(4-fluorophenyl)-6-isopropyl-pyrazolo[4,3-g]isoquinolin-8-yl] oxycyclobutanecarboxylic acid (245 mg, 79%) as a bright yellow/green oil. LCMS m/z 700.19 $[M+1]^+$.

Step 2. Synthesis of 3-[5-(4-fluorophenyl)-6-isopropyl-1-(2-phosphonooxyethoxycarbonyl)-pyrazolo[4,3-g]isoquinolin-8-yl]oxycyclobutanecarboxylic acid (129)

To a solution of 3-[1-(2-ditert-butoxyphosphoryloxyethoxycarbonyl)-5-(4-fluorophenyl)-6-isopropyl-pyrazolo[4,3-g]isoquinolin-8-yl]oxycyclobutanecarboxylic acid (240 mg, 0.3430 mmol) in DCM (10 mL) at room temperature was added TFA (3 mL). The reaction mixture was stirred at room temperature for 45 minutes, then concentrated. Purification by reverse-phase chromatography (Column: C18. Gradient: 0-100% MeCN in water with 0.1% trifluoroacetic acid) afforded the product. 3-[5-(4-fluorophenyl)-6-isopropyl-1-(2-phosphonooxyethoxycarbonyl)pyrazolo[4,3-g]isoquinolin-8-yl]oxycyclobutanecarboxylic acid (Trifluoroacetic Acid (0.5)) (70 mg, 31%) as a pale yellow solid. $^1$H NMR (400 MHz, Methanol-$d_4$) δ 9.08 (t, J=1.0 Hz, 1H), 8.45 (d, J=0.9 Hz, 1H), 7.73 (d, J=1.0 Hz, 1H), 7.38-7.28 (m, 4H), 5.80-5.69 (m, 1H), 4.84-4.77 (m, 2H), 4.50-4.41 (m, 2H), 3.31-3.23 (m, 1H), 3.00-2.86 (m, 3H), 2.72 (dtd, J=13.4, 6.7, 2.7 Hz, 2H), 1.24 (d, J=6.6 Hz, 6H). LCMS m/z 587.96 [M+H]$^+$.

Compound 130

2-[2-[[5-(4-fluorophenyl)-6-isopropyl-1H-pyrazolo[4,3-g]isoquinolin-8-yl]oxy]ethoxy]acetic acid (130)

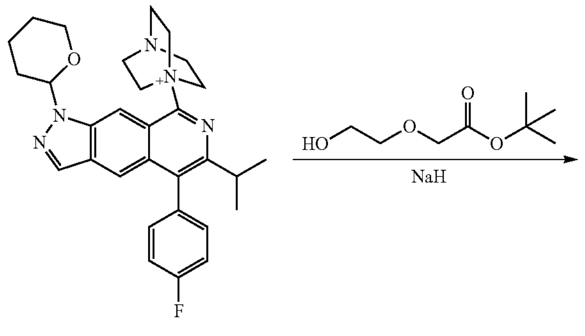

S13

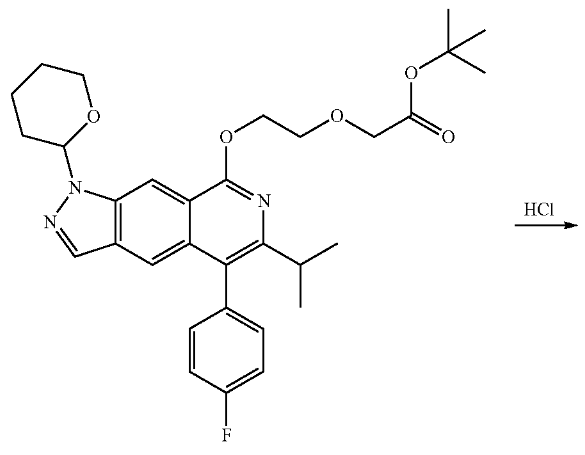

C39

-continued

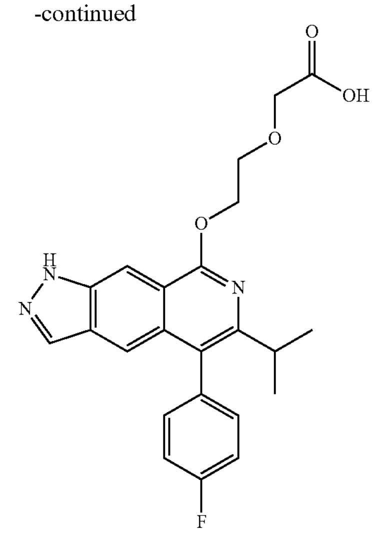

130

Compound 130 was prepared in two steps from S13 according to the method described for the preparation of compound 2 (Addition of tert-butyl 2-(2-hydroxyethoxy) acetate to S13 using NaH, then tandem THP deprotection and ester hydrolysis with HCl). 2-[2-[[5-(4-fluorophenyl)-6-isopropyl-1H-pyrazolo[4,3-g]isoquinolin-8-yl]oxy] ethoxy]acetic acid (8.4 mg, 37%). $^1$H NMR (400 MHz, Methanol-$d_4$) δ 8.47 (t, J=1.1 Hz, 1H), 8.13 (d, J=1.1 Hz, 1H), 7.59 (d, J=1.1 Hz, 1H), 7.33-7.25 (m, 4H), 4.84-4.77 (m, 2H), 4.24 (s, 2H), 4.15-4.06 (m, 2H), 2.83 (m, 1H), 1.20 (d, J=6.7 Hz, 6H). LCMS m/z 424.26 [M+H]$^+$.

Compound 131

(2S,4R)-1-acetyl-4-[[5-(4-fluorophenyl)-6-isopropyl-1H-pyrazolo[4,3-g]isoquinolin-8-yl]oxy]pyrrolidine-2-carboxylic acid (131)

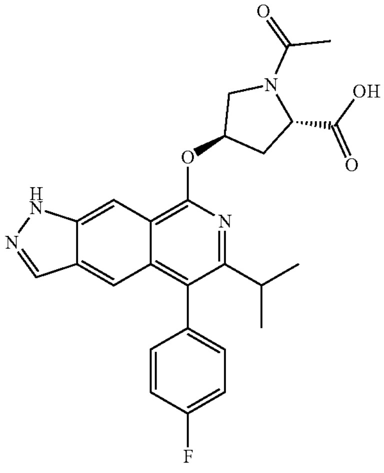 [SMILES: CC(=O)N1C[C@H](Oc2nc(C(C)C)c(-c3ccc(F)cc3)c3cc4cn[nH]c4cc23)C[C@H]1C(=O)O]

Compound 131 was prepared in two steps from S13 according to the method described for the preparation of compound 2(2S,4R)-1-acetyl-4-[[5-(4-fluorophenyl)-6-isopropyl-1H-pyrazolo[4,3-g]isoquinolin-8-yl]oxy]pyrrolidine-2-carboxylic acid (20.3 mg, 55%). $^1$H NMR (400 MHz, Methanol-$d_4$) δ 8.35 (m, 1H), 8.13 (d, J=1.1 Hz, 1H), 7.61 (m, 1H), 7.35-7.18 (m, 4H), 6.06-5.84 (m, 1H), 4.86-4.61 (m, 1H), 4.23 (dd, J=11.6, 4.9 Hz, 1H), 4.14-3.94 (m, 1H), 2.94-2.72 (m, 2H), 2.57 (m, 1H), 2.13 (m, 3H), 1.21 (m, 6H). LCMS m/z 477.33 $[M+H]^+$ Compound 132

2-[[3-[[5-(4-fluorophenyl)-6-isopropyl-1H-pyrazolo[4,3-g]isoquinolin-8-yl]oxy]cyclobutanecarbonyl]amino]propanoic acid (132)

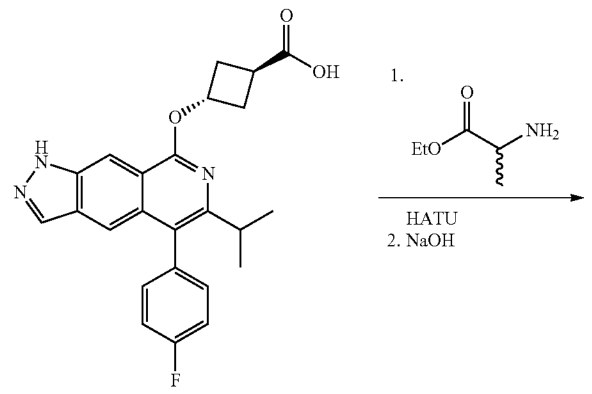

127

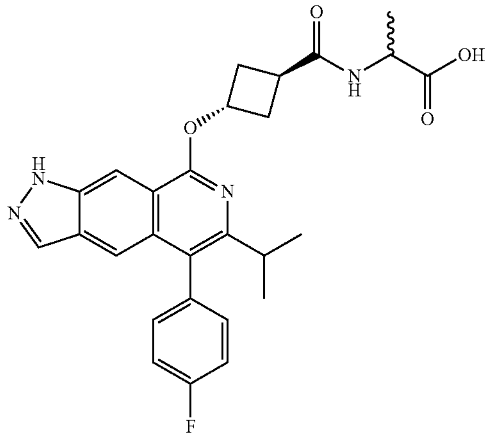

132

Compound 132 was prepared from compound 127 by HATU coupling in two steps using the method described for the preparation of compound 30. In the second step, the ethyl ester group was removed by hydrolysis with NaOH. 2-[[3-[[5-(4-fluorophenyl)-6-isopropyl-1H-pyrazolo[4,3-g]soquinolin-8-yl]oxy]cyclobutanecarbonyl]amino]propanoic acid (43 mg, 54%) as a colorless solid. $^1$H NMR (300 MHz, Methanol-$d_4$) δ 8.44 (t, J=1.1 Hz, 1H), 8.13 (d, J=1.1 Hz, 1H), 7.61 (d, J=1.0 Hz, 1H), 7.39-7.14 (m, 4H), 5.81-5.60 (m, 1H), 4.49 (qd, J=7.3, 2.7 Hz, 1H), 3.31-3.21 (m, 1H), 3.05-2.74 (m, 3H), 2.74-2.51 (m, 2H), 1.44 (d, J=7.4 Hz, 3H), 1.19 (d, J=6.7 Hz, 6H). LCMS m/z 491.0 $[M+H]^+$.

Compound 133

3-[[5-(3,4-difluorophenyl)-6-isopropyl-1H-pyrazolo[4,3-g]isoquinolin-8-yl]oxy]cyclobutanecarboxylic acid (133)

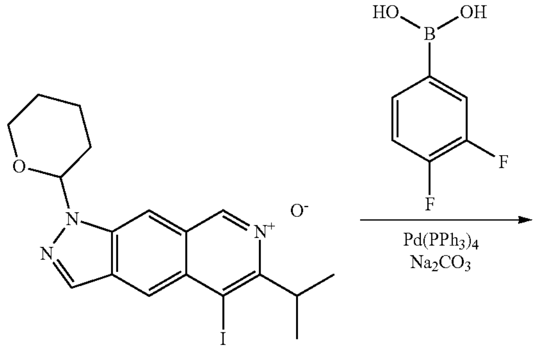

C11

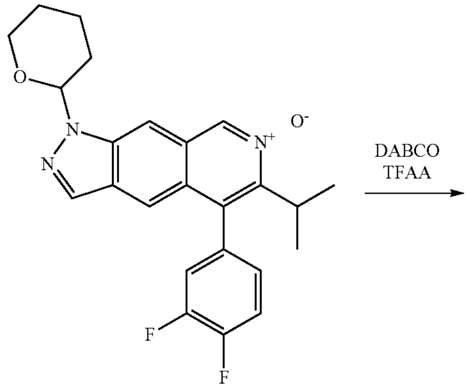

C41

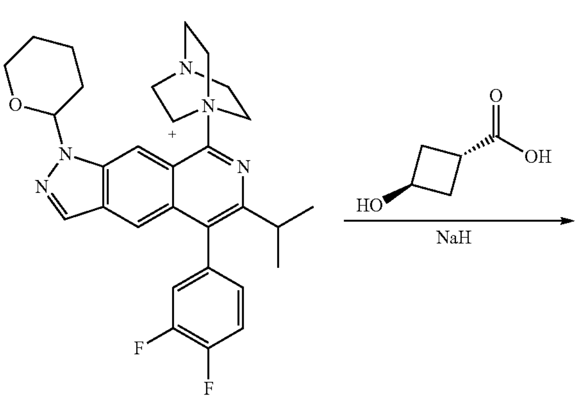

-continued

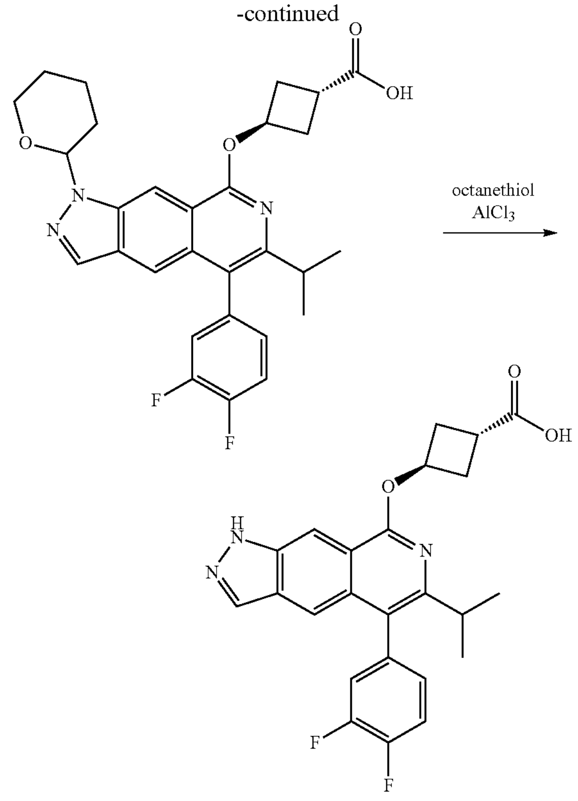

133

Compound 133 was prepared from C11 using the method described for the preparation of compound 1. Purification by reversed-phase chromatography (Column: C18. Gradient: 0-100% MeCN in water with 0.2% formic acid) afforded the product. A pale yellow solid was obtained. 3-[[5-(3,4-difluorophenyl)-6-isopropyl-1H-pyrazolo[4,3-g]isoquinolin-8-yl]oxy]cyclobutanecarboxylic acid (22.7 mg, 35%). $^1$H NMR (400 MHz, Methanol-$d_4$:Chloroform-d 3:1) δ 8.46 (s, 1H), 8.18 (s, 1H), 7.64 (s, 1H), 7.42 (q, J=9.0 Hz, 1H), 7.21 (t, J=9.4 Hz, 1H), 7.12 (m, 1H), 5.74 (q, J=6.9 Hz, 1H), 3.26 (m, 1H), 3.02-2.90 (m, 2H), 2.85 (p, J=6.6 Hz, 1H), 2.67 (m, 2H), 1.23 (m, 6H). LCMS m/z 438.21 $[M+H]^+$.

Compound 134

3-[[6-isopropyl-5-(2-methyl-4-pyridyl)-1H-pyrazolo[4,3-g]isoquinolin-8-yl]oxy]cyclobutanecarboxylic acid (134)

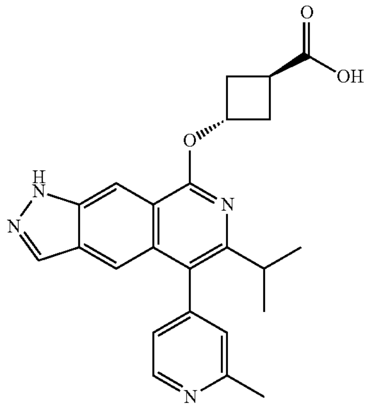 [SMILES: Cc1cc(-c2c(C(C)C)nc(O[C@H]3C[C@H](C(=O)O)C3)c3cc4[nH]ncc4cc23)ccn1]

Compound 134 was prepared from S15 and methyl 3-hydroxycyclobutanecarboxylate as described for the preparation of compound 27. KOtBu was used as the base in the displacement reaction. NaOH was used for hydrolysis of the methyl ester, and then TFA deprotection of the THP group afforded the product. $^1$H NMR (400 MHz, Methanol-$d_4$) δ 8.58 (dd, J=5.1, 0.8 Hz, 1H), 8.45 (dt, J=2.9, 1.1 Hz, 1H), 8.25 (s, 1H), 8.18 (t, J=1.2 Hz, 1H), 7.60 (d, J=1.1 Hz, 1H), 7.38-7.31 (m, 1H), 7.24 (dd, J=5.2, 1.7 Hz, 1H), 5.52-5.40 (m, 1H), 3.08-2.87 (m, 4H), 2.85-2.71 (m, 1H), 2.65 (s, 3H), 2.53 (dd, J=8.3, 2.7 Hz, 1H), 1.23 (ddd, J=6.6, 3.9, 2.5 Hz, 6H). LCMS m/z 417.05 $[M+H]^+$ Compound 135

4-[[6-isopropyl-5-(2-methyl-4-pyridyl)-1H-pyrazolo[4,3-g]isoquinolin-8-yl]oxy]benzoic acid (135)

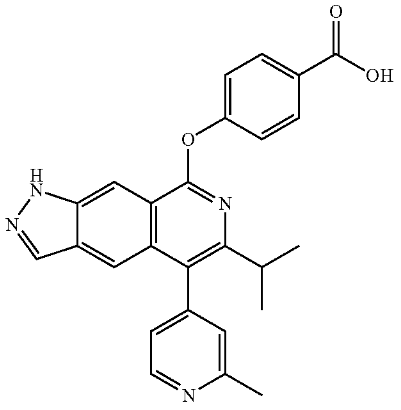 [SMILES: Cc1cc(-c2c(C(C)C)nc(Oc3ccc(C(=O)O)cc3)c3cc4[nH]ncc4cc23)ccn1]

Compound 135 was prepared from S14 and hydroxyl benzoic acid using the method as described for compound 6. $^1$H NMR (300 MHz, Methanol-$d_4$) δ 8.68-8.54 (m, 2H), 8.30-8.11 (m, 4H), 7.72 (d, J=1.1 Hz, 1H), 7.54-7.43 (m, 2H), 7.40-7.32 (m, 1H), 7.32-7.24 (m, 1H), 6.89-6.74 (m, 1H), 2.83-2.70 (m, 1H), 2.66 (s, 3H), 1.05 (dd, J=6.6, 1.2 Hz, 6H). LCMS m/z 439.0 $[M+H]^+$.

Compound 136

3-[[6-isopropyl-5-(2-methoxy-4-pyridyl)-1H-pyrazolo[4,3-g]isoquinolin-8-yl]oxy]cyclobutanecarboxylic acid (136)

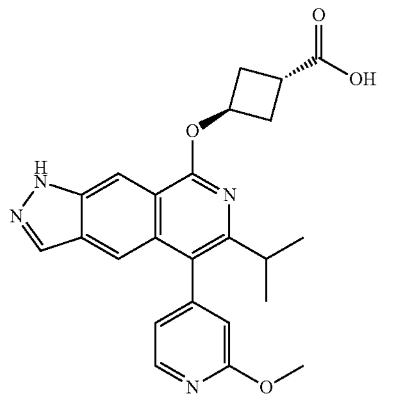 [SMILES: COc1cc(-c2c(C(C)C)nc(O[C@H]3C[C@H](C(=O)O)C3)c3cc4[nH]ncc4cc23)ccn1]

Compound 136 was prepared by addition of 3-hydroxy-cyclobutanecarboxylate to S16 using the using NaH in DMSO. $^1$H NMR (400 MHz, Methanol-$d_4$) δ 8.42 (t, J=1.1 Hz, 1H), 8.25 (dd, J=5.2, 0.7 Hz, 1H), 8.12 (d, J=1.1 Hz, 1H), 7.61 (d, J=1.1 Hz, 1H), 6.90 (dd, J=5.2, 1.4 Hz, 1H), 6.75 (t, J=1.0 Hz, 1H), 5.75-5.57 (m, 1H), 3.99 (s, 3H), 3.23 (m, 1H), 2.92 (m, 2H), 2.80 (p, J=6.6 Hz, 1H), 2.70-2.58 (m, 2H), 1.18 (m, 6H). LCMS m/z 433.26 $[M+H]^+$.

Compound 137

3-[[5-(4-fluorophenyl)-6-(1-hydroxycyclopropyl)-1H-pyrazolo[4,3-g]isoquinolin-8-yl]oxy]cyclobutanecarboxylic acid (137)

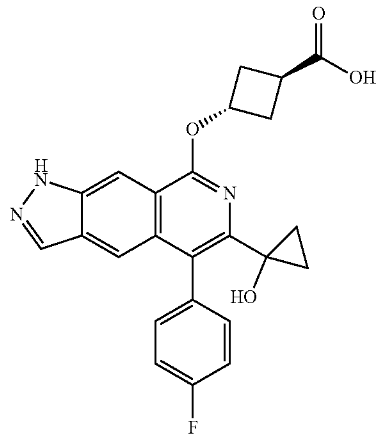 [SMILES: O=C(O)[C@H]1C[C@H](Oc2nc(C3(O)CC3)c(-c3ccc(F)cc3)c3cc4cn[nH]c4cc23)C1]

Compound 137 was prepared by addition of 3-hydroxy-cyclobutanecarboxylate to S17 using NaH in DMSO. The benzyl ester was removed by hydrogenation using a $Pd(OH)_2$ catalyst. LCMS m/z 434.09 $[M+H]^+$ Compound 138

4-[[5-(4-fluorophenyl)-6-(1-hydroxycyclopropyl)-1H-pyrazolo[4,3-g]isoquinolin-8-yl]oxy]benzoic acid (138)

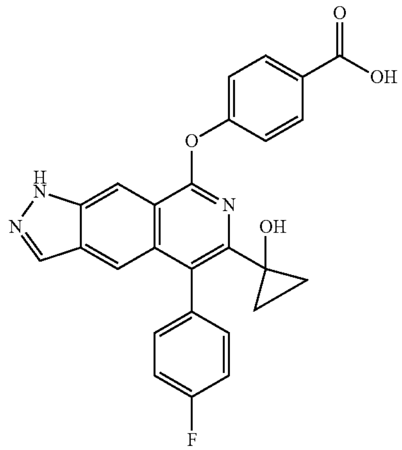 [SMILES: O=C(O)c1ccc(Oc2nc(C3(O)CC3)c(-c3ccc(F)cc3)c3cc4cn[nH]c4cc23)cc1]

Compound 138 was prepared by addition of 3-hydroxy-cyclobutanecarboxylate to S17 using NaH in DMSO. The benzyl ester was removed by hydrogenation using a $Pd(OH)_2$ catalyst. LCMS m/z 458.04 $[M+H]^+$ Compound 139

3-[[5-(3,4-difluorophenyl)-6-(1-hydroxycyclopropyl)-1H-pyrazolo[4,3-g]isoquinolin-8-yl]oxy]cyclobutanecarboxylic acid (139)

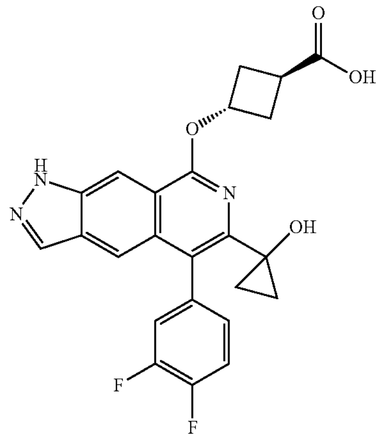 [SMILES: O=C(O)[C@H]1C[C@H](Oc2nc(C3(O)CC3)c(-c3ccc(F)c(F)c3)c3cc4cn[nH]c4cc23)C1]

Compound 139 was prepared by addition of 3-hydroxy-cyclobutanecarboxylate to S18 using NaH in DMSO. The benzyl ester was removed by hydrogenation using a $Pd(OH)_2$ catalyst.

$^1$H NMR (300 MHz, Methanol-$d_4$) δ 8.45 (t, J=1.1 Hz, 1H), 8.21 (d, J=1.1 Hz, 1H), 7.81 (d, J=1.1 Hz, 1H), 7.45-7.27 (m, 3H), 7.24-7.13 (m, 1H), 5.79-5.61 (m, 1H), 3.27-3.12 (m, 1H), 2.90 (dddd, J=11.2, 7.0, 4.0, 2.6 Hz, 2H), 2.70-2.57 (m, 1H), 1.00-0.80 (m, 4H). LCMS m/z 452.47 $[M+H]^+$.

Compound 140

3-[[5-(3,4-difluorophenyl)-6-[1-(trifluoromethyl)cyclopropyl]-1H-pyrazolo[4,3-g]isoquinolin-8-yl]oxy]cyclobutanecarboxylic acid (140)

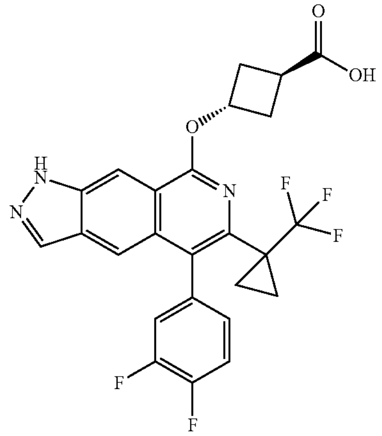 [SMILES: O=C(O)[C@H]1C[C@H](Oc2nc(C3(C(F)(F)F)CC3)c(-c3ccc(F)c(F)c3)c3cc4cn[nH]c4cc23)C1]

Compound 140 was prepared by addition of 3-hydroxycyclobutanecarboxylate to S19 using NaH in DMSO. $^1$HNMR (300 MHz, Acetone-$d_6$) δ 8.56 (t, J=1.1 Hz, 1H), 8.30 (d, J=1.1 Hz, 1H), 7.77 (d, J=1.1 Hz, 1H), 7.55 (dt, J=10.8, 8.5 Hz, 1H), 7.40 (ddd, J=10.5, 7.8, 2.1 Hz, 1H), 7.30-7.21 (m, 1H), 5.80-5.62 (m, 1H), 3.32-3.22 (m, 2H), 3.04-2.75 (m, 2H), 2.73-2.59 (m, 2H), 1.21-1.12 (m, 2H). LCMS m/z 504.39 $[M+H]^+$.

Compound 141

3-[[6-(1,1-difluoroethyl)-5-(4-fluorophenyl)-1H-pyrazolo[4,3-g]isoquinolin-8-yl]oxy]cyclobutanecarboxylic acid (141)

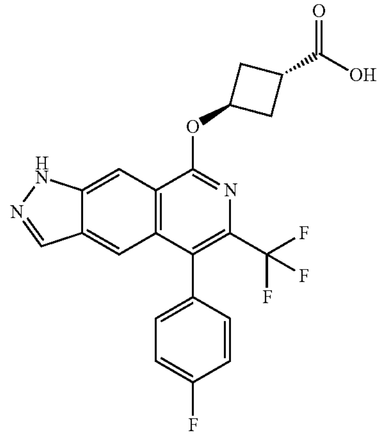

Compound 141 was prepared in two steps from S20. Compound S20 was converted to 8-(4-aza-1-azoniabicyclo[2.2.2]octan-1-yl)-6-(1,1-difluoroethyl)-5-(4-fluorophenyl)-1H-pyrazolo[4,3-g]isoquinoline by treatment with DABCO and TFAA. 3-hydroxycyclobutanecarboxylic acid was added to 8-(4-aza-1-azoniabicyclo[2.2.2]octan-1-yl)-6-(1,1-difluoroethyl)-5-(4-fluorophenyl)-1H-pyrazolo[4,3-g]isoquinoline using NaH in DMSO to afford the product. 3-[[6-(1,1-difluoroethyl)-5-(4-fluorophenyl)-1H-pyrazolo[4,3-g]isoquinolin-8-yl]oxy]cyclobutanecarboxylic acid. $^1$H NMR (300 MHz, Methanol-$d_4$) δ 8.47 (q, J=1.2 Hz, 1H), 8.22 (d, J=1.1 Hz, 1H), 7.72 (d, J=1.0 Hz, 1H), 7.35-7.16 (m, 4H), 5.75-5.60 (m, 1H), 3.24 (dtt, J=9.3, 4.0, 1.7 Hz, 1H), 2.97-2.84 (m, 2H), 2.67 (dtd, J=13.4, 6.6, 2.7 Hz, 2H), 2.07-1.88 (m, 3H). LCMS m/z 442.33 $[M+H]^+$.

Compound 142

3-[[5-(3,4-difluorophenyl)-6-(1-methoxycyclobutyl)-1H-pyrazolo[4,3-g]isoquinolin-8-yl]oxy]cyclobutanecarboxylic acid (142)

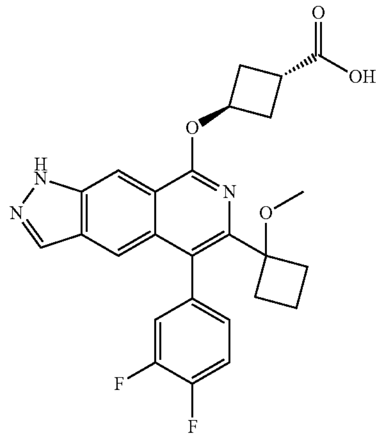 [SMILES: COC1(c2nc(O[C@H]3C[C@H](C(=O)O)C3)c3cc4[nH]ncc4cc3c2-c2ccc(F)c(F)c2)CCC1]

Compound 142 was prepared from S21 and 3-hydroxycyclobutanecarboxylic acid as described for the preparation of compound 127. HCl was used in the THP deprotection step. $^1$H NMR (400 MHz, Methanol-$d_4$) δ 8.47 (t, J=1.1 Hz, 1H), 8.22 (d, J=1.1 Hz, 1H), 7.76 (d, J=1.1 Hz, 1H), 7.36 (dt, J=10.7, 8.4 Hz, 1H), 7.25 (ddd, J=11.4, 7.8, 2.1 Hz, 1H), 7.16-7.09 (m, 1H), 5.74-5.62 (m, 1H), 3.29-3.19 (m, 1H), 3.06 (s, 3H), 2.91 (dddd, J=12.6, 5.4, 4.0, 2.0 Hz, 2H), 2.70-2.54 (m, 3H), 2.54-2.46 (m, 1H), 2.04-1.85 (m, 3H), 1.71-1.57 (m, 1H). LCMS m/z 480.42 $[M+H]^+$.

Compound 143

3-[[5-(3,4-difluorophenyl)-6-(2-methoxy-2-methylpropyl)-1H-pyrazolo[4,3-g]isoquinolin-8-yl]oxy]cyclobutanecarboxylic acid (143)

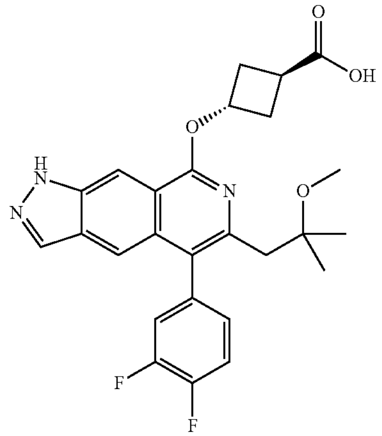 [SMILES: COC(C)(C)Cc1nc(O[C@H]2C[C@H](C(=O)O)C2)c2cc3[nH]ncc3cc2c1-c1ccc(F)c(F)c1]

Compound 143 was prepared from S22 and 3-hydroxycyclobutanecarboxylic acid as described for the preparation of compound 127. HCl was used in the THP deprotection step. $^1$H NMR (300 MHz, Methanol-$d_4$) δ 8.45 (t, J=1.1 Hz, 1H), 8.19 (d, J=1.1 Hz, 1H), 7.65 (d, J=1.1 Hz, 1H), 7.44 (dt, J=10.7, 8.4 Hz, 1H), 7.26 (ddd, J=11.3, 7.7, 2.1 Hz, 1H), 7.13 (ddd, J=8.6, 4.4, 1.9 Hz, 1H), 5.78-5.68 (m, 1H), 3.18 (s, 3H), 2.95-2.80 (m, 4H), 2.64 (dtd, J=13.3, 6.5, 2.8 Hz, 2H), 1.21 (d, J=3.6 Hz, 6H). LCMS m/z 482.49 $[M+H]^+$.

Compound 144

4-[[5-(3,4-difluorophenyl)-6-(2-hydroxy-1,1-dimethyl-ethyl)-1H-pyrazolo[4,3-g]isoquinolin-8-yl]oxy]benzoic acid (144)

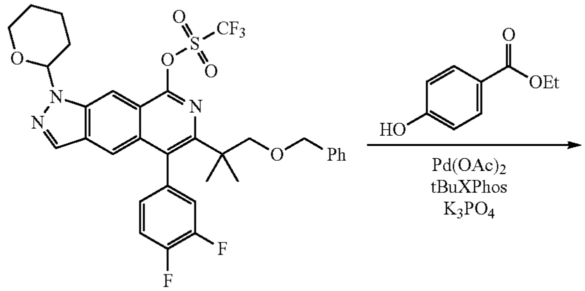

S23

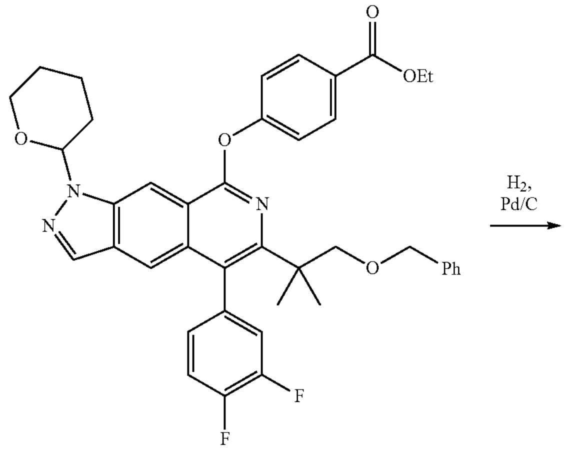

C42

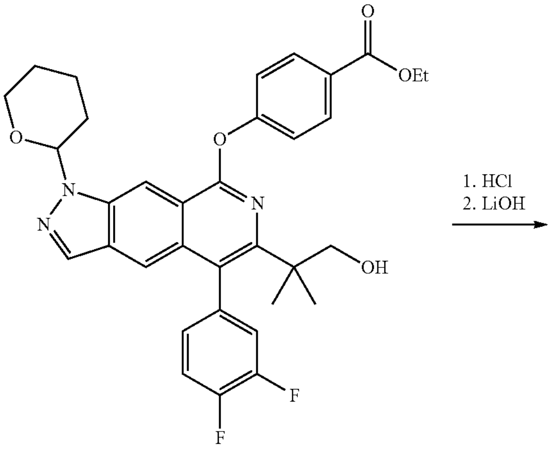

C43

-continued

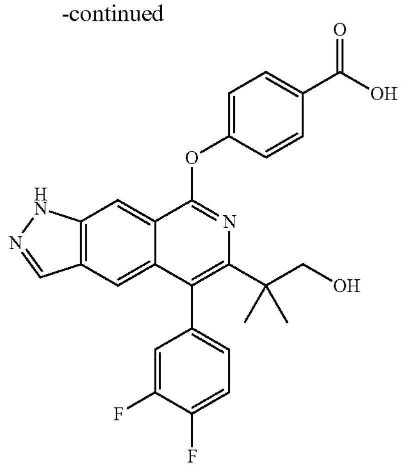

144

Step 1. Synthesis of ethyl 4-[5-(3,4-difluorophenyl)-6-(2-hydroxy-1,1-dimethyl-ethyl)-1-tetrahydropyran-2-yl-pyrazolo[4,3-g]isoquinolin-8-yl]oxybenzoate (C42)

To a vial was added ethyl 4-hydroxybenzoate (73.8 mg, 0.4441 mmol), [6-(2-benzyloxy-1,1-dimethyl-ethyl)-5-(3,4-difluorophenyl)-1-tetrahydropyran-2-yl-pyrazolo[4,3-g]isoquinolin-8-yl] trifluoromethanesulfonate (100 mg, 0.1480 mmol), $Pd(OAc)_2$ (3.32 mg, 0.01479 mmol), ditert-butyl-[2-(2,4,6-triisopropylphenyl)phenyl]phosphane (9.43 mg, 0.02221 mmol), and $K_3PO_4$ (94.2 mg, 0.4438 mmol). The vial was sealed and flushed with nitrogen. Toluene (1.2 mL) was added and the reaction was stirred at 100° C. overnight. After cooling to room temperature, the reaction was diluted with EtOAc and washed with $NH_4Cl$ sat. solution. Purification by silica gel chromatography (Gradient: 0-30% EtOAc in heptane) yielded the product. Ethyl 4-[6-(2-benzyloxy-1,1-dimethyl-ethyl)-5-(3,4-difluorophenyl)-1-tetrahydropyran-2-yl-pyrazolo[4,3-g]isoquinolin-8-yl]oxybenzoate (33 mg, 30%) LCMS m/z 691.78 $[M+H]^+$.

Step 2. Synthesis of ethyl 4-[5-(3,4-difluorophenyl)-6-(2-hydroxy-1,1-dimethyl-ethyl)-1-tetrahydropyran-2-yl-pyrazolo[4,3-g]isoquinolin-8-yl]oxybenzoate (C43)

Ethyl 4-[6-(2-benzyloxy-1,1-dimethyl-ethyl)-5-(3,4-difluorophenyl)-1-tetrahydropyran-2-yl-pyrazolo[4,3-g]isoquinolin-8-yl]oxybenzoate was dissolved in MeOH (5 mL). The solution was transferred into a vial containing Pd (7.87 mg, 0.007395 mmol). The vial was flushed with H2 and the reaction was stirred at room temperature overnight. The reaction mixture was filtered through a Celite® plug, concentrated, and purified (Gradient: 0-30% EtOAc in heptane) to afford the product. Ethyl 4-[5-(3,4-difluorophenyl)-6-(2-hydroxy-1,1-dimethyl-ethyl)-1-tetrahydropyran-2-yl-pyrazolo[4,3-g]isoquinolin-8-yl]oxybenzoate (17 mg, 19%) LCMS m/z 602.13 $[M+H]^+$.

Step 3. Synthesis of 4-[[5-(3,4-difluorophenyl)-6-(2-hydroxy-1,1-dimethyl-ethyl)-1H-pyrazolo[4,3-g]isoquinolin-8-yl]oxy]benzoic acid (144)

To a vial was added ethyl 4-[5-(3,4-difluorophenyl)-6-(2-hydroxy-1,1-dimethyl-ethyl)-1-tetrahydropyran-2-yl-pyrazolo[4,3-g]isoquinolin-8-yl]oxybenzoate (15 mg, 0.02191 mmol), followed by HCl (1000 μL of 4 M, 4.000 mmol) in 1,4-dioxane (500 The reaction was stirred at room temperature for 2 hours. The reaction mixture was poured into water and neutralized with $NaHCO_3$ sat. solution. The product was extracted with EtOAc. The reaction was concentrated in vacuo and purified by silica gel chromatography (Gradient: 0-10% MeOH in dichloromethane) to afford ethyl 4-[[5-(3,4-difluorophenyl)-6-(2-hydroxy-1,1-dimethyl-ethyl)-1H-pyrazolo[4,3-g]isoquinolin-8-yl]oxy]benzoate.

To a solution of ethyl 4-[[5-(3,4-difluorophenyl)-6-(2-hydroxy-1,1-dimethyl-ethyl)-1H-pyrazolo[4,3-g]isoquinolin-8-yl]oxy]benzoate in THF (1.2 mL)/MeOH (0.4 mL)/$H_2O$ (0.4 mL) was added LiOH (5.25 mg, 0.2192 mmol). The reaction was stirred at room temperature for 3 hours. The reaction mixture was diluted with $H_2O$ and acidified with 1 N HCl aq. solution. The product was extracted with EtOAc and concentrated to give 4-[[5-(3,4-difluorophenyl)-6-(2-hydroxy-1,1-dimethyl-ethyl)-1H-pyrazolo[4,3-g]isoquinolin-8-yl]oxy]benzoic acid (8.2 mg, 69%). $^1H$ NMR (300 MHz, Methanol-$d_4$) δ 8.60 (t, J=1.1 Hz, 1H), 8.23 (d, J=1.1 Hz, 1H), 8.21-8.12 (m, 2H), 7.57 (d, J=1.1 Hz, 1H), 7.51-7.37 (m, 3H), 7.31 (ddd, J=11.2, 7.7, 2.1 Hz, 1H), 7.17 (ddt, J=6.8, 4.9, 1.9 Hz, 1H), 3.45 (d, J=2.4 Hz, 2H), 0.97 (d, J=3.5 Hz, 7H). LCMS m/z 490.14 $[M+H]^+$.

Preparation of T1 and T2

5-(4-fluorophenyl)-6-isopropyl-8-oxido-1H-pyrazolo[4,3-g]quinolin-8-ium (T1) and 7-chloro-5-(4-fluorophenyl)-6-isopropyl-1H-pyrazolo[4,3-g]quinolone (T2)

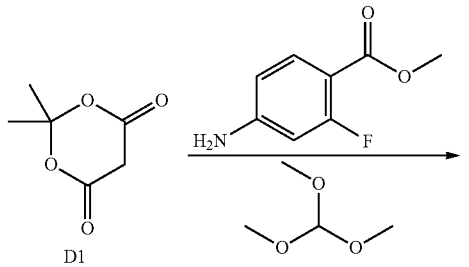

D1

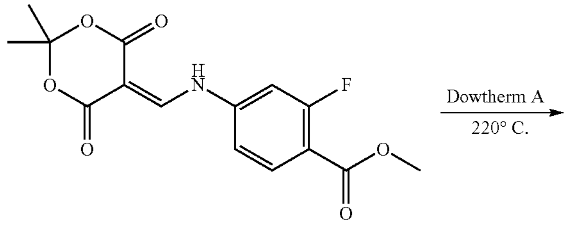

D2

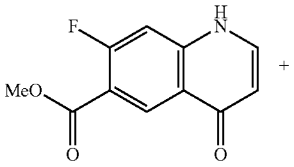

D3

-continued

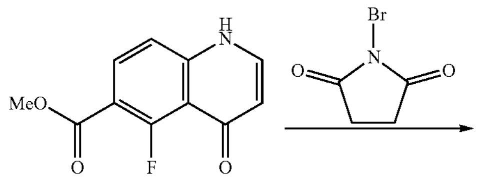

D4

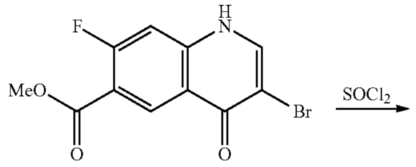

D5

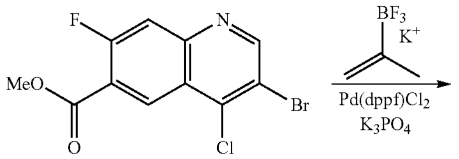

D6

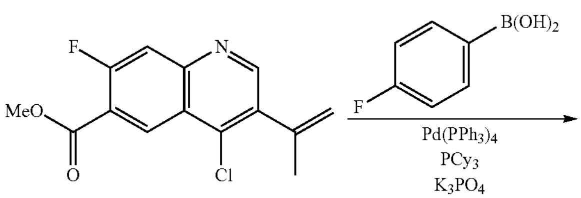

D7

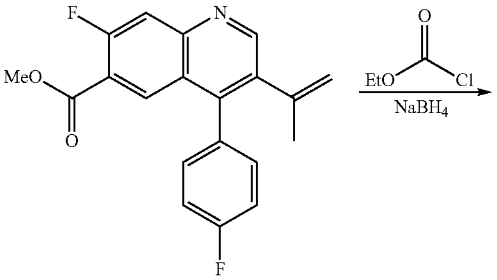

D8

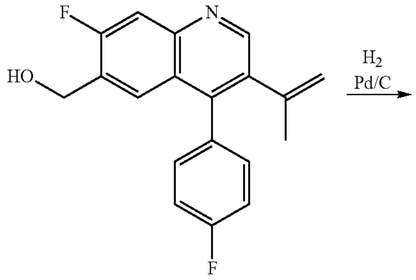

D9

-continued

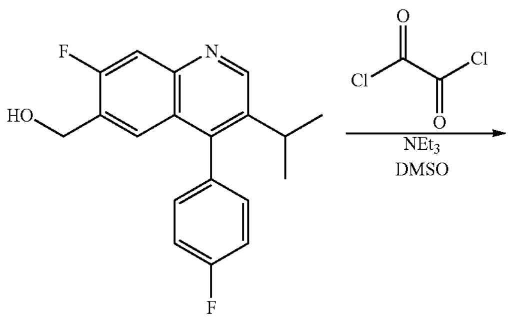

D10

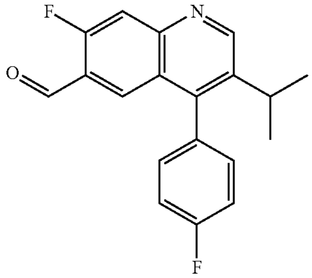

D11

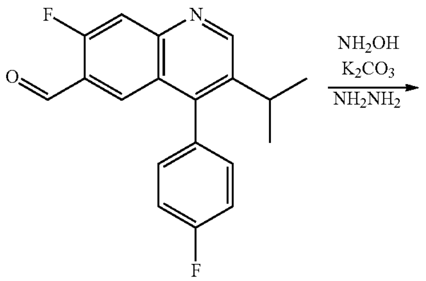

D11

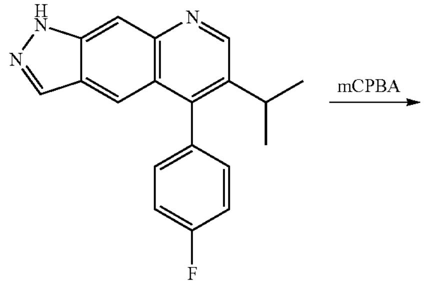

D12

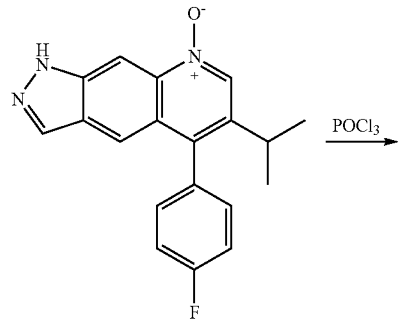

T1

-continued

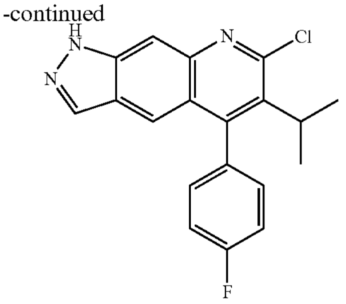

T2

Step 1. Synthesis of methyl 4-[(2,2-dimethyl-4,6-dioxo-1,3-dioxan-5-ylidene)methylamino]-2-fluoro-benzoate A suspension of 2,2-dimethyl-1,3-dioxane-4,6-dione (25.562 g, 177.36 mmol), trimethoxymethane (18.821 g, 177.36 mmol) and methyl 4-amino-2-fluoro-benzoate (25 g, 147.80 mmol) in ethanol (50 mL) was refluxed for 3 hours and then stirred at room temperature for another 2 hours. The resulting solid precipitate was filtered off and washed with ethanol to afford the product. methyl 4-[(2,2-dimethyl-4,6-dioxo-1,3-dioxan-5-ylidene)methylamino]-2-fluoro-benzoate (45 g, 92%). $^1$H NMR (400 MHz, DMSO-$d_6$) δ 11.29 (s, 1H), 8.66 (s, 1H), 7.92 (t, J=8.3 Hz, 1H), 7.73 (dd, J=12.9, 2.2 Hz, 1H), 7.54 (dd, J=8.7, 2.2 Hz, 1H), 3.85 (s, 3H), 1.68 (s, 6H). LCMS m/z 324.1 $[M+H]^+$.

Step 2. Synthesis of methyl 5-fluoro-4-oxo-1H-quinoline-6-carboxylate methyl 7-fluoro-4-oxo-1H-quinoline-6-carboxylate To Dowtherm A (200 mL) at 220° C. was added portion-wise methyl 4-[(2,2-dimethyl-4,6-dioxo-1,3-dioxan-5-ylidene)methylamino]-2-fluoro-benzoate (45 g, 139.20 mmol). After bubbling subsided, the mixture was heated for an additional 10 minutes, and then allowed to cool to room temperature. The mixture was diluted with hexane and the resulting solid was collected by filtration, washed with further hexane to afford the product as a regioisomeric mixture of methyl 7-fluoro-4-oxo-1H-quinoline-6-carboxylate D3 (25 g, 81%) and methyl 5-fluoro-4-oxo-1H-quinoline-6-carboxylate D4 (52:41 by LCMS). The mixture was advanced to the next step without separation. LCMS m/z 221.96 $[M+H]^+$.

Step 3. Synthesis of methyl 3-bromo-7-fluoro-4-oxo-1H-quinoline-6-carboxylate and methyl 3-bromo-5-fluoro-4-oxo-1H-quinoline-6-carboxylate (D5)

To a regioisomeric mixture of methyl 7-fluoro-4-oxo-1H-quinoline-6-carboxylate (29 g, 115.38 mmol) D3, and methyl 5-fluoro-4-oxo-1H-quinoline-6-carboxylate D4 (29.000 g, 115.38 mmol) in DMF (200 mL) was cooled to 0° C. and 1-bromopyrrolidine-2,5-dione (20.536 g, 115.38 mmol) was added portion wise. The reaction was allowed to stir at room temperature overnight. The reaction was quenched with ice cool water in stirring condition. The solid was filtered out and washed with cold water. The compound dried in vacuum to obtain a regioisomeric mixture of methyl 3-bromo-7-fluoro-4-oxo-1H-quinoline-6-carboxylate D5 (32 g, 49%) LCMS m/z 300.0 $[M+H]^+$ and methyl 3-bromo- 5-fluoro-4-oxo-1H-quinoline-6-carboxylate (32 g, 39%). LCMS m/z 302.0 $[M+H]^+$. The mixtures were used in the subsequent steps without separation.

Step 4. Synthesis of methyl 3-bromo-4-chloro-7-fluoro-quinoline-6-carboxylate and methyl 3-bromo-4-chloro-5-fluoro-quinoline-6-carboxylate (D6)

To a regioisomeric mixture of methyl 3-bromo-7-fluoro-4-oxo-1H-quinoline-6-carboxylate (30 g, 89.976 mmol) and methyl 3-bromo-5-fluoro-4-oxo-1H-quinoline-6-carboxylate (30.000 g, 89.976 mmol) was cooled to 0° C. and thionyl chloride (107.05 g, 65.635 mL, 899.76 mmol) was added dropwise and addition of DMF (6.58 g, 6.97 mL, 89.976 mmol). The mixture was refluxed for 4 h. The mixture was concentrated in vacuum, and neutralized by saturated solution of $NaHCO_3$ and extracted with dichloromethane (100 mL×3). The combined organic phase was dried over $Na_2SO_4$ and concentrated. The mixture was purified by silica gel chromatography (Gradient: 3% EtOAc in hexane) to afford methyl 3-bromo-4-chloro-7-fluoro-quinoline-6-carboxylate D6 (8.5 g, 28%). $^1H$ NMR (400 MHz, DMSO-$d_6$) δ 9.20 (s, 2H), 8.74 (d, J=7.4 Hz, 2H), 8.06 (d, J=11.6 Hz, 2H), 3.96 (s, 6H), 0.84 (s, 1H). LCMS m/z 317.8 $[M+H]^+$.

Eluting with 4% EtOAc in hexane afforded the second regioisomer, methyl 3-bromo-4-chloro-5-fluoro-quinoline-6-carboxylate (17 g, 59%). $^1H$ NMR (400 MHz, DMSO-$d_6$) δ 9.22 (s, 1H), 8.18 (dd, J=8.9, 7.0 Hz, 1H), 8.01 (d, J=8.9 Hz, 1H), 3.94 (s, 3H), 0.84 (s, 1H). LCMS m/z 320.0 $[M+H]^+$.

Step 5. Synthesis of methyl 4-chloro-7-fluoro-3-isopropenyl-quinoline-6-carboxylate (D7)

A stirred solution of methyl 3-bromo-4-chloro-7-fluoro-quinoline-6-carboxylate D6 (8.45 g, 26.528 mmol), $K_3PO_4$ (11.262 g, 53.056 mmol) and potassium trifluoro(isopropenyl)boranuide (4.3181 g, 29.181 mmol) in 1,4-dioxane (90 mL) and $H_2O$ (9 mL) was purged with Ar gas for 10 minutes. Then, $Pd(dppf)Cl_2{\cdot}CH_2Cl_2$ (2.1664 g, 2.6528 mmol) was added. The reaction mixture was heated at 100° C. overnight. The reaction mixture was filtered over Celite® washing with ethyl acetate. The filtrate was concentrated in vacuum. Purification by column chromatography (Gradient: 5-8% EtOAc/hexane) afforded the product. methyl 4-chloro-7-fluoro-3-isopropenyl-quinoline-6-carboxylate (4.5 g, 60%). $^1H$ NMR (400 MHz, DMSO-$d_6$) δ 8.90 (s, 2H), 8.78 (d, J=7.6 Hz, 2H), 8.00 (d, J=11.7 Hz, 2H), 6.96 (dd, J=18.3, 8.8 Hz, 1H), 5.55 (s, 2H), 5.22 (s, 2H), 3.96 (s, 7H), 2.29-2.20 (m, 1H), 2.21 (s, 1H), 2.18 (s, 6H), 2.17-2.06 (m, 2H), 1.23 (s, 2H), 1.14 (q, J=7.6 Hz, 1H), 0.85 (t, J=6.6 Hz, 1H). LCMS m/z 280.1 $[M+H]^+$.

Step 6. Synthesis of 7-fluoro-4-(4-fluorophenyl)-3-isopropenyl-quinoline-6-carboxylic acid (D8)

Methyl 4-chloro-7-fluoro-3-isopropenyl-quinoline-6-carboxylate (7 g, 25.0 mmol) and (4-fluorophenyl)boronic acid (6.3 g, 45.05 mmol) were dissolved in 1,4-dioxane (70 mL) and $K_3PO_4$ (10.63 g, 50.0 mmol) aqueous solution (6 mL) was added to it. The reaction mixture was purged with nitrogen for 10 minutes $Pd(PPh_3)_4$ (2.89 g, 2.50 mmol) and tricyclohexyl-phosphine (701.8 mg, 2.5 mmol) were then added to it and finally the reaction mixture was heated to 90° C. for 12 hours. After completion, the reaction mixture was passed through Celite® and washed with EtOAc. The combined organic layer was evaporated under reduced pressure. Purification was done by flash chromatography on silica gel (100-200 mesh) using (5-10% EtOAc in hexane) to afford the product. 7-fluoro-4-(4-fluorophenyl)-3-isopropenyl-quinoline-6-carboxylate (5.5 g, 64%). $^1H$ NMR (400 MHz, DMSO-D6): δ 8.96 (s, 1H), 7.10 (d, 1H, J=7.8 Hz), 7.95 (d, 1H, J=11.88), 7.48-7.39 (m, 4H), 5.24 (s, 1H), 5.10 (s, 1H), 3.92 (s, 3H), 1.69 (s, 3H). LCMS m/z 340.0 0 [M+H]+.

Step 7: Synthesis of [7-fluoro-4-(4-fluorophenyl)-3-isopropenyl-6-quinolyl]methanol (D9)

To a solution of 7-fluoro-4-(4-fluorophenyl)-3-isopropenyl-quinoline-6-carboxylic acid (1 g, 3.0740 mmol) in THF (15 mL) were added $Et_3N$ (373 mg, 0.5141 mL, 3.69 mmol) and Ethyl chloroformate (400 mg, 0.35 mL, 3.69 mmol) and stirred for 1 hour. The reaction mixture was filtered off and to the filtrate was added a solution of $NaBH_4$ (232 mg, 6.15 mmol) in $H_2O$ (3.5 mL) and stirred for 3 hours. The reaction mixture was carefully quenched with 1 N HCl, and extracted with EtOAc. The extract was washed with saturated $NaHCO_3$, brine, dried over $MgSO_4$, filtered, and concentrated. Purification by silica gel chromatography (Gradient: 30-50% EtOAc in hexane) to afford the product as a white solid [7-fluoro-4-(4-fluorophenyl)-3-isopropenyl-6-quinolyl]methanol (800 mg, 80%). LCMS m/z 312.0 $[M+1]^+$.

Step 7. Synthesis of [7-fluoro-4-(4-fluorophenyl)-3-isopropenyl-6-quinolyl]methanol (D9)

To an ice cold stirred solution of $LiAlH_4$ (201.33 mg, 0.2196 mL, 5.3045 mmol) in THF (20 mL) was added a solution of methyl 7-fluoro-4-(4-fluorophenyl)-3-isopropenyl-quinoline-6-carboxylate (1.2 g, 3.53 mmol) in THF (10 mL) as dropwise. After complete addition, the reaction mixture was stirred at room temperature for 6 hours. The reaction mixture was cooled to 0° C. and quenched with dropwise addition of water (0.2 mL), 15% NaOH (0.2 mL) and water (0.6 mL). The reaction mixture was filtered with celite bed and washed by EtOAc (20 mL). The filtrate was concentrated and crude was purified by column chromatography (silica gel 100-200 mesh) using 30-40% EtOAc/hexane to get desired product [7-fluoro-4-(4-fluorophenyl)-3-isopropenyl-6-quinolyl]methanol (800 mg, 66%). LCMS m/z 312.0 $[M+1]^+$.

Step 8. Synthesis of [7-fluoro-4-(4-fluorophenyl)-3-isopropyl-6-quinolyl]methanol (D10)

A stirred solution of [7-fluoro-4-(4-fluorophenyl)-3-isopropenyl-6-quinolyl]methanol (1 g, 3.2121 mmol) in Ethanol (10 mL) was degassed and Pd/C (500 mg, 4.6984 mmol) was added. The mixture was stirred at room temperature under hydrogen at balloon pressure for 12 hours. The reaction was filtered and washed with EtOAc (30 mL), concentrated. Purification by silica gel chromatography (Gradient: 0-30% EtOAc in heptane) yielded the product. [7-fluoro-4-(4-fluorophenyl)-3-isopropyl-6-quinolyl]methanol (975 mg, 93%). $^1H$ NMR (400 MHz, DMSO-$d_6$) δ 9.02 (s, 1H), 7.74 (d, J=11.4 Hz, 1H), 7.47-7.34 (m, 4H), 5.34 (t, J=5.5 Hz, 1H), 4.61 (d, J=5.7 Hz, 2H), 1.23 (d, J=7.0 Hz, 6H). LCMS m/z 313.7 $[M+H]^+$.

Step 9. Synthesis of 7-fluoro-4-(4-fluorophenyl)-3-isopropyl-quinoline-6-carbaldehyde (D11)

To a stirred solution of oxalyl chloride (785.85 mg, 0.5401 mL, 6.1914 mmol) in dichloromethane (10 mL) at −78° C. was added DMSO (967.54 mg, 0.8788 mL, 12.383 mmol) after 15 minutes, a solution of [7-fluoro-4-(4-fluorophenyl)-3-isopropyl-6-quinolyl]methanol (970 mg, 3.0957 mmol) in dichloromethane (3 mL) was added. The reaction mixture was then stirred 2 hours at −78° C. Triethyl amine (1.5662 g, 2.1573 mL, 15.478 mmol) was added and the reaction was stirred at −78° C. for 30 minutes. The reaction mixture was then partitioned between water (10 mL) and dichloromethane (20 mL×2), the combined organic fractions were washed with brine, dried ($Na_2SO_4$), filtered and the solvent was removed in vacuo.

Purification by silica gel chromatography (Gradient: 0-10% EtOAc in heptane) yielded the product.7-fluoro-4-(4-fluorophenyl)-3-isopropyl-quinoline-6-carbaldehyde (785 mg, 80%). $^1$H NMR (400 MHz, DMSO-$d_6$) δ 10.20 (s, 1H), 9.20 (s, 1H), 7.96 (d, J=11.8 Hz, 1H), 7.80 (d, J=7.7 Hz, 1H), 7.50-7.40 (m, 4H), 2.82 (p, J=7.0 Hz, 1H), 1.25 (d, J=7.0 Hz, 7H). LCMS m/z 312.03 [M+H]$^+$.

Step 10. Synthesis of 5-(4-fluorophenyl)-6-isopropyl-1H-pyrazolo[4,3-g]quinolone (D12)

A sealed tube 7-fluoro-4-(4-fluorophenyl)-3-isopropyl-quinoline-6-carbaldehyde (2.8 g, 8.9938 mmol), O-Methyl-hydroxylamine Hydrochloride (901.40 mg, 10.793 mmol) and $K_2CO_3$ (1.4917 g, 10.793 mmol) were mixed in DME (20 mL) for 4 h at 40° C. The reaction mixture was filtered, and concentrated in vacuo to reduce the volume (10 mL). Hydrazine hydrate (2.2512 g, 2.1920 mL of 65% w/v, 44.969 mmol) was added to the concentrated oxime solution, and the mixture was refluxed for 3 days. The reaction mixture was concentrated and partitioned between EtOAc (30 mL) and water (10 mL). The organic layer was dried over $Na_2SO_4$ and filtered and concentrated. Purification by silica gel chromatography (Gradient: 0-50% EtOAc in heptane) yielded the product. 5-(4-fluorophenyl)-6-isopropyl-1H-pyrazolo[4,3-g]quinoline (1.4 g, 50%) $^1$H NMR (400 MHz, DMSO-$d_6$) δ 13.19 (s, 1H), 9.03 (s, 1H), 8.31 (s, 1H), 8.11 (s, 1H), 7.69 (s, 1H), 7.43 (dd, J=7.4, 3.6 Hz, 4H), 2.84-2.75 (m, 1H), 1.25 (d, J=7.0 Hz, 7H). LCMS m/z 306.11 [M+H]$^+$.

Step 11. Synthesis of 5-(4-fluorophenyl)-6-isopropyl-8-oxido-1H-pyrazolo[4,3-g]quinolin-8-ium (T1)

In a vial, 5-(4-fluorophenyl)-6-isopropyl-1H-pyrazolo[4,3-g]quinoline (200 mg, 0.6550 mmol) in dichloromethane (20 mL) was cooled in an ice bath The vial was located in an ice bath, and mCPBA (225 mg, 1.304 mmol) was added. The reaction was warmed to room temperature and stirred for 16 hours. The reaction was worked up by addition of saturated $NaHCO_3$ solution and $CHCl_3$:IPA. The mixture was extracted with $CHCl_3$:IPA (×3). The organic phases were filtered through a phase separator, combined and the volatiles were evaporated in vacuo to afford the product. 5-(4-fluorophenyl)-6-isopropyl-8-oxido-1H-pyrazolo[4,3-g]quinolin-8-ium (205 mg, 97%). $^1$H NMR (400 MHz, DMSO-$d_6$) δ 13.51 (s, 1H), 8.79 (s, 1H), 8.72 (d, J=1.1 Hz, 1H), 8.40 (t, J=1.3 Hz, 1H), 7.81 (d, J=0.8 Hz, 1H), 7.46 (s, 2H), 7.44 (s, 2H), 2.77 (h, J=6.9 Hz, 1H), 1.20 (d, J=7.0 Hz, 6H). LCMS m/z 322.12 [M+H]$^+$.

Step 12. Synthesis of 7-chloro-5-(4-fluorophenyl)-6-isopropyl-1H-pyrazolo[4,3-g]quinolone (T2)

In a vial, 5-(4-fluorophenyl)-6-isopropyl-8-oxido-1H-pyrazolo[4,3-g]quinolin-8-ium (790 mg, 2.458 mmol) was weighted and suspended in $POCl_3$ (14 mL, 150.2 mmol). The reaction stirred at room temperature for 20 minutes. The reaction was worked up by evaporating the volatiles in vacuo. The residue was suspended in ice/water, then filtered, and the recovered solid was washed with cold water to afford the product. 7-chloro-5-(4-fluorophenyl)-6-isopropyl-1H-pyrazolo[4,3-g]quinoline (867 mg, 93%). $^1$H NMR (400 MHz, DMSO-$d_6$) δ 13.33 (s, 1H), 8.35 (d, J=1.1 Hz, 1H), 8.05 (t, J=1.1 Hz, 1H), 7.61 (d, J=1.0 Hz, 1H), 7.48-7.43 (m, 4H), 3.15 (br, 1H), 1.30 (d, J=5.6 Hz, 6H). LCMS m/z 340.03 [M+H]$^+$.

Preparation of T3

7-bromo-2-chloro-4-(4-fluorophenyl)-3-isopropyl-quinoline-6-carbaldehyde (T3)

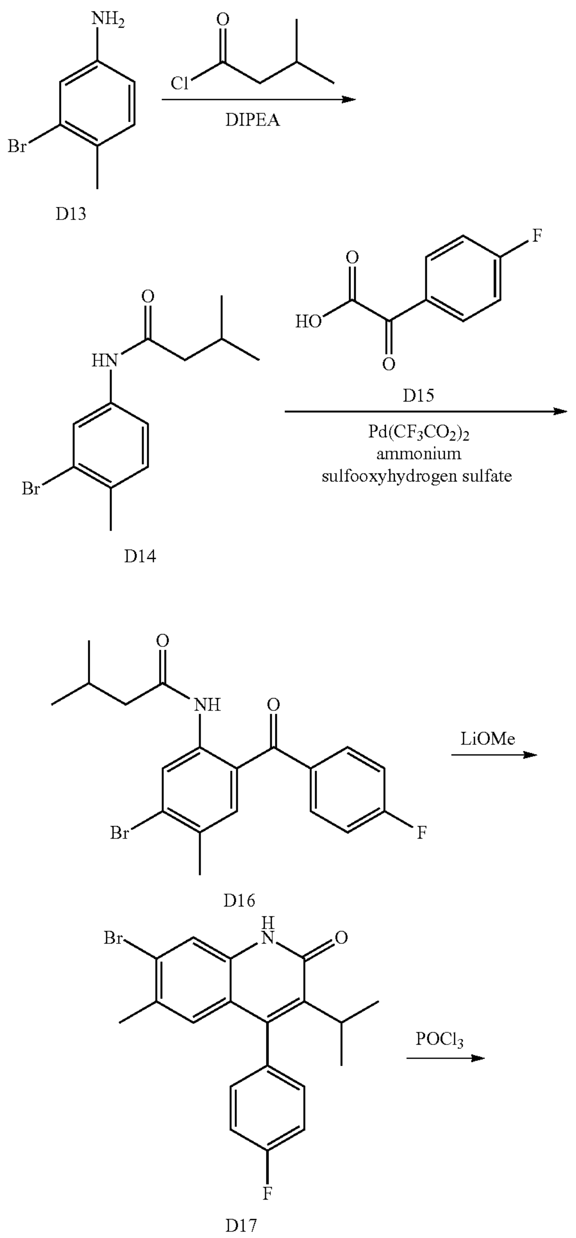

-continued

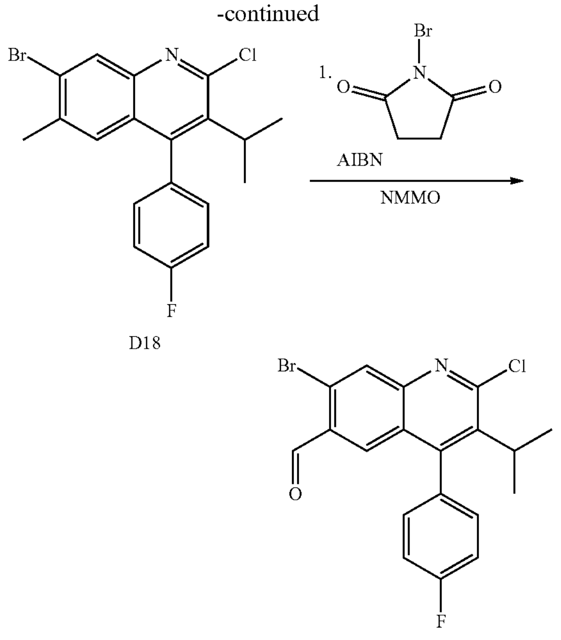

D18

T3

Step 1. Synthesis of N-(3-bromo-4-methyl-phenyl)-3-methyl-butanamide (D14)

A solution of 3-bromo-4-methyl-aniline (83 g, 446.1 mmol) and DIPEA (165 mL, 947.3 mmol) in dichloromethane (500 mL) was cooled on an ice bath. 3-methylbutanoyl chloride (60 mL, 492.1 mmol) was added portion-wise. After addition, the cooling bath was removed and the mixture allowed to stir for 30 minutes. After 2 hours, the mixture was washed with brine, 1N HCl (70 mL) and aqueous saturated sodium bicarbonate. The aqueous washings were re-extracted with dichloromethane (2×500 ml). The dichloromethane phase was dried over $Na_2SO_4$, filtered and evaporated. 10 g of this material was set aside. The remaining product was suspended in heptane plus ~5% MTBE, stirring for 1 hours. Purification by silica gel chromatography (Gradient: 0-50% EtOAc in heptane) afforded the product. N-(3-bromo-4-methyl-phenyl)-3-methyl-butanamide (118 g, 93%). $^1$H NMR (300 MHz, Chloroform-d) δ 7.80 (d, J=2.2 Hz, 1H), 7.56 (s, 1H), 7.39 (dd, J=8.3, 2.2 Hz, 1H), 7.15 (d, J=8.2 Hz, 1H), 2.35 (s, 3H), 2.30-2.11 (m, 3H), 1.15-0.80 (m, 6H). LCMS m/z 270.08 $[M+H]^+$.

Step 2. Synthesis of N-[5-bromo-2-(4-fluorobenzoyl)-4-methyl-phenyl]-3-methyl-butanamide (D16)

A suspension of N-(3-bromo-4-methyl-phenyl)-3-methyl-butanamide (35.1 g, 129.9 mmol), 2-(4-fluorophenyl)-2-oxo-acetic acid (24.3 g, 144.5 mmol) and $Pd(TFA)_2$ (2.53 g, 7.610 mmol) in diglyme (420 mL) was stirred for 5 min. Ammonia sulfooxy hydrogen sulfate (60 g, 262.9 mmol) was added. The mixture was bubbled with nitrogen and heated at 50° C. (internal temperature) for 7 hours. The solvent was distilled off under high vacuum. The residue was partitioned in EtOAc and aqueous sodium bicarbonate, extracted with EtOAc (3×). The organic phase was washed with aqueous sodium bicarbonate and brine, dried over $Na_2SO_4$, filtered and evaporated. Purification by silica gel chromatography (Gradient: 0-30% EtOAc in dichloromethane, then 0-20% EtOAc in dichloromethane) yielded the product. N-[5-bromo-2-(4-fluorobenzoyl)-4-methyl-phenyl]-3-methyl-butanamide (39.56 g, 78%). $^1$H NMR (300 MHz, Chloroform-d) δ 10.60 (s, 1H), 8.98 (s, 1H), 7.74 (dd, J=8.8, 5.3 Hz, 2H), 7.36 (d, J=0.8 Hz, 1H), 7.21 (t, J=8.6 Hz, 2H), 2.36 (s, 3H), 2.32-2.12 (m, 3H), 1.03 (d, J=6.3 Hz, 6H). LCMS m/z 392.24 $[M+H]^+$.

Step 3. Synthesis of 7-bromo-4-(4-fluorophenyl)-3-isopropyl-6-methyl-1H-quinolin-2-one (D17)

To a solution of N-[5-bromo-2-(4-fluorobenzoyl)-4-methyl-phenyl]-3-methyl-butanamide (18.39 g, 46.88 mmol) in DMF (320 mL) was added LiOMe (7.12 g, 187.5 mmol). The mixture was heated at 80° C. (internal) for 19 hours. The mixture was cooled in an ice bath, poured into water (500 mL), and acidified with 6 M HCl (30 mL). The mixture was diluted with water to 2 L, filtered. The resulting solid was washed with water (2×), then heptane. The aqueous filtrate and heptane washing were discarded. The solid was dried at 50° C. under vacuum overnight to afford the product. 7-bromo-4-(4-fluorophenyl)-3-isopropyl-6-methyl-1H-quinolin-2-one (13.8 g, 79%) $^1$H NMR (300 MHz, DMSO-$d_6$) δ 11.76 (s, 1H), 7.56 (s, 1H), 7.46-7.34 (m, 2H), 7.30 (dd, J=8.6, 5.7 Hz, 2H), 6.65 (s, 1H), 2.59 (q, J=7.0 Hz, 1H), 2.19 (s, 3H), 1.19 (d, J=6.9 Hz, 6H). LCMS m/z 374.23 $[M+H]^+$.

Step 4. Synthesis of 7-bromo-2-chloro-4-(4-fluorophenyl)-3-isopropyl-6-methyl-quinoline (D18)

A suspension of 7-bromo-4-(4-fluorophenyl)-3-isopropyl-6-methyl-1H-quinolin-2-one (13.8 g, 36.87 mmol) in phosphorus oxychloride (102.6 mL, 1.101 mol) was heated at 100° C. (sand bath) for 5 hours. The mixture was distilled under vacuum and co-distilled with toluene (100 mL) to dryness. The residue was suspended in ice water. Aqueous sodium bicarbonate was added till pH~8, extracted with dichloromethane (3×). The organic phase was dried over $Na_2SO_4$, filtered and evaporated. The residue was crystallized from dichloromethane/MTBE. The resulting precipitate was collected by filtration. The solid was washed with water (2×), and dried under high vacuum. The solid (~10 g) was purified by silica gel chromatography (Gradient: 0-100% EtOAc in heptane) to afford product in two batches 4.04 g (batch 1) and 5.67 g (batch 2), both as white solids. The filtrate (3.2 g) was purified by silica gel chromatography (Gradient: 0-100% dichloromethane in heptane) to afford 1.47 g additional product as a white solid.

7-bromo-2-chloro-4-(4-fluorophenyl)-3-isopropyl-6-methyl-quinoline (11.18 g, 77%) $^1$H NMR (300 MHz, Chloroform-d) δ 8.17 (s, 1H), 7.30-7.03 (m, 4H), 6.89 (d, J=1.1 Hz, 1H), 3.12 (br. s, 1H), 2.33 (d, J=0.9 Hz, 3H), 1.25 (d, J=7.2 Hz, 6H). LCMS m/z 392.15 $[M+H]^+$.

A by-product of this reaction was 7-bromo-2-chloro-3-isopropyl-4-(4-methoxyphenyl)-6-methyl-quinoline (D61) was also isolated. 7-bromo-2-chloro-3-isopropyl-4-(4-methoxyphenyl)-6-methyl-quinoline (170 mg, 1%). $^1$H NMR (300 MHz, Chloroform-d) δ 8.14 (s, 1H), 7.10-6.88 (m, 5H), 3.85 (s, 3H), 3.18 (s, 1H), 2.32 (d, J=0.9 Hz, 3H), 1.24 (d, J=7.2 Hz, 6H). LCMS m/z 404.22 $[M+1]^+$.

Step 5. Synthesis of 7-bromo-6-(bromomethyl)-2-chloro-4-(4-fluorophenyl)-3-isopropyl-quinoline 7-bromo-2-chloro-4-(4-fluorophenyl)-3-isopropyl-quinoline-6-carbaldehyde (T3)

A solution of 7-bromo-2-chloro-4-(4-fluorophenyl)-3-isopropyl-6-methyl-quinoline (11.07 g, 28.19 mmol), 1-bromopyrrolidine-2,5-dione (6.5 g, 36.52 mmol) and AIBN (630 mg, 3.837 mmol) in, 2-dichloroethane (110 mL) was heated at reflux under air for 3 hours. The mixture was concentrated. Purification by silica gel chromatography (Gradient: 0-100% dichloromethane in heptane) afforded the product. 7-bromo-6-(bromomethyl)-2-chloro-4-(4-fluorophenyl)-3-isopropyl-quinoline (12.4 g, 40%). LCMS m/z 469.92 $[M+H]^+$.

7-bromo-6-(bromomethyl)-2-chloro-4-(4-fluorophenyl)-3-isopropyl-quinoline was dissolved in $CH_3CN$ (110 mL). The resulting suspension was stirred with 4 Å 150° C. activated Molecular sieves (4 g) at room temperature for 10 minutes. 4-methyl-4-oxido-morpholin-4-ium (6.60 g, 56.34 mmol) was added. The mixture was stirred at 50° C. for 1 hours. The mixture was filtered through celite. The filtrate was evaporated. Purification by silica gel chromatography (Gradient: 0-20% EtOAc in heptane) yielded the product. 7-bromo-2-chloro-4-(4-fluorophenyl)-3-isopropyl-quinoline-6-carbaldehyde (6.36 g, 56%). $^1H$ NMR (300 MHz, Chloroform-d) δ 10.32 (s, 1H), 8.25 (s, 1H), 7.71 (s, 1H), 7.29-6.98 (m, 4H), 3.17 (br. s, 1H), 1.26 (d, J=7.2 Hz, 6H). LCMS m/z 405.98 $[M+H]^+$. LCMS m/z 406.2$[M+H]^+$.

Preparation of T4

7-chloro-5-(4-fluorophenyl)-6-isopropyl-9-methyl-1H-pyrazolo[4,3-g]quinolone (T4)

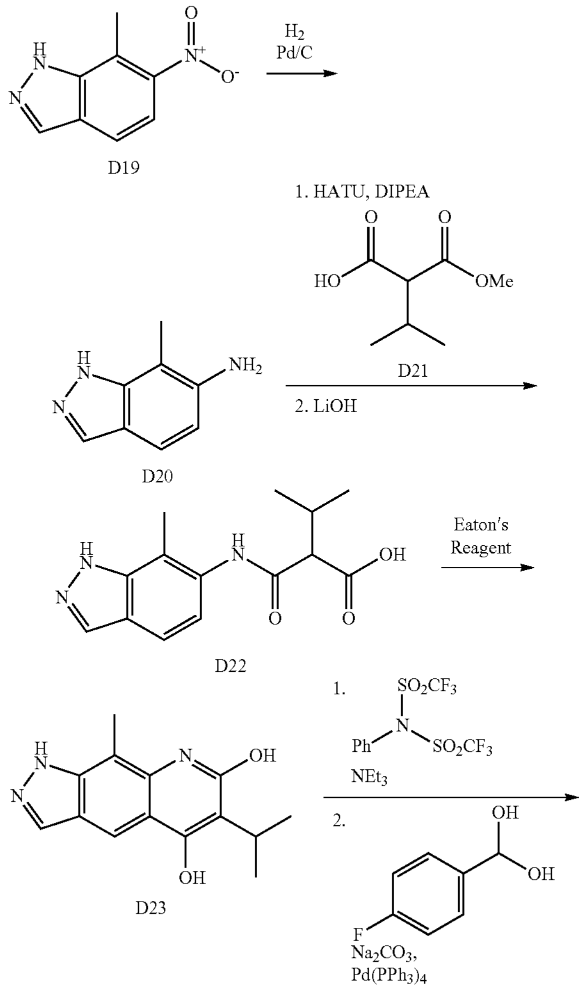

D19

D20

D22

D23

-continued

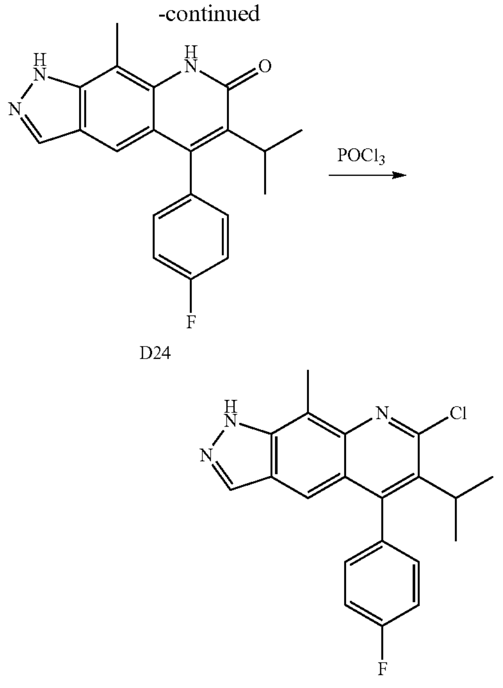

D24

T4

Step 1. Synthesis of 7-methyl-1H-indazol-6-amine (D20)

In a flask, palladium on carbon (750 mg of 10% w/w, 0.7048 mmol) was suspended in EtOH (10 mL). Then, a solution of 7-methyl-6-nitro-1H-indazole (5000 mg, 28.22 mmol) in EtOH (200 mL) was added. The flask was purged with nitrogen and then with hydrogen. The reaction was stirred at room temperature for 18 hours. The mixture was filtered through a glass fiber membrane, and the volatiles were evaporated in vacuo to obtain a cream solid. 7-methyl-1H-indazol-6-amine (4.120 g, 99%). $^1H$ NMR (400 MHz, DMSO-$d_6$) δ 12.38 (s, 1H), 7.73 (s, 1H), 7.22 (d, J=8.5 Hz, 1H), 6.54 (d, J=8.6 Hz, 1H), 4.95 (s, 2H), 2.18 (s, 3H). LCMS m/z 148.13 $[M+H]^+$.

Step 2. Synthesis of methyl 3-methyl-2-[(7-methyl-1H-indazol-6-yl)carbamoyl]butanoate 3-methyl-2-[(7-methyl-1H-indazol-6-yl)carbamoyl]butanoic acid (D22)

Part A: HATU (13.1 g, 34.45 mmol) was added to stirred solution of 7-methyl-1H-indazol-6-amine (4 g, 27.18 mmol), 2-methoxycarbonyl-3-methyl-butanoic acid (6.53 g, 40.77 mmol) and DIPEA (12 mL, 68.89 mmol) in DMF (30 mL). The solution was stirred at room temperature for 24 hours. The solution was poured into water (50 mL) and the aqueous layer was extracted with EtOAc (3×10 mL). The combined organic layers were dried and concentrated under reduced pressure to afford a yellow solid. The solid was suspended in ether (200 ml) and filtered. The solid was washed with further ether and dried in vacuo to afford methyl 3-methyl-2-[(7-methyl-1H-indazol-6-yl)carbamoyl]butanoate (7.5 g, 95%). LCMS m/z 290.6 $[M+H]^+$.

Part B: LiOH (6.5 g, 271.4 mmol) was added to a stirred solution of methyl 3-methyl-2-[(7-methyl-1H-indazol-6-yl)carbamoyl]butanoate (6 g) in MeOH (70 mL), THF (20 mL)

and water (10 mL). The solution was stirred at room temperature for 3 hours and the solvent was removed under reduced pressure. The crude product was dissolved in water (50 mL) and acidified with 6 M HCl. The white precipitate was extracted with EtOAc (3×100 mL). The combined organic layers were dried and concentrated under reduced pressure to afford 3-methyl-2-[(7-methyl-1H-indazol-6-yl) carbamoyl]butanoic acid (7 g, 91%) as yellow solid. $^1$H NMR (400 MHz, DMSO-$d_6$) δ 13.14 (s, 1H), 9.83 (s, 1H), 8.03 (d, J=1.3 Hz, 1H), 7.52 (d, J=8.5 Hz, 1H), 6.97 (d, J=8.5 Hz, 1H), 3.68 (m, 4H), 2.35 (m, 4H), 0.99 (t, J=6.6 Hz, 6H).

Step 3. Synthesis of 6-isopropyl-9-methyl-1H-pyrazolo[4,3-g]quinoline-5,7-diol (D23)

3-methyl-2-[(7-methyl-1H-indazol-6-yl)carbamoyl]butanoic acid (650 mg, 2.361 mmol) was suspended in Eaton's reagent (6 mL, 37.81 mmol) and the mixture was heated for 3 h at 150° C. The solution was poured into ice/water and slowly basified with 6N NaOH. A brown precipitate was formed and collected by filtration. The brown solid was dried at 60° C. for 2 h to afford 6-isopropyl-9-methyl-1H-pyrazolo[4,3-g]quinoline-5,7-diol (590 mg, 93%) as a brown powder. $^1$H NMR (400 MHz, DMSO-$d_6$) δ 13.03 (s, 1H), 10.12 (s, 1H), 9.91 (s, 1H), 8.17 (s, 1H), 3.44 (p, J=6.9 Hz, 1H), 2.56 (s, 3H), 1.30 (d, J=6.9 Hz, 6H). LCMS m/z 258.18 [M+H]$^+$.

Step 4. Synthesis of 7-chloro-5-(4-fluorophenyl)-6-isopropyl-9-methyl-1H-pyrazolo[4,3-g]quinolone (T4)

Part A. In a flask, 6-isopropyl-9-methyl-1H-pyrazolo[4,3-g]quinoline-5,7-diol (1.00 g, 3.887 mmol) was weighted and dissolved in a mixture of dichloromethane (15 mL) and DMF (5 mL). Then, $Et_3N$ (650 μL, 4.664 mmol) was added, followed by 1,1,1-trifluoro-N-phenyl-N-(trifluoromethylsulfonyl)methanesulfonamide (1.460 g, 4.087 mmol). The reaction was stirred for 2 hours. Water and dichloromethane were added. The mixture was extracted thrice with dichloromethane. The organic phases were filtered through a phase separator, combined and the volatiles were evaporated in vacuo. The crude mixture was triturated with cold water to afford a grey solid. (7-hydroxy-6-isopropyl-9-methyl-1H-pyrazolo[4,3-g]quinolin-5-yl) trifluoromethanesulfonate (1.4082 g, 72%) LCMS m/z 390.23 [M+H]$^+$.

Part B. (7-hydroxy-6-isopropyl-9-methyl-1H-pyrazolo[4,3-g]quinolin-5-yl) trifluoromethanesulfonate was added to a vial, together with (4-fluorophenyl)boronic acid (1.010 g, 7.218 mmol), $Pd(PPh_3)_4$ (418 mg, 0.3617 mmol) and sodium carbonate (1.150 g, 10.85 mmol). The solids were suspended in a mixture of 1,4-dioxane (8 mL) and DMF (8 mL). The mixture was heated at 160° C. μW for 60 minutes. The volatiles were evaporated in vacuo. Then, water was added to the solution to precipitate the product. The solid was filter and triturated with cold water to afford the product 5-(4-fluorophenyl)-6-isopropyl-9-methyl-1,8-dihydropyrazolo[4,3-g]quinolin-7-one (1199 mg, 99%). LCMS m/z 336.25 [M+H]$^+$.

Part C. 5-(4-fluorophenyl)-6-isopropyl-9-methyl-1,8-dihydropyrazolo[4,3-g]quinolin-7-one was suspended in phosphorus oxychloride (24.0 mL, 257.5 mmol). The suspension was heated at 100° C. for 20 minutes. Water and NaOH were added to adjust the pH to ~7. The mixture was extracted thrice with dichloromethane. The organic phases were filtered through a phase separator, combined and the volatiles were evaporated in vacuo. The product was obtained as green-yellow solid which was used without further purification. 7-chloro-5-(4-fluorophenyl)-6-isopropyl-9-methyl-1H-pyrazolo[4,3-g]quinoline (760 mg, 49%). LCMS m/z 354.26 [M+H]$^+$.

Preparation of T5 and T6

5,7-dichloro-6-isopropyl-9-methyl-1H-pyrazolo[4,3-g]quinolone (T5) and 1-[7-chloro-5-(4-fluorophenyl)-6-isopropyl-9-methyl-pyrazolo[4,3-g]quinolin-1-yl]-2,2-dimethyl-propan-1-one (T6)

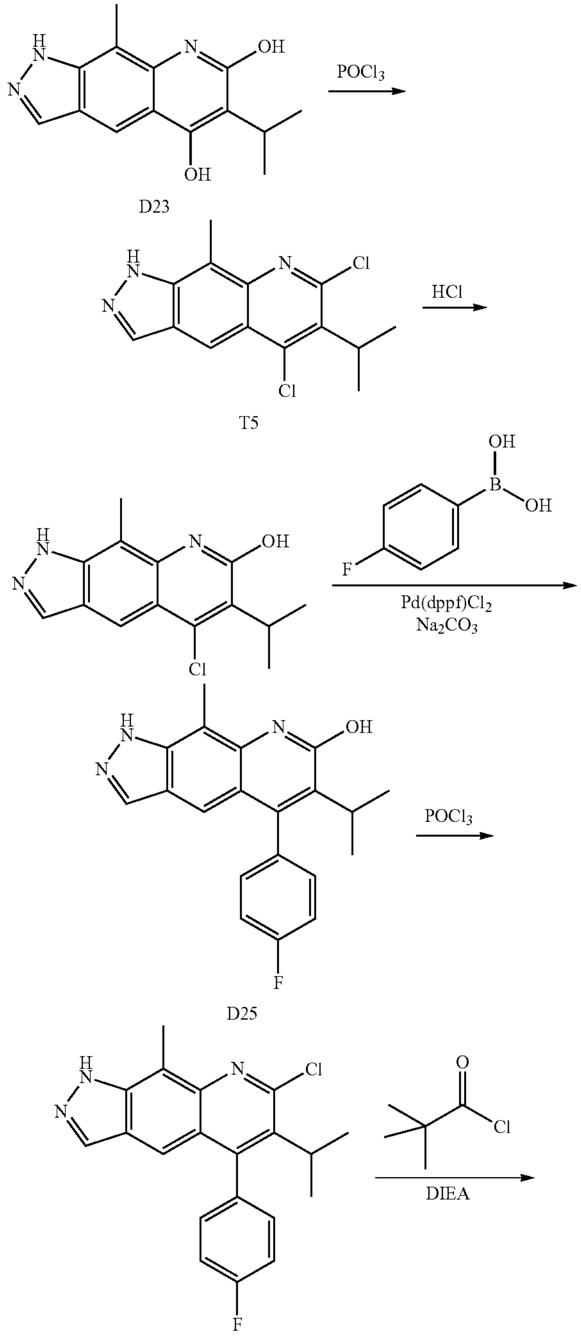

D23

T5

D25

T4

-continued

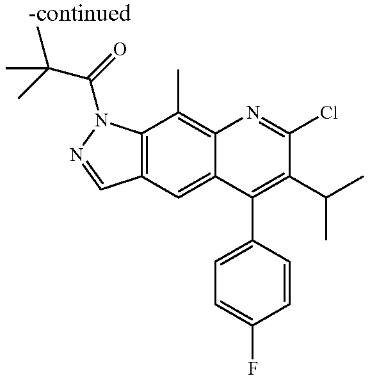

T6

Step 1. Synthesis of 5,7-dichloro-6-isopropyl-9-methyl-1H-pyrazolo[4,3-g]quinolone (T5)

6-isopropyl-9-methyl-1H-pyrazolo[4,3-g]quinoline-5,7-diol (2 g, 7.773 mmol) was suspended in $POCl_3$ (30 mL, 321.9 mmol). The brown suspension was heated at 150° C. for 3 h then cooled to room temperature. The solvent was removed under reduced pressure. The crude product was suspended in water (50 mL) and the basified with 6N NaOH. The precipitate was collected by filtration. The wet sold was lyophilized for 24 hours to afford. 5,7-dichloro-6-isopropyl-9-methyl-1H-pyrazolo[4,3-g]quinoline (2 g, 81%) as a brown solid. $^1H$ NMR (400 MHz, DMSO-$d_6$) δ 13.65 (s, 1H), 8.68 (s, 1H), 8.57 (s, 1H), 2.96 (d, J=0.9 Hz, 3H), 1.56 (d, J=7.2 Hz, 6H). LCMS m/z 294.05 $[M+H]^+$.

Step 2. Synthesis of 5-chloro-6-isopropyl-9-methyl-1H-pyrazolo[4,3-g]quinolin-7-ol HCl (25 mL of 12 M, 300.0 mmol) was added to a stirred yellow suspension of 5,7-dichloro-6-isopropyl-9-methyl-1H-pyrazolo[4,3-g]quinoline (3.5 g, 11.13 mmol) in 1,4-dioxane (100 mL). The solution was heated at 100° C. for 2 hours, then poured into ice/water to form white precipitate. The precipitate was filtered and washed with ether. The solid was lyophilized for 24 h to form 5-chloro-6-isopropyl-9-methyl-1H-pyrazolo[4,3-g]quinolin-7-ol (2.8 g, 86%) as a brown solid. LCMS m/z 276.14 $[M+H]^+$.

Step 3. Synthesis of 5-(4-fluorophenyl)-6-isopropyl-9-methyl-1H-pyrazolo[4,3-g]quinolin-7-ol (D25)

$Pd(PPh_3)_4$ (250 mg, 0.2163 mmol) was added to nitrogen purged suspension of 5-chloro-6-isopropyl-9-methyl-1H-pyrazolo[4,3-g]quinolin-7-ol (300 mg, 1.088 mmol), (4-fluorophenyl)boronic acid (380 mg, 1.086 mmol) and solid $Na_2CO_3$ (485 mg, 4.57 mmol) in DMF (2 mL) and 1,4-dioxane (8 mL). The solution was heated at 160° C. under microwave conditions for 45 minutes. The mixture was diluted with water (10 mL) and EtOAc (10 mL). The organic layer was separated and aq. layer was extracted with EtOAc. The combined organic layers were dried, and concentrated under reduced pressure. Purification by reversed-phase HPLC. Method: C18 Waters Sunfire column (30×150 mm, 5 micron). Gradient: MeCN in $H_2O$ with 0.2% formic acid to afford the product. 5-(4-fluorophenyl)-6-isopropyl-9-methyl-1H-pyrazolo[4,3-g]quinolin-7-ol (220 mg, 56%) as a white solid. $^1H$ NMR (400 MHz, DMSO-$d_6$) δ 13.28 (s, 1H), 10.83 (s, 1H), 8.29 (s, 1H), 8.26 (d, J=1.2 Hz, 1H), 3.83-3.53 (m, 1H), 2.67 (s, 3H), 1.37 (d, J=7.0 Hz, 6H). LCMS m/z 336.55 $[M+H]^+$.

Step 4. Synthesis of 7-chloro-5-(4-fluorophenyl)-6-isopropyl-9-methyl-1H-pyrazolo[4,3-g]quinolone (T4)

A solution of 5-(4-fluorophenyl)-6-isopropyl-9-methyl-1H-pyrazolo[4,3-g]quinolin-7-ol (220 mg, 0.6560 mmol) in $POCl_3$ (5 mL, 53.64 mmol) was heated at 150° C. for 2 hours and the reaction was cooled. $POCl_3$ was removed under reduced pressure and the brown solid was suspended with water (5 mL) and EtOAc (10 mL). The organic layer was dried and concentrated under reduced pressure. Purification by reversed-phase HPLC. Method: C18 Waters Sunfire column (30×150 mm, 5 micron). Gradient: MeCN in $H_2O$ with 0.2% formic acid afforded the product. 7-chloro-5-(4-fluorophenyl)-6-isopropyl-9-methyl-1H-pyrazolo[4,3-g]quinoline (90 mg, 38%) as a white solid. $^1H$ NMR (400 MHz, DMSO-$d_6$) δ 13.42 (s, 1H), 8.32 (d, J=1.4 Hz, 1H), 7.54-7.22 (m, 5H), 3.13 (m, 1H), 2.92 (d, J=0.8 Hz, 3H), 1.30 (d, J=7.0 Hz, 6H). LCMS m/z 354.11 $[M+H]^+$.

Step 5. Synthesis of 1-[7-chloro-5-(4-fluorophenyl)-6-isopropyl-9-methyl-pyrazolo[4,3-g]quinolin-1-yl]-2,2-dimethyl-propan-1-one (T6)

In a flask, 7-chloro-5-(4-fluorophenyl)-6-isopropyl-9-methyl-1H-pyrazolo[4,3-g]quinoline (120 mg, 0.3392 mmol) was dissolved in THF (3 mL). DIPEA (180 1.033 mmol) was added and the mixture was stirred for 10 minutes at room temperature. Then, 2,2-dimethylpropanoyl chloride (130 μL, 1.057 mmol) was added dropwise. The reaction was stirred at room temperature for 20 hours. The reaction was worked up by evaporating the volatiles in vacuo. Water and dichloromethane were added, and the mixture was extracted with dichloromethane (×3). The organic phases were filtered through a phase separator, combined and the volatiles were evaporated in vacuo. Purification by silica gel chromatography (Gradient: 0-2% EtOAc in heptane) yielded the product. 1-[7-chloro-5-(4-fluorophenyl)-6-isopropyl-9-methyl-pyrazolo[4,3-g]quinolin-1-yl]-2,2-dimethyl-propan-1-one (143.7 mg, 97%). LCMS m/z 438.35 $[M+H]^+$.

Preparation of T7

9-fluoro-5-hydroxy-6-isopropyl-1,8-dihydropyrazolo[4,3-g]quinolin-7-one (T7)

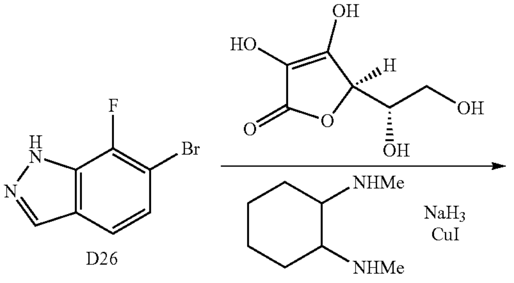

-continued

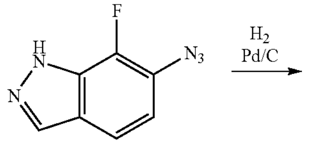

D27

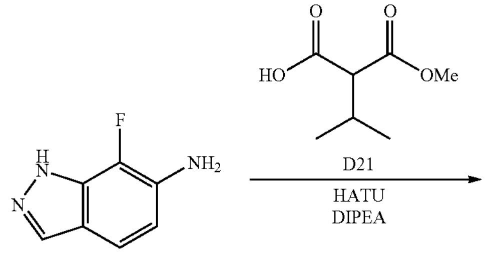

D28

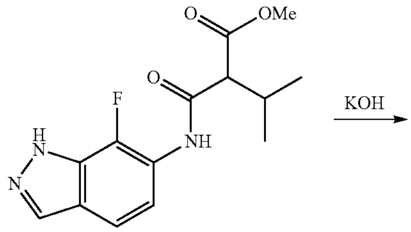

D29

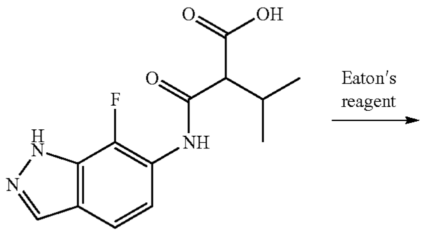

D30

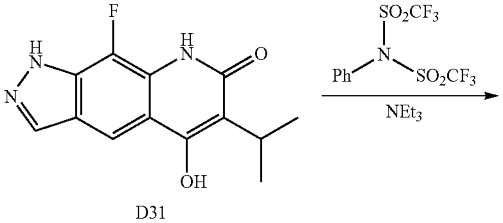

D31

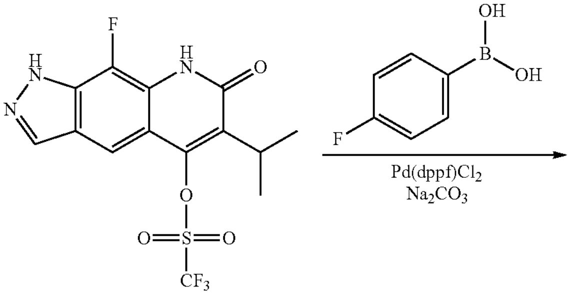

D32

-continued

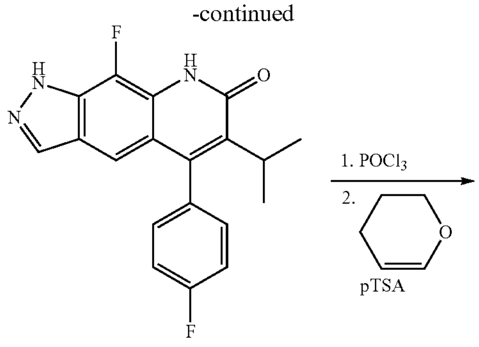

D33

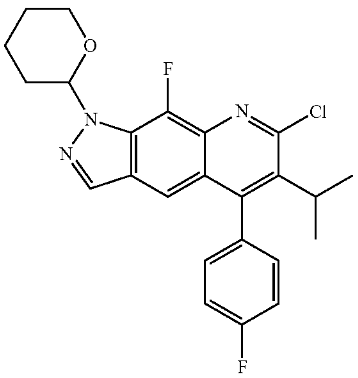

T7

Step 1. Synthesis of 6-azido-7-fluoro-1H-indazole (D27)

In a microwave vial, 6-bromo-7-fluoro-1H-indazole (1000 mg, 4.651 mmol), $NaN_3$ (605 mg, 9.306 mmol), CuI (90 mg, 0.4726 mmol) and (2R)-2-[(1S)-1,2-dihydroxyethyl]-4-hydroxy-5-oxo-2H-furan-3-olate (Sodium salt) (45 mg, 0.2272 mmol) were dissolved in degassed EtOH (7 mL)/Water (3 mL) containing N1, N2-dimethylcyclohexane-1,2-diamine (100 mg, 0.7030 mmol). The vial was sealed and heated at 80° C. for 4 hours. Water and dichloromethane were added. The mixture was extracted with dichloromethane (×3). The organic phases were combined, dried with $MgSO_4$, filtered and the volatiles were evaporated in vacuo. Purification by reversed-phase chromatography (Column: C18. Gradient: 0-100% MeCN in water with 0.2% formic acid) afforded the product. 6-azido-7-fluoro-1H-indazole (650 mg, 79%). $^1$H NMR (400 MHz, Methanol-$d_4$) δ 8.05 (d, J=3.4 Hz, 1H), 7.55 (d, J=8.6 Hz, 1H), 6.91 (dd, J=8.6, 6.8 Hz, 1H). LCMS m/z 178.12 $[M+H]^+$.

Step 2. Synthesis of 7-fluoro-1H-indazol-6-amine (D28)

In a flask, 6-azido-7-fluoro-1H-indazole (120 mg, 0.6774 mmol) were weighted and dissolved in Ethanol (7 mL). Then, palladium on carbon (36 mg, 0.03383 mmol) was added. The flask was purged with nitrogen three times, and then placed under a hydrogen atmosphere. The reaction was stirred at room temperature for 16 hours. The reaction was worked up by filtering the mixture through a short pad of Celite®, and removing the volatiles in vacuo. The product was used without further purification. 7-fluoro-1H-indazol-6-amine (100 mg, 98%). LCMS m/z 152.09 $[M+H]^+$.

Step 3. Synthesis of methyl 2-[(7-fluoro-1H-indazol-6-yl)carbamoyl]-3-methyl-butanoate (D29)

In a flask, 7-fluoro-1H-indazol-6-amine (90 mg, 0.5955 mmol) was suspended in dichloromethane (6 mL). Then, 2-methoxycarbonyl-3-methyl-butanoic acid (160 mg, 0.8991 mmol) was added, followed by HATU (270 mg, 0.7101 mmol) and finally DIPEA (300 μL, 1.722 mmol). The mixture was stirred at room temperature for 30 minutes. The reaction was worked up by addition of water and dichloromethane and then extracted with dichloromethane (×3). The organic phases were filtered through a phase separator, combined and the volatiles were evaporated in vacuo. The crude was purified by flash column chromatography Purification by silica gel chromatography (Gradient: 0-7% MeOH in dichloromethane) yielded the product. Methyl 2-[(7-fluoro-1H-indazol-6-yl)carbamoyl]-3-methyl-butanoate (224.2 mg, 90%, purity 70%). LCMS m/z 282.05 $[M+H]^+$.

Step 4. Synthesis of 2-[(7-fluoro-1H-indazol-6-yl) carbamoyl]-3-methyl-butanoic acid (D30)

In a flask, methyl 2-[(7-fluoro-1H-indazol-6-yl)carbamoyl]-3-methyl-butanoate (1350 mg, 3.237 mmol) and KOH (545 mg, 9.714 mmol) were added and dissolved in EtOH (27 mL) and $H_2O$ (3 mL). The reaction was stirred at room temperature for 16 hours. The reaction was worked up by evaporating the volatiles, then adding water and bringing the pH to 2. The mixture was extracted with $CHCl_3$:IPA (×3). The organic phases were filtered through a phase separator, combined and the volatiles were evaporated in vacuo to afford the product as a white. 2-[(7-fluoro-1H-indazol-6-yl) carbamoyl]-3-methyl-butanoic acid (875 mg, 97%). LCMS m/z 280.15 $[M+H]^+$.

Step 5. Synthesis of 9-fluoro-5-hydroxy-6-isopropyl-1,8-dihydropyrazolo[4,3-g]quinolin-7-one (D31)

In a vial, 2-[(7-fluoro-1H-indazol-6-yl)carbamoyl]-3-methyl-butanoic acid (135 mg, 0.4834 mmol) was weighted and suspended in Eaton's reagent (2000 μL, 12.60 mmol). The reaction was heated at 80° C. for 96 hours (decarboxylation outcompetes the cyclization when heated at higher temperatures). The reaction was worked up by addition of brine, and bringing the pH to 7 with aqueous 6M NaOH, and performing successive extractions with $CHCl_3$:IPA. The organic phases were combined, dried with $MgSO_4$, filtered and the volatiles were evaporated in vacuo. Purification by silica gel chromatography (Gradient: 0-5% dichloromethane in MeOH) yielded the product. 9-fluoro-5-hydroxy-6-isopropyl-1,8-dihydropyrazolo[4,3-g]quinolin-7-one (46.4 mg, 37%). $^1H$ NMR (400 MHz, DMSO-$d_6$) δ 13.50 (s, 1H), 11.00 (s, 1H), 10.14 (s, 1H), 8.28 (dd, J=3.4, 1.5 Hz, 1H), 8.17 (s, 1H), 3.43 (heptet, J=6.9 Hz, 1H), 1.30 (d, J=7.0 Hz, 6H). LCMS m/z 262.19 $[M+H]^+$.

Step 6. Synthesis of (9-fluoro-6-isopropyl-7-oxo-1,8-dihydropyrazolo[4,3-g]quinolin-5-yl)trifluoromethanesulfonate (D32)

In a flask, 9-fluoro-5-hydroxy-6-isopropyl-1,8-dihydropyrazolo[4,3-g]quinolin-7-one (210 mg, 0.7835 mmol) was weighted was dissolved in DMF (6 mL). Then, $Et_3N$ (130 μL, 0.9327 mmol) was added followed by $PhN(SO_2CF_3)_2$ (330 mg, 0.9237 mmol). The reaction was stirred at room temperature for 1 hour. The reaction was worked up by addition of water and dichloromethane. The mixture was extracted with dichloromethane (×3). The organic phases were filtered through a phase separator, combined and the volatiles were evaporated in vacuo. Purification by silica gel chromatography (Gradient: 0-5% dichloromethane in MeOH) yielded the product as a white solid. (9-fluoro-6-isopropyl-7-oxo-1,8-dihydropyrazolo[4,3-g]quinolin-5-yl) trifluoromethanesulfonate (255.5 mg, 92%). $^1H$ NMR (400 MHz, DMSO-$d_6$) δ 13.83 (s, 1H), 12.13 (s, 1H), 8.45 (dd, J=3.3, 1.3 Hz, 1H), 7.93 (s, 1H), 3.28-3.12 (m, 1H), 1.39 (d, J=6.9 Hz, 6H). LCMS m/z 394.23 $[M+H]^+$.

Step 7. Synthesis of 9-fluoro-5-(4-fluorophenyl)-6-isopropyl-1,8-dihydropyrazolo[4,3-g]quinolin-7-one (D33)

In a vial, (9-fluoro-6-isopropyl-7-oxo-1,8-dihydropyrazolo[4,3-g]quinolin-5-yl) trifluoromethanesulfonate (276 mg, 0.70 mmol), 4-Fluorophenylboronic acid (300 mg, 2.14 mmol), $Na_2CO_3$ (225 mg, 2.123 mmol) and $Pd(PPh_3)_4$ (80 mg, 0.069 mmol) were suspended in 1,4-dioxane (4.5 mL). The reaction was heated at 160° C. for 2 hours. The volatiles were evaporated in vacuo, then water and dichloromethane were added. The mixture was extracted with dichloromethane (×3). The organic phases were filtered through a phase separator, combined and the volatiles were evaporated in vacuo. Purification by silica gel chromatography (Gradient: 0-5% dichloromethane in MeOH) afforded the product as a pale orange solid. 9-fluoro-5-(4-fluorophenyl)-6-isopropyl-1,8-dihydropyrazolo[4,3-g]quinolin-7-one (72.9 mg, 31%). LCMS m/z 340.26 $[M+H]^+$.

Step 8. Synthesis of 7-chloro-9-fluoro-5-(4-fluorophenyl)-6-isopropyl-1-tetrahydropyran-2-yl-pyrazolo [4,3-g]quinolone (T7)

Part A. In a vial, 9-fluoro-5-(4-fluorophenyl)-6-isopropyl-1,8-dihydropyrazolo[4,3-g]quinolin-7-one (78 mg, 0.2299 mmol) was weighted and suspended in phosphorus oxychloride (1.0 mL, 10.73 mmol). The reaction was heated at 100° C. for 5 minutes. The reaction was worked up by addition of water and dichloromethane. The mixture was extracted with dichloromethane (×3). The organic phases were filtered through a phase separator, combined and the volatiles were evaporated in vacuo. The crude was used without further purification. LCMS m/z 358.22 $[M+H]^+$.

Part B. In a flask, the crude from Part A was re-suspended in dichloromethane (2.5 mL). Then, 3,4-dihydro-2H-pyran (105 1.15 mmol) was added, followed by 4-methylbenzenesulfonic acid monohydrate (2.5 mg, 0.01314 mmol). The reaction was stirred at room temperature for 30 minutes. Water and dichloromethane were added. The mixture was extracted with dichloromethane (×3). The organic phases were filtered through a phase separator, combined, and the volatiles were evaporated in vacuo. Purification by silica gel column chromatography (Gradient: 0-20% of EtOAc in Heptane) afforded the product. 7-chloro-9-fluoro-5-(4-fluorophenyl)-6-isopropyl-1-tetrahydropyran-2-yl-pyrazolo[4,3-g]quinoline (103.4 mg, 100%) LCMS m/z 442.35 $[M+H]^+$.

Preparation of T8 and T9

7-bromo-2-chloro-4-(4-fluorophenyl)-6-methyl-3-tetrahydropyran-4-yl-quinoline (T8) and 7-bromo-6-(bromomethyl)-2-chloro-4-(4-fluorophenyl)-3-tetrahydropyran-4-yl-quinoline (T9)

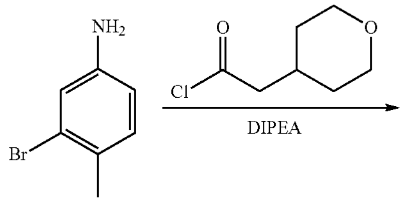

D13

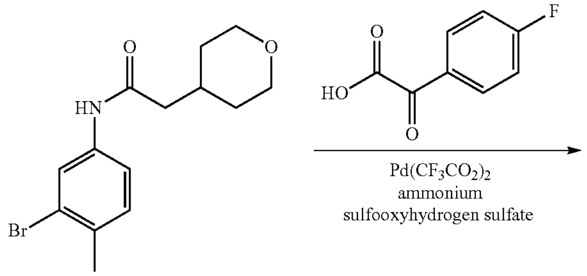

D34

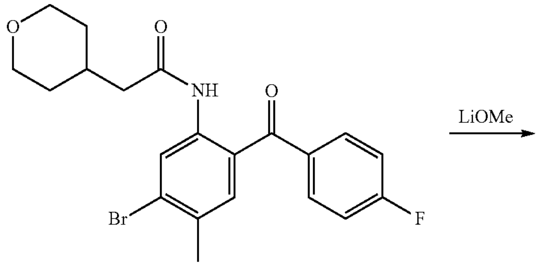

D35

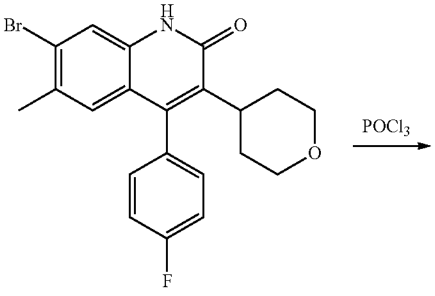

D36

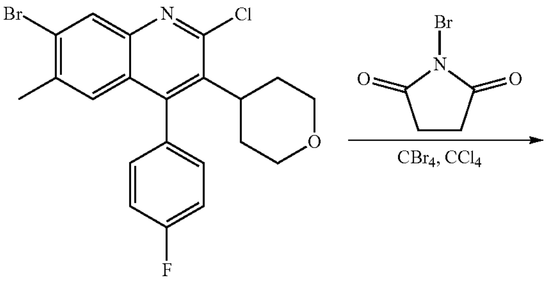

D37

-continued

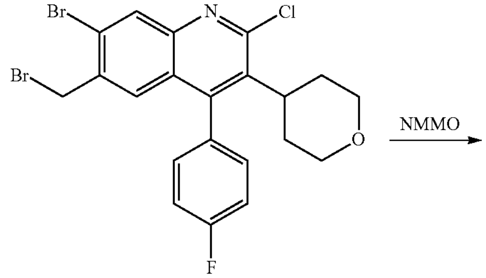

D38

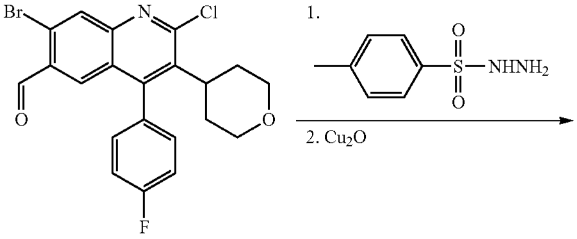

T8

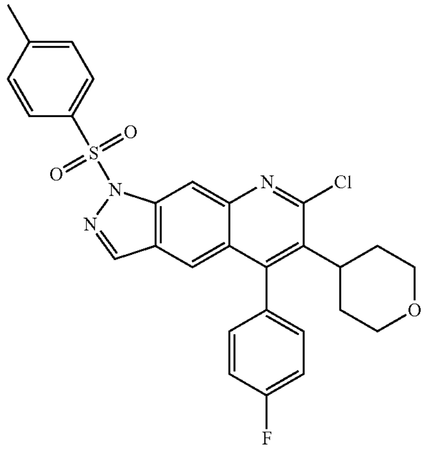

T9

Step 1. N-(3-bromo-4-methyl-phenyl)-2-tetrahydropyran-4-yl-acetamide (D34)

In a flask containing 3-bromo-4-methyl-aniline (1.78 g, 9.376 mmol) in DMF (21.6 mL) was added 2-tetrahydropyran-4-ylacetic acid (1.38 g, 9.381 mmol), HATU (4.26 g, 11.20 mmol) and DIPEA (5.6 mL, 32.15 mmol). The solution was then stirred overnight at rt and was quenched with a large amount of water and diluted with AcOEt. The phases were separated and the aqueous phase was extracted twice with AcOEt. The combined organic layers were dried over $Na_2SO_4$, filtered and evaporated. Purification by silica gel chromatography (Gradient: 0-100% EtOAc/Heptane) gave N-(3-bromo-4-methyl-phenyl)-2-tetrahydropyran-4-yl-acetamide (2.52 g, 85%) 1H NMR (400 MHz, DMSO-$d_6$) δ 9.99 (s, 1H), 7.98 (d, J=2.1 Hz, 1H), 7.38 (dd, J=8.3, 2.1 Hz, 1H), 7.25 (d, J=8.7 Hz, 1H), 3.81 (dd, J=11.4, 2.5 Hz, 2H), 3.29 (td, J=11.7, 2.1 Hz, 2H), 2.27 (s, 3H), 2.22 (d, J=7.2 Hz, 2H), 1.97 (dtq, J=14.9, 7.4, 3.7 Hz, 1H), 1.62-1.51 (m, 2H), 1.22 (qd, J=12.1, 4.6 Hz, 2H). ESI-MS m/z calc. 311.0521, found 312.04 $(M+1)^+$ Step 2. N-[5-bromo-2-(4-fluorobenzoyl)-4-methyl-phenyl]-2-tetrahydropyran-4-yl-acetamide (D35)

A vial was charged with N-(3-bromo-4-methyl-phenyl)-2-tetrahydropyran-4-yl-acetamide (886 mg, 2.838 mmol), 2-(4-fluorophenyl)-2-oxo-acetic acid (716 mg, 4.259 mmol), bis[(2,2,2-trifluoroacetyl)oxy]palladium (94 mg, 0.2827 mmol) and ammonium sulfoxyhydrogen sulfate (1.3 g, 5.697 mmol). The vial was sealed and purged with one vacuum/$N_2$ cycle then diglyme (9.5 mL) was added and the reaction was stirred a t 70° C. for 3 hours. The mixture was evaporated at 80° C. under high vacuum and the residue was suspended in DCM, filtered through celite and evaporated to dryness. Purification by silica gel chromatography (Gradient: 0-100% EtOAc/Heptane) gave N-[5-bromo-2-(4-fluorobenzoyl)-4-methyl-phenyl]-2-tetrahydropyran-4-yl-acetamide (1.23 g, 100%). $^1$H NMR (400 MHz, Chloroform-d) δ 10.62 (s, 1H), 8.92 (s, 1H), 7.76-7.68 (m, 2H), 7.34 (s, 1H), 7.22-7.15 (m, 2H), 3.94 (dd, J=10.7, 3.6 Hz, 2H), 3.42 (td, J=12.0, 2.2 Hz, 2H), 2.36-2.31 (m, 5H), 2.22-2.05 (m, 1H), 1.73-1.65 (m, 2H), 1.47-1.32 (m, 2H). ESI-MS m/z calc. 433.06888, found 434.1 $(M+1)^+$ Step 3. Synthesis of 7-bromo-4-(4-fluorophenyl)-6-methyl-3-tetrahydropyran-4-yl-1H-quinolin-2-one (D36)

To a solution of N-[5-bromo-2-(4-fluorobenzoyl)-4-methyl-phenyl]-2-tetrahydropyran-4-yl-acetamide (1.23 g, 2.832 mmol) in DMF (9.4 mL) was added LiOMe (419 mg, 11.03 mmol).

The mixture was heated overnight at 80° C. The mixture was cooled to room temperature, poured into aqueous saturated $NH_4Cl$ (400 mL) yielding a yellow precipitate was formed. Solid was collected through filtration, washed with water and heptane. The solid was solubilized in dichloromethane and the solution was dried over sodium sulfate, filtered and evaporated to afford the product. 7-bromo-4-(4-fluorophenyl)-6-methyl-3-tetrahydropyran-4-yl-1H-quinolin-2-one (1.027 g, 78%). $^1$H NMR (400 MHz, DMSO-$d_6$) δ 11.87 (s, 1H), 7.56 (s, 1H), 7.40 (t, J=8.8 Hz, 2H), 7.35-7.29 (m, 2H), 6.66 (s, 1H), 3.79 (d, J=10.5 Hz, 2H), 3.04-2.95 (m, 2H), 2.47-2.40 (m, 2H), 2.20 (s, 3H), 2.16 (t, J=5.9 Hz, 1H), 1.28-1.19 (m, 2H). LCMS m/z 416.06 $[M+H]^+$.

Step 4. Synthesis of 7-bromo-2-chloro-4-(4-fluorophenyl)-6-methyl-3-tetrahydropyran-4-yl-quinoline (D37)

A suspension of 7-bromo-4-(4-fluorophenyl)-6-methyl-3-tetrahydropyran-4-yl-1H-quinolin-2-one (3.9 g, 9.163 mmol) in phosphorus oxychloride (12.8 mL, 137.3 mmol) was heated at 100° C. for 3 hours. The mixture was evaporated to dryness and co-evaporated twice with toluene. The residue was solubilized in dichloromethane and an excess of a saturated solution of $NaHCO_3$ was added. The biphasic solution was stirred for 15 minutes and pH was checked to make sure the aqueous phase remained basic. The phases were separated and the aqueous phase was extracted twice with dichloromethane. The combined organic layers were dried over $Na_2SO_4$, filtered and evaporated to afford the product. 7-bromo-2-chloro-4-(4-fluorophenyl)-6-methyl-3-tetrahydropyran-4-yl-quinoline (3.89 g, 92%). $^1$H NMR (400 MHz, DMSO-$d_6$) δ 8.27 (s, 1H), 7.49-7.35 (m, 4H), 7.05 (s, 1H), 3.90-3.77 (m, 2H), 3.16-2.92 (m, 3H), 2.38 (s, 3H), 1.46 (d, J=11.5 Hz, 2H). (2H are missing in $^1$H NMR corresponding to $CH_2$ from THP ring). LCMS m/z 434.05 $[M+H]^+$.

Step 5. Synthesis of 7-bromo-6-(bromomethyl)-2-chloro-4-(4-fluorophenyl)-3-tetrahydropyran-4-yl-quinoline (D38)

7-bromo-2-chloro-4-(4-fluorophenyl)-6-methyl-3-tetrahydropyran-4-yl-quinoline (1 g, 2.169 mmol), $CBr_4$ (71 mg, 0.2141 mmol) and N-bromosuccinimide (425 mg, 2.388 mmol) were added to a vial. The vial was sealed and was purged with one vacuum/nitrogen cycle. $CCl_4$ (21.7 mL) was added and the reaction was stirred under compact fluorescent white light for 1 hour. The solvent was evaporated to dryness. Purification by silica gel chromatography (Gradient: 0-100% EtOAc in dichloromethane) yielded the product 7-bromo-6-(bromomethyl)-2-chloro-4-(4-fluorophenyl)-3-tetrahydropyran-4-yl-quinoline (966 mg, 72%). LCMS m/z 511.88 $[M+H]^+$.

Step 6. Synthesis of 7-bromo-2-chloro-4-(4-fluorophenyl)-3-tetrahydropyran-4-yl-quinoline-6-carbaldehyde (T8)

To a solution of 7-bromo-6-(bromomethyl)-2-chloro-4-(4-fluorophenyl)-3-tetrahydropyran-4-yl-quinoline (906 mg, 1.376 mmol) in acetonitrile (13.8 mL) were added 6 activated molecular sieves and 4-methylmorpholine N-oxide (322 mg, 2.749 mmol). The reaction was stirred at room temperature for 2 hours and then filtered. The filtrate was evaporated and purified by Purification by silica gel chromatography (Gradient: 0-100% EtOAc in dichloromethane) yielded the product. 7-bromo-2-chloro-4-(4-fluorophenyl)-3-tetrahydropyran-4-yl-quinoline-6-carbaldehyde (644 mg, 99%). LCMS m/z 448.13 $[M+H]^+$.

Step 7. Synthesis of 7-chloro-5-(4-fluorophenyl)-1-(p-tolylsulfonyl)-6-tetrahydropyran-4-yl-pyrazolo[4,3-g]quinolone (T9)

To a solution of 7-bromo-2-chloro-4-(4-fluorophenyl)-3-tetrahydropyran-4-yl-quinoline-6-carbaldehyde (215 mg, 0.4552 mmol) in Ethanol (2.3 mL) was added 4-methylbenzenesulfonohydrazide (87 mg, 0.4531 mmol) and acetic acid (26 μL, 0.4572 mmol).

The reaction was heated at 50° C. for 1 hours. LCMS showed the formation of the desired N-[(E)-[7-bromo-2-chloro-4-(4-fluorophenyl)-3-tetrahydropyran-4-yl-6-quinolyl]methyleneamino]-4-methyl-benzenesulfonamide (280 mg, 100%). LCMS m/z 616.13 $[M+1]^+$. The reaction was evaporated to dryness and trace acetic acid was removed by co-evaporating with toluene.

The white solid was transferred to a vial with cupriooxycopper (33 mg, 0.2306 mmol). The vial was sealed and was purged with one vacuum/$N_2$ cycle. 3-methylbutan-1-ol (4.6 mL) was added and the reaction was heated at 130° C. for 30 min. The reaction was cooled to room temperature and was directly subjected to purification by silica gel chromatography (Gradient: 0-100% EtOAc/Heptane) and yielded 7-chloro-5-(4-fluorophenyl)-1-(p-tolylsulfonyl)-6-tetrahydropyran-4-yl-pyrazolo[4,3-g]quinoline (198 mg, 77%). $^1$H NMR (400 MHz, Chloroform-d) δ 8.85 (s, 1H), 8.25 (d, J=1.0 Hz, 1H), 7.92-7.87 (m, 2H), 7.53 (s, 1H), 7.30-7.27 (m, 2H), 7.25-7.14 (m, 4H), 4.04-3.91 (m, 2H), 3.37-3.15 (m, 3H), 2.33 (s, 3H), 1.49-1.37 (m, 2H), 1.34-1.16 (m, 2H). LCMS m/z 536.09 $[M+H]^+$.

Preparation of T10

7-chloro-5-(4-fluorophenyl)-1H-pyrazolo[4,3-g]quinoline-6-carboxylic acid (T10)

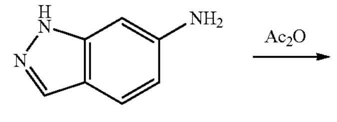

D39

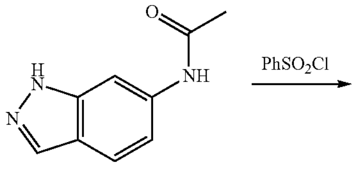

D40

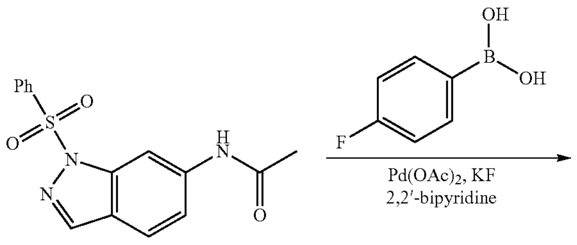

D41

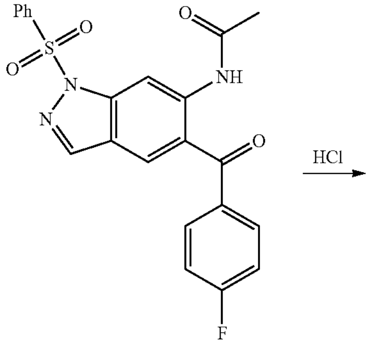

D42

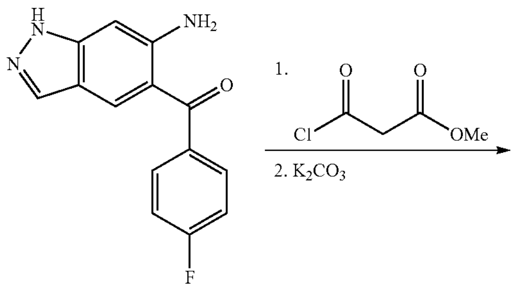

D43

-continued

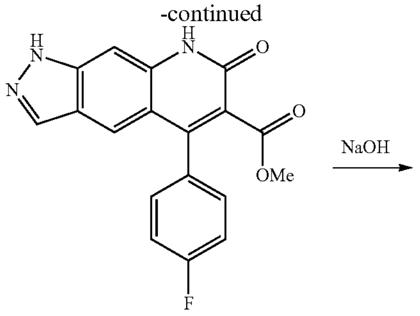

D44

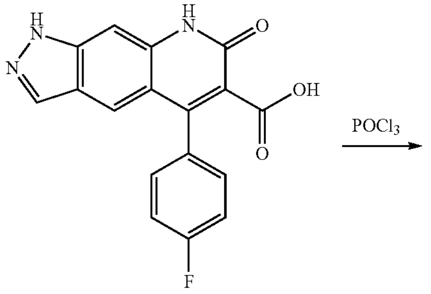

D45

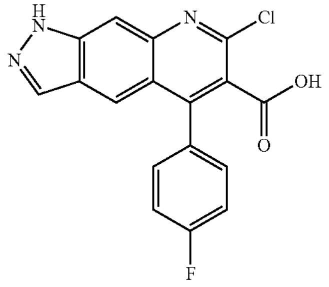

T10

Step 1. Synthesis of N-(1H-indazol-6-yl)acetamide (D40)

In a three-necked flask equipped with and addition funnel and a temperature probe, to a suspension of 1H-indazol-6-amine (100.2 g, 752.53 mmol) in anhydrous THF (1 L) at room temperature was added dropwise acetic anhydride (78.986 g, 73 mL, 773.70 mmol) over 2.25 hours. The mixture was stirred at room temperature for an additional 20 hours. Then a solution of sodium hydroxide (32.98 g, 824.56 mmol) in water (500 mL) was added over 15 minutes at room temperature. The mixture was vigorously stirred for 30 minutes. The THF was removed under reduced pressure. More water (180 mL) was added and the suspension was stirred for 1 hour at 0° C. The solid was filtered, washed with water (2×100 mL) and dried under vacuum to afford N-(1H-indazol-6-yl)acetamide (128.82 g, 98%) as beige solid.

Note: Acetic anhydride was added dropwise over 2.25 hours. During this addition the internal temperature increased from 18° C. to 29° C. During the addition of aqueous NaOH, the internal temperature reached 33° C. $^{1}H$ NMR (300 MHz, DMSO-$d_6$): δ 12.86 (s, 1H), 10.08 (s, 1H), 8.16 (s, 1H), 7.94 (s, 1H), 7.63 (d, J=8.6 Hz, 1H), 7.04 (dd, J=8.6, 1.6 Hz, 1H), 2.07 (s, 3H). LCMS m/z 176.2 $[M+H]^+$.

Step 2. Synthesis of N-[1-(benzenesulfonyl)indazol-6-yl]acetamide (D41)

To a suspension of N-(1H-indazol-6-yl)acetamide (31.8 g, 181.52 mmol) in anhydrous dichloroethane (400 mL) was added anhydrous pyridine (29.340 g, 30 mL, 370.92 mmol) and benzenesulfonyl chloride (33.216 g, 24 mL, 188.06 mmol) at room temperature. The mixture was heated at 25-27° C. and maintained at this temperature for 72 hours. More benzenesulfonyl chloride (6.2280 g, 4.5 mL, 35.3 mmol) was added and after an additional 24 hours at 25-27° C., the solvent was removed under reduced pressure. The solid was triturated in water (1×250 mL) for 20 minutes at 0° C. then filtered, washed with water (3×75 mL) and dried under vacuum. The residue was triturated in MTBE (1×125 mL) and in a mixture of MTBE and THF (125 mL/10 mL) filtered and dried to afford N-[1-(benzenesulfonyl)indazol-6-yl]acetamide (56.04 g, 96%) as pink solid. $^1H$ NMR (300 MHz, DMSO-$d_6$) δ 10.40 (br s, 1H), 8.69-8.64 (m, 1H), 8.43 (d, J=0.9 Hz, 1H), 7.90-7.83 (m, 2H), 7.78-7.67 (m, 2H), 7.64-7.55 (m, 2H), 7.51 (dd, J=8.7, 1.7 Hz, 1H), 2.12 (s, 3H), LCMS m/z 316.1 $[M+H]^+$.

Step 3. Synthesis of N-[1-(benzenesulfonyl)-5-(4-fluorobenzoyl)indazol-6-yl]acetamide (D42)

In a flask, N-[1-(benzenesulfonyl)indazol-6-yl]acetamide (8.3 g, 26.32 mmol), 2-(4-fluorophenyl)-2-oxo-acetic acid (5.300 g, 31.52 mmol), bis[(2,2,2-trifluoroacetyl)oxy]palladium (1.750 g, 5.264 mmol) and ammonia sulfooxy hydrogen sulfate (24.00 g, 105.2 mmol) were added and suspended in 1-methoxy-2-(2-methoxyethoxy)ethane (110 mL). The reaction was stirred at 65° C. for 5 hours. An additional 0.2 equivalents of the catalyst was added and allowed to stir for an additional 40 hours of reaction.

The reaction was worked up by addition of water and dichloromethane. The mixture was extracted thrice with dichloromethane. The organic phases were filtered through a phase separator, combined and the volatiles were evaporated in vacuo. The crude was triturated with cold water, cold methanol and heptane. A brown solid was obtained. N-[1-(benzenesulfonyl)-5-(4-fluorobenzoyl)indazol-6-yl] acetamide (12.59 g, 77%). LCMS m/z 438.3 $[M+H]^+$.

Step 4. Synthesis of (6-amino-1H-indazol-5-yl)-(4-fluorophenyl)methanone (D43)

To a suspension of N-[1-(benzenesulfonyl)-5-(4-fluorobenzoyl)indazol-6-yl]acetamide (2.45 g, 5.5335 mmol) in water (20 mL) was added concentrated hydrogen chloride (40 mL of 12 M, 480.00 mmol) (12 M solution in water). The mixture was heated to 85° C. for 17 hours. After being cooled to room temperature, more concentrated hydrogen chloride (15 mL of 12 M, 180.00 mmol) (12 M solution in water) was added. The mixture was heated to 95° C. and maintained at this temperature for 7 hours. It was cooled to room temperature and stirred overnight. After being cooled to 0-5° C., 25% w/w aqueous NaOH, then 1 N aqueous NaOH were added dropwise to adjust pH to ~pH 6-7. The precipitated solid was filtered, washed with water (3×15 mL), then dried under vacuum to afford (6-amino-1H-indazol-5-yl)-(4-fluorophenyl)methanone (1.41 g, 100%) as brown solid. $^1H$ NMR (300 MHz, DMSO-$d_6$) δ 12.56 (br s, 1H), 7.90 (s, 1H), 7.77 (s, 1H), 7.74-7.64 (m, 2H), 7.42-7.29 (m, 2H), 6.79-6.58 (m, 3H), 19F NMR (282 MHz, DMSO-$d_6$) δ −108.7-109.0 (m, 1F), LCMS m/z 256.1 $[M+H]^+$.

Step 5. Synthesis of methyl 5-(4-fluorophenyl)-7-oxo-1,8-dihydropyrazolo[4,3-g]quinoline-6-carboxylate (D44)

Part A. In a vial, (6-amino-1H-indazol-5-yl)-(4-fluorophenyl)methanone (2000 mg, 7.555 mmol) was weighted and suspended in dichloromethane (30 mL). Then, pyridine (610 μL, 7.542 mmol) was added and the mixture was stirred at room temperature for 5 minutes. After this time, methyl 3-chloro-3-oxo-propanoate (1.550 g, 11.35 mmol) was added dropwise. The reaction was stirred for 1 hour. An additional equivalent of acyl chloride was added. The reaction was stirred at room temperature for an additional hour. The reaction was worked up by addition of water and $CHCl_3$:IPA (3:1). The mixture was extracted with CHCl3: IPA (3:1) (×3). The organic phases were filtered through a phase separator, combined and the volatiles were evaporated in vacuo. The crude product was used in the next step without further purification.

Part B. The crude product from part A was re-suspended in DMF (30 mL) and $K_2CO_3$ (1.360 g, 9.840 mmol) was added. The reaction was stirred at 70° C. for 3 hours. Water and $CHCl_3$:IPA (3:1) were added. The mixture was extracted with CHCl3:IPA (3:1) (×3). The organic phases were filtered through a phase separator, combined and the volatiles were evaporated in vacuo. The crude was suspended in water and precipitated by addition of 1M HCl. The solid was filtered and washed with cold water. A pale yellow solid was obtained. methyl 5-(4-fluorophenyl)-7-oxo-1,8-dihydropyrazolo[4,3-g]quinoline-6-carboxylate (2.3972 g, 94%). $^1H$ NMR (400 MHz, DMSO-$d_6$) δ 13.11 (s, 1H), 12.12 (s, 1H), 8.16 (t, J=1.2 Hz, 1H), 7.58 (s, 1H), 7.45-7.37 (m, 5H), 3.50 (s, 3H). LCMS m/z 338.05 $[M+H]^+$.

Step 6. Synthesis of 5-(4-fluorophenyl)-7-oxo-1,8-dihydropyrazolo[4,3-g]quinoline-6-carboxylic acid (D45)

In a vial, methyl 5-(4-fluorophenyl)-7-oxo-1,8-dihydropyrazolo[4,3-g]quinoline-6-carboxylate (650 mg, 1.912 mmol) was suspended in a mixture of EtOH (12.0 mL) and water (4 mL). Then, NaOH (385 mg, 9.626 mmol) was added. The reaction was heated at 70° C. for 4 hours. After this time, LC-MS showed formation of product and almost complete consumption of the starting material. The mixture was concentrated in vacuo to remove the volatiles. The crude product was suspended in water and precipitated by the addition of 1 M HCl until the pH was ~pH 2. The precipitate was filtered and triturated with cold water to obtain the product as a cream solid. 5-(4-fluorophenyl)-7-oxo-1,8-dihydropyrazolo[4,3-g]quinoline-6-carboxylic acid (615.2 mg, 100%) $^1H$ NMR (400 MHz, DMSO-$d_6$) δ 13.20 (s, 2H), 12.19 (s, 1H), 8.15 (d, J=1.0 Hz, 1H), 7.52 (s, 1H), 7.47 (t, J=0.9 Hz, 1H), 7.46-7.36 (m, 4H). LCMS m/z 324.01 $[M+H]^+$.

Step 7. Synthesis of 7-chloro-5-(4-fluorophenyl)-1H-pyrazolo[4,3-g]quinoline-6-carboxylic acid (T10)

In a vial, 5-(4-fluorophenyl)-7-oxo-1,8-dihydropyrazolo[4,3-g]quinoline-6-carboxylic acid (100 mg, 0.2898 mmol) was weighted and suspended in $POCl_3$ (1 mL, 10.73 mmol). The reaction was heated at 80° C. for 2 hours. The reaction was worked up be evaporating the volatiles in vacuo. Then, ice was added and allowed to melt. The solid was suspended in the water and filtered. Then, the solid was washed with cold water to afford the product which was used without further purification. 7-chloro-5-(4-fluorophenyl)-1H-pyrazolo[4,3-g]quinoline-6-carboxylic acid (75.6 mg, 40%) LCMS m/z 342.0 $[M+H]^+$.

Preparation of T11

7-bromo-2-chloro-4-(4-fluorophenyl)-6-methyl-3-methylsulfonyl-quinoline (T11)

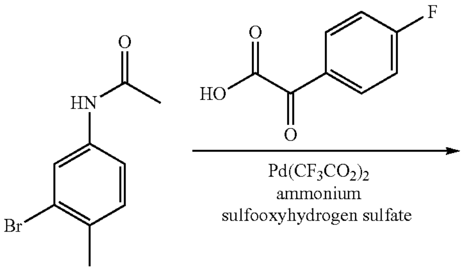

D46

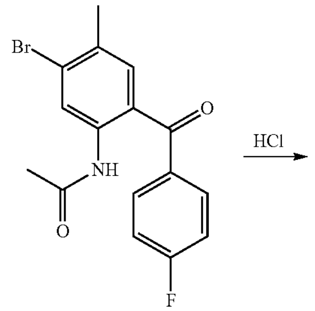

D47

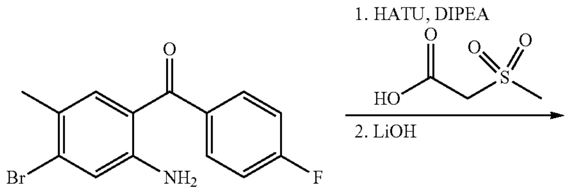

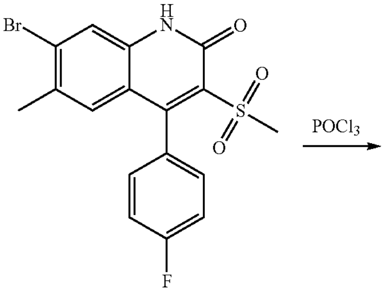

D49

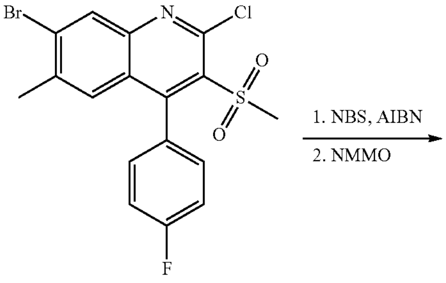

D50

-continued

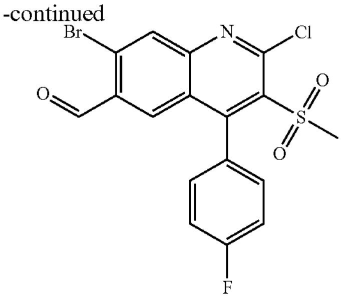

T11

Step 1. Synthesis of N-[5-bromo-2-(4-fluorobenzoyl)-4-methyl-phenyl]acetamide (D47)

A suspension of N-(3-bromo-4-methyl-phenyl)acetamide (62.73 g, 275.0 mmol), 2-(4-fluorophenyl)-2-oxo-acetic acid (63.37 g, 376.9 mmol) and ammonia sulfooxy hydrogen sulfate (125 g, 547.8 mmol) in diglyme (750 mL) was bubbled with nitrogen. $Pd(TFA)_2$ (5 g, 15.04 mmol) was added. The mixture was stirred at 50° C. (internal temperature) under $N_2$ for 11 hours. Saturated aqueous sodium bicarbonate (700 mL) was added slowly. The mixture was then extracted with EtOAc (3×). The extracts were washed with aqueous sodium bicarbonate, then brine, and concentrated. The residue was distilled under high vacuum to remove diglyme. The product was used in subsequent steps without further purification. N-[5-bromo-2-(4-fluorobenzoyl)-4-methyl-phenyl]acetamide (96.3 g, 100%). LCMS m/z 350.07 $[M+H]^+$.

Step 2. Synthesis of (2-amino-4-bromo-5-methyl-phenyl)-(4-fluorophenyl)methanone (D48)

To a suspension of N[5-bromo-2-(4-fluorobenzoyl)-4-methyl-phenyl]acetamide (1.92 g, 5.483 mmol) in EtOH (15 mL) was added aqueous HCl (10 mL of 6 M, 60.00 mmol), and the reaction was heated at 70° C. (internal T) for 5 hours. The reaction mixture was cooled to room temperature overnight. The resulting precipitate came out was collected by filtration and the solid cake was washed with water, dried under high vacuum to afford the product as a yellow solid. 1.14 g. (2-amino-4-bromo-5-methyl-phenyl)-(4-fluorophenyl)methanone (Hydrochloride salt) (1.70 g, 90%). LCMS m/z 308.08 $[M+H]^+$. The filtrate was basified with 1N NaOH, extracted with dichloromethane (3×). The organic phase was evaporated. 570 mg.

Step 3. Synthesis of 7-bromo-4-(4-fluorophenyl)-6-methyl-3-methylsulfonyl-1H-quinolin-2-one (D49)

Part A. A solution of (2-amino-4-bromo-5-methyl-phenyl)-(4-fluorophenyl)methanone (511 mg, 1.562 mmol) and 2-methylsulfonylacetic acid (250 mg, 1.810 mmol) in DMF (5 mL) was treated with HATU (804 mg, 2.115 mmol) and DIPEA (750 μL, 4.306 mmol) at room temperature for 1 hour, then at 60° C. for 1 hour. The mixture was partitioned in aqueous $NH_4Cl$ and EtOAc, extracted with EtOAc (3×), washed with brine. The organic phase was dried over $Na_2SO_4$, filtered and evaporated. Purification by silica gel chromatography (Gradient: 0-100% EtOAc in heptane) yielded the product. N-[5-bromo-2-(4-fluorobenzoyl)-4-methyl-phenyl]-2-methylsulfonyl-acetamide (1.02 g, 32%). LCMS m/z 428.16 $[M+H]^+$.

Part B. To a solution of N-[5-bromo-2-(4-fluorobenzoyl)-4-methyl-phenyl]-2-methylsulfonyl-acetamide (1.02 g, 1.089 mmol) in DMF (8 mL) was added LiOMe (86 mg, 2.265 mmol). The mixture was heated at 70° C. (internal) for 15 min. The mixture was evaporated to dryness under high vacuum. Aqueous saturated $NH_4Cl$ was added. A yellow precipitate was formed and the solid was collected through filtration, and washed with water. Purification by silica gel chromatography (Gradient: 0-30% EtOAc in dichloromethane) yielded the product. 7-bromo-4-(4-fluorophenyl)-6-methyl-3-methylsulfonyl-1H-quinolin-2-one (356 mg, 80%) $^1$H NMR (300 MHz, Chloroform-d) δ 7.59 (s, 1H), 7.26-7.14 (m, 4H), 6.88 (d, J=1.0 Hz, 1H), 3.36 (s, 3H), 2.31 (d, J=0.8 Hz, 3H). LCMS m/z 410.11 $[M+H]^+$.

Step 4. Synthesis of 7-bromo-2-chloro-4-(4-fluorophenyl)-6-methyl-3-methylsulfonyl-quinoline (D50)

A suspension of 7-bromo-4-(4-fluorophenyl)-6-methyl-3-methylsulfonyl-1H-quinolin-2-one (4.83 g, 11.77 mmol) in phosphorus oxychloride (20 mL, 214.6 mmol) was heated under reflux. The suspension turned to a solution after approximately 1 hour. After 3 hours, the mixture was evaporated, co-evaporated with toluene to dryness. The residue was suspended in ice water. Aqueous sodium bicarbonate was added until the mixture was ~pH 8, then the mixture was extracted with dichloromethane (3×). The organic phase was dried over $Na_2SO_4$, filtered and evaporated. Purification by silica gel chromatography (Gradient: 0-50% MeOH in dichloromethane) yielded the product. 7-bromo-2-chloro-4-(4-fluorophenyl)-6-methyl-3-methylsulfonyl-quinoline (4.16 g, 82%) $^1$H NMR (300 MHz, DMSO-$d_6$) δ 8.43 (s, 1H), 7.50-7.39 (m, 2H), 7.39-7.26 (m, 2H), 7.16 (d, J=1.1 Hz, 1H), 3.42 (s, 3H), 2.41 (d, J=0.9 Hz, 3H). LCMS m/z 428.07 $[M+H]^+$.

Step 5. Synthesis of 7-bromo-2-chloro-4-(4-fluorophenyl)-3-methylsulfonyl-quinoline-6-carbaldehyde (T11)

Part A. A solution of 7-bromo-2-chloro-4-(4-fluorophenyl)-6-methyl-3-methylsulfonyl-quinoline (2.92 g, 6.811 mmol), 1-bromopyrrolidine-2,5-dione (1.50 g, 8.428 mmol) and AIBN (150 mg, 0.9135 mmol) in 1,2-dichloroethane (60 mL) was heated at reflux under air for 23 hours. AIBN (100 mg) and N-bromosuccinimide (500 mg) were added. The mixture was stirred under reflux for 24 hours. The mixture was concentrated to dryness. Purification by silica gel chromatography (Gradient: 0-50% EtOAc/heptane) afforded 7-bromo-6-(bromomethyl)-2-chloro-4-(4-fluorophenyl)-3-methylsulfonyl-quinoline (2.91 g, 72%). The product was used in part B without further purification. LCMS m/z 505.79 $[M+H]^+$.

Part B. 7-bromo-6-(bromomethyl)-2-chloro-4-(4-fluorophenyl)-3-methylsulfonyl-quinoline was dissolved in acetonitrile (50 mL), 4 Å Molecular sieves (1 g) (activated at 150° C.) was added and the mixture was stirred at room temperature for 10 minutes. 4-methyl-4-oxido-morpholin-4-ium (1.5 g, 12.80 mmol) was added. After 10 minutes, the mixture was heated at 50° C. for 30 minutes. The mixture was cooled to room temperature, filtered through Celite®, and washed with dichloromethane. Purification by silica gel chromatography (Gradient: 0-50% EtOAc in heptane) yielded the product. 7-bromo-2-chloro-4-(4-fluorophenyl)-3-methylsulfonyl-quinoline-6-carbaldehyde (1.33 g, 44%) $^1$H NMR (300 MHz, Chloroform-d) δ 10.34 (s, 1H), 8.36 (d, J=0.5 Hz, 1H), 7.86 (d, J=0.5 Hz, 1H), 7.26-7.08 (m, 4H), 3.29 (s, 3H). LCMS m/z 441.88 $[M+H]^+$.

Compound 145

4-[9-fluoro-5-(4-fluorophenyl)-6-tetrahydropyran-4-yl-1H-pyrazolo[4,3-g]quinolin-7-yl]-3-methoxy-benzoic acid (145)

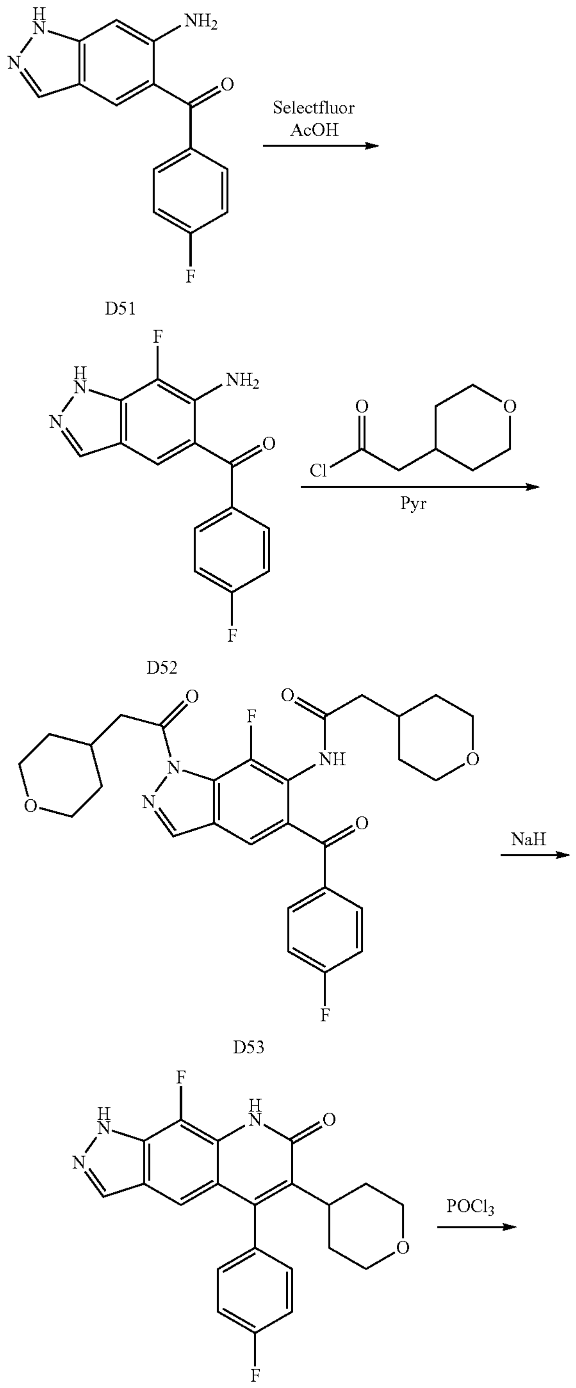

D51 D52 D53 D55

-continued

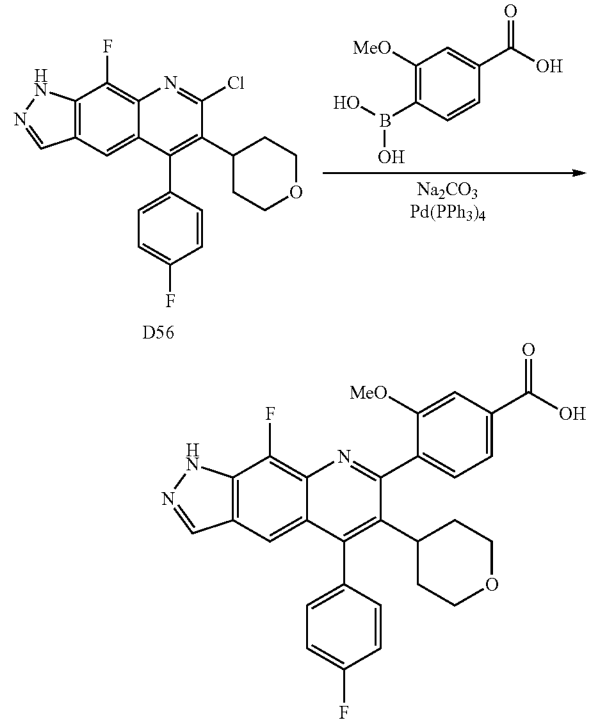

D56

145

Step 1. Synthesis of (6-amino-7-fluoro-1H-indazol-5-yl)-(4-fluorophenyl)methanone (D52)

A suspension of Selectfluor (140 mg, 0.3952 mmol) in acetic acid (3 mL) was added dropwise to a solution of 6-amino-1H-indazol-5-yl)-(4-fluorophenyl)methanone (100 mg, 0.3918 mmol) in acetic acid (3 mL). The reaction was allowed to stir at room temperature for 18 hours. The reaction was concentrated. Water and dichloromethane were added. The mixture was extracted with dichloromethane (3×). The organic phases were passed through a phase separator, combined and concentrated in vacuo. The crude was advanced to the next step. (6-amino-7-fluoro-1H-indazol-5-yl)-(4-fluorophenyl)methanone $^1$H NMR (400 MHz, DMSO-$d_6$) δ 13.26 (s, 1H), 8.06 (d, J=3.4 Hz, 1H), 7.77-7.71 (m, 2H), 7.68 (s, 1H), 7.42-7.35 (m, 2H), 6.43 (s, 2H). LCMS m/z 273.98 $[M+H]^+$.

Step 2. Synthesis of N-[7-fluoro-5-(4-fluorobenzoyl)-1-(2-tetrahydropyran-4-ylacetyl)indazol-6-yl]-2-tetrahydropyran-4-yl-acetamide (D53)

(6-amino-7-fluoro-1H-indazol-5-yl)-(4-fluorophenyl) methanone was dissolved in dichloromethane (5 mL), then Pyridine (40 μL, 0.4946 mmol) was added, followed by 2-tetrahydropyran-4-ylacetyl chloride (140 μL, 0.9746 mmol). The mixture was stirred at room temperature for 2 hours. Water and dichloromethane were added. The mixture was extracted with dichloromethane (3×). The organic phases were passed through a phase separator, combined and concentrated in vacuo. The crude product was advanced into the next step without further purification. N-[7-fluoro-5-(4-fluorobenzoyl)-1-(2-tetrahydropyran-4-ylacetyl)indazol-6-yl]-2-tetrahydropyran-4-yl-acetamide LCMS m/z 526.12 $[M+H]^+$.

Step 3. Synthesis of 9-fluoro-5-(4-fluorophenyl)-6-tetrahydropyran-4-yl-1,8-dihydropyrazolo[4,3-g]quinolin-7-one (D55)

(6-amino-7-fluoro-1H-indazol-5-yl)-(4-fluorophenyl) methanone was dissolved in DMF (4 mL). Then, NaH (32 mg, 0.8001 mmol) was added and the reaction was heated at 70° C. for 6 hours. Water and dichloromethane were added. The mixture was extracted with dichloromethane (3×). The organic phases were passed through a phase separator, combined and concentrated in vacuo. The crude was purified by flash column chromatography (15.5 g C18, 0-50% of $CH_3CN$ in water, additive: formic acid 0.2%) to afford a pale yellow solid. 9-fluoro-5-(4-fluorophenyl)-6-tetrahydropyran-4-yl-1,8-dihydropyrazolo[4,3-g]quinolin-7-one (15.2 mg, 10%) $^1$H NMR (400 MHz, DMSO-$d_6$) δ 13.56 (s, 1H), 11.68 (s, 1H), 8.17 (s, 1H), 7.48-7.33 (m, 4H), 7.01 (s, 1H), 3.81 (d, J=10.3 Hz, 2H), 3.01 (t, J=11.2 Hz, 2H), 1.35-1.18 (m, 4H). Tertiary proton of THP seems that overlaps with the DMSO solvent peak. LCMS m/z 382.0 $[M+H]^+$.

Standard Procedure A: Aryl Chloride Formation with $POCl_3$

Step 4. Synthesis of 7-chloro-9-fluoro-5-(4-fluorophenyl)-6-tetrahydropyran-4-yl-1H-pyrazolo[4,3-g]quinolone (D56)

9-fluoro-5-(4-fluorophenyl)-6-tetrahydropyran-4-yl-1,8-dihydropyrazolo[4,3-g]quinolin-7-one (11.2 mg, 0.02937 mmol) was suspended in $POCl_3$ (250 μL, 2.682 mmol) in a reaction vial. The mixture was heated at 100° C. for 15 minutes. The volatiles were evaporated in vacuo. Ice was added to quench remnants of $POCl_3$. The ice was allowed to melt, and the resulting solid was suspended, filtered and washed with cold water to afford a pale red solid was obtained. The solid was used as is in the next reaction. 7-chloro-9-fluoro-5-(4-fluorophenyl)-6-tetrahydropyran-4-yl-1H-pyrazolo[4,3-g]quinoline (7.1 mg, 44%). LCMS m/z 400.04 $[M+H]^+$.

Standard Procedure B: Suzuki Coupling

Step 5. Synthesis of 4-[9-fluoro-5-(4-fluorophenyl)-6-tetrahydropyran-4-yl-1H-pyrazolo[4,3-g]quinolin-7-yl]-3-methoxy-benzoic acid (145)

In a vial, 7-chloro-9-fluoro-5-(4-fluorophenyl)-6-tetrahydropyran-4-yl-1H-pyrazolo[4,3-g]quinoline (7 mg, 0.01751 mmol), 4-borono-3-methoxy-benzoic acid (7 mg, 0.03572 mmol), $Na_2CO_3$ (6 mg, 0.05661 mmol) and $Pd(PPh_3)_4$ (1 mg) were suspended in a mixture of DMF (250 μL) and 1,4-dioxane (250 The mixture was heated at 160° C. μW for 1 hour. A solution of HCl (1.0 M) and $CHCl_3$:IPA (3:1) were added. The mixture was extracted thrice with CHC13: IPA (3:1). The organic phases were filtered through a phase separator, combined and the volatiles were evaporated in vacuo. Purification by reversed-phase HPLC. Method: C18 Waters Sunfire column (30×150 mm, 5 micron). Gradient: MeCN in $H_2O$ containing 0.1% ammonium hydroxide afforded the product as a pale yellow solid. 4-[9-fluoro-5-(4-fluorophenyl)-6-tetrahydropyran-4-yl-1H-pyrazolo[4,3-g]quinolin-7-yl]-3-methoxy-benzoic acid (2.0 mg, 22%) LCMS m/z 516.01 $[M+H]^+$.

Compound 146

4-[6-ethylsulfonyl-5-(4-fluorophenyl)-1H-pyrazolo[4,3-g]quinolin-7-yl]-3-methoxy-benzoic acid (146)

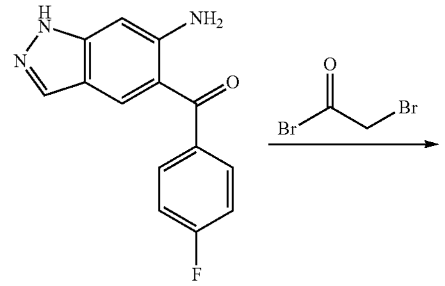

D51

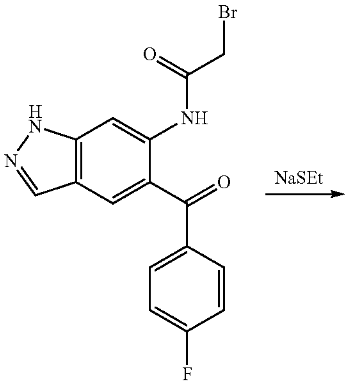

D57

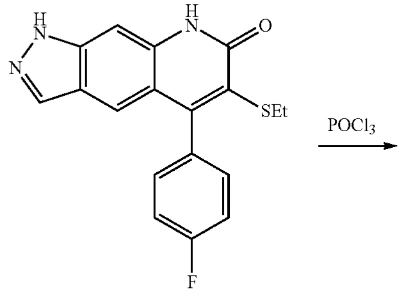

D58

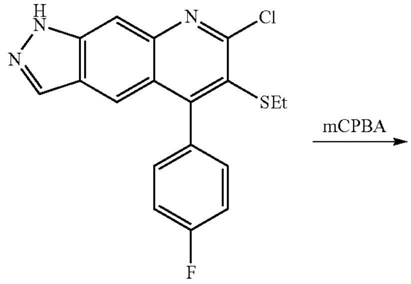

D59

-continued

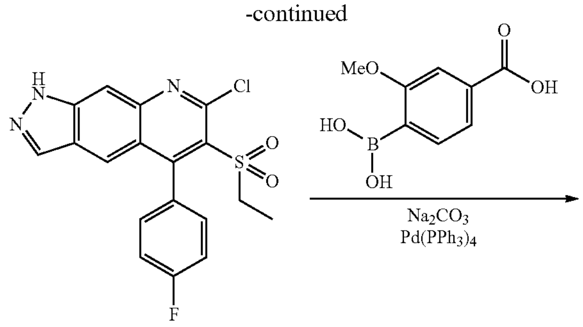

D60

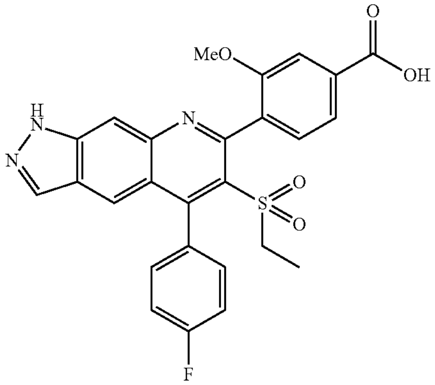

146

Step 1. Synthesis of 2-bromo-N-[5-(4-fluorobenzoyl)-1H-indazol-6-yl]acetamide (D57)

To a suspension of (6-amino-1H-indazol-5-yl)-(4-fluorophenyl)methanone (100 mg, 0.3863 mmol) in anhydrous dichloromethane (2 mL) cooled at 0° C. was added bromoacetyl bromide (81.095 mg, 35 μL, 0.4018 mmol). The mixture was stirred for 10 minutes at 0° C. then for 5 hours at room temperature. Additional bromoacetyl bromide (23.170 mg, 10 μL, 0.1148 mmol) was added at room temperature and the mixture was stirred for 18 hours. The solvent was removed under reduced pressure and the residue was dried under vacuum to afford 181 mg of 2-bromo-N-[5-(4-fluorobenzoyl)-1H-indazol-6-yl]acetamide (Hydrobromic Acid) as beige solid, which was used without further purification. LCMS m/z 376.0 $[M+H]^+$.

Step 2. Synthesis of 6-ethylsulfanyl-5-(4-fluorophenyl)-1,8-dihydropyrazolo[4,3-g]quinolin-7-one (D58)

2-bromo-N-[5-(4-fluorobenzoyl)-1H-indazol-6-yl]acetamide (262 mg, 0.5433 mmol) was dissolved in DMF (4 mL). Then, sodium ethanethiolate (90 mg, 1.070 mmol) was added. The reaction was stirred at 70° C. for 3 hours. Water and dichloromethane were added. The mixture was extracted thrice with dichloromethane. The organic phases were filtered through a phase separator, combined and the volatiles were evaporated in vacuo. The crude was re-suspended in water, filtered and washed with cold water to obtain a cream solid. 6-ethylsulfanyl-5-(4-fluorophenyl)-1,8-dihydropyrazolo[4,3-g]quinolin-7-one (37.6 mg, 17%, purity 80%). $^1$H NMR (400 MHz, DMSO-$d_6$) δ 13.02 (s, 1H), 11.93 (s, 1H), 8.11 (s, 1H), 7.35 (m, 6H), 2.88 (q, J=7.5 Hz, 2H), 1.01 (t, J=7.3 Hz, 3H). LCMS m/z 339.98 $[M+H]^+$.

Step 3. 7-chloro-6-ethylsulfanyl-5-(4-fluorophenyl)-1H-pyrazolo[4,3-g]quinolone (D59)

In a vial, 6-ethylsulfanyl-5-(4-fluorophenyl)-1,8-dihydro-pyrazolo[4,3-g]quinolin-7-one (35 mg, 0.08422 mmol) was suspended in $POCl_3$ (400 μL, 4.291 mmol). The reaction was stirred for 10 minutes at 80° C. Evaporation of volatiles in vacuo, followed by addition of ice resulted in precipitate formation. The precipitate was filtered and washed with cold water to afford a yellow solid. 7-chloro-6-ethylsulfanyl-5-(4-fluorophenyl)-1H-pyrazolo[4,3-g]quinoline (34.3 mg, 91%) $^1$H NMR (400 MHz, DMSO-$d_6$) δ 13.45 (s, 1H), 8.41 (s, 1H), 8.10 (s, 1H), 7.82 (s, 1H), 7.45 (m, 4H), 2.74 (q, J=7.7 Hz, 2H), 1.00 (t, J=7.4 Hz, 3H). LCMS m/z 357.93 $[M+H]^+$.

Step 4. Synthesis of 7-chloro-6-ethylsulfonyl-5-(4-fluorophenyl)-1H-pyrazolo[4,3-g]quinolone (D60)

In a vial, 7-chloro-6-ethylsulfanyl-5-(4-fluorophenyl)-1H-pyrazolo[4,3-g]quinoline (30 mg, 0.08384 mmol) was dissolved in $CHCl_3$ (600 μL). Then, mCPBA (45 mg, 0.1799 mmol) was added and the reaction was stirred at room temperature for 2 hours. The reaction was worked up by addition of water and dichloromethane. The mixture was extracted thrice with dichloromethane. The organic phases were filtered through a phase separator, combined, and the volatiles were evaporated in vacuo. The crude was purified by flash column chromatography (Teledyne ISCO, 15.5 g silica gel, 0-40% of $CH_3CN$ in water, additive: TFA). A pale yellow solid was obtained, 7-chloro-6-ethylsulfonyl-5-(4-fluorophenyl)-1H-pyrazolo[4,3-g]quinoline (Trifluoroacetate salt) (19.1 mg, 45%). $^1$H NMR (400 MHz, Methanol-$d_4$) δ 8.32 (d, J=1.1 Hz, 1H), 8.13 (t, J=1.0 Hz, 1H), 7.88 (d, J=0.9 Hz, 1H), 7.40-7.33 (m, 2H), 7.31-7.24 (m, 2H), 3.59 (q, J=7.4 Hz, 2H), 1.28 (t, J=7.4 Hz, 3H). LCMS m/z 389.97 $[M+H]^+$.

Step 5. Synthesis of 4-[6-ethylsulfonyl-5-(4-fluorophenyl)-1H-pyrazolo[4,3-g]quinolin-7-yl]-3-methoxy-benzoic acid (146)

7-chloro-6-ethylsulfonyl-5-(4-fluorophenyl)-1H-pyrazolo[4,3-g]quinoline (Trifluoroacetate salt) (18 mg, 0.03556 mmol), 4-borono-3-methoxy-benzoic acid (10 mg, 0.05103 mmol), $Na_2CO_3$ (10 mg, 0.09435 mmol) and $Pd(PPh_3)_4$ (2 mg, 0.001731 mmol) were suspended in a mixture of DMF (0.3 mL) and 1,4-dioxane (0.3 mL). The reaction was heated at 160° C. for 1 hour. A solution of HCl (1.0 M) and $CHCl_3$:IPA (3:1). The mixture was extracted thrice with CHCl3: IPA (3:1). The organic phases were filtered through a phase separator, combined and the volatiles were evaporated in vacuo. Purification by reversed-phase HPLC. Method: C18 Waters Sunfire column (30×150 mm, 5 micron). Gradient: MeCN in $H_2O$ with 0.2% formic acid afforded the product as a white solid was obtained, 4-[6-ethylsulfonyl-5-(4-fluorophenyl)-1H-pyrazolo[4,3-g]quinolin-7-yl]-3-methoxy-benzoic acid (4.1 mg, 23%). $^1$H NMR (400 MHz, DMSO-$d_6$) δ 13.55 (s, 1H), 13.10 (s, 1H), 8.48 (s, 1H), 8.21 (s, 1H), 7.83 (s, 1H), 7.70-7.62 (m, 1H), 7.56 (m, 3H), 7.49 (d, J=7.7 Hz, 1H), 7.42 (t, J=8.8 Hz, 2H), 3.78 (s, 3H), 2.80-3.05 (m, 2H), 0.97 (t, J=7.4 Hz, 3H). LCMS m/z 506.2 $[M+H]^+$.

Compound 147 and Compound 148

3-[[6-isopropyl-5-(4-methoxyphenyl)-1H-pyrazolo[4,3-g]quinolin-7-yl]oxy]cyclobutanecarboxylic acid (147) and 3-[[6-isopropyl-5-(4-methoxyphenyl)-1H-pyrazolo[4,3-g]quinolin-7-yl]oxy]cyclobutanecarboxylic acid (148)

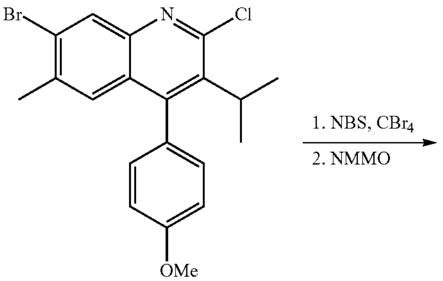

D61

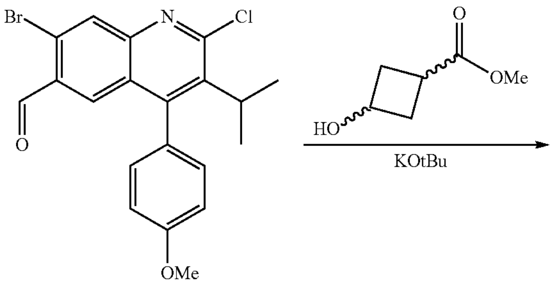

D62

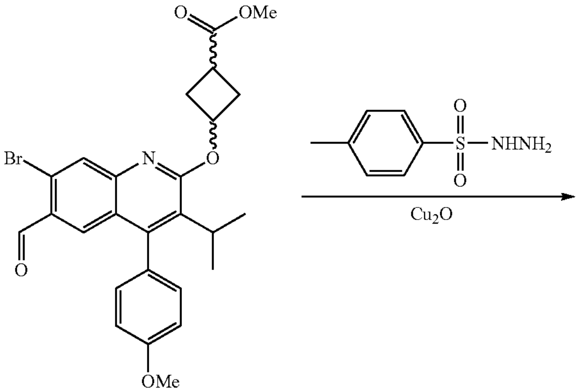

D63

-continued

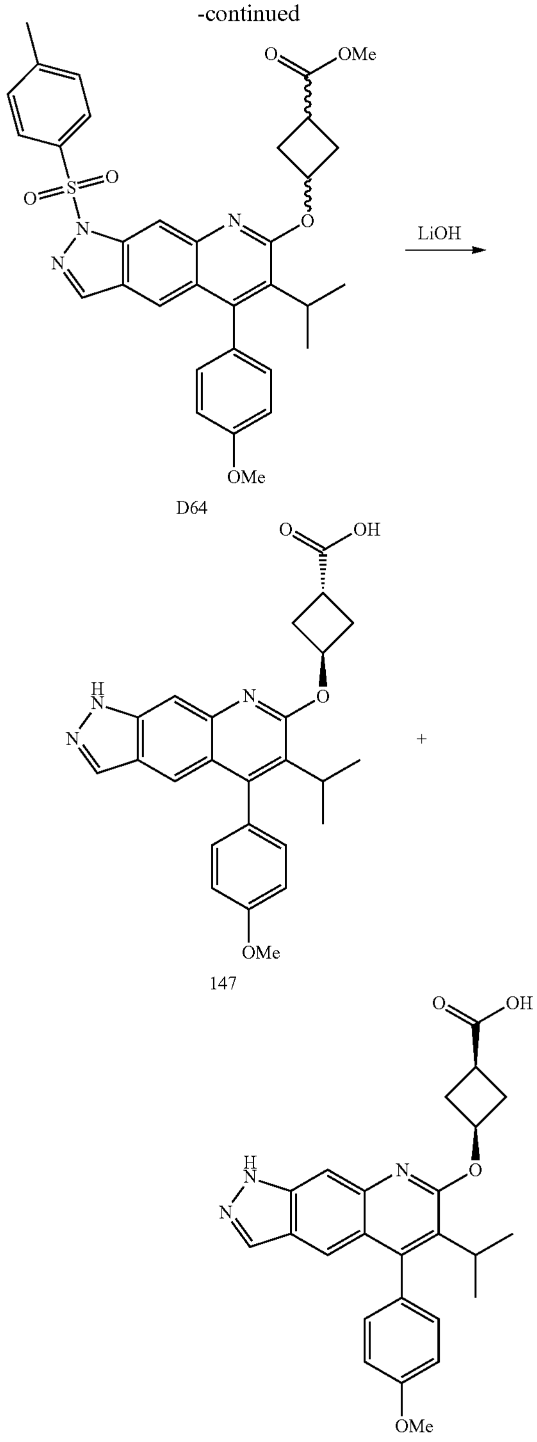

D64

147

148

Standard Procedure D: Aryl Methyl Bromination and Aldehyde Formation

Step 1. Synthesis of 7-bromo-2-chloro-3-isopropyl-4-(4-methoxyphenyl)quinoline-6-carbaldehyde (D62)

A solution of 7-bromo-2-chloro-3-isopropyl-4-(4-methoxyphenyl)-6-methyl-quinoline (157 mg, 0.3879 mmol), NBS (83 mg, 0.4663 mmol) and carbon tetrabromide (27 mg, 0.08142 mmol) in $CCl_4$ (8 mL) was irradiated for 2 hours. The mixture was then purified by silica gel chromatography (Gradient: 0-100% dichloromethane in heptane) to afford 7-bromo-6-(bromomethyl)-2-chloro-3-isopropyl-4-(4-methoxyphenyl)quinoline (186 mg, 59%). LCMS m/z 484.18 $[M+H]^+$. 7-bromo-6-(bromomethyl)-2-chloro-3-isopropyl-4-(4-methoxyphenyl)quinoline was dissolved in $CH_3CN$ (8 mL). The resulting suspension was stirred with 4 Å 150° C. activated Molecular sieves (200 mg) for 10 min. 4-methyl-4-oxido-morpholin-4-ium (92 mg, 0.7853 mmol) was added. After 1 hour at room temperature, the reaction mixture was stirred at 50° C. for 1 hour, and filtered through Celite. The solid pad was washed with dichloromethane and the filtrate was evaporated. The residue was dissolved in minimal dichloromethane, and purified by silica gel chromatography (Gradient: 0-100% dichloromethane in heptane) to afford 7-bromo-2-chloro-3-isopropyl-4-(4-methoxyphenyl)quinoline-6-carbaldehyde (55 mg, 34%) as a white solid, which was used without further purification. LCMS m/z 419.26 $[M+H]^+$.

Standard Procedure E: Addition of Alcohols to Chloropyridines

Step 2. Synthesis of 6-isopropyl-7-methoxy-5-(4-methoxyphenyl)-1-(p-tolylsulfonyl)pyrazolo[4,3-g]quinolone (D62)

A solution of 7-bromo-2-chloro-3-isopropyl-4-(4-methoxyphenyl)quinoline-6-carbaldehyde (55 mg, 0.1314 mmol) and methyl 3-hydroxycyclobutanecarboxylate (52 mg, 0.3996 mmol) in THF (2 mL) was treated with KOtBu (0.16 mL of 1 M, 0.1600 mmol) at 60° C. for 30 min. The mixture was cooled to room temperature, partitioned in EtOAc and saturated $NH_4Cl$, and then extracted with EtOAc (3×). The organic phase was dried over $Na_2SO_4$, filtered and evaporated. methyl 3-[[7-bromo-6-formyl-3-isopropyl-4-(4-methoxyphenyl)-2-quinolyl]oxy]cyclobutanecarboxylate (90 mg, 65%). LCMS m/z 512.32 $[M+H]^+$.

Standard Procedure F: Tosyl Protected Pyrazole Formation

Step 3. Synthesis of methyl 3-[6-isopropyl-5-(4-methoxyphenyl)-1-(p-tolylsulfonyl)pyrazolo[4,3-g]quinolin-7-yl]oxycyclobutanecarboxylate (D63)

methyl 3-[[7-bromo-6-formyl-3-isopropyl-4-(4-methoxyphenyl)-2-quinolyl]oxy]cyclobutanecarboxylate was dissolved in EtOH (5 mL), and treated with 4-methylbenzenesulfonohydrazide (27 mg, 0.1450 mmol) at room temperature for 1 hour. The reaction mixture was evaporated. Purification by silica gel chromatography (Gradient: 0-30% EtOAc in heptane) yielded the product methyl 3-[[7-bromo-3-isopropyl-4-(4-methoxyphenyl)-6-[(E)-(p-tolylsulfonylhydrazono)methyl]-2-quinolyl]oxy]cyclobutanecarboxylate (21 mg, 13%) LCMS m/z 680.51 $[M+H]^+$, and undesired product N-[(E)-[7-bromo-3-isopropyl-2-methoxy-4-(4-methoxyphenyl)-6-quinolyl]methyleneamino]-4-methyl-benzenesulfonamide (11 mg, 9%) LCMS m/z 582.4 $[M+H]^+$. methyl 3-[[7-bromo-3-isopropyl-4-(4-methoxyphenyl)-6-[(E)-(p-tolylsulfonylhydrazono)methyl]-2-quinolyl]oxy]cyclobutanecarboxylate (21 mg, 13%) was dissolved in 3-methylbutan-1-ol (4 mL), and treated with $Cu_2O$ (18 mg, 0.1258 mmol) at 130° C. under nitrogen for 1 h. The mixture was evaporated and the residue was purified by Purification by silica gel chromatography (Gradient: 0-100% EtOAc in heptane) yielded the product, methyl 3-[6-isopropyl-5-(4-methoxyphenyl)-1-(p-tolylsulfonyl)pyrazolo[4,3-g]quinolin-7-yl]oxycyclobutanecarboxylate (15 mg, 2%), which was used without further purification. LCMS m/z 600.38 $[M+H]^+$.

Standard Procedure G: Ester Hydrolysis

Step 4. Synthesis of 3-[[6-isopropyl-5-(4-methoxyphenyl)-1H-pyrazolo[4,3-g]quinolin-7-yl]oxy]cyclobutanecarboxylic acid [TRANS] (147) and 3-[[6-isopropyl-5-(4-methoxyphenyl)-1H-pyrazolo[4,3-g]quinolin-7-yl]oxy]cyclobutanecarboxylic acid [CIS] (148)

A suspension of methyl 3-[6-isopropyl-5-(4-methoxyphenyl)-1-(p-tolylsulfonyl)pyrazolo[4,3-g]quinolin-7-yl]oxycyclobutanecarboxylate (15 mg, 0.008299 mmol) in MeOH (3 mL), THF (1 mL), water (0.2 mL) was treated with LiOH (50 μL of 5 M, 0.2500 mmol) at 50° C. for 2 h. The mixture was evaporated and the residue was dissolved in MeOH (1 mL), treated with 6 N HCl (50 μl). Purification by reversed-phase HPLC, Method: C18 Waters Sunfire column (30×150 mm, 5 micron). Gradient: MeCN in $H_2O$ with 0.2% formic acid afforded the products. 3-[[6-isopropyl-5-(4-methoxyphenyl)-1H-pyrazolo[4,3-g]quinolin-7-yl]oxy]cyclobutanecarboxylic acid [TRANS] (2.0 mg, 53%) LCMS m/z 432.34 $[M+H]^+$. 3-[[6-isopropyl-5-(4-methoxyphenyl)-1H-pyrazolo[4,3-g]quinolin-7-yl]oxy]cyclobutanecarboxylic acid [CIS] (3.5 mg, 88%) LCMS m/z 432.3 $[M+H]^+$.

Compound 149

(2S)-2-[[5-(4-fluorophenyl)-6-isopropyl-1H-pyrazolo[4,3-g]quinolin-7-yl]amino]propanoic acid (149)

lp;5p

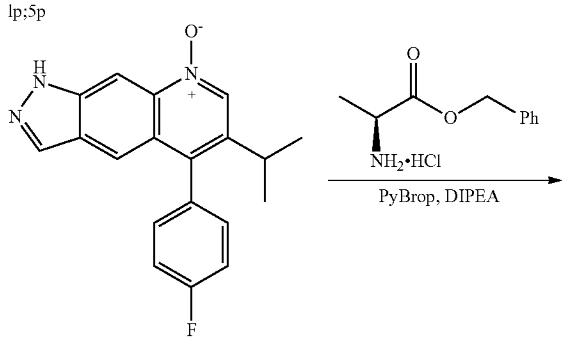

T1

-continued

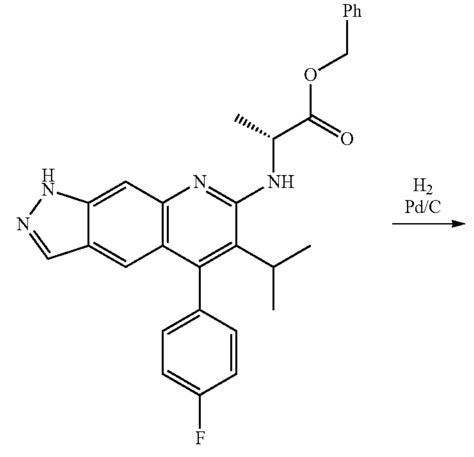

D65

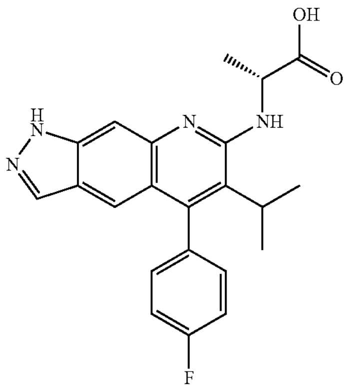

149

Standard Procedure H: PyBrop Mediated Addition of Amines to Pyridine N-oxides

Step 1. Synthesis of benzyl(2S)-2-[[5-(4-fluorophenyl)-6-isopropyl-1H-pyrazolo[4,3-g]quinolin-7-yl]amino]propanoate (D65)

To a stirred solution of 5-(4-fluorophenyl)-6-isopropyl-8-oxido-1H-pyrazolo[4,3-g]quinolin-8-ium (50 mg, 0.1556 mmol), benzyl (2S)-2-aminopropanoate; hydrochloride (100.68 mg, 0.4668 mmol) in dichloromethane (4 mL) in a sealed tube was added DIPEA (100.55 mg, 0.1355 mL, 0.7780 mmol) and PyBrop (217.61 mg, 0.4668 mmol). The reaction mixture was stirred at 50° C. overnight. The mixture was diluted with dichloromethane (5 mL), water (1 mL), and the organic phase was dried over $Na_2SO_4$ and concentrated. Purified by chromatography on neutral aluminum oxide (Gradient: 15-20% EtOAc/hexane) afforded the product benzyl (2S)-2-[[5-(4-fluorophenyl)-6-isopropyl-1H-pyrazolo[4,3-g]quinolin-7-yl]amino]propanoate (35 mg, 43%). LCMS m/z 483.25 $[M+H]^+$.

Standard Procedure I: Benzyl Group Removal by Palladium Catalyzed Hydrogenation

Step 2. Synthesis of (2S)-2-[[5-(4-fluorophenyl)-6-isopropyl-1H-pyrazolo[4,3-g]quinolin-7-yl]amino] propanoic acid (149)

To a stirred solution of benzyl (2S)-2-[[5-(4-fluorophenyl)-6-isopropyl-1H-pyrazolo[4,3-g]quinolin-7-yl]amino] propanoate (30 mg, 0.0622 mmol) in Ethanol (5 mL) was degassed pursing with Ar and Pd/C (20 mg, 0.1879 mmol) was added. The reaction mixture was stirred at room temperature in $H_2$ balloon pressure for 2 hours. The reaction mixture was filtered over Celite® and washed with EtOAc. The filtrate was concentrated in vacuo and purified by prep-HPLC to afford the product as an off white solid (2S)-2-[[5-(4-fluorophenyl)-6-isopropyl-1H-pyrazolo[4,3-g]quinolin-7-yl]amino]propanoic acid (4 mg, 16%). $^1H$ NMR (400 MHz, DMSO-$d_6$): δ 12.45 (brs, 1H), 8.07 (s, 1H), 7.49 (s, 1H), 7.40 (d, 2H, J=8.84 Hz), 7.35-7.32 (m, 2H), 7.21 (s, 1H), 6.11 (brs, 1H), 4.78 (s, 1H), 3.05 (t, 1H, J=7.56 Hz), 1.54 (d, 3H, J=7.04 Hz), 1.20 (t, 6H, J=6.44 Hz). LCMS m/z 393.11 $[M+H]^+$.

Compound 150

(2R)-2-[[5-(4-fluorophenyl)-6-isopropyl-1H-pyrazolo[4,3-g]quinolin-7-yl]amino]propanoic acid (150)

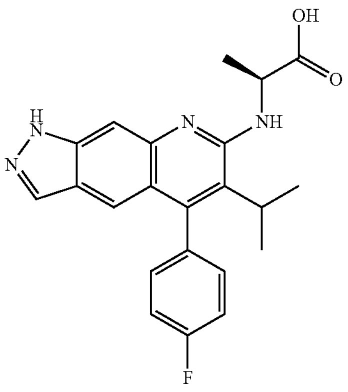 [SMILES: CC(C)c1c(N[C@@H](C)C(=O)O)nc2cc3[nH]ncc3cc2c1-c1ccc(F)cc1]

Compound 150 was prepared from T1 and benzyl (2R)-2-aminopropanoate hydrochloride using the method described for compound 149. Purification by prep-HPLC afforded the product compound as off white solid (2R)-2-[[5-(4-fluorophenyl)-6-isopropyl-1H-pyrazolo[4,3-g]quinolin-7-yl]amino]propanoic acid (34 mg, 31%) NMR (400 MHz, DMSO-$d_6$): δ 12.79 (brs, 1H), 8.07 (s, 1H), 7.49 (s, 1H), 7.40 (t, 2H, J=8.84 Hz), 7.35-7.32 (m, 2H), 7.21 (s, 1H), 6.08 (brs, 1H), 4.82 (t, 1H, J=6.68 Hz), 3.06 (t, 1H, J=7.36 Hz), 1.54 (d, 3H, J=7.04 Hz), 1.20 (t, 6H, J=6.44 Hz). LCMS m/z 393.11 $[M+H]^+$.

Compound 151

1-[5-(4-fluorophenyl)-6-isopropyl-1H-pyrazolo[4,3-g]quinolin-7-yl]azetidine-3-carboxylic acid (151)

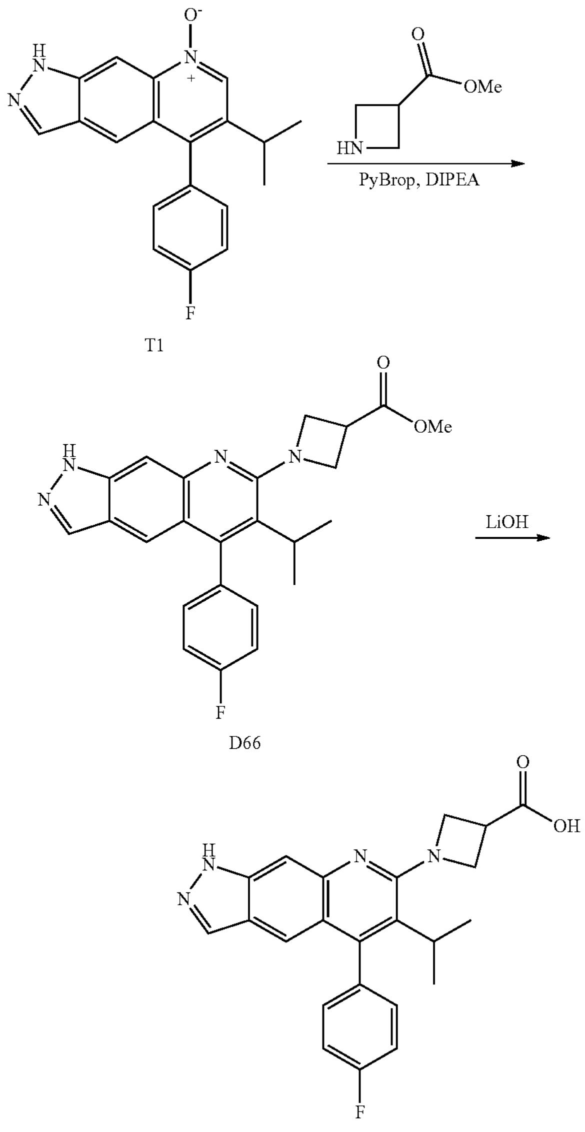

T1
D66
151

Standard Procedure H: PyBrop Addition of Amines to Pyridine N-oxides

Step 1. Synthesis of methyl 1-[5-(4-fluorophenyl)-6-isopropyl-1H-pyrazolo[4,3-g]quinolin-7-yl]azetidine-3-carboxylate (D66)

To a stirred solution of 5-(4-fluorophenyl)-6-isopropyl-8-oxido-1H-pyrazolo[4,3-g]quinolin-8-ium (183 mg, 0.5695 mmol), methyl 3-azetidinecarboxylate hydrochloride (1:1) (258.99 mg, 1.7085 mmol) in dichloromethane (7 mL) and a sealed tube was added DIPEA (368.02 mg, 0.4960 mL, 2.8475 mmol) and reaction mixture was stirred at that time PyBrop (796.47 mg, 1.7085 mmol) was added. The reaction mixture was stirred at 50° C. overnight. The reaction mixture was diluted with dichloromethane (10 mL) and washed with water (5 mL), the organic part was dried over $Na_2SO_4$ and concentrated. The crude was purified by column chromatography on silica gel (100-200 mesh) using 50-70% EtOAc/hexane to get methyl 1-[5-(4-fluorophenyl)-6-isopropyl-1H-pyrazolo[4,3-g]quinolin-7-yl]azetidine-3-carboxylate (28 mg, 11%) LCMS m/z 419.1 $[M+H]^+$.

Step 2. Synthesis of 1-[5-(4-fluorophenyl)-6-isopropyl-1H-pyrazolo[4,3-g]quinolin-7-yl]azetidine-3-carboxylic acid (151)

To a stirred solution of methyl 145-(4-fluorophenyl)-6-isopropyl-1H-pyrazolo[4,3-g]quinolin-7-yl]azetidine-3-carboxylate (30 mg, 0.0717 mmol) in THF (0.5 mL), Methanol (0.2 mL) and Water (0.1 mL) was added LiOH at 0° C. The reaction mixture stirred at room temperature for 4 h. The mixture was concentrated and diluted with water (2 mL) and then acidified with saturated citric acid solution. The compound was extracted with ethyl acetate (5 mL×2), the organic part was dried over $Na_2SO_4$ and concentrated in vacuum. The crude was purified by prep-HPLC to afford the product as an off white solid 1-[5-(4-fluorophenyl)-6-isopropyl-1H-pyrazolo[4,3-g]quinolin-7-yl]azetidine-3-carboxylic acid (5.8 mg, 20%) NMR (400 MHz, DMSO-$d_6$): δ 12.86 (brs, 1H), 8.10 (s, 1H), 7.62 (s, 1H), 7.37 (d, 2H, J=7.32 Hz), 7.21 (s, 1H), 4.30 (d, 2H, J=7.72 Hz), 3.23-3.18 (m, 1H), 0.96 (d, 6H, J=7 Hz). LCMS m/z 405.017 $[M+H]^+$.

Compound 152

3-[[5-(4-fluorophenyl)-6-isopropyl-1H-pyrazolo[4,3-g]quinolin-7-yl]amino]cyclobutanecarboxylic acid (152)

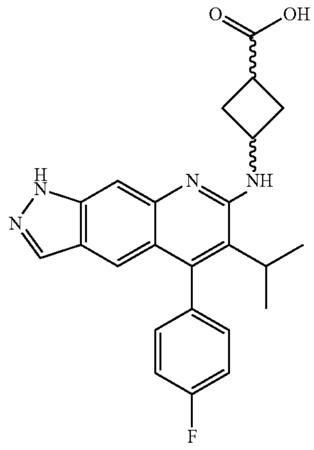 [SMILES: CC(C)c1c(NC2CC(C(=O)O)C2)nc2cc3[nH]ncc3cc2c1-c1ccc(F)cc1]

Compound 152 was prepared from T1 and methyl 3-aminocyclobutanecarboxylate hydrochloride according to the method described for the preparation of compound 151. Purification by prep-HPLC afforded the product as an off white solid 3-[[5-(4-fluorophenyl)-6-isopropyl-1H-pyrazolo[4,3-g]quinolin-7-yl]amino]cyclobutanecarboxylic acid (7.5 mg, 31%). $^1$H NMR (400 MHz, DMSO-$d_6$): δ 12.81 (brs, 1H), 8.04 (s, 1H), 7.49 (brs, 1H), 7.40-7.32 (m, 4H), 7.51 (brs, 1H), 6.29 (brs, 1H), 5.97 (brs, 1H), 4.93 (q, 1H, J=6.21 Hz), 4.75 (d, 1H, J=7.68 Hz), 3.05 (brs, 1H), 2.87 (brs, 1H), 2.69 (t, 2H, J=10.2 Hz), 2.20 (d, 1H, J=9.2 Hz), 2.19 (brs, 1H), 1.18 (brs, 6H). LCMS m/z 419.1 $[M+H]^+$.

Compound 153

(3S)-1-[5-(4-fluorophenyl)-6-isopropyl-1H-pyrazolo[4,3-g]quinolin-7-yl]pyrrolidine-3-carboxylic acid (153)

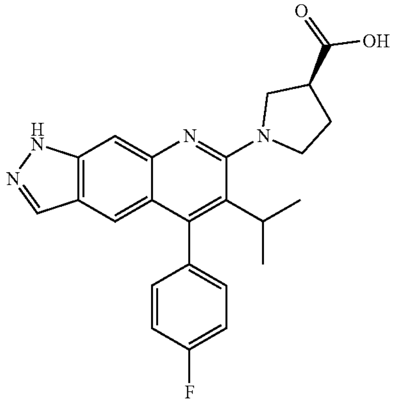 [SMILES: CC(C)c1c(N2CC[C@H](C(=O)O)C2)nc2cc3[nH]ncc3cc2c1-c1ccc(F)cc1]

Compound 153 was prepared from T1 and methyl (3S)-pyrrolidine-3-carboxylate according to the method described for the preparation of compound 151. Purification by prep-HPLC afforded the product as an off white solid (3S)-1-[5-(4-fluorophenyl)-6-isopropyl-1H-pyrazolo[4,3-g]quinolin-7-yl]pyrrolidine-3-carboxylic acid (10.5 mg, 42%). $^1$H NMR (400 MHz, DMSO-$d_6$): δ 12.90 (brs, 1H), 12.42 (brs, 1H), 8.13 (s, 1H), 7.67 (s, 1H), 7.39 (d, 4H, J=7.84 Hz), 7.25 (s, 1H), 3.81 (t, 1H, J=7 Hz), 3.71-3.62 (m, 2H), 3.55-3.51 (m, 1H), 3.46-3.41 (m, 1H), 3.18-3.11 (m, 1H), 2.11-2.08 (m, 2H), 0.96 (d, 6H, J=7 Hz). LCMS m/z 419.1 $[M+H]^+$.

Compound 154

(3R)-1-[5-(4-fluorophenyl)-6-isopropyl-1H-pyrazolo[4,3-g]quinolin-7-yl]pyrrolidine-3-carboxylic acid (154)

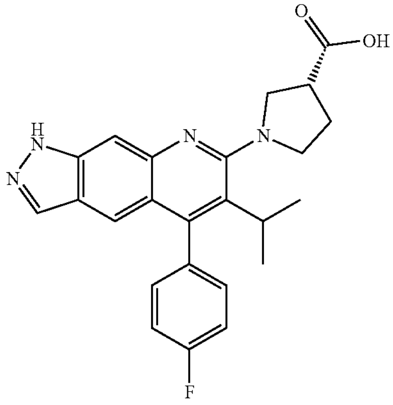

Compound 154 was prepared from T1 and methyl (3R)-pyrrolidine-3-carboxylate according to the method described for the preparation of compound 151. Purification by prep-HPLC afforded the product as an off white solid. (3R)-1-[5-(4-fluorophenyl)-6-isopropyl-1H-pyrazolo[4,3-g]quinolin-7-yl]pyrrolidine-3-carboxylic acid (16 mg, 27%). $^1$H NMR (400 MHz, DMSO-$d_6$): δ 12.90 (brs, 1H), 12.42 (brs, 1H), 8.13 (s, 1H), 7.67 (s, 1H), 7.39 (d, 4H, J=7.84 Hz), 7.25 (s, 1H), 3.81 (t, 1H, J=7 Hz), 3.71-3.62 (m, 2H), 3.55-3.51 (m, 1H), 3.46-3.41 (m, 1H), 3.18-3.11 (m, 1H), 2.11-2.08 (m, 2H), 0.96 (d, 6H, J=7 Hz). LCMS m/z 419.1 $[M+H]^+$.

Compound 155

4-[5-(4-fluorophenyl)-6-isopropyl-1H-pyrazolo[4,3-g]quinolin-7-yl]benzoic acid (155)

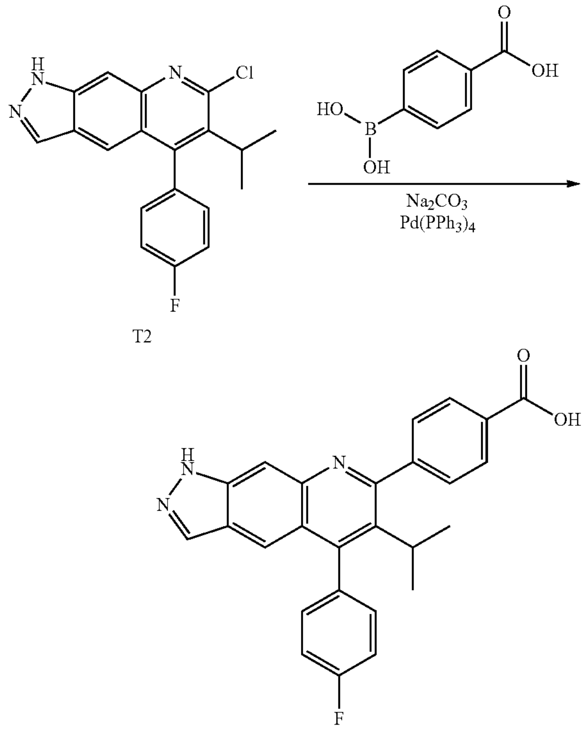

T2

155

Standard Procedure B: Suzuki Coupling

Synthesis of 4-[5-(4-fluorophenyl)-6-isopropyl-1H-pyrazolo[4,3-g]quinolin-7-yl]benzoic acid (155)

To a nitrogen purged suspension of 7-chloro-5-(4-fluorophenyl)-6-isopropyl-1H-pyrazolo[4,3-g]quinoline (20 mg, 0.055 mmol), 4-boronobenzoic acid (25 mg, 0.1507 mmol) and solid $Na_2CO_3$ (26 mg, 0.2453 mmol) in DMF (250 μL) and 1,4-dioxane (750 μL) was added $Pd(PPh_3)_4$ (15 mg, 0.01298 mmol). The solution was heated at 160° C. for 1 hour in a Biotage microwave oven. The mixture was diluted with water (5 mL) and EtOAc (5 mL). The organic layer was separated and the aq. layer was extracted with EtOAc. The combined organic layers were dried, and concentrated under reduced pressure. Purification by reverse-phase HPLC. Method: C18 Waters Sunfire column (30×150 mm, 5 micron). Gradient: MeCN in $H_2O$ with 0.2% formic acid afforded the product as a yellow solid. 4-[5-(4-fluorophenyl)-6-isopropyl-1H-pyrazolo[4,3-g]quinolin-7-yl]benzoic acid (12 mg, 51%). $^1$H NMR (400 MHz, Acetone-$d_6$) δ 8.31 (d, J=1.2 Hz, 1H), 8.25-8.13 (m, 3H), 7.78-7.68 (m, 3H), 7.57-7.50 (m, 2H), 7.48-7.35 (m, 2H), 3.27 (p, J=7.2 Hz, 1H), 1.02 (d, J=7.2 Hz, 6H). LCMS m/z 426.22 $[M+H]^+$.

Compound 156

4-[5-(4-fluorophenyl)-6-isopropyl-1H-pyrazolo[4,3-g]quinolin-7-yl]-3-methoxy-benzoic acid (156)

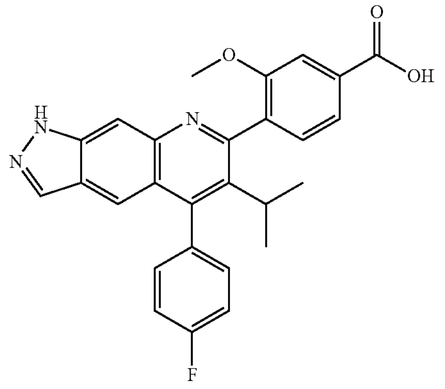

Compound 156 was prepared from T2 and 4-borono-3-methoxy-benzoic acid according to standard procedure B, as described for the preparation of compound 155. The crude product was purified by reversed-phase HPLC. Method: C18 Waters Sunfire column (30×150 mm, 5 micron). Gradient: MeCN in $H_2O$ with 0.2% formic acid to afford 4-[5-(4-fluorophenyl)-6-isopropyl-1H-pyrazolo[4,3-g]quinolin-7-yl]-3-methoxy-benzoic acid (6 mg, 24%) as a white solid. $^1$H NMR (300 MHz, Acetone-$d_6$) δ 8.34 (s, 2H), 7.86-7.81 (m, 2H), 7.77 (d, J=1.4 Hz, 1H), 7.64-7.51 (m, 3H), 7.47-7.25 (m, 2H), 3.90 (s, 3H), 3.23-3.05 (m, 1H), 1.02 (d, J=7.2 Hz, 3H), 0.97 (d, J=7.2 Hz, 3H). LCMS m/z 456.19 $[M+H]^+$.

Compound 157

3-fluoro-4-[5-(4-fluorophenyl)-6-isopropyl-1H-pyrazolo[4,3-g]quinolin-7-yl]benzoic acid (157)

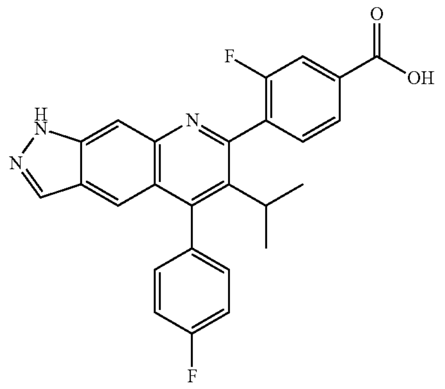

Compound 157 was prepared from T2 and 4-borono-3-fluoro-benzoic acid according to standard procedure B, as described for the preparation of compound 155. The crude product was purified by reverse-phase HPLC. Method: C18 Waters Sunfire column (30×150 mm, 5 micron). Gradient: MeCN in $H_2O$ with 0.2% formic acid to afford 3-fluoro-4-[5-(4-fluorophenyl)-6-isopropyl-1H-pyrazolo[4,3-g]quinolin-7-yl]benzoic acid (8 mg, 29%) as a white solid. LCMS m/z 444.17 $[M+H]^+$. $^1H$ NMR (300 MHz, Acetone-$d_6$) δ 8.31 (d, J=1.0 Hz, 1H), 8.21-8.20 (m, 1H), 8.05 (dd, J=7.9, 1.5 Hz, 1H), 7.89 (dd, J=10.0, 1.5 Hz, 1H), 7.77-7.62 (m, 2H), 7.57-7.26 (m, 4H), 3.24-2.98 (m, 1H), 1.03 (d, J=7.2 Hz, 3H), 1.01-0.95 (d, J=7.0 Hz, 3H).

Compound 158

5-[5-(4-fluorophenyl)-6-isopropyl-1H-pyrazolo[4,3-g]quinolin-7-yl]-6-methoxy-pyridine-2-carboxylic acid (158)

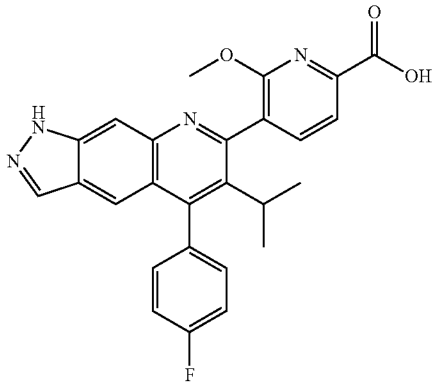

Compound 158 was prepared from T2 according to standard procedure B. The crude product was purified by reversed-phase HPLC. Method: C18 Waters Sunfire column (30×150 mm, 5 micron). Gradient: MeCN in $H_2O$ with 0.2% formic acid to afford 5-[5-(4-fluorophenyl)-6-isopropyl-1H-pyrazolo[4,3-g]quinolin-7-yl]-6-methoxy-pyridine-2-carboxylic acid (5.2 mg, 9%). $^1H$ NMR (400 MHz, DMSO-$d_6$) δ 13.30 (s, 1H), 8.36 (d, J=1.1 Hz, 1H), 8.12 (s, 1H), 8.00 (d, J=7.4 Hz, 1H), 7.87 (d, J=7.4 Hz, 1H), 7.63 (s, 1H), 7.55-7.46 (m, 2H), 7.47-7.42 (m, 2H), 3.91 (s, 3H), 2.94 (h, J=7.1 Hz, 1H), 0.89 (m, 6H). LCMS m/z 457.15 $[M+H]^+$.

Compound 159

4-[5-(4-fluorophenyl)-6-isopropyl-1H-pyrazolo[4,3-g]quinolin-7-y]benzamide (159)

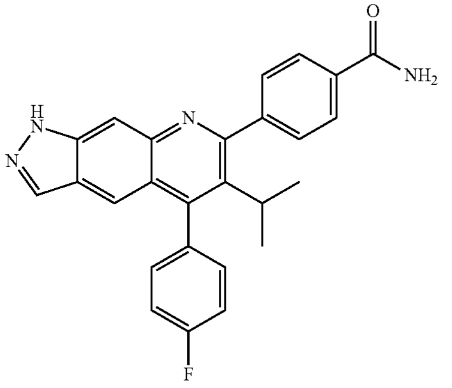 [SMILES: CC(C)c1c(-c2ccc(C(N)=O)cc2)nc2cc3[nH]ncc3cc2c1-c1ccc(F)cc1]

Compound 159 was prepared from T2 according to standard procedure B. The crude product was purified by reverse-phase HPLC. Method: C18 Waters Sunfire column (30×150 mm, 5 micron). Gradient: MeCN in $H_2O$ with 0.2% formic acid to afford 4-[5-(4-fluorophenyl)-6-isopropyl-1H-pyrazolo[4,3-g]quinolin-7-yl]benzamide (10.8 mg, 34%). $^1H$ NMR (400 MHz, Methanol-$d_4$) δ 8.22 (d, J=1.1 Hz, 1H), 8.13 (s, 1H), 8.05 (d, J=7.9 Hz, 2H), 7.71 (s, 1H), 7.65 (d, J=8.0 Hz, 2H), 7.44 (m, 2H), 7.35 (m, 2H), 3.21 (h, J=7.3 Hz, 1H), 0.98 (d, J=7.2 Hz, 6H). LCMS m/z 425.16 $[M+H]^+$.

Compound 160

4-[5-(4-fluorophenyl)-6-isopropyl-1H-pyrazolo[4,3-g]quinolin-7-yl]-N-methyl-benzamide (160)

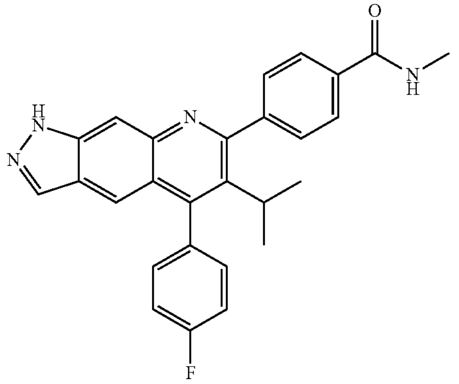 [SMILES: CNC(=O)c1ccc(-c2nc3cc4[nH]ncc4cc3c(-c3ccc(F)cc3)c2C(C)C)cc1]

Compound 160 was prepared from T2 according to standard procedure B. The crude product was purified by reverse-phase HPLC. Method: C18 Waters Sunfire column (30×150 mm, 5 micron). Gradient: MeCN in $H_2O$ with 0.2% formic acid to afford 4-[5-(4-fluorophenyl)-6-isopropyl-1H-pyrazolo[4,3-g]quinolin-7-yl]-N-methyl-benzamide (7.8 mg, 24%). $^1H$ NMR (400 MHz, Methanol-$d_4$) δ 8.22 (d, J=1.2 Hz, 1H), 8.13 (d, J=1.2 Hz, 1H), 8.04-7.94 (m, 2H), 7.70 (d, J=1.1 Hz, 1H), 7.68-7.61 (m, 2H), 7.44 (m, 2H), 7.35 (m, 2H), 3.19 (h, J=7.3 Hz, 1H), 2.97 (s, 3H), 0.97 (d, J=7.2 Hz, 6H). LCMS m/z 439.13 [M+H]$^+$.

Compound 161

[4-[5-(4-fluorophenyl)-6-isopropyl-1H-pyrazolo[4,3-g]quinolin-7-yl]phenyl]-morpholino-methanone (161)

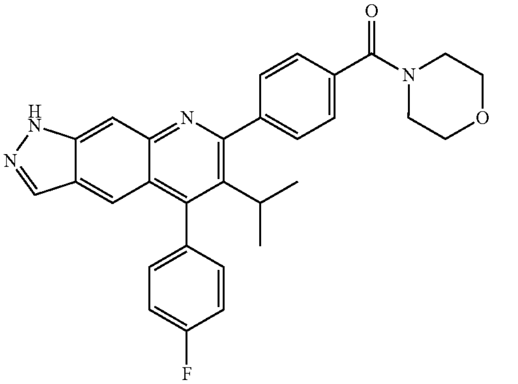 [SMILES: CC(C)c1c(-c2ccc(C(=O)N3CCOCC3)cc2)nc2cc3[nH]ncc3cc2c1-c1ccc(F)cc1]

Compound 161 was prepared from T2 according to standard procedure B. The crude product was purified by reverse-phase HPLC. Method: C18 Waters Sunfire column (30×150 mm, 5 micron). Gradient: MeCN in $H_2O$ with 0.2% formic acid to afford [4-[5-(4-fluorophenyl)-6-isopropyl-1H-pyrazolo[4,3-g]quinolin-7-yl]phenyl]-morpholino-methanone (7.3 mg, 20%). $^1H$ NMR (400 MHz, Methanol-$d_4$) δ 8.22 (s, 1H), 8.13 (s, 1H), 7.70 (s, 1H), 7.64 (m, 4H), 7.43 (m, 2H), 7.35 (m, 2H), 3.88-3.52 (m, 8H), 3.22 (m, 1H, obscured by solvent peak), 0.98 (d, J=7.2 Hz, 6H). LCMS m/z 495.16 [M+H]$^+$.

Compound 162

5-(4-fluorophenyl)-6-isopropyl-7-(6-methylsulfonyl-3-pyridyl)-1H-pyrazolo[4,3-g]quinoline (162)

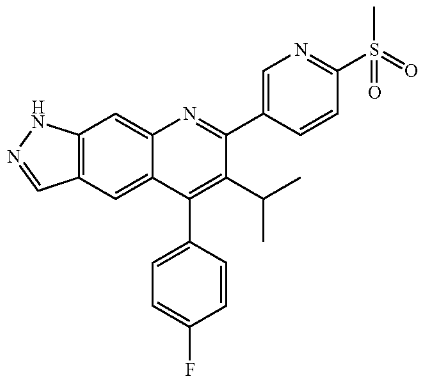 [SMILES: CC(C)c1c(-c2ccc(S(C)(=O)=O)nc2)nc2cc3[nH]ncc3cc2c1-c1ccc(F)cc1]

Compound 162 was prepared from T2 according to standard procedure B. The crude product was purified by reverse-phase HPLC. Method: C18 Waters Sunfire column (30×150 mm, 5 micron). Gradient: MeCN in $H_2O$ with 0.1% trifluoroacetic acid to afford the product 5-(4-fluorophenyl)-64 sopropyl-7-(6-methylsulfonyl-3-pyridyl)-1H-pyrazolo[4,3-g]quinoline (Trifluoroacetate salt) (11.30 mg, 15%). $^1H$ NMR (400 MHz, DMSO-$d_6$) δ 13.28 (s, 1H), 9.00 (dd, J=2.2, 0.8 Hz, 1H), 8.40-8.33 (m, 2H), 8.22 (dd, J=8.0, 0.8 Hz, 1H), 8.15-8.09 (m, 1H), 7.64 (d, J=1.0 Hz, 1H), 7.51-7.43 (m, 4H), 3.40 (s, 3H), 3.08 (h, J=7.1 Hz, 1H), 0.94 (d, J=7.2 Hz, 6H). LCMS m/z 460.96 [M+H]$^+$.

Compound 163 and Compound 164

3-[5-(4-fluorophenyl)-6-isopropyl-1H-pyrazolo[4,3-g]quinolin-7-yl]cyclobutanecarboxylic acid (163) and 3-[5-(4-fluorophenyl)-6-isopropyl-1H-pyrazolo[4,3-g]quinolin-7-yl]cyclobutanecarboxylic acid (164)

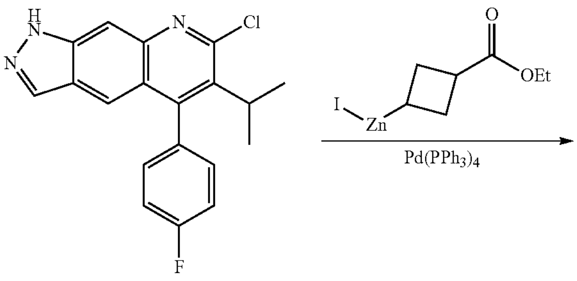

T2

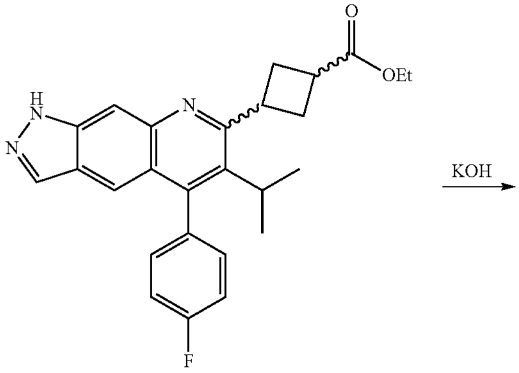

D67

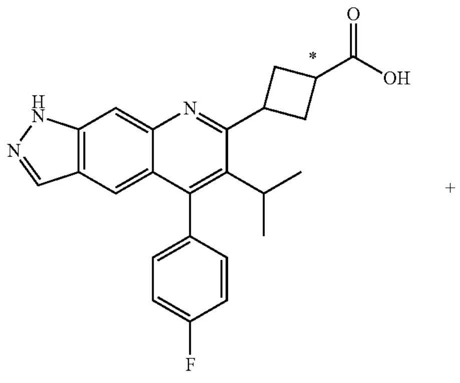

163
[ENANT-1]

-continued

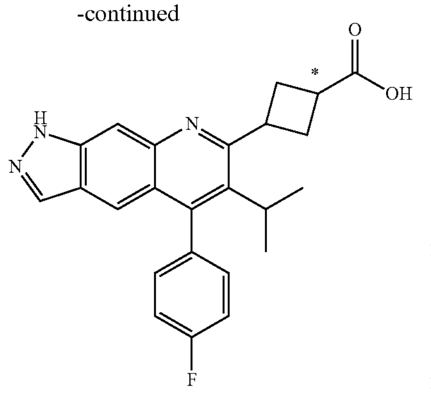

164
[ENANT-2]

Step 1. Synthesis of ethyl 3-(5-(4-fluorophenyl)-6-isopropyl-1H-pyrazolo[4,3-g]quinolin-7-yl)cyclobutane-1-carboxylate (D67)

To a mixture of copper-zinc (290 mg, 2.249 mmol) in toluene (1.8 mL) and N,N-dimethylacetamide (450 μL) under $N_2$ was added ethyl 3-iodocyclobutanecarboxylate (190 mg, 0.7478 mmol). The reaction mixture was heated at 85° C. for 3 hours and cooled to room temperature. 7-chloro-5-(4-fluorophenyl)-6-isopropyl-1H-pyrazolo[4,3-g]quinoline (85 mg, 0.2502 mmol) and $Pd(PPh_3)_4$ (43 mg, 0.03721 mmol) were added to the reaction mixture. The reaction was heated at 85° C. for 16 hours and cooled to room temperature. The reaction was worked up by addition of water and dichloromethane. The mixture was extracted with dichloromethane (×3). The organic phases were filtered through a phase separator, combined and the volatiles were evaporated in vacuo. The product was used in the next reaction without further purification.

Step 2. Synthesis of 3-[5-(4-fluorophenyl)-6-isopropyl-1H-pyrazolo[4,3-g]quinolin-7-yl]cyclobutanecarboxylic acid [ENANT-1] (163) and 3-[5-(4-fluorophenyl)-6-isopropyl-1H-pyrazolo[4,3-g]quinolin-7-yl]cyclobutanecarboxylic acid [ENANT-2](164)

ethyl 3-(5-(4-fluorophenyl)-6-isopropyl-1H-pyrazolo[4,3-g]quinolin-7-yl)cyclobutane-1-carboxylate was suspended in a mixture of EtOH (1.5 mL) and water (0.5 mL), and KOH (56 mg, 0.9981 mmol) was added. The reaction was heated at 50° C. for 2 hours. The reaction mixture was concentrated in vacuo to remove the volatiles. The mixture was re-suspended in HCl 1.0 M and the mixture was extracted with dichloromethane (×3). The organic phases were filtered through a phase separator, combined and the volatiles were evaporated in vacuo. The mixture was dissolved in dichloromethane, and filter through a plug of silica gel. The filtrate was recovered and the volatiles were evaporated in vacuo. SFC purification (Column: Daicel Chiralpak® AD-H. Mobile Phase: 30% Methanol (containing 5 mM Ammonia), 70% carbon dioxide) afforded the two products, cis and trans isomers.

Peak A. 3-[5-(4-fluorophenyl)-6-isopropyl-1H-pyrazolo[4,3-g]quinolin-7-yl]cyclobutanecarboxylic acid [ENANT-1] (163) (15.2 mg, 29%). $^1$H NMR (400 MHz, Methanol-$d_4$) δ 8.17 (s, 2H), 7.56 (s, 1H), 7.30 (m, 4H), 4.36 (m, 1H), 3.43-3.32 (m, 1H), 3.20 (m, 1H), 2.94 (m, 2H), 2.64 (m, 2H), 1.27-1.17 (m, 6H). LCMS m/z 404.14 $[M+H]^+$.

Peak B. 3-[5-(4-fluorophenyl)-6-isopropyl-1H-pyrazolo[4,3-g]quinolin-7-yl]cyclobutanecarboxylic acid (164) [ENANT-2] (8.4 mg, 16%). $^1$H NMR (400 MHz, Methanol-$d_4$) δ 8.17 (m, 2H), 7.58 (s, 1H), 7.35-7.27 (m, 4H), 4.15 (m, 1H), 3.26 (m, 2H), 2.90 (m, 2H), 2.72 (m, 2H), 1.23 (m, 6H). LCMS m/z 404.14 $[M+H]^+$.

Compound 165

[3-[5-(4-fluorophenyl)-6-isopropyl-1H-pyrazolo[4,3-g]quinolin-7-yl]cyclobutyl]-(3-hydroxyazetidin-1-yl)methanone (165)

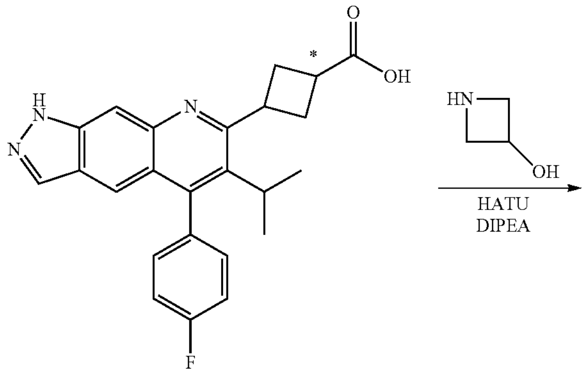

163

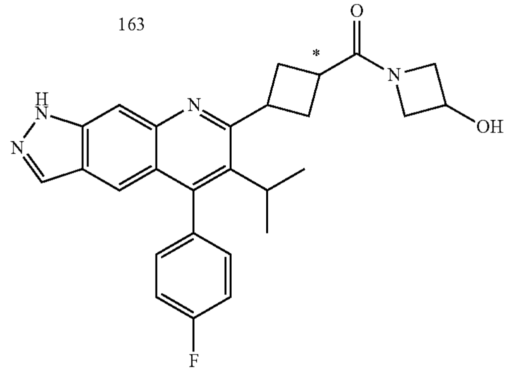

165

Step 1. Synthesis of [3-[5-(4-fluorophenyl)-6-isopropyl-1H-pyrazolo[4,3-g]quinolin-7-yl]cyclobutyl]-(3-hydroxyazetidin-1-yl)methanone (165)

3-[5-(4-fluorophenyl)-6-isopropyl-1H-pyrazolo[4,3-g]quinolin-7-yl]cyclobutanecarboxylic acid (5.5 mg, 0.01334 mmol) and HATU (6 mg, 0.01578 mmol) were dissolved in DMF (200 μL). Then, DIPEA (10 μL, 0.05741 mmol) was added and the reaction was stirred for 5 minutes. Azetidin-3-ol Hydrochloride salt (3 mg, 0.02738 mmol) was added and the reaction was stirred for 10 minutes. The reaction was worked up by addition of water and dichloromethane. The mixture was extracted with dichloromethane (×3). The organic phases were filtered through a phase separator, combined and the volatiles were evaporated in vacuo. Purification by reverse-phase HPLC. Method: C18 Waters Sunfire column (30×150 mm, 5 micron). Gradient: MeCN in $H_2O$ with 0.1% trifluoroacetic acid afforded [3-[5-(4-fluorophenyl)-6-isopropyl-1H-pyrazolo[4,3-g]quinolin-7-yl]cyclobutyl]-(3-hydroxyazetidin-1-yl)methanone (Trifluoroacetate salt) (4.4 mg, 55%). $^1$H NMR (400 MHz, DMSO-$d_6$)

δ 13.29 (s, 1H), 8.33 (s, 1H), 8.20 (s, 1H), 7.55 (s, 1H), 7.48-7.34 (m, 4H), 4.48 (m, 1H), 4.28 (t, J=7.8 Hz, 2H), 4.18-4.06 (m, 2H), 3.24 (m, 1H), 3.18-3.06 (m, 1H), 2.90-2.76 (m, 2H), 1.15 (d, J=7.4 Hz, 6H). *CH2 and CH from cyclobutyl are obscured by solvent peaks. LCMS m/z 459.2 $[M+H]^+$.

Compound 166

1-[5-(4-fluorophenyl)-6-isopropyl-1H-pyrazolo[4,3-g]quinolin-7-yl]piperidine-4-carboxylic acid (166)

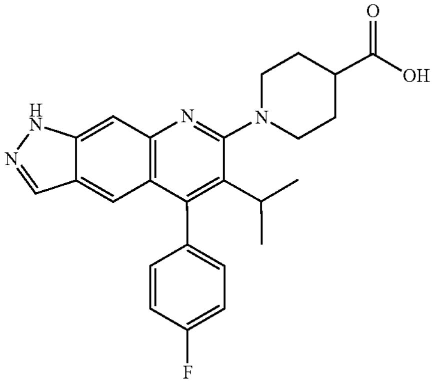 [SMILES: CC(C)c1c(N2CCC(C(=O)O)CC2)nc2cc3[nH]ncc3cc2c1-c1ccc(F)cc1]

7-chloro-5-(4-fluorophenyl)-6-isopropyl-1H-pyrazolo[4,3-g]quinoline (41 mg, 0.08446 mmol), piperidine-4-carboxylic acid (22 mg, 0.1703 mmol) and NaOtBu (33 mg, 0.3434 mmol) were added to a vial under nitrogen. The solids were suspended in t-Butanol (300 μL), and nitrogen was bubbled through the mixture for 10 minutes. Then, BrettPhos Palladacycle Gen. 4 (2.5 mg, 0.002716 mmol) was added. The reaction was stirred at 120° C. for 20 hours.

The volatiles were removed in vacuo and the reaction was resuspended in dichloromethane/HCl 1M (1:2). The mixture was extracted dichloromethane (×3), and the organic phases were filtered through a phase separator and then combined and evaporated in vacuo. Purification by reversed-phase HPLC. Method: C18 Waters Sunfire column (30×150 mm, 5 micron). Gradient: MeCN in $H_2O$ with 0.2% formic acid afforded the product. 1-[5-(4-fluorophenyl)-6-isopropyl-1H-pyrazolo[4,3-g]quinolin-7-yl]piperidine-4-carboxylic acid (1.0 mg, 3%) LCMS m/z 433.07 $[M+H]^+$.

Compound 167

2-[[5-(4-fluorophenyl)-6-isopropyl-1H-pyrazolo[4,3-g]quinolin-7-yl]oxy]acetic acid (167)

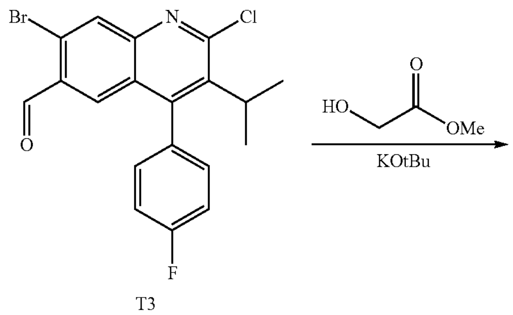

T3

-continued

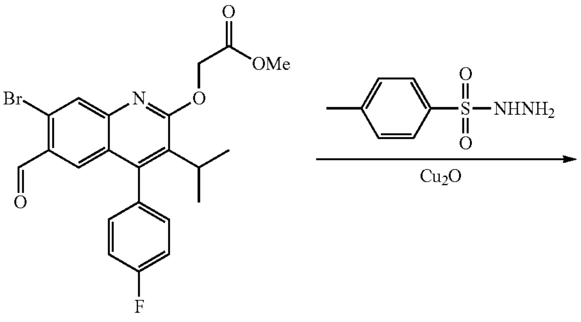

D68

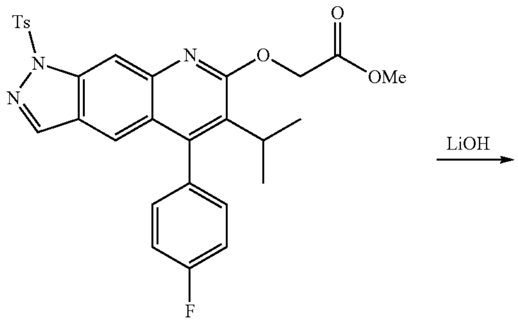

D69

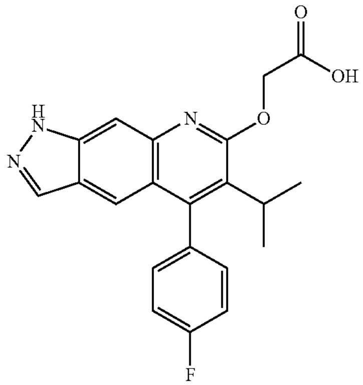

167

Compound 167 was prepared in three steps form compound T3 and methyl 2-hydroxyacetate using standard procedures E, F and G, as described for the preparation of compound 3.

Purification by reversed-phase HPLC. Method: C18 Waters Sunfire column (30×150 mm, 5 micron). Gradient:

MeCN in $H_2O$ with 0.2% formic acid. 2-[[5-(4-fluorophenyl)-6-isopropyl-1H-pyrazolo[4,3-g]quinolin-7-yl]oxy]acetic acid (10 mg, 50%). $^1$H NMR (300 MHz, DMSO-$d_6$) δ 13.05 (s, 1H), 8.21 (d, J=1.1 Hz, 1H), 7.72 (t, J=1.1 Hz, 1H), 7.53-7.30 (m, 5H), 5.10 (s, 2H), 2.85 (p, J=6.9 Hz, 1H), 1.29 (d, J=7.0 Hz, 6H). LCMS m/z 380.17 $[M+H]^+$.

Compound 168

4-[[5-(4-fluorophenyl)-6-isopropyl-1H-pyrazolo[4,3-g]quinolin-7-yl]oxy]-3-methoxy-benzoic acid (168)

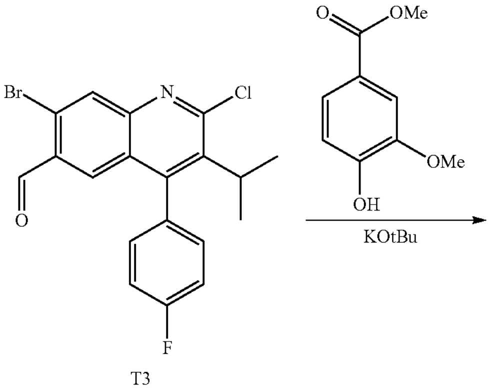

T3

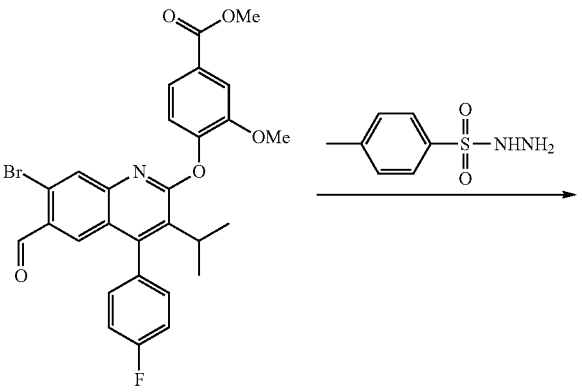

D69

-continued

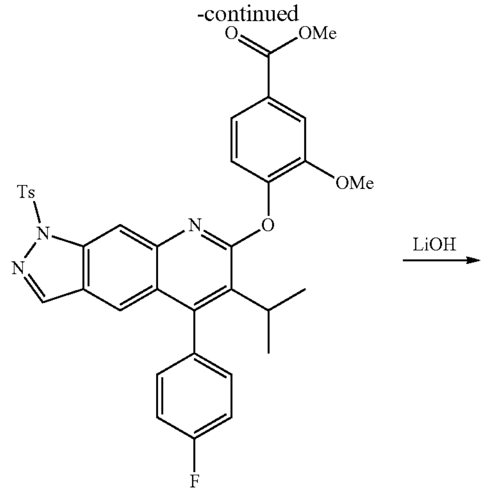

D70

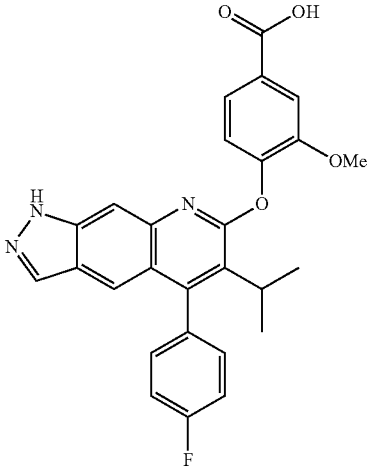

168

Compound 168 was prepared in three steps from T3 and methyl 4-hydroxy-3-methoxy-benzoate using standard procedures E, F and G, as described for the preparation of compound 147. Step 1 may also be performed using NaH as base in DMF solvent. Purification by reverse-phase HPLC. Method: C18 Waters Sunfire column (30×150 mm, 5 micron). Gradient: MeCN in $H_2O$ with 0.2% formic acid afforded the product 4-[[5-(4-fluorophenyl)-6-isopropyl-1H-pyrazolo[4,3-g]quinolin-7-yl]oxy]-3-methoxy-benzoic acid. $^1$H NMR (300 MHz, DMSO-$d_6$) δ 13.05 (s, 2H), 8.23 (d, J=1.0 Hz, 1H), 7.74-7.66 (m, 2H), 7.53 (q, J=1.1 Hz, 2H), 7.49-7.43 (m, 4H), 7.39 (d, J=8.1 Hz, 1H), 3.80 (s, 3H), 2.96 (p, J=7.0 Hz, 1H), 1.37 (d, J=7.0 Hz, 6H). LCMS m/z 472.13 $[M+H]^+$.

Compounds 169-173

Compounds 169-173 (Table 9) were prepared from T3, as described for the preparation of compound 168. The ester hydrolysis step was omitted in the preparation of compound 173.

TABLE 9

Method of preparation, structure and physicochemical data for compounds 169-173

| Compound | Product | Reagent | $^{1}H$ NMR; LCMS m/z $[M + H]^+$ |
| --- | --- | --- | --- |
| 169 | 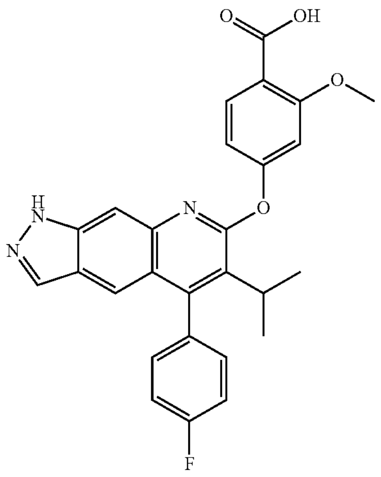 [SMILES: COc1cc(Oc2nc3cc4[nH]ncc4cc3c(-c3ccc(F)cc3)c2C(C)C)ccc1C(=O)O] | 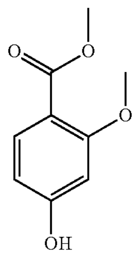 | $^{1}H$ NMR (300 MHz, DMSO-$d_6$) δ 13.11 (s, 1H), 12.58 (s, 1H), 8.25 (d, J = 1.1 Hz, 1H), 7.82 (d, J = 8.5 Hz, 1H), 7.67 (t, J = 1.1 Hz, 1H), 7.56 (d, J = 0.9 Hz, 1H), 7.52-7.36 (m, 4H), 7.11 (d, J = 2.2 Hz, 1H), 6.90 (dd, J = 8.5, 2.1 Hz, 1H), 3.86 (s, 3H), 2.96 (p, J = 7.0 Hz, 1H), 1.35 (d, J = 7.0 Hz, 6H). LCMS m/z 472.16 $[M + H]^+$. |
| 170 | 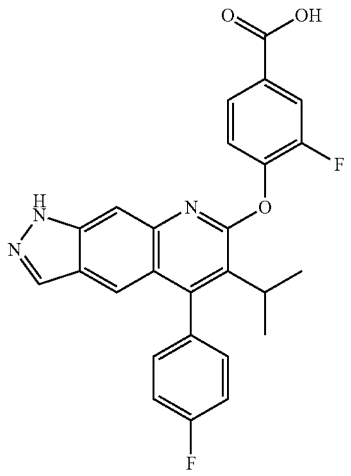 [SMILES: CC(C)c1c(Oc2ccc(C(=O)O)cc2F)nc2cc3[nH]ncc3cc2c1-c1ccc(F)cc1] | 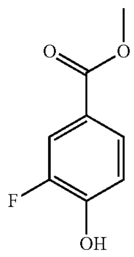 | $^{1}H$ NMR (300 MHz, DMSO-$d_6$) δ 13.33 (s, 1H), 13.11 (s, 1H), 8.26 (d, J = 1.1 Hz, 1H), 8.04-7.82 (m, 2H), 7.73-7.53 (m, 3H), 7.48 (d, J = 7.2 Hz, 4H), 2.98 (p, J = 7.0 Hz, 1H), 1.37(d, J = 7.1 Hz, 6H). LCMS m/z 460.24 $[M + H]^+$. |
| 171 | 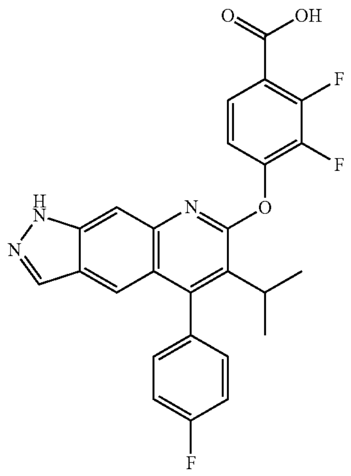 [SMILES: CC(C)c1c(Oc2ccc(C(=O)O)c(F)c2F)nc2cc3[nH]ncc3cc2c1-c1ccc(F)cc1] | 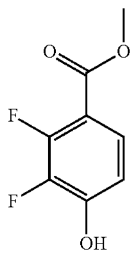 | $^{1}H$ NMR (300 MHz, DMSO-$d_6$) δ 13.63 (s, 1H), 13.14 (s, 1H), 8.27 (d, J = 1.1 Hz, 1H), 7.86 (td, J = 8.3, 7.7, 2.2 Hz, 1H), 7.64 (t, J = 1.1 Hz, 1H), 7.58 (d, J = 0.9 Hz, 1H), 7.52-7.27 (m, 5H), 2.98 (p, J = 7.0 Hz, 1H), 1.36 (d, J = 7.0 Hz, 6H). LCMS m/z 478.12 $[M + H]^+$. |

TABLE 9-continued

| Method of preparation, structure and physicochemical data for compounds 169-173 | | | |
|---|---|---|---|
| Compound | Product | Reagent | $^1$H NMR; LCMS m/z $[M + H]^+$ |
| 172 | 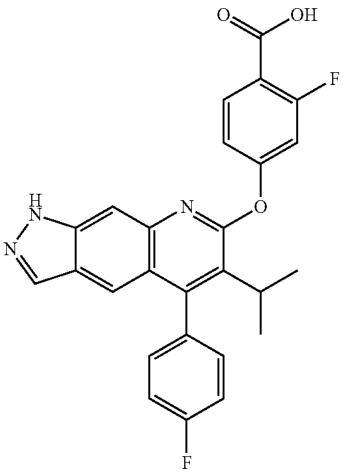 [SMILES: CC(C)c1c(Oc2ccc(C(=O)O)c(F)c2)nc2cc3[nH]ncc3cc2c1-c1ccc(F)cc1] | 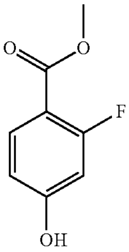 | $^1$H NMR (300 MHz, DMSO-$d_6$) δ 13.24 (s, 1H), 13.14 (s, 1H), 8.27 (s, 1H), 8.02 (t, J = 8.6 Hz, 1H), 7.70 (t, J = 1.1 Hz, 1H), 7.58 (d, J = 0.9 Hz, 1H), 7.51-7.43 (m, 4H), 7.39 (dd, J = 11.9, 2.2 Hz, 1H), 7.26 (dd, J = 8.6, 2.4 Hz, 1H), 2.95 (p, J = 7.0 Hz, 1H), 1.33 (d, J = 7.1 Hz, 6H). LCMS m/z 460.29 $[M + H]^+$. |
| 173 | 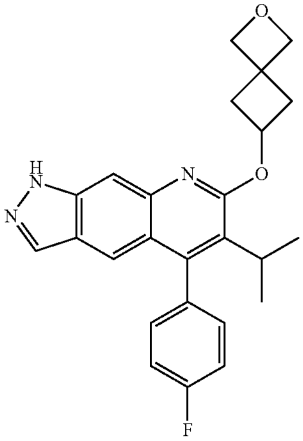 [SMILES: CC(C)c1c(OC2CC3(COC3)C2)nc2cc3[nH]ncc3cc2c1-c1ccc(F)cc1] | 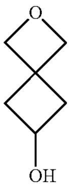 | $^1$H NMR (300 MHz, Chloroform-$d_6$) δ 10.18 (br. s, 1H), 7.81 (s, 1H), 7.43 (d, J = 0.8 Hz, 1H), 7.22-7.00 (m, 5H), 5.36 (p, J = 7.0 Hz, 1H), 4.80 (s, 2H), 4.69 (s, 2H), 3.08-2.70 (m, 3H), 2.36 (ddd, J = 12.5, 6.1, 2.7 Hz, 2H), 1.19 (d, J = 7.0 Hz, 6H). LCMS m/z 418.21 $[M + H]^+$. |

Compound 174

7-(azetidin-3-yloxy)-5-(4-fluorophenyl)-6-isopropyl-1H-pyrazolo[4,3-g]quinoline (174)

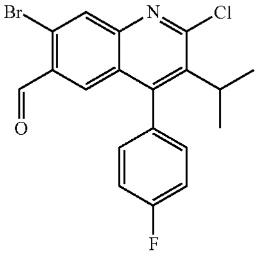

T3

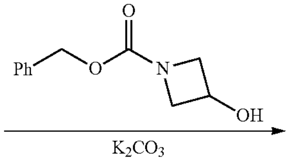

-continued

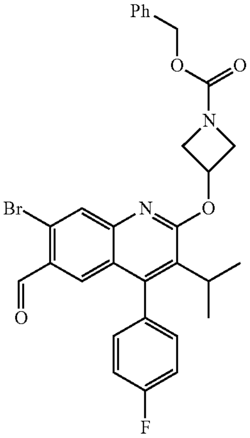

D71

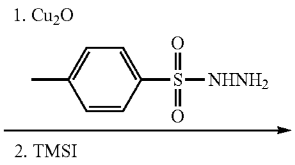

-continued

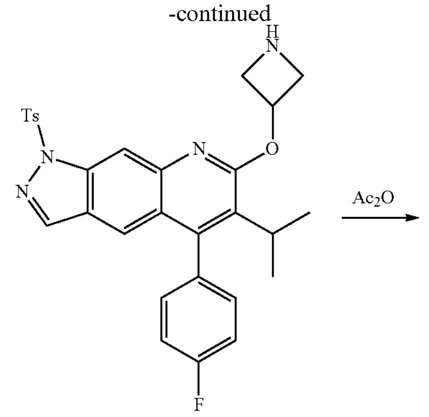

D72

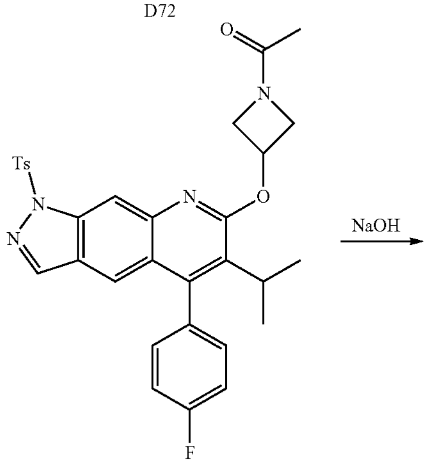

D73

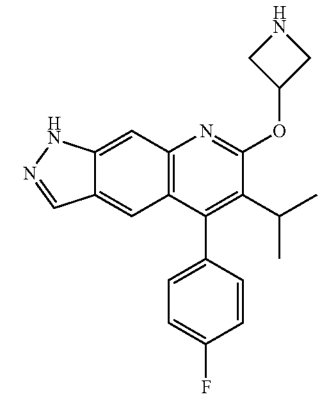

174

Step 1. Synthesis of benzyl 3-[[7-bromo-4-(4-fluorophenyl)-6-formyl-3-isopropyl-2-quinolyl]oxy]azetidine-1-carboxylate (D71)

A suspension of $K_2CO_3$ (633 mg, 4.580 mmol) and benzyl 3-hydroxyazetidine-1-carboxylate (834 mg, 4.025 mmol) in DMF (21 mL) was added to 7-bromo-2-chloro-4-(4-fluorophenyl)-3-isopropyl-quinoline-6-carbaldehyde (1.19 g, 2.830 mmol). The mixture was heated at 100° C. for 24 hours. Additional $K_2CO_3$ (400 mg) was added and the mixture was stirred at 100° C. for 4 hours. The mixture was cooled to room temperature, added to 100 mL aqueous $NH_4Cl$ with stirring. 1N HCl (6 mL) was added, and the mixture was filtered and washed with water to afford the product as a white solid. benzyl 3-[[7-bromo-4-(4-fluorophenyl)-6-formyl-3-isopropyl-2-quinolyl]oxy]azetidine-1-carboxylate (2.4 g, 71%). LCMS m/z 577.07 $[M+H]^+$.

Step 2. Synthesis of 3-[5-(4-fluorophenyl)-6-isopropyl-1-(p-tolylsulfonyl)pyrazolo[4,3-g]quinolin-7-yl]oxyazetidine-1-carboxylate benzyl 3-[[7-bromo-4-(4-fluorophenyl)-6-formyl-3-isopropyl-2-quinolyl]oxy]azetidine-1-carboxylate was suspended in EtOH (30 mL) and treated with 4-methylbenzenesulfonohydrazide (600 mg, 3.222 mmol) at 50° C. for 1 hour. The mixture was evaporated to afford benzyl 3-[[7-bromo-4-(4-fluorophenyl)-3-isopropyl-6-[(E)-(p-tolylsulfonylhydrazono)methyl]-2-quinolyl]oxy]azetidine-1-carboxylate, which was used without further purification. LCMS m/z 745.05 $[M+H]^+$.

Benzyl 3-[[7-bromo-4-(4-fluorophenyl)-3-isopropyl-6-[(E)-(p-tolylsulfonylhydrazono)methyl]-2-quinolyl]oxy]azetidine-1-carboxylate, was suspended in 3-methylbutan-1-ol (40 mL), and $Cu_2O$ (498 mg, 3.480 mmol) was added. The mixture was bubbled with $N_2$, and heated under $N_2$ at 120° C. for 2 h. The mixture was filtered through Celite®, washed with DMF, and evaporated.

Benzyl 3-[5-(4-fluorophenyl)-6-isopropyl-1-(p-tolylsulfonyl)pyrazolo[4,3-g]quinolin-7-yl]oxyazetidine-1-carboxylate (1.3 g, 55%). $^1$H NMR (400 MHz, Chloroform-d) δ 8.45 (t, J=0.9 Hz, 1H), 8.10 (d, J=1.0 Hz, 1H), 7.82 (s, 1H), 7.80 (s, 1H), 7.43-7.26 (m, 4H), 7.17-6.95 (m, 8H), 5.65 (tt, J=6.7, 4.3 Hz, 1H), 5.10 (s, 2H), 4.57 (t, J=8.4 Hz, 2H), 4.15 (dt, J=10.2, 2.5 Hz, 2H), 2.86 (p, J=7.0 Hz, 1H), 2.26 (s, 3H), 1.20 (m, 6H). LCMS m/z 665.31 $[M+H]^+$.

Step 3. Synthesis of 7-(azetidin-3-yloxy)-5-(4-fluorophenyl)-6-isopropyl-1-(p-tolylsulfonyl)pyrazolo[4,3-g]quinolone (D72)

Iodo(trimethyl)silane (200 μL, 1.405 mmol) was added to a solution of benzyl 3-[5-(4-fluorophenyl)-6-isopropyl-1-(p-tolylsulfonyl)pyrazolo[4,3-g]quinolin-7-yl]oxyazetidine-1-carboxylate (320 mg, 0.4814 mmol) in dichloromethane (10 mL) at room temperature. The mixture was stirred at room temperature for 22 hours. MeOH (0.5 mL) was added. After stirring for 1 h, the mixture was evaporated. Purification by silica gel chromatography (Gradient: 0-30% MeOH in dichloromethane) yielded the product. 7-(azetidin-3-yloxy)-5-(4-fluorophenyl)-6-isopropyl-1-(p-tolylsulfonyl)pyrazolo[4,3-g]quinoline (180 mg, 70%) LCMS m/z 531.21 $[M+H]^+$.

Step 4. Synthesis of 1-[3-[5-(4-fluorophenyl)-6-isopropyl-1-(p-tolylsulfonyl)pyrazolo[4,3-g]quinolin-7-yl]oxyazetidin-1-yl]ethanone (D73)

A solution of 7-(azetidin-3-yloxy)-5-(4-fluorophenyl)-6-isopropyl-1-(p-tolylsulfonyl)pyrazolo[4,3-g]quinoline (190 mg, 0.3581 mmol) and $NEt_3$ (150 μL, 1.076 mmol) in THF (6 mL) was divided into two parts. One part was used in the preparation of compound D74. The remaining half of the mixture was treated with acetic anhydride (60 μL, 0.6359 mmol) and stirred at 50° C. for 5 hours. After 24 hours, the mixture was cooled to room temperature, and partitioned between EtOAc and brine, then extracted with EtOAc (2×). The organic phase was dried over $Na_2SO_4$, filtered and evaporated. Purification by silica gel chromatography (Gradient: 0-20% MeOH in dichloromethane) yielded the product. 1-[3-[5-(4-fluorophenyl)-6-isopropyl-1-(p-tolylsulfonyl)pyrazolo[4,3-g]quinolin-7-yl]oxyazetidin-1-yl] ethanone (54 mg, 48%) LCMS m/z 573.2 $[M+H]^+$.

Step 5. Synthesis of 1-[3-[[5-(4-fluorophenyl)-6-isopropyl-1H-pyrazolo[4,3-g]quinolin-7-yl]oxy] azetidin-1-yl]ethanone (174)

NaOH (0.5 mL of 1 M, 0.5000 mmol) was added to a solution of 1-[3-[5-(4-fluorophenyl)-6-isopropyl-1-(p-tolyl sulfonyl)pyrazolo[4,3-g]quinolin-7-yl]oxyazetidin-1-yl] ethanone (54 mg, 0.08623 mmol) in MeOH (5 ml)/dichloromethane (2 ml). After 3 h, 1N HCl (0.45 mL) was added. The mixture was evaporated and the residue was dissolved in DMSO. Purification by reversed-phase HPLC. Method: C18 Waters Sunfire column (30×150 mm, 5 micron). Gradient: MeCN in $H_2O$ with 0.2% formic acid afforded the product. 7-(azetidin-3-yloxy)-5-(4-fluorophenyl)-6-isopropyl-1H-pyrazolo[4,3-g]quinoline (13.2 mg, 37%). LCMS m/z 377.14 $[M+H]^+$.

Compound 175

5-(4-fluorophenyl)-6-isopropyl-7-(1-methylsulfonylazetidin-3-yl)oxy-1H-pyrazolo[4,3-g]quinoline (175)

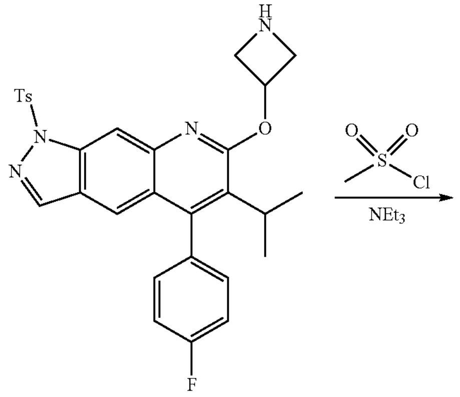

174

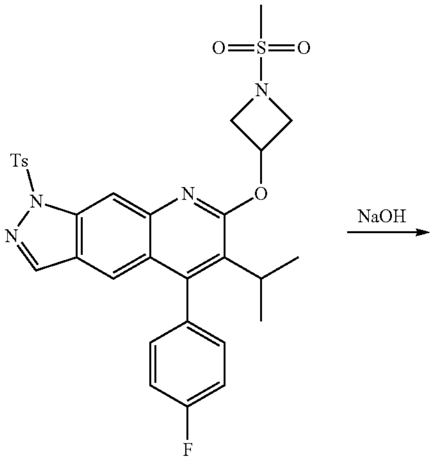

D74

-continued

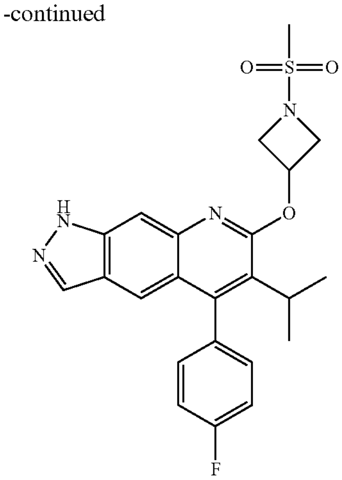

175

Step 1. Synthesis of 5-(4-fluorophenyl)-6-isopropyl-7-(1-methylsulfonylazetidin-3-yl)oxy-1-(p-tolylsulfonyl)pyrazolo[4,3-g]quinolone (D74)

A solution of 7-(azetidin-3-yloxy)-5-(4-fluorophenyl)-6-isopropyl-1-(p-tolylsulfonyl)pyrazolo[4,3-g]quinoline (95 mg) and triethylamine (75 μL) in THF (1.5 mL). Methanesulfonyl chloride (60 μL, 0.7752 mmol) was added and the mixture was stirred at 50° C. for 5 hours. The mixture was cooled to room temperature, and partitioned between EtOAc and brine, then extracted with EtOAc (2×). The organic phase was dried over $Na_2SO_4$, filtered and evaporated. Purification by silica gel chromatography (Gradient: 0-100% EtOAc in heptane, then 0-20% MeOH in dichloromethane) afforded the product. 5-(4-fluorophenyl)-6-isopropyl-7-(1-methylsulfonylazetidin-3-yl)oxy-1-(p-tolylsulfonyl)pyrazolo[4,3-g]quinoline (44 mg, 39%) LCMS m/z 609.24 $[M+H]^+$.

Step 2. Synthesis of 5-(4-fluorophenyl)-6-isopropyl-7-(1-methylsulfonylazetidin-3-yl)oxy-1H-pyrazolo [4,3-g]quinolone (175)

NaOH (0.5 mL of 1 M, 0.5000 mmol) was added to a solution of 5-(4-fluorophenyl)-6-isopropyl-7-(1-methylsulfonylazetidin-3-yl)oxy-1-(p-tolylsulfonyl)pyrazolo[4,3-g]quinoline (44 mg, 0.07034 mmol) in MeOH (5 mL)/dichloromethane (2 ml) at room temperature for 4 hours. The mixture was neutralized with 1M HCl (0.5 mL), evaporated. Purification by reverse-phase HPLC. Method: C18 Waters Sunfire column (30×150 mm, 5 micron). Gradient: MeCN in $H_2O$ with 0.2% formic acid afforded the product. 5-(4-fluorophenyl)-6-isopropyl-7-(1-methylsulfonylazetidin-3-yl)oxy-1H-pyrazolo[4,3-g]quinoline (11 mg, 31%) LCMS m/z 454.96 $[M+H]^+$.

Compound 176 and Compound 177

3-[[5-(4-fluorophenyl)-6-isopropyl-1H-pyrazolo[4,3-g]quinolin-7-yl]oxy]cyclobutanecarboxylic acid (176) and 3-[[5-(4-fluorophenyl)-6-isopropyl-1H-pyrazolo[4,3-g]quinolin-7-yl]oxy]cyclobutanecarboxylic acid (177)

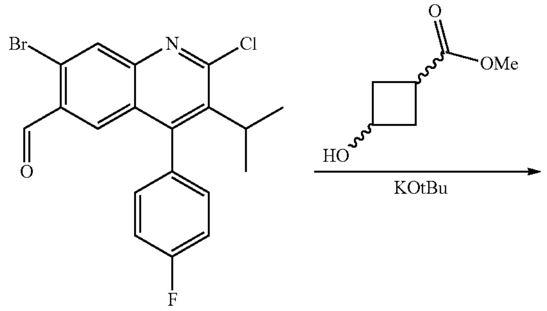

T3

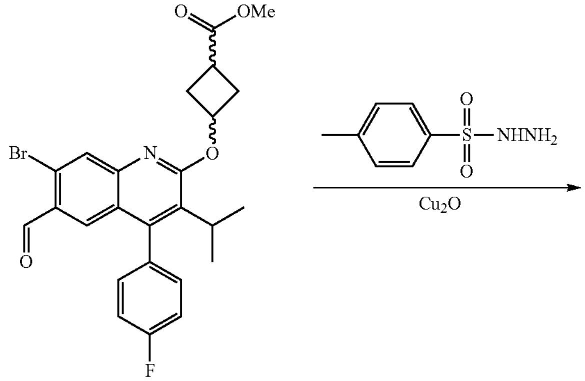

D75

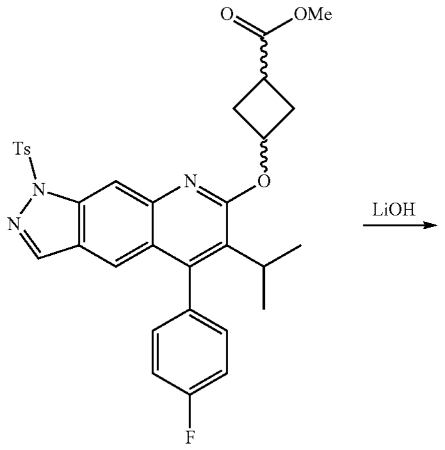

D76

-continued

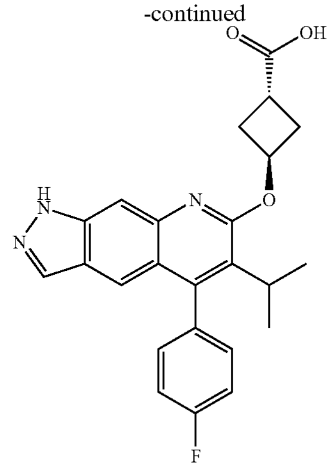

176

+

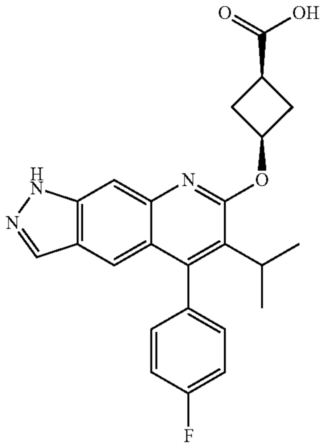

177

Compounds 176 and 177 were prepared from T3 according to the method described for the preparation of compounds 146 and 147. Purification by reverse-phase HPLC. Method: C18 Waters Sunfire column (30×150 mm, 5 micron). Gradient: MeCN in $H_2O$ with 0.2% formic acid afforded products 176 and 177. (1S, 3S)-3-[[5-(4-fluorophenyl)-6-isopropyl-1H-pyrazolo[4,3-g]quinolin-7-yl]oxy]cyclobutanecarboxylic acid (21.8 mg, 21%). $^{1}$H NMR (300 MHz, Chloroform-d+5% $CD_3OD$) δ 7.98 (d, J=1.1 Hz, 1H), 7.78 (d, J=1.1 Hz, 1H), 7.42 (d, J=0.9 Hz, 1H), 7.21-7.03 (m, 4H), 5.52-5.27 (m, 1H), 2.93-2.69 (m, 4H), 2.53-2.36 (m, 2H), 1.21 (d, J=7.0 Hz, 6H). LCMS m/z 420.33 $[M+H]^+$. (1R, 3R)-3-[[5-(4-fluorophenyl)-6-isopropyl-1H-pyrazolo[4,3-g]quinolin-7-yl]oxy]cyclobutanecarboxylic acid (19.6 mg, 19%). $^{1}$H NMR (300 MHz, Chloroform-d+5% $CD_3OD$) δ 8.06 (d, J=1.1 Hz, 1H), 7.87 (d, J=1.1 Hz, 1H), 7.50 (d, J=0.9 Hz, 1H), 7.28-7.14 (m, 4H), 5.75 (pd, J=6.6, 3.3 Hz, 1H), 3.34-3.16 (m, 1H), 3.08-2.80 (m, 3H), 2.58 (dddd, J=13.5, 10.0, 6.2, 2.8 Hz, 2H), 1.30 (d, J=7.0 Hz, 6H). LCMS m/z 420.28 $[M+H]^+$.

Compound 178

4-[[5-(4-fluorophenyl)-6-isopropyl-1H-pyrazolo[4,3-g]quinolin-7-yl]oxy]benzoic acid (178)

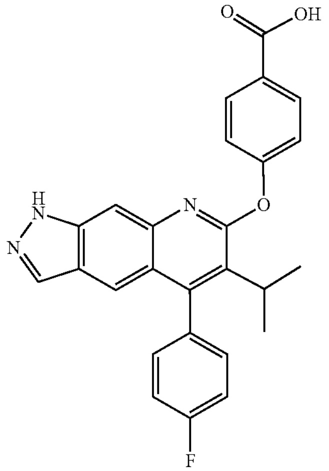 [SMILES: CC(C)c1c(Oc2ccc(C(=O)O)cc2)nc2cc3[nH]ncc3cc2c1-c1ccc(F)cc1]

Prepared from T3 and methyl 4-hydroxybenzoate as described for compound 168. 4-[[5-(4-fluorophenyl)-6-isopropyl-1H-pyrazolo[4,3-g]quinolin-7-yl]oxy]benzoic acid (8.7 mg, 31%). $^1$H NMR (300 MHz, DMSO-$d_6$) δ 13.10 (s, 1H), 12.97 (s, 1H), 8.26 (d, J=1.1 Hz, 1H), 8.08 (d, J=8.7 Hz, 2H), 7.63 (t, J=1.0 Hz, 1H), 7.56 (d, J=0.9 Hz, 1H), 7.51-7.37 (m, 6H), 2.96 (p, J=7.0 Hz, 1H), 1.35 (d, J=7.0 Hz, 6H). LCMS m/z 442.42 $[M+H]^+$.

Compounds 179-192

Compounds 179-192 (Table 10) were prepared from T4 by Suzuki coupling with the appropriate boronic ester according to standard procedure B, or Negishi coupling with the alkyl zinc reagent as described for the preparation of compound 163. In some examples, an ester hydrolysis step was performed according to standard procedure G. Any other modifications are noted in the table foot notes. Compound 185 was prepared by addition of the appropriate phenol reagent to T4.

TABLE 10

Method of preparation, structure and physicochemical data for compounds 179-192

| Compound | Product | Reagent | $^1$H NMR; LCMS m/z $[M + H]^+$ |
|---|---|---|---|
| 179 | 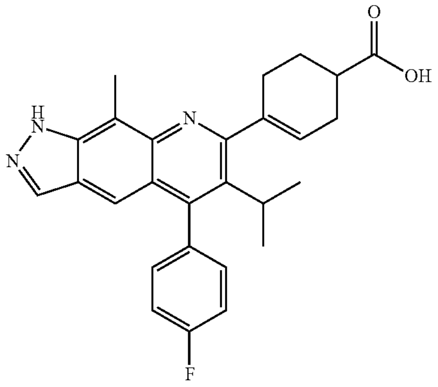 [SMILES: Cc1c2nc(C3=CCC(C(=O)O)CC3)c(C(C)C)c(-c3ccc(F)cc3)c2cc2cn[nH]c12] | 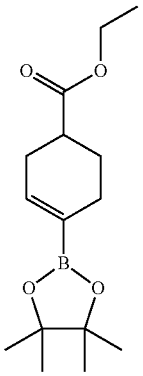 | 1H NMR (400 MHz, Acetone-d6) δ 8.25 (s, 1H), 7.53 (d, J = 1.0 Hz, 1H), 7.48-7.25 (m, 4H), 5.96 (s, 1H), 3.54-3.32 (m, 1H), 3.07 (d, J = 0.9 Hz, 3H), 2.84-2.45 (m, 4H), 2.32-2.12 (m, 1H), 2.01-1.82 (m, 1H), 1.18 (d, J = 4.1 Hz, 3H), 1.15 (d, J = 4.1 Hz, 3H). LCMS m/z 444.17 $[M + H]^+$. |
| 180 | 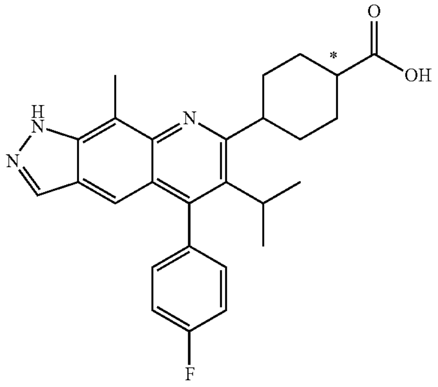 [SMILES: Cc1c2nc(C3CCC(C(=O)O)CC3)c(C(C)C)c(-c3ccc(F)cc3)c2cc2cn[nH]c12] | 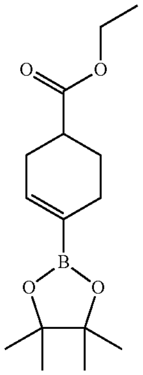 | $^1$H NMR (400 MHz, Acetone-d6) δ 8.17 (s, 1H), 7.40 (s, 1H), 7.38 (s, 2H), 7.36 (s, 2H), 3.34-3.37 (m, 1H), 3.23-3.19 (m, 1H), 3.03 (d, J = 0.8 Hz, 3H), 2.82 (d, J = 4.1 Hz, 1H), 2.47-2.40 (m, 2H), 2.37-2.24 (m, 2H), 1.89-1.71 (m, 4H), 1.33 (d, J = 7.1 Hz, 6H). LCMS m/z 446.2 $[M + H]^+$. CIS isomer |

TABLE 10-continued

| Method of preparation, structure and physicochemical data for compounds 179-192 | | | |
|---|---|---|---|
| Compound | Product | Reagent | $^1$H NMR; LCMS m/z [M + H]$^+$ |
| 181 | 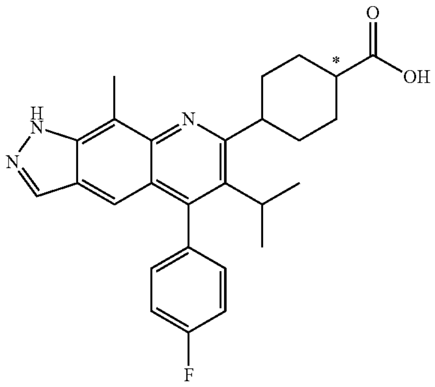 [SMILES: Cc1c2nc(C3CCC(C(=O)O)CC3)c(C(C)C)c(-c3ccc(F)cc3)c2cc2cn[nH]c12] | 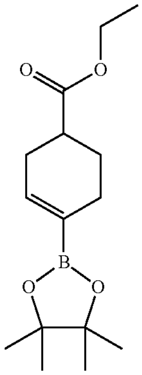 | $^1$H NMR (400 MHz, Methanol-$d_4$) δ 8.16 (s, 1H), 7.49 (s, 1H), 7.34 (s, 2H), 7.32 (s, 3H), 3.06 (s, 3H), 2.56 (m, 1H), 2.26-1.94 (m, 6H), 1.69-1.66 (m, 2H), 1.42-1.26 (m, 6H). 0.90-0.87 (m, 1H). LCMS m/z 446.2 [M + H]$^+$. TRANS isomer |
| 182 | 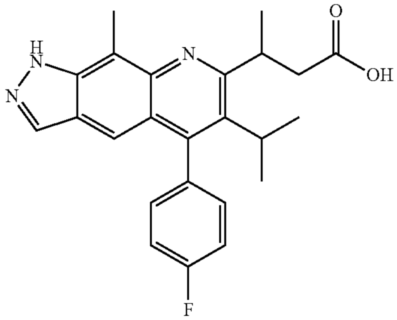 [SMILES: Cc1c2nc(C(C)CC(=O)O)c(C(C)C)c(-c3ccc(F)cc3)c2cc2cn[nH]c12] | 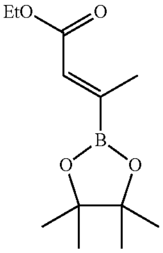 | $^1$H NMR (400 MHz, Acetone-$d_6$) δ 8.25-8.11 (m, 1H), 7.52-7.24 (m, 5H), 4.13-3.79 (m, 1H), 3.08 (d, J = 0.8 Hz, 3H), 1.50 (d, J = 6.6 Hz, 2H), 1.33 (d, J = 8 Hz, 3H), 1.17 (d, J = 7.2 Hz, 3H). LCMS m/z 406.11 [M + H]$^+$. |
| 183 | 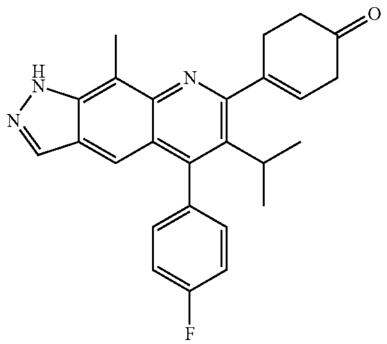 [SMILES: Cc1c2nc(C3=CCC(=O)CC3)c(C(C)C)c(-c3ccc(F)cc3)c2cc2cn[nH]c12] | 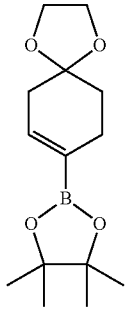 | $^1$H NMR (400 MHz, Chloroform-d) δ 10.06 (s, 1H), 8.17 (s, 1H), 7.43 (s, 1H), 7.36-7.15 (m, 4H), 5.92 (dd, J = 4.4, 3.0 Hz, 1H), 3.37 (p, J = 7.2 Hz, 1H), 3.19-3.16 (m, 2H), 3.09-3.06 (m, 4H), 2.82 (t, J = 6.9 Hz, 2H), 1.17 (d, J = 7.2 Hz, 6H). LCMS m/z 414.17 [M + H]$^+$ |
| 184 | 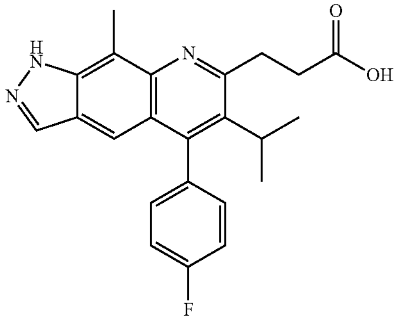 [SMILES: Cc1c2nc(CCC(=O)O)c(C(C)C)c(-c3ccc(F)cc3)c2cc2cn[nH]c12] | 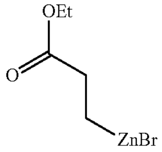 | $^1$H NMR (400 MHz, Acetone-$d_6$) δ 8.20 (s, 1H), 7.40 (s, 1H), 7.38 (d, J = 1.2 Hz, 2H), 3.56 (t, J = 6.6 Hz, 2H), 3.19-3.13 (m, 2H), 3.09 (s, 3H), 1.38-1.25 (m, 6H). LCMS m/z 392.17 [M + H]$^+$. |

TABLE 10-continued

| Method of preparation, structure and physicochemical data for compounds 179-192 | | | |
|---|---|---|---|
| Compound | Product | Reagent | $^1$H NMR; LCMS m/z [M + H]$^+$ |
| 185[1] | 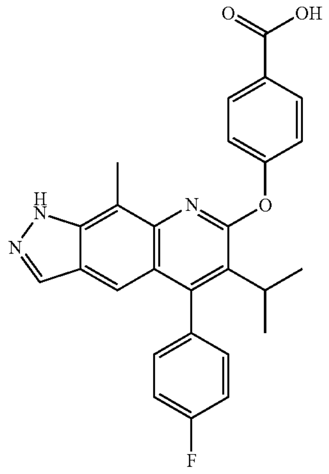 [SMILES: Cc1c2nc(Oc3ccc(C(=O)O)cc3)c(C(C)C)c(-c3ccc(F)cc3)c2cc2cn[nH]c12] | 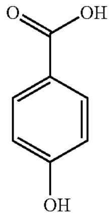 | $^1$H NMR (400 MHz, Methanol-$d_4$) δ 8.19-8.12 (m, 2H), 8.08 (s, 1H), 7.46-7.38 (m, 3H), 7.34 (m, 4H), 3.03 (hept, J = 7.0 Hz, 1H), 2.61 (d, J = 0.8 Hz, 3H), 1.41 (d, J = 7.0 Hz, 6H). LCMS m/z 456.19 [M + H]$^+$. |
| 186 | 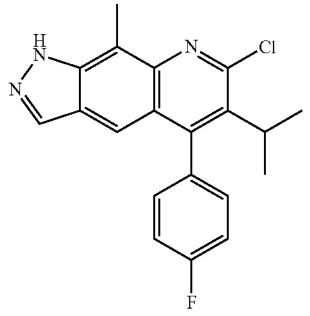 [SMILES: Cc1c2nc(Cl)c(C(C)C)c(-c3ccc(F)cc3)c2cc2cn[nH]c12] | = T4 | $^1$H NMR (400 MHz, DMSO-$d_6$) δ 13.42 (s, 1H), 8.32 (d, J = 1.4 Hz, 1H), 7.54-7.22 (m, 5H), 3.13 (m, 1H), 2.92 (d, J = 0.8 Hz, 3H), 1.30 (d, J = 7.0 Hz, 6H). LCMS m/z 354.11 [M + H]$^+$. |
| 187 | 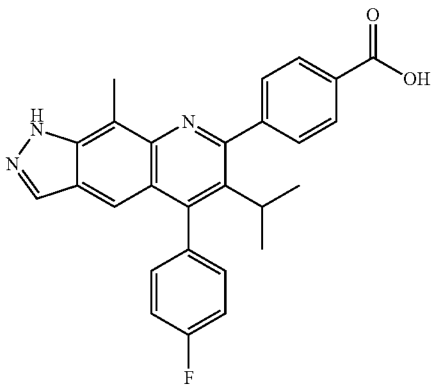 [SMILES: Cc1c2nc(-c3ccc(C(=O)O)cc3)c(C(C)C)c(-c3ccc(F)cc3)c2cc2cn[nH]c12] | 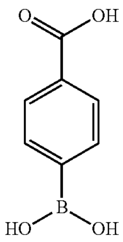 | $^1$H NMR (400 MHz, Acetone-d6) δ 8.29-8.10 (m, 3H), 7.78-7.69 (m, 2H), 7.54-7.48 (m, 3H), 7.40 (t, J = 8.9 Hz, 2H), 3.33-3.18 (m, 1H), 3.01 (d, J = 0.9 Hz, 3H), 1.01 (d, J = 7.2 Hz, 6H). LCMS m/z 440.33 [M + H]$^+$. |

TABLE 10-continued

Method of preparation, structure and physicochemical data for compounds 179-192

| Compound | Product | Reagent | $^1$H NMR; LCMS m/z $[M + H]^+$ |
|---|---|---|---|
| 188 | 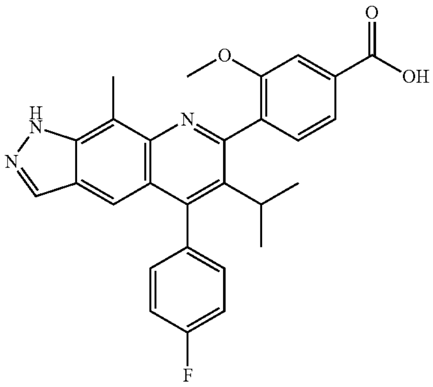 [SMILES: COc1cc(C(=O)O)ccc1-c1nc2c(C)c3[nH]ncc3cc2c(-c2ccc(F)cc2)c1C(C)C] | 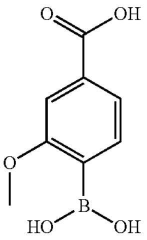 | $^1$H NMR (400 MHz, DMSO-$d_6$) δ 13.28 (s, 1H), 8.29 (s, 1H), 7.71 (dd, J = 7.7, 1.5 Hz, 1H), 7.64 (d, J = 1.5 Hz, 1H), 7.49 (d, J = 7.7 Hz, 1H), 7.47-7.39 (m, 4H), 7.37 (s, 1H), 3.80 (s, 3H), 2.96 (h, J = 7.3 Hz, 1H), 2.88 (s, 3H), 0.86 (m, 6H). LCMS m/z 470.44 $[M + H]^+$. |
| 189 | 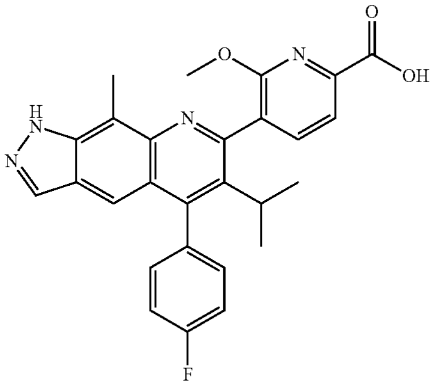 [SMILES: COc1nc(C(=O)O)ccc1-c1nc2c(C)c3[nH]ncc3cc2c(-c2ccc(F)cc2)c1C(C)C] | 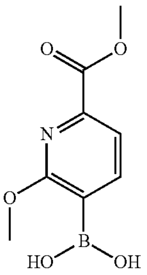 | $^1$H NMR (400 MHz, DMSO-$d_6$) δ 13.30 (s, 1H), 13.22 (s, 1H), 8.31 (d, J = 1.3 Hz, 1H), 7.99 (d, J = 7.4 Hz, 1H), 7.86 (d, J = 7.4 Hz, 1H), 7.51-7.35 (m, 5H), 3.90 (s, 3H), 2.97-2.90 (m, 1H), 2.89 (s, 3H), 0.88 (m, 6H). LCMS m/z 471.39 $[M + H]^+$. |
| 190 | 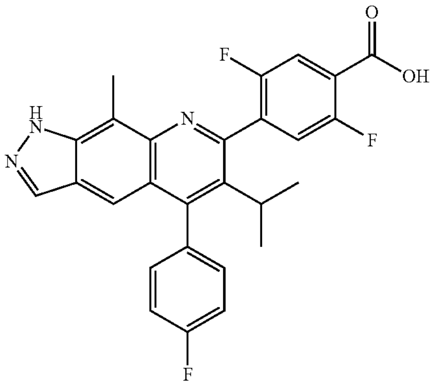 [SMILES: Cc1c2nc(-c3cc(F)c(C(=O)O)cc3F)c(C(C)C)c(-c3ccc(F)cc3)c2cc2cn[nH]c12] | 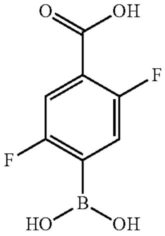 [SMILES: O=C(O)c1cc(F)c(B(O)O)cc1F] | $^1$H NMR (400 MHz, Acetone-d6) δ 8.26 (s, 1H), 7.83 (dd, J = 9.2, 5.7 Hz, 1H), 7.58-7.08 (m, 6H), 3.23-3.11 (m, 1H), 3.01 (d, J = 0.9 Hz, 3H), 1.04 (t, J = 8.5 Hz, 3H), 1.02(d, J = 8.5 Hz, 3H). LCMS m/z 476.07 $[M + H]^+$. |
| 191 | 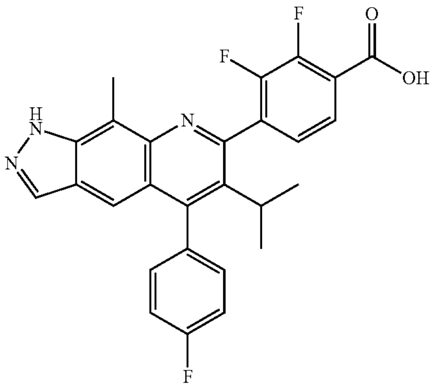 [SMILES: Cc1c2nc(-c3ccc(C(=O)O)c(F)c3F)c(C(C)C)c(-c3ccc(F)cc3)c2cc2cn[nH]c12] | 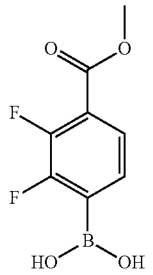 | $^1$H NMR (400 MHz, Acetone-d6) δ 8.27 (s, 1H), 7.94 (ddd, J = 8.3, 6.5, 1.8 Hz, 1H), 7.58-7.36 (m, 4H), 3.20-3.16 (m, 1H), 3.00 (d, J = 0.8 Hz, 3H), 1.05-1.00 (m, 6H). LCMS m/z 476.12 $[M + H]^+$. |

TABLE 10-continued

Method of preparation, structure and physicochemical data for compounds 179-192

| Compound | Product | Reagent | $^1H$ NMR; LCMS m/z $[M + H]^+$ |
|---|---|---|---|
| 192 | 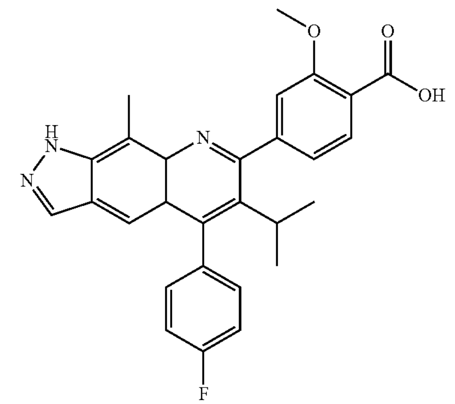 | 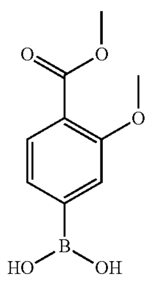 | $^1H$ NMR (400 MHz, Acetone-d6) δ 8.25 (s, 1H), 8.06 (d, J = 7.9 Hz, 1H), 7.76-7.67 (m, 1H), 7.58-7.39 (m, 5H), 7.32 (dd, J = 7.9, 1.5 Hz, 1H), 4.10 (s, 3H), 3.37-3.20 (m, 1H), 3.02 (d, J = 0.9 Hz, 3H), 1.04 (d, J = 7.2 Hz, 6H). LCMS m/z 470.13 $[M + H]^+$. |

*Compound 185 was prepared from a THP protected analog of T4.

Compound 193

4-(5-chloro-6-isopropyl-9-methyl-1H-pyrazolo[4,3-g]quinolin-7-yl)benzoic acid (193)

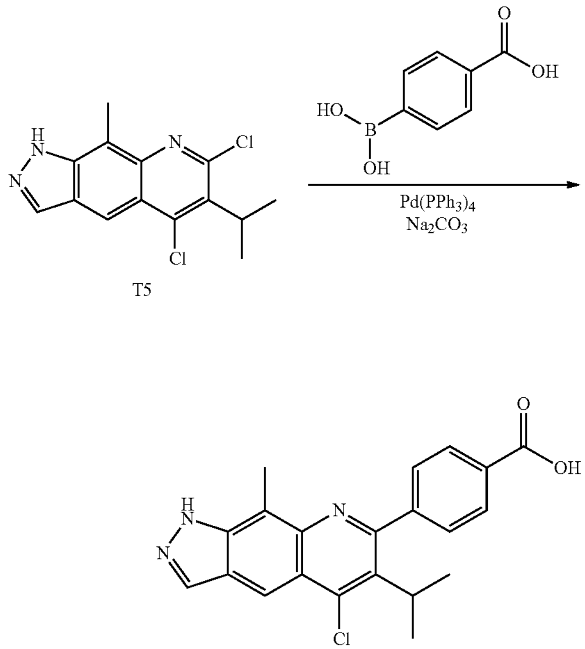

T5

193

Compound 193 was prepared from T5 and 4-boronobenzoic acid by Suzuki coupling using standard procedure B. Purification by reverse-phase HPLC. Method: C18 Waters Sunfire column (30×150 mm, 5 micron). Gradient: MeCN in $H_2O$ with 0.2% formic acid afforded the product. 4-(5-chloro-6-isopropyl-9-methyl-1H-pyrazolo[4,3-g]quinolin-7-yl)benzoic acid (2.9 mg, 12%) $^1H$ NMR (400 MHz, DMSO-$d_6$) δ 13.49 (s, 1H), 8.70 (s, 1H), 8.52 (s, 1H), 8.16-8.00 (m, 2H), 7.67 (d, J=8.2 Hz, 2H), 3.00 (br s), 2.91 (s, 3H), 1.41 (d, J=7.2 Hz, 6H). LCMS m/z 380.1 $[M+H]^+$. *The secondary proton in the isopropyl chain appears as a broad singlet.

Compound 194

4-[5-(3,4-difluorophenyl)-6-isopropyl-9-methyl-1H-pyrazolo[4,3-g]quinolin-7-yl]benzoic acid (194)

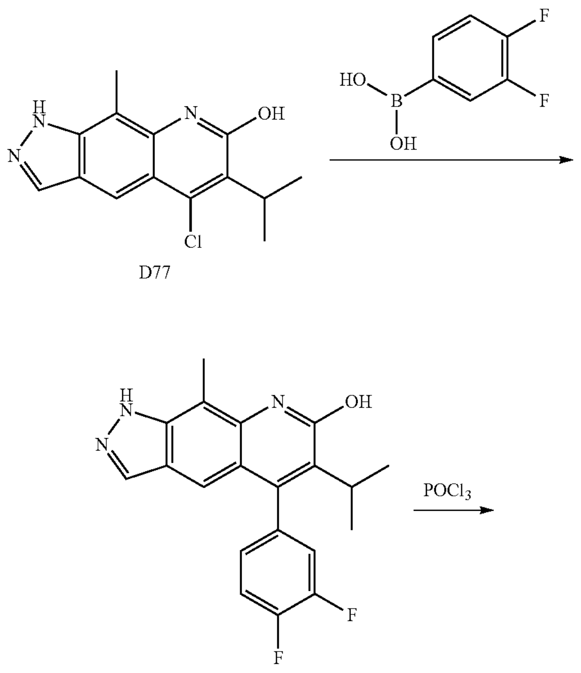

D77

D78

-continued

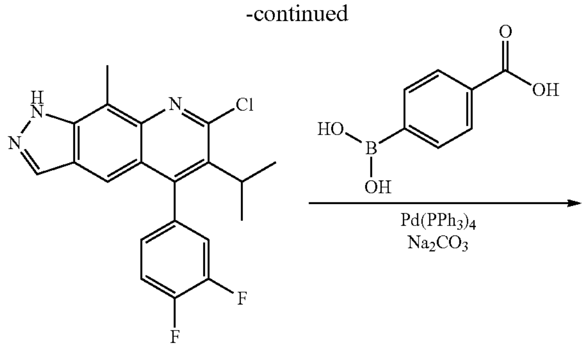

D79

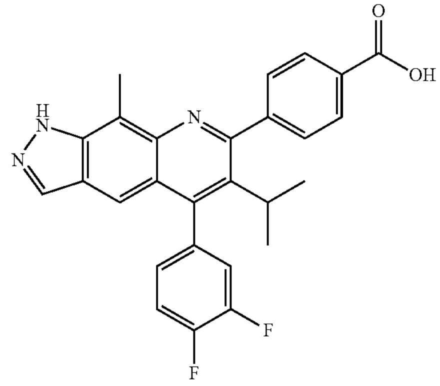

194

Compound 194 was prepared in three steps from D77 using a Suzuki coupling with (3,4-difluorophenyl)boronic acid (Standard procedure B), conversion of the quinolinone to the pyridyl chloride (Standard procedure A), followed by a second Suzuki coupling reaction with 4-boronobenzoic acid (Standard procedure B). Purification by reverse-phase HPLC. Method: C18 Waters Sunfire column (30×150 mm, 5 micron). Gradient: MeCN in $H_2O$ with 0.2% formic acid afforded the product as an orange solid. 4-[5-(3,4-difluoro-phenyl)-6-isopropyl-9-methyl-1H-pyrazolo[4,3-g]quinolin-7-yl]benzoic acid (14 mg, 27%). $^1H$ NMR (400 MHz, Acetone-d6) δ 8.25 (s, 1H), 8.30-8.22 (m, 2H), 8.23-8.05 (m, 1H), 7.80-7.71 (m, 2H), 7.2-7.58 m, 1H), 7.54-7.45 (m, 1H), 7.33-7.30 (m, 1H), 3.34-3.12 (m, 1H), 3.01 (d, J=0.9 Hz, 3H), 1.03 (d, J=8.0 Hz, 6H). LCMS m/z 458.17 $[M+H]^+$.

Compounds 195-201

Compound 195-201 (Table 11) were prepared from T5 and the appropriate boronic acid or ester by Suzuki coupling using standard procedure B. Any other modifications are noted in the table foot notes.

TABLE 11

Method of preparation, structure and physicochemical data for Compounds 195-201

| Compound | Product | Reagent | $^1H$ NMR; LCMS m/z $[M + H]^+$ |
|---|---|---|---|
| 195 | 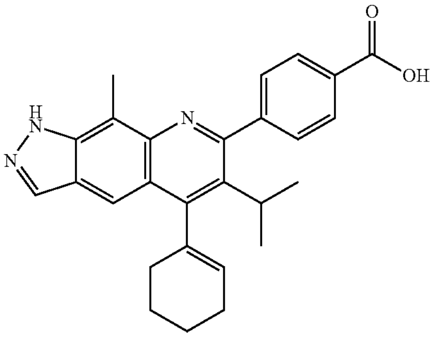 [SMILES: Cc1c2nc(-c3ccc(C(=O)O)cc3)c(C(C)C)c(C3=CCCCC3)c2cc2cn[nH]c12] | 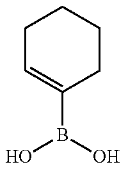 | $^1H$ NMR (400 MHz, DMSO-$d_6$) δ 13.24 (s, 1H), 8.42 (s, 1H), 8.23 (s, 1H), 8.06 (d, J = 8.2 Hz, 2H), 7.60 (d, J = 8.0 Hz, 2H), 5.79 (s, 1H), 2.85 (s, 3H), 2.45-2.13 (m, 4H), 1.81 (s, 4H), 1.12 (m, 6H). *isopropyl C—H obscured by solvent. LCMS m/z 426.23 $[M + H]^+$ |
| 196 | 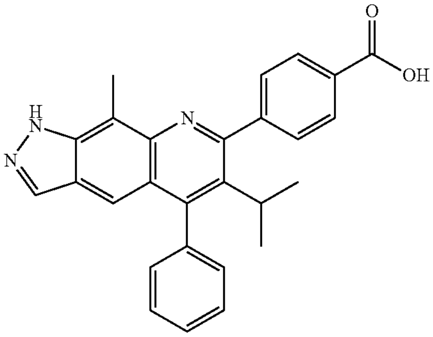 [SMILES: Cc1c2nc(-c3ccc(C(=O)O)cc3)c(C(C)C)c(-c3ccccc3)c2cc2cn[nH]c12] | 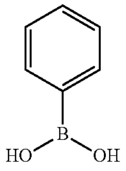 | $^1H$ NMR (400 MHz, DMSO-$d_6$) δ 13.28 (s, 1H), 13.08 (s, 1H), 8.29 (d, J = 1.1 Hz, 1H), 8.14-8.03 (m, 2H), 7.72-7.65 (m, 2H), 7.64-7.53 (m, 3H), 7.45-7.39 (m, 2H), 7.38 (s, 1H), 3.13 (h, J = 7.1 Hz, 1H), 2.90 (d, J = 0.9 Hz, 3H), 0.91 (d, J = 7.2 Hz, 6H). LCMS m/z 422.19 $[M + H]^+$ |

TABLE 11-continued

Method of preparation, structure and physicochemical data for Compounds 195-201

| Compound | Product | Reagent | $^1$H NMR; LCMS m/z [M + H]$^+$ |
| --- | --- | --- | --- |
| 197 | 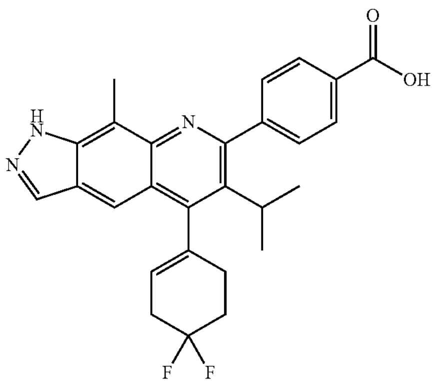 [SMILES: Cc1c2nc(-c3ccc(C(=O)O)cc3)c(C(C)C)c(C3=CCC(F)(F)CC3)c2cc2cn[nH]c12] | 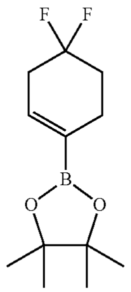 | $^1$H NMR (400 MHz, DMSO-$d_6$) δ 13.30 (s, 1H), 8.40 (s, 1H), 8.17 (s, 1H), 8.07 (d, J = 8.1 Hz, 2H), 7.61 (d, J = 8.1 Hz, 2H), 5.73 (s, 1H), 3.31 (s, J = 7.2 Hz, 1H), 2.93 (m, 5H), 2.65 (m, 2H), 2.47-2.19 (m, 2H), 1.13 (m, 6H). LCMS m/z 462.18 [M + H]$^+$ |
| 198 | 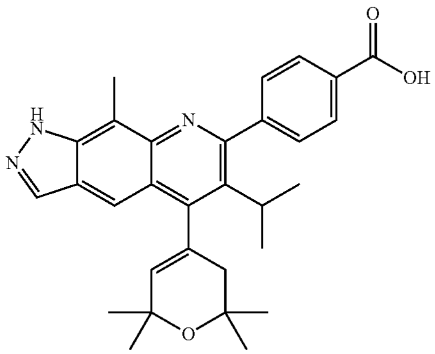 [SMILES: Cc1c2nc(-c3ccc(C(=O)O)cc3)c(C(C)C)c(C3=CC(C)(C)OC(C)(C)C3)c2cc2cn[nH]c12] | 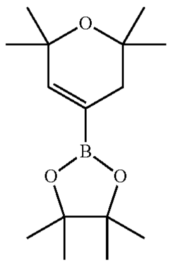 | LCMS m/z 484.18 [M + H]+ |
| 199 | 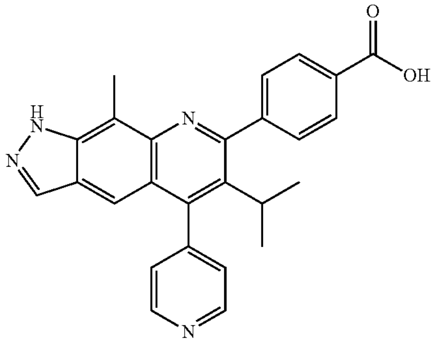 | 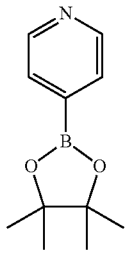 | $^1$H NMR (400 MHz, DMSO-$d_6$) δ 13.39 (s, 1H), 8.96 (d, J = 5.2 Hz, 2H), 8.29 (s, 1H), 8.16-8.06 (m, 2H), 7.80 (d, J = 5.4 Hz, 2H), 7.68 (d, J = 8.1 Hz, 3H), 7.37 (s, 1H), 3.07 (heptet, J = 7.2 Hz, 1H), 2.92 (s, 3H), 0.93 (d, J = 7.2 Hz, 6H). LCMS m/z 423.17 [M + H]$^+$ |
| 200 | 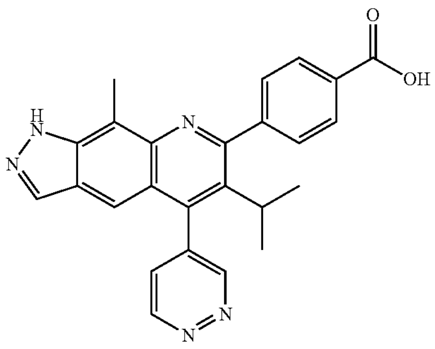 | 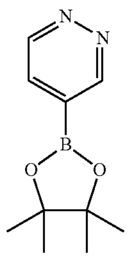 | $^1$H NMR (400 MHz, DMSO-$d_6$) δ 13.40 (s, 1H), 9.60-9.46 (m, 1H), 9.40 (d, J = 1.9 Hz, 1H), 8.30 (s, 1H), 8.11 (d, J = 8.1 Hz, 2H), 7.94 (dd, J = 5.3, 2.4 Hz, 1H), 7.68 (d, J = 8.0 Hz, 2H), 7.33 (s, 1H), 3.05 (heptet, J = 7.2 Hz, 1H), 2.93 (s, 3H), 0.91 (m, 6H). LCMS m/z 423.98 [M + H]$^+$ |

TABLE 11-continued

Method of preparation, structure and physicochemical data for Compounds 195-201

| Compound | Product | Reagent | $^1$H NMR; LCMS m/z $[M + H]^+$ |
|---|---|---|---|
| 201 | 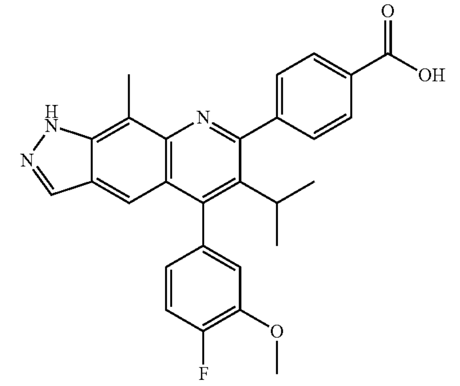 [SMILES: COc1cc(-c2c(C(C)C)c(-c3ccc(C(=O)O)cc3)nc3c(C)c4[nH]ncc4cc23)ccc1F] | 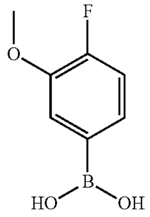 | $^1$H NMR (400 MHz, Methanol-$d_4$) δ 8.17 (s, 1H), 8.16-8.11 (m, 2H), 7.65-7.58 (m, 2H), 7.55 (d, J = 1.0 Hz, 1H), 7.30 (dd, J = 11.4, 8.2 Hz, 1H), 7.12 (dd, J = 8.2, 2.0 Hz, 1H), 6.93 (m, 1H), 3.87 (s, 3H), 3.25 (hept, J = 7.2 Hz, 1H), 2.96 (d, J = 0.9 Hz, 3H), 1.00 (m, 6H). LCMS m/z 470.19 $[M + H]^+$ |

Compound 202

2-fluoro-4-[5-(4-fluorophenyl)-6-isopropyl-9-methyl-1H-pyrazolo[4,3-g]quinolin-7-yl]benzoic acid (202)

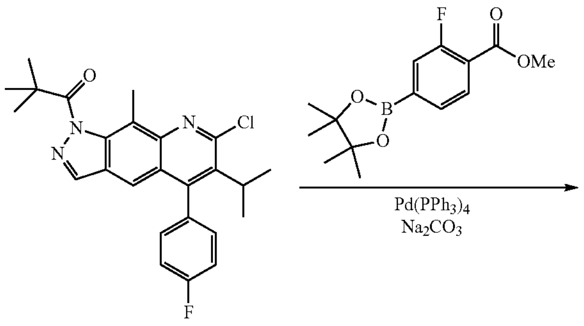

T6

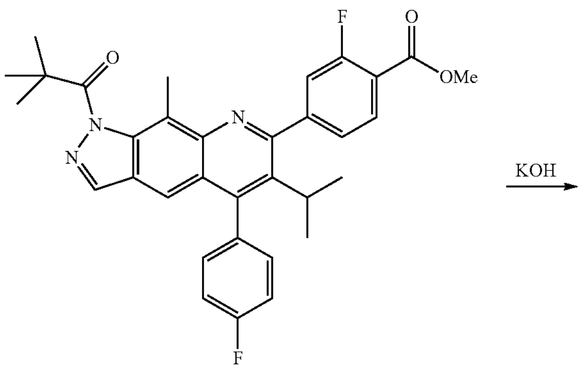

D80

-continued

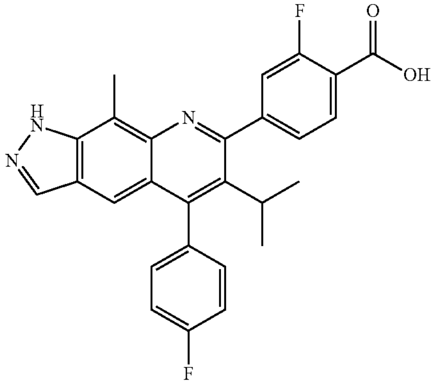

202

Compound 202 was prepared from T6 in two steps by Suzuki coupling (standard procedure B) then ester hydrolysis (Standard procedure G using KOH as the base). Purification by reverse-phase HPLC. Method: C18 Waters Sunfire column (30×150 mm, 5 micron). Gradient: MeCN in $H_2O$ with 0.2% formic acid afforded the product. 2-fluoro-4-[5-(4-fluorophenyl)-6-isopropyl-9-methyl-1H-pyrazolo[4,3-g]quinolin-7-yl]benzoic acid (15.9 mg, 57%) $^1$H NMR (400 MHz, Methanol-$d_4$:Chloroform-d (3:1) δ 8.11 (s, 1H), 8.03 (t, J=7.7 Hz, 1H), 7.44 (d, J=1.0 Hz, 1H), 7.40 (dd, J=7.9, 1.6 Hz, 1H), 7.37-7.31 (m, 3H), 7.31-7.22 (m, 2H), 3.21 (septet, J=7.2 Hz, 1H), 2.96 (d, J=0.9 Hz, 3H), 0.97 (d, J=7.2 Hz, 6H). LCMS m/z 458.33 $[M+H]^+$.

Compound 203

3-[5-(4-fluorophenyl)-6-isopropyl-9-methyl-1H-pyrazolo[4,3-g]quinolin-7-yl]benzoic acid (203)

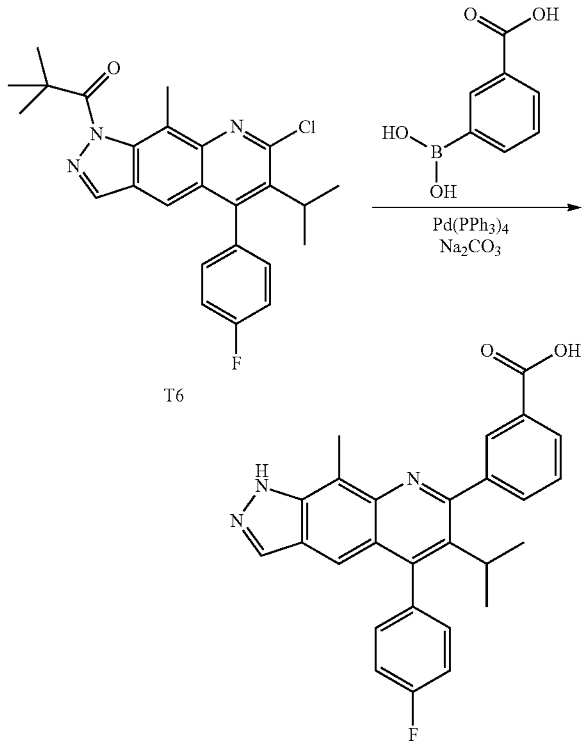

T6

203

Compound 203 was prepared from T6 by Suzuki coupling with 3-boronobenzoic acid according to standard procedure B. Purification by reverse-phase HPLC. Method: C18 Waters Sunfire column (30×150 mm, 5 micron). Gradient: MeCN in $H_2O$ with 0.2% formic acid afforded the product. 3-[5-(4-fluorophenyl)-6-isopropyl-9-methyl-1H-pyrazolo [4,3-g]quinolin-7-yl]benzoic acid (12.7 mg, 48%). $^1H$ NMR (400 MHz, Methanol-$d_4$) δ 8.19 (m, 1H), 8.15 (m, 2H), 7.79 (dt, J=7.6, 1.4 Hz, 1H), 7.63 (t, J=7.7 Hz, 1H), 7.49 (d, J=1.0 Hz, 1H), 7.41 (m, 2H), 7.37-7.28 (m, 2H), 3.27-3.18 (m, 1H), 2.98 (d, J=0.9 Hz, 3H), 0.97 (d, J=7.2 Hz, 6H). LCMS m/z 440.33 $[M+H]^+$.

Compound 204

5-[5-(4-fluorophenyl)-6-isopropyl-9-methyl-1H-pyrazolo[4,3-g]quinolin-7-yl]-6-methoxy-pyridine-2-carboxamide (204)

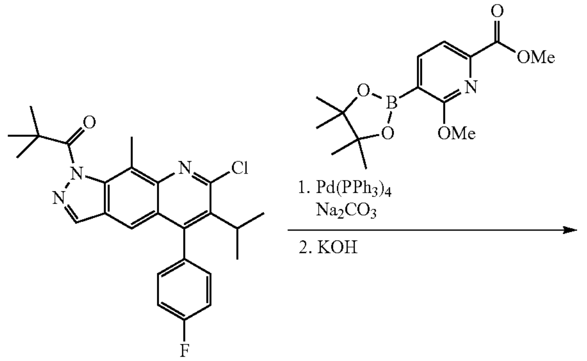

T6

-continued

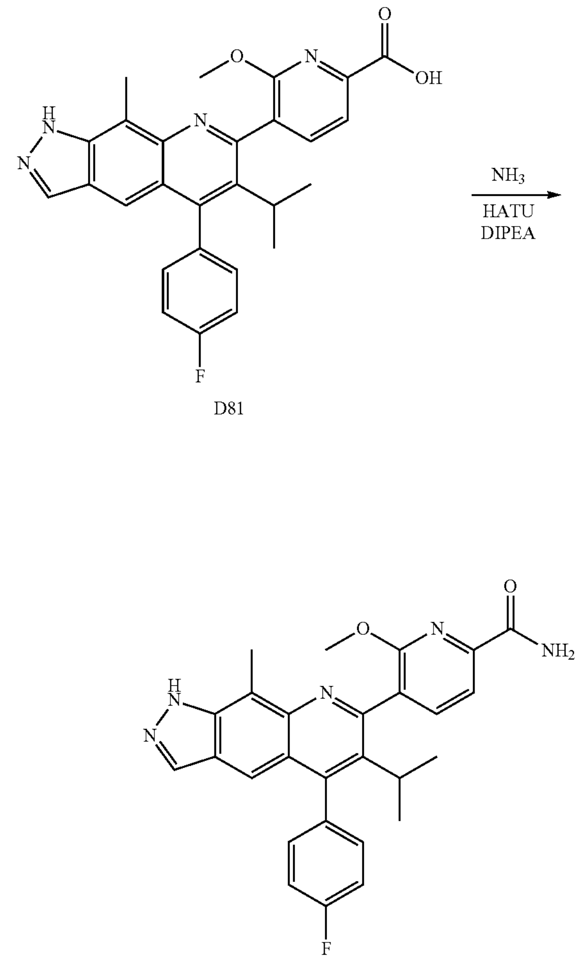

D81

204

Step 1 and 2. 5-[5-(4-fluorophenyl)-6-isopropyl-9-methyl-1H-pyrazolo[4,3-g]quinolin-7-yl]-6-methoxy-pyridine-2-carboxylic acid (D81=compound 189)

Compound 204 was prepared from T6 by Suzuki coupling then ester hydrolysis using standard procedure B and standard procedure G (KOH was used instead of LiOH). Purification by reverse-phase HPLC. Method: C18 Waters Sunfire column (30×150 mm, 5 micron). Gradient: MeCN in $H_2O$ with 0.2% formic acid afforded the product. 5-[5-(4-fluorophenyl)-6-isopropyl-9-methyl-1H-pyrazolo[4,3-g] quinolin-7-yl]-6-methoxy-pyridine-2-carboxylic acid (10.6 mg, 38%) $^1H$ NMR (400 MHz, Methanol-$d_4$) δ 8.15 (s, 1H), 7.91 (m, 2H), 7.48 (d, J=0.9 Hz, 1H), 7.42 (m, 1H), 7.38-7.26 (m, 3H), 3.99 (s, 3H), 3.02 (septet, J=7.2 Hz, 1H), 2.95 (d, J=0.9 Hz, 3H), 0.94 (m, 6H). LCMS m/z 471.39 $[M+H]^+$.

Step 3. Synthesis of 5-[5-(4-fluorophenyl)-6-isopropyl-9-methyl-1H-pyrazolo[4,3-g]quinolin-7-yl]-6-methoxy-pyridine-2-carboxamide (204)

5-[5-(4-fluorophenyl)-6-isopropyl-9-methyl-1H-pyrazolo [4,3-g]quinolin-7-yl]-6-methoxy-pyridine-2-carboxylic acid (5 mg, 0.01063 mmol) was dissolved in DMF (200 μL). Then, HATU (5 mg, 0.01315 mmol) was added, followed by DIPEA (6 μL, 0.03445 mmol). The reaction was stirred for 5 minutes, then ammonia (2 μL of 30% w/w, 0.03171 mmol) was added. Purification by reverse-phase HPLC. Method: C18 Waters Sunfire column (30×150 mm, 5 micron). Gradient: MeCN in $H_2O$ with 0.2% formic acid afforded the product. 5-[5-(4-fluorophenyl)-6-isopropyl-9-methyl-1H-pyrazolo[4,3-g]quinolin-7-yl]-6-methoxy-pyridine-2-carboxamide (2.7 mg, 50%) $^1$H NMR (400 MHz, DMSO-$d_6$) δ 13.32 (s, 1H), 8.31 (d, J=1.3 Hz, 1H), 8.14 (d, J=2.6 Hz, 1H), 7.98 (d, J=7.4 Hz, 1H), 7.81 (d, J=7.4 Hz, 1H), 7.76 (d, J=2.5 Hz, 1H), 7.51-7.35 (m, 5H), 3.96 (s, 3H), 2.95 (h, J=7.2 Hz, 1H), 2.89 (s, 3H), 0.88 (m, 6H, conformers). LCMS m/z 470.15 $[M+H]^+$.

Compound 205

3-fluoro-4-[5-(4-fluorophenyl)-6-tetrahydropyran-4-yl-1H-pyrazolo[4,3-g]quinolin-7-yl]benzoic acid (205)

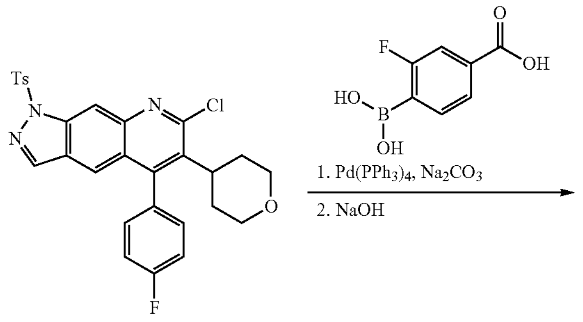

T9

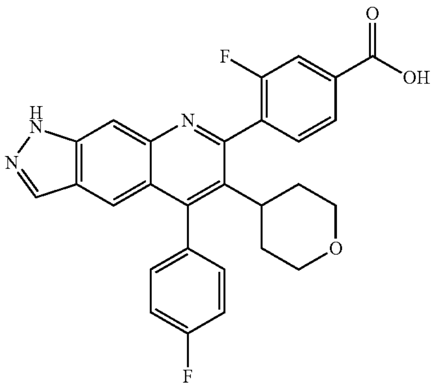

205

Compound 205 was prepared from T9 by Suzuki coupling then ester hydrolysis using standard procedure B and standard procedure G. Purification by reverse-phase HPLC. Method: C18 Waters Sunfire column (30×150 mm, 5 micron). Gradient: MeCN in $H_2O$ with 0.2% formic acid afforded the product. 3-fluoro-4-[5-(4-fluorophenyl)-6-tetrahydropyran-4-yl-1H-pyrazolo[4,3-g]quinolin-7-yl]benzoic acid (2.3 mg, 5%). LCMS m/z 486.15 $[M+H]^+$.

Compound 206

4-[5-(4-fluorophenyl)-6-tetrahydropyran-4-yl-1H-pyrazolo[4,3-g]quinolin-7-yl]benzoic acid (206)

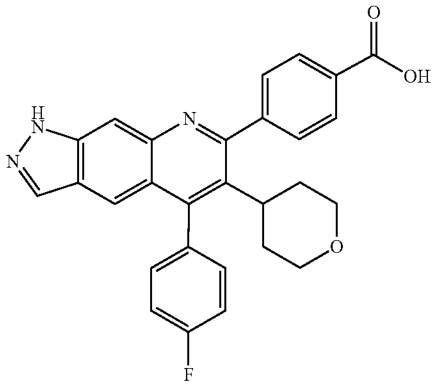 [SMILES: O=C(O)c1ccc(-c2nc3cc4[nH]ncc4cc3c(-c3ccc(F)cc3)c2C2CCOCC2)cc1]

Compound 206 was prepared from T9 by Suzuki coupling then ester hydrolysis using standard procedure B and standard procedure G (NaOH was used as base). Purification by reverse-phase HPLC. Method: C18 Waters Sunfire column (30×150 mm, 5 micron). Gradient: MeCN in $H_2O$ with 0.2% formic acid afforded the product. 4-[5-(4-fluorophenyl)-6-tetrahydropyran-4-yl-1H-pyrazolo[4,3-g]quinolin-7-yl]benzoic acid (1.6 mg, 4%). $^1$H NMR (400 MHz, DMSO-$d_6$) δ 13.25 (s, 1H), 8.35 (s, 1H), 8.12-8.05 (m, 3H), 7.67 (d, J=7.8 Hz, 2H), 7.60 (s, 1H), 7.52-7.44 (m, 4H), 3.62 (m, 2H), 3.00-2.90 (m, 1H), 2.81 (t, J=11.3 Hz, 2H), 2.52-2.48 (m, 2H), 1.54-1.38 (m, 2H). LCMS m/z 468.19 $[M+H]^+$.

Compound 207-210

Compounds 207-210 (Table 12) were prepared from T8 and the appropriate phenol or alcohol reagent using standard procedures E, F and G, as described in the preparation of compound 168.

TABLE 12

Method of preparation, structure and physicochemical data for Compounds 207-210

| Compound | Product | Reagent | $^1H$ NMR; LCMS m/z $[M + H]^+$ |
|---|---|---|---|
| 207 | 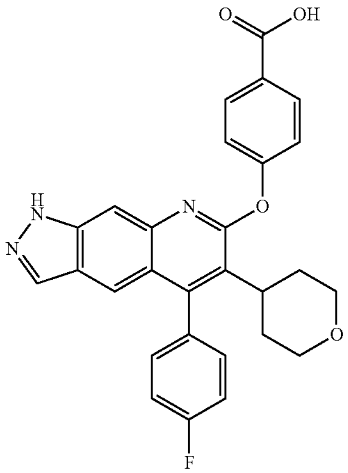 [SMILES: O=C(O)c1ccc(Oc2nc3cc4[nH]ncc4cc3c(-c3ccc(F)cc3)c2C2CCOCC2)cc1] | 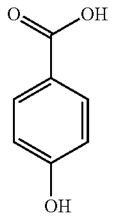 | $^1H$ NMR (400 MHz, DMSO-$d_6$) δ 13.13 (s, 1H), 8.26 (s, 1H), 8.09 (d, J = 8.7 Hz, 2H), 7.63 (s, 1H), 7.57 (s, 1H), 7.48 (d, J = 7.2 Hz, 4H), 7.42 (d, J = 8.7 Hz, 2H), 3.87 (dd, J = 10.7, 3.6 Hz, 2H), 3.09 (t, J = 11.7 Hz, 2H), 2.84-2.79 (m, 1H), 2.45-2.37 (m, 2H), 1.54 (d, J = 12.6 Hz, 2H). LCMS m/z 484.12 $[M + H]^+$ |
| 208 | 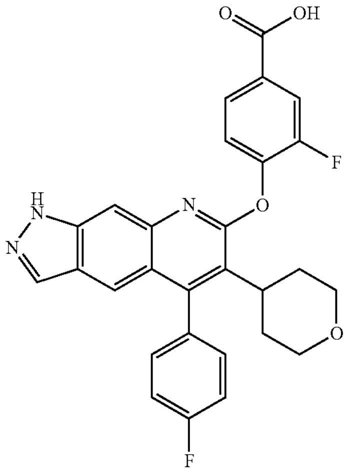 [SMILES: O=C(O)c1ccc(Oc2nc3cc4[nH]ncc4cc3c(-c3ccc(F)cc3)c2C2CCOCC2)c(F)c1] | 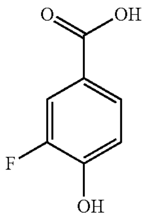 | $^1H$ NMR (400 MHz, DMSO-$d_6$) δ 13.56 (s, 1H), 8.67 (s, 1H), 8.41 (m, 2H), 8.12-8.04 (m, 3H), 7.99-7.88 (m, 4H), 4.36 (dd, J = 11.5, 4.1 Hz, 2H), 3.60 (t, J = 12.0 Hz, 2H), 3.37 (t, J = 12.2 Hz, 1H), 2.97-2.92 (m, 2H), 2.03 (d, J = 12.9 Hz, 2H). LCMS m/z 502.23 $[M + H]^+$ |
| 209 | 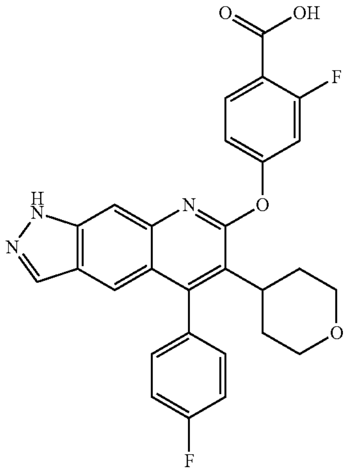 [SMILES: O=C(O)c1ccc(Oc2nc3cc4[nH]ncc4cc3c(-c3ccc(F)cc3)c2C2CCOCC2)cc1F] | 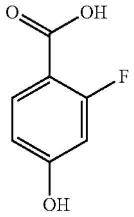 [SMILES: O=C(O)c1ccc(O)cc1F] | $^1H$ NMR (400 MHz, DMSO-$d_6$) δ 13.60 (s, 1H), 8.68 (s, 1H), 8.53 (t, J = 8.6 Hz, 1H), 8.19 (s, 1H), 8.09 (s, 1H), 7.92 (m, 4H), 7.84-7.72 (m, 2H), 4.40-4.29 (m, 2H), 3.58 (m 2H), 3.34 (t, J =12.0 Hz, 1H), 2.94-2.84 (m, 2H), 2.02 (d, J = 12.9 Hz, 2H). LCMS m/z 502.03 $[M + H]^+$ |

TABLE 12-continued

| Method of preparation, structure and physicochemical data for Compounds 207-210 | | | |
|---|---|---|---|
| Compound | Product | Reagent | $^1H$ NMR; LCMS m/z $[M + H]^+$ |
| 210 | 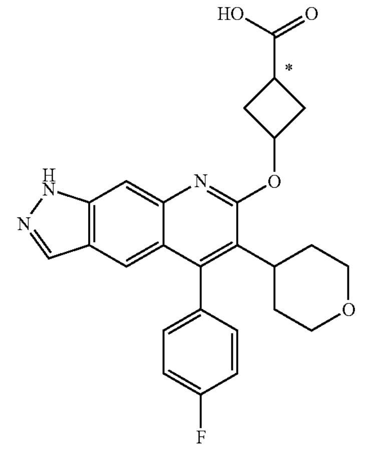 [SMILES: O=C(O)C1CC(Oc2nc3cc4[nH]ncc4cc3c(-c3ccc(F)cc3)c2C2CCOCC2)C1] | 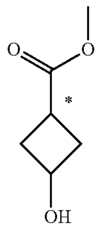 | $^1H$ NMR (400 MHz, DMSO-$d_6$) δ 13.49 (s, 1H), 8.62 (s, 1H), 8.27 (s, 1H), 7.95 (s, 1H), 7.91-7.79 (m, 4H), 5.91 (m, 1H), 4.33 (m, 2H), 3.53 (t, J = 11.7 Hz, 2H), 3.42-3.26 (m, 3H), 3.24-3.12 (m, 1H), 2.99-2.80 (m, 4H), 1.85 (d, J = 13.0 Hz, 2H). LCMS m/z 462.13 $[M + H]^+$; Trans stereoisomer. |

Compound 211

4-[9-fluoro-5-(4-fluorophenyl)-6-isopropyl-1H-pyrazolo[4,3-g]quinolin-7-yl]-3-methoxy-benzoic acid (211)

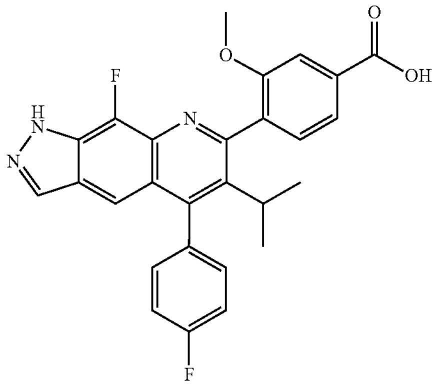

Prepared from compound T7 by Suzuki coupling (standard procedure B) and then THP removal by treatment with 4 M HCl in 1,4-dioxane at room temperature. Purification by reverse-phase HPLC. Method: C18 Waters Sunfire column (30×150 mm, 5 micron). Gradient: MeCN in $H_2O$ with 0.2% formic acid afforded the product. 4-[9-fluoro-5-(4-fluorophenyl)-6-isopropyl-1H-pyrazolo[4,3-g]quinolin-7-yl]-3-methoxy-benzoic acid (7.0 mg, 26%). $^1H$ NMR (400 MHz, Methanol-$d_4$) δ 8.24 (d, J=3.2 Hz, 1H), 7.80 (dd, J=7.7, 1.4 Hz, 1H), 7.75 (d, J=1.4 Hz, 1H), 7.52-7.28 (m, 6H), 3.85 (s, 3H), 3.09 (septet, J=7.2 Hz, 1H), 0.94 (m, 6H). LCMS m/z 474.4 $[M+H]^+$.

Compound 212

2-fluoro-4-[[5-(4-fluorophenyl)-6-methylsulfonyl-1H-pyrazolo[4,3-g]quinolin-7-yl]oxy]benzoic acid (212)

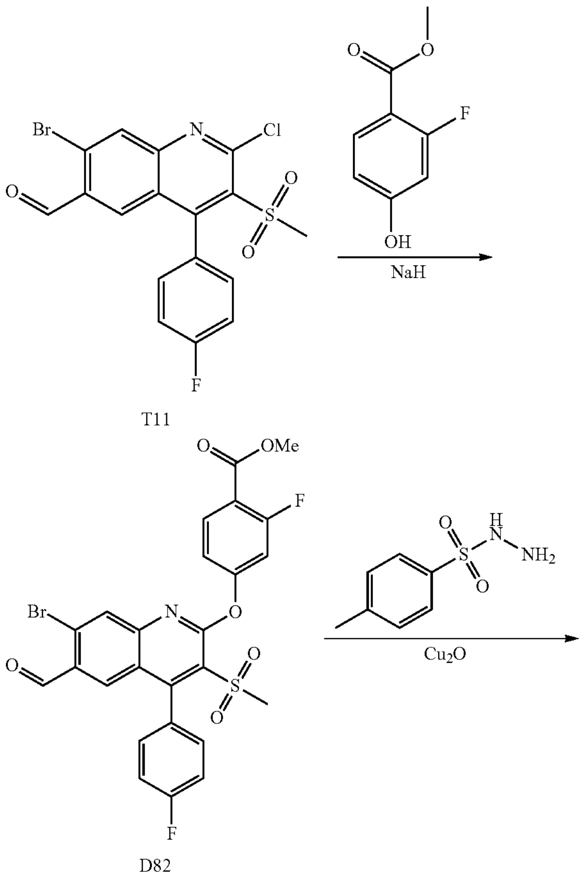

-continued

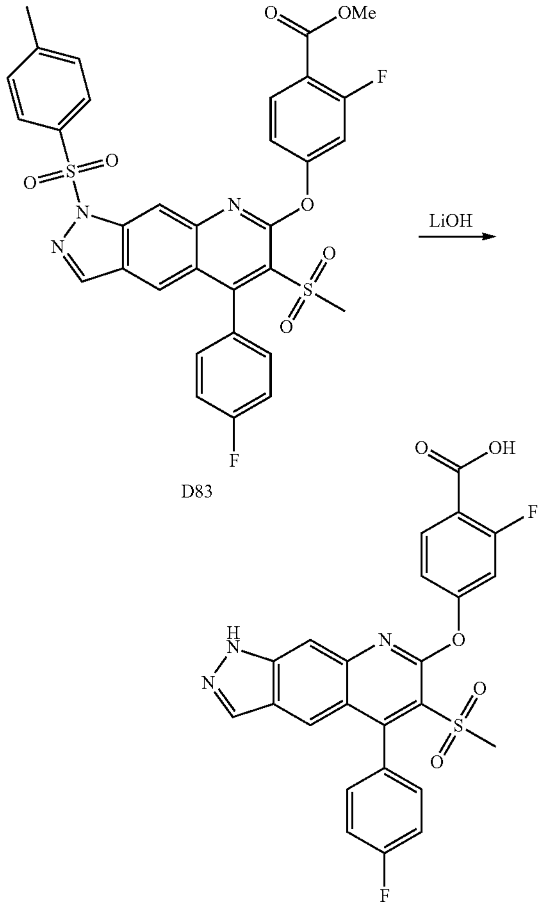

D83

212

Compound 212 was prepared from T11 in three steps using the method described for the preparation of compound 168. LCMS m/z 496.17 $[M+H]^+$.

Compounds 213-217

Compound 213-217 (Table 13) were prepared from T11 as described for the preparation of compound 212 using the reactants below in Step 1.

TABLE 13

Method of preparation, structure and physicochemical data for compounds 213-217

| Compound | Product | Reactants | $^1H$ NMR; LCMS m/z $[M + H]^+$ |
|---|---|---|---|
| 213 | 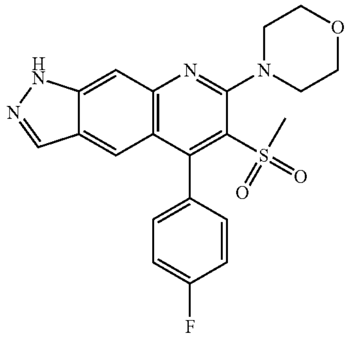 [SMILES: CS(=O)(=O)c1c(N2CCOCC2)nc2cc3[nH]ncc3cc2c1-c1ccc(F)cc1] | 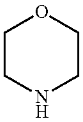 | $^1H$ NMR (300 MHz, Chloroform-d + 5% $CD_3OD$) δ 8.21 (d, J = 1.2 Hz, 1H), 8.03 (t, J = 1.1 Hz, 1H), 7.95 (d, J = 0.9 Hz, 1H), 7.47-7.35 (m, 2H), 7.33-7.19 (m, 2H), 4.06-3.86 (m, 4H), 3.54 (dd, J = 5.7, 3.6 Hz, 4H), 3.29 (s, 3H). LCMS m/z 427.17 $[M + H]^+$ |

TABLE 13-continued

Method of preparation, structure and physicochemical data for compounds 213-217

| Compound | Product | Reactants | $^1$H NMR; LCMS m/z $[M + H]^+$ |
|---|---|---|---|
| 214 | 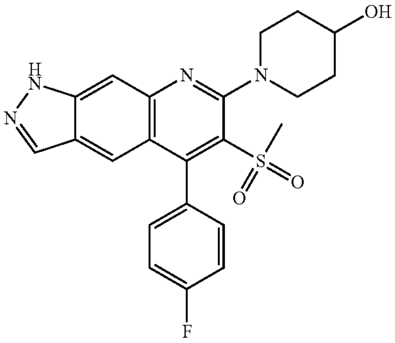 [SMILES: CS(=O)(=O)c1c(N2CCC(O)CC2)nc2cc3[nH]ncc3cc2c1-c1ccc(F)cc1] | 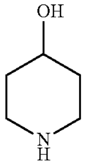 | $^1$H NMR (300 MHz, Chloroform-d + 5% $CD_3OD$) δ 11.27 (s, 1H), 8.22 (s, 1H), 8.05 (s, 1H), 7.98 (s, 1H), 7.94 (s, 1H), 7.40 (dd, J = 8.7, 5.3 Hz, 2H), 7.32-7.23 (m, 2H), 4.05-3.91 (m, 1H), 3.84 (dt, J = 10.0, 4.0 Hz, 2H), 3.26 (s, 3H), 3.26-3.17 (m, 2H), 2.14 (dd, J = 10.2, 5.1 Hz, 2H), 1.87 (dtd, J = 12.9, 9.4, 3.6 Hz, 2H). LCMS m/z 441.21 $[M + H]^+$ |
| 215 | 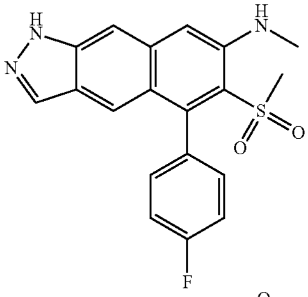 | | $^1$H NMR (400 MHz, Chloroform-d + 5% $CD_3OD$) δ 7.97 (d, J = 1.2 Hz, 1H), 7.68 (t, J = 1.0 Hz, 1H), 7.38 (d, J = 0.9 Hz, 1H), 7.30-7.06 (m, 4H), 3.11 (s, 3H), 2.95 (s, 3H). LCMS m/z 371.14 $[M + H]^+$ |
| 216 | 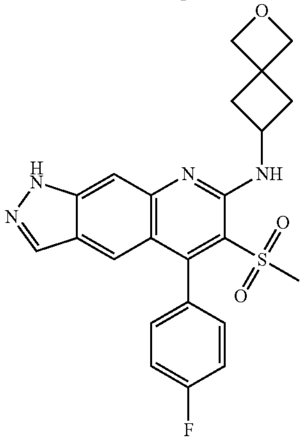 | 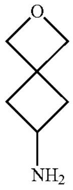 | LCMS m/z 453.04 $[M + H]^+$ |
| 217 | 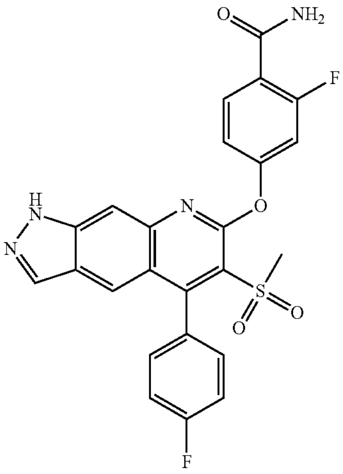 [SMILES: CS(=O)(=O)c1c(Oc2ccc(C(N)=O)c(F)c2)nc2cc3[nH]ncc3cc2c1-c1ccc(F)cc1] | 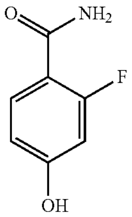 [SMILES: NC(=O)c1ccc(O)cc1F] | $^1$H NMR (300 MHz, Chloroform-d + 5% $CD_3OD$) δ 8.21 (s, 1H), 7.89 (d, J = 8.9 Hz, 1H), 7.86 (dd, J = 6.6, 1.0 Hz, 1H), 7.40 (s, 1H), 7.38-7.23 (m, 4H), 6.71 (dd, J = 8.7, 2.3 Hz, 1H), 6.59 (dd, J = 14.0, 2.3 Hz, 1H), 3.42 (s, 3H). LCMS m/z 495.62 $[M + H]^+$ |

Compound 218

4-[5-(4-fluorophenyl)-6-methoxycarbonyl-1H-pyrazolo[4,3-g]quinolin-7-yl]benzoic acid (218)

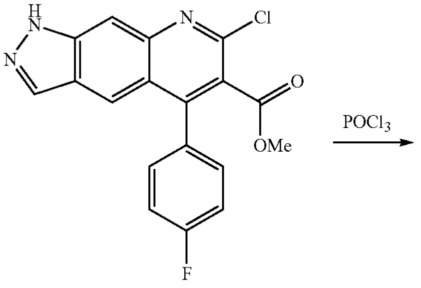

D84

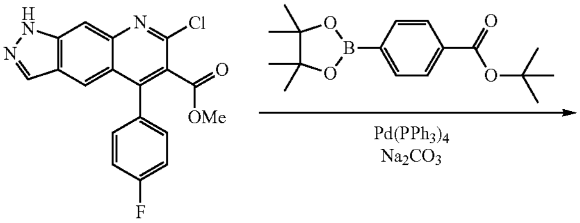

D85

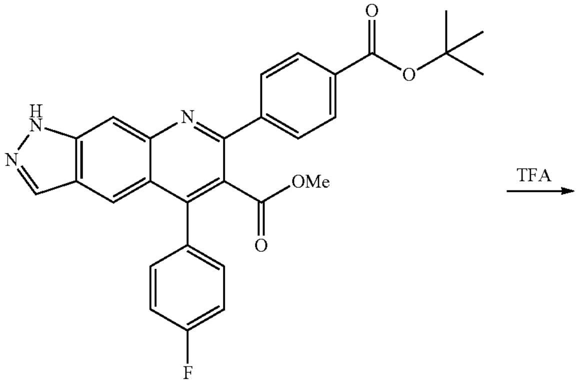

D86

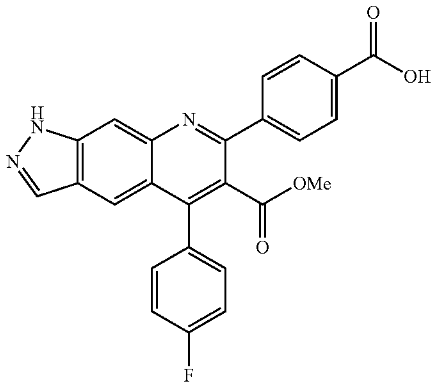

218

Step 1. Synthesis of methyl 7-chloro-5-(4-fluorophenyl)-1H-pyrazolo[4,3-g]quinoline-6-carboxylate (D85)

Compound D85 was prepared from D84 according to standard procedure A to afford the product. methyl 7-chloro-5-(4-fluorophenyl)-1H-pyrazolo[4,3-g]quinoline-6-carboxylate (2376.9 mg, 71%). $^1H$ NMR (400 MHz, DMSO-$d_6$) δ 13.54 (s, 1H), 8.46 (d, J=1.1 Hz, 1H), 8.18 (t, J=1.1 Hz, 1H), 8.10 (d, J=0.9 Hz, 1H), 7.55-7.50 (m, 2H), 7.49-7.43 (m, 2H), 3.62 (s, 3H). LCMS m/z 355.95 $[M+H]^+$.

Step 2 & 3: 4-[5-(4-fluorophenyl)-6-methoxycarbonyl-1H-pyrazolo[4,3-g]quinolin-7-yl]benzoic acid (218)

Compound 218 was prepared from D85 by Suzuki coupling with tert-butyl 4-(4,4,5,5-tetramethyl-1,3,2-dioxaborolan-2-yl)benzoate as described in standard procedure B, followed by treatment with trifluoroacetic acid in dichloromethane. Purification by reverse-phase HPLC. Method: C18 Waters Sunfire column (30×150 mm, 5 micron). Gradient: MeCN in $H_2O$ with 0.2% formic acid afforded the product. 4-[5-(4-fluorophenyl)-6-methoxycarbonyl-1H-pyrazolo[4,3-g]quinolin-7-yl]benzoic acid (9.7 mg, 15%). $^1H$ NMR (400 MHz, DMSO-$d_6$) δ 13.48 (s, 1H), 8.46 (s, 1H), 8.28 (s, 1H), 8.16-8.06 (m, 3H), 7.82 (d, J=8.2 Hz, 2H), 7.53 (m, 2H), 7.45 (m, 2H), 3.38 (s, 3H). LCMS m/z 441.87 $[M+H]^+$.

Compound 219

4-[6-(dimethylcarbamoyl)-5-(4-fluorophenyl)-1H-pyrazolo[4,3-g]quinolin-7-yl]-3-methoxy-benzoic acid (219)

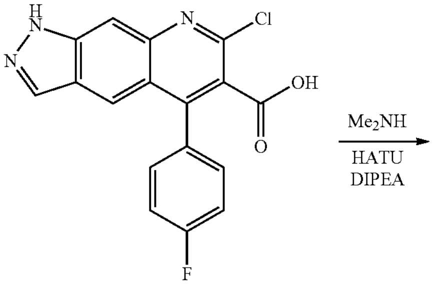

T10

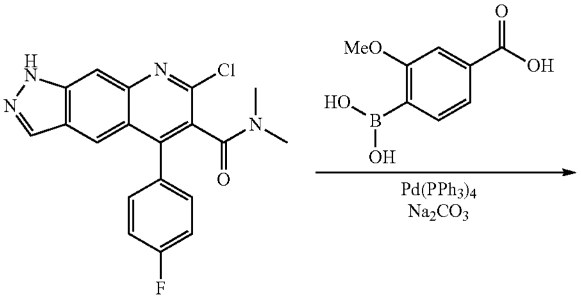

D87

-continued

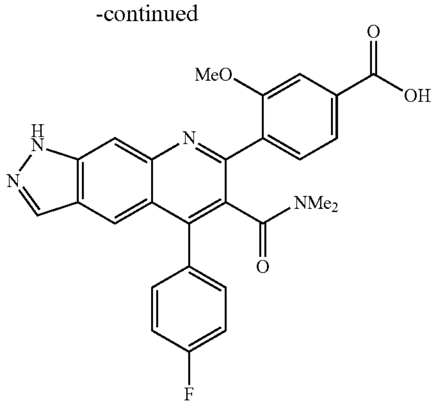

219

Step 1. Synthesis of 7-chloro-5-(4-fluorophenyl)-N,N-dimethyl-1H-pyrazolo[4,3-g]quinoline-6-carboxamide (D87)

In a vial, 7-chloro-5-(4-fluorophenyl)-1H-pyrazolo[4,3-g]quinoline-6-carboxylic acid (60 mg, 0.1756 mmol), HATU (70 mg, 0.1841 mmol) and N-methylmethanamine (Hydrochloride salt) (45 mg, 0.5518 mmol) were dissolved in dichloromethane (3 mL). Then, DIPEA (90 μL, 0.5167 mmol) was added. The reaction was stirred for 30 minutes at room temperature. Water and dichloromethane were added. The mixture was extracted thrice with dichloromethane. The organic phases were filtered through a phase separator, combined and the volatiles were evaporated in vacuo. The crude was purified by flash column chromatography (Gradient: 0-40% of EtOAc in dichloromethane) to afford the product. 7-chloro-5-(4-fluorophenyl)-N,N-dimethyl-1H-pyrazolo[4,3-g]quinoline-6-carboxamide (53.5 mg, 60%). LCMS m/z 369.04 $[M+H]^+$.

Step 2. Synthesis of 4-[6-(dimethylcarbamoyl)-5-(4-fluorophenyl)-1H-pyrazolo[4,3-g]quinolin-7-yl]-3-methoxy-benzoic acid (219)

Compound 219 was prepared from compound T10 by Suzuki coupling using standard procedure B. Purification by reversed-phase HPLC. Method: C18 Waters Sunfire column (30×150 mm, 5 micron). Gradient: MeCN in $H_2O$ with 0.1% trifluoroacetic acid afforded the product. 4-[6-(dimethylcarbamoyl)-5-(4-fluorophenyl)-1H-pyrazolo[4,3-g]quinolin-7-yl]-3-methoxy-benzoic acid (Trifluoroacetate salt) (3.7 mg, 6%) $^1H$ NMR (400 MHz, DMSO-$d_6$) δ 13.37 (s, 1H), 8.43 (s, 1H), 8.20 (t, J=1.1 Hz, 1H), 8.14 (d, J=1.0 Hz, 1H), 7.71 (m, 1H), 7.63 (dd, J=7.7, 1.5 Hz, 1H), 7.59 (d, J=1.5 Hz, 1H), 7.50-7.36 (m, 4H), 3.76 (s, 3H), 2.55 (s, 3H), 2.43 (s, 3H). LCMS m/z 485.13 $[M+H]^+$.

Compound 220

5-(4-fluorophenyl)-6-isopropyl-1H-pyrazolo[4,3-g]quinoline (220)

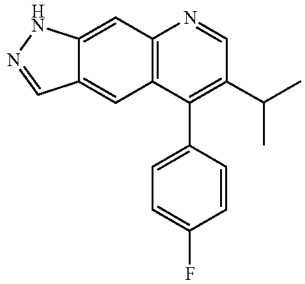 [SMILES: CC(C)c1cnc2cc3[nH]ncc3cc2c1-c1ccc(F)cc1]

Compound 220 was prepared as described for D12. $^1H$ NMR (400 MHz, DMSO-$d_6$) δ 13.21 (s, 1H), 9.04 (s, 1H), 8.32 (t, J=1.3 Hz, 1H), 8.12 (d, J=1.0 Hz, 1H), 7.70 (d, J=0.8 Hz, 1H), 7.54-7.30 (m, 4H), 2.80 (hept, J=6.9 Hz, 1H), 1.26 (d, J=7.0 Hz, 6H). LCMS m/z 306.22 $[M+H]^+$ Compound 221

5-(4-fluorophenyl)-6-isopropyl-9-methyl-1H-pyrazolo[4,3-g]quinolin-7-ol (221)

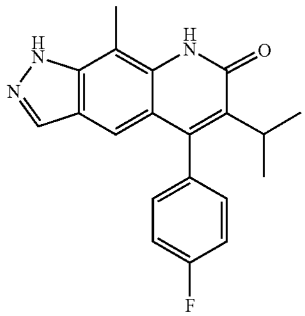 [SMILES: Cc1c2[nH]ncc2cc2c(-c3ccc(F)cc3)c(C(C)C)c(=O)[nH]c12]

Compound 221 was prepared as shown for D24. $^1H$ NMR (400 MHz, DMSO-$d_6$) δ 13.28 (s, 1H), 10.83 (s, 1H), 8.29 (s, 1H), 8.26 (d, J=1.2 Hz, 1H), 3.83-3.53 (m, 1H), 2.67 (s, 3H), 1.37 (d, J=7.0 Hz, 6H). LCMS m/z 336.55 $[M+H]^+$.

Preparation of W1-W3

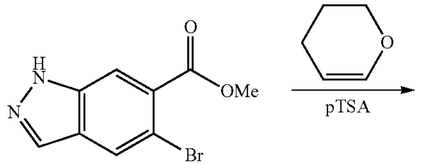

F1

-continued

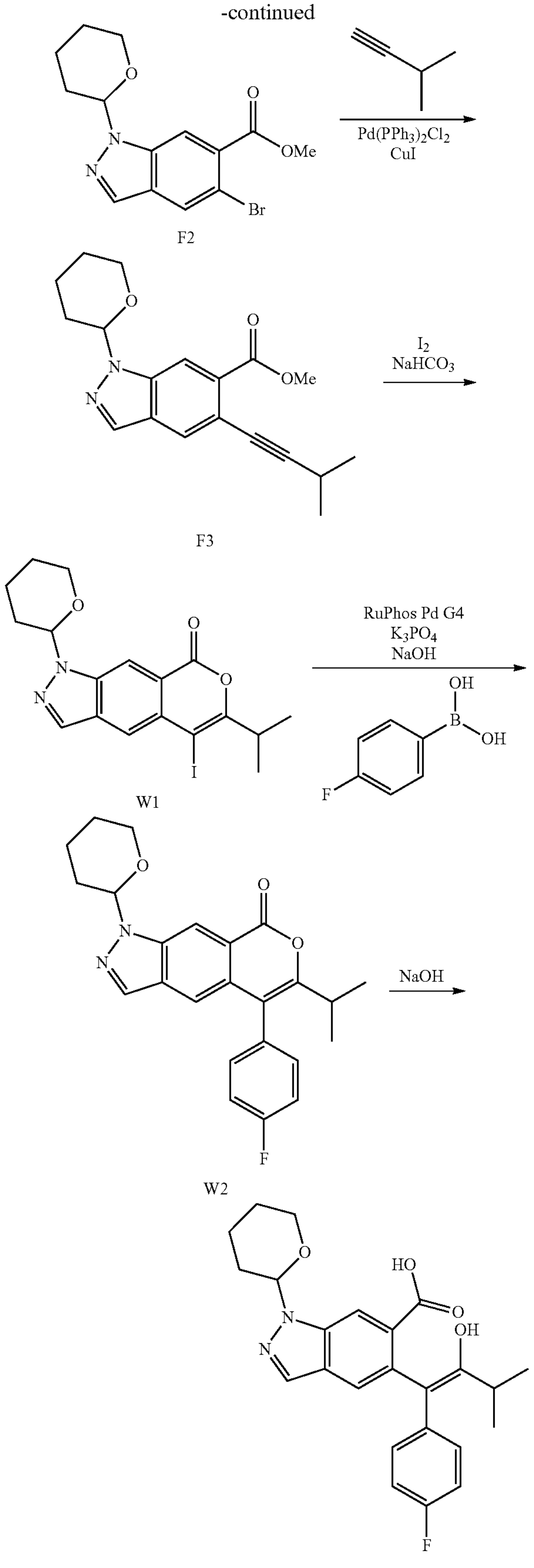

F2

F3

W1

W2

W3

Step 1. Synthesis of Synthesis of methyl 5-bromo-1-tetrahydropyran-2-yl-indazole-6-carboxylate and methyl 5-bromo-2-tetrahydropyran-2-yl-indazole-6-carboxylate (F2)

Methyl 5-bromo-1H-indazole-6-carboxylate (1.05 g, 3.70 mmol) was dissolved in anhydrous THF (24 mL). 3,4-Dihydro-2H-pyran (843.2 mg, 0.85 mL, 10.02 mmol) and p-toluenesulfonic acid (monohydrate) (36.2 mg, 0.19 mmol) were added and the reaction was stirred at 60° C. for 18 hours. The reaction mixture was allowed to cool to room temperature then ethyl acetate (125 mL) was added. The organic phase was washed with 5% aqueous $NaHCO_3$ (3×25 mL) and brine (2×25 mL), dried over $Na_2SO_4$, filtered and the solvent was removed under reduced pressure. Purification by silica gel chromatography (Gradient: 0-35% EtOAc in heptane) yielded the product as an inseparable mixture of isomers. Methyl 5-bromo-1-tetrahydropyran-2-yl-indazole-6-carboxylate and methyl 5-bromo-2-tetrahydropyran-2-yl-indazole-6-carboxylate (1.04 g, 82%) as yellow oil. $^1H$ NMR (300 MHz, $CDCl_3$) δ 8.09-7.53 (m, 3H), 5.78-5.69 (m, 1H), 4.06-3.93 (m, 4H), 3.82-3.68 (m, 1H), 2.62-2.42 (m, 1H), 2.23-1.99 (m, 2H), 1.97-1.59 (m, 3H), LCMS m/z 339.1 $[M+H]^+$.

Step 2. Synthesis of methyl 5-(3-methylbut-1-ynyl)-1-tetrahydropyran-2-yl-indazole-6-carboxylate; methyl 5-(3-methylbut-1-ynyl)-2-tetrahydropyran-2-yl-indazole-6-carboxylate (F2)

In a sealed tube, nitrogen was bubbled through a mixture of triethylamine (84 mL) and methyl 5-bromo-1-tetrahydropyran-2-yl-indazole-6-carboxylate, methyl 5-bromo-2-tetrahydropyran-2-yl-indazole-6-carboxylate (6.03 g, 17.7 mmol) for 30 minutes. CuI (255 mg, 1.33 mmol), $Pd(PPh_3)_2Cl_2$ (1.3 g, 1.78 mmol) were added followed by 3-methylbut-1-yne (3.46 g, 5.2 mL, 50.8 mmol). The tube was sealed then transferred to a pre-heated oil bath set to 80° C. After being stirred at 77.6° C. for 17 hours, then 80° C. for 4.5 hours, the reaction was cooled, diluted with ethyl acetate (150 mL) and the solvent was evaporated. The residue was dissolved in ethyl acetate (500 mL). The organic phase was washed with 1 N aq HCl (1×150 mL), water/brine (2/1) (2×150 mL), saturated aqueous $NaHCO_3$ (2×200 mL) and brine (1×200 mL), dried over $Na_2SO_4$, filtered and concentrated under reduced pressure. The residue was adsorbed on silica gel and purified by flash chromatography on silica gel (Gradient: 0-20% ethyl acetate in heptanes) to give a brown solid. This solid was diluted with cold diethyl ether (200 mL), stirred at room temperature for 0.5 hours, filtered over Buchner and dried under rotavapor vacuum to afford methyl 5-(3-methylbut-1-ynyl)-1-tetrahydropyran-2-yl-indazole-6-carboxylate and methyl 5-(3-methylbut-1-ynyl)-2-tetrahydropyran-2-yl-indazole-6-carboxylate (5.23 g, 86%) as an inseparable mixture. LCMS m/z 327.2 $[M+H]^+$. $^1H$ NMR (300 MHz, $CDCl_3$) δ 8.13 (s, 1H), 8.01 (s, 1H), 7.89 (s, 1H), 5.74 (dd, J=9.5, 2.5 Hz, 1H), 4.11-4.00 (m, 1H), 3.97 (s, 3H), 3.85-3.69 (m, 1H), 2.84 (dt, J=13.7, 7.0 Hz, 1H), 2.62-2.47 (m, 1H), 2.19-2.04 (m, 2H), 1.87-1.63 (m, 3H), 1.30 (d, J=6.8 Hz, 6H).

Step 3. Synthesis of 5-iodo-6-isopropyl-1-tetrahydropyran-2-yl-pyrano[4,3-f]indazol-8-one; 5-iodo-6-isopropyl-2-tetrahydropyran-2-yl-pyrano[4,3-f]indazol-8-one (W1)

To a solution of methyl 5-(3-methylbut-1-ynyl)-1-tetrahydropyran-2-yl-indazole-6-carboxylate and methyl 5-(3- methylbut-1-ynyl)-2-tetrahydropyran-2-yl-indazole-6-carboxylate (1.91 g, 5.85 mmol) in dry dichloromethane (40 mL) was added a solution of iodine (1.68 g, 0.34 mL, 6.62 mmol) in dry dichloromethane (60 mL) at room temperature under a nitrogen atmosphere. The reaction mixture was stirred at room temperature for 1 hours, diluted with dichloromethane (100 mL), then quenched with an aqueous solution of saturated $NaHCO_3$ and 10% $Na_2S_2O_3$ (80/20, 280 mL) at 0° C. Layers were separated and the aqueous layer was extracted with dichloromethane (2×200 mL). Combined organic layers were dried over $Na_2SO_4$, filtered and evaporated. The yellow solid was triturated in a minimum of acetonitrile (30 mL), filtered over Buchner and dried under vacuum. The filtrate was concentrated, adsorbed over silica gel and purified by flash chromatography on silica gel (Gradient: 0-10% ethyl acetate in heptanes).

The resulting solid was triturated in acetonitrile (20 mL), filtered, washed with heptanes and dried in vacuo to afford 5-iodo-6-isopropyl-1-tetrahydropyran-2-yl-pyrano[4,3-f]indazol-8-one and 5-iodo-6-isopropyl-2-tetrahydropyran-2-yl-pyrano[4,3-f]indazol-8-one as an inseparable mixture of isomers (1 g, 37%). LCMS m/z 439.1[M+H]$^+$. $^1H$ NMR (300 MHz, $CDCl_3$) δ 8.57 (s, 1H), 8.23 (s, 1H), 8.15 (s, 1H), 5.83 (dd, J=9.7, 2.3 Hz, 1H), 4.11-4.01 (m, 1H), 3.81 (td, J=11.1, 3.1 Hz, 1H), 3.61 (sept., J=7.0 Hz, 1H), 2.65-2.50 (m, 1H), 2.23-2.06 (m, 2H), 1.89-1.66 (m, 3H), 1.31 (d, J=7.0 Hz, 6H).

Step 4. Synthesis of 5-(4-fluorophenyl)-6-isopropyl-1-tetrahydropyran-2-yl-pyrano[4,3-f]indazol-8-one (W2) and 5-[(Z)-1-(4-fluorophenyl)-2-hydroxy-3-methyl-but-1-enyl]-1-tetrahydropyran-2-yl-indazole-6-carboxylic acid (W3)

In a sealed tube, were added water (1.75 mL) and potassium phosphate (1.40 g, 6.60 mmol). The mixture was stirred for 10 minutes at room temperature then toluene (24 mL) was added. Nitrogen was bubbled through the mixture for 15 minutes then 5-iodo-6-isopropyl-1-tetrahydropyran-2-yl-pyrano[4,3-f]indazol-8-one (1.5 g, 3.10 mmol), (4-fluorophenyl)boronic acid (650 mg, 4.65 mmol) and RuPhos Pd G4 (260 mg, 0.3057 mmol) were added. The tube was sealed then transferred to a pre-heated oil bath set to 70° C. and stirred at this temperature for 2 hours. Additional RuPhos Pd G4 (260 mg, 0.3057 mmol) was added and the reaction mixture was stirred for another two hours. The reaction mixture was cooled to room temperature then diluted with ethyl acetate (500 mL). The organic phase was washed with 5% aqueous $NaHCO_3$ (3×100 mL) and brine (2×100 mL), dried over $Na_2SO_4$, filtered and the solvent was removed under reduced pressure. Purification by silica gel chromatography (Gradient: 0-30% EtOAc in heptane) yielded the product 5-(4-fluorophenyl)-6-isopropyl-1-tetrahydropyran-2-yl-pyrano[4,3-f]indazol-8-one (1.09 g, 87%) as a white solid. The 5-(4-fluorophenyl)-6-isopropyl-1-tetrahydropyran-2-yl-pyrano[4,3-f]indazol-8-one (1.09 g, 87%) was taken up in EtOH (20 mL) and NaOH (8 mL of 2 M, 16.00 mmol) and refluxed for 1 hour. The EtOH was evaporated and then liquid was washed with dichloromethane (discarded). The mixture was acidified with 8 mL 2 M HCl and brought to pH 2 with citrate buffer solution. The final product was extracted from the water layer with dichloromethane (3×15 mL) on a phase separator. The volatiles were evaporated to yield 5-[(Z)-1-(4-fluorophenyl)-2-hydroxy-3-methyl-but-1-enyl]-1-tetrahydropyran-2-yl-indazole-6-carboxylic acid (1.08 g, 82%). $^1H$ NMR (300 MHz, Chloroform-d) δ 8.44 (d, J=5.5 Hz, 1H), 7.89 (d, J=10.6 Hz, 1H), 7.28 (d, J=6.3 Hz, 2H), 7.18-7.14 (m, OH), 7.10-6.97 (m, 2H), 6.87 (d, J=8.5 Hz, OH), 5.77-5.68 (m, 1H), 4.53 (d, J=66.5 Hz, 1H), 4.00 (d, J=12.0 Hz, 1H), 3.72 (t, J=10.2 Hz, 1H), 3.12 (d, J=16.8 Hz, 1H), 2.49 (d, J=11.4 Hz, 1H), 2.16-1.54 (m, 4H), 1.12-0.93 (m, 6H) (exists as a mixture of enol isomers in chloroform). LCMS m/z 326.33 [M+H]$^+$.

Preparation of W4

(Z)-5-(1-(3,4-difluorophenyl)-2-hydroxy-3-methyl-but-1-en-1-yl)-1-(tetrahydro-2H-pyran-2-yl)-1H-indazole-6-carboxylic acid (W4)

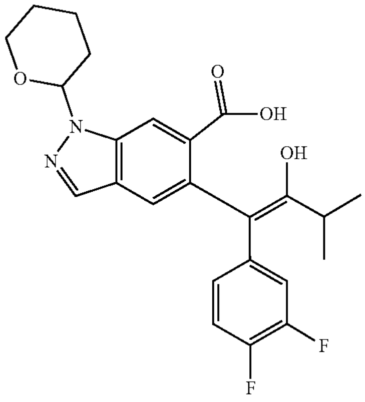 [SMILES: CC(C)/C(O)=C(\c1ccc(F)c(F)c1)c1cc2cnn(C3CCCCO3)c2cc1C(=O)O]

W4 was prepared from W1 using the method described for the preparation of W3. W4 was used in the preparation of compound 232-239 (Table 2) without further purification.

Compound 222

3-(6-isopropyl-8-oxo-1H-mrazolo[4,3-g]isoquinolin-7-yl)cyclobutanecarboxlic acid (222)

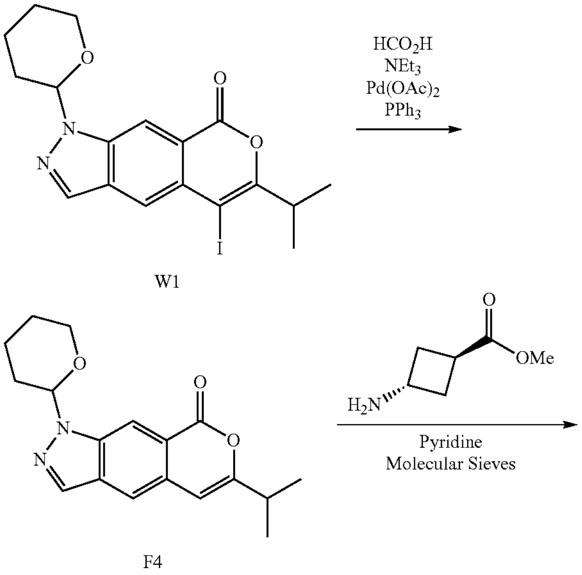

-continued

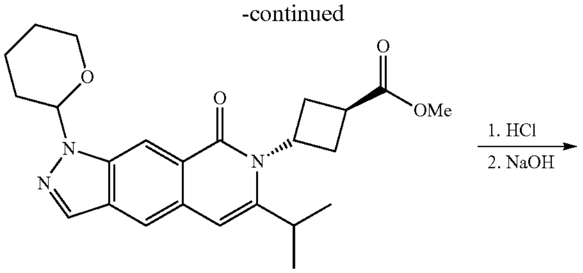

F5

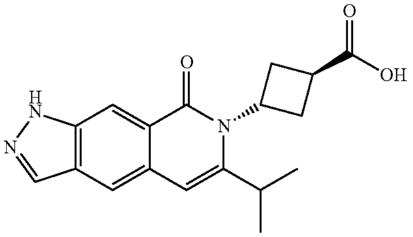

222

Step 1. Synthesis of 6-isopropyl-1-tetrahydropyran-2-yl-pyrano[4,3-f]indazol-8-one (F4)

5-iodo-6-isopropyl-1-tetrahydropyran-2-yl-pyrano[4,3-f]indazol-8-one (1.5 g, 3.423 mmol) $Pd(OAc)_2$ (40 mg, 0.1782 mmol) and $PPh_3$ (90 mg, 0.3431 mmol) were suspended in MeCN (50 mL) and $NEt_3$ (1.5 mL, 10.76 mmol). The mixture was purged with nitrogen for 30 minutes, then formic acid (250 μL, 6.627 mmol) was added. The mixture was sealed, then heated to 60° C. for 5 hours. Upon cooling water (200 mL) was added, and the mixture was extracted with EtOAc (×3). The organic layer was dried using a phase separator, then concentrated under vacuum. Purification by silica gel chromatography (Gradient: 0-100% EtOAc in heptane) yielded the product. 6-isopropyl-1-tetrahydropyran-2-yl-pyrano[4,3-f]indazol-8-one (900 mg, 84%) as a brown solid. 1H NMR (300 MHz, Chloroform-d) δ 8.62 (s, 1H), 8.17 (d, J=1.0 Hz, 1H), 7.74 (d, J=0.9 Hz, 1H), 6.35 (s, 1H), 5.84 (dd, J=9.8, 2.5 Hz, 1H), 4.14-4.02 (m, 1H), 3.82 m, 1H), 2.83 (m, 1H), 2.61 (d, J=9.1 Hz, 1H), 2.25-2.10 (m, 2H), 1.78 (m, 3H), 1.34 (d, J=6.9 Hz, 6H).

Step 2. Synthesis of 3-(6-isopropyl-8-oxo-1H-pyrazolo[4,3-g]isoquinolin-7-yl)cyclobutanecarboxylic acid (222)

A solution of 6-isopropyl-1-tetrahydropyran-2-yl-pyrano[4,3-f]indazol-8-one (105 mg, 0.3361 mmol) and methyl 3-aminocyclobutanecarboxylate (Hydrochloride salt) (120 mg, 0.7246 mmol) in Pyridine (2 mL) in a 5 mL biotage microwave vial was purged with nitrogen. Molecular sieves (200 mg) (4 Å Powder Dried at 100° C.) were added. The mixture was heated at 140° C. under microwave conditions for 16 hours. Purification by silica gel chromatography (Gradient: 0-50% EtOAc in heptane) yielded the product F5. Methyl 3-(6-isopropyl-8-oxo-1-tetrahydropyran-2-yl-pyrazolo[4,3-g]isoquinolin-7-yl)cyclobutanecarboxylate (140 mg, 73%). A small portion of F5 was deprotected by treated with 1 M HCl, then 10 M KOH to afford the product. 3-(6-isopropyl-8-oxo-1H-pyrazolo[4,3-g]isoquinolin-7-yl) cyclobutanecarboxylic acid (2.9 mg, 3%). LCMS m/z 326.33 $[M+H]^+$.

Compound 223

3-[5-(4-fluorophenyl)-6-isopropyl-8-oxo-1H-pyrazolo[4,3-g]isoquinolin-7-yl]cyclobutanecarboxylic acid (223)

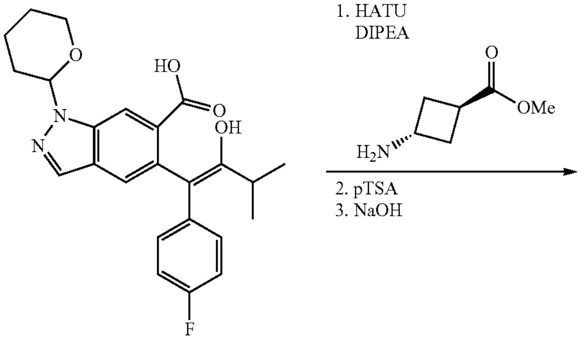

W3

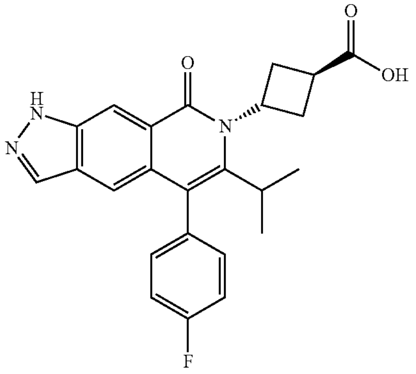

223

Preparation of 3-[5-(4-fluorophenyl)-6-isopropyl-8-oxo-1H-pyrazolo[4,3-g]isoquinolin-7-yl]cyclobutanecarboxylic acid (223)

Standard Method J.

To a solution of 5-[(Z)-1-(4-fluorophenyl)-2-hydroxy-3-methyl-but-1-enyl]-1-tetrahydropyran-2-yl-indazole-6-carboxylic acid (200 mg, 0.47 mmol) in DMF (3 mL) with methyl 3-aminocyclobutanecarboxylate (80 mg, 0.62 mmol) and DIPEA (250 μL, 1.44 mmol). HATU (270 mg, 0.71 mmol) was added and the mixture was stirred overnight at room temperature. Diluted with dichloromethane and washed with water (×2) and 2 M HCl (2×) on a phase separator. The residue was dissolved in dichloromethane (3 mL) andp-toluene sulfonic acid (monohydrate) (300 mg, 1.57 mmol) was added. The mixture was heated to 65° C. in the microwave for 30 minutes. The mixture was washed with water and citrate buffer solution, concentrated and DMF (3 mL) and NaOH (500 μL of 10 M, 5.0 mmol) added. The mixture was stirred overnight at room temperature, filtered and purified by reverse-phase chromatography (Column: C18. Gradient: 0-100% MeCN in water with 0.1% trifluoroacetic acid) afforded the product. 3-[5-(4-fluorophenyl)-6-isopropyl-8-oxo-1H-pyrazolo[4,3-g]isoquinolin-7-yl]cyclobutanecarboxylic acid (23.4 mg, 11%). $^1H$ NMR (400 MHz, DMSO-$d_6$) δ 8.48 (s, 1H), 8.20 (s, 1H), 7.37 (q, J=6.9, 5.0 Hz, 4H), 7.08 (s, 1H), 5.19 (s, 1H), 3.56 (q, J=9.9 Hz, 2H), 3.16 (dd, J=17.5, 10.1 Hz, 2H), 2.41 (m, 2H), 1.33-1.21 (m, 6H). LCMS m/z 420.39 $[M+H]^+$.

Compounds 224-231
Standard Method J was used in the preparation of compounds 224-231 (Table 14) from W3 and the appropriate amine reagent.
TABLE 14
| Method of preparation, structure and physicochemical data for compounds 224-231 | | | |
|---|---|---|---|
| Compound | Structure | Amine Reagent | LCMS m/z $[M+H]^+$ |
| 224 | 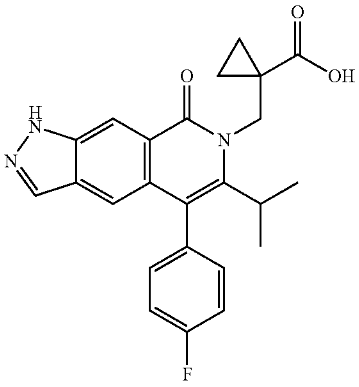 [SMILES: CC(C)c1c(-c2ccc(F)cc2)c2cc3cn[nH]c3cc2c(=O)n1CC1(C(=O)O)CC1] | 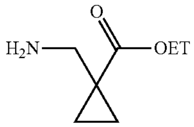 | LCMS m/z 420.16 $[M+H]^+$ |
| 225 | 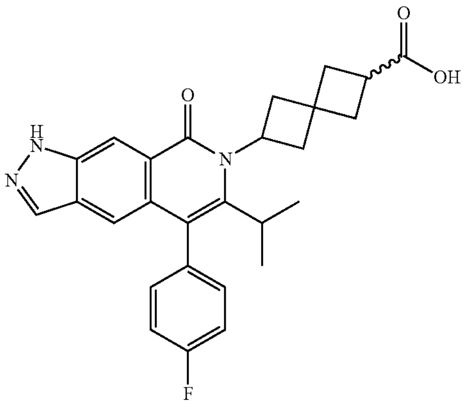 [SMILES: CC(C)c1c(-c2ccc(F)cc2)c2cc3cn[nH]c3cc2c(=O)n1C1CC2(CC(C(=O)O)C2)C1] | 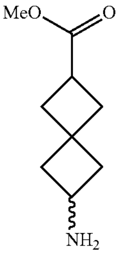 | LCMS m/z 460.29 $[M+H]^+$ |
| 226 | 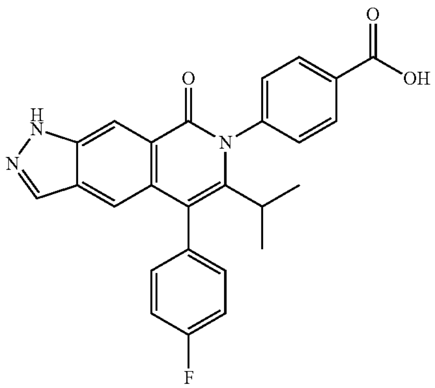 [SMILES: CC(C)c1c(-c2ccc(F)cc2)c2cc3cn[nH]c3cc2c(=O)n1-c1ccc(C(=O)O)cc1] | 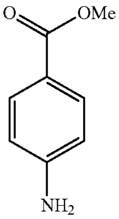 | LCMS m/z 440.1 $[M+H]^+$ |

TABLE 14-continued
Method of preparation, structure and physicochemical data for compounds 224-231
| Compound | Structure | Amine Reagent | LCMS m/z [M + H]$^+$ |
|---|---|---|---|
| 227 | 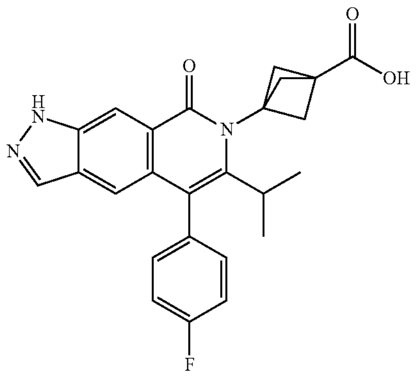 | 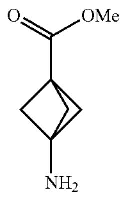 | LCMS m/z 460.29 [M + H]$^+$. |
| 228 | 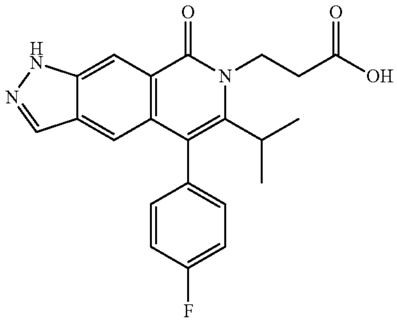 [SMILES: CC(C)c1c(-c2ccc(F)cc2)c2cc3cn[nH]c3cc2c(=O)n1CCC(=O)O] | 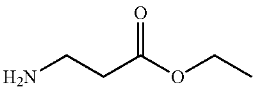 | LCMS m/z 394.18 [M + H]$^+$. |
| 229 | 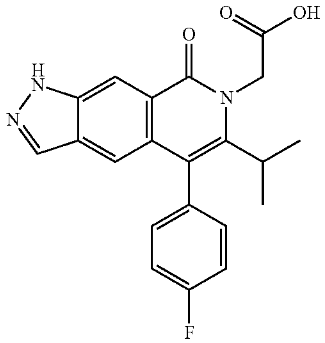 [SMILES: CC(C)c1c(-c2ccc(F)cc2)c2cc3cn[nH]c3cc2c(=O)n1CC(=O)O] | 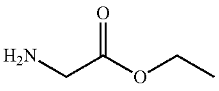 | LCMS m/z 380.14 [M + H]$^+$. |
| 230 | 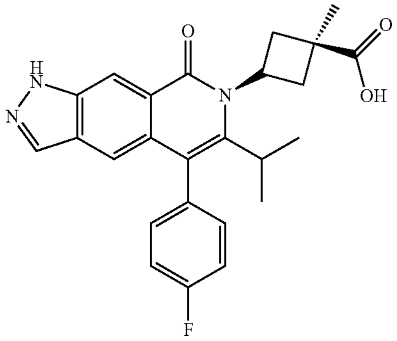 | 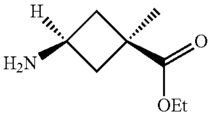 | LCMS m/z 434.18 [M + H]$^+$. |

TABLE 14-continued

| Method of preparation, structure and physicochemical data for compounds 224-231 | | | |
|---|---|---|---|
| Compound | Structure | Amine Reagent | LCMS m/z [M + H]+ |
| 231 | 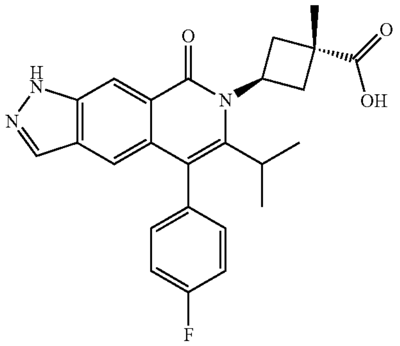 [SMILES: CC(C)c1c(-c2ccc(F)cc2)c2cc3cn[nH]c3cc2c(=O)n1[C@H]1C[C@](C)(C(=O)O)C1] | 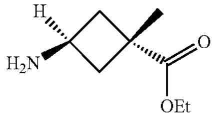 | LCMS m/z 434.38 [M + H]+. |

Standard Method K. To a solution of (Z)-5-(1-(3,4-difluorophenyl)-2-hydroxy-3-methylbut-1-en-1-yl)-1-(tetrahydro-2H-pyran-2-yl)-1H-indazole-6-carboxylic acid (W4) (50 mg) in DMF (1.5 mL) with the appropriate amine and DIPEA. HATU was added and allowed to stir overnight at room temperature. The mixture was diluted with dichloromethane and washed with water (×2) and 2 M HCl (×2) on a phase separator. Dichloromethane (3 mL) and p-toluenesulfonic acid (monohydrate) were added. The mixture was heated to 65° C. in the microwave for 30 minutes. The mixture was washed with water and citrate buffer solution. DMF (1.5 mL) and NaOH were added and the mixture was stirred overnight at room temperature. The reaction was filtered and Purification by reversed-phase chromatography (Column: C18. Gradient: 0-100% MeCN in water with 0.2% trifluoroacetic acid) afforded the product.

Compounds 232-239

Standard method K was used in the preparation of compounds 232-239 (Table 15) from W4.

TABLE 15

| Method of preparation, structure and physicochemical data for compounds 232-239 | | | |
|---|---|---|---|
| Compound | Structure | Amine Reagent | LCMS m/z [M + H]+ |
| 232 | 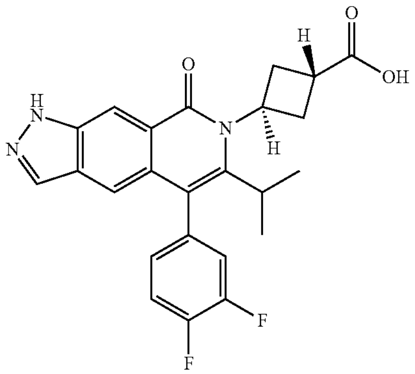 [SMILES: CC(C)c1c(-c2ccc(F)c(F)c2)c2cc3cn[nH]c3cc2c(=O)n1[C@H]1C[C@H](C(=O)O)C1] | 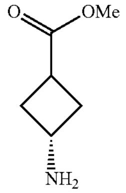 | $^1$H NMR (400 MHz, DMSO-$d_6$) δ 13.44 (s, 1H), 8.49 (s, 1H), 8.20 (s, 1H), 7.70-7.40 (m, 2H), 7.15 (d, J = 18.2 Hz, 2H), 5.16 (t, J = 8.7 Hz, 1H), 3.55 (q, J = 10.0 Hz, 2H), 3.29-3.05 (m, 2H), 2.45-2.35 (m, 2H), 1.27 (t, J = 6.9 Hz, 6H). LCMS m/z 438.12 [M + H]+. |
| 233 | 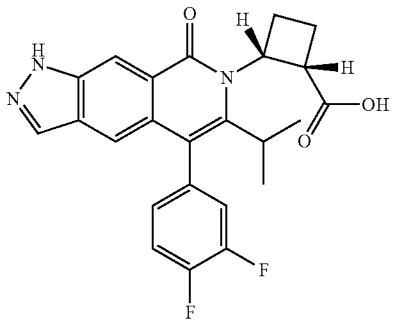 [SMILES: CC(C)c1c(-c2ccc(F)c(F)c2)c2cc3cn[nH]c3cc2c(=O)n1[C@@H]1CC[C@@H]1C(=O)O] | 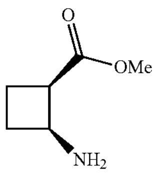 | LCMS m/z 438.02 [M + H]+. |

TABLE 15-continued

Method of preparation, structure and physicochemical data for compounds 232-239

| Compound | Structure | Amine Reagent | LCMS m/z [M + H]$^+$ |
|---|---|---|---|
| 234 | 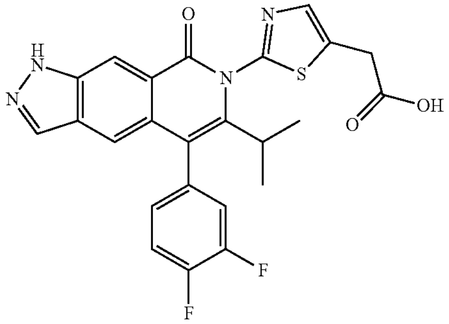 [SMILES: CC(C)c1c(-c2ccc(F)c(F)c2)c2cc3cn[nH]c3cc2c(=O)n1-c1ncc(CC(=O)O)s1] | 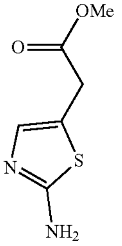 [SMILES: COC(=O)Cc1cnc(N)s1] | LCMS m/z 480.96 [M + H]$^+$. |
| 235 | 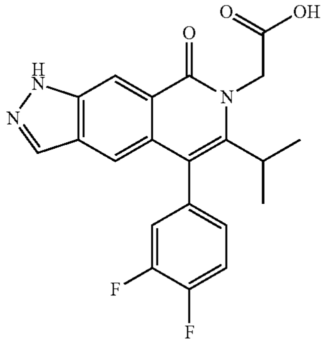 [SMILES: CC(C)c1c(-c2ccc(F)c(F)c2)c2cc3cn[nH]c3cc2c(=O)n1CC(=O)O] | 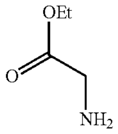 | $^1$H NMR (400 MHz, DMSO-d$_6$) δ 13.43 (s, 1H), 8.45 (t, J = 1.0 Hz, 1H), 8.22 (d, J = 1.1 Hz, 1H), 7.62 (q, J = 9.2 Hz, 1H), 7.49 (t, J = 9.5 Hz, 1H), 7.20 (s, 2H), 4.81 (s, 2H), 3.17-3.05 (m, 1H), 1.19 (s, 6H). LCMS m/z 398.28 [M + H]$^+$. |
| 236 | 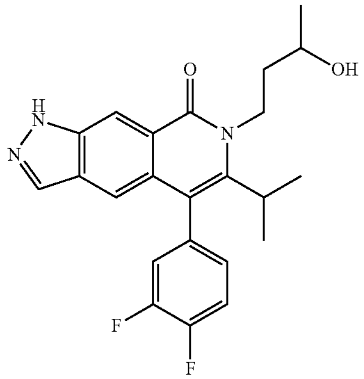 [SMILES: CC(O)CCn1c(C(C)C)c(-c2ccc(F)c(F)c2)c2cc3cn[nH]c3cc2c1=O] | 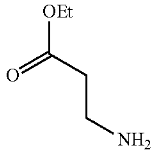 | $^1$H NMR (400 MHz, DMSO-d$_6$) δ 13.42 (s, 1H), 8.47 (s, 1H), 8.26-8.17 (m, 1H), 7.70-7.55 (m, 1H), 7.51-7.44 (m, 1H), 7.19 (d, J = 12.0 Hz, 2H), 4.35 (t, J = 7.8 Hz, 2H), 3.25-3.13 (m, 1H), 2.74 (t, J = 8.3 Hz, 2H), 1.23 (s, 6H). LCMS m/z 412.13 [M + H]$^+$. |
| 237 | 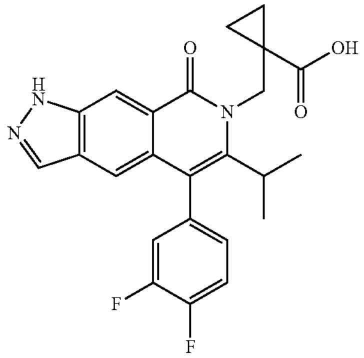 [SMILES: CC(C)c1c(-c2ccc(F)c(F)c2)c2cc3cn[nH]c3cc2c(=O)n1CC1(C(=O)O)CC1] | 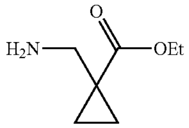 | $^1$H NMR (400 MHz, DMSO-d$_6$) δ 13.43 (s, 1H), 8.44 (s, 1H), 8.21 (s, 1H), 7.68-7.47 (m, 2H), 7.17 (d, J = 24.9 Hz, 2H), 4.82 (q, J = 14.9 Hz, 2H), 3.19 (s, 1H), 1.08 (s, 8H), 0.75 (s, 2H). LCMS m/z 438.12 [M + H]$^+$. |

TABLE 15-continued

Method of preparation, structure and physicochemical data for compounds 232-239

| Compound | Structure | Amine Reagent | LCMS m/z [M + H]$^+$ |
|---|---|---|---|
| 238 | 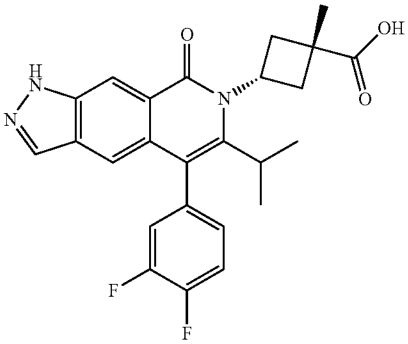 [SMILES: CC(C)c1c(-c2ccc(F)c(F)c2)c2cc3cn[nH]c3cc2c(=O)n1[C@H]1C[C@@](C)(C(=O)O)C1] | 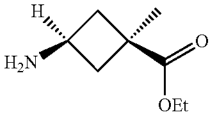 | $^1$H NMR (400 MHz, DMSO-$d_6$) δ 13.45 (s, 1H), 12.22 (s, 1H), 8.44 (s, 1H), 8.21-8.17 (m, 1H), 7.61 (dt, J = 10.7, 8.5 Hz, 1H), 7.49 (ddd, J = 10.9, 7.8, 2.0 Hz, 1H), 7.18 (s, 1H), 7.14-7.09 (m, 1H), 4.84 (p, J = 8.7 Hz, 1H), 3.64 (t, J = 9.7 Hz, 2H), 3.14 (p, J = 7.3 Hz, 1H), 2.17-2.08 (m, 2H), 1.46 (s, 3H), 1.28 (t, J = 6.9 Hz, 6H). LCMS m/z 452.16 [M + H]$^+$. |
| 239 | 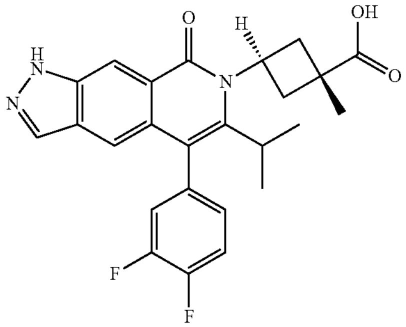 [SMILES: CC(C)c1c(-c2ccc(F)c(F)c2)c2cc3cn[nH]c3cc2c(=O)n1[C@H]1C[C@](C)(C(=O)O)C1] | 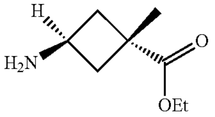 | $^1$H NMR (400 MHz, DMSO-$d_6$) δ 13.45 (s, 1H), 8.49 (s, 1H), 8.20 (s, 1H), 7.61 (dt, J = 10.8, 8.5 Hz, 1H), 7.54-7.44 (m, 1H), 7.15 (d, J = 21.1 Hz, 2H), 5.08 (t, J = 9.1 Hz, 1H), 3.40 (m, 4H), 3.14 (p, J = 7.3 Hz, 1H), 1.55 (s, 3H), 1.28 (t, J = 7.0 Hz, 6H). LCMS m/z 452.16 [M + H]$^+$. |

Compound 240

4-(6-(dimethylamino)-5-(4-fluorophenyl)-7,8-dihydro-1H-pyrazolo[4,3-g]quinolin-7-yl)-3-methoxybenzoic acid (240)

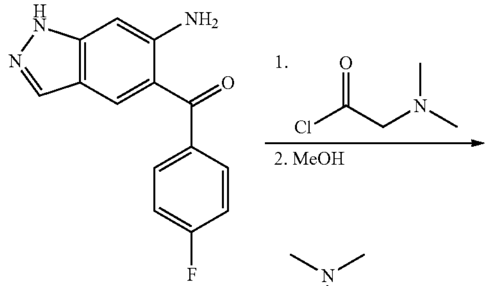

D51

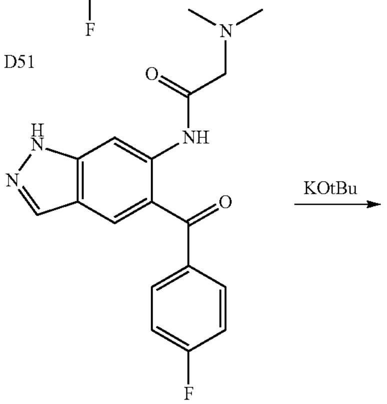

G1

-continued

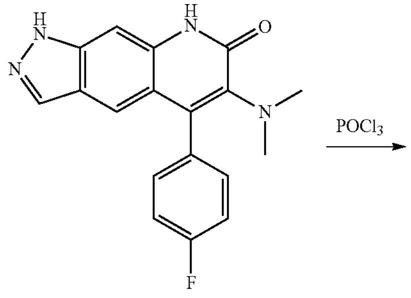

G2

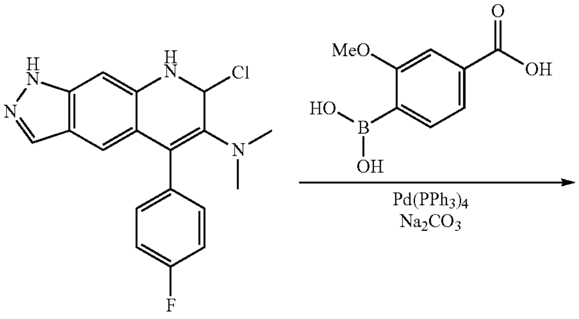

G3

-continued

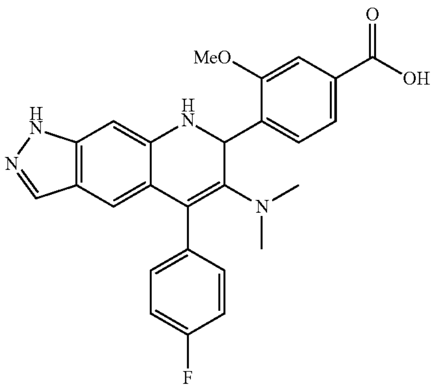

240

Compound 240 was prepared from D51 using the method described for the preparation of compound 145, omitting the fluorination Step 1. $^{1}$H NMR (400 MHz, Methanol-$d_4$) δ 8.21 (d, J=1.1 Hz, 1H), 8.12 (t, J=1.1 Hz, 1H), 7.95 (d, J=1.0 Hz, 1H), 7.79 (dd, J=7.7, 1.5 Hz, 1H), 7.75 (d, J=1.4 Hz, 1H), 7.49 (m, 3H), 7.35 (m, 2H), 3.85 (s, 3H), 2.27 (s, 6H). LCMS m/z 457.36 [M+1]$^{+}$.

Compound 241

4-(5-(4-fluorophenyl)-6-methoxy-1H-pyrazolo[4,3-g]quinolin-7-yl)benzoic acid (241)

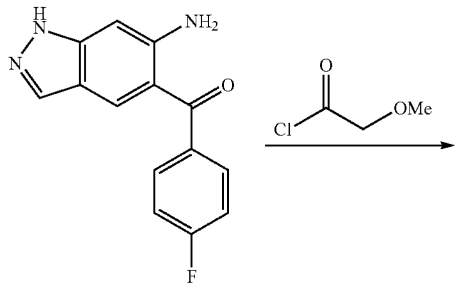

D51

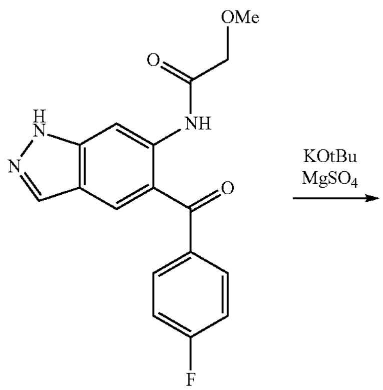

G4

-continued

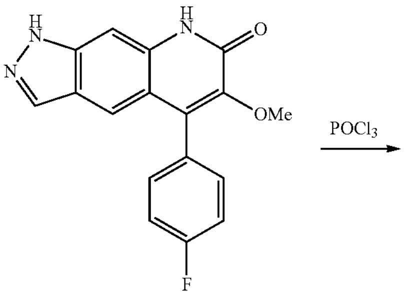

G5

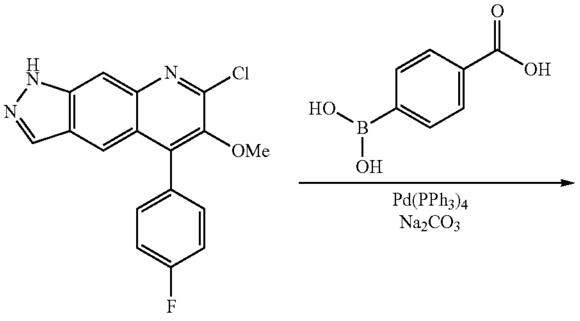

G6

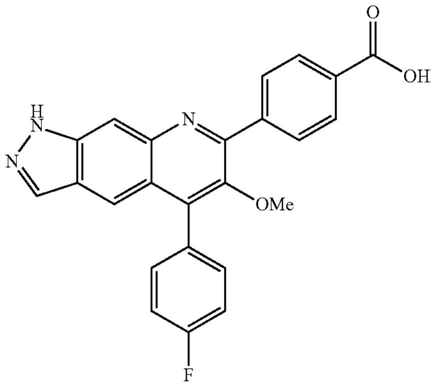

241

Compound 241 was prepared from D51 and 2-methoxyacetyl chloride using the method described for the preparation of compound 145. $^{1}$H NMR (400 MHz, Methanol-$d_4$) δ 8.30 (m, 2H), 8.25-8.20 (m, 2H), 8.14-8.09 (m, 3H), 7.66-7.58 (m, 2H), 7.44-7.34 (m, 2H), 3.23 (s, 3H). LCMS m/z 414.29 [M+1]$^{+}$.

Compounds 242-244

Compounds 242-244 were prepared from G6 using the method described for the preparation of compound 241 (Table 16).

TABLE 16

Method of preparation, structure and physicochemical data for compounds 242-244

| Compound | Product | Reagent | $^1$H NMR; LCMSm/z [M + H]$^+$ |
|---|---|---|---|
| 242 | 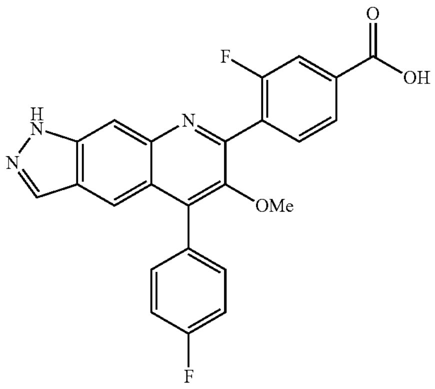 [SMILES: COc1c(-c2ccc(C(=O)O)cc2F)nc2cc3[nH]ncc3cc2c1-c1ccc(F)cc1] | 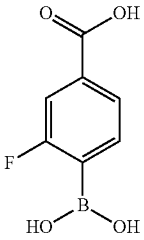 | $^1$H NMR (400 MHz, Methanol-$d_4$) δ 8.27 (t, J = 1.1 Hz, 1H), 8.26 (d, J = 1.2 Hz, 1H), 8.10 (t, J = 7.8 Hz, 1H), 8.04 (d, J = 1.0 Hz, 1H), 7.96 (dd, J = 8.2, 1.6 Hz, 1H), 7.89 (dd, J = 11.9, 1.6 Hz, 1H), 7.65-7.53 (m, 2H), 7.42-7.31 (m, 2H), 3.26 (s, 3H). LCMS m/z 432.21 [M + 1]$^+$. |
| 243 | 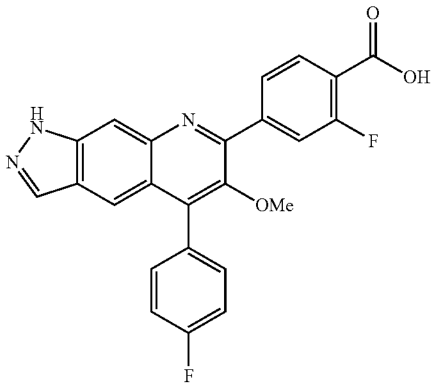 [SMILES: COc1c(-c2ccc(C(=O)O)c(F)c2)nc2cc3[nH]ncc3cc2c1-c1ccc(F)cc1] | 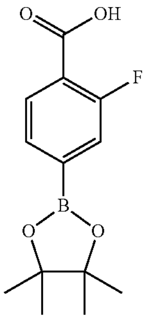 | $^1$H NMR (400 MHz, Methanol-$d_4$) δ 8.35 (d, J = 1.2 Hz, 1H), 8.32 (t, J = 1.1 Hz, 1H), 8.19 (d, J = 1.0 Hz, 1H), 8.10 (dd, J = 7.9, 1.5 Hz, 1H), 7.95 (dd, J = 10.2, 1.5 Hz, 1H), 7.87 (dd, J = 7.9, 6.9 Hz, 1H), 7.70-7.64 (m, 2H), 7.50-7.40 (m, 2H), 3.30 (s, 3H). LCMS m/z 432.17 [M + 1]$^+$. |
| 244 | 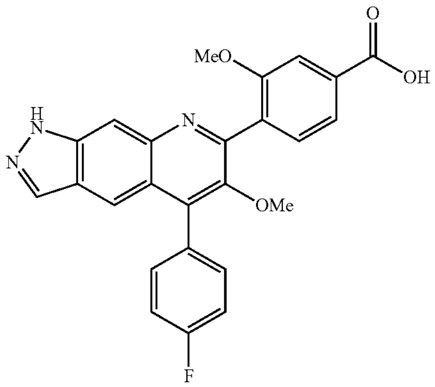 [SMILES: COc1cc(C(=O)O)ccc1-c1nc2cc3[nH]ncc3cc2c(-c2ccc(F)cc2)c1OC] | 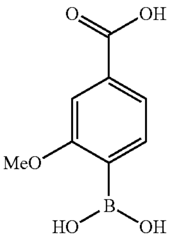 [SMILES: COc1cc(C(=O)O)ccc1B(O)O] | $^1$H NMR (400 MHz, Methanol-$d_4$) δ 8.26 (d, J = 1.1 Hz, 1H), 8.19 (t, J = 1.1 Hz, 1H), 8.08 (d, J = 1.0 Hz, 1H), 7.79 (m, 2H), 7.58 (m, 2H), 7.55-7.51 (m, 1H), 7.36 (m, 2H), 3.88 (s, 3H), 3.21 (s, 3H). LCMS m/z 444.36 [M + 1]$^+$. |

Compound 245

4-[5-(4-fluorophenyl)-6-isopropylsulfonyl-1H-pyrazolo[4,3-g]quinolin-7-yl]benzamide (245)

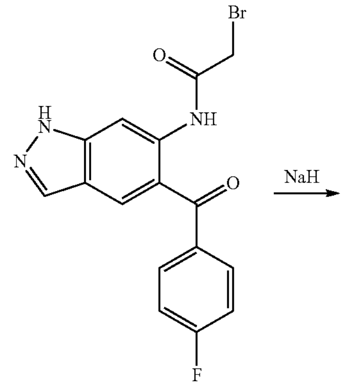

D57

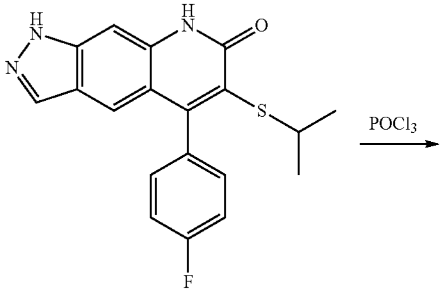

G7

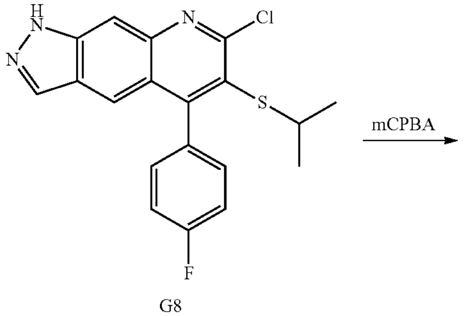

G8

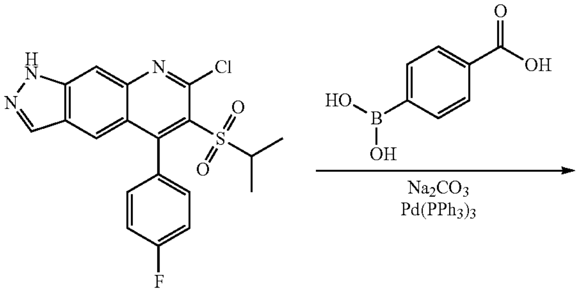

G9

-continued

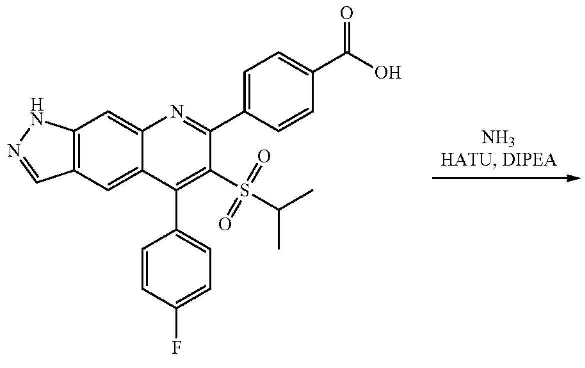

G10

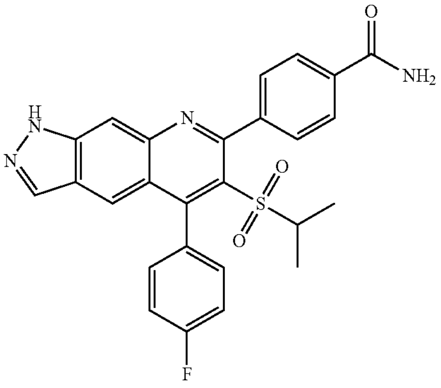

245

Compound G10 was prepared from D57 and bromoacetyl chloride using the methods described for the preparation of compound 146. Compound 245 was prepared from G10 by coupling of ammonia with HATU and DIPEA. $^1$H NMR (400 MHz, DMSO-$d_6$) δ 13.56 (s, 1H), 8.50 (d, J=1.3 Hz, 1H), 8.22 (t, J=1.1 Hz, 1H), 8.12 (s, 1H), 7.98 (d, J=8.1 Hz, 2H), 7.90 (s, 1H), 7.70 (d, J=8.2 Hz, 2H), 7.61-7.54 (m, 2H), 7.49 (s, 1H), 7.44 (m, 2H), 2.66 (hept, J=6.5 Hz, 1H), 0.93 (d, J=6.7 Hz, 6H). LCMS m/z 489.33 $[M+1]^+$.

Compounds 246-248

Compound 246-248 (Table 17) were prepared from S6 by addition of the phenol reagent in the presence of $Cs_2CO_3$ in DMF at 150° C. under microwave conditions, followed by THP deprotection with TFA using an analogous method to that described for the preparation of compound 65.

TABLE 17

Method of preparation, structure and physicochemical data for compounds 246-248

| Compound | Product | Reagent | $^1$H NMR; LCMS m/z [M + H]$^+$ |
|---|---|---|---|
| 246 | 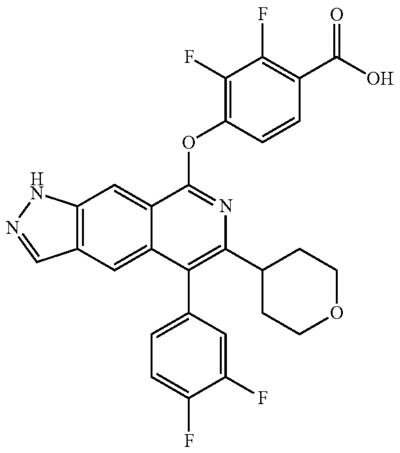 [SMILES: O=C(O)c1ccc(Oc2nc(C3CCOCC3)c(-c3ccc(F)c(F)c3)c3cc4cn[nH]c4cc23)c(F)c1F] | 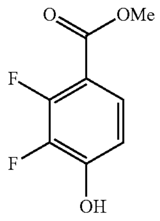 [SMILES: COC(=O)c1ccc(O)c(F)c1F] | $^1$H NMR (300 MHz, $CDCl_3$ + Methanol-$d_4$) δ 8.62 (d, J = 1.2 Hz, 1H), 8.21 (d, J = 1.1 Hz, 1H), 7.89 (ddd, J = 9.3, 7.4, 2.2 Hz, 1H), 7.72 (d, J = 1.1 Hz, 1H),7.41 (d, J = 8.4 Hz, 1H), 7.34-7.26 (m, 1H), 7.17 (ddd, J = 10.3, 7.6, 2.1 Hz, 1H), 7.08 (ddd, J = 8.6, 4.3, 2.0 Hz, 1H), 3.90 (d, J = 11.0 Hz, 2H), 3.29 (ddd, J = 12.3, 10.7, 6.2 Hz, 2H), 2.76-2.60 (m, 1H), 1.87 (q, J = 12.9 Hz, 2H), 1.51-1.33 (m, 2H) ppm. LCMS m/z 538.09 [M + 1]$^+$. |
| 247 | 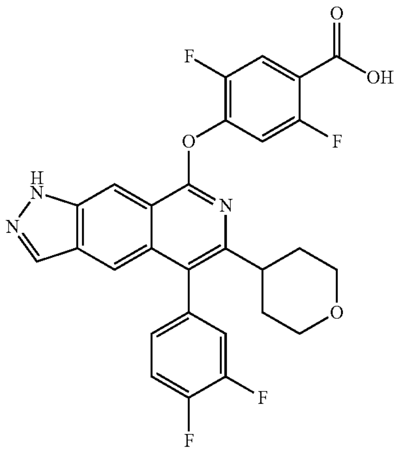 [SMILES: O=C(O)c1cc(F)c(Oc2nc(C3CCOCC3)c(-c3ccc(F)c(F)c3)c3cc4cn[nH]c4cc23)cc1F] | 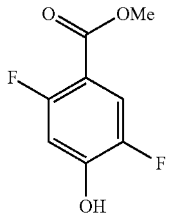 | $^1$H NMR (300 MHz, $CDCl_3$ + Methanol-$d_4$) δ 8.61 (t, J = 1.1 Hz, 1H), 8.22 (d, J = 1.1 Hz, 1H), 7.88 (dd, J = 10.4, 6.6 Hz, 1H), 7.73 (d, J = 1.1 Hz, 1H), 7.45-7.28 (m, 2H), 7.25-7.03 (m, 2H), 3.91 (d, J = 11.2 Hz, 2H), 3.29 (dd, J = 11.3, 6.3 Hz, 2H), 2.77-2.63 (m, 1H), 1.89 (q, J = 12.3 Hz, 2H), 1.44 (d, J = 13.3 Hz, 2H) ppm. LCMS m/z 538.13 [M + 1]$^+$. |
| 248* | 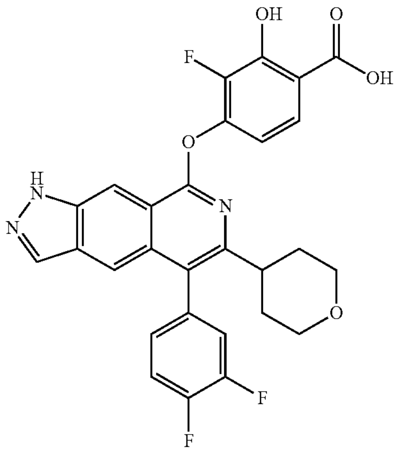 | 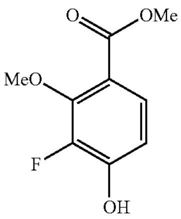 [SMILES: COC(=O)c1ccc(O)c(F)c1OC] | $^1$H NMR (300 MHz, $CDCl_3$ + Methanol-$d_4$) δ 8.64 (t, J = 1.1 Hz, 1H), 8.21 (d, J = 1.1 Hz, 1H), 7.79 (dd, J = 8.9, 2.1 Hz, 1H), 7.72 (d, J = 1.1 Hz, 1H), 7.43-7.31 (m, 1H), 7.27-7.04 (m, 2H), 6.97 (dd, J = 8.9, 6.5 Hz, 1H), 3.90 (d, J = 11.3 Hz, 2H), 3.30 (dt, J = 11.2, 5.6 Hz, 2H), 2.74-2.61 (m, 1H), 1.91 (q, J = 12.4, 11.7 Hz, 2H), 1.43 (d, J = 13.2 Hz, 2H) ppm. LCMS m/z 536.37 [M + 1]$^+$. |

*Prepared from C33 by deprotection with TFA

Compound 249

2-fluoro-4-[5-(4-fluorophenyl)-6-isopropoxy-1H-pyrazolo[4,3-g]quinolin-7-yl]benzoic acid (249)

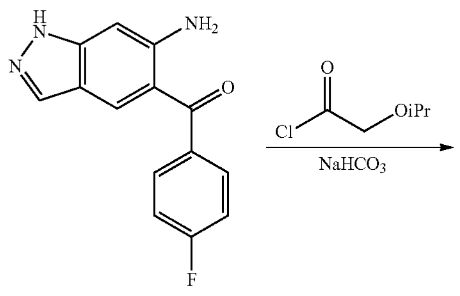

D51

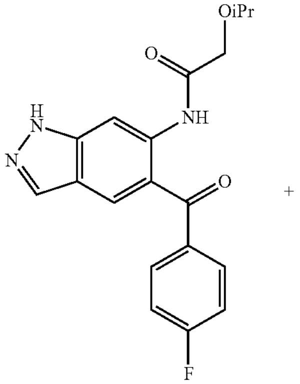

G11

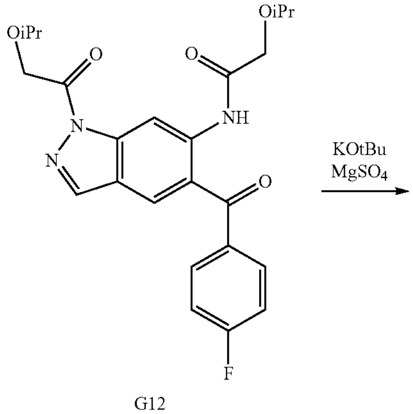

G12

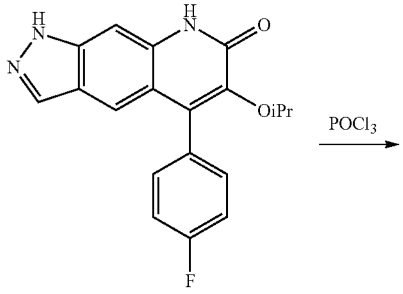

G13

-continued

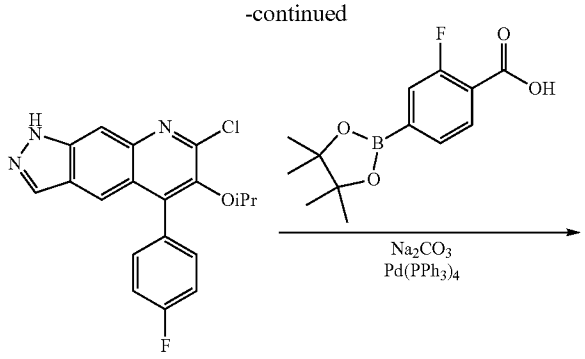

G14

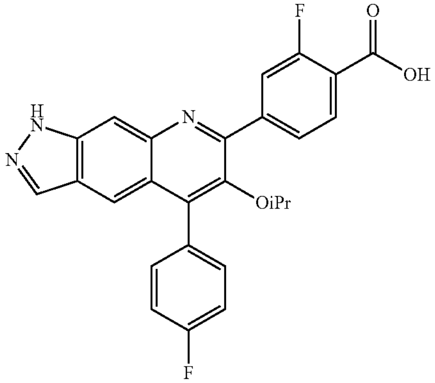

249

Compound 249 was prepared from D51 as described for the preparation of compound 145. $^{1}H$ NMR (400 MHz, Methanol-$d_4$) δ 8.26 (m, 2H), 8.12 (d, J=0.9 Hz, 1H), 8.06 (t, J=7.8 Hz, 1H), 7.93 (dd, J=8.1, 1.6 Hz, 1H), 7.86 (dd, J=11.9, 1.5 Hz, 1H), 7.68-7.59 (m, 2H), 7.42-7.33 (m, 2H), 3.66 (hep, J=6.1 Hz, 1H), 0.73 (d, J=6.1 Hz, 6H). LCMS m/z 460.3 $[M+1]^+$.

Compound 250

3-fluoro-4-[5-(4-fluorophenyl)-6-isopropoxy-1H-pyrazolo[4,3-g]quinolin-7-yl]benzoic acid (250)

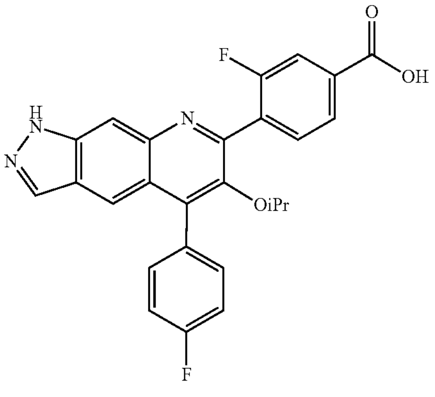 [SMILES: CC(C)Oc1c(-c2ccc(C(=O)O)cc2F)nc2cc3[nH]ncc3cc2c1-c1ccc(F)cc1]

Compound 250 was prepared from D51 via G14 as described for the preparation of compound 145. $^{1}H$ NMR (400 MHz, Methanol-$d_4$) δ 8.28 (d, J=1.1 Hz, 1H), 8.24 (t, J=1.1 Hz, 1H), 8.17 (d, J=1.0 Hz, 1H), 8.01 (dd, J=7.9, 1.5

Hz, 1H), 7.86 (dd, J=10.2, 1.5 Hz, 1H), 7.81 (m, 1H), 7.66-7.57 (m, 2H), 7.42-7.31 (m, 2H), 3.63 (hept, J=6.1 Hz, 1H), 0.65 (d, J=6.1 Hz, 6H). LCMS m/z 460.3 $[M+1]^+$.

Compound 251

4-[5-(4-fluorophenyl)-6-isopropoxy-1H-pyrazolo[4,3-g]quinolin-7-yl]benzoic acid (251)

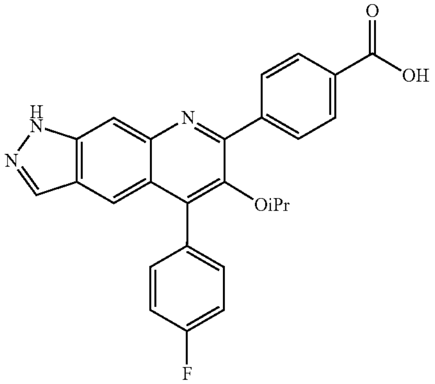 [SMILES: CC(C)Oc1c(-c2ccc(C(=O)O)cc2)nc2cc3[nH]ncc3cc2c1-c1ccc(F)cc1]

Compound 251 was prepared from D51 via G14 as described for the preparation of compound 145. $^1H$ NMR (400 MHz, Methanol-$d_4$) δ 8.26 (m, 2H), 8.21-8.16 (m, 2H), 8.12 (d, J=0.9 Hz, 1H), 8.11-8.05 (m, 2H), 7.65-7.61 (m, 2H), 7.37 (t, J=8.8 Hz, 2H), 3.63 (h, J=6.2 Hz, 1H), 0.68 (d, J=6.2 Hz, 6H). LCMS m/z 442.33 $[M+1]^+$.

Compound 252

Ethyl 4-[5-(4-fluoro-3-methoxy-phenyl)-6-isopropyl-1H-pyrazolo[4,3-g]quinolin-7-yl]benzoate 4-[5-(4-fluoro-3-methoxy-phenyl)-6-isopropyl-1H-pyrazolo[4,3-g]quinolin-7-yl]benzoic acid (252)

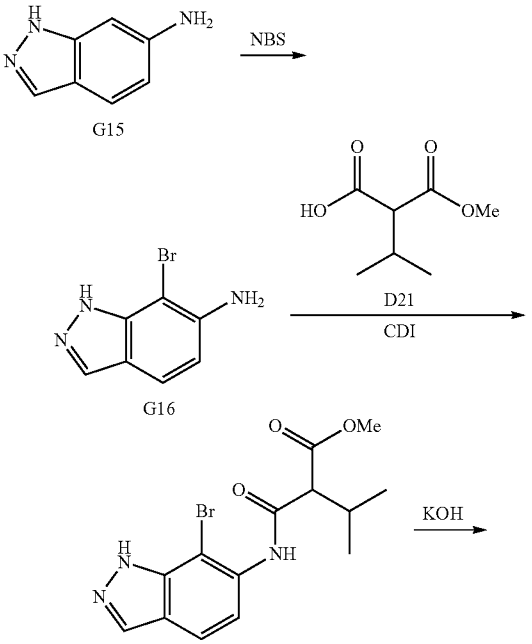

G15

G16

G17

-continued

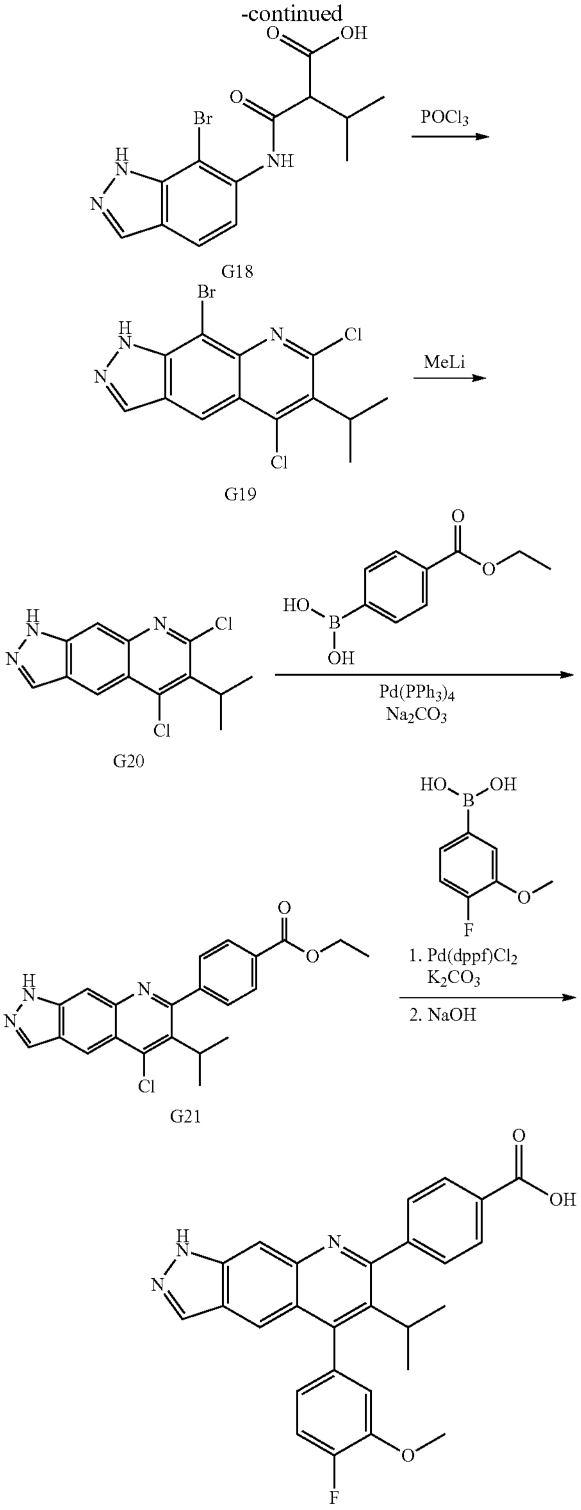

G18

G19

G20

G21

252

Step 1: 7-bromo-1H-indazol-6-amine

To a solution of 1H-indazol-6-amine (5 g, 37.551 mmol) in anhydrous DMF (30 mL) cooled at −15° C. (internal temperature), a solution of NBS (6.74 g, 37.869 mmol) in anhydrous DMF (15 mL+2 mL rinse) was added drop wise over 30 minutes. The mixture was stirred from −4.5° C. to −2.7° C. over 1 hour. Water (150 mL) and an aqueous solution of $NaHCO_3$ 5% (30 mL) were added. The mixture was extracted with a 1:1 mixture of MTBE and EtOAc (5×150 mL). The organic phases were combined, washed successively with water (3×50 mL) and brine (1×150 mL), dried over $Na_2SO_4$, filtered and concentrated to afford 7-bromo-1H-indazol-6-amine (7.66 g, 94%) as an orange solid. 1H NMR (300 MHz, DMSO-d6) δ 12.69 (br s, 1H), 7.88 (d, J=1.4 Hz, 1H), 7.40 (d, J=8.5 Hz, 1H), 6.65 (d, J=8.5 Hz, 1H), 5.51 (br s, 2H), ESI-MS m/z calc. 210.9745, found 212.1 (M+1)+; Retention time: 1.34 minutes.

Step 2: ethyl 2-[(7-bromo-1H-indazol-6-yl)carbamoyl]-3-methyl-butanoate

To a solution of 2-ethoxycarbonyl-3-methyl-butanoic acid (14.74 g, 67.695 mmol) in anhydrous DCE (120 mL), CDI (10.95 g, 67.530 mmol) portion-wise was added over 10 minutes 0° C. and the reaction was stirred for 30 minutes at 0° C. then for 1.5 hours at room temperature. 7-Bromo-1H-indazol-6-amine (10.2 g, 46.082 mmol) was added and the suspension was heated to 50° C. for 18 hours. The mixture was concentrated and the residue was triturated in water (1×160 mL), filtered, washed successively with water (2×40 mL), with heptanes (2×40 mL) and with a mixture of heptanes and MTBE (1:4, 1×50 mL), and dried to afford ethyl 2-[(7-bromo-1H-indazol-6-yl)carbamoyl]-3-methyl-butanoate (16.78 g, 96%) as a beige solid. 1H NMR (300 MHz, DMSO-$d_6$) δ 13.45 (br s, 1H), 9.97 (s, 1H), 8.19 (d, J=1.2 Hz, 1H), 7.74 (d, J=8.4 Hz, 1H), 7.18 (d, J=8.4 Hz, 1H), 4.15 (q, J=7.1 Hz, 2H), 3.37 (d, J=9.8 Hz, 1H), 2.40-2.24 (m, 1H), 1.22 (t, J=7.1 Hz, 3H), 1.06-0.94 (m, 6H), ESI-MS m/z calc. 367.0532, found 368.1 (M+1)+; Retention time: 1.81 minutes.

Step 3: 2-[(7-bromo-1H-indazol-6-yl)carbamoyl]-3-methyl-butanoic acid

To a suspension of ethyl 2-[(7-bromo-1H-indazol-6-yl) carbamoyl]-3-methyl-butanoate (7.34 g, 18.937 mmol) in EtOH (150 mL) was added water (35 mL), followed by KOH (4.22 g, 75.215 mmol) and the reaction was stirred at room temperature for 19 hours. The mixture was concentrated and water (50 mL) was added. The mixture was cooled to 0° C. and an aqueous solution of HCl 1.0 M was added until pH 2 was reached. The solid was filtered, washed with water (3×25 mL) and the residue was triturated in water (1×50 mL) at 0° C. for 15 minutes, filtered and dried to afford 2-[(7-bromo-1H-indazol-6-yl)carbamoyl]-3-methyl-butanoic acid (6.38 g, 97%) as a pink solid. 1H NMR (300 MHz, DMSO-$d_6$) δ 13.42 (br s, 1H), 12.69 (br s, 1H), 9.90 (s, 1H), 8.20 (s, 1H), 7.73 (d, J=8.5 Hz, 1H), 7.23 (d, J=8.5 Hz, 1H), 3.27 (d, J=9.5 Hz, 1H), 2.36-2.19 (m, 1H), 1.05-0.95 (m, 6H), ESI-MS m/z calc. 339.0219, found 340.0 (M+1)+; Retention time: 1.57 minutes.

Step 4: 9-bromo-5,7-dichloro-6-isopropyl-1H-pyrazolo[4,3-g]quinoline

A mixture of 2-[(7-bromo-1H-indazol-6-yl)carbamoyl]-3-methyl-butanoic acid (2.5 g, 7.3492 mmol) and $POCl_3$ (46.060 g, 28 mL, 300.40 mmol) was heated to 95° C. for 24 hours. The was concentrated and the residue was taken up in a mixture of DCM (150 mL) and EtOAc (450 mL) then, under stirring, was added an aqueous solution of $NaHCO_3$ 5% (300 mL) and brine (150 mL). The organic phase was washed with brine (2×100 mL), dried over $MgSO_4$, filtered and concentrated. The residue was suspended in acetonitrile (175 mL) and heated at reflux for 1 minute. The insoluble solid was removed by filtration while the solution was still hot. When the solution reached room temperature, water (300 mL) was added under stirring, and the solid was filtered and dried to afford 9-bromo-5,7-dichloro-6-isopropyl-1H-pyrazolo[4,3-g]quinoline (1.37 g, 44%) as a yellow solid. 1H NMR (300 MHz, DMSO-d6) δ 13.87 (br s, 1H), 8.85 (s, 1H), 8.67 (d, J=1.3 Hz, 1H), 4.16-3.90 (m, 1H), 1.49 (d, J=7.2 Hz, 6H), ESI-MS m/z calc. 356.9435, found 358.0 (M+1)+; Retention time: 2.34 minutes.

Step 5: 5,7-dichloro-6-isopropyl-1H-pyrazolo[4,3-g]quinoline

A solution of 9-bromo-5,7-dichloro-6-isopropyl-1H-pyrazolo[4,3-g]quinoline (7.58 g, 21.111 mmol) in anhydrous THF (60 mL+20 mL rinse) was added drop wise over 1.25 hours to a solution of methyllithium (14 mL of 1.6 M, 22.400 mmol) (1.6M in diethyl ether) in anhydrous THF (40 mL) cooled at −78° C. Then, 15 minutes after finishing the addition, a solution of butyllithium (8.5 mL of 2.5 M, 21.250 mmol) (2.5 M solution in hexanes) was added within 10 minutes. The reaction was stirred at −78° C. for 30 minutes more. An aqueous solution of aqueous citric acid 5% (50 mL) and the mixture was allowed to warm to room temperature. Ethyl acetate (500 mL), dichloromethane (100 mL) and 2-Methyl-THF (250 mL) were added. The organic phase was washed successively with an aqueous solution of $NaHCO_3$ 5% (2×200 mL) and brine (2×100 mL), dried over $MgSO_4$, filtered and concentrated. The residue was triturated in acetonitrile (1×40 mL), filtered and dried to afford 5,7-dichloro-6-isopropyl-1H-pyrazolo[4,3-g]quinoline (5.25 g, 83%) as a yellow solid. $^1$H NMR (300 MHz, DMSO-d6) δ 13.49 (s, 1H), 8.80 (s, 1H), 8.54 (s, 1H), 8.06 (s, 1H), 4.14-3.90 (m, 1H), 1.49 (d, J=7.0 Hz, 6H), ESI-MS m/z calc. 279.033, found 280.1 (M+1)+; Retention time: 3.2 minutes.

Step 6: ethyl 4-(5-chloro-6-isopropyl-1H-pyrazolo[4,3-g]quinolin-7-yl)benzoate

To a suspension of 5,7-dichloro-6-isopropyl-1H-pyrazolo[4,3-g]quinoline (1000 mg, 3.320 mmol), (4-ethoxycarbonylphenyl)boronic acid (700 mg, 3.608 mmol) and Tetrakis (triphenylphosphane)palladium(0) (190 mg, 0.1644 mmol) in a mixture of Dioxane (5.0 mL) and DMF (5 mL), an aqueous solution of $Na_2CO_3$ (4.1 mL of 2 M, 8.200 mmol) was added and the reaction was heated at 100° C. for 4 hours. An aqueous solution of HCl 1.0 M and DCM were added. The mixture was extracted with DCM (3×), dried through a phase separator, combined and concentrated to afford ethyl 4-(5-chloro-6-isopropyl-1H-pyrazolo[4,3-g]quinolin-7-yl)benzoate (1421.3 mg, 48%). 1H NMR (400 MHz, Chloroform-d) δ 10.67 (s, 1H), 8.88 (d, J=0.9 Hz, 1H), 8.42 (d, J=1.2 Hz, 1H), 8.22-8.19 (m, 2H), 8.18 (t, J=1.1 Hz, 1H), 7.65-7.53 (m, 2H), 4.45 (q, J=7.1 Hz, 2H), 3.41 (p, J=7.2 Hz, 1H), 1.51-1.41 (m, 9H). ESI-MS m/z calc. 393.1244, found 394.2 $(M+1)^+$; Retention time: 0.84 minutes Step 7: ethyl 4-[5-(4-fluoro-3-methoxy-phenyl)-6-isopropyl-1H-pyrazolo[4,3-g]quinolin-7-yl]benzoate 4-[5-(4-fluoro-3-methoxy-phenyl)-6-isopropyl-1H-pyrazolo[4,3-g]quinolin-7-yl]benzoic acid (252)

A suspension of ethyl 4-(5-chloro-6-isopropyl-1H-pyrazolo[4,3-g]quinolin-7-yl)benzoate (30 mg, 0.05061 mmol), (4-fluoro-3-methoxy-phenyl)boronic acid (15 mg, 0.08826 mmol), K2CO3 (15 mg, 0.1085 mmol) and Pd(dppf)$Cl_2$ (2 mg, 0.002449 mmol) in a mixture of 1,4-dioxane (400 μL) and water (100 μL), was heated at 110° C. for 5 hours. The reaction was cooled to room temperature, an aqueous solution of NaOH (200 μL of 2 M, 0.4000 mmol) was added and the reaction was stirred at room temperature for 2 hours. An aqueous solution of HCl 1.0 M and $CHCl_3$:IPA (3:1) were added. The mixture was extracted with $CHCl_3$:IPA (3:1) (3×). The organic phases were dried through a phase separator, combined and concentrated. Purification by reverse-phase HPLC (Method: C18 Waters Sunfire column, 30×150 mm, 5 micron. Gradient: MeCN in $H_2O$ with 0.2% formic acid) afforded 4-[5-(4-fluoro-3-methoxy-phenyl)-6-isopropyl-1H-pyrazolo[4,3-g]quinolin-7-yl]benzoic acid (19.9 mg, 85%). $^1$H NMR (400 MHz, Methanol-$d_4$) δ 8.24 (d, J=1.1 Hz, 1H), 8.22-8.16 (m, 2H), 8.13 (d, J=1.2 Hz, 1H), 7.79 (d, J=1.0 Hz, 1H), 7.70-7.62 (m, 2H), 7.33 (dd, J=11.4, 8.2 Hz, 1H), 7.16 (dd, J=8.2, 2.0 Hz, 1H), 6.96 (ddd, J=8.2, 4.2, 2.0 Hz, 1H), 3.88 (s, 3H), 3.22 (h, J=7.2 Hz, 1H), 1.01 (m, 6H). ESI-MS m/z calc. 455.16452, found 456.2 $(M+1)^+$; Retention time: 1.07

Compounds 253-262

Compounds 253-262 (Table 18) were prepared in two steps from intermediate G21 and the appropriate boronic acid according to the method described for compound 252, followed by demethylation and ester hydrolysis with $BBr_3$ according to the method described for compound 252. Any modifications to methods are noted in Table 18 and accompanying footnotes.

TABLE 18

Method of preparation, structure and physicochemical data for compounds 253-261.

| Cmpd | Product | Boronic acid | Method | $^1$H NMR; LCMS m/z $[M + H]^+$ |
|---|---|---|---|---|
| 253 | 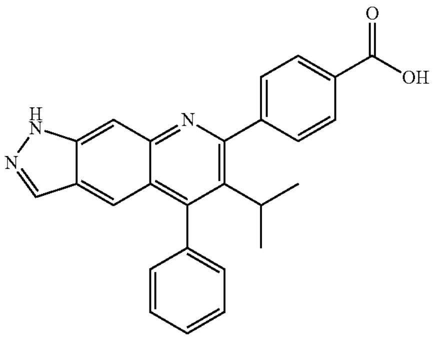 [SMILES: CC(C)c1c(-c2ccc(C(=O)O)cc2)nc2cc3[nH]ncc3cc2c1-c1ccccc1] | 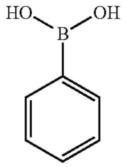 | As for compound 252 from intermediate G21 | $^1$H NMR (400 MHz, Methanol-d4) δ 8.24-8.16 (m, 3H), 8.13 (t, J = 1.1 Hz, 1H), 7.70 (d, J = 1.1Hz, 1H), 7.69-7.63 (m, 2H), 7.62-7.56 (m, 3H), 7.44-7.38 (m, 2H), 3.21 (hept, J = 7.2 Hz, 1H), 0.97 (d, J = 7.2 Hz, 6H). LCMS m/z 408.2 [M + H+] |
| 254 | 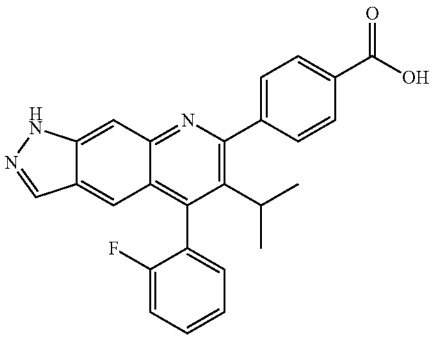 [SMILES: CC(C)c1c(-c2ccc(C(=O)O)cc2)nc2cc3[nH]ncc3cc2c1-c1ccccc1F] | 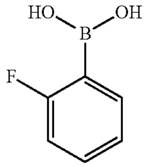 | As for compound 252 from intermediate G21 | 1H NMR (400 MHz, Methanol-d4) δ 8.35 (d, J = 1.1 Hz, 1H), 8.30-8.25 (m, 2H), 8.24 (d, J = 1.1 Hz, 1H), 7.92 (s, 1H), 7.80 (m, 2H), 7.76-7.67 (m, 1H), 7.52-7.47 (m, 2H), 7.43 (m, 1H), 3.23 (h, J = 7.4 Hz, 1H), 1.02 (m, 6H). LCMS m/z 426.17 [M + H+] |
| 255 | 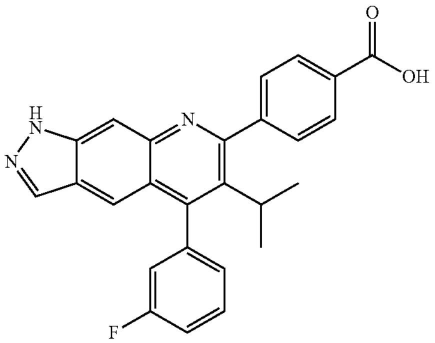 [SMILES: CC(C)c1c(-c2ccc(C(=O)O)cc2)nc2cc3[nH]ncc3cc2c1-c1cccc(F)c1] | 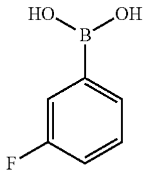 | As for compound 252 from intermediate G21 | 1H NMR (400 MHz, Methanol-d4) δ 8.24 (d, J = 1.1 Hz, 1H), 8.23-8.18 (m, 2H), 8.15 (t, J = 1.1 Hz, 1H), 7.74 (d, J = 1.0 Hz, 1H), 7.71-7.66 (m, 2H), 7.66-7.59 (m, 1H), 7.38-7.30 (m, 1H), 7.26 (dt, J = 7.6, 1.2 Hz, 1H), 7.24-7.19 (m, 1H), 3.20 (h, J = 7.2 Hz, 1H), 0.99 (d, J = 7.2 Hz, 6H). LCMS m/z 426.17 [M + H+] |

TABLE 18-continued

Method of preparation, structure and physicochemical data for compounds 253-261.

| Cmpd | Product | Boronic acid | Method | $^1$H NMR; LCMS m/z [M + H]$^+$ |
|---|---|---|---|---|
| 256 | 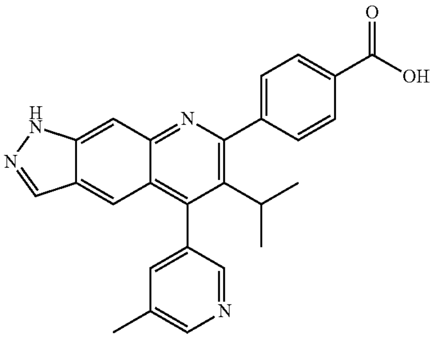 [SMILES: Cc1cncc(-c2c(C(C)C)c(-c3ccc(C(=O)O)cc3)nc3cc4[nH]ncc4cc23)c1] | 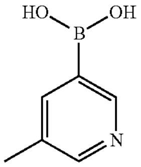 | As for compound 252 from intermediate G21 | 1H NMR (400 MHz, Methanol-d4) δ 8.70 (m, 1H), 8.51 (m, 1H), 8.30 (d, J = 1.1 Hz, 1H), 8.27-8.22 (m, 2H), 8.21 (t, J = 1.1 Hz, 1H), 7.92 (m, 1H), 7.79 (d, J = 1.0 Hz, 1H), 7.77-7.69 (m, 2H), 3.19 (h, J = 7.2 Hz, 1H), 2.56 (s, 3H), 0.99 (dd, J = 7.2, 2.3 Hz, 6H). LCMS m/z 423.19 [M + H+] |
| 257 | 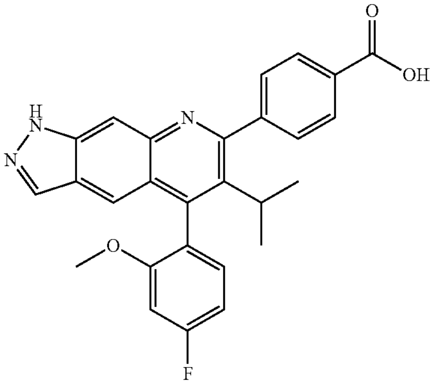 [SMILES: COc1cc(F)ccc1-c1c(C(C)C)c(-c2ccc(C(=O)O)cc2)nc2cc3[nH]ncc3cc12] | 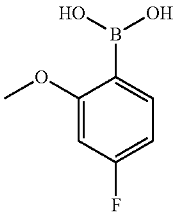 | As for compound 252 from intermediate G21 | 1H NMR (400 MHz, Methanol-d4) δ 8.41 (d, J = 1.1 Hz, 1H), 8.35-8.27 (m, 2H), 8.24 (d, J = 1.1 Hz, 1H), 8.07 (d, J = 1.0 Hz, 1H), 7.90-7.81 (m, 2H), 7.36 (dd, J = 8.4, 6.4 Hz, 1H), 7.15 (dd, J = 11.0, 2.4 Hz, 1H), 7.02 (td, J = 8.3, 2.4 Hz, 1H), 3.73 (s, 3H), 3.23 (h, J = 7.3 Hz, 1H), 1.01 (m, J = 30.3, 7.2 Hz, 6H). LCMS m/z 456.2 [M + H+] |
| 258 | 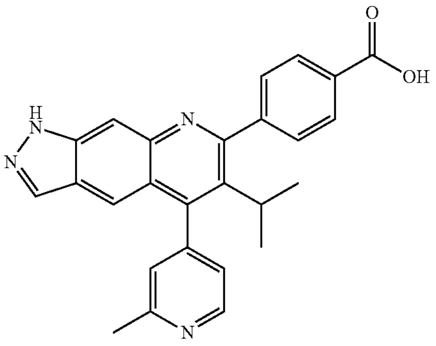 [SMILES: Cc1cc(-c2c(C(C)C)c(-c3ccc(C(=O)O)cc3)nc3cc4[nH]ncc4cc23)ccn1] | 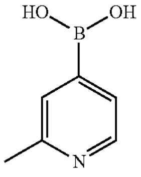 | As for compound 252 from intermediate G21 | 1H NMR (400 MHz, Methanol-d4) δ 8.99 (d, J = 5.9 Hz, 1H), 8.40 (d, J = 1.1 Hz, 1H), 8.33 (m, 1H), 8.31 (d, J = 8.2 Hz, 2H), 8.15 (m, 1H), 8.06 (d, J = 6.0 Hz, 1H), 8.02 (m, 1H), 7.89-7.82 (m, 2H), 3.22-3.09 (m, 1H), 2.95 (s, 3H), 1.05 (dd, J = 7.2, 5.9 Hz, 6H). LCMS m/z 423.19 [M + H+] |
| 259 | 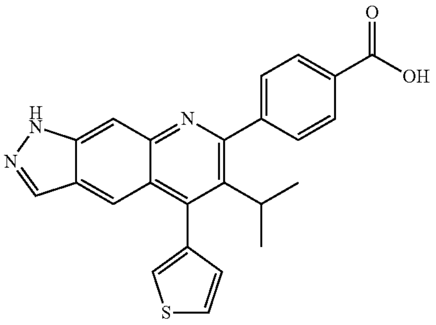 [SMILES: CC(C)c1c(-c2ccc(C(=O)O)cc2)nc2cc3[nH]ncc3cc2c1-c1ccsc1] | 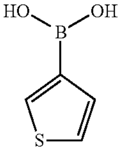 | As for compound 252 from intermediate G21 | 1H NMR (400 MHz, Methanol-d4) δ 8.41 (d, J = 1.7 Hz, 1H), 8.29 (m, 2H), 8.23 (d, J = 1.1 Hz, 1H), 8.10 (m, 1H), 7.88-7.76 (m, 3H), 7.71-7.64 (m, 1H), 7.30 (m, 1H), 3.26 (d, J = 7.2 Hz, 1H), 1.04 (m, 6H). LCMS m/z 414.12 [M + H+] |

TABLE 18-continued

Method of preparation, structure and physicochemical data for compounds 253-261.

| Cmpd | Product | Boronic acid | Method | $^1$H NMR; LCMS m/z $[M + H]^+$ |
|---|---|---|---|---|
| 260 | 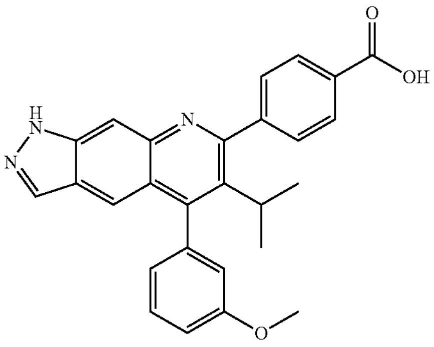 [SMILES: COc1cccc(-c2c(C(C)C)c(-c3ccc(C(=O)O)cc3)nc3cc4[nH]ncc4cc23)c1] | 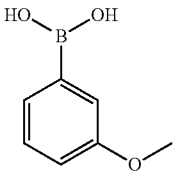 | As for compound 252 from intermediate G21 | 1H NMR (400 MHz, Methanol-d4) δ 8.37 (d, J = 1.1 Hz, 1H), 8.33-8.24 (m, 2H), 8.22 (t, J = 1.1 Hz, 1H), 8.02 (d, J = 1.0 Hz, 1H), 7.86-7.78 (m, 2H), 7.63-7.54 (m, 1H), 7.21 (ddd, J = 8.4, 2.5, 1.0 Hz, 1H), 7.04 (ddt, J = 4.9, 2.4, 1.3 Hz, 2H), 3.88 (s, 3H), 3.29-3.21 (m, 1H), 1.02 (d, J = 7.2, 6H). LCMS m/z 438.18 [M + H+] |
| 261 | 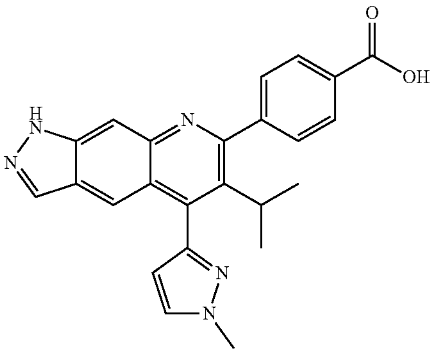 [SMILES: CC(C)c1c(-c2ccc(C(=O)O)cc2)nc2cc3[nH]ncc3cc2c1-c1ccn(C)n1] | 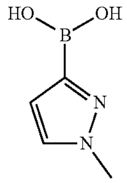 | As for compound 252 from intermediate G21 | 1H NMR (400 MHz, Methanol-d4) δ 8.33 (d, J = 1.1 Hz, 1H), 8.28-8.21 (m, 2H), 8.17 (t, J = 1.1 Hz, 1H), 8.08 (d, J = 1.0 Hz, 1H), 7.94 (d, J = 2.3 Hz, 1H), 7.77-7.69 (m, 2H), 6.57 (d, J = 2.2 Hz, 1H), 4.10 (s, 3H), 3.25 (h, J = 7.2 Hz, 1H), 1.05 (d, J = 7.2 Hz, 6H). LCMS m/z 412.22 [M + H+] |
| 262 | 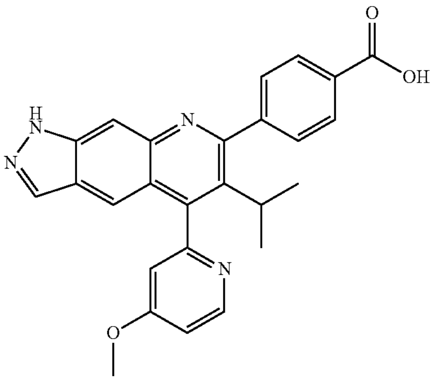 [SMILES: COc1ccnc(-c2c(C(C)C)c(-c3ccc(C(=O)O)cc3)nc3cc4[nH]ncc4cc23)c1] | 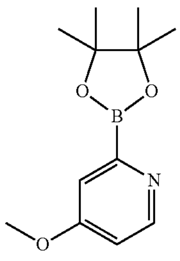 | As for compound 252 from intermediate G21 | 1H NMR (400 MHz, Methanol-d4) δ 8.53 (d, J = 2.7 Hz, 1H), 8.33 (d, J = 1.1 Hz, 1H), 8.29-8.23 (m, 3H), 8.22 (t, J = 1.1 Hz, 1H), 7.87 (d, J = 1.1 Hz, 1H), 7.79-7.73 (m, 2H), 7.62 (dd, J = 2.8, 1.6 Hz, 1H), 3.98 (s, 3H), 3.21 (h, J = 7.2 Hz, 1H), 1.01 (dd, J = 7.2, 1.9 Hz, 6H). LCMS m/z 439.22 [M + H+] |
| 263 | 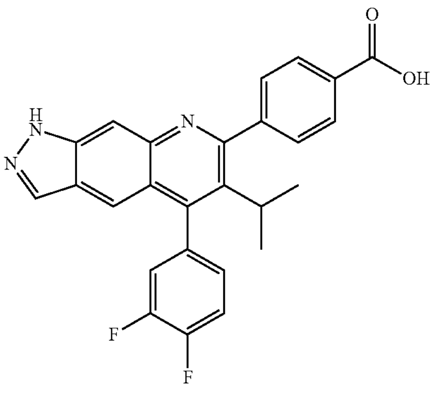 [SMILES: CC(C)c1c(-c2ccc(C(=O)O)cc2)nc2cc3[nH]ncc3cc2c1-c1ccc(F)c(F)c1] | 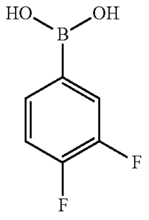 [SMILES: OB(O)c1ccc(F)c(F)c1] | As for compound 252 from intermediate G21 | 1H NMR (400 MHz, Methanol-d4) δ 8.31 (d, J = 1.1 Hz, 1H), 8.28-8.20 (m, 2H), 8.19 (t, J = 1.1 Hz, 1H), 7.86 (d, J = 1.0 Hz, 1H), 7.78-7.70 (m, 2H), 7.56 (dt, J = 10.5, 8.3 Hz, 1H), 7.45 (ddd, J = 10.9, 7.6, 2.1 Hz, 1H), 7.32-7.23 (m, 1H), 3.22 (h, J = 7.2 Hz, 1H), 1.01 (m, 6H). LCMS m/z 444.19 [M + H+] |

TABLE 18-continued

| Method of preparation, structure and physicochemical data for compounds 253-261. | | | | |
|---|---|---|---|---|
| Cmpd | Product | Boronic acid | Method | $^1$H NMR; LCMS m/z $[M + H]^+$ |
| 264 | 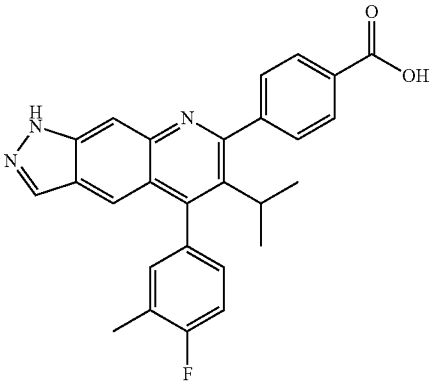 [SMILES: Cc1cc(-c2c(C(C)C)c(-c3ccc(C(=O)O)cc3)nc3cc4[nH]ncc4cc23)ccc1F] | 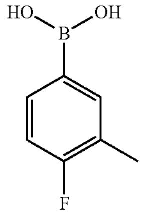 | As for compound 252 from intermediate G21 | 1H NMR (400 MHz, Methanol-d4) δ 8.35 (d, J = 1.1 Hz, 1H), 8.27 (d, J = 8.2 Hz, 2H), 8.21 (d, J = 1.1 Hz, 1H), 7.95 (s, 1H), 7.79 (d, J = 8.1 Hz, 2H), 7.40-7.29 (m, 3H), 3.24 (h, J = 7.1 Hz, 1H), 2.41 (d, J = 1.9 Hz, 3H), 1.00 (m). LCMS m/z 440.17 [M + H+] |

Assays for Detecting and Measuring AAT Modulator Properties of Compounds

Example 1: AAT Function Assay (MSD Assay NL20-SI Cell Line)

Alpha-1 antitrypsin (AAT) is a SERPIN (serine protease inhibitor) that inactivates enzymes by binding to them covalently. This assay measured the amount of functionally active AAT in a sample in the presence of the disclosed compounds 1-262 by determining the ability of AAT to form an irreversible complex with human neutrophil Elastase (hNE). In practice, the sample (cell supernatant, blood sample, or other) was incubated with excess hNE to allow AAT-Elastase complex to be formed with all functional AAT in the sample. This complex was then captured to a microplate coated with an anti-AAT antibody. The complex captured to the plate was detected with a labeled anti-Elastase antibody and quantitated using a set of AAT standards spanning the concentration range present in the sample. Meso Scale Discovery (MSD) plate reader, Sulfo-tag labeling, and microplates were used to provide high sensitivity and wide dynamic range.

Materials:

| Reagents/Plates | Concentration |
|---|---|
| Goat anti-human Alpha-1-Antitrypsin Polyclonal Antibody | 1 mL @ 1 mg/mL |
| Use at 5 µg/mL in phosphate buffered saline (PBS) | |
| Human Neutrophil Elastase | 100 µg lyophilized |
| Stock at 3.4 µM (0.1 mg + 1 mL PBS) | |
| Working at 1 µg/mL (34 nm) in MSD Assay buffer (1% bovine serum albumin (BSA)) | |
| Mouse anti-human Neutrophil Elastase Monoclonal Antibody | 900 µg/mL |
| Sulfo-tagged @ 12:1 using MSD Gold Sulfo-tag N-hydroxysuccinimide (NHS) ester; use at 0.45 µg/mL in MSD Assay buffer (1% BSA) | |
| M-AAT (Alpha-1-Antitrypsin) | 5 mg lyophilized |
| MSD Blocker A (BSA) | 250 mL |
| 5% solution in PBS for blocking | |
| 1% solution in PBS for assay buffer | |
| MSD Read Buffer T (4X) with Surfactant | 1 L or 250 mL |
| MSD 384 high bind plates | |

-continued

| Reagents/Plates | Concentration |
|---|---|
| Polypropylene for dilution 384 well plate | |
| Tissue culture treated black well 384 well plate | |

Instrument(s):
- Meso Sector S600
- Bravo
- Washer dispenser
- Multidrop Combi

Assay Protocol

Day 1 Cell Culture
1. Harvest NL20 human bronchial epithelial cells expressing human Z-AAT in OptiMEM™ containing Pen/Strep (P/S)
2. Seed at 16,000 cells/well in 30 µL (384 well plate)
3. Centrifuge plates briefly up to speed (1200 rpm) and place into 37° C. incubator overnight Day 2: Compound Addition and Coating Plates with Capture Antibody Compound Addition:
1. Dispense 40 µL of OptiMEM™ (P/S) with doxycycline (1:1000 stock=0.1 µM final) to each well of the compound plate using a multidrop Combi in hood
2. Remove cell plate from incubator, flip/blot and take immediately to Bravo to transfer compounds
3. Return plates to incubator overnight Coat MSD Plates
1. Dilute capture antibody (Polyclonal Goat anti-AAT) to 5 µg/mL (1:200) in PBS (no BSA).
2. Dispense 25 µL of diluted capture antibody into all wells of MSD 384-well High Bind plate using the Multidrop equipped with a standard cassette.
3. Incubate overnight at 4° C.

Prepare Blocker A (BSA) Solutions
1. Prepare solution of 5% MSD Blocker A (BSA) following the manufacturer's instructions.
2. Further dilute the 5% MSD Blocker A in PBS to 1% (Blocker A) as needed.

Day 3: Run MSD Assay

Block Plates
1. Wash plate 1× with 50 µL Wash buffer (PBS+0.5% Tween 20), and adds 35 µL 5% Block A buffer to block non-specific binding on washer dispenser
2. Rotate plates on shaker for 1 hour at 600 rpm Prepare M-AAT Standards 1. Dilute M-AAT stock to 1.6 μg/mL in 1% BSA Blocker A (Stock in −70° C.); then prepare 12×1:2 serial dilutions in 1% Blocker A
2. The top starting final concentration on MSD plate is 320 ng/mL. These dilutions correspond to a final concentration of 320, 160, 80, 40, 20, 10, 5, 2.5, 1.25, 0.625, 0.312, 0.156 ng/mL.

Dilution Plate

1. Add 80 μL of 1% Assay buffer to all wells except columns 1/24 (standards) with Multidrop Combi
2. Add diluted standards to columns 1 and 24
3. Centrifuge dilution plates 1200 rpm briefly Cell Plate 1. Aspirate columns which will have the standards from the cell plates in the hood using 16-pin aspirator Prepare Human Neutrophil Elastase (hNE)

1. Prepare 1 μg/mL Human Neutrophil Elastase by diluting in 1% Blocker A.
   a. Small 100 μg vial—add 1 mL PBS (100 μg/mL)
      i. This can then be diluted 1:100 in 1% Assay Buffer for a final 1 μg/mL concentration MSD—Add hNE (20 μL/Well)

1. After the MSD plate has blocked for at least 1 hour, wash plate 1× with 50 μL Wash buffer (PBS+0.5% Tween 20) and then add 20 μL hNE to each well Bravo—Cell Plate—Dilution Plate—MSD Plate Using the Bravo aspirate 10 μL from the cell plate, transfer to the dilution plate (9-fold dilution)

1. Mix 25 μL 3×, then aspirate 5 μL, transfer to MSD plate (5-fold dilution)
2. Mix 10 μL 3×. Total dilution is 45 fold.
3. Shake plates at 600 rpm for 1.5 hours Add Functional Detection hNE Antibody 1. Wash plate 1× with wash buffer
2. Add 25 μL Sulfo-tagged anti-Elastase Monoclonal Mouse anti-Elastase) diluted to 0.45 μg/mL (1:2000) in 1% Blocker A into all wells of the functional activity MSD plates using the washer/dispenser Note: The dilution required for sufficient signal must be determined for each new lot of labeled antibody.
3. Incubate at RT shaking at 600 rpm for 1 hour.

Final Wash and MSD Imager Read

1. Wash the plate 1×, and add 25 μL of Wash Buffer to the plate.
2. Make 2× Read buffer
3. Remove wash buffer from MSD plate
4. Transfer 35 μL 2× Read Buffer to MSD plate using Bravo and take to MSD to read immediately Data analysis in MSD Discovery Workbench 4.0 software and $EC_{50}$ values were determined using Genedata. See Table 19 for data.

Example 2: Biochemical Assay (Z-AAT Elastase Activity Assay)

This assay measured the modulation of compounds 1-262 on Z-AAT SERPIN activity using purified Z-AAT protein and purified human neutrophil elastase (hNE). Normally, when active monomeric Z-AAT encounters a protease such as trypsin or elastase, it forms a 1:1 covalent "suicide" complex in which both the AAT and protease are irreversibly inactivated. However, compounds binding to Z-AAT can lead to a decrease in SERPIN activity. In such cases, when a protease encounters compound-bound Z-AAT, the protease cleaves and inactivates Z-AAT without itself being inactivated.

Materials

Reagents

PBS buffer (media prep)+0.01% BRIJ35 detergent (Calbiochem catalog #203728)

Opti-MEM media (Fisher 11058-021)

Human neutrophil elastase (hNE, Athens Research #16-14-051200)

3.4 μM stock (0.1 mg/mL) prepared in 50 mM Na Acetate, pH 5.5, 150 mM NaCl, stored at −80° C.

Elastase substrate V (ES V, fluorescent peptide substrate MeOSuc-Ala-Ala-Pro-Val-AMC, Calbiochem catalog #324740)

20 mM stock in DMSO, stored at −20° C.

Purified Z-AAT protein from human plasma;

12.9 μM (0.67 mg/mL) Z-AAT Vertex Cambridge Sample 4942, from patient #061-SSN, stored at −80 C Plates Corning 4511 (384 well black low volume)

Instruments

PerkinElmer® EnVision™

Assay Protocol

Pre-Incubation of Z-AAT with Compounds 1. 7.5 μL of Z-AAT (20 nM) was incubated with compounds 1-215 in a GCA plate for 1 hour at room temperature Addition of hNE 1. 7.5 μL of HNE solution (3 nM in PBS+0.01% BRIJ35) added into GCA plate
2. Incubate plate for 30 minutes to allow Z-AAT/HNE suicide complex formation.

Addition of Substrate and Read Plate on PE Envision 1. 7.5 μL of substrate (300 μM solution of elastase substrate (ES V) in PBS+0.01%

BRIJ35) dispensed per well into GCA plate

2. Immediately read on Envision.

Compounds 1-87, 89-140, 143-151, 154, 158, 160, 164-167, 170, 171, 173-183, 186, 189-208, and 210-215 had an $IC_{50}/EC_{50}$ ratio of greater than 10 or an $IC_{50}$ of greater than 10 μM. Compounds 161, 162, 163, 172, and 209 had an $IC_{50}$ of greater than 3.33 μM.

Example 3: EC50 and Z-AAT Elastase Activity Data for Compounds 1-262

The compounds of formula (I) are useful as modulators of AAT activity. Table 19 below illustrates the $EC_{50}$ of the compounds 1-262 using procedures described in Example 1. In Table 19 below, the following meanings apply. Table 19 below also provides the Z-AAT elastase activity using procedures described in Example 2. For both $EC_{50}$ and $IC_{50}$: "+++" means<1.16 μM; "++" means between 1.16 μM and 3.0 μM; "+" means greater than 3.0 μM; and "N/A" means activity not assessed. For $IC_{50}$, "N.D." means activity not detected up to 30 μM.

TABLE 19

$EC_{50}$ and $IC_{50}$ data for Compounds 1-262

| Compound No. | NL20 Functional $EC_{50}$ (μM) | Z-AAT Elastase Activity $IC_{50}$ (μM) |
|---|---|---|
| 1 | +++ | + |
| 2 | +++ | + |

TABLE 19-continued

EC50 and IC50 data for Compounds 1-262

| Compound No. | NL20 Functional $EC_{50}$ (μM) | Z-AAT Elastase Activity $IC_{50}$ (μM) |
|---|---|---|
| 3 | +++ | N.D. |
| 4 | +++ | N.D. |
| 5 | + | N.D. |
| 6 | +++ | + |
| 7 | + | + |
| 8 | ++ | + |
| 9 | ++ | N.D. |
| 10 | +++ | N.D. |
| 11 | ++ | + |
| 12 | +++ | + |
| 13 | ++ | N.D. |
| 14 | ++ | N.D. |
| 15 | +++ | N.D. |
| 16 | +++ | N.D. |
| 17 | +++ | N.D. |
| 18 | ++ | N.D. |
| 19 | + | N.D. |
| 20 | + | N.D. |
| 21 | ++ | N.D. |
| 22 | + | + |
| 23 | + | N/A |
| 24 | + | N.D. |
| 25 | ++ | N.D. |
| 26 | + | N.D. |
| 27 | ++ | + |
| 28 | ++ | N.D. |
| 29 | ++ | N.D. |
| 30 | ++ | N/A |
| 31 | + | N.D. |
| 32 | +++ | + |
| 33 | + | N.D. |
| 34 | + | N.D. |
| 35 | + | N.D. |
| 36 | + | N.D. |
| 37 | + | N.D. |
| 38 | + | N.D. |
| 39 | +++ | + |
| 40 | + | N.D. |
| 41 | ++ | N.D. |
| 42 | +++ | + |
| 43 | + | N.D. |
| 44 | +++ | ++ |
| 45 | +++ | + |
| 46 | +++ | N.D. |
| 47 | +++ | + |
| 48 | +++ | N.D. |
| 49 | ++ | N.D. |
| 50 | + | N.D. |
| 51 | ++ | + |
| 52 | +++ | ++ |
| 53 | ++ | + |
| 54 | ++ | N.D. |
| 55 | + | + |
| 56 | +++ | + |
| 57 | ++ | +++ |
| 58 | ++ | + |
| 59 | ++ | + |
| 60 | + | N/A |
| 61 | +++ | ++ |
| 62 | + | N.D. |
| 63 | +++ | + |
| 64 | +++ | + |
| 65 | ++ | + |
| 66 | + | N.D. |
| 67 | ++ | N.D. |
| 68 | +++ | ++ |
| 69 | +++ | ++ |
| 70 | + | N.D. |
| 71 | +++ | ++ |
| 72 | +++ | + |
| 73 | + | + |
| 74 | +++ | N.D. |
| 75 | +++ | ++ |
| 76 | + | + |
| 77 | +++ | ++ |
| 78 | + | + |
| 79 | +++ | ++ |
| 80 | +++ | ++ |
| 81 | +++ | ++ |
| 82 | +++ | + |
| 83 | +++ | +++ |
| 84 | +++ | +++ |
| 85 | +++ | N/A |
| 86 | +++ | N/A |
| 87 | + | N.D. |
| 88 | +++ | N.D. |
| 89 | + | N/A |
| 90 | ++ | N.D. |
| 91 | + | N.D. |
| 92 | ++ | N.D. |
| 93 | +++ | +++ |
| 94 | +++ | +++ |
| 95 | ++ | + |
| 96 | +++ | + |
| 97 | +++ | + |
| 98 | +++ | +++ |
| 99 | +++ | +++ |
| 100 | +++ | +++ |
| 101 | +++ | +++ |
| 102 | + | N.D. |
| 103 | + | N.D. |
| 104 | +++ | +++ |
| 105 | +++ | +++ |
| 106 | +++ | +++ |
| 107 | +++ | +++ |
| 108 | +++ | + |
| 109 | +++ | + |
| 110 | +++ | ++ |
| 111 | +++ | ++ |
| 112 | +++ | + |
| 113 | +++ | ++ |
| 114 | +++ | + |
| 115 | +++ | ++ |
| 116 | +++ | +++ |
| 117 | +++ | + |
| 118 | ++ | + |
| 119 | + | + |
| 120 | +++ | N.D. |
| 121 | +++ | N.D. |
| 122 | ++ | ++ |
| 123 | +++ | ++ |
| 124 | ++ | N.D. |
| 125 | +++ | + |
| 126 | + | N.D. |
| 127 | +++ | N.D. |
| 128 | +++ | +++ |
| 129 | +++ | N.D. |
| 130 | +++ | ++ |
| 131 | ++ | + |
| 132 | +++ | +++ |
| 133 | +++ | +++ |
| 134 | +++ | + |
| 135 | +++ | ++ |
| 136 | +++ | + |
| 137 | ++ | N.D. |
| 138 | ++ | + |
| 139 | ++ | + |
| 140 | +++ | N.D. |
| 141 | +++ | +++ |
| 142 | +++ | N.D. |
| 143 | +++ | + |
| 144 | +++ | ++ |
| 145 | + | + |
| 146 | + | N.D. |
| 147 | + | N.D. |
| 148 | + | N.D. |
| 149 | ++ | N.D. |
| 150 | ++ | N.D. |
| 151 | + | N.D. |
| 152 | ++ | N.D. |

TABLE 19-continued

EC$_{50}$ and IC$_{50}$ data for Compounds 1-262

| Compound No. | NL20 Functional EC$_{50}$ (μM) | Z-AAT Elastase Activity IC$_{50}$ (μM) |
|---|---|---|
| 153 | ++ | + |
| 154 | ++ | + |
| 155 | +++ | +++ |
| 156 | +++ | +++ |
| 157 | +++ | +++ |
| 158 | +++ | +++ |
| 159 | + | N.D. |
| 160 | + | N.D. |
| 161 | + | N.D. |
| 162 | ++ | N.D. |
| 163 | +++ | ++ |
| 164 | ++ | N.D. |
| 165 | +++ | N.D. |
| 166 | +++ | N/A |
| 167 | +++ | N.D. |
| 168 | +++ | +++ |
| 169 | +++ | +++ |
| 170 | +++ | +++ |
| 171 | +++ | +++ |
| 172 | +++ | +++ |
| 173 | ++ | N.D. |
| 174 | + | N.D. |
| 175 | + | N.D. |
| 176 | +++ | ++ |
| 177 | +++ | +++ |
| 178 | +++ | +++ |
| 179 | +++ | +++ |
| 180 | + | N.D. |
| 181 | +++ | +++ |
| 182 | +++ | +++ |
| 183 | + | + |
| 184 | ++ | N.D. |
| 185 | +++ | ++ |
| 186 | + | N.D. |
| 187 | +++ | +++ |
| 188 | +++ | +++ |
| 189 | +++ | +++ |
| 190 | +++ | +++ |
| 191 | +++ | +++ |
| 192 | +++ | +++ |
| 193 | + | N.D. |
| 194 | +++ | ++ |
| 195 | + | N.D. |
| 196 | +++ | +++ |
| 197 | + | + |
| 198 | + | N/A |
| 199 | ++ | ++ |
| 200 | + | N.D. |
| 201 | +++ | ++ |
| 202 | +++ | +++ |
| 203 | +++ | ++ |
| 204 | ++ | N.D. |
| 205 | + | + |
| 206 | + | N.D. |
| 207 | +++ | N.D. |
| 208 | +++ | ++ |
| 209 | + | + |
| 210 | +++ | + |
| 211 | +++ | +++ |
| 212 | + | N.D. |
| 213 | + | N.D. |
| 214 | + | N.D. |
| 215 | + | + |
| 216 | ++ | ++ |
| 217 | + | + |
| 218 | + | N.D. |
| 219 | + | N.D. |
| 220 | + | N.D. |
| 221 | + | N.D. |
| 222 | + | N.D. |
| 223 | +++ | + |
| 224 | +++ | + |
| 225 | +++ | + |
| 226 | +++ | +++ |
| 227 | ++ | + |
| 228 | ++ | N.D. |
| 229 | + | N.D. |
| 230 | ++ | N.D. |
| 231 | +++ | + |
| 232 | +++ | + |
| 233 | + | N.D. |
| 234 | + | ++ |
| 235 | + | N.D. |
| 236 | ++ | + |
| 237 | +++ | ++ |
| 238 | ++ | N.D. |
| 239 | +++ | + |
| 240 | +++ | + |
| 241 | +++ | N.D. |
| 242 | + | + |
| 243 | + | + |
| 244 | + | + |
| 245 | + | N.D. |
| 246 | +++ | + |
| 247 | +++ | + |
| 248 | +++ | N.D. |
| 249 | ++ | N.D. |
| 250 | ++ | + |
| 251 | ++ | + |
| 252 | +++ | ++ |
| 253 | +++ | ++ |
| 254 | ++ | N.D. |
| 255 | +++ | ++ |
| 256 | + | N.D. |
| 257 | ++ | + |
| 258 | + | N.D. |
| 259 | ++ | + |
| 260 | +++ | + |
| 261 | + | N.D. |
| 262 | + | N.D. |
| 263 | +++ | +++ |
| 264 | +++ | ++ |

Other Embodiments

This description provides merely exemplary embodiments of the disclosed subject matter. One skilled in the art will readily recognize from the disclosure and accompanying claims, that various changes, modifications and variations can be made therein without departing from the spirit and scope of the disclosure as defined in the following claims.

What is claimed is:

1. A compound represented by Formula II (II)

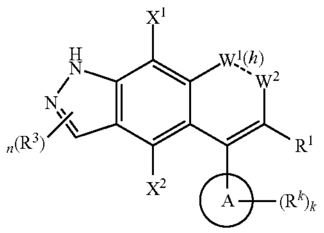

a tautomer thereof, a deuterated derivative of that compound or tautomer, or a pharmaceutically acceptable salt of any of the foregoing, wherein:

$W^1$ and $W^2$ are each independently selected from —C═O, —$CR^2$, N, and —$NR^2$, wherein:

when $W^1$ is —$CR^2$, then $W^2$ is N;
when $W^2$ is —$CR^2$, then $W^1$ is N;
when $W^1$ is —C═O, then $W^2$ is —$NR^2$; and
when $W^2$ is —C═O, then $W^1$ is —$NR^2$ (h) is a double bond except that when one of $W^1$ and $W^2$ is —C═O, then (h) is a single bond;

Ring A is $C_3$-$C_{12}$ carbocyclyl, 3 to 12-membered heterocyclyl, $C_6$ or $C_{10}$ aryl, or 5 to 10-membered heteroaryl;

$R^1$ is halogen, $C_1$-$C_6$ alkyl, $C_1$-$C_6$ alkoxy, $C_1$-$C_6$ haloalkoxy, —C(═O)$R^z$, —C(═O)O$R^z$, —C(═O)N$R^wR^x$, —N$R^wR^x$, —N$R^w$C(═O)$R^z$, —N$R^w$C(═O)O$R^z$, —N$R^w$C(═O)N$R^xR^y$, —O$R^z$, —OC(═O)$R^z$, —OC(═O)N$R^wR^x$, S(═O)$_2R^z$, $C_3$-$C_6$ cycloalkyl, or 3 to 6-membered heterocyclyl; wherein:

the $C_1$-$C_6$ alkyl, the $C_3$-$C_6$ cycloalkyl, or the 3 to 6-membered heterocyclyl of $R^1$ is optionally substituted with 1 to 3 groups independently selected from —O$R^z$, $C_1$-$C_3$ haloalkyl, —CN, and halogen; and $R^w$, $R^x$, $R^y$, and $R^z$ are each independently hydrogen or $C_1$-$C_4$ alkyl;

$X^1$ and $X^2$ are each independently hydrogen, halogen, —CN, $C_1$-$C_3$ alkyl, $C_1$-$C_3$ haloalkyl, $C_1$-$C_3$ alkoxy, $C_1$-$C_3$ haloalkoxy, $C_3$-$C_6$ cycloalkyl, or 5 or 6-membered heteroaryl;

$R^2$ is hydrogen, halogen,

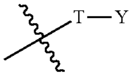
or
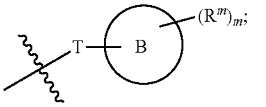

wherein:

T is absent, or is selected from —O—, —$OCH_2$—, —NH—, —NS(═O)$_2CH_3$, —S—, and —$CH_2$—;

Y is selected from $C_1$-$C_6$ alkyl, —$(CR^aR^a)_p$COOH, —$(CR^aR^a)_p$N$R^b$S(═O)$_2(CR^cR^c)_q$OH, —$(CR^aR^a)_p$C(═O)N$R^b(CR^cR^c)_g$COOH, and —$(CR^aR^a)_p$(O)$(CR^cR^c)_q$COOH; wherein:

$R^a$, for each occurrence, is independently hydrogen, halogen, —OH, or $C_1$-$C_4$ alkyl optionally substituted with 1 to 3 groups independently selected from halogen and —OH;

or alternatively, when $R^a$, for each occurrence, is independently $C_1$-$C_4$ alkyl, two $R^a$ groups together with their intervening carbon atom form cyclopropyl or cyclobutyl;

$R^b$ and $R^c$, for each occurrence, are each independently hydrogen or $C_1$-$C_2$ alkyl; and p and q are each independently an integer selected from 1 and 2;

Ring B is $C_3$-$C_{12}$ carbocyclyl, 3 to 12-membered heterocyclyl, $C_6$ or $C_{10}$ aryl, or 5 to 10-membered heteroaryl;

$R^3$ is —C(═O)O$R^d$; wherein $R^d$ is $C_1$-$C_4$ alkyl optionally substituted with —OC(O)$R^e$, —OC(═O)O$R^e$, or —OP(═O)$R^fR^f$; wherein:

$R^e$, for each occurrence, is independently hydrogen or —$CH_3$;

$R^f$, for each occurrence, is independently —OH, —$CH_3$, or —$OCH_3$;

$R^k$ is halogen, —CN, $C_1$-$C_2$ alkyl, $C_1$-$C_2$ haloalkyl, $C_1$-$C_2$ alkoxy, $C_1$-$C_2$ haloalkoxy, or O—($C_3$-$C_6$ cycloalkyl);

$R^m$, for each occurrence, is independently halogen, —CN, ═O, $C_1$-$C_6$ alkyl, $C_1$-$C_6$ alkoxy, —C(═O)$R^r$, —C(═O)O$R^r$, —C(═O)N$R^pR^q$, —C(═O)N$R^p$O$R^r$, —N$R^pR^q$, —N$R^p$C(═O)$R^r$, —N$R^p$S(═O)$_2R^r$, —O$R^r$, S(═O)$_2R^r$, —S(═O)$_2$N$R^pR^q$, —P(═O)$R^sR^t$, $C_3$-$C_6$ cycloalkyl, 3 to 6-membered heterocyclyl, phenyl, or 5 or 6-membered heteroaryl, wherein the $C_1$-$C_6$ alkyl, the phenyl, or the 5 or 6-membered heteroaryl of $R^m$ is optionally substituted with 1 to 3 groups independently selected from halogen, CN, —C(═O)O$R^r$, —N$R^pR^q$, and —O$R^r$; and wherein the $C_3$-$C_6$ cycloalkyl or the 3 to 6-membered heterocyclyl of $R^m$ is optionally substituted with 1 to 3 groups independently selected from halogen, CN, ═O, —C(═O)O$R^r$, —N$R^pR^q$, and —O$R^r$;

wherein $R^p$ and $R^q$, for each occurrence, are each independently hydrogen or $C_1$-$C_4$ alkyl optionally substituted with 1 to 3 groups independently selected from —OH, —$OCH_3$, —$OC_2H_5$, and —COOH;

wherein $R^r$, for each occurrence, is independently hydrogen, $C_1$-$C_4$ alkyl, $C_3$-$C_6$ cycloalkyl, or 3 to 6-membered heterocyclyl; wherein the $C_1$-$C_4$ alkyl, $C_3$-$C_6$ cycloalkyl, or 3 to 6-membered heterocyclyl of $R^r$ is optionally substituted with 1 to 3 groups independently selected from —OH, —$OCH_3$, —$OC_2H_5$, —$CH_2$OH, —C(═O)OH, —(O)C(═O)OH, and —(O)P(═O)(OH)$_2$; and wherein $R^s$ and $R^t$, for each occurrence, are each independently hydrogen, $C_1$-$C_4$ alkyl, $C_1$-$C_4$ alkoxy, or —OH;

k and m are each independently an integer selected from 0, 1, 2, 3, 4, and 5; and n is an integer selected from 0and 1.

2. The compound, tautomer, deuterated derivative, or pharmaceutically acceptable salt according to claim 1, wherein the compound is represented by Formula IIIa, IIIb, IIIc, or IIId:

(IIIa)

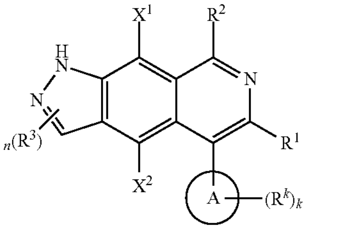

(IIIb)

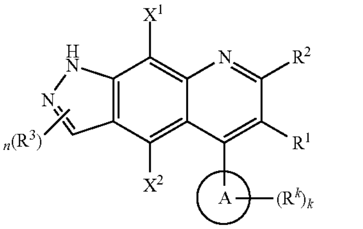

(IIIc)

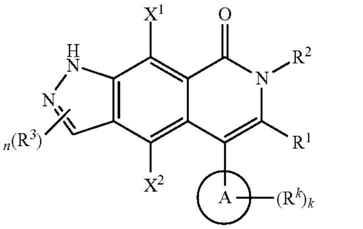

-continued (IIId)

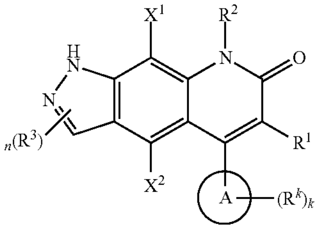

wherein:

Ring A is optionally substituted with $R^k$ and Ring A is 5 or 6-membered carbocyclyl, phenyl, or 5 or 6-membered heteroaryl;

$R^1$ is $C_1$-$C_6$ alkyl, $C_1$-$C_6$ alkoxy, —C(═O)OR$^z$, —C(═O)NR$^w$R$^x$, —NR$^w$R$^x$, —OR$^z$, —S(═O)$_2$R$^z$, $C_3$-$C_6$ cycloalkyl, or 3 to 6-membered heterocyclyl; wherein:

the $C_1$-$C_6$ alkyl, the $C_3$-$C_6$ cycloalkyl, or the 3 to 6-membered heterocyclyl of $R^1$ is optionally substituted with 1 to 3 groups independently selected from —OR$^z$ and halogen; and $R^w$, $R^x$, and $R^z$ are each independently hydrogen or $C_1$-$C_4$ alkyl;

$X^1$ and $X^2$ are each independently hydrogen, halogen, —CN, $C_1$-$C_2$ alkyl, $C_1$-$C_2$ haloalkyl, $C_1$-$C_2$ alkoxy, $C_1$-$C_2$ haloalkoxy or $C_3$-$C_4$ cycloalkyl;

$R^2$ is as defined in claim 1, except when $R^2$ is

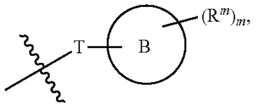

Ring B is optionally substituted with $R^m$ and Ring B is $C_4$-$C_9$ carbocyclyl, phenyl, 4 to 9-membered heterocyclyl, or 5 to 6-membered heteroaryl;

$R^3$ is absent or is —C(═O)O(CH$_2$)$_2$(O)P(═O)(OH)$_2$; and $R^k$ is halogen, —CN, —CH$_3$, $C_1$ haloalkyl, or —OCH$_3$.

3. The compound, tautomer, deuterated derivative, or pharmaceutically acceptable salt according to claim 1, wherein the compound is represented by Formula IVa, IVb, or IVc:

(IVa)

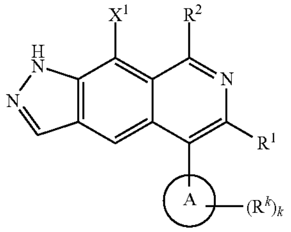

-continued (IVb)

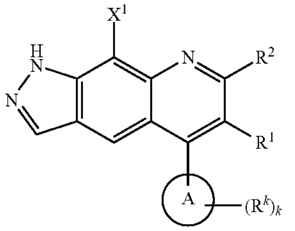

(IVc)

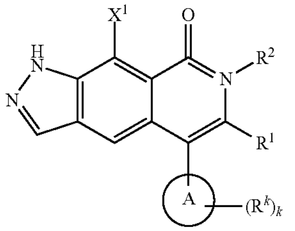

wherein $X^1$ is hydrogen, halogen, —OH$_3$, —OHF$_2$, —OH$_2$F, or —OCH$_3$.

4. The compound, tautomer, deuterated derivative, or pharmaceutically acceptable salt according to claim 1, wherein the compound is represented by Formula Va, Vb, or Vc:

(Va)

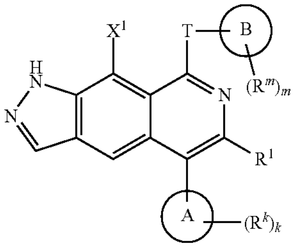

(Vb)

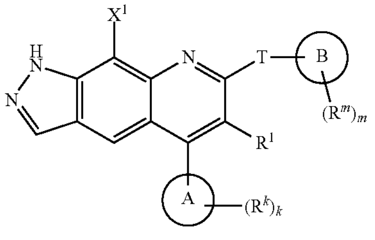

(Vc)

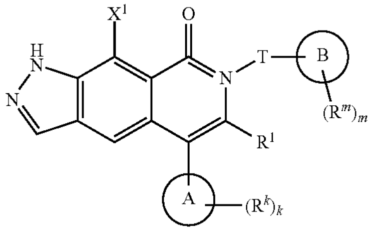

wherein:

$R^1$ is $C_1$-$C_4$ alkyl, $C_1$-$C_4$ alkoxy, —C(═O)OR$^z$, —C(═O)NR$^w$R$^x$, —NR$^w$R$^x$, —OR$^z$, —S(═O)$_2$R$^z$, cyclopropyl, cyclobutyl or 5 or 6-membered heterocyclyl; wherein:

the $C_1$-$C_4$ alkyl, the cyclopropyl, the cyclobutyl, or the 5 or 6-membered heterocyclyl of $R^1$ is optionally substituted with 1 to 3 groups independently selected from —$OR^z$ and halogen; and $R^w$, $R^x$, and $R^z$ are each independently hydrogen or $C_1$-$C_2$ alkyl; and T is absent, or is selected from —O—, —$OCH_2$—, —NH—, and —$CH_2$—.

5. The compound, tautomer, deuterated derivative, or pharmaceutically acceptable salt according to claim 1, wherein Ring A is optionally substituted with $R^k$ and Ring A is phenyl, cyclohexenyl, 3,6-dihydro-2H-pyranyl, pyridinyl, pyridazinyl, thiophenyl, or pyrazolyl.

6. The compound, tautomer, deuterated derivative, or pharmaceutically acceptable salt according to claim 1, wherein Ring A is optionally substituted with $R^k$ and Ring A is selected from:

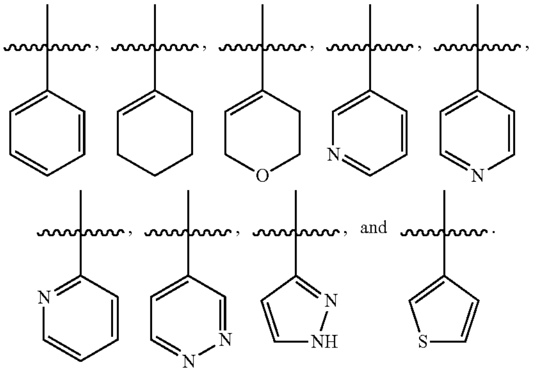

and

7. The compound, tautomer, deuterated derivative, or pharmaceutically acceptable salt according to claim 1, wherein Ring A is optionally substituted with $R^k$ and Ring A is selected from

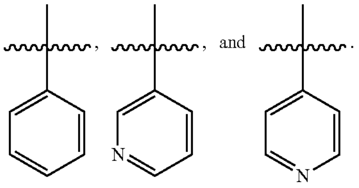

and

8. The compound, tautomer, deuterated derivative, or pharmaceutically acceptable salt according to claim 1, wherein when $R^2$ is

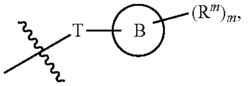

Ring B is optionally substituted with $R^m$ and Ring B is selected from isoindolinyl, azaspiro[3.4]octanyl, spiro[3.3]heptanyl, azaspiro[3.3]heptanyl, oxaspiro[3.3]heptanyl, azabicyclo[3.2.0]heptanyl, phenyl, cyclohexenyl, cyclohexyl, pyridinyl, piperidinyl, morpholinyl, tetrahydro-2H-pyranyl, thiazolyl, pyrazolyl, furanyl, tetrahydrofuranyl, cyclopentyl, bicyclo[1.1.1]pentanyl, pyrrolidinyl, cyclobutyl, azetidinyl, and cyclopropyl.

9. The compound, tautomer, deuterated derivative, or pharmaceutically acceptable salt according to claim 1, wherein $R^2$ is

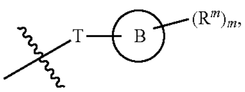

and

Ring B is optionally substituted with $R^m$ and Ring B is selected from:

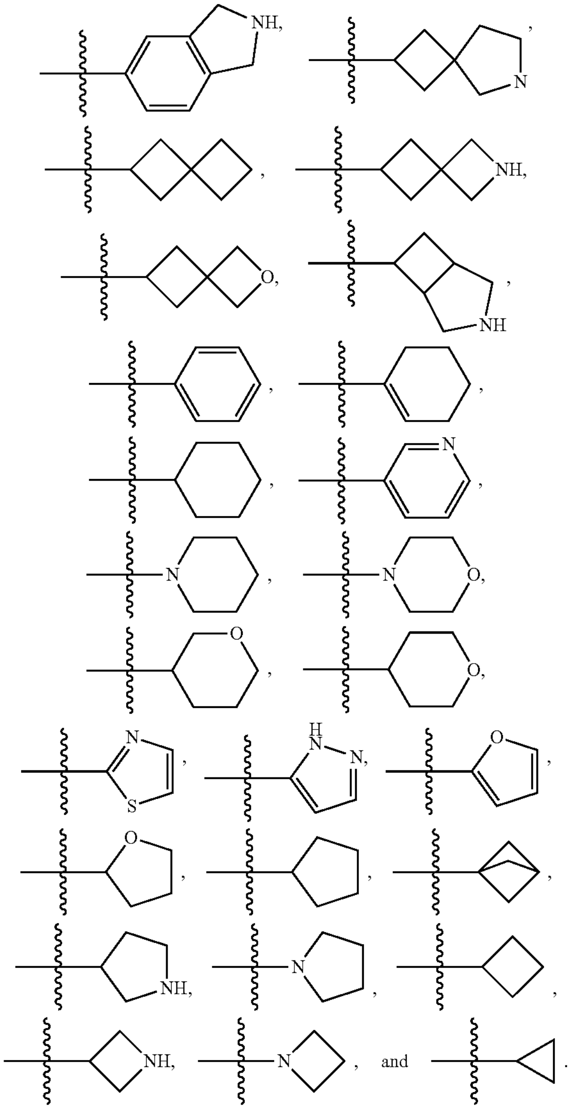

and

10. The compound, tautomer, deuterated derivative, or pharmaceutically acceptable salt according to claim 1, wherein $R^2$ is

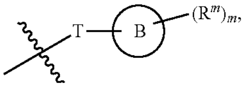

and

Ring B is optionally substituted with $R^m$ and Ring B is selected from:

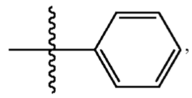, 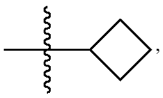, and

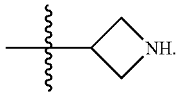

11. The compound, tautomer, deuterated derivative, or pharmaceutically acceptable salt according to claim 1, wherein $R^m$, for each occurrence, is independently halogen, —CN, =O, $C_1$-$C_6$ alkyl, $C_1$-$C_4$ alkoxy, —C(=O)$R^r$, —C(=O)O$R^r$, —C(=O)N$R^pR^q$, —C(=O)N$R^p$O$R^r$, —N$R^pR^q$, —N$R^p$C(=O)$R^r$, —N$R^p$S(=O)$_2R^r$, —O$R^r$, S(=O)$_2R^r$, —S(=O)$_2$N$R^pR^q$, —P(=O)$R^sR^t$, or 5 or 6-membered heterocyclyl; wherein:

the $C_1$-$C_6$ alkyl of $R^m$ is optionally substituted with 1 to 3 groups independently selected from —C(=O)OH, —C(=O)$OCH_3$, —C(=O)$OC_2H_5$, —OH, —$OCH_3$, and —$OC_2H_5$; and the 5 or 6-membered heterocyclyl of $R^m$ is optionally substituted with 1 to 3 groups independently selected from halogen, =O, —C(=O)OH, and —OH; wherein:

$R^p$ and $R^q$, for each occurrence, are each independently hydrogen or $C_1$-$C_3$ alkyl optionally substituted with 1 to 3 groups independently selected from —OH, —$OCH_3$, and —C(=O)OH;

$R^r$, for each occurrence, is independently hydrogen, $C_1$-$C_4$ alkyl, $C_3$-$C_6$ cycloalkyl, or 4 to 6-membered heterocyclyl; wherein the $C_1$-$C_4$ alkyl, $C_3$-$C_6$ cycloalkyl, or 4 to 6-membered heterocyclyl of $R^r$ is optionally substituted with 1 to 3 groups independently selected from —OH, —$OCH_3$, —$OC_2H_5$, —C(=O)OH, —(O)C(=O)OH, and —(O)P(=O)$(OH)_2$; and $R^s$ and $R^t$, for each occurrence, are each independently hydrogen, $C_1$-$C_2$ alkyl, $C_1$-$C_2$ alkoxy, or —OH.

12. The compound, tautomer, deuterated derivative, or pharmaceutically acceptable salt according to claim 1, wherein $R^m$, for each occurrence, is independently halogen, CN, =O, $C_1$-$C_4$ alkyl, $C_1$-$C_4$ alkoxy, —C(=O)$R^r$, —C(=O)O$R^r$, —C(=O)N$R^pR^q$, —C(=O)N$R^p$O$R^r$, —N$R^pR^q$, —N$R^p$C(=O)$R^r$, —N$R^p$S(=O)$_2R^r$, —O$R^r$, S(=O)$_2R^r$, —S(=O)$_2$N$R^pR^q$, —P(=O)$R^sR^t$, imidazolidinyl, or morpholinyl; wherein:

the $C_1$-$C_4$ alkyl of $R^m$ is optionally substituted with 1 to 3 groups independently selected from —C(=O)OH, —C(=O)$OCH_3$, —C(=O)$OC_2H_5$, —OH, —$OCH_3$, and —$OC_2H_5$; and the imidazolidinyl or the morpholinyl of $R^m$ is optionally substituted with 1 to 3 groups independently selected from oxo (=O) and —OH; wherein:

$R^p$ and $R^q$, for each occurrence, are each independently hydrogen or $C_1$-$C_3$ alkyl optionally substituted with 1 to 3 groups independently selected from —OH, —$OCH_3$, and —C(=O)OH;

$R^r$, for each occurrence, is independently hydrogen, $C_1$-$C_2$ alkyl, cyclopropyl, oxetanyl, or azetidinyl; wherein the $C_1$-$C_2$ alkyl, cyclopropyl, oxetanyl, or azetidinyl of $R^r$ is optionally substituted with 1 to 3 groups independently selected from —OH, —$CH_2$OH, —C(=O)OH, and —(O)P(=O)$(OH)_2$; and $R^s$ and $R^t$, for each occurrence, are each independently —$CH_3$, —$OCH_3$, or —OH.

13. The compound, tautomer, deuterated derivative, or pharmaceutically acceptable salt according to claim 1, wherein $R^m$, for each occurrence, is independently selected from —COOH, —C(=O)CH(OH)$CH_3$, F, —$CH_3$, —C(=O)$NH_2$, —C(=O)NH($OCH_3$), S(=O)$_2NH_2$, —NHS(=O)$_2CH_3$, =O, —OH, —P(=O)$(CH_3)_2$, —P(=O)$(OH)_2$, —P(=O)$(OCH_3)_2$, —OH, imidazolidin-4-yl, —$CH_2$OH, —NH$CH_3$, morpholin-4-yl, —(C=O)NHCH($CH_3$)$CH_2$OH, —C(=O)N($CH_3$)CH($CH_3$)$CH_2$OH, —N$CH_3$C(=O)CH(OH)$CH_3$, —C(=O)CH($CH_3$)$CH_2$OH, —C(=O)CH(OH)$CH_2$OH, —C(=O)(hydroxymethyl)oxetan-3-yl, —C(=O)(hydroxy)cyclopropyl, —C(=O)CH(OH)$CH_3$, —C(=O)$OCH_3$, —$OCH_3$, —$CH_2$COOH, —CN, —$OCH_2$COOH, —OCH($CH_3$)COOH, —CH($CH_3$)COOH, Cl, S(=O)$_2CH_3$, S(=O)$_2$NH$CH_3$, —$CH_2$C(=O)$OC_2H_5$, —C(=O)$OCH_2$(O)P(=O)$(OH)_2$, —C(=O)NHCH($CH_3$)COOH, —C(=O)NH$CH_3$, —C(=O)(3-hydroxyazetidin-1-yl), and —C(=O)(morpholin-4-yl).

14. The compound, tautomer, deuterated derivative, or pharmaceutically acceptable salt according to claim 1, wherein at least one occurrence of $R^m$ is —COOH, —$CH_2$COOH, —$OCH_2$COOH, —OCH($CH_3$)COOH, —CH($CH_3$)COOH, —C(=O)$OCH_2$(O)P(=O)$(OH)_2$, or —C(=O)NHCH($CH_3$)COOH.

15. The compound, tautomer, deuterated derivative, or pharmaceutically acceptable salt according to claim 1, wherein the compound is represented by Formula VIa, VIb, or VIc:

(VIa)

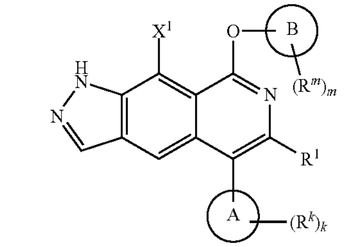

(VIb)

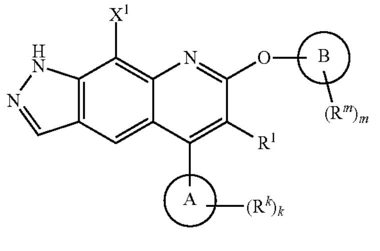

(VIc)

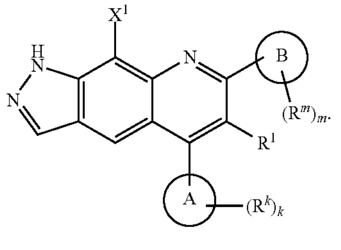

16. The compound, tautomer, deuterated derivative, or pharmaceutically acceptable salt according to claim 1, wherein $R^1$ is $C_1$-$C_3$ alkyl, $C_1$-$C_3$ alkoxy, —C(═O)$OR^z$, —C(═O)$NR^wR^x$, —$NR^wR^x$, —$OR^z$, —S(═O)$_2R^z$, cyclopropyl, cyclobutyl, or a 6-membered heterocyclyl; wherein:

the $C_1$-$C_3$ alkyl, the cyclopropyl, the cyclobutyl, or the 6-membered heterocyclyl of $R^1$ is optionally substituted with 1 to 3 groups independently selected from —OH, —$OCH_3$, $C_1$-$C_2$ haloalkyl, —CN, and halogen; and $R^w$, $R^x$, $R^y$, and $R^z$ are each independently hydrogen or —$CH_3$.

17. The compound, tautomer, deuterated derivative, or pharmaceutically acceptable salt according to claim 1, wherein $R^1$ is —$C(CH_3)_2$, —$CF_3$, —$CH_2C(CH_3)_2OCH_3$, —$C(CH_3)_2CH_2OH$, —$OCH_3$, —$O(CH)(CH_3)_2$, —C(═O)$OCH_3$, —C(═O)$N(CH_3)_2$, $N(CH_3)_2$, —S(═O)$_2CH_3$, S(═O)$_2C_2H_5$, —S(═O)$_2CH(CH_3)_2$, tetrahydro-2H-pyran-4-yl, cyclopropyl, or cyclobutyl; and wherein the cyclopropyl or the cyclobutyl of $R^1$ is optionally substituted with —OH, —$OCH_3$, or —$CF_3$.

18. The compound, tautomer, deuterated derivative, or pharmaceutically acceptable salt according to claim 1, wherein the compound is represented by Formula VIIa, VIIb, VIIc, VIId, VIIe, or VIIf:

(VIIa)

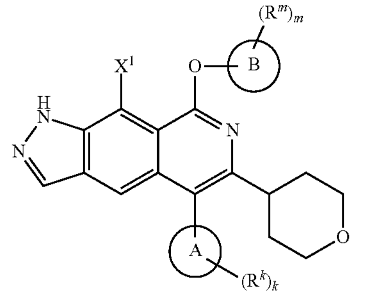

(VIIb)

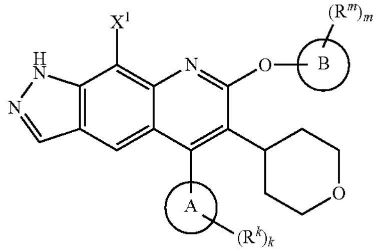

(VIIc)

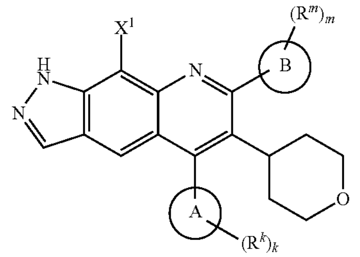

-continued (VIId)

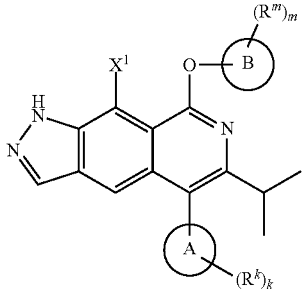

(VIIe)

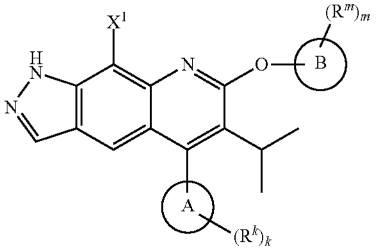

(VIIf)

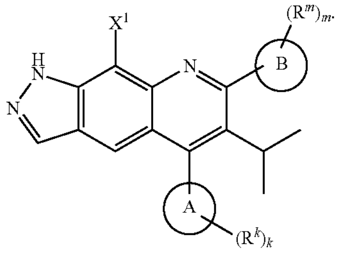

19. The compound, tautomer, deuterated derivative, or pharmaceutically acceptable salt according to claim 1, wherein the compound is represented by Formula VIIIa, VIIIb, or VIIIc:

(VIIIa)

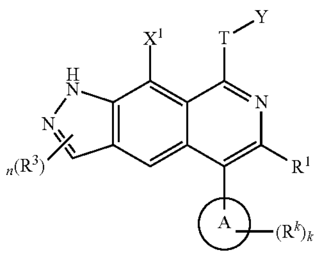

(VIIIb)

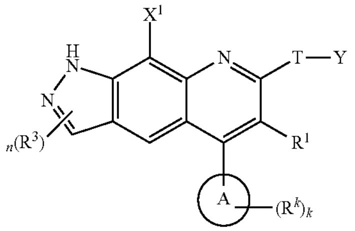

-continued (VIIIc)

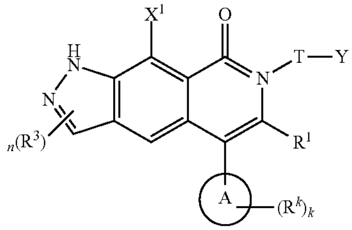

wherein:

Ring A is optionally substituted with $R^k$ and Ring A is phenyl or 5 or 6-membered heteroaryl;

T is absent, or is selected from —O—, —NH—, and $—CH_2—$;

Y is $C_1$-$C_2$ alkyl, $—(CR^aR^a)_pCOOH$, $—(CR^aR^a)_pNR^bS(=O)_2(CR^cR^c)_qOH$, $—(CR^aR^a)_pC(=O)NR^b(CR^cR^c)_qCOOH$, or $—(CR^aR^a)_p(O)(CR^cR^c)_qCOOH$; wherein:

$R^a$, for each occurrence, is independently hydrogen, —OH, $—CH_3$, or $—CH_2OH$; and $R^b$ and $R^c$, for each occurrence, are each independently hydrogen or $—CH_3$.

20. The compound, tautomer, deuterated derivative, or pharmaceutically acceptable salt according to claim 1, wherein

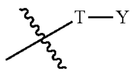

is $—NHCH_3$, $—CH_2COOH$, $—(CH_2)_2COOH$, $—CH(CH_3)CH_2COOH$, $—NHCH(CH_3)COOH$, $—OCH_2COOH$, $—O(CH_2)_2(O)CH_2COOH$, $—CH_2CH(CH_3)COOH$, $—OCH(CH_3)C(=O)NHCH_2COOH$, or $—OCH(CH_2OH)CH_2NHS(=O)_2(CH_2)_2OH$.

21. The compound, tautomer, deuterated derivative, or pharmaceutically acceptable salt according to claim 1, wherein Ring A is optionally substituted with $R^k$ and Ring A is phenyl or pyridinyl.

22. The compound, tautomer, deuterated derivative, or pharmaceutically acceptable salt according to claim 1, wherein Ring A is optionally substituted with $R^k$ and Ring A is

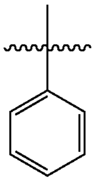 or 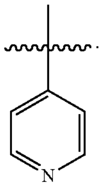.

23. The compound, tautomer, deuterated derivative, or pharmaceutically acceptable salt according to claim 1, wherein Ring A is selected from:

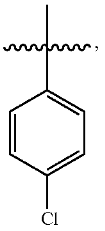, 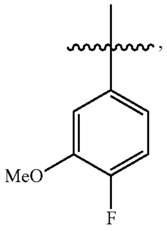, 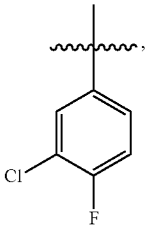, 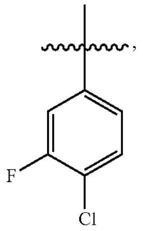,

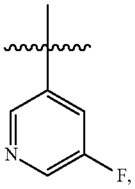, 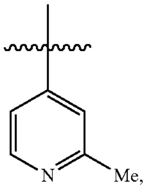, 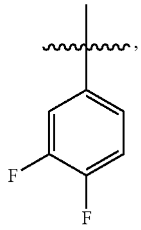, and

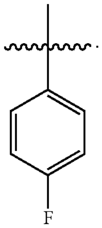.

24. The compound, tautomer, deuterated derivative, or pharmaceutically acceptable salt according to claim 1, wherein Ring A is selected from:

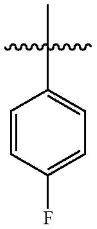, 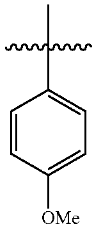, 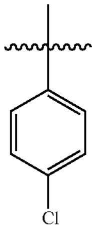, 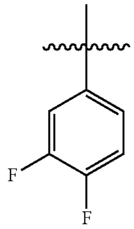,

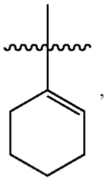, 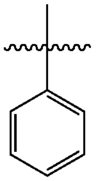, 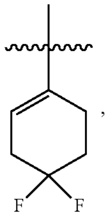, 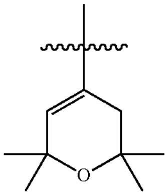,

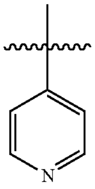, 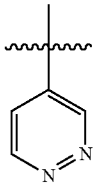, 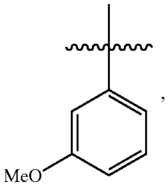,

-continued

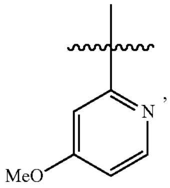 , 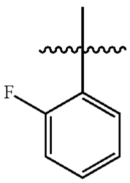 , 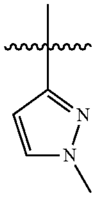 ,

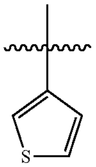 , and 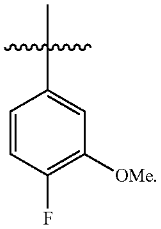

25. The compound, tautomer, deuterated derivative, or pharmaceutically acceptable salt according to claim 1, wherein $R^1$ is halogen, $C_1$-$C_3$ alkyl, $C_1$-$C_3$ alkoxy, —$NR^wR^x$, —$OR^z$, $C_3$-$C_6$ cycloalkyl, or 5 or 6-membered heterocyclyl; wherein:

the $C_1$-$C_3$ alkyl, the $C_3$-$C_6$ cycloalkyl, or the 5 or 6-membered heterocyclyl of $R^1$ is optionally substituted with 1 to 3 groups independently selected from —OH, —$OCH_3$, $C_1$-$C_2$ haloalkyl, —CN, and halogen; and $R^w$, $R^x$, and $R^z$ are each independently hydrogen or —$CH_3$.

26. The compound, tautomer, deuterated derivative, or pharmaceutically acceptable salt according to claim 1, wherein $R^1$ is $C_1$-$C_3$ alkyl or 6-membered heterocyclyl; wherein:

the $C_1$-$C_3$ alkyl or the 6-membered heterocyclyl of $R^1$ is optionally substituted with 1 to 3 groups independently selected from —OH, —$OCH_3$, $C_1$-$C_2$ haloalkyl, and halogen.

27. The compound, tautomer, deuterated derivative, or pharmaceutically acceptable salt according to claim 1, wherein $R^1$ is —$CH(CH_3)_2$ or tetrahydro-2H-pyran-4-yl.

28. The compound, tautomer, deuterated derivative, or pharmaceutically acceptable salt according to claim 1, wherein $R^1$ is selected from:

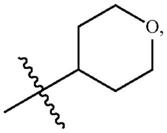 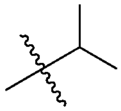 , 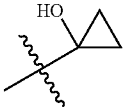 ,

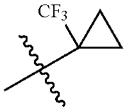 , 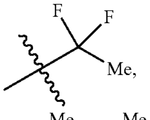 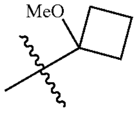 ,

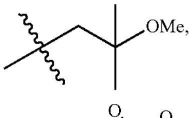 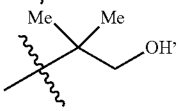 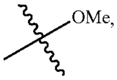

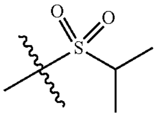 , and 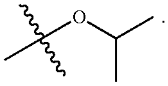 .

29. The compound, tautomer, deuterated derivative, or pharmaceutically acceptable salt according to claim 1, wherein $R^1$ is selected from:

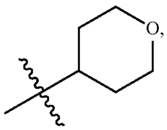 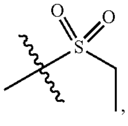 , 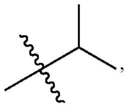 ,

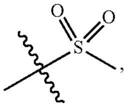 , 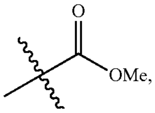 and 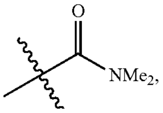

30. The compound, tautomer, deuterated derivative, or pharmaceutically acceptable salt according to claim 1, wherein $R^2$ is selected from:

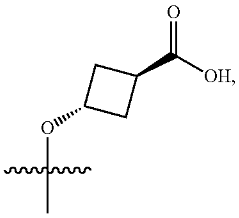 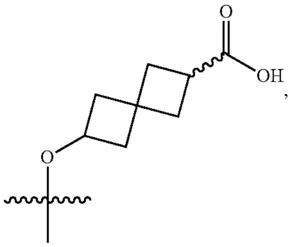 ,

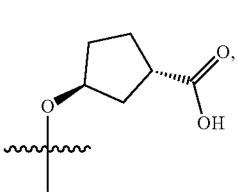 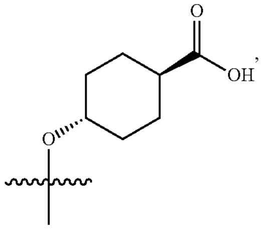 ,

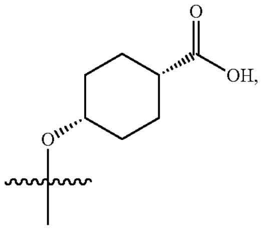 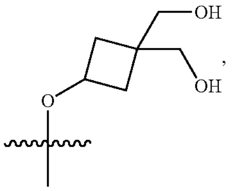 ,

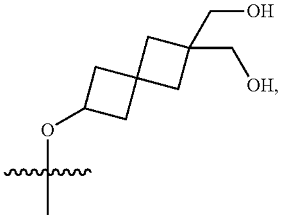 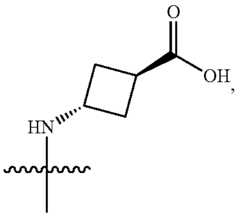 ,

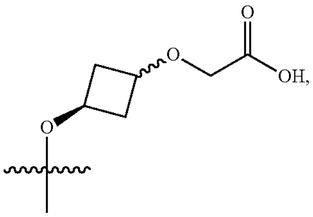

-continued

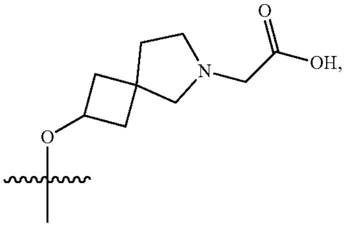

and

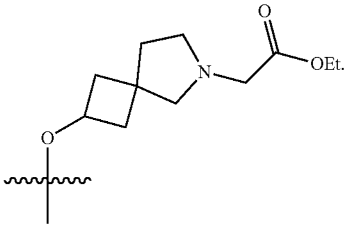

31. The compound, tautomer, deuterated derivative, or pharmaceutically acceptable salt according to claim 1, wherein $R^2$ is selected from

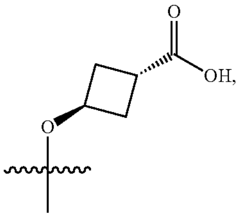

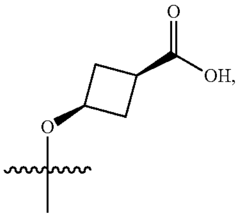

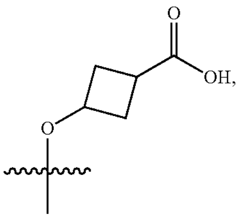

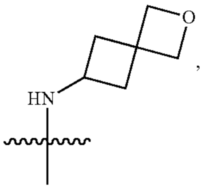

,

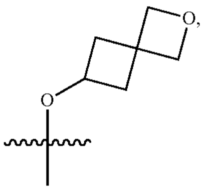

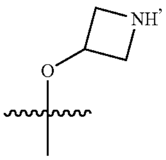

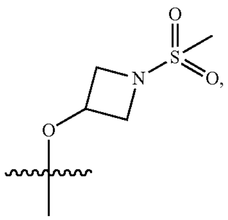

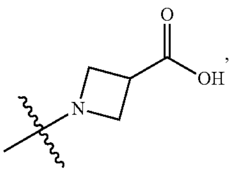

,

-continued

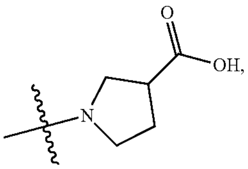

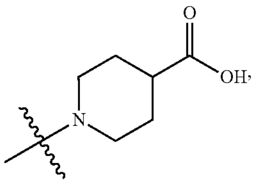

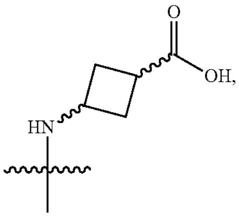

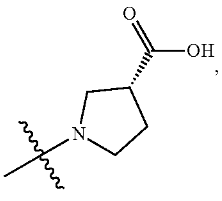

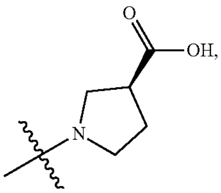

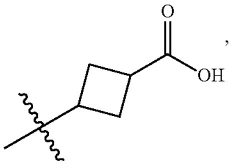

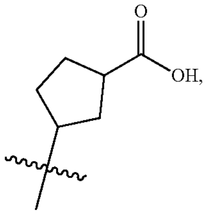

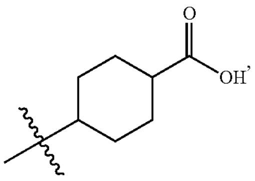

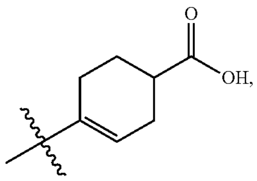

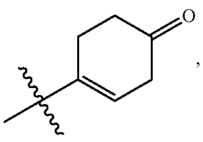

,

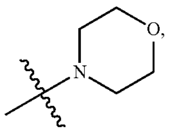

and

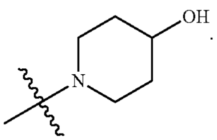

32. The compound, tautomer, deuterated derivative, or pharmaceutically acceptable salt according to claim 1, wherein:

$X^1$ is hydrogen, F, or —$CH_3$;

$R^k$ is F, Cl, —$CH_3$, or —$OCH_3$; and k is an integer selected from 0, 1, and 2.

33. The compound, tautomer, deuterated derivative, or pharmaceutically acceptable salt according to claim 1, wherein the compound is selected from TABLE I
| Compounds 1-262 |
|---|
Compound 1
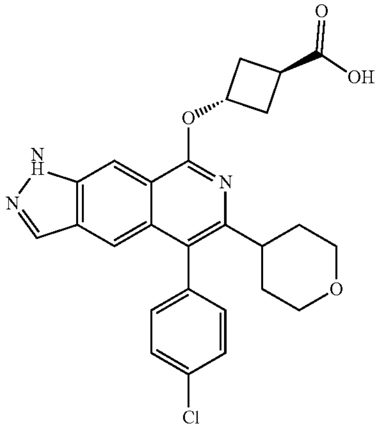 [SMILES: O=C(O)[C@H]1C[C@H](Oc2nc(C3CCOCC3)c(-c3ccc(Cl)cc3)c3cc4cn[nH]c4cc23)C1]
Compound 2
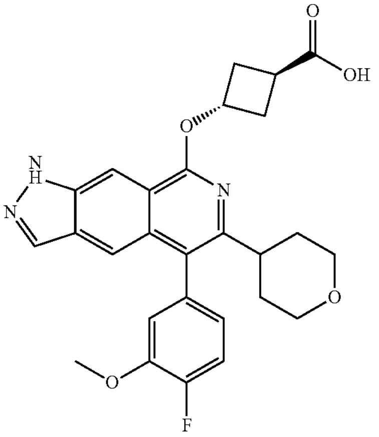 [SMILES: COc1cc(-c2c(C3CCOCC3)nc(O[C@H]3C[C@H](C(=O)O)C3)c3cc4[nH]ncc4cc23)ccc1F]
Compound 3
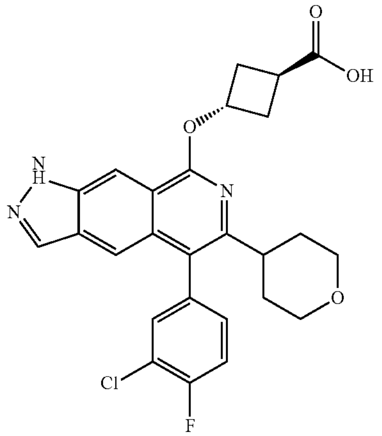 [SMILES: O=C(O)[C@H]1C[C@H](Oc2nc(C3CCOCC3)c(-c3ccc(F)c(Cl)c3)c3cc4cn[nH]c4cc23)C1]

TABLE I-continued
| Compounds 1-262 |
|---|
Compound 4
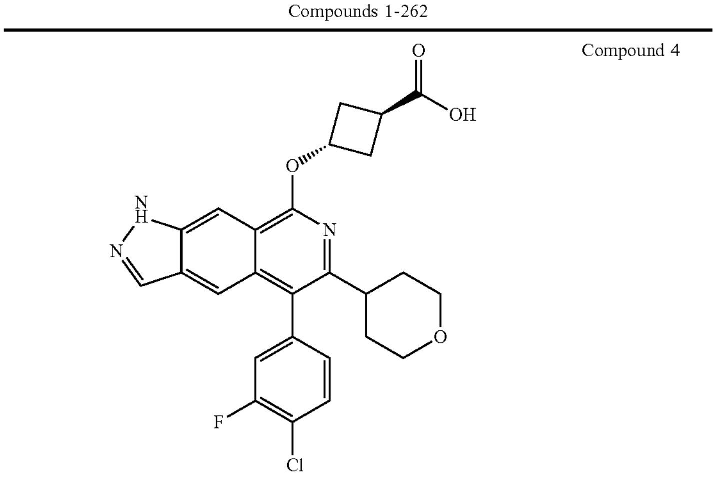
Compound 5
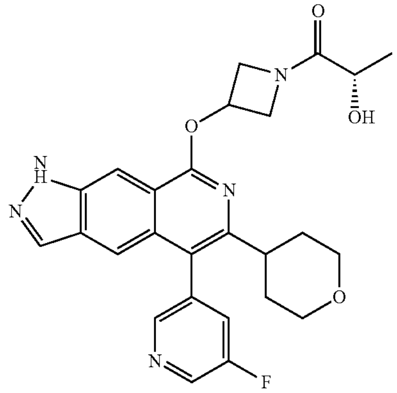 [SMILES: C[C@H](O)C(=O)N1CC(Oc2nc(C3CCOCC3)c(-c3cncc(F)c3)c3cc4cn[nH]c4cc23)C1]
Compound 6
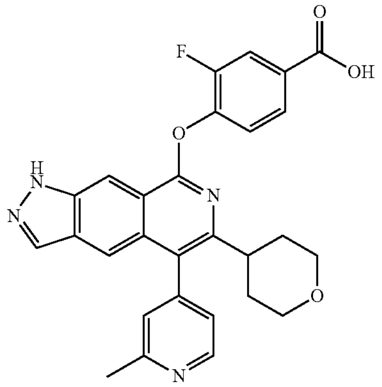 [SMILES: Cc1cc(-c2c(C3CCOCC3)nc(Oc3ccc(C(=O)O)cc3F)c3cc4[nH]ncc4cc23)ccn1]
Compound 7
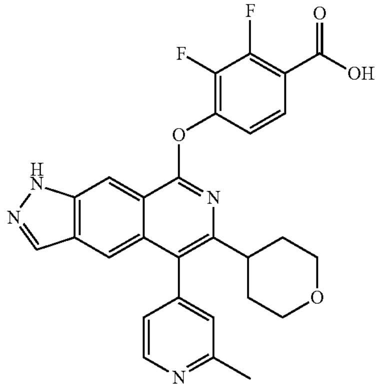 [SMILES: Cc1cc(-c2c(C3CCOCC3)nc(Oc3ccc(C(=O)O)c(F)c3F)c3cc4[nH]ncc4cc23)ccn1]

TABLE I-continued
Compounds 1-262
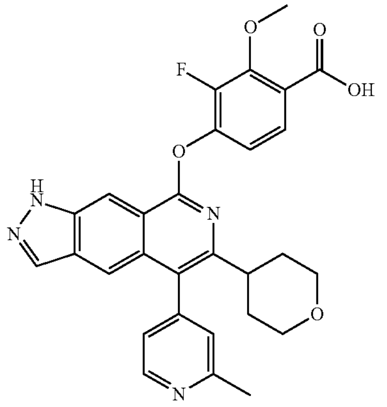 [SMILES: COc1c(C(=O)O)ccc(Oc2nc(C3CCOCC3)c(-c3ccnc(C)c3)c3cc4cn[nH]c4cc23)c1F]
Compound 8
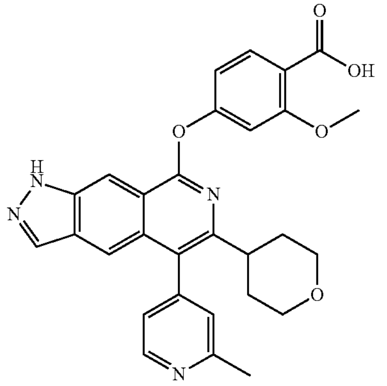 [SMILES: COc1cc(Oc2nc(C3CCOCC3)c(-c3ccnc(C)c3)c3cc4cn[nH]c4cc23)ccc1C(=O)O]
Compound 9
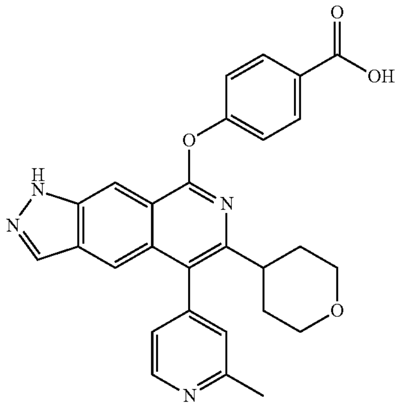 [SMILES: Cc1cc(-c2c(C3CCOCC3)nc(Oc3ccc(C(=O)O)cc3)c3cc4[nH]ncc4cc23)ccn1]
Compound 10
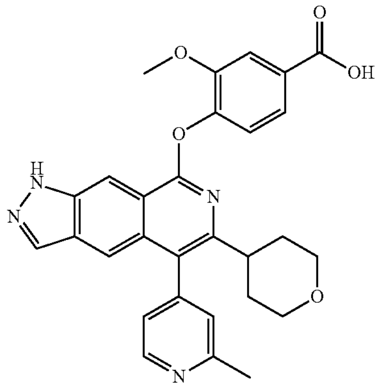 [SMILES: COc1cc(C(=O)O)ccc1Oc1nc(C2CCOCC2)c(-c2ccnc(C)c2)c2cc3cn[nH]c3cc12]
Compound 11

TABLE I-continued
| Compounds 1-262 |
| --- |
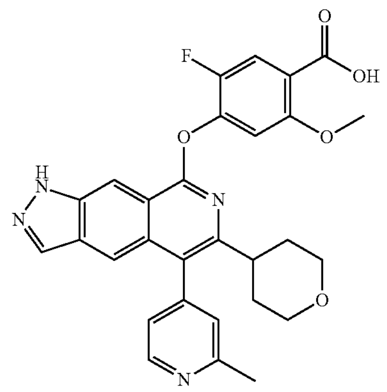 [SMILES: COc1cc(Oc2nc(C3CCOCC3)c(-c3ccnc(C)c3)c3cc4cn[nH]c4cc23)c(F)cc1C(=O)O]
Compound 12
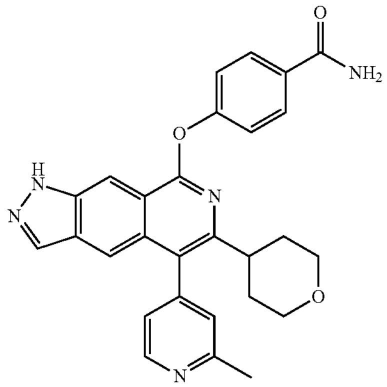 [SMILES: Cc1cc(-c2c(C3CCOCC3)nc(Oc3ccc(C(N)=O)cc3)c3cc4[nH]ncc4cc23)ccn1]
Compound 13
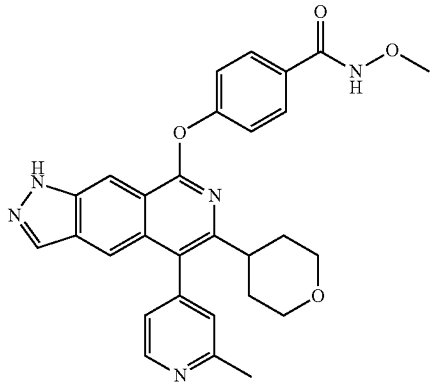 [SMILES: CONC(=O)c1ccc(Oc2nc(C3CCOCC3)c(-c3ccnc(C)c3)c3cc4cn[nH]c4cc23)cc1]
Compound 14
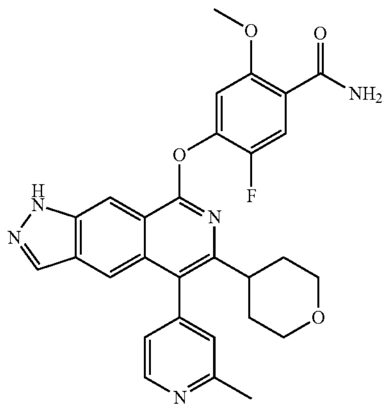 [SMILES: COc1cc(Oc2nc(C3CCOCC3)c(-c3ccnc(C)c3)c3cc4cn[nH]c4cc23)c(F)cc1C(N)=O]
Compound 15

TABLE I-continued
| Compounds 1-262 |
| --- |
Compound 16
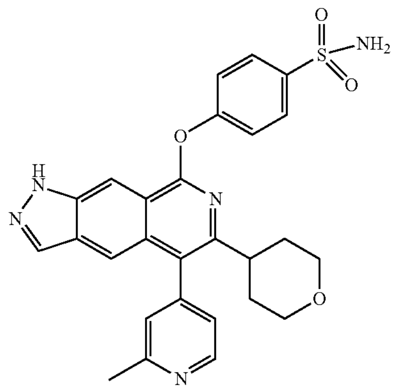 [SMILES: Cc1cc(-c2c(C3CCOCC3)nc(Oc3ccc(S(N)(=O)=O)cc3)c3cc4[nH]ncc4cc23)ccn1]
Compound 17
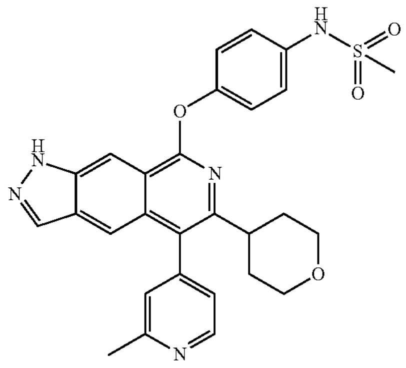 [SMILES: Cc1cc(-c2c(C3CCOCC3)nc(Oc3ccc(NS(C)(=O)=O)cc3)c3cc4[nH]ncc4cc23)ccn1]
Compound 18
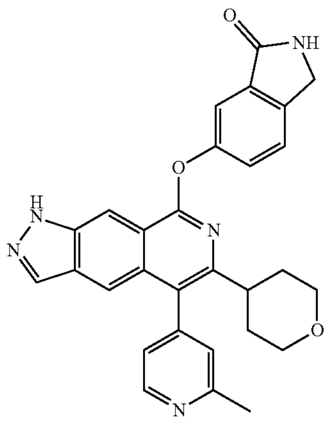 [SMILES: Cc1cc(-c2c(C3CCOCC3)nc(Oc3ccc4c(c3)C(=O)NC4)c3cc4[nH]ncc4cc23)ccn1]
Compound 19
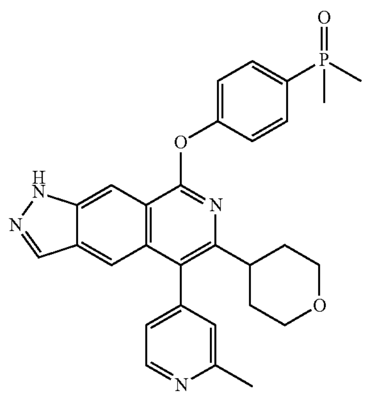 [SMILES: Cc1cc(-c2c(C3CCOCC3)nc(Oc3ccc(P(C)(C)=O)cc3)c3cc4[nH]ncc4cc23)ccn1]

TABLE I-continued
| Compounds 1-262 |
| --- |
Compound 20
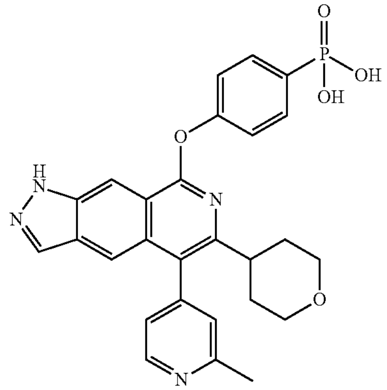 [SMILES: Cc1cc(-c2c(C3CCOCC3)nc(Oc3ccc(P(=O)(O)O)cc3)c3cc4[nH]ncc4cc23)ccn1]
Compound 21
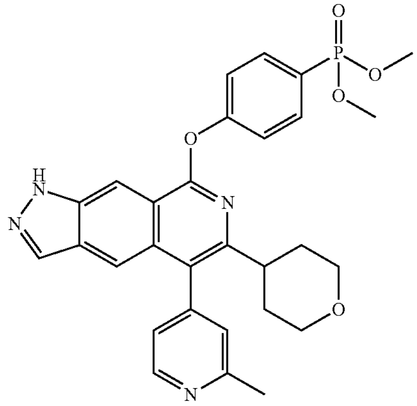 [SMILES: COP(=O)(OC)c1ccc(Oc2nc(C3CCOCC3)c(-c3ccnc(C)c3)c3cc4cn[nH]c4cc23)cc1]
Compound 22
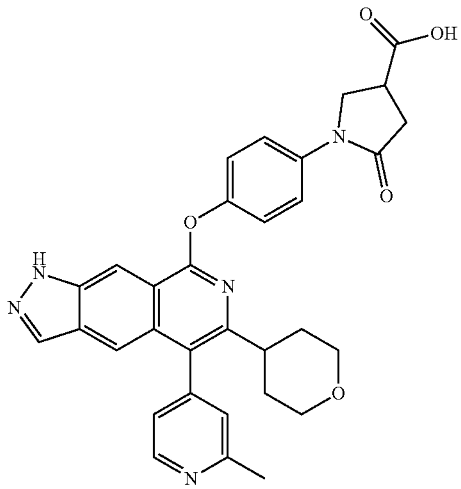 [SMILES: Cc1cc(-c2c(C3CCOCC3)nc(Oc3ccc(N4CC(C(=O)O)CC4=O)cc3)c3cc4[nH]ncc4cc23)ccn1]

TABLE I-continued
| Compounds 1-262 |
| --- |
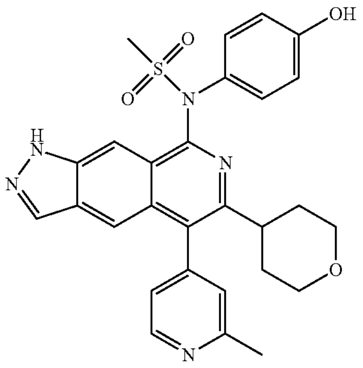 [SMILES: Cc1cc(-c2c(C3CCOCC3)nc(N(c3ccc(O)cc3)S(C)(=O)=O)c3cc4[nH]ncc4cc23)ccn1]
Compound 23
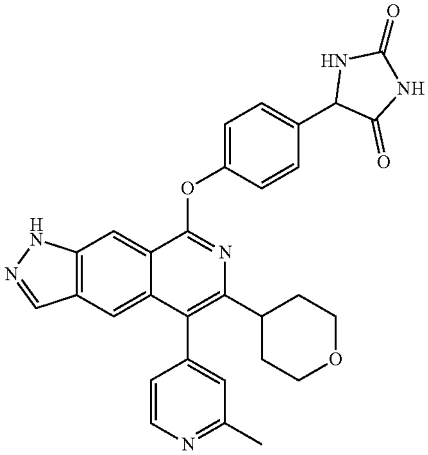 [SMILES: Cc1cc(-c2c(C3CCOCC3)nc(Oc3ccc(C4NC(=O)NC4=O)cc3)c3cc4[nH]ncc4cc23)ccn1]
Compound 24
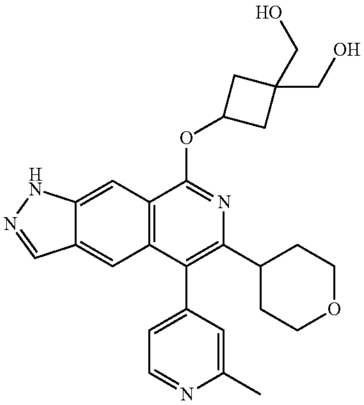 [SMILES: Cc1cc(-c2c(C3CCOCC3)nc(OC3CC(CO)(CO)C3)c3cc4[nH]ncc4cc23)ccn1]
Compound 25
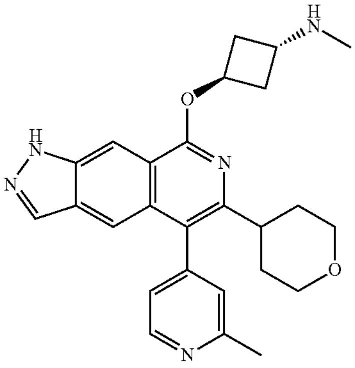 [SMILES: CN[C@H]1C[C@H](Oc2nc(C3CCOCC3)c(-c3ccnc(C)c3)c3cc4cn[nH]c4cc23)C1]
Compound 26

TABLE I-continued
| Compounds 1-262 |
|---|
Compound 27
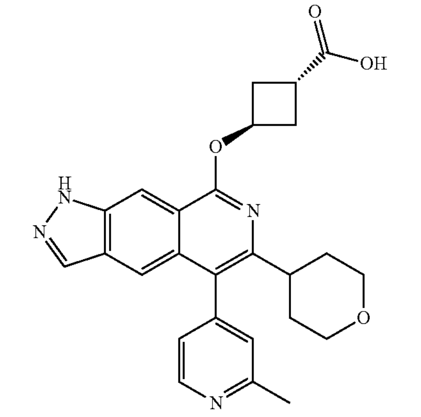 [SMILES: Cc1cc(-c2c(C3CCOCC3)nc(O[C@H]3C[C@H](C(=O)O)C3)c3cc4[nH]ncc4cc23)ccn1]
Compound 28
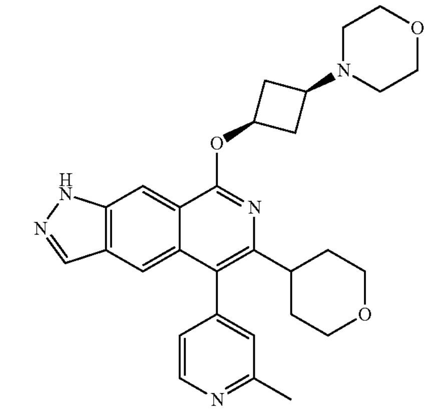 [SMILES: Cc1cc(-c2c(C3CCOCC3)nc(O[C@H]3C[C@@H](N4CCOCC4)C3)c3cc4[nH]ncc4cc23)ccn1]
Compound 29
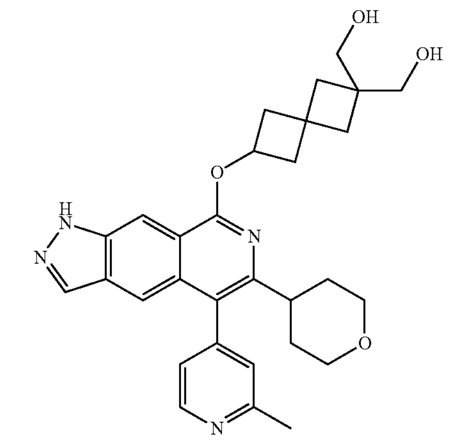 [SMILES: Cc1cc(-c2c(C3CCOCC3)nc(OC3CC4(C3)CC(CO)(CO)C4)c3cc4[nH]ncc4cc23)ccn1]

TABLE I-continued
| Compounds 1-262 |
| --- |
| 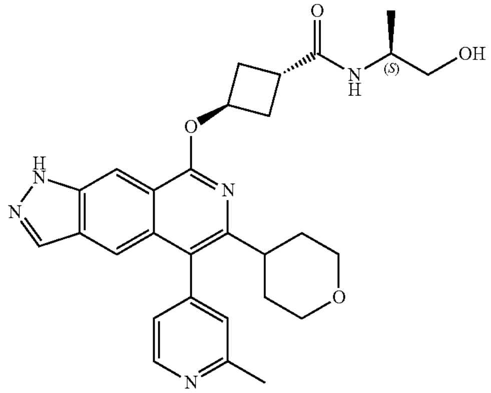 Compound 30 |
| 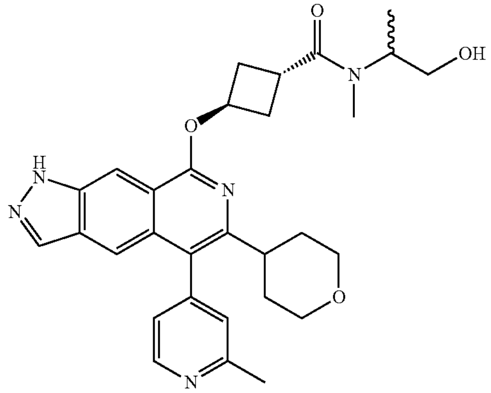 [SMILES: Cc1cc(-c2c(C3CCOCC3)nc(O[C@H]3C[C@H](C(=O)N(C)C(C)CO)C3)c3cc4[nH]ncc4cc23)ccn1] Compound 31 |
| 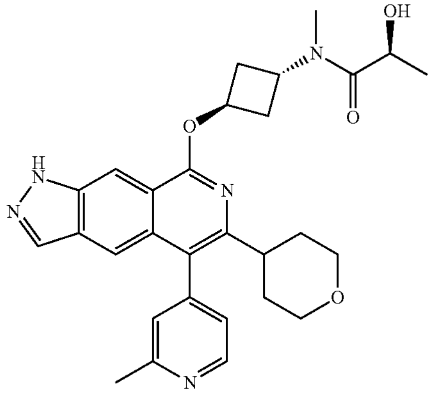 [SMILES: Cc1cc(-c2c(C3CCOCC3)nc(O[C@H]3C[C@H](N(C)C(=O)[C@H](C)O)C3)c3cc4[nH]ncc4cc23)ccn1] Compound 32 |
| 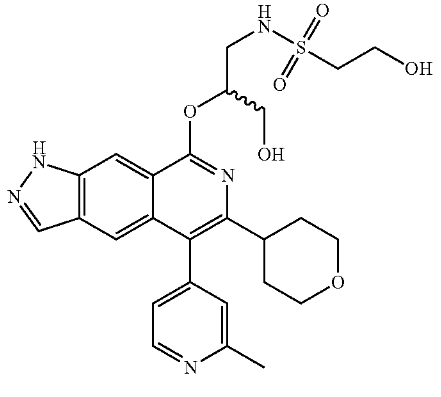 [SMILES: Cc1cc(-c2c(C3CCOCC3)nc(OC(CO)CNS(=O)(=O)CCO)c3cc4[nH]ncc4cc23)ccn1] Compound 33 |

TABLE I-continued
| Compounds 1-262 |
| --- |
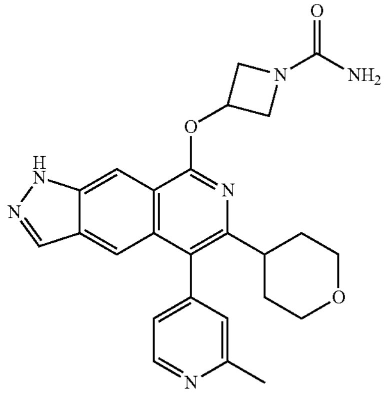 [SMILES: Cc1cc(-c2c(C3CCOCC3)nc(OC3CN(C(N)=O)C3)c3cc4[nH]ncc4cc23)ccn1]
Compound 34
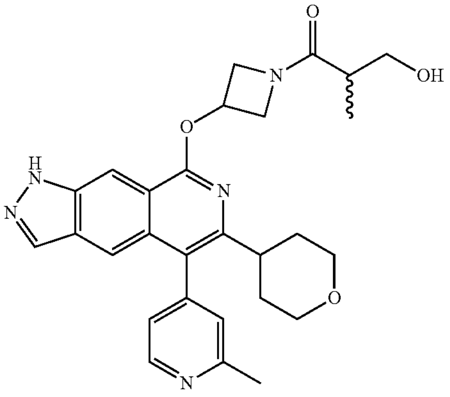 [SMILES: Cc1cc(-c2c(C3CCOCC3)nc(OC3CN(C(=O)C(C)CO)C3)c3cc4[nH]ncc4cc23)ccn1]
Compound 35
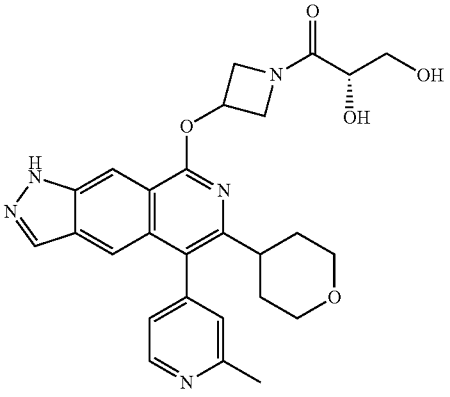 [SMILES: Cc1cc(-c2c(C3CCOCC3)nc(OC3CN(C(=O)[C@@H](O)CO)C3)c3cc4[nH]ncc4cc23)ccn1]
Compound 36
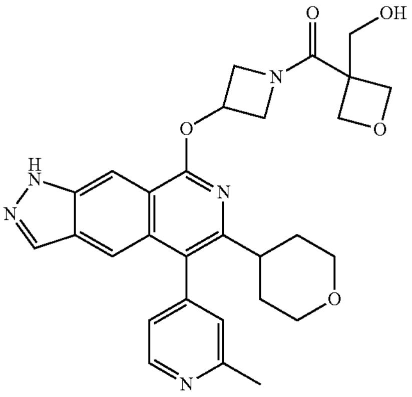 [SMILES: Cc1cc(-c2c(C3CCOCC3)nc(OC3CN(C(=O)C4(CO)COC4)C3)c3cc4[nH]ncc4cc23)ccn1]
Compound 37

TABLE I-continued
| Compounds 1-262 |
| --- |
| 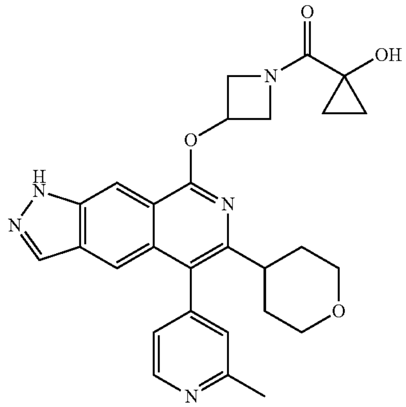 [SMILES: Cc1cc(-c2c(C3CCOCC3)nc(OC3CN(C(=O)C4(O)CC4)C3)c3cc4[nH]ncc4cc23)ccn1] Compound 38 |
| 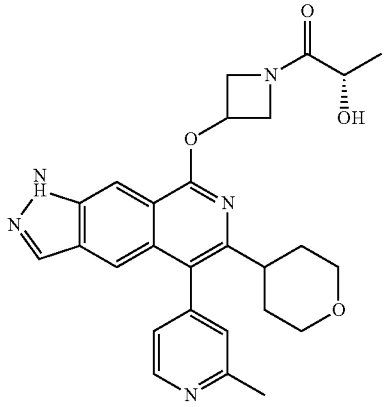 [SMILES: Cc1cc(-c2c(C3CCOCC3)nc(OC3CN(C(=O)[C@H](C)O)C3)c3cc4[nH]ncc4cc23)ccn1] Compound 39 |
| 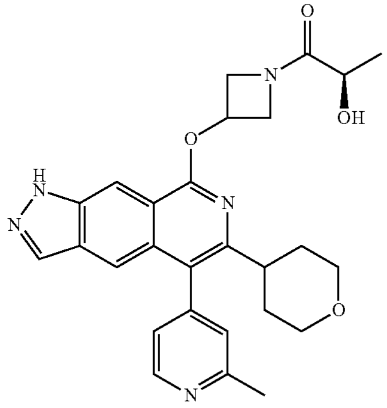 Compound 40 |

TABLE I-continued
| Compounds 1-262 |
| --- |
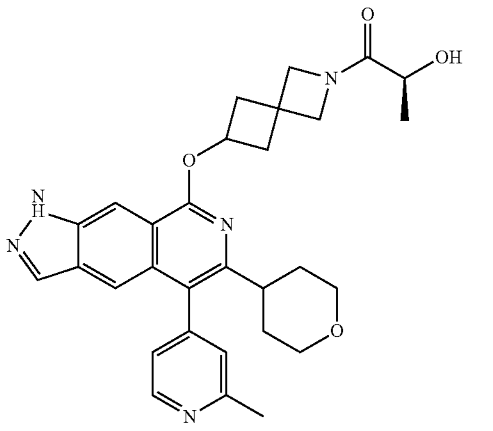 [SMILES: Cc1cc(-c2c(C3CCOCC3)nc(OC3CC4(C3)CN(C(=O)[C@H](C)O)C4)c3cc4[nH]ncc4cc23)ccn1]
Compound 41
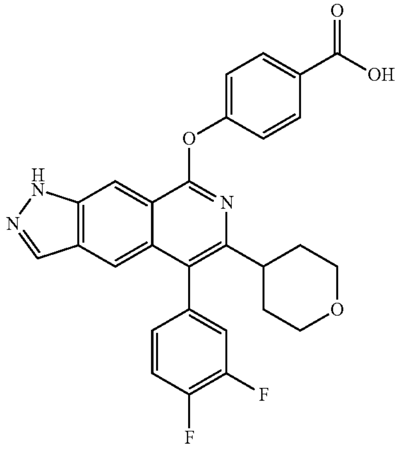 [SMILES: O=C(O)c1ccc(Oc2nc(C3CCOCC3)c(-c3ccc(F)c(F)c3)c3cc4cn[nH]c4cc23)cc1]
Compound 42
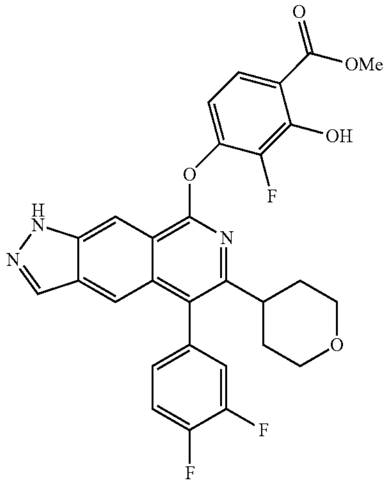 [SMILES: COC(=O)c1ccc(Oc2nc(C3CCOCC3)c(-c3ccc(F)c(F)c3)c3cc4cn[nH]c4cc23)c(F)c1O]
Compound 43

TABLE I-continued
| Compounds 1-262 |
| --- |
Compound 44
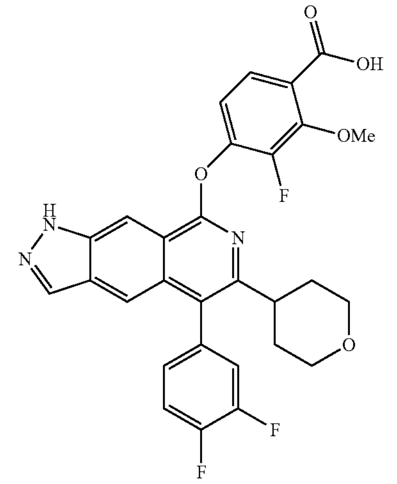 [SMILES: COc1c(C(=O)O)ccc(Oc2nc(C3CCOCC3)c(-c3ccc(F)c(F)c3)c3cc4cn[nH]c4cc23)c1F]
Compound 45
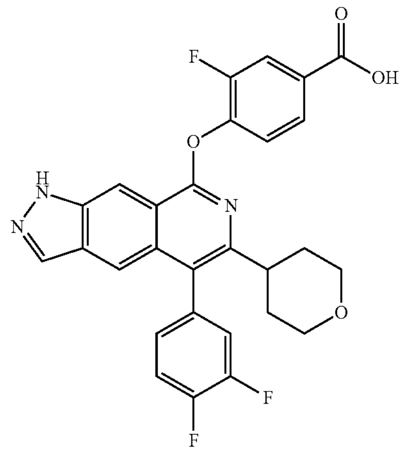 [SMILES: O=C(O)c1ccc(Oc2nc(C3CCOCC3)c(-c3ccc(F)c(F)c3)c3cc4cn[nH]c4cc23)c(F)c1]
Compound 46
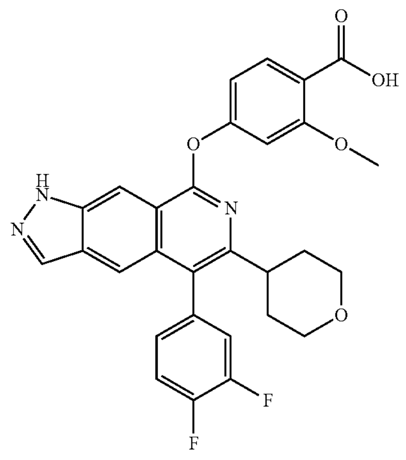 [SMILES: COc1cc(Oc2nc(C3CCOCC3)c(-c3ccc(F)c(F)c3)c3cc4cn[nH]c4cc23)ccc1C(=O)O]

TABLE I-continued
| Compounds 1-262 |
| --- |
Compound 47
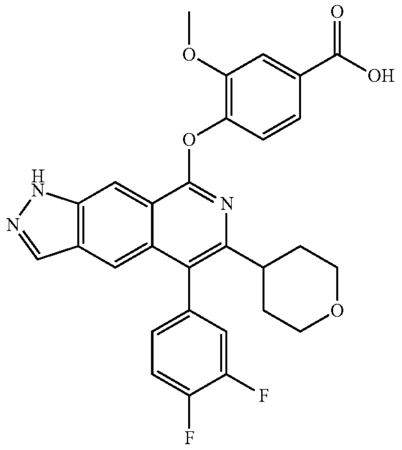 [SMILES: COc1cc(C(=O)O)ccc1Oc1nc(C2CCOCC2)c(-c2ccc(F)c(F)c2)c2cc3cn[nH]c3cc12]
Compound 48
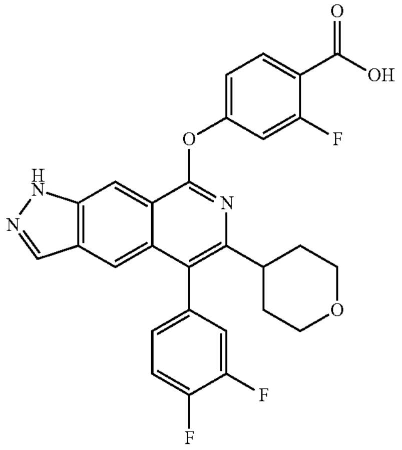 [SMILES: O=C(O)c1ccc(Oc2nc(C3CCOCC3)c(-c3ccc(F)c(F)c3)c3cc4cn[nH]c4cc23)cc1F]
Compound 49
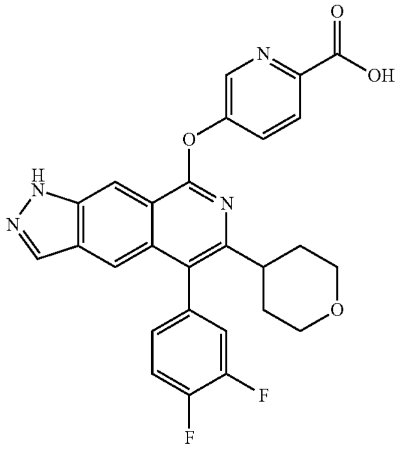 [SMILES: O=C(O)c1ccc(Oc2nc(C3CCOCC3)c(-c3ccc(F)c(F)c3)c3cc4cn[nH]c4cc23)cn1]

TABLE I-continued
| Compounds 1-262 |
|---|
| 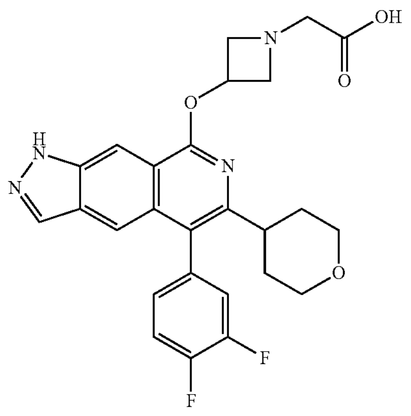 [SMILES: O=C(O)CN1CC(Oc2nc(C3CCOCC3)c(-c3ccc(F)c(F)c3)c3cc4cn[nH]c4cc23)C1] Compound 50 |
| 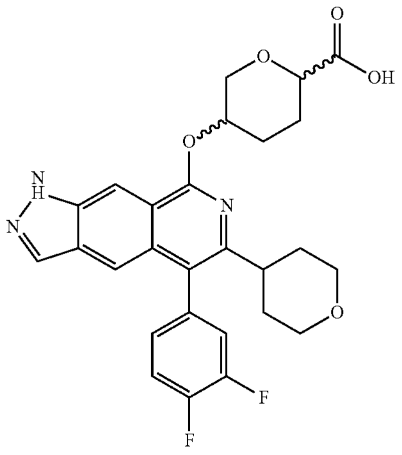 [SMILES: O=C(O)C1CCC(Oc2nc(C3CCOCC3)c(-c3ccc(F)c(F)c3)c3cc4cn[nH]c4cc23)CO1] Compound 51 |
| 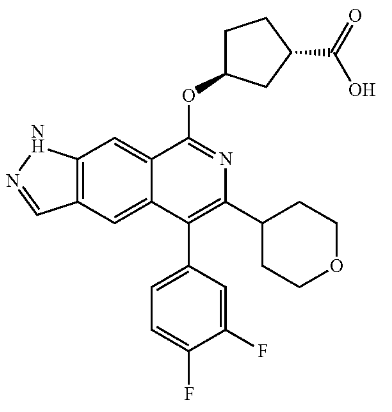 [SMILES: O=C(O)[C@H]1CC[C@H](Oc2nc(C3CCOCC3)c(-c3ccc(F)c(F)c3)c3cc4cn[nH]c4cc23)C1] Compound 52 |

TABLE I-continued
| Compounds 1-262 |
| --- |
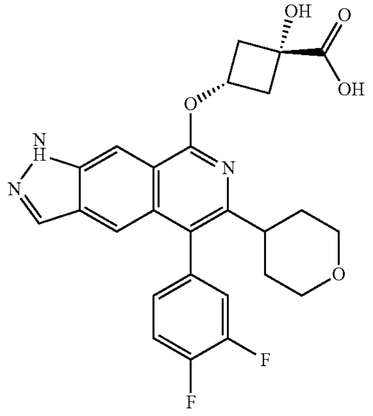 [SMILES: O=C(O)[C@]1(O)C[C@@H](Oc2nc(C3CCOCC3)c(-c3ccc(F)c(F)c3)c3cc4cn[nH]c4cc23)C1]
Compound 53
Compound 54
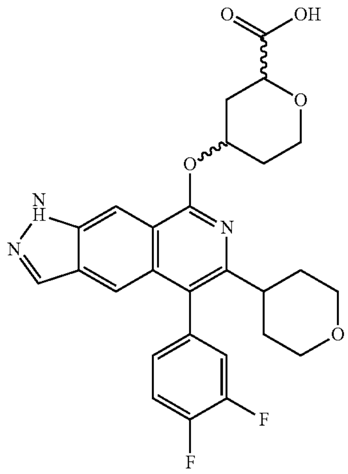 [SMILES: O=C(O)C1CC(Oc2nc(C3CCOCC3)c(-c3ccc(F)c(F)c3)c3cc4cn[nH]c4cc23)CCO1]
Compound 55
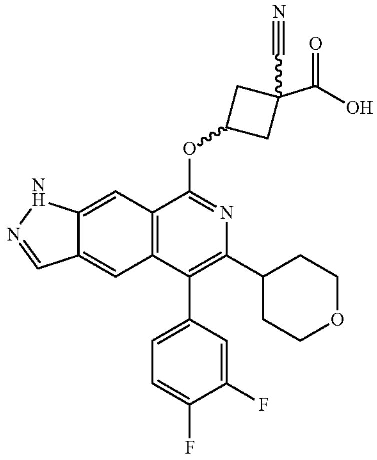 [SMILES: N#CC1(C(=O)O)CC(Oc2nc(C3CCOCC3)c(-c3ccc(F)c(F)c3)c3cc4cn[nH]c4cc23)C1]

TABLE I-continued
| Compounds 1-262 |
| --- |
Compound 56
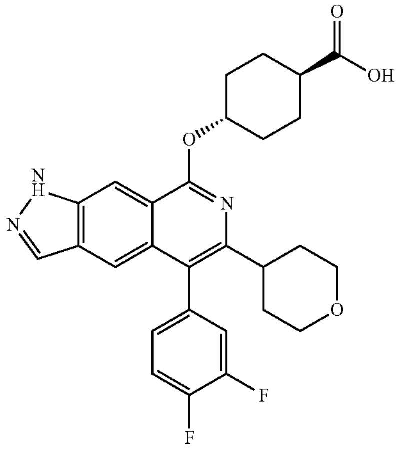 [SMILES: O=C(O)[C@H]1CC[C@H](Oc2nc(C3CCOCC3)c(-c3ccc(F)c(F)c3)c3cc4cn[nH]c4cc23)CC1]
Compound 57
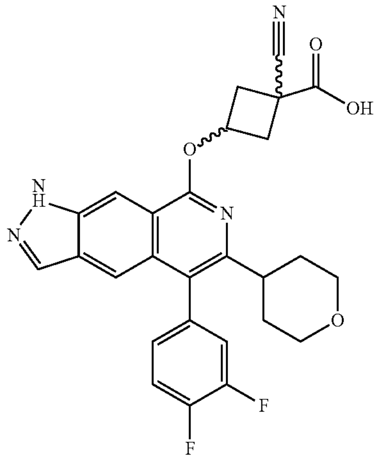 [SMILES: N#CC1(C(=O)O)CC(Oc2nc(C3CCOCC3)c(-c3ccc(F)c(F)c3)c3cc4cn[nH]c4cc23)C1]
Compound 58
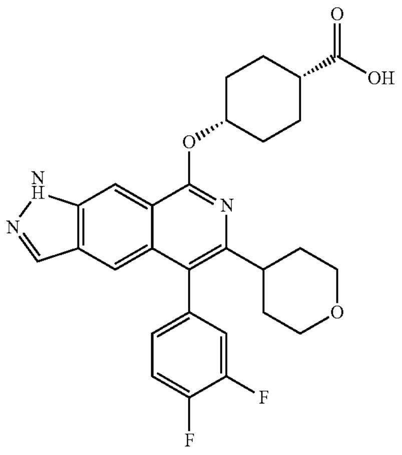 [SMILES: O=C(O)[C@H]1CC[C@@H](Oc2nc(C3CCOCC3)c(-c3ccc(F)c(F)c3)c3cc4cn[nH]c4cc23)CC1]

TABLE I-continued
| Compounds 1-262 |
| --- |
Compound 59
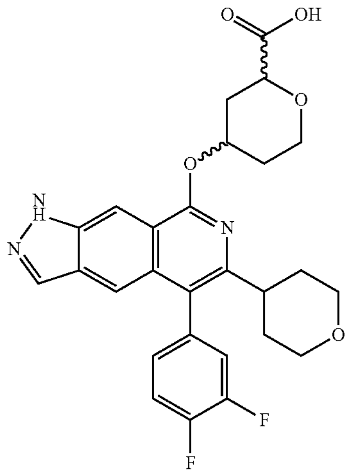 [SMILES: O=C(O)C1CC(Oc2nc(C3CCOCC3)c(-c3ccc(F)c(F)c3)c3cc4cn[nH]c4cc23)CCO1]
Compound 60
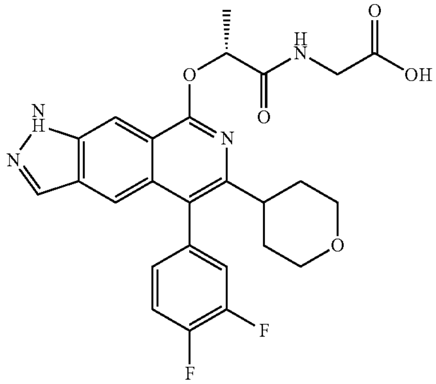 [SMILES: C[C@@H](Oc1nc(C2CCOCC2)c(-c2ccc(F)c(F)c2)c2cc3cn[nH]c3cc12)C(=O)NCC(=O)O]
Compound 61
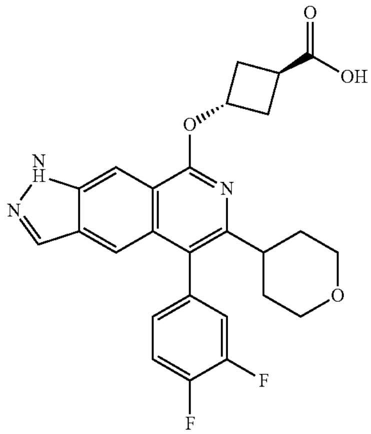 [SMILES: O=C(O)[C@H]1C[C@H](Oc2nc(C3CCOCC3)c(-c3ccc(F)c(F)c3)c3cc4cn[nH]c4cc23)C1]

TABLE I-continued
| Compounds 1-262 |
| --- |
Compound 62
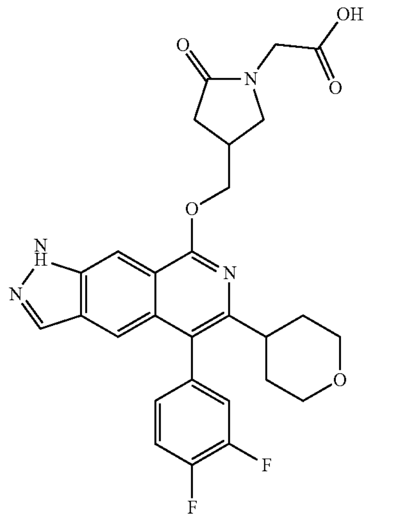 [SMILES: O=C(O)CN1CC(COc2nc(C3CCOCC3)c(-c3ccc(F)c(F)c3)c3cc4cn[nH]c4cc23)CC1=O]
Compound 63
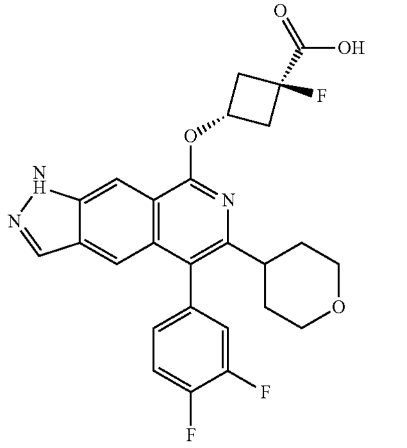 [SMILES: O=C(O)[C@]1(F)C[C@H](Oc2nc(C3CCOCC3)c(-c3ccc(F)c(F)c3)c3cc4cn[nH]c4cc23)C1]
Compound 64
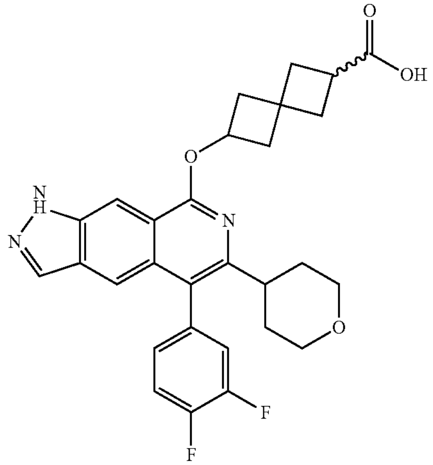 [SMILES: O=C(O)C1CC2(CC(Oc3nc(C4CCOCC4)c(-c4ccc(F)c(F)c4)c4cc5cn[nH]c5cc34)C2)C1]

TABLE I-continued
| Compounds 1-262 |
| --- |
| 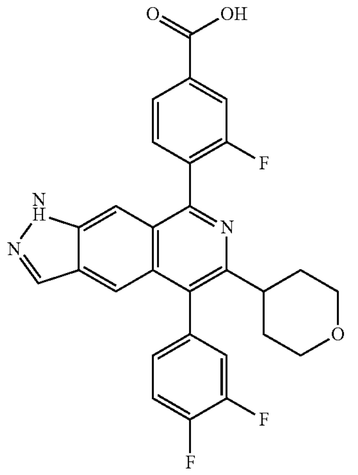 [SMILES: O=C(O)c1ccc(-c2nc(C3CCOCC3)c(-c3ccc(F)c(F)c3)c3cc4cn[nH]c4cc23)c(F)c1] Compound 65 |
| 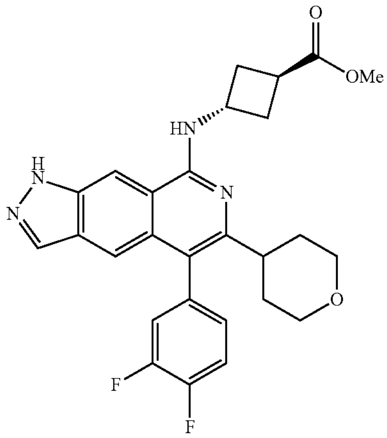 [SMILES: COC(=O)[C@H]1C[C@H](Nc2nc(C3CCOCC3)c(-c3ccc(F)c(F)c3)c3cc4cn[nH]c4cc23)C1] Compound 66 |
| 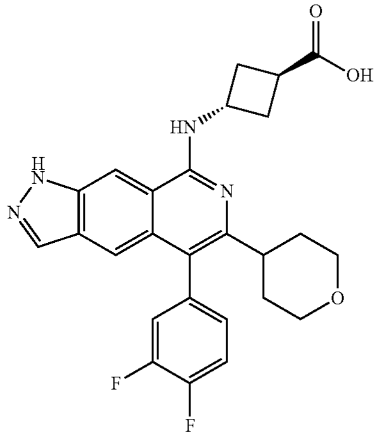 [SMILES: O=C(O)[C@H]1C[C@H](Nc2nc(C3CCOCC3)c(-c3ccc(F)c(F)c3)c3cc4cn[nH]c4cc23)C1] Compound 67 |

TABLE I-continued
| Compounds 1-262 |
| --- |
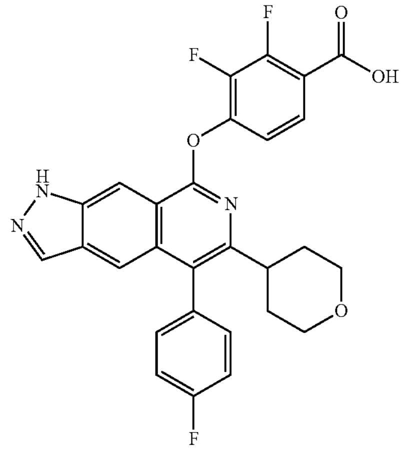
Compound 68
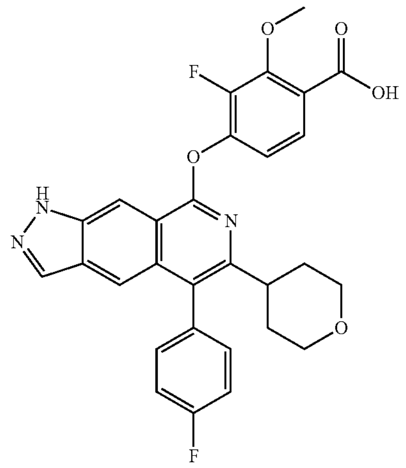
Compound 69
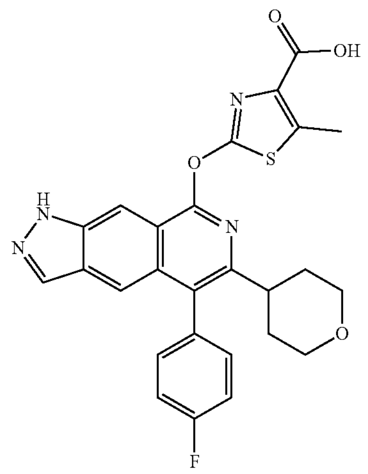 [SMILES: Cc1sc(Oc2nc(C3CCOCC3)c(-c3ccc(F)cc3)c3cc4cn[nH]c4cc23)nc1C(=O)O]
Compound 70

TABLE I-continued
| Compounds 1-262 |
| --- |
| Compound 71 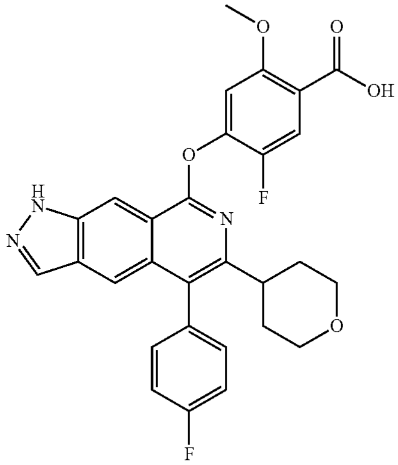 [SMILES: COc1cc(Oc2nc(C3CCOCC3)c(-c3ccc(F)cc3)c3cc4cn[nH]c4cc23)c(F)cc1C(=O)O] |
| Compound 72 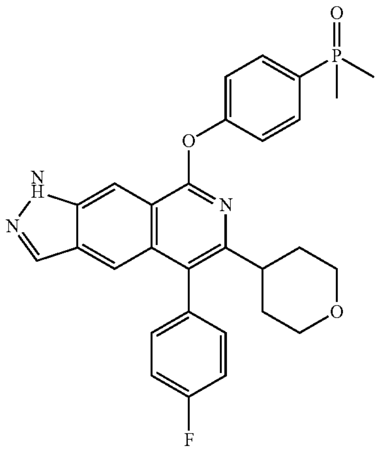 [SMILES: CP(C)(=O)c1ccc(Oc2nc(C3CCOCC3)c(-c3ccc(F)cc3)c3cc4cn[nH]c4cc23)cc1] |
| Compound 73 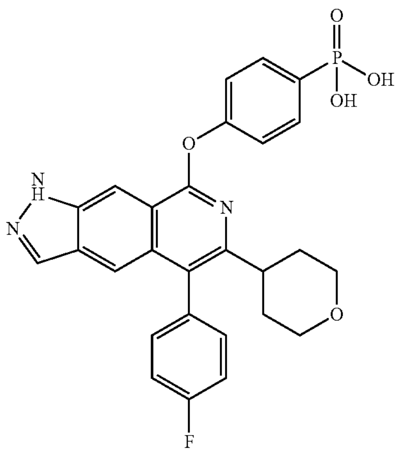 |

TABLE I-continued
| Compounds 1-262 |
|---|
| Compound 74 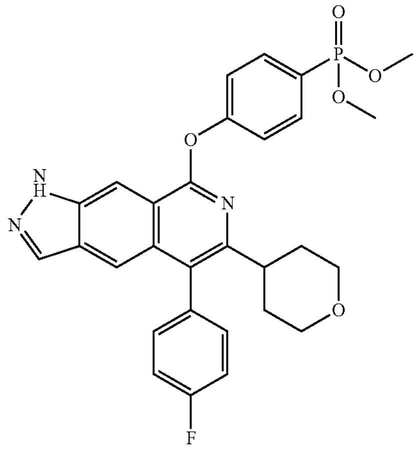 [SMILES: COP(=O)(OC)c1ccc(Oc2nc(C3CCOCC3)c(-c3ccc(F)cc3)c3cc4cn[nH]c4cc23)cc1] |
| Compound 75 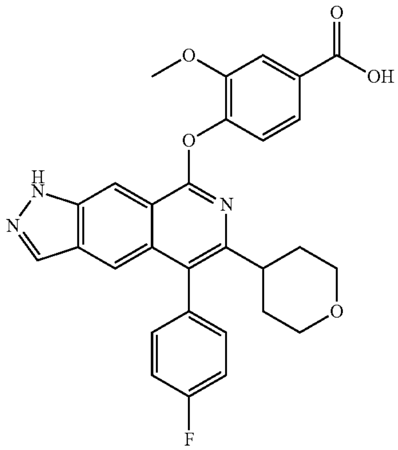 [SMILES: COc1cc(C(=O)O)ccc1Oc1nc(C2CCOCC2)c(-c2ccc(F)cc2)c2cc3cn[nH]c3cc12] |
| Compound 76 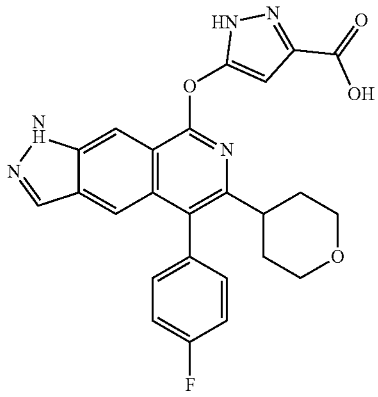 [SMILES: O=C(O)c1cc(Oc2nc(C3CCOCC3)c(-c3ccc(F)cc3)c3cc4cn[nH]c4cc23)[nH]n1] |

TABLE I-continued
| Compounds 1-262 |
| --- |
| 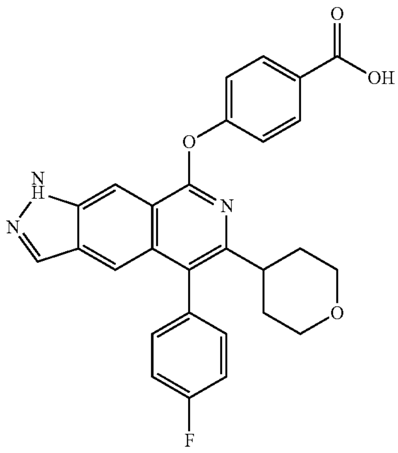 Compound 77 |
| 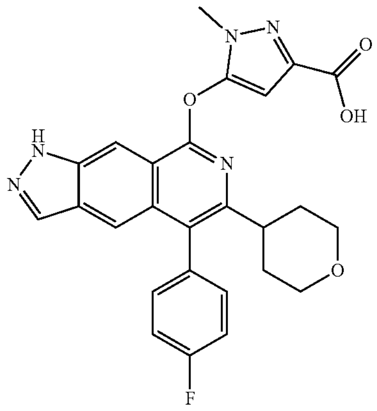 [SMILES: Cn1nc(C(=O)O)cc1Oc1nc(C2CCOCC2)c(-c2ccc(F)cc2)c2cc3cn[nH]c3cc12] Compound 78 |
| 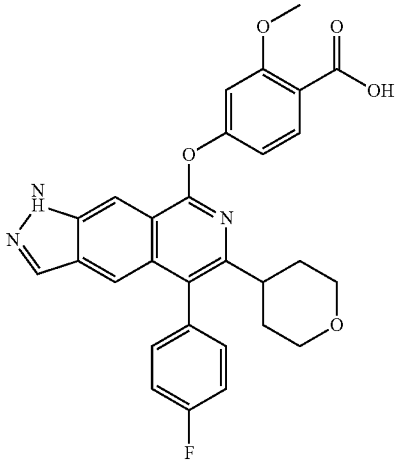 Compound 79 |

TABLE I-continued
| Compounds 1-262 |
| --- |
Compound 80
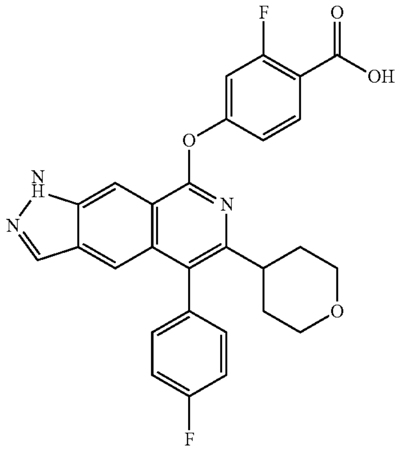
Compound 81
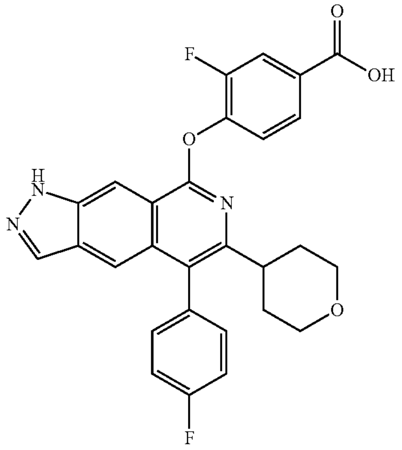 [SMILES: O=C(O)c1ccc(Oc2nc(C3CCOCC3)c(-c3ccc(F)cc3)c3cc4cn[nH]c4cc23)c(F)c1]
Compound 82
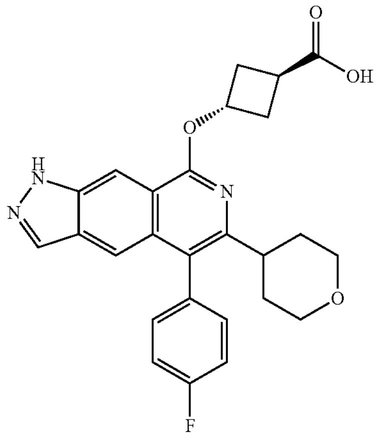 [SMILES: O=C(O)[C@H]1C[C@H](Oc2nc(C3CCOCC3)c(-c3ccc(F)cc3)c3cc4cn[nH]c4cc23)C1]

TABLE I-continued
| Compounds 1-262 |
| --- |
Compound 83
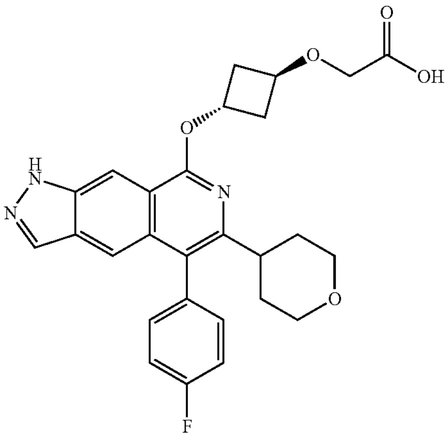 [SMILES: O=C(O)CO[C@H]1C[C@H](Oc2nc(C3CCOCC3)c(-c3ccc(F)cc3)c3cc4cn[nH]c4cc23)C1]
Compound 84
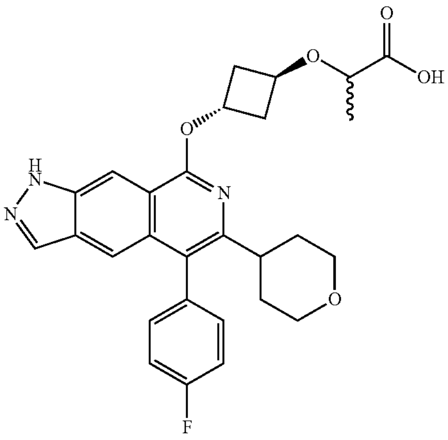
Compound 85
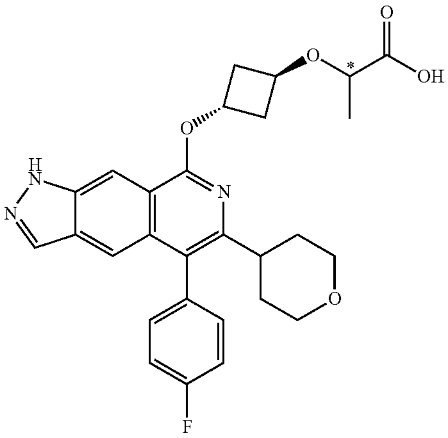 [SMILES: CC(O[C@H]1C[C@H](Oc2nc(C3CCOCC3)c(-c3ccc(F)cc3)c3cc4cn[nH]c4cc23)C1)C(=O)O]

TABLE I-continued
| Compounds 1-262 |
| --- |
Compound 86
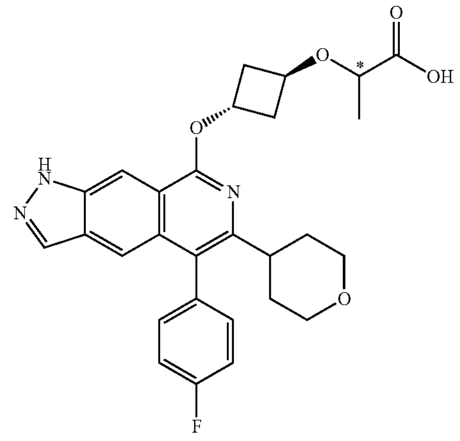 [SMILES: CC(O[C@H]1C[C@H](Oc2nc(C3CCOCC3)c(-c3ccc(F)cc3)c3cc4cn[nH]c4cc23)C1)C(=O)O]
Compound 87
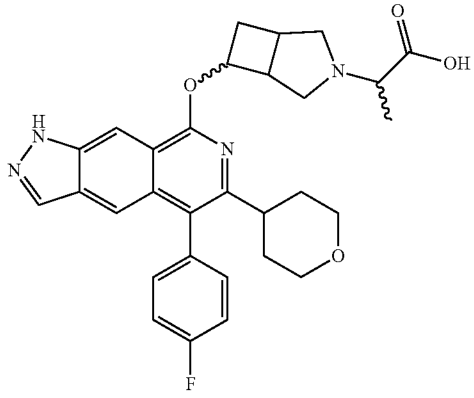 [SMILES: CC(C(=O)O)N1CC2CC(Oc3nc(C4CCOCC4)c(-c4ccc(F)cc4)c4cc5cn[nH]c5cc34)C2C1]
Compound 88
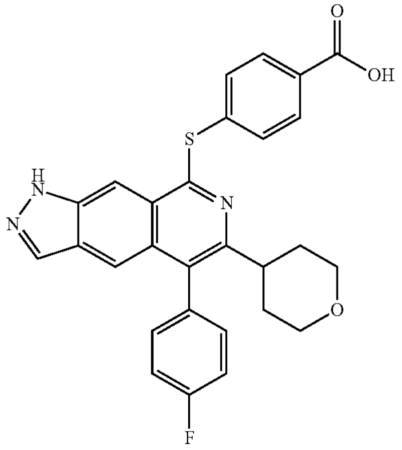

TABLE I-continued
| Compounds 1-262 |
| --- |
Compound 89
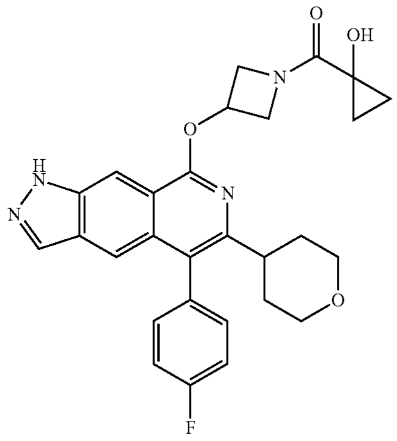 [SMILES: O=C(N1CC(Oc2nc(C3CCOCC3)c(-c3ccc(F)cc3)c3cc4cn[nH]c4cc23)C1)C1(O)CC1]
Compound 90
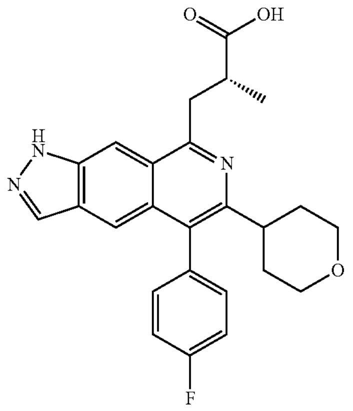 [SMILES: C[C@H](Cc1nc(C2CCOCC2)c(-c2ccc(F)cc2)c2cc3cn[nH]c3cc12)C(=O)O]
Compound 91
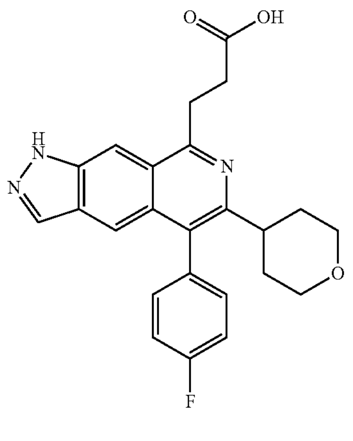 [SMILES: O=C(O)CCc1nc(C2CCOCC2)c(-c2ccc(F)cc2)c2cc3cn[nH]c3cc12]

TABLE I-continued
| Compounds 1-262 |
| --- |
Compound 92
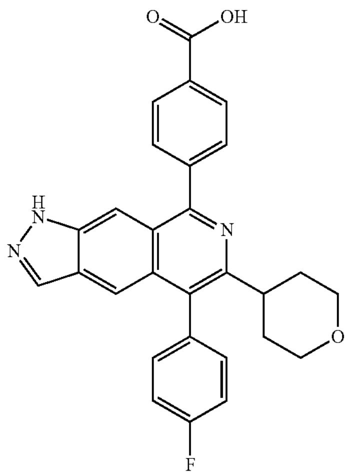 [SMILES: O=C(O)c1ccc(-c2nc(C3CCOCC3)c(-c3ccc(F)cc3)c3cc4cn[nH]c4cc23)cc1]
Compound 93
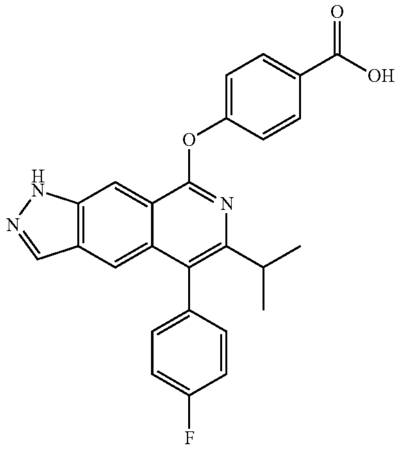 [SMILES: CC(C)c1nc(Oc2ccc(C(=O)O)cc2)c2cc3[nH]ncc3cc2c1-c1ccc(F)cc1]
Compound 94
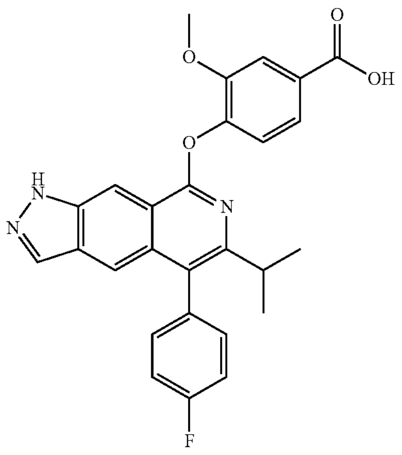 [SMILES: COc1cc(C(=O)O)ccc1Oc1nc(C(C)C)c(-c2ccc(F)cc2)c2cc3cn[nH]c3cc12]

TABLE I-continued
| Compounds 1-262 |  |
| --- | --- |
| 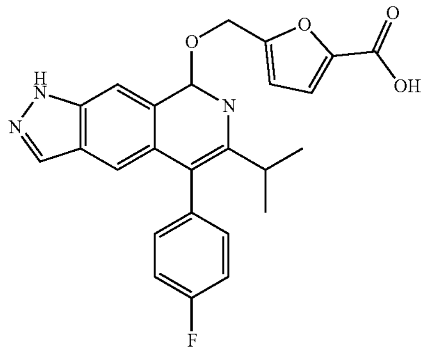 [SMILES: CC(C)C1=C(c2ccc(F)cc2)c2cc3cn[nH]c3cc2C(OCc2ccc(C(=O)O)o2)N1] | Compound 95 |
| 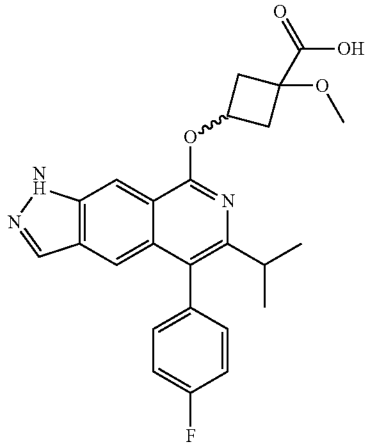 [SMILES: COC1(C(=O)O)CC(Oc2nc(C(C)C)c(-c3ccc(F)cc3)c3cc4cn[nH]c4cc23)C1] | Compound 96 |
| 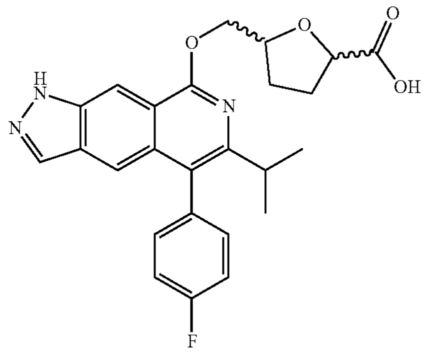 [SMILES: CC(C)c1nc(OCC2CCC(C(=O)O)O2)c2cc3[nH]ncc3cc2c1-c1ccc(F)cc1] | Compound 97 |
| 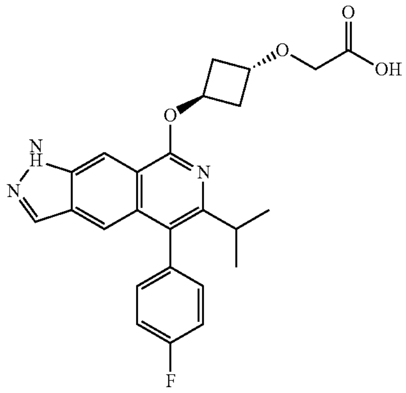 [SMILES: CC(C)c1nc(O[C@H]2C[C@H](OCC(=O)O)C2)c2cc3[nH]ncc3cc2c1-c1ccc(F)cc1] | Compound 98 |

TABLE I-continued
| Compounds 1-262 |
| --- |
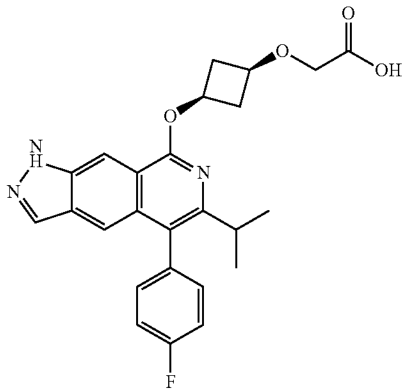 [SMILES: CC(C)c1nc(O[C@H]2C[C@@H](OCC(=O)O)C2)c2cc3[nH]ncc3cc2c1-c1ccc(F)cc1]
Compound 99
Compound 100
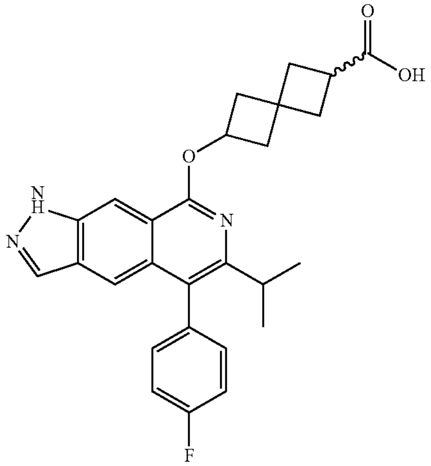 [SMILES: CC(C)c1nc(OC2CC3(C2)CC(C(=O)O)C3)c2cc3[nH]ncc3cc2c1-c1ccc(F)cc1]
Compound 101
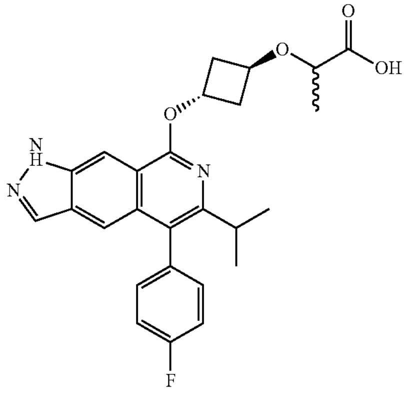 [SMILES: CC(O[C@H]1C[C@H](Oc2nc(C(C)C)c(-c3ccc(F)cc3)c3cc4cn[nH]c4cc23)C1)C(=O)O]

TABLE I-continued
| Compounds 1-262 |
|---|
Compound 102
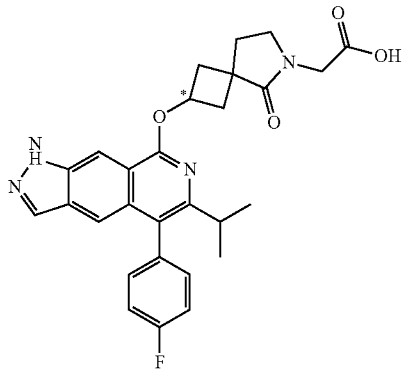 [SMILES: CC(C)c1nc(OC2CC3(CCN(CC(=O)O)C3=O)C2)c2cc3[nH]ncc3cc2c1-c1ccc(F)cc1]
Compound 103
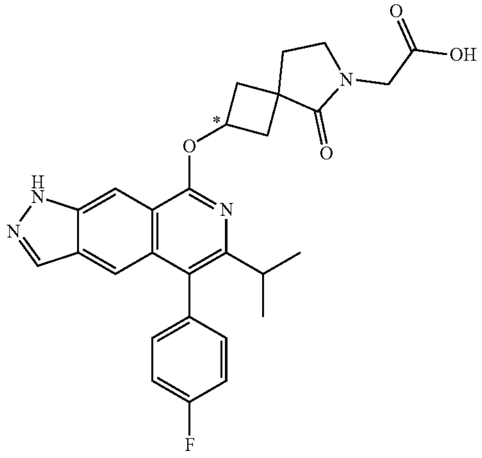 [SMILES: CC(C)c1nc(OC2CC3(CCN(CC(=O)O)C3=O)C2)c2cc3[nH]ncc3cc2c1-c1ccc(F)cc1]
Compound 104
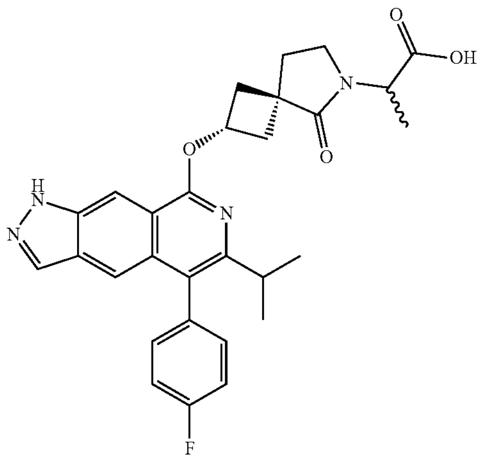 [SMILES: CC(C)c1nc(O[C@H]2C[C@@]3(CCN(C(C)C(=O)O)C3=O)C2)c2cc3[nH]ncc3cc2c1-c1ccc(F)cc1]

TABLE I-continued
| Compounds 1-262 |
| --- |
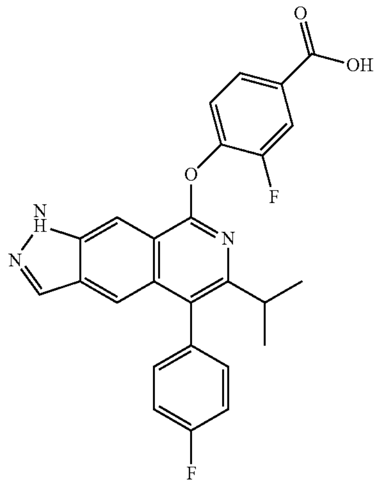 [SMILES: CC(C)c1nc(Oc2ccc(C(=O)O)cc2F)c2cc3[nH]ncc3cc2c1-c1ccc(F)cc1]
Compound 105
Compound 106
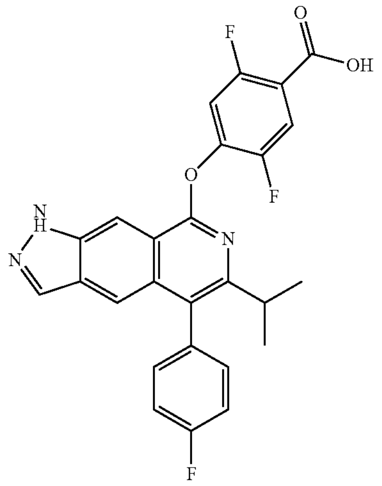 [SMILES: CC(C)c1nc(Oc2cc(F)c(C(=O)O)cc2F)c2cc3[nH]ncc3cc2c1-c1ccc(F)cc1]
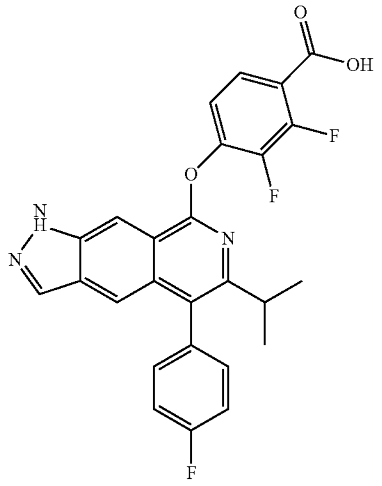 [SMILES: CC(C)c1nc(Oc2ccc(C(=O)O)c(F)c2F)c2cc3[nH]ncc3cc2c1-c1ccc(F)cc1]
Compound 107

TABLE I-continued
| Compounds 1-262 |
| --- |
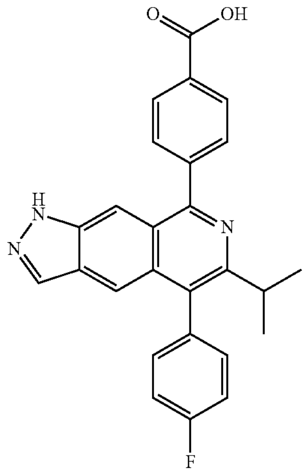 [SMILES: CC(C)c1nc(-c2ccc(C(=O)O)cc2)c2cc3[nH]ncc3cc2c1-c1ccc(F)cc1]
Compound 108
Compound 109
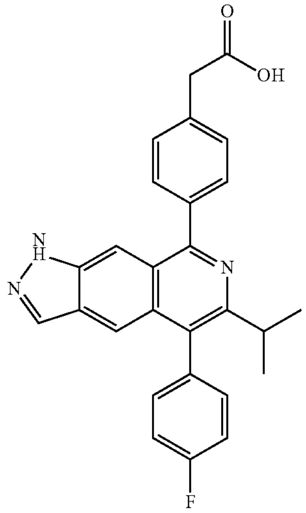 [SMILES: CC(C)c1nc(-c2ccc(CC(=O)O)cc2)c2cc3[nH]ncc3cc2c1-c1ccc(F)cc1]
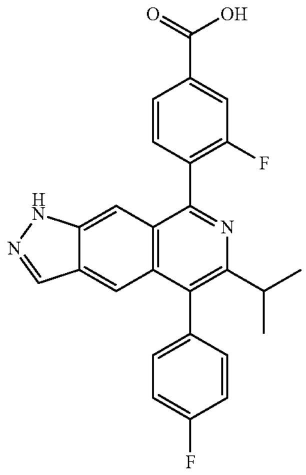 [SMILES: CC(C)c1nc(-c2ccc(C(=O)O)cc2F)c2cc3[nH]ncc3cc2c1-c1ccc(F)cc1]
Compound 110

TABLE I-continued
| Compounds 1-262 |
| --- |
| 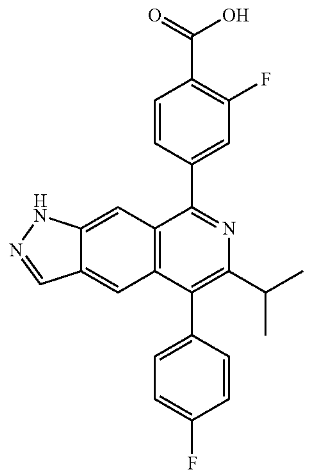 [SMILES: CC(C)c1nc(-c2ccc(C(=O)O)c(F)c2)c2cc3[nH]ncc3cc2c1-c1ccc(F)cc1] Compound 111 |
| Compound 112 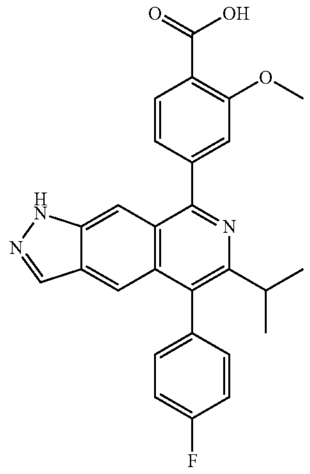 [SMILES: COc1cc(-c2nc(C(C)C)c(-c3ccc(F)cc3)c3cc4cn[nH]c4cc23)ccc1C(=O)O] |
| Compound 113 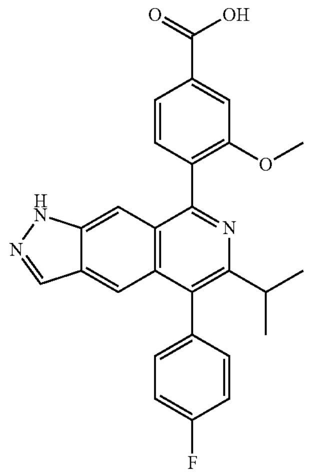 [SMILES: COc1cc(C(=O)O)ccc1-c1nc(C(C)C)c(-c2ccc(F)cc2)c2cc3cn[nH]c3cc12] |

TABLE I-continued
| Compounds 1-262 |
| --- |
Compound 114
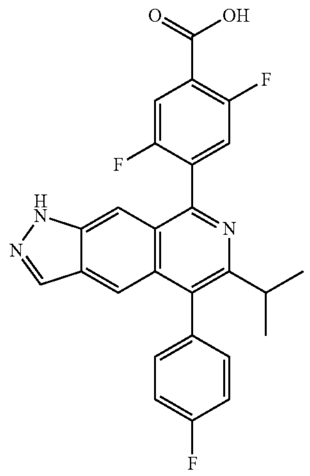 [SMILES: CC(C)c1nc(-c2cc(F)c(C(=O)O)cc2F)c2cc3[nH]ncc3cc2c1-c1ccc(F)cc1]
Compound 115
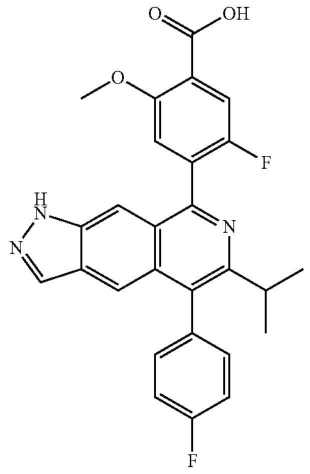 [SMILES: COc1cc(-c2nc(C(C)C)c(-c3ccc(F)cc3)c3cc4cn[nH]c4cc23)c(F)cc1C(=O)O]
Compound 116
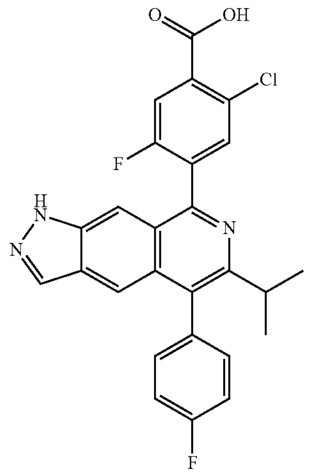 [SMILES: CC(C)c1nc(-c2cc(Cl)c(C(=O)O)cc2F)c2cc3[nH]ncc3cc2c1-c1ccc(F)cc1]

TABLE I-continued
| Compounds 1-262 |
| --- |
Compound 117
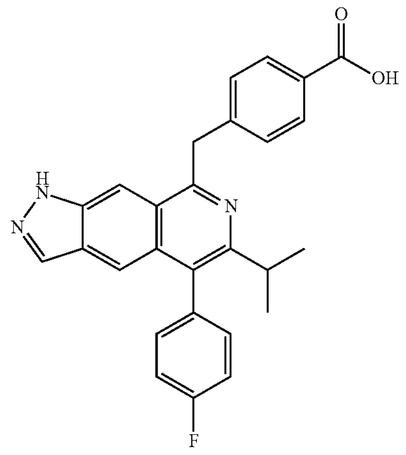 [SMILES: CC(C)c1nc(Cc2ccc(C(=O)O)cc2)c2cc3[nH]ncc3cc2c1-c1ccc(F)cc1]
Compound 118
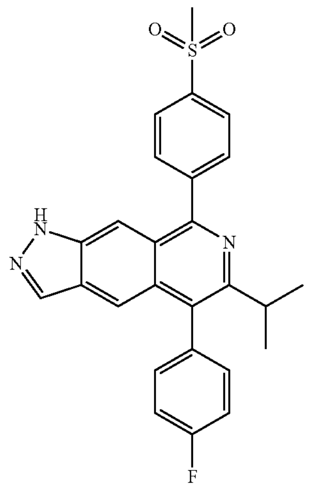 [SMILES: CC(C)c1nc(-c2ccc(S(C)(=O)=O)cc2)c2cc3[nH]ncc3cc2c1-c1ccc(F)cc1]
Compound 119
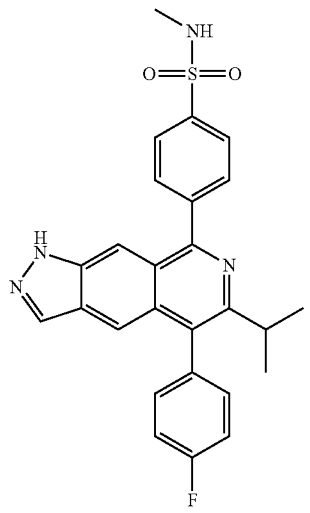 [SMILES: CNS(=O)(=O)c1ccc(-c2nc(C(C)C)c(-c3ccc(F)cc3)c3cc4cn[nH]c4cc23)cc1]

TABLE I-continued
| Compounds 1-262 |
| --- |
Compound 120
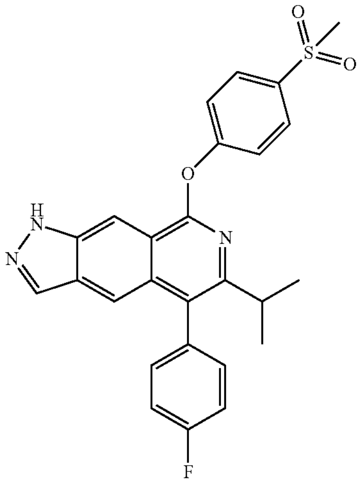 [SMILES: CC(C)c1nc(Oc2ccc(S(C)(=O)=O)cc2)c2cc3[nH]ncc3cc2c1-c1ccc(F)cc1]
Compound 121
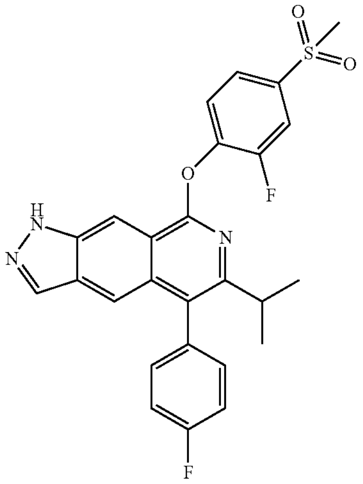 [SMILES: CC(C)c1nc(Oc2ccc(S(C)(=O)=O)cc2F)c2cc3[nH]ncc3cc2c1-c1ccc(F)cc1]
Compound 122
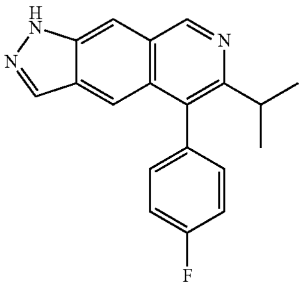 [SMILES: CC(C)c1ncc2cc3[nH]ncc3cc2c1-c1ccc(F)cc1]

TABLE I-continued
Compounds 1-262
Compound 123
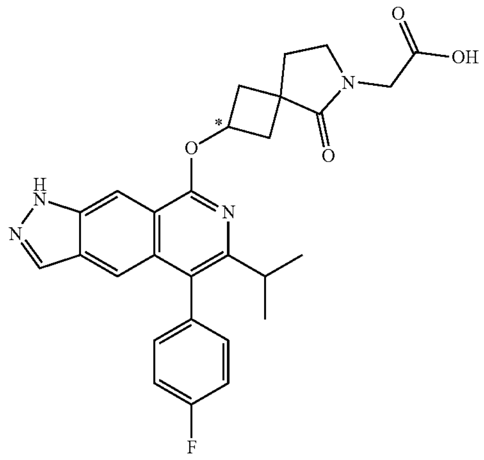 [SMILES: CC(C)c1nc(OC2CC3(CCN(CC(=O)O)C3=O)C2)c2cc3[nH]ncc3cc2c1-c1ccc(F)cc1]
Compound 124
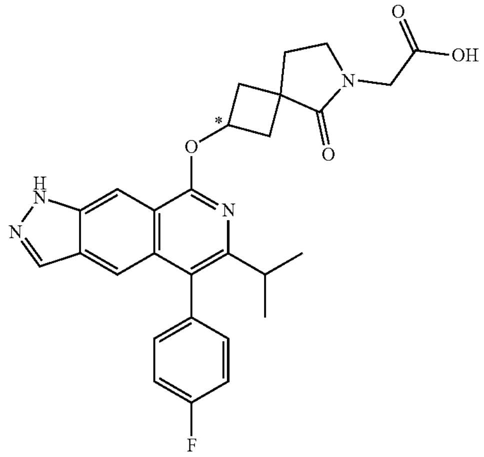 [SMILES: CC(C)c1nc(OC2CC3(CCN(CC(=O)O)C3=O)C2)c2cc3[nH]ncc3cc2c1-c1ccc(F)cc1]
Compound 125
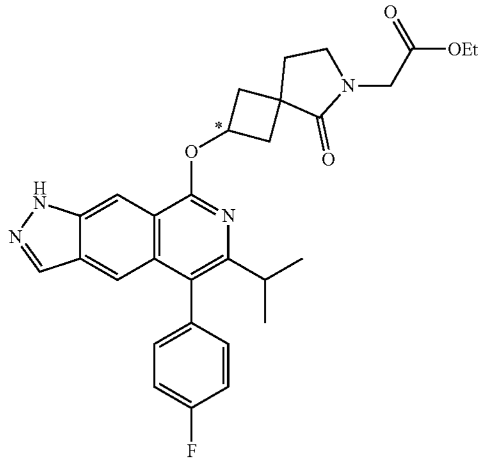 [SMILES: CCOC(=O)CN1CCC2(CC(Oc3nc(C(C)C)c(-c4ccc(F)cc4)c4cc5cn[nH]c5cc34)C2)C1=O]

TABLE I-continued
| Compounds 1-262 |
| --- |
| Compound 126 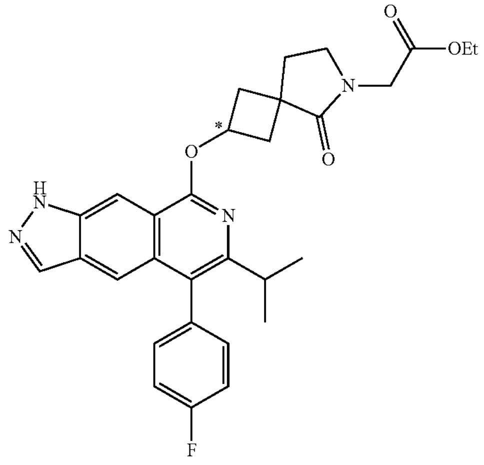 [SMILES: CCOC(=O)CN1CCC2(CC(Oc3nc(C(C)C)c(-c4ccc(F)cc4)c4cc5cn[nH]c5cc34)C2)C1=O] |
| Compound 127 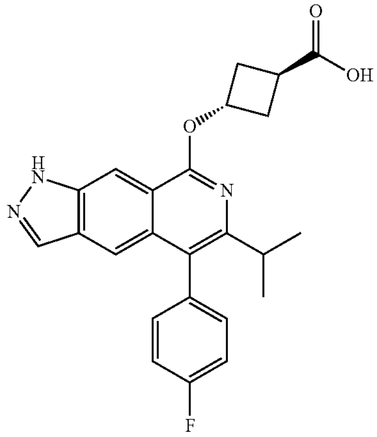 [SMILES: CC(C)c1nc(O[C@H]2C[C@H](C(=O)O)C2)c2cc3[nH]ncc3cc2c1-c1ccc(F)cc1] |
| Compound 128 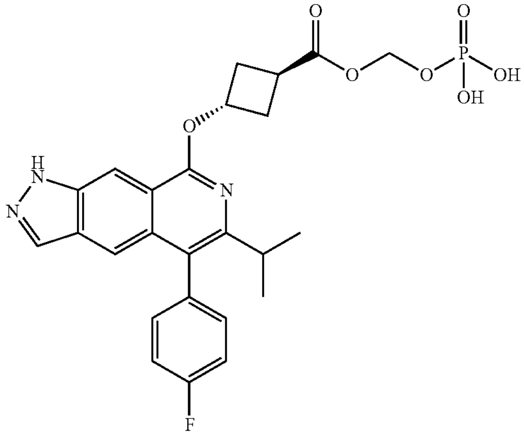 [SMILES: CC(C)c1nc(O[C@H]2C[C@H](C(=O)OCOP(=O)(O)O)C2)c2cc3[nH]ncc3cc2c1-c1ccc(F)cc1] |

TABLE I-continued
| Compounds 1-262 |
| --- |
| 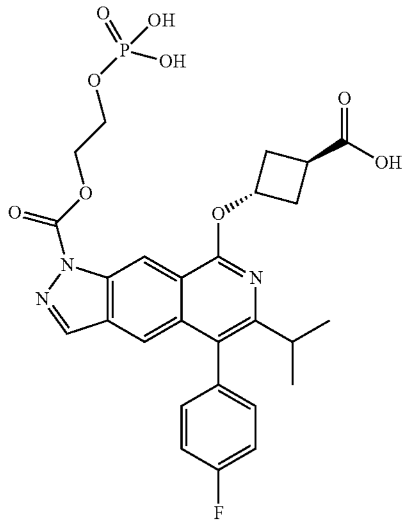 [SMILES: CC(C)c1nc(O[C@H]2C[C@H](C(=O)O)C2)c2cc3c(cnn3C(=O)OCCOP(=O)(O)O)cc2c1-c1ccc(F)cc1] Compound 129 |
| 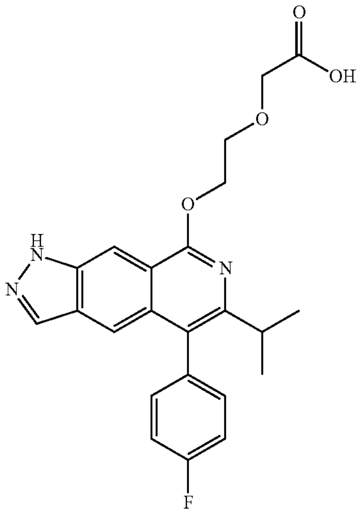 [SMILES: CC(C)c1nc(OCCOCC(=O)O)c2cc3[nH]ncc3cc2c1-c1ccc(F)cc1] Compound 130 |
| 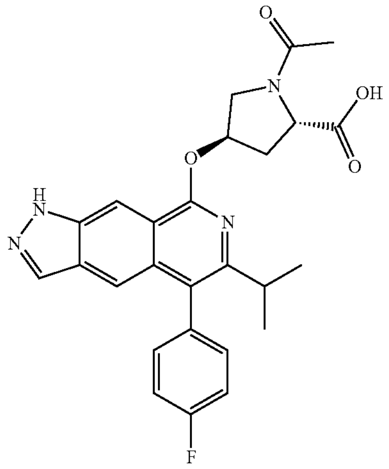 [SMILES: CC(=O)N1C[C@H](Oc2nc(C(C)C)c(-c3ccc(F)cc3)c3cc4cn[nH]c4cc23)C[C@H]1C(=O)O] Compound 131 |

TABLE I-continued
| Compounds 1-262 |
| --- |
Compound 132
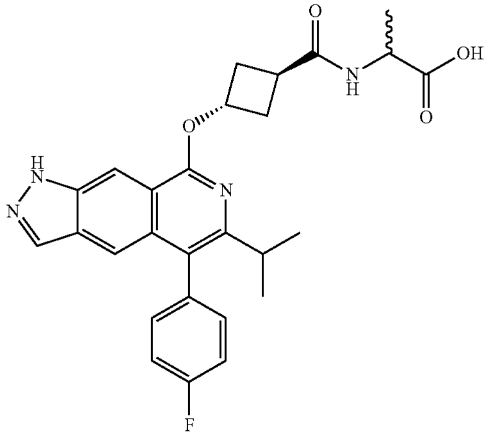 [SMILES: CC(NC(=O)[C@H]1C[C@H](Oc2nc(C(C)C)c(-c3ccc(F)cc3)c3cc4cn[nH]c4cc23)C1)C(=O)O]
Compound 133
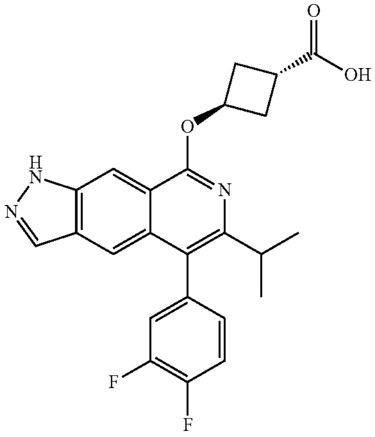 [SMILES: CC(C)c1nc(O[C@H]2C[C@H](C(=O)O)C2)c2cc3[nH]ncc3cc2c1-c1ccc(F)c(F)c1]
Compound 134
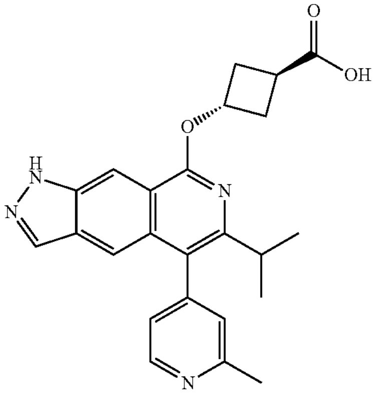 [SMILES: Cc1cc(-c2c(C(C)C)nc(O[C@H]3C[C@H](C(=O)O)C3)c3cc4[nH]ncc4cc23)ccn1]

TABLE I-continued
| Compounds 1-262 |
| --- |
Compound 135
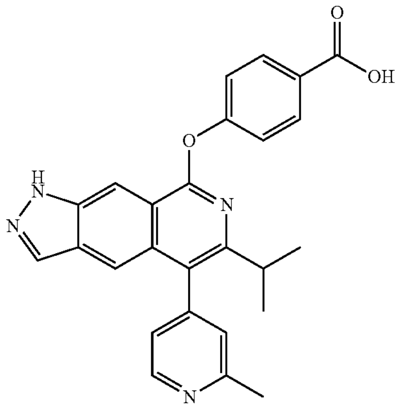 [SMILES: Cc1cc(-c2c(C(C)C)nc(Oc3ccc(C(=O)O)cc3)c3cc4[nH]ncc4cc23)ccn1]
Compound 136
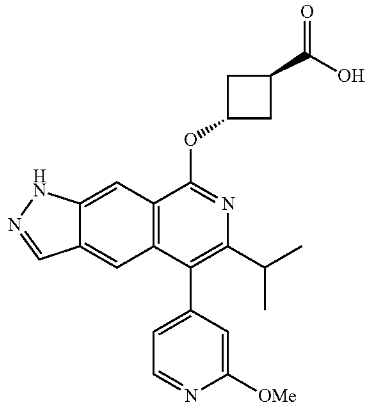 [SMILES: COc1cc(-c2c(C(C)C)nc(O[C@H]3C[C@H](C(=O)O)C3)c3cc4[nH]ncc4cc23)ccn1]
Compound 137
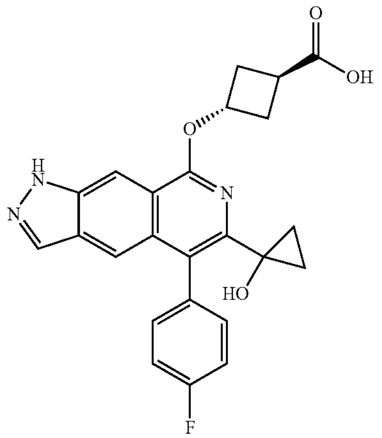 [SMILES: O=C(O)[C@H]1C[C@H](Oc2nc(C3(O)CC3)c(-c3ccc(F)cc3)c3cc4cn[nH]c4cc23)C1]

TABLE I-continued
| Compounds 1-262 |
| --- |
Compound 138
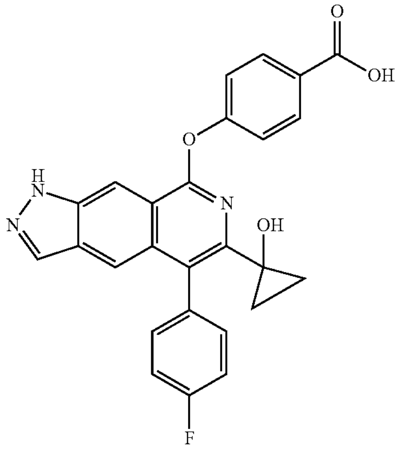 [SMILES: O=C(O)c1ccc(Oc2nc(C3(O)CC3)c(-c3ccc(F)cc3)c3cc4cn[nH]c4cc23)cc1]
Compound 139
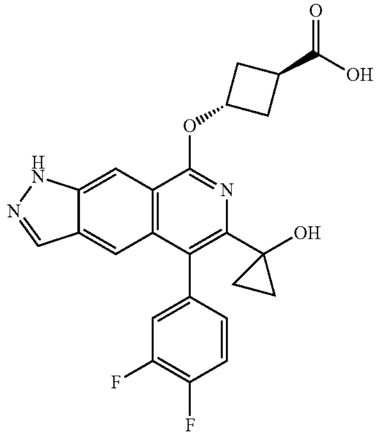 [SMILES: O=C(O)[C@H]1C[C@H](Oc2nc(C3(O)CC3)c(-c3ccc(F)c(F)c3)c3cc4cn[nH]c4cc23)C1]
Compound 140
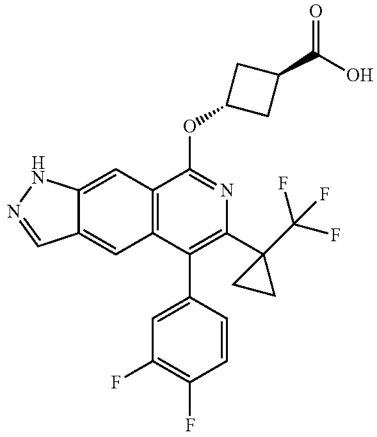 [SMILES: O=C(O)[C@H]1C[C@H](Oc2nc(C3(C(F)(F)F)CC3)c(-c3ccc(F)c(F)c3)c3cc4cn[nH]c4cc23)C1]

TABLE I-continued
| Compounds 1-262 |
|---|
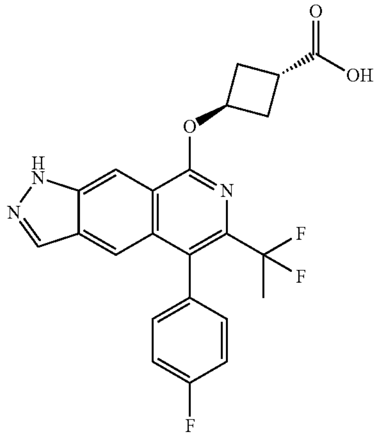 [SMILES: CC(F)(F)c1nc(O[C@H]2C[C@H](C(=O)O)C2)c2cc3[nH]ncc3cc2c1-c1ccc(F)cc1]
Compound 141
Compound 142
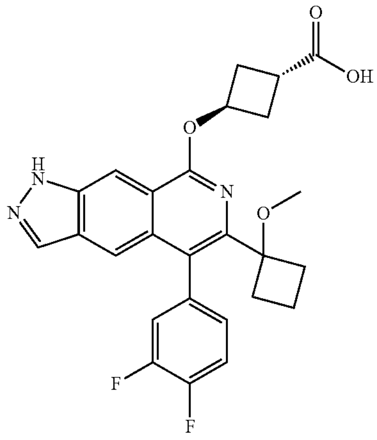 [SMILES: COC1(c2nc(O[C@H]3C[C@H](C(=O)O)C3)c3cc4[nH]ncc4cc3c2-c2ccc(F)c(F)c2)CCC1]
Compound 143
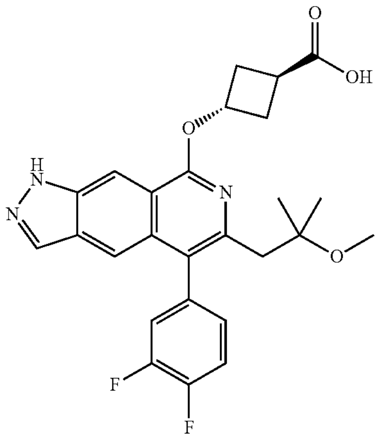 [SMILES: COC(C)(C)Cc1nc(O[C@H]2C[C@H](C(=O)O)C2)c2cc3[nH]ncc3cc2c1-c1ccc(F)c(F)c1]

TABLE I-continued
| Compounds 1-262 |
|---|
Compound 144
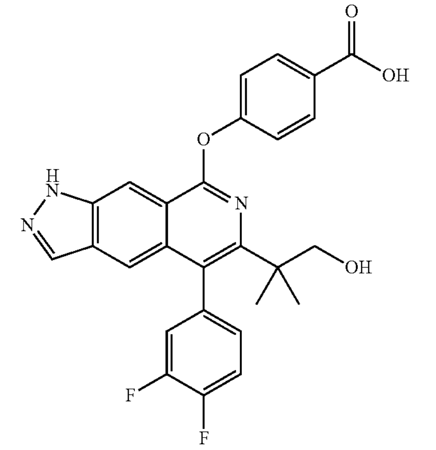 [SMILES: CC(C)(CO)c1nc(Oc2ccc(C(=O)O)cc2)c2cc3[nH]ncc3cc2c1-c1ccc(F)c(F)c1]
Compound 145
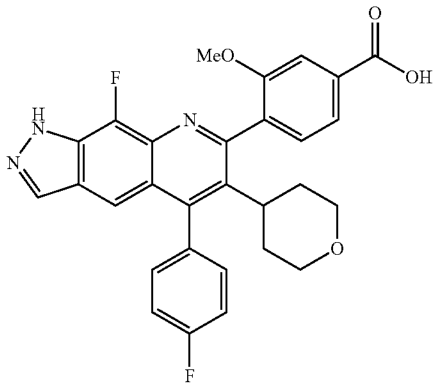 [SMILES: COc1cc(C(=O)O)ccc1-c1nc2c(F)c3[nH]ncc3cc2c(-c2ccc(F)cc2)c1C1CCOCC1]
Compound 146
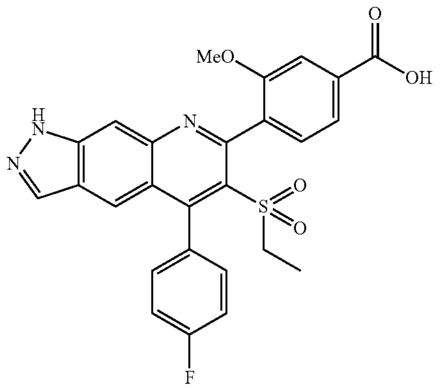 [SMILES: CCS(=O)(=O)c1c(-c2ccc(C(=O)O)cc2OC)nc2cc3[nH]ncc3cc2c1-c1ccc(F)cc1]

TABLE I-continued
| Compounds 1-262 |
| --- |
Compound 147
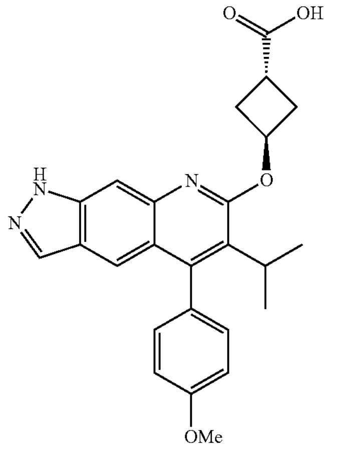 [SMILES: COc1ccc(-c2c(C(C)C)c(O[C@H]3C[C@H](C(=O)O)C3)nc3cc4[nH]ncc4cc23)cc1]
Compound 148
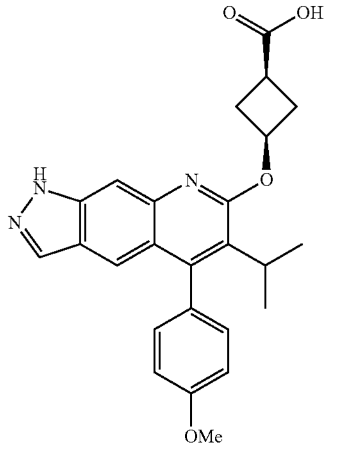 [SMILES: COc1ccc(-c2c(C(C)C)c(O[C@H]3C[C@@H](C(=O)O)C3)nc3cc4[nH]ncc4cc23)cc1]
Compound 149
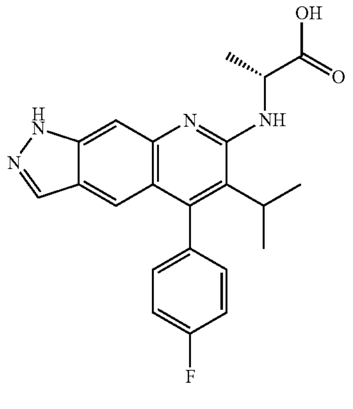 [SMILES: CC(C)c1c(N[C@H](C)C(=O)O)nc2cc3[nH]ncc3cc2c1-c1ccc(F)cc1]

TABLE I-continued
| Compounds 1-262 | |
|---|---|
| 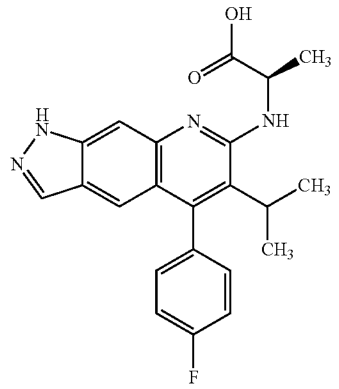 [SMILES: CC(C)c1c(N[C@H](C)C(=O)O)nc2cc3[nH]ncc3cc2c1-c1ccc(F)cc1] | Compound 150 |
| 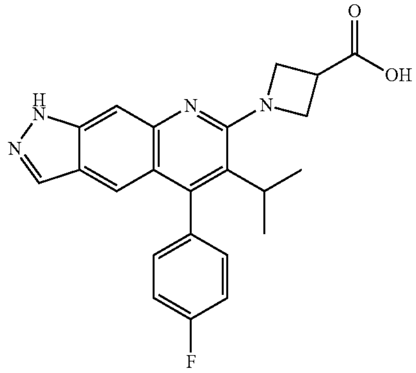 [SMILES: CC(C)c1c(N2CC(C(=O)O)C2)nc2cc3[nH]ncc3cc2c1-c1ccc(F)cc1] | Compound 151 |
| 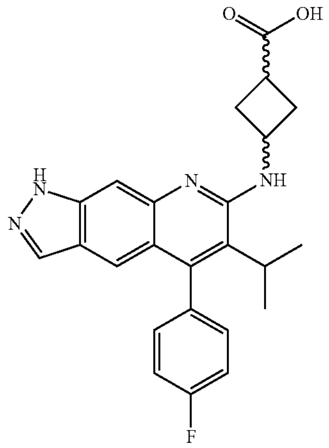 [SMILES: CC(C)c1c(NC2CC(C(=O)O)C2)nc2cc3[nH]ncc3cc2c1-c1ccc(F)cc1] | Compound 152 |
| 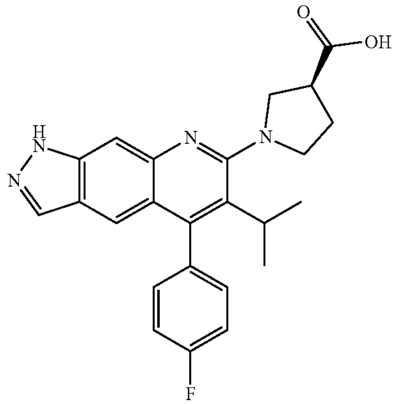 [SMILES: CC(C)c1c(N2CC[C@H](C(=O)O)C2)nc2cc3[nH]ncc3cc2c1-c1ccc(F)cc1] | Compound 153 |

TABLE I-continued
| Compounds 1-262 |
|---|
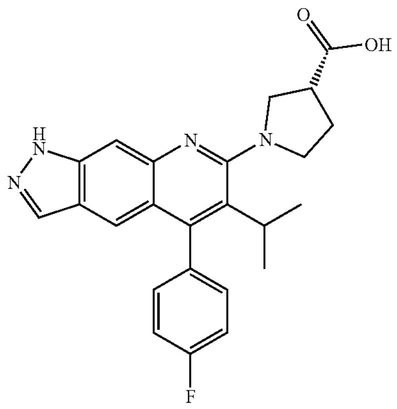
Compound 154
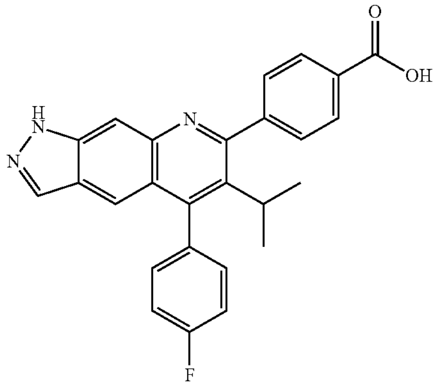 [SMILES: CC(C)c1c(-c2ccc(C(=O)O)cc2)nc2cc3[nH]ncc3cc2c1-c1ccc(F)cc1]
Compound 155
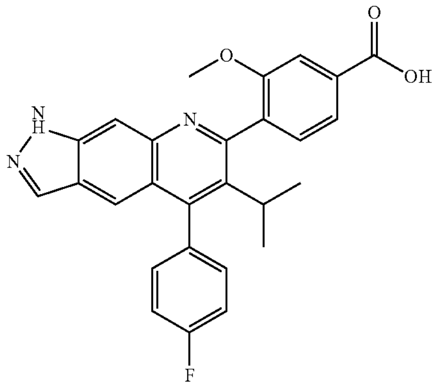
Compound 156
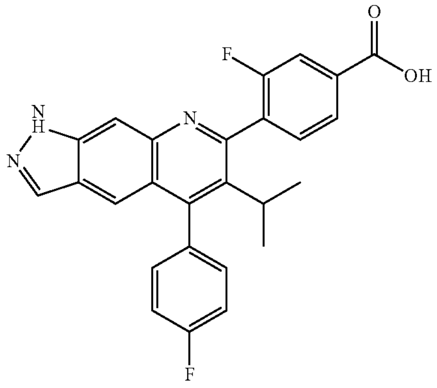
Compound 157

TABLE I-continued
Compounds 1-262
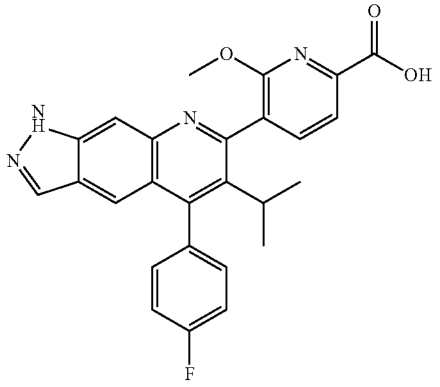
Compound 158
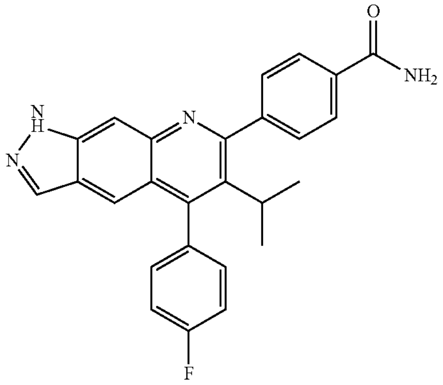 [SMILES: CC(C)c1c(-c2ccc(C(N)=O)cc2)nc2cc3[nH]ncc3cc2c1-c1ccc(F)cc1]
Compound 159
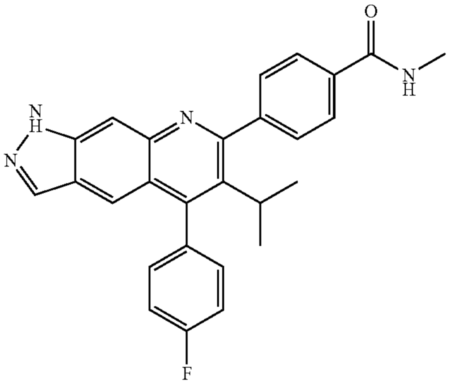 [SMILES: CNC(=O)c1ccc(-c2nc3cc4[nH]ncc4cc3c(-c3ccc(F)cc3)c2C(C)C)cc1]
Compound 160
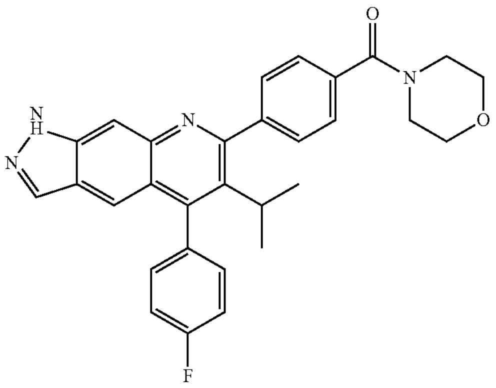 [SMILES: CC(C)c1c(-c2ccc(C(=O)N3CCOCC3)cc2)nc2cc3[nH]ncc3cc2c1-c1ccc(F)cc1]
Compound 161

TABLE I-continued
| Compounds 1-262 |
| --- |
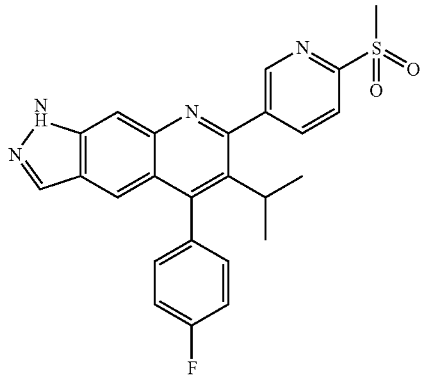 [SMILES: CC(C)c1c(-c2ccc(S(C)(=O)=O)nc2)nc2cc3[nH]ncc3cc2c1-c1ccc(F)cc1]
Compound 162
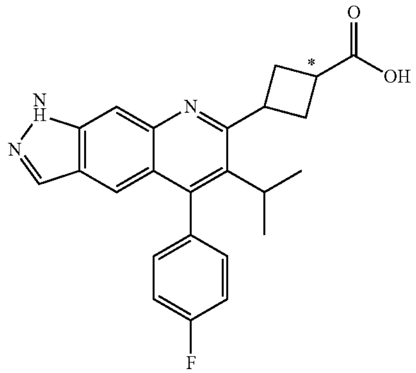 [SMILES: CC(C)c1c(C2CC(C(=O)O)C2)nc2cc3[nH]ncc3cc2c1-c1ccc(F)cc1]
Compound 163
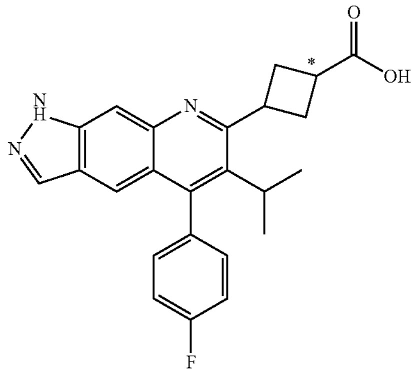 [SMILES: CC(C)c1c(C2CC(C(=O)O)C2)nc2cc3[nH]ncc3cc2c1-c1ccc(F)cc1]
Compound 164
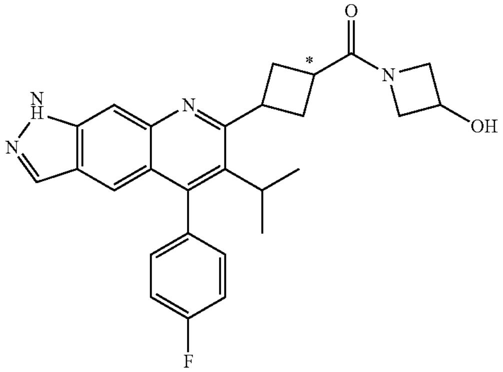 [SMILES: CC(C)c1c(C2CC(C(=O)N3CC(O)C3)C2)nc2cc3[nH]ncc3cc2c1-c1ccc(F)cc1]
Compound 165

TABLE I-continued
| Compounds 1-262 |
| --- |
| Compound 166 |
| 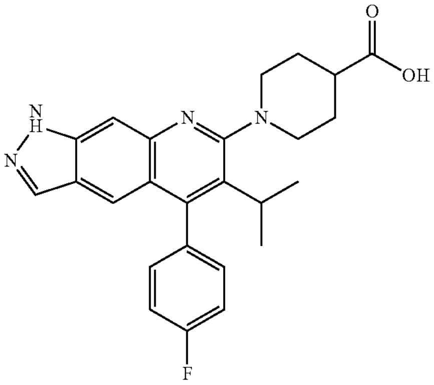 [SMILES: CC(C)c1c(N2CCC(C(=O)O)CC2)nc2cc3[nH]ncc3cc2c1-c1ccc(F)cc1] |
| Compound 167 |
| 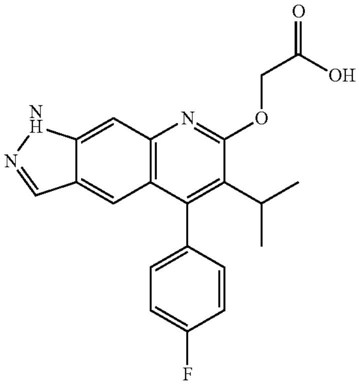 [SMILES: CC(C)c1c(OCC(=O)O)nc2cc3[nH]ncc3cc2c1-c1ccc(F)cc1] |
| Compound 168 |
| 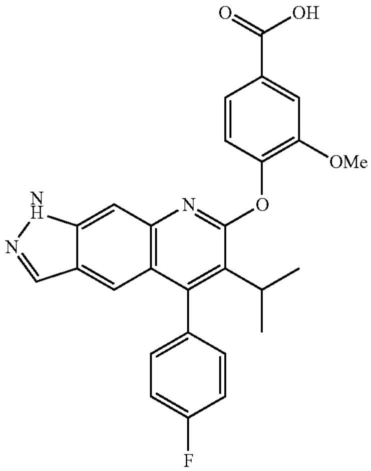 [SMILES: COc1cc(C(=O)O)ccc1Oc1nc2cc3[nH]ncc3cc2c(-c2ccc(F)cc2)c1C(C)C] |

TABLE I-continued
| Compounds 1-262 |
| --- |
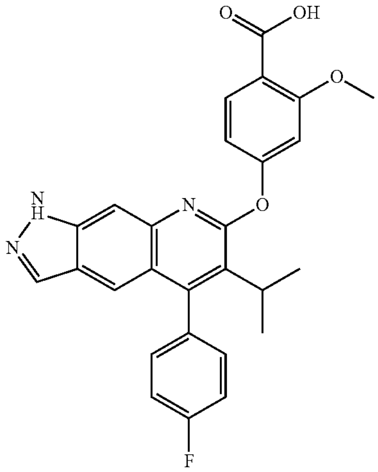 [SMILES: COc1cc(Oc2nc3cc4[nH]ncc4cc3c(-c3ccc(F)cc3)c2C(C)C)ccc1C(=O)O]
Compound 169
Compound 170
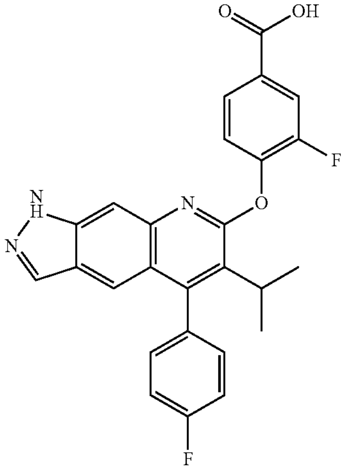 [SMILES: CC(C)c1c(Oc2ccc(C(=O)O)cc2F)nc2cc3[nH]ncc3cc2c1-c1ccc(F)cc1]
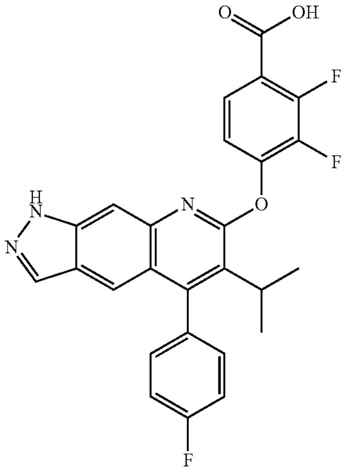 [SMILES: CC(C)c1c(Oc2ccc(C(=O)O)c(F)c2F)nc2cc3[nH]ncc3cc2c1-c1ccc(F)cc1]
Compound 171

TABLE I-continued
| Compounds 1-262 |
| --- |
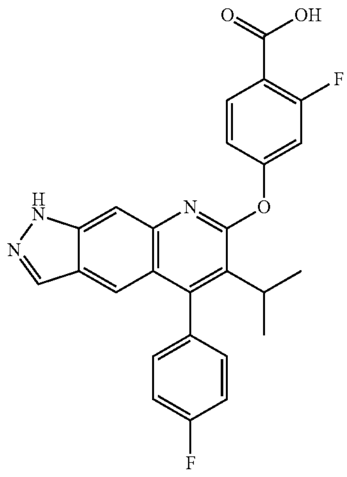 [SMILES: CC(C)c1c(Oc2ccc(C(=O)O)c(F)c2)nc2cc3[nH]ncc3cc2c1-c1ccc(F)cc1]
Compound 172
Compound 173
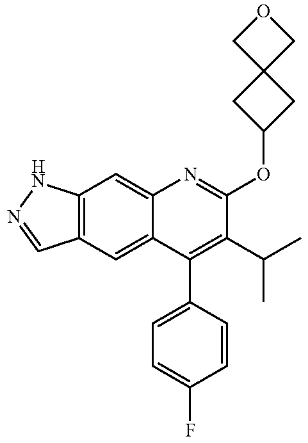 [SMILES: CC(C)c1c(OC2CC3(COC3)C2)nc2cc3[nH]ncc3cc2c1-c1ccc(F)cc1]
Compound 174
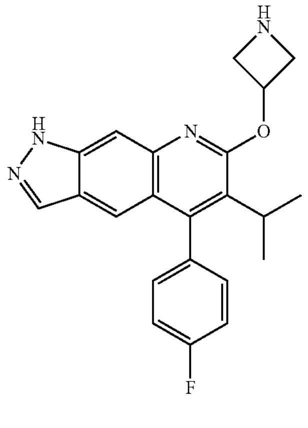 [SMILES: CC(C)c1c(OC2CNC2)nc2cc3[nH]ncc3cc2c1-c1ccc(F)cc1]

TABLE I-continued
| Compounds 1-262 |
| --- |
| Compound 175 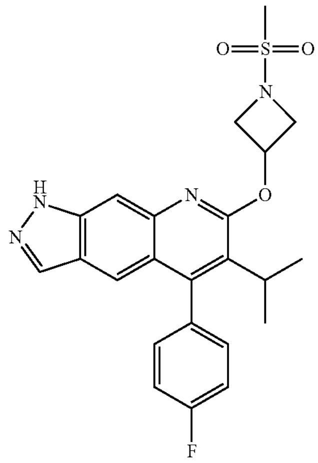 [SMILES: CC(C)c1c(OC2CN(S(C)(=O)=O)C2)nc2cc3[nH]ncc3cc2c1-c1ccc(F)cc1] |
| Compound 176 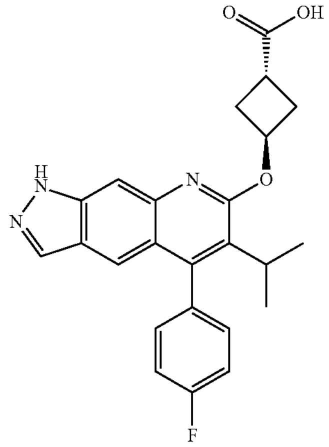 [SMILES: CC(C)c1c(O[C@H]2C[C@H](C(=O)O)C2)nc2cc3[nH]ncc3cc2c1-c1ccc(F)cc1] |
| Compound 177 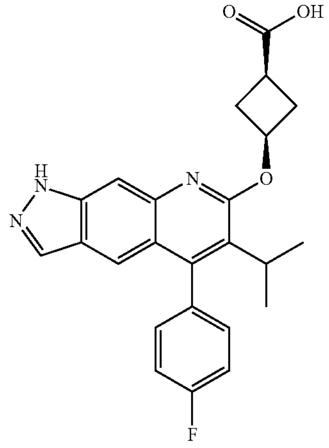 [SMILES: CC(C)c1c(O[C@H]2C[C@@H](C(=O)O)C2)nc2cc3[nH]ncc3cc2c1-c1ccc(F)cc1] |

TABLE I-continued
| Compounds 1-262 |
| --- |
| Compound 178 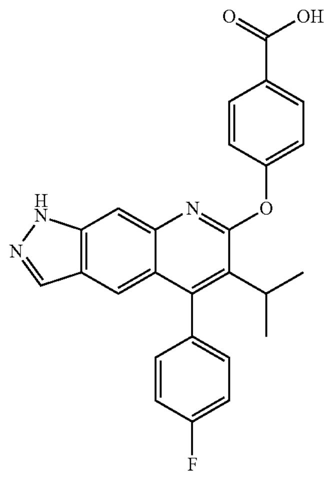 [SMILES: CC(C)c1c(Oc2ccc(C(=O)O)cc2)nc2cc3[nH]ncc3cc2c1-c1ccc(F)cc1] |
| Compound 179 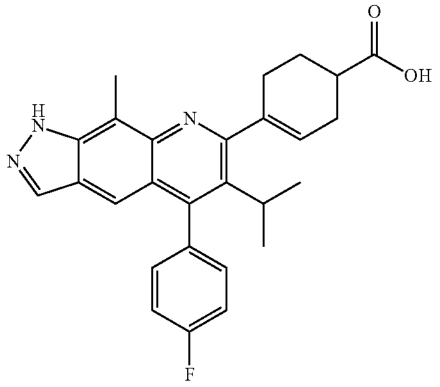 [SMILES: Cc1c2nc(C3=CCC(C(=O)O)CC3)c(C(C)C)c(-c3ccc(F)cc3)c2cc2cn[nH]c12] |
| Compound 180 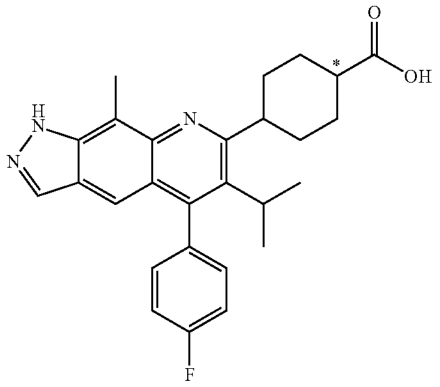 [SMILES: Cc1c2nc(C3CCC(C(=O)O)CC3)c(C(C)C)c(-c3ccc(F)cc3)c2cc2cn[nH]c12] |

TABLE I-continued
| Compounds 1-262 |
| --- |
Compound 181
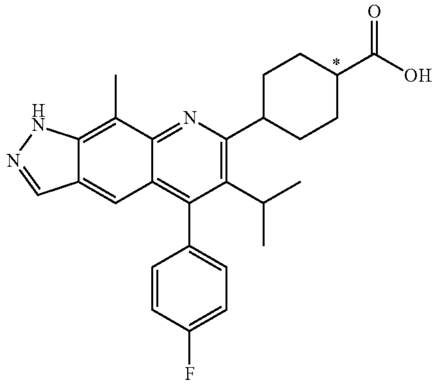 [SMILES: Cc1c2nc(C3CCC(C(=O)O)CC3)c(C(C)C)c(-c3ccc(F)cc3)c2cc2cn[nH]c12]
Compound 182
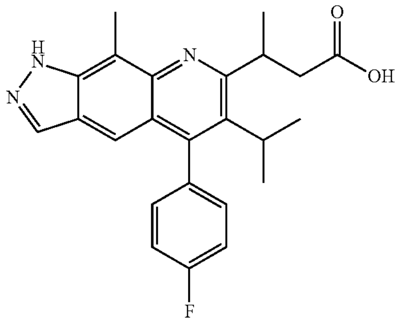 [SMILES: Cc1c2nc(C(C)CC(=O)O)c(C(C)C)c(-c3ccc(F)cc3)c2cc2cn[nH]c12]
Compound 183
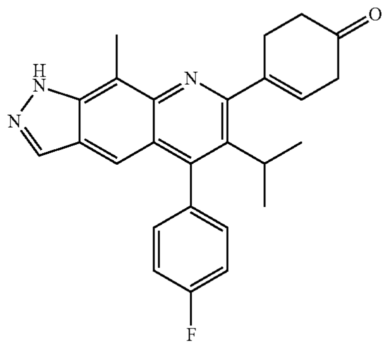 [SMILES: Cc1c2nc(C3=CCC(=O)CC3)c(C(C)C)c(-c3ccc(F)cc3)c2cc2cn[nH]c12]
Compound 184
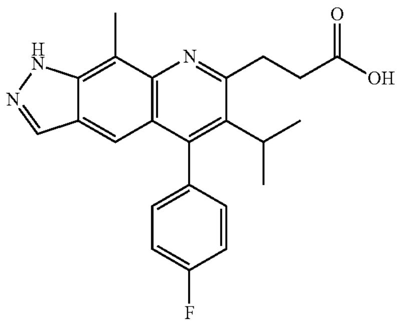 [SMILES: Cc1c2nc(CCC(=O)O)c(C(C)C)c(-c3ccc(F)cc3)c2cc2cn[nH]c12]

TABLE I-continued
| Compounds 1-262 | |
|---|---|
| 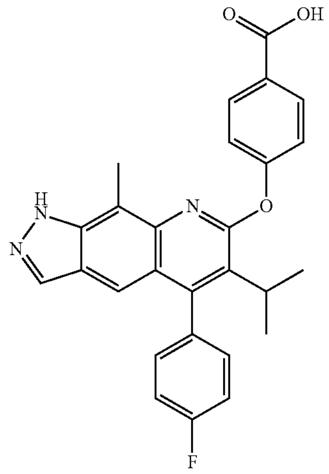 [SMILES: Cc1c2nc(Oc3ccc(C(=O)O)cc3)c(C(C)C)c(-c3ccc(F)cc3)c2cc2cn[nH]c12] | Compound 185 |
| 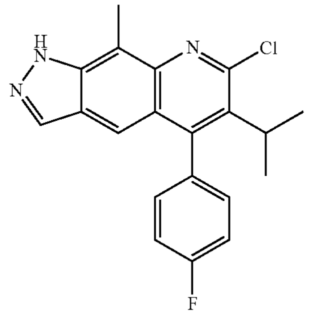 [SMILES: Cc1c2nc(Cl)c(C(C)C)c(-c3ccc(F)cc3)c2cc2cn[nH]c12] | Compound 186 |
| 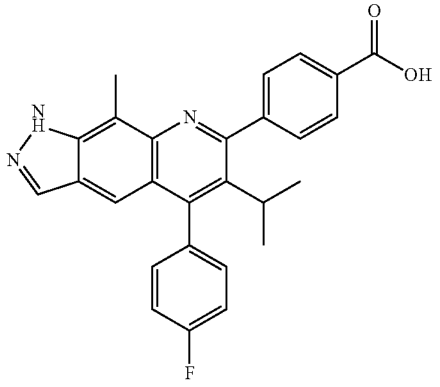 [SMILES: Cc1c2nc(-c3ccc(C(=O)O)cc3)c(C(C)C)c(-c3ccc(F)cc3)c2cc2cn[nH]c12] | Compound 187 |
| 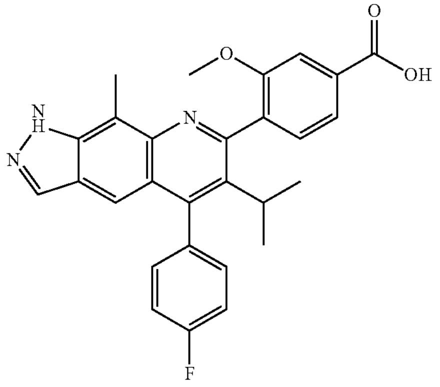 [SMILES: COc1cc(C(=O)O)ccc1-c1nc2c(C)c3[nH]ncc3cc2c(-c2ccc(F)cc2)c1C(C)C] | Compound 188 |

TABLE I-continued
| Compounds 1-262 |
|---|
| 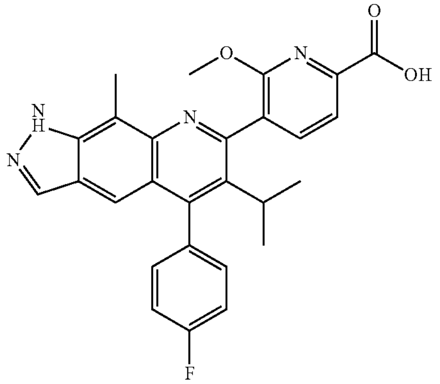 [SMILES: COc1nc(C(=O)O)ccc1-c1nc2c(C)c3[nH]ncc3cc2c(-c2ccc(F)cc2)c1C(C)C] Compound 189 |
| 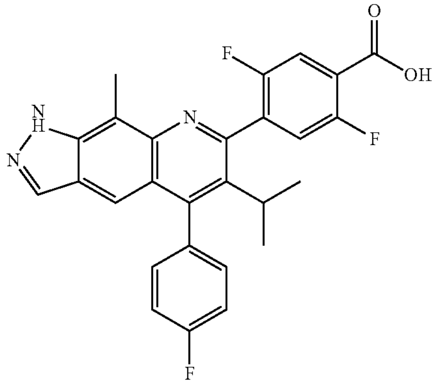 [SMILES: Cc1c2nc(-c3cc(F)c(C(=O)O)cc3F)c(C(C)C)c(-c3ccc(F)cc3)c2cc2cn[nH]c12] Compound 190 |
| 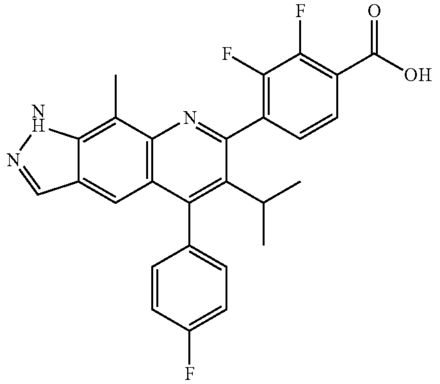 [SMILES: Cc1c2nc(-c3ccc(C(=O)O)c(F)c3F)c(C(C)C)c(-c3ccc(F)cc3)c2cc2cn[nH]c12] Compound 191 |
| 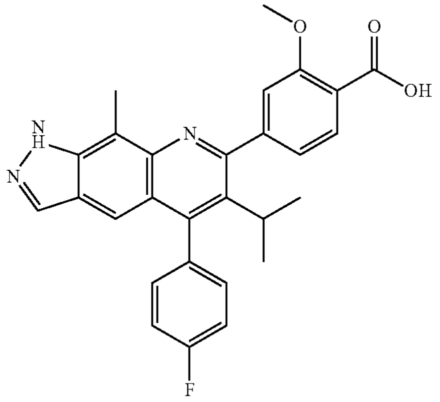 [SMILES: COc1cc(-c2nc3c(C)c4[nH]ncc4cc3c(-c3ccc(F)cc3)c2C(C)C)ccc1C(=O)O] Compound 192 |

TABLE I-continued
| Compounds 1-262 |
| --- |
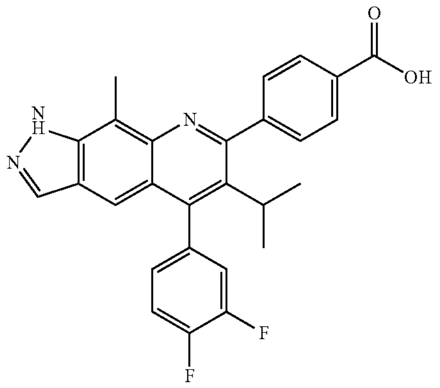 [SMILES: Cc1c2nc(-c3ccc(C(=O)O)cc3)c(C(C)C)c(-c3ccc(F)c(F)c3)c2cc2cn[nH]c12]
Compound 194
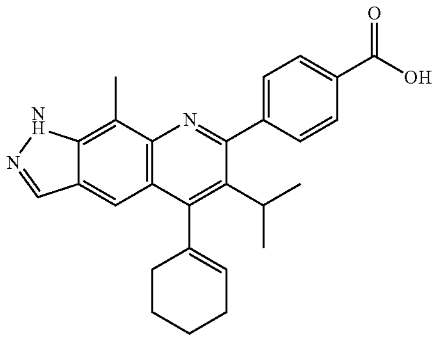 [SMILES: Cc1c2nc(-c3ccc(C(=O)O)cc3)c(C(C)C)c(C3=CCCCC3)c2cc2cn[nH]c12]
Compound 195
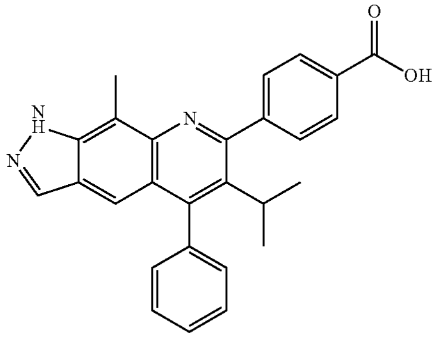 [SMILES: Cc1c2nc(-c3ccc(C(=O)O)cc3)c(C(C)C)c(-c3ccccc3)c2cc2cn[nH]c12]
Compound 196
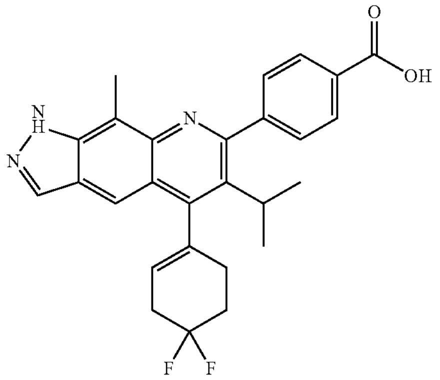 [SMILES: Cc1c2nc(-c3ccc(C(=O)O)cc3)c(C(C)C)c(C3=CCC(F)(F)CC3)c2cc2cn[nH]c12]
Compound 197

TABLE I-continued
| Compounds 1-262 | |
| --- | --- |
| 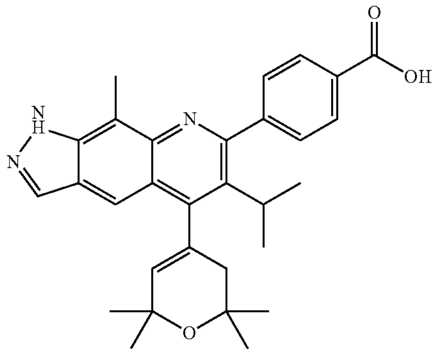 [SMILES: Cc1c2nc(-c3ccc(C(=O)O)cc3)c(C(C)C)c(C3=CC(C)(C)OC(C)(C)C3)c2cc2cn[nH]c12] | Compound 198 |
| 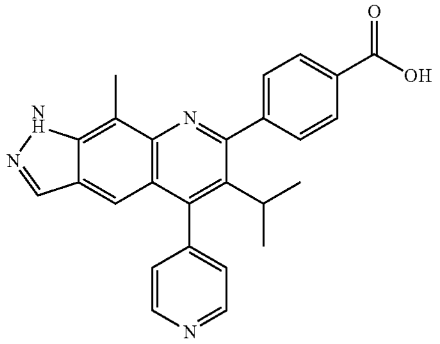 [SMILES: Cc1c2nc(-c3ccc(C(=O)O)cc3)c(C(C)C)c(-c3ccncc3)c2cc2cn[nH]c12] | Compound 199 |
| 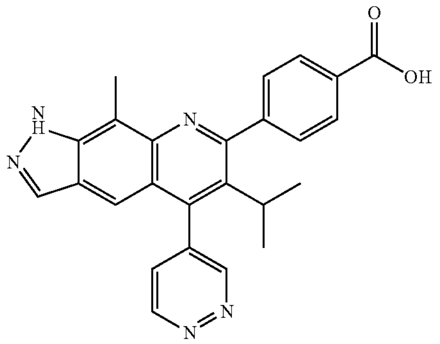 | Compound 200 |
| 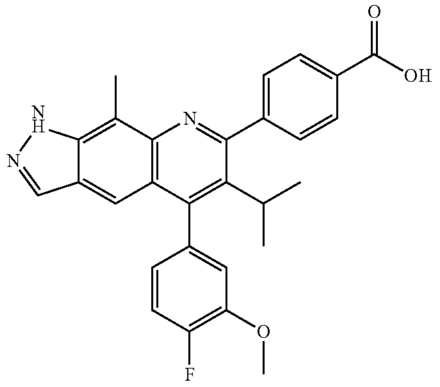 [SMILES: COc1cc(-c2c(C(C)C)c(-c3ccc(C(=O)O)cc3)nc3c(C)c4[nH]ncc4cc23)ccc1F] | Compound 201 |

TABLE I-continued
| Compounds 1-262 | |
|---|---|
| 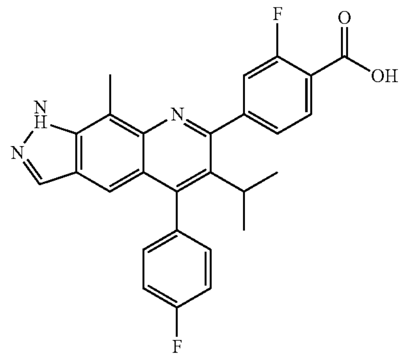 [SMILES: Cc1c2nc(-c3ccc(C(=O)O)c(F)c3)c(C(C)C)c(-c3ccc(F)cc3)c2cc2cn[nH]c12] | Compound 202 |
| 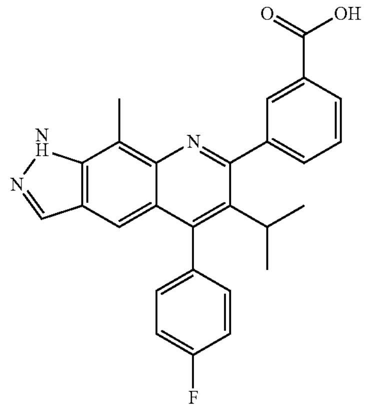 [SMILES: Cc1c2nc(-c3cccc(C(=O)O)c3)c(C(C)C)c(-c3ccc(F)cc3)c2cc2cn[nH]c12] | Compound 203 |
| 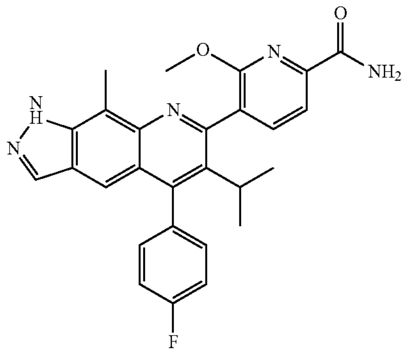 [SMILES: COc1nc(C(N)=O)ccc1-c1nc2c(C)c3[nH]ncc3cc2c(-c2ccc(F)cc2)c1C(C)C] | Compound 204 |
| 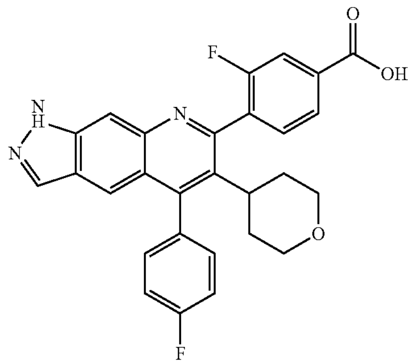 [SMILES: O=C(O)c1ccc(-c2nc3cc4[nH]ncc4cc3c(-c3ccc(F)cc3)c2C2CCOCC2)c(F)c1] | Compound 205 |

TABLE I-continued
| Compounds 1-262 |
|---|
Compound 206
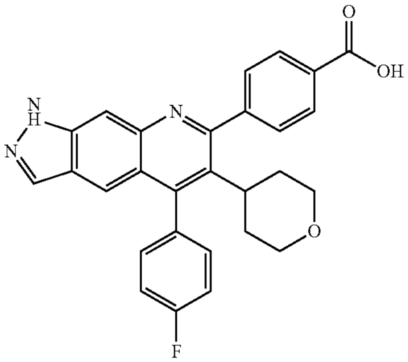 [SMILES: O=C(O)c1ccc(-c2nc3cc4[nH]ncc4cc3c(-c3ccc(F)cc3)c2C2CCOCC2)cc1]
Compound 207
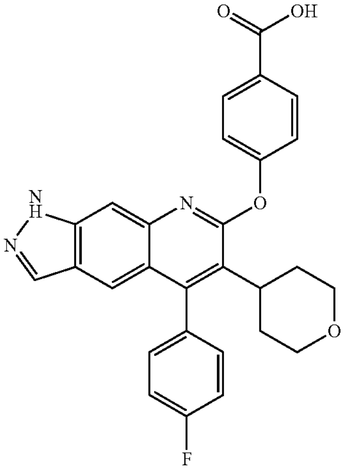 [SMILES: O=C(O)c1ccc(Oc2nc3cc4[nH]ncc4cc3c(-c3ccc(F)cc3)c2C2CCOCC2)cc1]
Compound 208
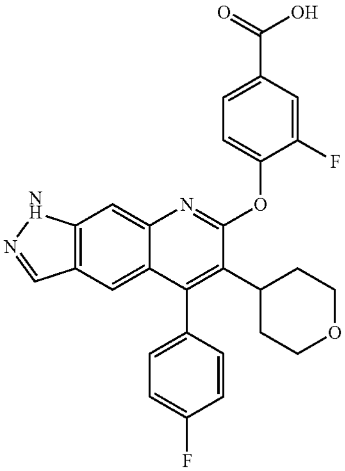 [SMILES: O=C(O)c1ccc(Oc2nc3cc4[nH]ncc4cc3c(-c3ccc(F)cc3)c2C2CCOCC2)c(F)c1]

TABLE I-continued
| Compounds 1-262 |
| --- |
Compound 209
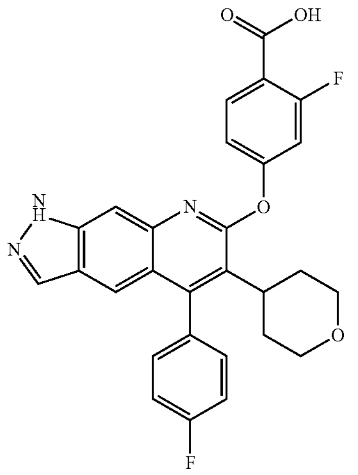 [SMILES: O=C(O)c1ccc(Oc2nc3cc4[nH]ncc4cc3c(-c3ccc(F)cc3)c2C2CCOCC2)cc1F]
Compound 210
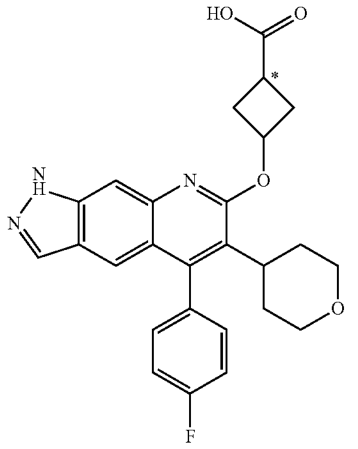 [SMILES: O=C(O)C1CC(Oc2nc3cc4[nH]ncc4cc3c(-c3ccc(F)cc3)c2C2CCOCC2)C1]
Compound 211
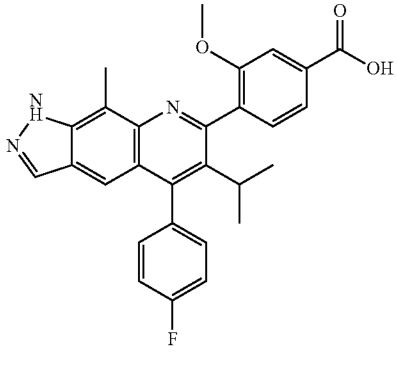 [SMILES: COc1cc(C(=O)O)ccc1-c1nc2c(C)c3[nH]ncc3cc2c(-c2ccc(F)cc2)c1C(C)C]

TABLE I-continued
| Compounds 1-262 | |
|---|---|
| 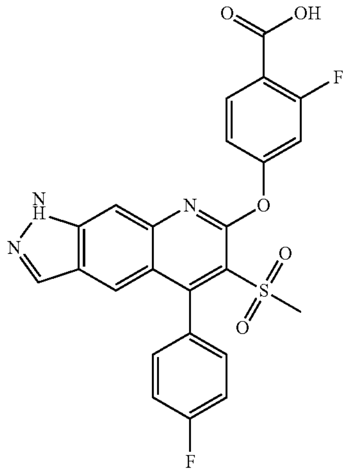 [SMILES: CS(=O)(=O)c1c(Oc2ccc(C(=O)O)c(F)c2)nc2cc3[nH]ncc3cc2c1-c1ccc(F)cc1] | Compound 212 |
| 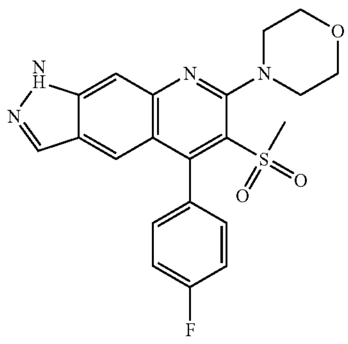 [SMILES: CS(=O)(=O)c1c(N2CCOCC2)nc2cc3[nH]ncc3cc2c1-c1ccc(F)cc1] | Compound 213 |
| 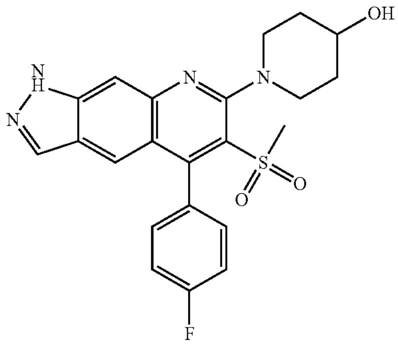 [SMILES: CS(=O)(=O)c1c(N2CCC(O)CC2)nc2cc3[nH]ncc3cc2c1-c1ccc(F)cc1] | Compound 214 |
| 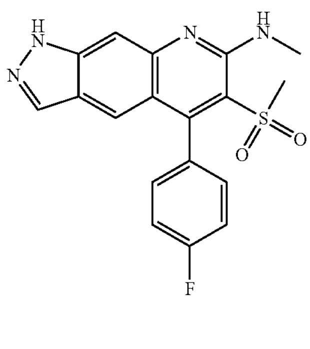 [SMILES: CNc1nc2cc3[nH]ncc3cc2c(-c2ccc(F)cc2)c1S(C)(=O)=O] | Compound 215 |

TABLE I-continued
| Compounds 1-262 |
| --- |
Compound 216
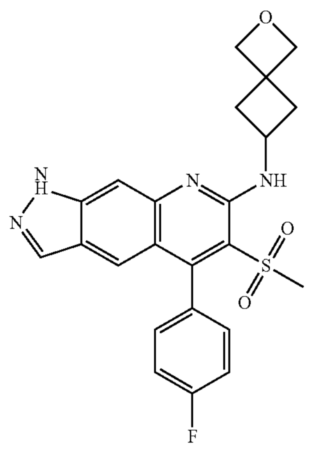 [SMILES: CS(=O)(=O)c1c(NC2CC3(COC3)C2)nc2cc3[nH]ncc3cc2c1-c1ccc(F)cc1]
Compound 217
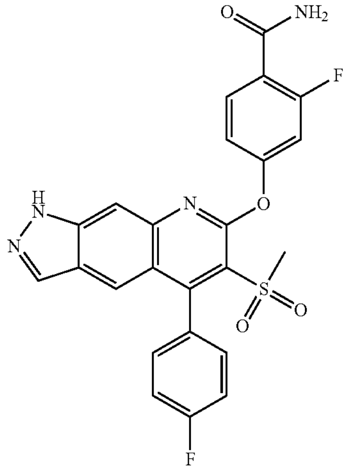 [SMILES: CS(=O)(=O)c1c(Oc2ccc(C(N)=O)c(F)c2)nc2cc3[nH]ncc3cc2c1-c1ccc(F)cc1]
Compound 218
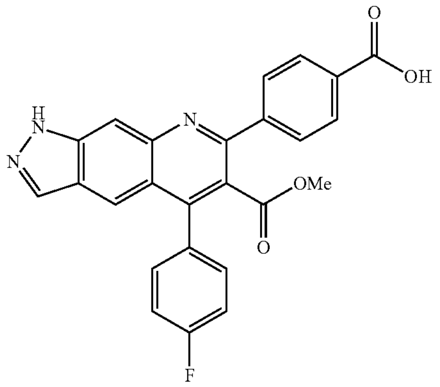 [SMILES: COC(=O)c1c(-c2ccc(C(=O)O)cc2)nc2cc3[nH]ncc3cc2c1-c1ccc(F)cc1]

TABLE I-continued
| Compounds 1-262 |
|---|
Compound 219
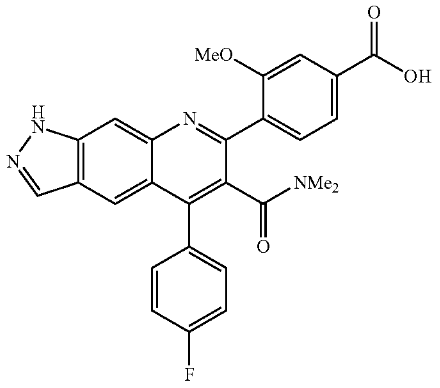 [SMILES: COc1cc(C(=O)O)ccc1-c1nc2cc3[nH]ncc3cc2c(-c2ccc(F)cc2)c1C(=O)N(C)C]
Compound 220
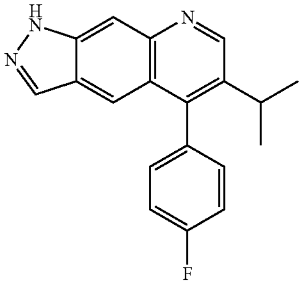 [SMILES: CC(C)c1cnc2cc3[nH]ncc3cc2c1-c1ccc(F)cc1]
Compound 221
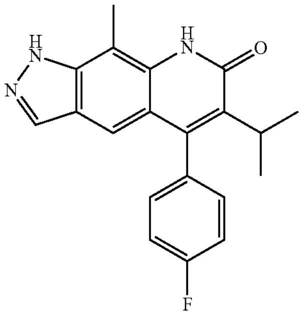 [SMILES: Cc1c2[nH]ncc2cc2c(-c3ccc(F)cc3)c(C(C)C)c(=O)[nH]c12]
Compound 223
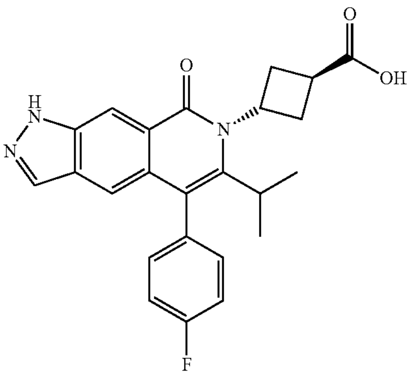

TABLE I-continued
| Compounds 1-262 | |
|---|---|
| 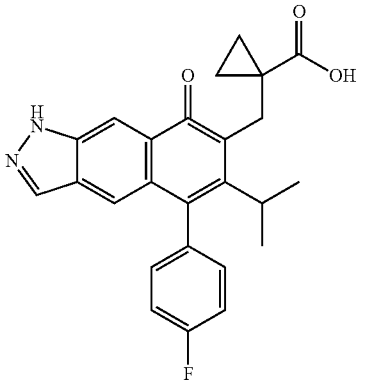 | Compound 224 |
| 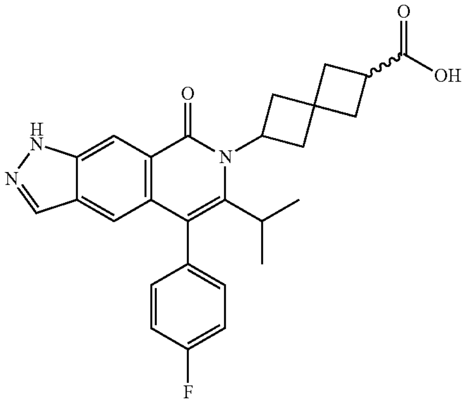 [SMILES: CC(C)c1c(-c2ccc(F)cc2)c2cc3cn[nH]c3cc2c(=O)n1C1CC2(CC(C(=O)O)C2)C1] | Compound 225 |
| 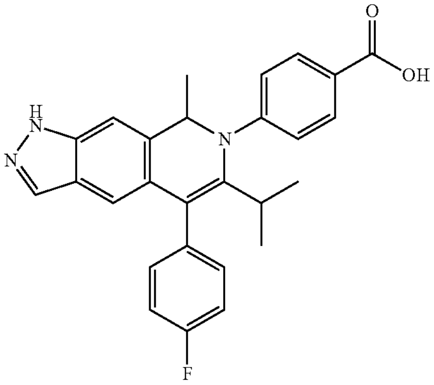 [SMILES: CC(C)C1=C(c2ccc(F)cc2)c2cc3cn[nH]c3cc2C(C)N1c1ccc(C(=O)O)cc1] | Compound 226 |
| 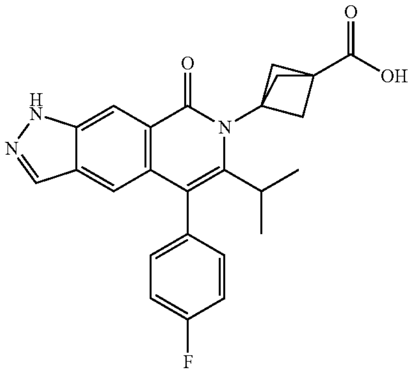 [SMILES: CC(C)c1c(-c2ccc(F)cc2)c2cc3cn[nH]c3cc2c(=O)n1C12CC(C(=O)O)(C1)C2] | Compound 227 |

TABLE I-continued
| Compounds 1-262 |
| --- |
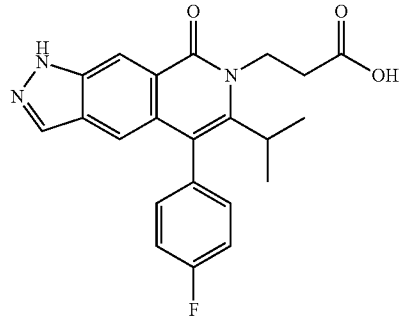 [SMILES: CC(C)c1c(-c2ccc(F)cc2)c2cc3cn[nH]c3cc2c(=O)n1CCC(=O)O]
Compound 228
Compound 229
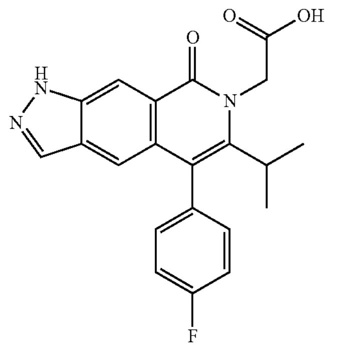 [SMILES: CC(C)c1c(-c2ccc(F)cc2)c2cc3cn[nH]c3cc2c(=O)n1CC(=O)O]
Compound 230
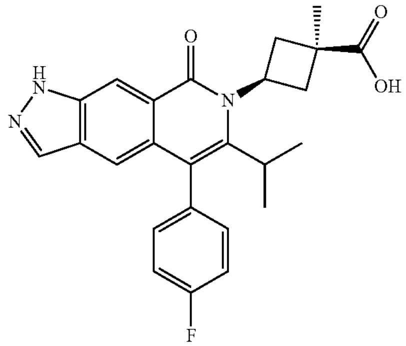 [SMILES: CC(C)c1c(-c2ccc(F)cc2)c2cc3cn[nH]c3cc2c(=O)n1[C@H]1C[C@@](C)(C(=O)O)C1]
Compound 231
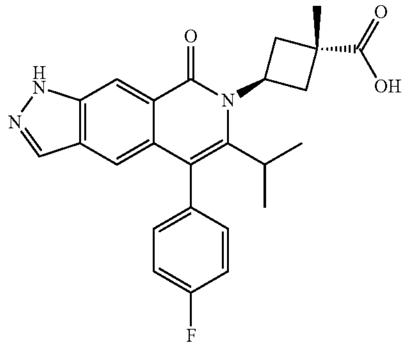 [SMILES: CC(C)c1c(-c2ccc(F)cc2)c2cc3cn[nH]c3cc2c(=O)n1[C@H]1C[C@](C)(C(=O)O)C1]

TABLE I-continued
| Compounds 1-262 |
| --- |
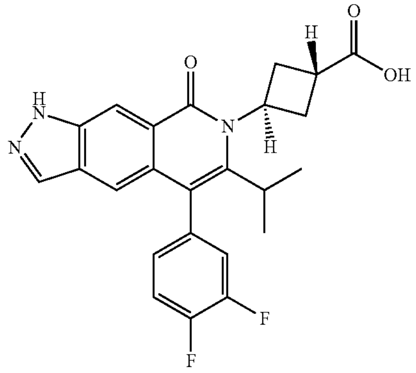 [SMILES: CC(C)c1c(-c2ccc(F)c(F)c2)c2cc3cn[nH]c3cc2c(=O)n1[C@H]1C[C@H](C(=O)O)C1]
Compound 232
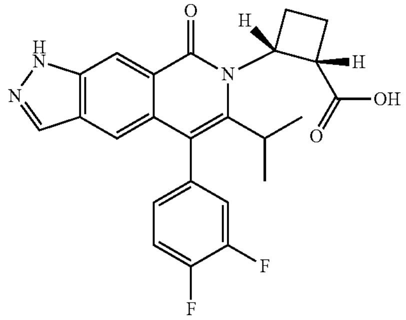 [SMILES: CC(C)c1c(-c2ccc(F)c(F)c2)c2cc3cn[nH]c3cc2c(=O)n1[C@@H]1CC[C@@H]1C(=O)O]
Compound 233
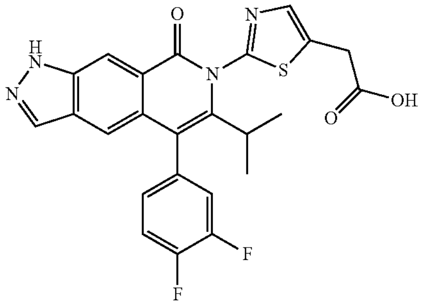 [SMILES: CC(C)c1c(-c2ccc(F)c(F)c2)c2cc3cn[nH]c3cc2c(=O)n1-c1ncc(CC(=O)O)s1]
Compound 234
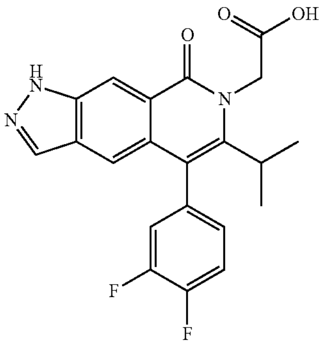 [SMILES: CC(C)c1c(-c2ccc(F)c(F)c2)c2cc3cn[nH]c3cc2c(=O)n1CC(=O)O]
Compound 235

TABLE I-continued
| Compounds 1-262 | |
|---|---|
| 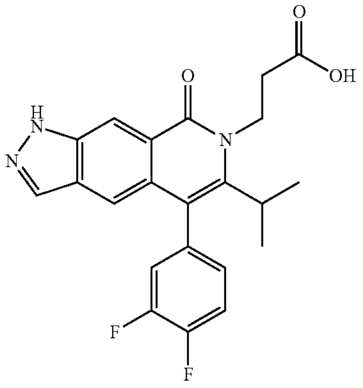 [SMILES: CC(C)c1c(-c2ccc(F)c(F)c2)c2cc3cn[nH]c3cc2c(=O)n1CCC(=O)O] | Compound 236 |
| 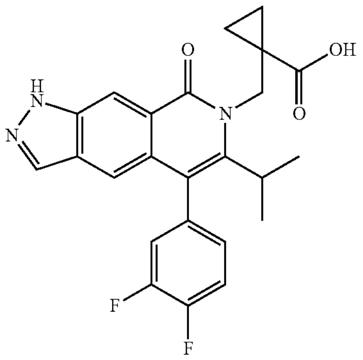 [SMILES: CC(C)c1c(-c2ccc(F)c(F)c2)c2cc3cn[nH]c3cc2c(=O)n1CC1(C(=O)O)CC1] | Compound 237 |
| 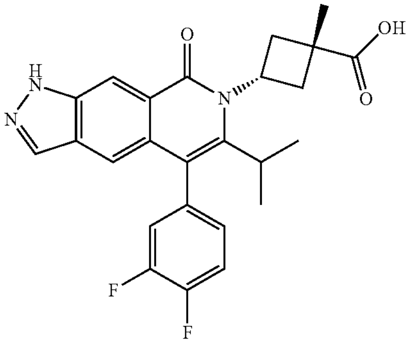 [SMILES: CC(C)c1c(-c2ccc(F)c(F)c2)c2cc3cn[nH]c3cc2c(=O)n1[C@H]1C[C@@](C)(C(=O)O)C1] | Compound 238 |
| 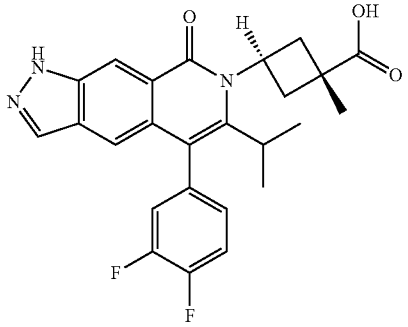 [SMILES: CC(C)c1c(-c2ccc(F)c(F)c2)c2cc3cn[nH]c3cc2c(=O)n1[C@H]1C[C@](C)(C(=O)O)C1] | Compound 239 |

TABLE I-continued
| Compounds 1-262 |
| --- |
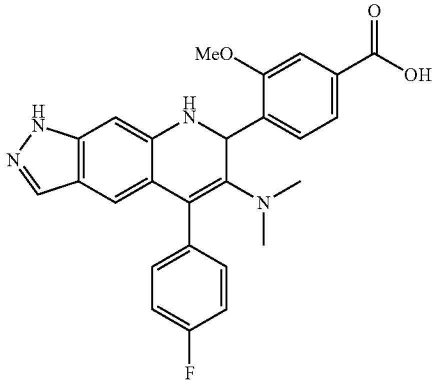 [SMILES: COc1cc(C(=O)O)ccc1C1Nc2cc3[nH]ncc3cc2C(c2ccc(F)cc2)=C1N(C)C]
Compound 240
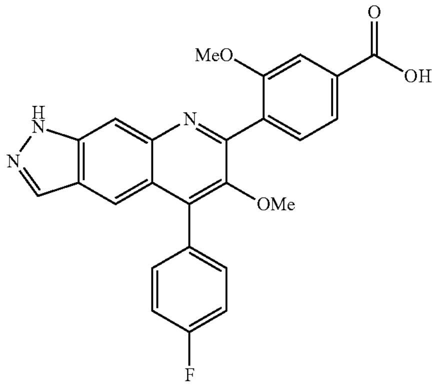 [SMILES: COc1cc(C(=O)O)ccc1-c1nc2cc3[nH]ncc3cc2c(-c2ccc(F)cc2)c1OC]
Compound 241
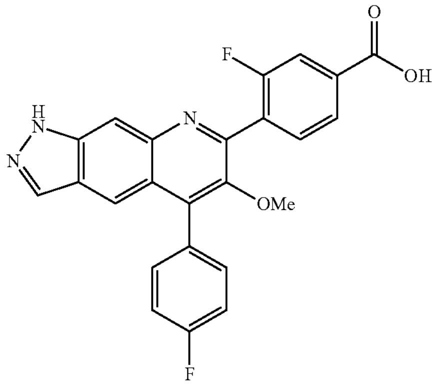 [SMILES: COc1c(-c2ccc(C(=O)O)cc2F)nc2cc3[nH]ncc3cc2c1-c1ccc(F)cc1]
Compound 242
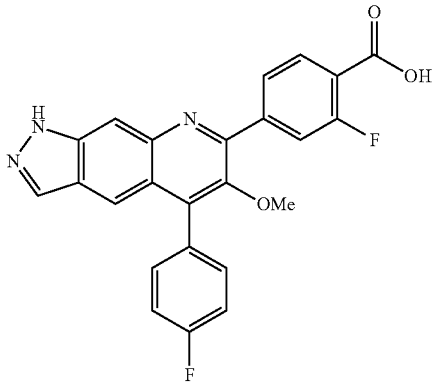 [SMILES: COc1c(-c2ccc(C(=O)O)c(F)c2)nc2cc3[nH]ncc3cc2c1-c1ccc(F)cc1]
Compound 243

TABLE I-continued
| Compounds 1-262 |
| --- |
Compound 244
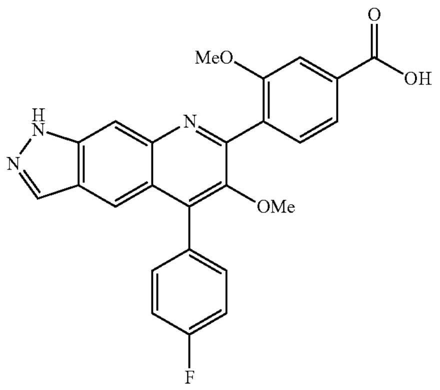
Compound 245
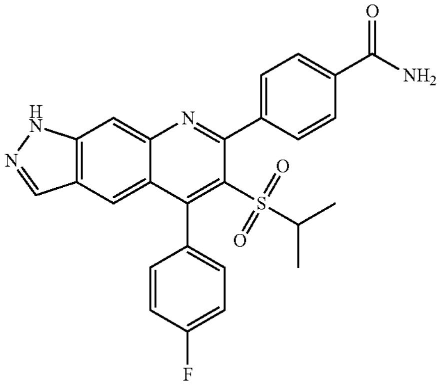 [SMILES: CC(C)S(=O)(=O)c1c(-c2ccc(C(N)=O)cc2)nc2cc3[nH]ncc3cc2c1-c1ccc(F)cc1]
Compound 246
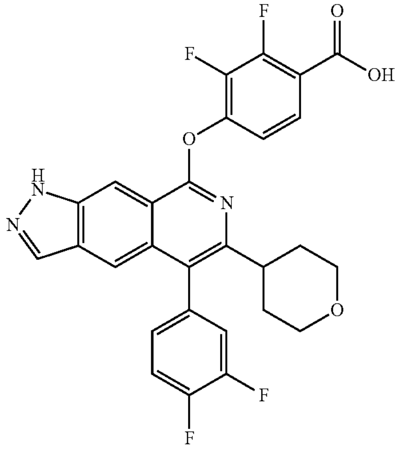 [SMILES: O=C(O)c1ccc(Oc2nc(C3CCOCC3)c(-c3ccc(F)c(F)c3)c3cc4cn[nH]c4cc23)c(F)c1F]

TABLE I-continued
| Compounds 1-262 |
| --- |
Compound 247
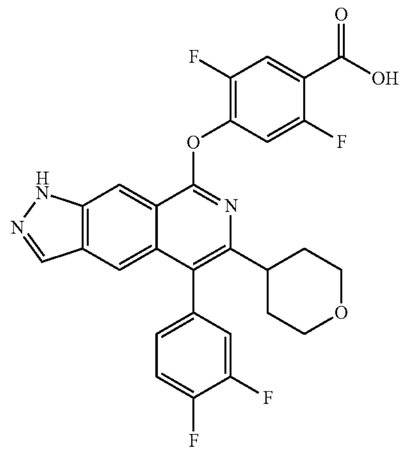 [SMILES: O=C(O)c1cc(F)c(Oc2nc(C3CCOCC3)c(-c3ccc(F)c(F)c3)c3cc4cn[nH]c4cc23)cc1F]
Compound 248
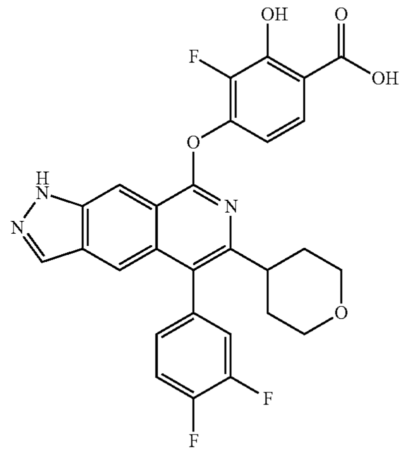 [SMILES: O=C(O)c1ccc(Oc2nc(C3CCOCC3)c(-c3ccc(F)c(F)c3)c3cc4cn[nH]c4cc23)c(F)c1O]
Compound 249
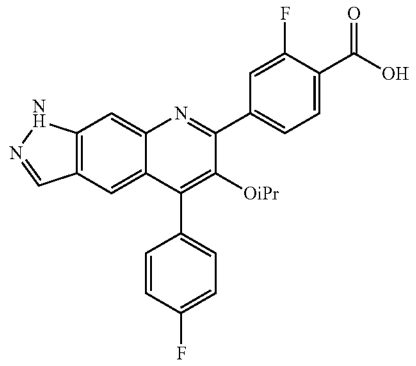 [SMILES: CC(C)Oc1c(-c2ccc(C(=O)O)c(F)c2)nc2cc3[nH]ncc3cc2c1-c1ccc(F)cc1]

TABLE I-continued
| Compounds 1-262 |
|---|
Compound 250
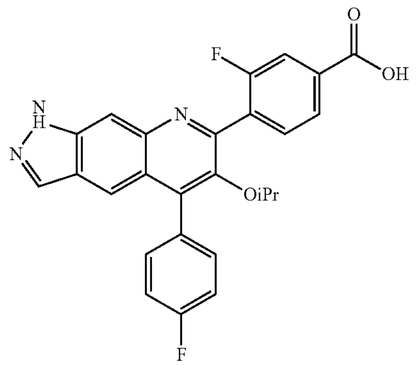 [SMILES: CC(C)Oc1c(-c2ccc(C(=O)O)cc2F)nc2cc3[nH]ncc3cc2c1-c1ccc(F)cc1]
Compound 251
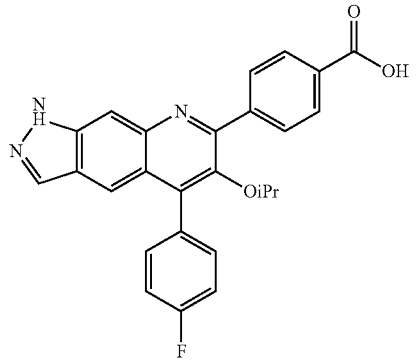 [SMILES: CC(C)Oc1c(-c2ccc(C(=O)O)cc2)nc2cc3[nH]ncc3cc2c1-c1ccc(F)cc1]
Compound 252
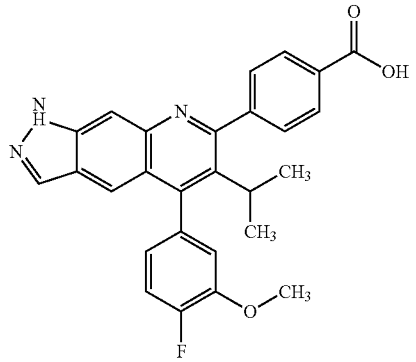 [SMILES: COc1cc(-c2c(C(C)C)c(-c3ccc(C(=O)O)cc3)nc3cc4[nH]ncc4cc23)ccc1F]
Compound 253
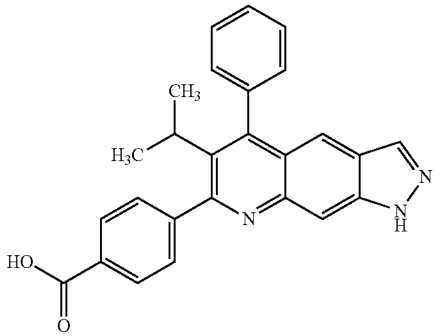 [SMILES: CC(C)c1c(-c2ccc(C(=O)O)cc2)nc2cc3[nH]ncc3cc2c1-c1ccccc1]

TABLE I-continued
| Compounds 1-262 |
| --- |
Compound 254
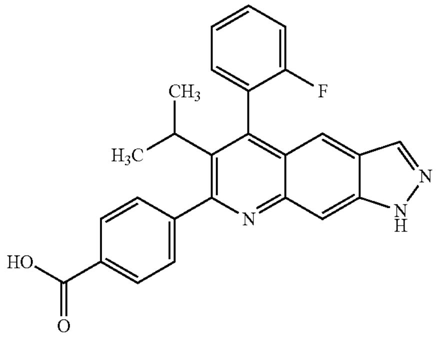 [SMILES: CC(C)c1c(-c2ccc(C(=O)O)cc2)nc2cc3[nH]ncc3cc2c1-c1ccccc1F]
Compound 255
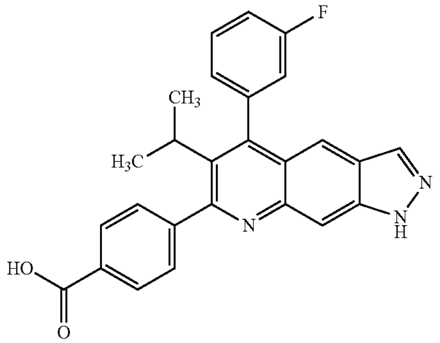 [SMILES: CC(C)c1c(-c2ccc(C(=O)O)cc2)nc2cc3[nH]ncc3cc2c1-c1cccc(F)c1]
Compound 256
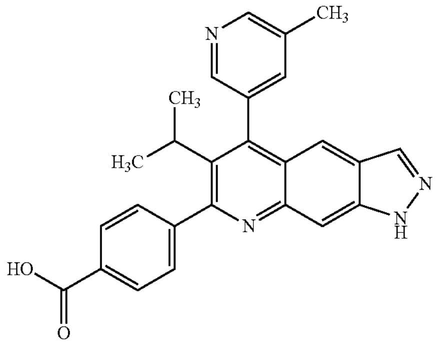 [SMILES: Cc1cncc(-c2c(C(C)C)c(-c3ccc(C(=O)O)cc3)nc3cc4[nH]ncc4cc23)c1]
Compound 257
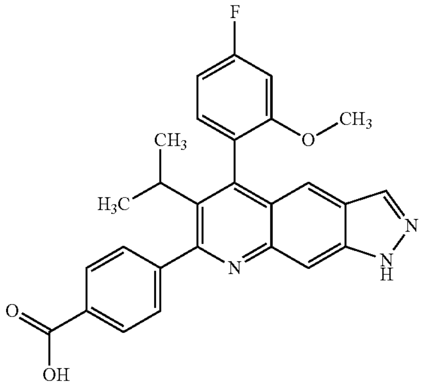 [SMILES: COc1cc(F)ccc1-c1c(C(C)C)c(-c2ccc(C(=O)O)cc2)nc2cc3[nH]ncc3cc12]

TABLE I-continued
| Compounds 1-262 |
| --- |
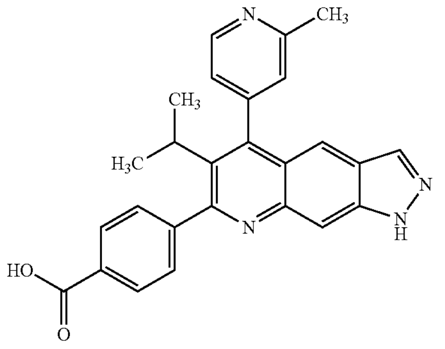 [SMILES: Cc1cc(-c2c(C(C)C)c(-c3ccc(C(=O)O)cc3)nc3cc4[nH]ncc4cc23)ccn1]
Compound 258
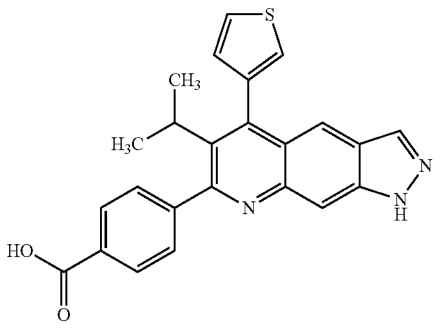 [SMILES: CC(C)c1c(-c2ccc(C(=O)O)cc2)nc2cc3[nH]ncc3cc2c1-c1ccsc1]
Compound 259
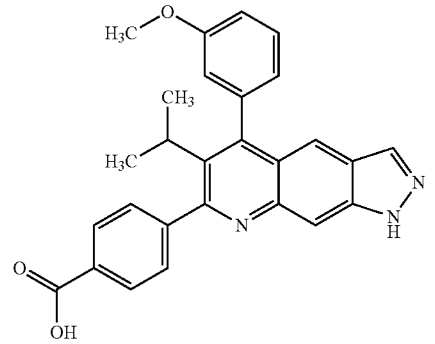 [SMILES: COc1cccc(-c2c(C(C)C)c(-c3ccc(C(=O)O)cc3)nc3cc4[nH]ncc4cc23)c1]
Compound 260
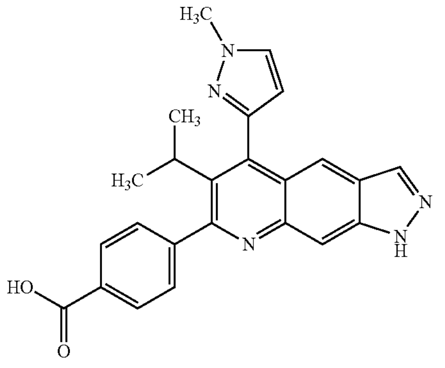 [SMILES: CC(C)c1c(-c2ccc(C(=O)O)cc2)nc2cc3[nH]ncc3cc2c1-c1ccn(C)n1]
Compound 261

TABLE I-continued

| Compounds 1-262 |
| --- |
| 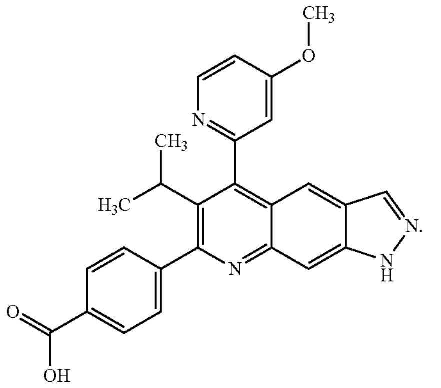 [SMILES: COc1ccnc(-c2c(C(C)C)c(-c3ccc(C(=O)O)cc3)nc3cc4[nH]ncc4cc23)c1] Compound 262 |

34. A pharmaceutical composition comprising the compound, tautomer, deuterated derivative, or pharmaceutically acceptable salt according to claim 1 and a pharmaceutically acceptable carrier.

35. A method of modulating alpha-1 antitrypsin (AAT) activity in a subject comprising administering the compound, tautomer, deuterated derivative, or pharmaceutically acceptable salt according to claim 1.

36. A method of treating alpha-1 antitrypsin deficiency (AATD) in a subject comprising administering the compound, tautomer, deuterated derivative, or pharmaceutically acceptable salt according to claim 1.

* * * * *